US012624033B2

(12) United States Patent
Fink et al.

(10) Patent No.: US 12,624,033 B2
(45) Date of Patent: May 12, 2026

(54) KRAS INHIBITORS

(71) Applicant: Bristol-Myers Squibb Company, Princeton, NJ (US)

(72) Inventors: Brian Edward Fink, Yardley, PA (US); Pravin S. Shirude, Mumbai (IN); Amit Kumar Chattopadhyay, Bangalore (IN); Laxmi Narayan Nanda, Bangalore (IN); Vishweshwaraiah Baligar, Bangalore (IN); Balaji Seshadri, Bangalore (IN); T.G. Murali Dhar, Princeton, NJ (US); Li-Qiang Sun, Princeton, NJ (US); Zhizhen Barbara Zheng, Princeton, NJ (US); Manoranjan Panda, Bangalore (IN); Maximilian David Palkowitz, Cambridge, MA (US); Sirish Kaushik Lakkaraju, Princeton, NJ (US); Moloy Banerjee, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 19/072,656

(22) Filed: Mar. 6, 2025

(65) Prior Publication Data

US 2025/0250271 A1 Aug. 7, 2025

Related U.S. Application Data

(63) Continuation of application No. 18/759,708, filed on Jun. 28, 2024.

(60) Provisional application No. 63/655,965, filed on Jun. 4, 2024, provisional application No. 63/551,905, filed on Feb. 9, 2024, provisional application No. 63/588,239, filed on Oct. 5, 2023, provisional application No. 63/511,455, filed on Jun. 30, 2023.

(51) Int. Cl.

| | |
|---|---|
| ***C07D 471/04*** | (2006.01) |
| ***A61K 31/519*** | (2006.01) |
| ***A61K 31/5377*** | (2006.01) |
| ***A61K 31/538*** | (2006.01) |
| ***A61K 31/5386*** | (2006.01) |
| ***A61K 31/553*** | (2006.01) |
| ***A61K 31/554*** | (2006.01) |
| ***A61P 35/00*** | (2006.01) |
| ***C07D 519/00*** | (2006.01) |

(52) U.S. Cl.

CPC .......... *C07D 471/04* (2013.01); *A61K 31/519* (2013.01); *A61K 31/5377* (2013.01); *A61K 31/538* (2013.01); *A61K 31/5386* (2013.01); *A61K 31/553* (2013.01); *A61K 31/554* (2013.01); *A61P 35/00* (2018.01); *C07D 519/00* (2013.01)

(58) Field of Classification Search

CPC ...... C07D 471/04; A61K 31/553; A61P 35/00

See application file for complete search history.

(56) References Cited

U.S. PATENT DOCUMENTS

| | | | |
|---|---|---|---|
| 10,011,600 | B2 | 7/2018 | Li et al. |
| 2019/0127336 | A1 | 5/2019 | Li et al. |
| 2020/0223817 | A1 | 7/2020 | Piazza et al. |
| 2020/0239479 | A1 | 7/2020 | Garland et al. |
| 2021/0154198 | A1 | 5/2021 | Deng et al. |
| 2022/0194961 | A1 | 6/2022 | Wang et al. |
| 2022/0324862 | A1 | 10/2022 | Yu et al. |
| 2023/0072276 | A1 | 3/2023 | Wang et al. |
| 2023/0226061 | A1 | 7/2023 | Vilenchik et al. |
| 2023/0339952 | A1 | 10/2023 | Wu et al. |
| 2024/0025907 | A1 | 1/2024 | Wang et al. |
| 2024/0067662 | A1 | 2/2024 | Condakes et al. |
| 2024/0199584 | A1 | 6/2024 | Fink et al. |
| 2024/0217982 | A1 | 7/2024 | Fink et al. |
| 2024/0317769 | A1 | 9/2024 | Fink et al. |
| 2024/0343736 | A1 | 10/2024 | Kercher et al. |
| 2024/0368191 | A1 | 11/2024 | Li et al. |
| 2024/0376127 | A1 | 11/2024 | Wang et al. |
| 2024/0383922 | A1 | 11/2024 | Cortopassi Coelho et al. |
| 2025/0154148 | A1 | 5/2025 | Fink et al. |
| 2025/0163046 | A1 | 5/2025 | Fink et al. |

FOREIGN PATENT DOCUMENTS

| | | | |
|---|---|---|---|
| CN | 111773225 | A | 10/2020 |
| CN | 112047937 | A | 12/2020 |
| CN | 112110918 | A | 12/2020 |
| CN | 113999226 | A | 2/2022 |
| CN | 114907387 | A | 8/2022 |
| CN | 115028644 | A | 9/2022 |
| CN | 115304623 | A | 11/2022 |
| CN | 115611888 | A | 1/2023 |
| CN | 115677701 | A | 2/2023 |

(Continued)

OTHER PUBLICATIONS

Mortison, J.D., et al., "Rapid Evaluation of Small Molecule Cellular Target Engagement with a Luminescent Thermal Shift Assay," ACS Medicinal Chemistry Letters 12(8):1288-1294, American Chemical Society, United States (Jul. 2021).

(Continued)

*Primary Examiner* — Renee Claytor

*Assistant Examiner* — Elena Vladimirovna Vishnyakova

(74) *Attorney, Agent, or Firm* — Sterne, Kessler, Goldstein & Fox P.L.L.C.

(57) ABSTRACT

The present disclosure provides KRAS inhibitors. Methods of treating cancers using the compounds are also provided.

15 Claims, No Drawings

(56) References Cited

FOREIGN PATENT DOCUMENTS

| | | | |
|---|---|---|---|
| CN | 115745955 | A | 3/2023 |
| CN | 115813930 | A | 3/2023 |
| CN | 116102559 | A | 5/2023 |
| CN | 116332948 | A | 6/2023 |
| CN | 116478184 | A | 7/2023 |
| CN | 116574104 | A | 8/2023 |
| CN | 116731044 | A | 9/2023 |
| CN | 116768858 | A | 9/2023 |
| CN | 116829151 | A | 9/2023 |
| CN | 116969977 | A | 10/2023 |
| CN | 117120058 | A | 11/2023 |
| CN | 117263959 | A | 12/2023 |
| CN | 117425658 | A | 1/2024 |
| CN | 117645627 | A | 3/2024 |
| CN | 117683051 | A | 3/2024 |
| CN | 117736226 | A | 3/2024 |
| CN | 117794940 | A | 3/2024 |
| CN | 118221700 | A | 6/2024 |
| CN | 118496300 | A | 8/2024 |
| CN | 118660880 | A | 9/2024 |
| CN | 118754899 | A | 10/2024 |
| CN | 118786129 | A | 10/2024 |
| CN | 119661539 | A | 3/2025 |
| EP | 4389751 | A1 | 6/2024 |
| WO | WO-2008080056 | A2 | 7/2008 |
| WO | WO-2008103470 | A2 | 8/2008 |
| WO | WO-2010093849 | A2 | 8/2010 |
| WO | WO-2012088030 | A1 | 6/2012 |
| WO | WO-2016099452 | A1 | 6/2016 |
| WO | WO-2016100542 | A1 | 6/2016 |
| WO | WO-2016100546 | A1 | 6/2016 |
| WO | WO-2016161361 | A1 | 10/2016 |
| WO | WO-2017114500 | A1 | 7/2017 |
| WO | WO-2017127442 | A1 | 7/2017 |
| WO | WO-2017172979 | A1 | 10/2017 |
| WO | WO-2018115380 | A1 | 6/2018 |
| WO | WO-2018237084 | A1 | 12/2018 |
| WO | WO-2020156285 | A1 | 8/2020 |
| WO | WO-2020177629 | A1 | 9/2020 |
| WO | WO-2020214537 | A1 | 10/2020 |
| WO | WO-2020221239 | A1 | 11/2020 |
| WO | WO-2020254451 | A1 | 12/2020 |
| WO | WO-2021026349 | A1 | 2/2021 |
| WO | WO-2021031952 | A1 | 2/2021 |
| WO | WO-2021057867 | A1 | 4/2021 |
| WO | WO-2021108683 | A1 | 6/2021 |
| WO | WO-2021109737 | A1 | 6/2021 |
| WO | WO-2021175199 | A1 | 9/2021 |
| WO | WO-2021203768 | A1 | 10/2021 |
| WO | WO-2021228161 | A1 | 11/2021 |
| WO | WO-2021231526 | A1 | 11/2021 |
| WO | WO-2021243280 | A2 | 12/2021 |
| WO | WO-2021247859 | A1 | 12/2021 |
| WO | WO-2021262962 | A1 | 12/2021 |
| WO | WO-2022017519 | A1 | 1/2022 |
| WO | WO-2022031952 | A2 | 2/2022 |
| WO | WO-2022042630 | A1 | 3/2022 |
| WO | WO-2022047093 | A1 | 3/2022 |
| WO | WO-2022047260 | A1 | 3/2022 |
| WO | WO-2022060836 | A1 | 3/2022 |
| WO | WO-2022061251 | A1 | 3/2022 |
| WO | WO-2022061348 | A1 | 3/2022 |
| WO | WO-2022068921 | A1 | 4/2022 |
| WO | WO-2022078414 | A1 | 4/2022 |
| WO | WO-2022079226 | A1 | 4/2022 |
| WO | WO-2022087335 | A1 | 4/2022 |
| WO | WO-2022095960 | A1 | 5/2022 |
| WO | WO-2022109307 | A1 | 5/2022 |
| WO | WO-2022132200 | A1 | 6/2022 |
| WO | WO-2022133038 | A1 | 6/2022 |
| WO | WO-2022140427 | A1 | 6/2022 |
| WO | WO-2022170802 | A1 | 8/2022 |
| WO | WO-2022173870 | A1 | 8/2022 |
| WO | WO-2022187236 | A1 | 9/2022 |
| WO | WO-2022187527 | A1 | 9/2022 |
| WO | WO-2022192790 | A1 | 9/2022 |
| WO | WO-2022192794 | A1 | 9/2022 |
| WO | WO-2022197862 | A1 | 9/2022 |
| WO | WO-2022212894 | A1 | 10/2022 |
| WO | WO-2022221866 | A1 | 10/2022 |
| WO | WO-2022223033 | A1 | 10/2022 |
| WO | WO-2022228543 | A1 | 11/2022 |
| WO | WO-2022228568 | A1 | 11/2022 |
| WO | WO-2022237649 | A1 | 11/2022 |
| WO | WO-2022246092 | A1 | 11/2022 |
| WO | WO-2022247760 | A1 | 12/2022 |
| WO | WO-2022247770 | A1 | 12/2022 |
| WO | WO-2022248885 | A2 | 12/2022 |
| WO | WO-2022250170 | A1 | 12/2022 |
| WO | WO-2022251292 | A1 | 12/2022 |
| WO | WO-2022256459 | A1 | 12/2022 |
| WO | WO-2022258974 | A1 | 12/2022 |
| WO | WO-2022266015 | A1 | 12/2022 |
| WO | WO-2022266248 | A1 | 12/2022 |
| WO | WO-2022268209 | A1 | 12/2022 |
| WO | WO-2022271823 | A1 | 12/2022 |
| WO | WO-2023001123 | A1 | 1/2023 |
| WO | WO-2023274324 | A1 | 1/2023 |
| WO | WO-2023008577 | A1 | 2/2023 |
| WO | WO-2023018809 | A1 | 2/2023 |
| WO | WO-2023018810 | A1 | 2/2023 |
| WO | WO-2023018812 | A1 | 2/2023 |
| WO | WO-2023020518 | A1 | 2/2023 |
| WO | WO-2023020519 | A1 | 2/2023 |
| WO | WO-2023020521 | A1 | 2/2023 |
| WO | WO-2023020523 | A1 | 2/2023 |
| WO | WO-2023022912 | A1 | 2/2023 |
| WO | WO-2023039240 | A1 | 3/2023 |
| WO | WO-2023045960 | A1 | 3/2023 |
| WO | WO-2023046135 | A1 | 3/2023 |
| WO | WO-2023056951 | A1 | 4/2023 |
| WO | WO-2023061294 | A1 | 4/2023 |
| WO | WO-2023061463 | A1 | 4/2023 |
| WO | WO-2023077441 | A1 | 5/2023 |
| WO | WO-2023081476 | A1 | 5/2023 |
| WO | WO-2023097227 | A1 | 6/2023 |
| WO | WO-2023098425 | A1 | 6/2023 |
| WO | WO-2023098426 | A1 | 6/2023 |
| WO | WO-2023098832 | A1 | 6/2023 |
| WO | WO-2023105491 | A1 | 6/2023 |
| WO | WO-2023114733 | A1 | 6/2023 |
| WO | WO-2023117681 | A1 | 6/2023 |
| WO | WO-2023122154 | A1 | 6/2023 |
| WO | WO-2023122662 | A1 | 6/2023 |
| WO | WO-2023125627 | A1 | 7/2023 |
| WO | WO-2023125989 | A1 | 7/2023 |
| WO | WO-2023133183 | A1 | 7/2023 |
| WO | WO-2023134465 | A1 | 7/2023 |
| WO | WO-2023137223 | A1 | 7/2023 |
| WO | WO-2023138583 | A1 | 7/2023 |
| WO | WO-2023140846 | A1 | 7/2023 |
| WO | WO-2023141300 | A1 | 7/2023 |
| WO | WO-2023141570 | A2 | 7/2023 |
| WO | WO-2023143312 | A1 | 8/2023 |
| WO | WO-2023143352 | A1 | 8/2023 |
| WO | WO-2023143623 | A1 | 8/2023 |
| WO | WO-2023150284 | A2 | 8/2023 |
| WO | WO-2023159086 | A1 | 8/2023 |
| WO | WO-2023159087 | A1 | 8/2023 |
| WO | WO-2023165618 | A1 | 9/2023 |
| WO | WO-2023172737 | A1 | 9/2023 |
| WO | WO-2023173014 | A1 | 9/2023 |
| WO | WO-2023173016 | A1 | 9/2023 |
| WO | WO-2023173017 | A1 | 9/2023 |
| WO | WO-2023179703 | A1 | 9/2023 |
| WO | WO-2023183585 | A1 | 9/2023 |
| WO | WO-2023190748 | A1 | 10/2023 |
| WO | WO-2023197984 | A1 | 10/2023 |
| WO | WO-2023215256 | A1 | 11/2023 |
| WO | WO-2023215801 | A1 | 11/2023 |
| WO | WO-2023215802 | A1 | 11/2023 |
| WO | WO-2023225302 | A1 | 11/2023 |
| WO | WO-2023240188 | A1 | 12/2023 |

(56) References Cited

FOREIGN PATENT DOCUMENTS

| | | | | |
|---|---|---|---|---|
| WO | WO-2023240189 A1 | 12/2023 | | |
| WO | WO-2023244599 A1 | 12/2023 | | |
| WO | WO-2023244600 A1 | 12/2023 | | |
| WO | WO-2023244604 A1 | 12/2023 | | |
| WO | WO-2023244615 A1 | 12/2023 | | |
| WO | WO-2023246777 A1 | * | 12/2023 | ............. A61P 35/00 |
| WO | WO-2024002373 A1 | 1/2024 | | |
| WO | WO-2024008068 A1 | 1/2024 | | |
| WO | WO-2024009191 A1 | 1/2024 | | |
| WO | WO-2024012519 A1 | 1/2024 | | |
| WO | WO-2024015262 A1 | 1/2024 | | |
| WO | WO-2024022444 A1 | 2/2024 | | |
| WO | WO-2024022471 A1 | 2/2024 | | |
| WO | WO-2024029613 A1 | 2/2024 | | |
| WO | WO-2024030633 A1 | 2/2024 | | |
| WO | WO-2024030647 A1 | 2/2024 | | |
| WO | WO-2024031088 A1 | 2/2024 | | |
| WO | WO-2024032702 A1 | 2/2024 | | |
| WO | WO-2024032703 A1 | 2/2024 | | |
| WO | WO-2024032704 A1 | 2/2024 | | |
| WO | WO-2024032747 A1 | 2/2024 | | |
| WO | WO-2024034591 A1 | 2/2024 | | |
| WO | WO-2024034593 A1 | 2/2024 | | |
| WO | WO-2024036270 A1 | 2/2024 | | |
| WO | WO-2024040109 A2 | 2/2024 | | |
| WO | WO-2024040131 A1 | 2/2024 | | |
| WO | WO-2024041589 A1 | 2/2024 | | |
| WO | WO-2024041606 A1 | 2/2024 | | |
| WO | WO-2024041621 A1 | 2/2024 | | |
| WO | WO-2024044667 A2 | 2/2024 | | |
| WO | WO-2024050351 A1 | 3/2024 | | |
| WO | WO-2024051763 A1 | 3/2024 | | |
| WO | WO-2024054926 A1 | 3/2024 | | |
| WO | WO-2024056063 A1 | 3/2024 | | |
| WO | WO-2024061333 A1 | 3/2024 | | |
| WO | WO-2024061365 A1 | 3/2024 | | |
| WO | WO-2024063576 A1 | 3/2024 | | |
| WO | WO-2024063578 A1 | 3/2024 | | |
| WO | WO-2024067575 A1 | 4/2024 | | |
| WO | WO-2024083246 A1 | 4/2024 | | |
| WO | WO-2024083255 A1 | 4/2024 | | |
| WO | WO-2024083256 A1 | 4/2024 | | |
| WO | WO-2024083258 A1 | 4/2024 | | |
| WO | WO-2024085661 A1 | 4/2024 | | |
| WO | WO-2024088069 A1 | 5/2024 | | |
| WO | WO-2024097559 A1 | 5/2024 | | |
| WO | WO-2024104425 A1 | 5/2024 | | |
| WO | WO-2024104453 A1 | 5/2024 | | |
| WO | WO-2024107686 A1 | 5/2024 | | |
| WO | WO-2024118966 A1 | 6/2024 | | |
| WO | WO-2024119278 A1 | 6/2024 | | |
| WO | WO-2024120424 A1 | 6/2024 | | |
| WO | WO-2024120433 A1 | 6/2024 | | |
| WO | WO-2024153180 A1 | 7/2024 | | |
| WO | WO-2024178304 A1 | 8/2024 | | |
| WO | WO-2024178313 A1 | 8/2024 | | |
| WO | WO-2024187174 A2 | 9/2024 | | |
| WO | WO-2024206747 A1 | 10/2024 | | |
| WO | WO-2024206766 A1 | 10/2024 | | |
| WO | WO-2024207892 A1 | 10/2024 | | |
| WO | WO-2024209339 A1 | 10/2024 | | |
| WO | WO-2024213122 A1 | 10/2024 | | |
| WO | WO-2024213979 A1 | 10/2024 | | |
| WO | WO-2024215754 A1 | 10/2024 | | |
| WO | WO-2024218686 A1 | 10/2024 | | |
| WO | WO-2024220440 A1 | 10/2024 | | |
| WO | WO-2024230734 A1 | 11/2024 | | |
| WO | WO-2024233703 A2 | 11/2024 | | |
| WO | WO-2024233838 A1 | 11/2024 | | |
| WO | WO-2024235225 A1 | 11/2024 | | |
| WO | WO-2024235286 A1 | 11/2024 | | |
| WO | WO-2024238343 A1 | 11/2024 | | |
| WO | WO-2024238633 A2 | 11/2024 | | |
| WO | WO-2024243025 A1 | 11/2024 | | |
| WO | WO-2024254334 A1 | 12/2024 | | |
| WO | WO-2024254404 A2 | 12/2024 | | |
| WO | WO-2024255827 A1 | 12/2024 | | |
| WO | WO-2024261256 A1 | 12/2024 | | |
| WO | WO-2024263586 A1 | 12/2024 | | |
| WO | WO-2025006753 A2 | 1/2025 | | |
| WO | WO-2025006783 A2 | 1/2025 | | |
| WO | WO-2025006967 A1 | 1/2025 | | |
| WO | WO-2025007000 A1 | 1/2025 | | |
| WO | WO-2025039676 A1 | 2/2025 | | |
| WO | WO-2025045141 A1 | 3/2025 | | |
| WO | WO-2025051242 A1 | 3/2025 | | |
| WO | WO-2025054347 A1 | 3/2025 | | |
| WO | WO-2025054530 A1 | 3/2025 | | |
| WO | WO-2025059040 A1 | 3/2025 | | |
| WO | WO-2025064542 A1 | 3/2025 | | |
| WO | WO-2025076044 A1 | 4/2025 | | |
| WO | WO-2025077770 A1 | 4/2025 | | |
| WO | WO-2025085748 A1 | 4/2025 | | |
| WO | WO-2025090809 A1 | 5/2025 | | |
| WO | WO-2025092798 A1 | 5/2025 | | |
| WO | WO-2025096738 A1 | 5/2025 | | |
| WO | WO-2025096855 A1 | 5/2025 | | |

OTHER PUBLICATIONS

Popow, J., et al., "Targeting Cancer With Small-molecule Pan-KRAS Degraders," BioRxiv Preprint, 141 pages, Cold Spring Harbor Laboratory, United States (Jul. 2024).

Song, J., et al., "Click Chemistry for Improvement in Selectivity of Quinazoline-Based Kinase Inhibitors for Mutant Epidermal Growth Factor Receptors," Bioorganic & Medicinal Chemistry Letters 29(3):477-480, Elsevier Science Ltd, United Kingdom (Feb. 2019).

Vasu, K.K., et al., "Imidazo[1,2-a]pyridines Linked With Thiazoles/thiophene Motif Through Keto Spacer as Potential Cytotoxic Agents and NF-κB Inhibitors," Bioorganic & Medicinal Chemistry Letters 27(24):5463-5466, Elsevier Science Ltd, United Kingdom (Dec. 2017).

International Search Report and Written Opinion for International Application No. PCT/US2024/036126, European Patent Office, Netherlands, mailed on Sep. 27, 2024, 10 pages.

International Search Report and Written Opinion for International Application No. PCT/US2024/036131, European Patent Office, Netherlands, mailed on Sep. 27, 2024, 10 pages.

Kuduk, S.D., et al., "SAR studies in the sulfonyl carboxamide class of HBV capsid assembly modulators," Bioorganic & Medicinal Chemistry Letters 29(16):2405-2409, Pergamon Press, United Kingdom (Aug. 2019).

Co-pending, U.S. Appl. No. 18/873,229, inventors Fink, B.E., et al., filed Dec. 9, 2024 (Not yet Published).

Co-pending, U.S. Appl. No. 18/875,573, inventors Kulyk, S., et al., filed Dec. 16, 2024 (Not yet Published).

Co-pending, U.S. Appl. No. 18/875,584, inventors Marx, M.A., et al., filed Dec. 16, 2024 (Not yet Published).

Co-pending, U.S. Appl. No. 18/875,603, inventors Wang, X., et al., filed Dec. 16, 2024 (Not yet Published).

Co-pending, U.S. Appl. No. 18/875,610, inventors Wang, X., et al., filed Dec. 16, 2024 (Not yet Published).

Kessler, D., et al., "Drugging an Undruggable Pocket on KRAS," Proceedings of the National Academy of Sciences of the United States of America 116(32):15823-15829, National Academy of Sciences, United States (Aug. 2019).

Liu, L., et al., "Discovery of Novel Indazole Derivatives as SOS1 Agonists that Activate KRAS Signaling," Bioorganic and Medicinal Chemistry 93:117457, Elsevier Science, United Kingdom (Oct. 2023).

Liu, M., et al., "Design, Synthesis, and Bioevaluation of Pyrido[2,3-d]pyrimidin-7-ones as Potent SOS1 Inhibitors," ACS Medicinal Chemistry Letters 14(2):183-190, American Chemical Society, United States (Jan. 2023).

Nilewski, C., et al., "Structure-Based Design and Evaluation of Reversible KRAS G13D Inhibitors," ACS Medicinal Chemistry Letters 15(1):21-28, American Chemical Society, United States (Dec. 2023).

(56) References Cited

OTHER PUBLICATIONS

Zhou, Z., et al., "Discovery of a Potent, Cooperative, and Selective SOS1 Protac ZZ151 with In Vivo Antitumor Efficacy in KRAS-Mutant Cancers," Journal of Medicinal Chemistry 66(6):4197-4214, American Chemical Society, United States (Mar. 2023).

Co-pending, U.S. Appl. No. 19/225,733 inventors Wang, X., et al., filed Jun. 2, 2025 (Not yet Published).

* cited by examiner

KRAS INHIBITORS

CROSS-REFERENCE TO RELATED APPLICATIONS

This application is a continuation of U.S. application Ser. No. 18/759,708, filed on Jun. 28, 2024, which claims the priority benefit of U.S. Provisional Application No. 63/511,455, filed Jun. 30, 2023; U.S. Provisional Application No. 63/588,239, filed Oct. 5, 2023; U.S. Provisional Application No. 63/551,905, filed Feb. 9, 2024; and U.S. Provisional Application No. 63/655,965, filed Jun. 4, 2024, which are each incorporated by reference herein in their entireties.

FIELD

The present disclosure provides KRAS inhibitors. Methods of treating cancers using the inhibitors are also provided.

BACKGROUND

The KRAS oncogene is a member of the RAS family of GTPases that are involved in numerous cellular signaling processes. KRAS mutations are gain-of-function mutations that are present in up to 30% of all tumors, including as many as 90% of pancreatic cancers. Single nucleotide substitutions that result in missense mutations at codons 12 and 13 of the KRAS primary amino acid sequence comprise approximately 40% of KRAS driver mutations in lung adenocarcinoma, with a G12C transversion being the most common activating mutation. KRAS G12C mutations occur in about 13% of lung adenocarcinomas and about 3% of colorectal adenocarcinomas and are also present in cancers of the breast, bladder, cervix, ovaries, pancreas and uterus. KRAS G12D mutations occur in 28% of all pancreatic ductal adenocarcinoma patients, 13% of all colorectal carcinoma patients, 4% of all non-small cell lung carcinoma patients and 3% of all gastric carcinoma patients. See, for example, https://www.mycancergenome.org/content/alteration/kras-g12d/. Due to the clinical significance of this protein, many attempts have been made to develop RAS inhibitors, but such attempts have been mostly unsuccessful. Accordingly, agents that inhibit mutant KRAS are desired.

SUMMARY

In some aspects, the present disclosure provides a compound of formula (I):

(I)

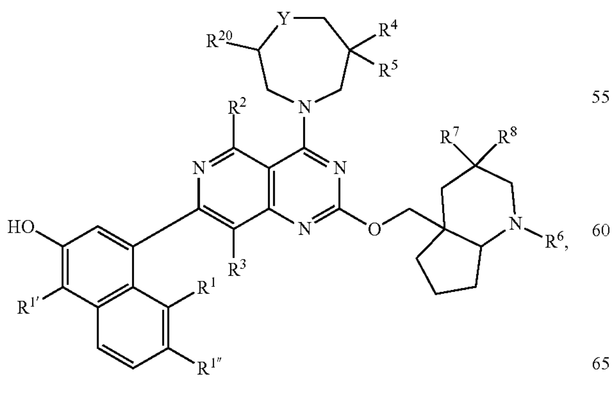

or a pharmaceutically acceptable salt thereof, wherein:

Y is O or $SO_2$, $R^1$ is hydrogen, halo, ethynyl or ethyl;

$R^{1'}$ is hydrogen, halo, or $C_{1-3}$ alkyl;

$R^{1''}$ is selected from hydrogen, $C_{2-3}$alkenyl, $C_{1-3}$ alkyl, $C_{2-3}$ alkynyl, halo, and hydroxy;

$R^2$ is hydrogen;

$R^3$ is halo;

$R^4$ and $R^5$ are the same or different and each is hydrogen, $C_{1-4}$ alkyl, hydroxy, $C_{1-4}$ hydroxyalkyl, or $C_{1-4}$ haloalkyl;

$R^{20}$ is selected from hydrogen and hydroxy$C_{1-4}$alkyl;

$R^6$ is $C_{1-6}$ alkyl optionally substituted with one or more deuterium atoms; $C_{3-6}$ cycloalkyl optionally substituted with $C_1$-$C_3$alkoxy, $C_1$-$C_3$alkoxy$C_{1-6}$ alkyl, amino, or cyanoethynyl; hydroxy$C_{1-6}$ alkyl; halo$C_{1-6}$ alkyl; hydroxy-halo$C_{1-6}$ alkyl; methylsulfonyl$C_1$-$C_6$alkyl; or —$(CH_2)_n$-A;

wherein A is a cyclic moiety selected from $C_{3-6}$ cycloalkyl, $C_{3-7}$ heterocycloalkyl, aryl, heteroaryl, spiro structures of any of these rings, and bicyclic structures of any of these rings, and n is 0, 1, 2, or 3;

wherein A is optionally substituted with one or more substituents selected from $C_{1-4}$ alkyl, $C_{1-4}$ alkylcarbonyl, $C_{3-6}$ cycloalkylcarbonyl, hydroxy, halo, cyano, halo$C_{1-6}$ alkyl, $C_{1-4}$ alkoxy, $C_{1-4}$ alkoxy $C_{1-4}$alkyl, $C_{1-4}$ alkoxycarbonyl, halo$C_{1-4}$ alkoxycarbonyl, hydroxy$C_1$-$C_4$alkyl, $C_{1-4}$ alkylcarbamato, amido, $C_{1-4}$ alkylamido, oxo, cyclopropylsulfonyl, ethylsulfonyl, and methylsulfonyl; and $R^7$ and $R^8$ are the same or different and each is hydrogen, hydroxy, $C_1$-$C_4$hydroxyalkyl, $C_{1-6}$ alkyl, $C_{1-6}$ alkylsulfonyl, or halo.

In some aspects the present disclosure provides a compound of formula (I), or a pharmaceutically acceptable salt thereof, wherein:

Y is O or $SO_2$;

$R^1$ is ethynyl or ethyl;

$R^{1'}$ is hydrogen, halo, or $C_{1-3}$ alkyl, and $R^{1''}$ is hydrogen;

$R^2$ is hydrogen;

$R^3$ is halo;

$R^4$ and $R^5$ are the same or different and each is hydrogen, $C_{1-4}$ alkyl, hydroxy, or $C_{1-4}$ haloalkyl;

$R^6$ is $C_{1-6}$ alkyl, $C_{3-6}$ cycloalkyl, hydroxy$C_{1-6}$ alkyl, halo$C_{1-6}$ alkyl, hydroxy-halo$C_{1-6}$ alkyl, methylsulfonyl$C_1$-$C_6$alkyl, or —$(CH_2)_n$-A;

wherein A is a cyclic moiety selected from $C_{3-6}$ cycloalkyl, $C_{3-7}$ heterocycloalkyl, aryl, heteroaryl, spiro structures of any of these rings, and bicyclic structures of any of these rings, and n is 0, 1, 2, or 3;

wherein A is optionally substituted with one or more substituents selected from $C_{1-4}$ alkyl, $C_{1-4}$ alkylcarbonyl, $C_{3-6}$ cycloalkylcarbonyl, hydroxy, halo, cyano, halo$C_{1-6}$ alkyl, $C_{1-4}$ alkoxy, $C_{1-4}$ alkoxy $C_{1-4}$alkyl, $C_{1-4}$ alkoxycarbonyl, halo$C_{1-4}$ alkoxycarbonyl, $C_{1-4}$ alkylcarbamato, amido, $C_{1-4}$ alkylamido, oxo, and methylsulfonyl; and $R^7$ and $R^8$ are the same or different and each is hydrogen, hydroxy, $C_{1-6}$ alkyl, $C_{1-6}$ alkylsulfonyl, or halo.

In some aspects of formula (I), $R^1$ is ethynyl. In some aspects of formula (I), $R^1$ is ethyl. In some aspects of formula (I), $R^1$ is hydrogen. In some aspects of formula (I), $R^1$ is halo.

In some aspects of formula (I), $R^{1''}$ is halo. In some aspects of formula (I), $R^{1''}$ is fluoro.

In some aspects of formula (I), $R^3$ is fluoro.

In some aspects of formula (I), $R^4$ and $R^5$ are both hydrogen. In other aspects, one of $R^4$ and $R^5$ is hydroxy and the other is methyl.

In some aspects of formula (I), Y is O. In some aspects of formula (I), Y is $SO_2$.

In some aspects of formula (I), $R^{1'}$ is hydrogen. In some aspects of formula (I), $R^{1'}$ is halo (e.g., fluoro).

In some aspects of formula (I), $R^6$ is $C_{2-6}$ alkyl, hydroxy$C_{1-6}$ alkyl, halo$C_{1-6}$ alkyl, hydroxy-halo$C_{1-6}$ alkyl, or methylsulfonyl$C_1$-$C_6$alkyl.

In some aspects of formula (I), $R^6$ is —$(CH_2)_n$-A, where n and A are as defined above. In some aspects, n is 0. In some aspects, n is 1. A is a cyclic moiety selected from $C_{4-6}$ cycloalkyl, $C_{3-10}$ heterocycloalkyl, aryl, heteroaryl, spiro structures of any of these rings, and bicyclic structures of any of these rings.

In some aspects of formula (I), $R^7$ and $R^8$ are hydrogen. In some aspects, one of $R^7$ and $R^8$ is hydrogen and one is halo.

In some aspects, the present disclosure provides a compound of formula (II):

(II)

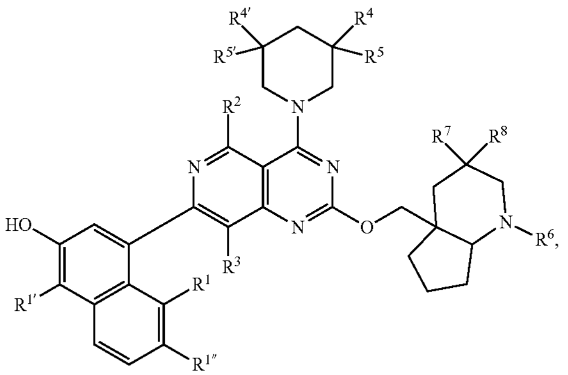

or a pharmaceutically acceptable salt thereof, wherein:

$R^1$ is ethynyl or ethyl;

$R^{1'}$ is hydrogen or halo (e.g., fluoro);

$R^{1''}$ is selected from hydrogen, $C_{2-3}$alkenyl, $C_{1-3}$ alkyl, $C_{2-3}$ alkynyl, halo, and hydroxy;

$R^2$ is hydrogen;

$R^3$ is halo (e.g., fluoro);

$R^4$, $R^5$ $R^{4'}$, and $R^{5'}$ are the same or different and each is hydrogen, halo$C_{1-4}$ alkyl, $C_{1-4}$ alkyl, hydroxy, or hydroxy$C_{1-4}$alkyl, or, $R^{4'}$ and $R^{5'}$, together with the atom to which they are attached, form a five-membered heterocycloalkyl ring optionally substituted with oxo;

$R^6$ is $C_{1-6}$ alkyl, hydroxy$C_{1-6}$ alkyl, halo$C_{1-6}$ alkyl, hydroxy-halo$C_{1-6}$ alkyl, methylsulfonyl$C_1$-$C_6$alkyl, or —$(CH_2)_n$-A;

wherein A is a cyclic moiety selected from $C_{3-6}$ cycloalkyl, $C_{3-7}$ heterocycloalkyl, spiro structures of either of these rings, and bicyclic structures of either of these rings, and n is 0, 1, or 2;

wherein A is optionally substituted with one or more substituents selected from $C_{1-4}$ alkyl, $C_{1-4}$ alkylcarbonyl, $C_{3-6}$ cycloalkylcarbonyl, hydroxy, halo, hydroxy$C_{1-6}$ alkyl, halo$C_{1-6}$ alkyl, $C_{1-4}$ alkoxy, $C_{1-4}$ alkoxy $C_{1-4}$alkyl, $C_{1-4}$ alkoxycarbonyl, halo$C_{1-4}$ alkoxycarbonyl, $C_{1-4}$ alkylcarbamato, amido, $C_{1-4}$ alkylamido, oxo (=O), and methylsulfonyl; and $R^7$ and $R^8$ are the same or different and each is hydrogen, $C_{1-6}$ alkyl, $C_{1-6}$ alkylsulfonyl, or halo.

In some aspects of formula (II), $R^1$ is ethynyl. In some aspects of formula (I), $R^1$ is ethyl.

In some aspects, and A is optionally substituted with one or more substituents selected from $C_{1-4}$ alkyl, $C_{1-4}$ alkylcarbonyl, $C_{3-6}$ cycloalkylcarbonyl, hydroxy, halo, halo$C_{1-6}$ alkyl, $C_{1-4}$ alkoxy, $C_{1-4}$ alkoxy $C_{1-4}$alkyl, $C_{1-4}$ alkoxycarbonyl, halo$C_{1-4}$ alkoxycarbonyl, $C_{1-4}$ alkylcarbamato, amido, $C_{1-4}$ alkylamido, oxo (=O), and methylsulfonyl.

In some aspects of formula (II), $R^3$ is fluoro.

In some aspects of formula (II), $R^4$ and $R^5$ are both hydrogen. In other aspects, one of $R^4$ and $R^5$ is hydroxy and the other is methyl or ethyl.

In some aspects of formula (II), $R^{4'}$ and $R^{5'}$ are both hydrogen. In other aspects, $R^{4'}$ and $R^{5'}$ are both halo.

In some aspects of formula (II), $R^{1'}$ is hydrogen. In some aspects of formula (I), $R^{1'}$ is halo (e.g., fluoro).

In some aspects of formula (II), $R^{1''}$ is halo. In some aspects of formula (II), $R^{1''}$ is fluoro.

In some aspects of formula (II), $R^6$ is $C_{2-6}$ alkyl, hydroxy$C_{1-6}$ alkyl, halo$C_{1-6}$ alkyl, hydroxy-halo$C_{1-6}$ alkyl, or methylsulfonyl$C_1$-$C_6$alkyl.

In some aspects of formula (II), $R^6$ is —$(CH_2)_n$-A, where n and A are as defined above. In some aspects, n is 0. In some aspects, n is 1. In some aspects, A is a cyclic moiety selected from $C_{4-6}$ cycloalkyl, $C_{3-10}$ heterocycloalkyl, aryl, heteroaryl, spiro structures of any of these rings, and bicyclic structures of any of these rings.

In some aspects of formula (II), $R^7$ and $R^8$ are hydrogen. In some aspects, one of $R^7$ and $R^8$ is hydrogen and one is halo.

In some aspects, the present disclosure provides a compound of formula (III):

(III)

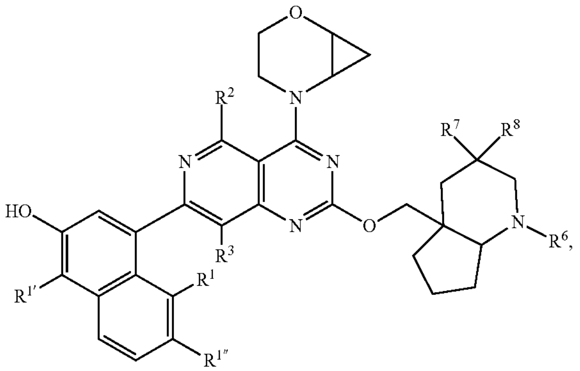

or a pharmaceutically acceptable salt thereof, wherein:

$R^1$ is ethynyl or ethyl;

$R^{1'}$ is hydrogen or halo (e.g., fluoro);

$R^{1''}$ is selected from hydrogen, $C_{2-3}$alkenyl, $C_{1-3}$ alkyl, $C_{2-3}$ alkynyl, halo, and hydroxy;

$R^2$ is hydrogen $R^3$ is halo (e.g., fluoro);

$R^6$ is $C_{1-6}$ alkyl, hydroxy$C_{1-6}$ alkyl, halo$C_{1-6}$ alkyl, hydroxy-halo$C_{1-6}$ alkyl, methylsulfonyl$C_1$-$C_6$alkyl, or —$(CH_2)_n$-A;

wherein A is a cyclic moiety selected from $C_{3-6}$ cycloalkyl, $C_{3-7}$ heterocycloalkyl, spiro structures of either of these rings, and bicyclic structures of any of these rings, and n is 0, 1, or 2;

wherein A is optionally substituted with one or more substituents selected from $C_{1-4}$ alkyl, $C_{1-4}$ alkylcarbonyl, $C_{3-6}$ cycloalkylcarbonyl, hydroxy, halo, halo$C_{1-6}$ alkyl, $C_{1-4}$ alkoxy, $C_{1-4}$ alkoxy $C_{1-4}$alkyl, $C_{1-4}$ alkoxycarbonyl, halo$C_{1-4}$ alkoxycarbonyl, $C_{1-4}$ alkylcarbamato, amido, $C_{1-4}$ alkylamido, oxo (=O), and methylsulfonyl; and $R^7$ and $R^8$ are the same or different and each is hydrogen, $C_{1-6}$ alkyl, $C_{1-6}$ alkylsulfonyl, or halo.

In some aspects of formula (III), $R^1$ is ethynyl. In some aspects of formula (I), $R^1$ is ethyl.

In some aspects of formula (III), $R^3$ is fluoro.

In some aspects of formula (III), $R^{1'}$ is hydrogen. In some aspects of formula (I), $R^{1'}$ is halo (e.g., fluoro).

In some aspects of formula (III), $R^{1''}$ is halo. In some aspects of formula (III), $R^{1''}$ is fluoro.

In some aspects of formula (III), $R^6$ is $C_{2-6}$ alkyl, hydroxy$C_{1-6}$ alkyl, halo$C_{1-6}$ alkyl, hydroxy-halo$C_{1-6}$ alkyl, or methylsulfonyl$C_1$-$C_6$alkyl.

In some aspects of formula (III), $R^6$ is $-(CH_2)_n$-A, where n and A are as defined above. In some aspects, n is 0. In some aspects, n is 1. In some aspects, A is a cyclic moiety selected from $C_{4-6}$ cycloalkyl, $C_{3-10}$ heterocycloalkyl, aryl, heteroaryl, spiro structures of any of these rings, and bicyclic structures of any of these rings.

In some aspects of formula (III), $R^7$ and $R^8$ are hydrogen. In some aspects, one of $R^7$ and $R^8$ is hydrogen and one is halo.

In some aspects, the present disclosure provides a compound of formula (IV):

(IV)

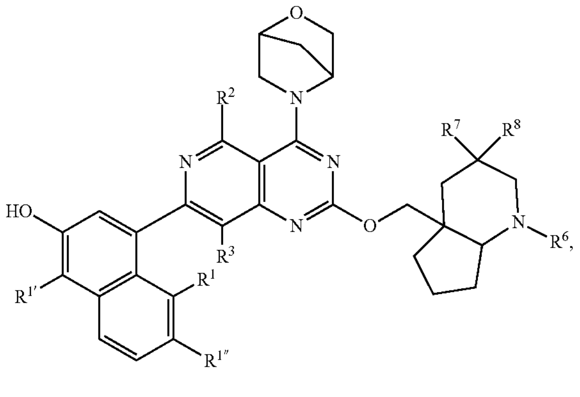

or a pharmaceutically acceptable salt thereof, wherein:

$R^1$ is ethynyl or ethyl;

$R^{1'}$ is hydrogen or halo (e.g., fluoro);

$R^{1''}$ is selected from hydrogen, $C_{2-3}$alkenyl, $C_{1-3}$ alkyl, $C_{2-3}$ alkynyl, halo, and hydroxy;

$R^2$ is hydrogen;

$R^3$ is halo (e.g., fluoro);

$R^6$ is $C_{1-6}$ alkyl, hydroxy$C_{1-6}$ alkyl, halo$C_{1-6}$ alkyl, hydroxy-halo$C_{1-6}$ alkyl, methylsulfonyl$C_1$-$C_6$alkyl, or $-(CH_2)_n$-A;

wherein A is a cyclic moiety selected from $C_{3-6}$ cycloalkyl, $C_{3-7}$ heterocycloalkyl, spiro structures of either of these rings, and bicyclic structures of either of these rings, and n is 0, 1, or 2;

wherein A is optionally substituted with one or more substituents selected from $C_{1-4}$ alkyl, $C_{1-4}$ alkylcarbonyl, $C_{3-6}$ cycloalkylcarbonyl, hydroxy, halo, halo$C_{1-6}$ alkyl, $C_{1-4}$ alkoxy, $C_{1-4}$ alkoxy $C_{1-4}$alkyl, $C_{1-4}$ alkoxycarbonyl, halo$C_{1-4}$ alkoxycarbonyl, $C_{1-4}$ alkylcarbamato, amido, $C_{1-4}$ alkylamido, oxo (=O), and methylsulfonyl; and $R^7$ and $R^8$ are the same or different and each is hydrogen, $C_{1-6}$ alkyl, $C_{1-6}$ alkylsulfonyl, or halo.

In some aspects of formula (IV), $R^1$ is ethynyl. In some aspects of formula (I), $R^1$ is ethyl.

In some aspects of formula (IV), $R^3$ is fluoro.

In some aspects of formula (IV), $R^{1'}$ is hydrogen. In some aspects of formula (I), $R^{1'}$ is halo (e.g., fluoro).

In some aspects of formula (IV), $R^{1''}$ is halo. In some aspects of formula (IV), $R^{1''}$ is fluoro.

In some aspects of formula (IV), $R^6$ is $C_{2-6}$ alkyl, hydroxy$C_{1-6}$ alkyl, halo$C_{1-6}$ alkyl, hydroxy-halo$C_{1-6}$ alkyl, or methylsulfonyl$C_1$-$C_6$alkyl.

In some aspects of formula (IV), $R^6$ is $-(CH_2)_n$-A, where n and A are as defined above. In some aspects, n is 0. In some aspects, n is 1. In some aspects, A is a cyclic moiety selected from $C_{4-6}$ cycloalkyl, $C_{3-10}$ heterocycloalkyl, aryl, heteroaryl, spiro structures of any of these rings, and bicyclic structures of any of these rings.

In some aspects of formula (IV), $R^7$ and $R^8$ are hydrogen. In some aspects, one of $R^7$ and $R^8$ is hydrogen and one is halo.

In some aspects, the present disclosure provides a compound of formula (V):

(V)

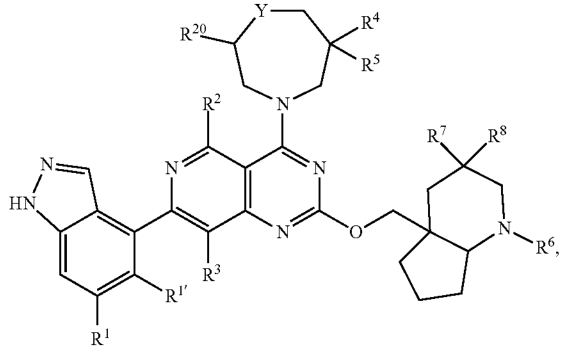

or a pharmaceutically acceptable salt thereof, wherein:

Y is O or $SO_2$;

$R^1$ and $R^{1'}$ are the same or different and each is hydrogen, halo, $C_{1-4}$ alkyl, $C_{2-4}$ alkenyl, $C_{3-6}$ cycloalkyl, $C_{1-4}$ haloalkyl, $C_{1-4}$ alkoxy, or $C_{1-4}$ haloalkoxy;

$R^2$ is hydrogen;

$R^3$ is halo (e.g., fluoro);

$R^4$ and $R^5$ are the same or different and each is hydrogen, $C_{1-4}$ alkyl, or hydroxy;

$R^{20}$ is selected from hydrogen and hydroxy$C_{1-4}$alkyl;

$R^6$ is $C_{1-6}$ alkyl, hydroxy$C_{1-6}$ alkyl, halo$C_{1-6}$ alkyl, hydroxy-halo$C_{1-6}$ alkyl, methylsulfonyl$C_1$-$C_6$alkyl, or $-(CH_2)_n$-A;

wherein A is a cyclic moiety selected from $C_{3-6}$ cycloalkyl, $C_{3-7}$ heterocycloalkyl, spiro structures of either of these rings, and bicyclic structures of either of these rings, and n is 0, 1, or 2;

wherein A is optionally substituted with one or more substituents selected from $C_{1-4}$ alkyl, $C_{1-4}$ alkylcarbonyl, cyano, $C_{3-6}$ cycloalkylcarbonyl, hydroxy, halo, halo$C_{1-6}$ alkyl, $C_{1-4}$ alkoxy, $C_{1-4}$ alkoxy $C_{1-4}$alkyl, $C_{1-4}$ alkoxycarbonyl, halo$C_{1-4}$ alkoxycarbonyl, $C_{1-4}$ alkylcarbamato, amido, $C_{1-4}$ alkylamido, oxo (=O), hydroxy $C_{1-4}$alkyl, and methylsulfonyl; and $R^7$ and $R^8$ are the same or different and each is hydrogen, $C_{1-6}$ alkyl, $C_{1-6}$ alkylsulfonyl, or halo.

In some aspects of formula (V), $R^1$ and $R^{1'}$ are the same or different and each is hydrogen, halo, $C_{1-4}$ alkyl, $C_{3-6}$ cycloalkyl, $C_{1-4}$ haloalkyl, $C_{1-4}$ alkoxy, or $C_{1-4}$ haloalkoxy.

In some aspects of formula (V), $R^3$ is fluoro.

In some aspects of formula (V), $R^4$ and $R^5$ are both H. In other aspects, one of $R^4$ and $R^5$ is hydroxy and the other is methyl.

In some aspects of formula (V), Y is O. In some aspects of formula (I), Y is $SO_2$.

In some aspects of formula (V), $R^6$ is $C_{2-6}$ alkyl, hydroxy$C_{1-6}$ alkyl, halo$C_{1-6}$ alkyl, hydroxy-halo$C_{1-6}$ alkyl, or methylsulfonyl$C_1$-$C_6$alkyl.

In some aspects of formula (V), $R^6$ is $-(CH_2)_n$-A, where n and A are as defined above. In some aspects, n is 0. In some aspects, n is 1. In some aspects, A is a cyclic moiety selected from $C_{4-6}$ cycloalkyl, $C_{3-10}$ heterocycloalkyl, aryl, heteroaryl, spiro structures of any of these rings, and bicyclic structures of any of these rings.

In some aspects of formula (V), A is optionally substituted with one or more substituents selected from $C_{1-4}$ alkyl, $C_{1-4}$ alkylcarbonyl, $C_{3-6}$ cycloalkylcarbonyl, hydroxy, halo, halo$C_{1-6}$ alkyl, $C_{1-4}$ alkoxy, $C_{1-4}$ alkoxy $C_{1-4}$alkyl, $C_{1-4}$ alkoxycarbonyl, halo$C_{1-4}$ alkoxycarbonyl, $C_{1-4}$ alkylcarbamato, amido, $C_{1-4}$ alkylamido, oxo (=O), and methylsulfonyl.

In some aspects of formula (V), A is optionally substituted with one or more substituents selected from $C_{1-4}$ alkyl, $C_{1-4}$ alkylcarbonyl, $C_{3-6}$ cycloalkylcarbonyl, hydroxy, halo, halo$C_{1-6}$ alkyl, $C_{1-4}$ alkoxy, $C_{1-4}$ alkoxy $C_{1-4}$alkyl, $C_{1-4}$ alkoxycarbonyl, halo$C_{1-4}$ alkoxycarbonyl, $C_{1-4}$ alkylcarbamato, amido, $C_{1-4}$ alkylamido, oxo, hydroxy $C_{1-4}$alkyl, and methylsulfonyl.

In some aspects of formula (V), $R^7$ and $R^8$ are hydrogen. In some aspects, one of $R^7$ and $R^8$ is hydrogen and one is halo.

In some aspects, the present disclosure provides a compound of formula (VI):

(VI)

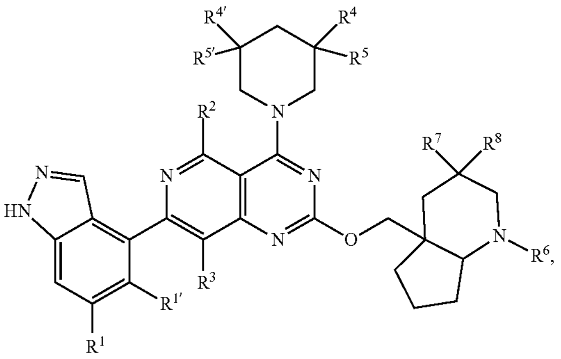

or a pharmaceutically acceptable salt thereof, wherein:

$R^1$ and $R^{1'}$ are the same or different and each is hydrogen, halo, $C_{1-4}$ alkyl, $C_{3-6}$ cycloalkyl, $C_{1-4}$ haloalkyl, $C_{1-4}$ alkoxy, or $C_{1-4}$ haloalkoxy;

$R^2$ is hydrogen;

$R^3$ is halo (e.g., fluoro);

$R^4$, $R^5$, $R^{4'}$, and $R^{5'}$ are the same or different and each is hydrogen, halo$C_{1-4}$ alkyl, $C_{1-4}$ alkyl, hydroxy, or hydroxy$C_{1-4}$alkyl, or, $R^{4'}$ and $R^{5'}$, together with the atom to which they are attached, form a five-membered heterocycloalkyl ring optionally substituted with oxo;

$R^6$ is $C_{1-6}$ alkyl, hydroxy$C_{1-6}$ alkyl, halo$C_{1-6}$ alkyl, hydroxy-halo$C_{1-6}$ alkyl, methylsulfonyl$C_1$-$C_6$alkyl, or $-(CH_2)_n$-A;

wherein A is a cyclic moiety selected from $C_{3-6}$ cycloalkyl, $C_{3-7}$ heterocycloalkyl, spiro structures of either of these rings, and bicyclic structures of either of these rings, and n is 0, 1, or 2;

wherein A is optionally substituted with one or more substituents selected from $C_{1-4}$ alkyl, $C_{1-4}$ alkylcarbonyl, $C_{3-6}$ cycloalkylcarbonyl, hydroxy, halo, halo$C_{1-6}$ alkyl, $C_{1-4}$ alkoxy, $C_{1-4}$ alkoxy $C_{1-4}$alkyl, $C_{1-4}$ alkoxycarbonyl, halo$C_{1-4}$ alkoxycarbonyl, $C_{1-4}$ alkylcarbamato, amido, $C_{1-4}$ alkylamido, oxo (=O), and methylsulfonyl; and $R^7$ and $R^8$ are the same or different and each is hydrogen, $C_{1-6}$ alkyl, $C_{1-6}$ alkylsulfonyl, or halo.

In some aspects of formula (VI), $R^3$ is fluoro.

In some aspects of formula (VI), $R^4$ and $R^5$ are both hydrogen. In other aspects, one of $R^4$ and $R^5$ is hydroxy and the other is methyl or ethyl.

In some aspects of formula (VI), $R^{4'}$ and $R^{5'}$ are both hydrogen. In other aspects, $R^{4'}$ and $R^{5'}$ are both halo.

In some aspects of formula (VI), $R^6$ is $C_{2-6}$ alkyl, hydroxy$C_{1-6}$ alkyl, halo$C_{1-6}$ alkyl, hydroxy-halo$C_{1-6}$ alkyl, or methylsulfonyl$C_1$-$C_6$alkyl.

In some aspects of formula (VI), $R^6$ is $-(CH_2)_n$-A, where n and A are as defined above. In some aspects, n is 0. In some aspects, n is 1. In some aspects, A is a cyclic moiety selected from $C_{4-6}$ cycloalkyl, $C_{3-10}$ heterocycloalkyl, aryl, heteroaryl, spiro structures of any of these rings, and bicyclic structures of any of these rings.

In some aspects of formula (VI), $R^7$ and $R^8$ are hydrogen. In some aspects, one of $R^7$ and $R^8$ is hydrogen and one is halo.

In some aspects, the present disclosure provides a compound selected from the group consisting of:
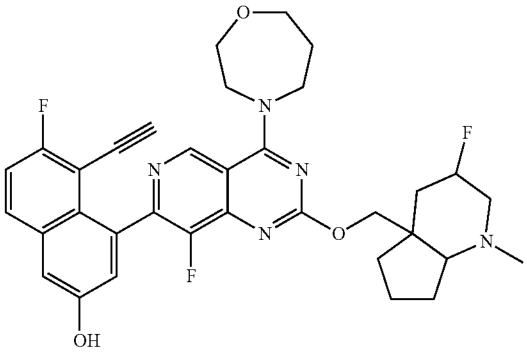
,
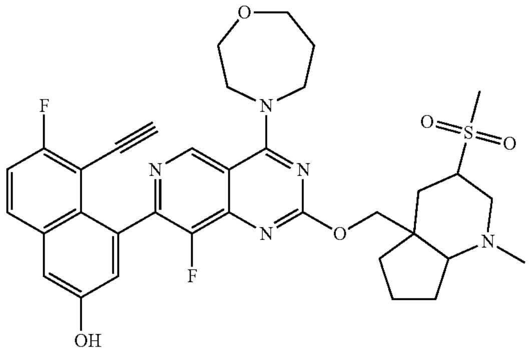
,
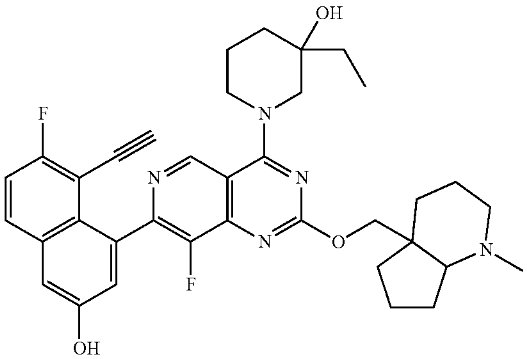
,
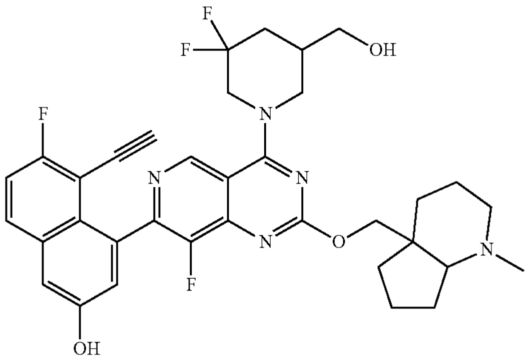
,
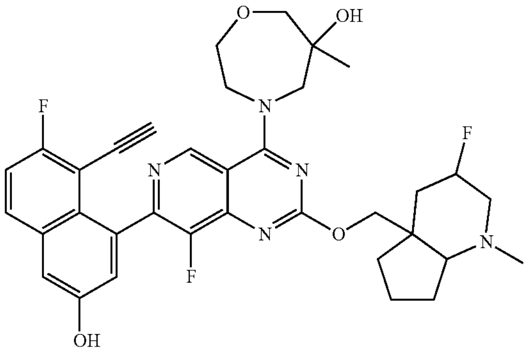
,
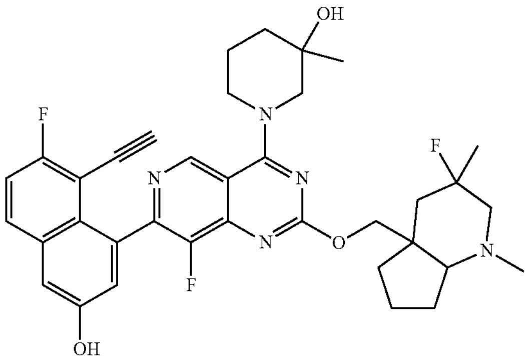
,
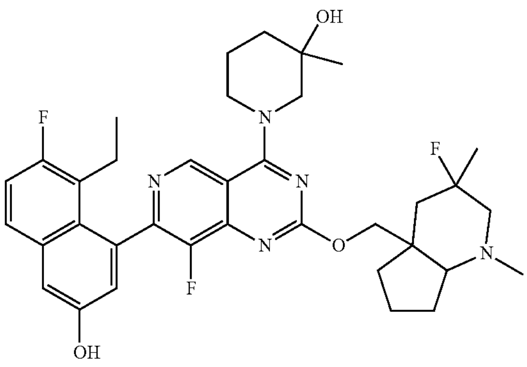
,
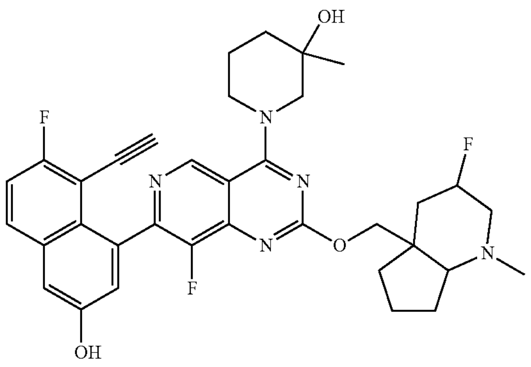
, -continued
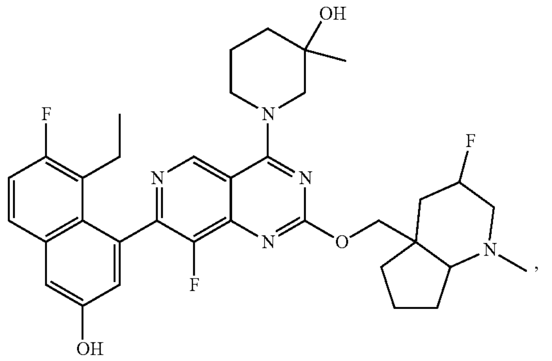
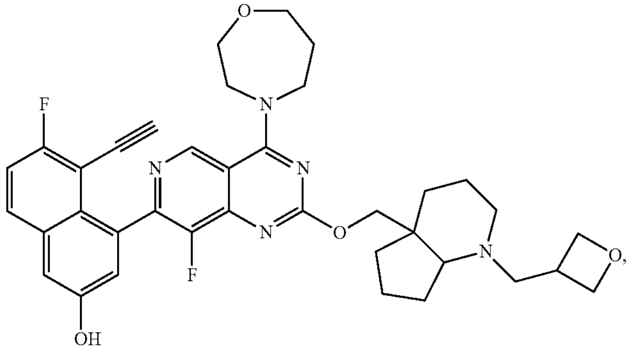
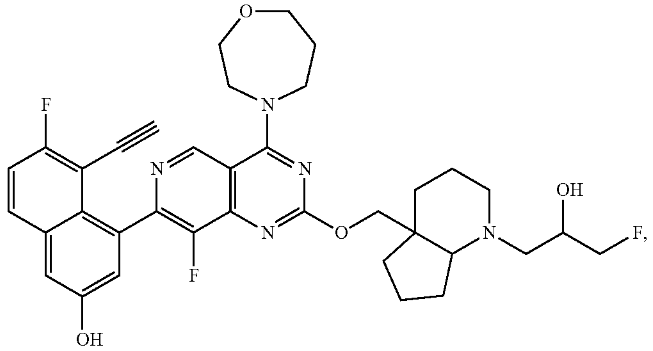
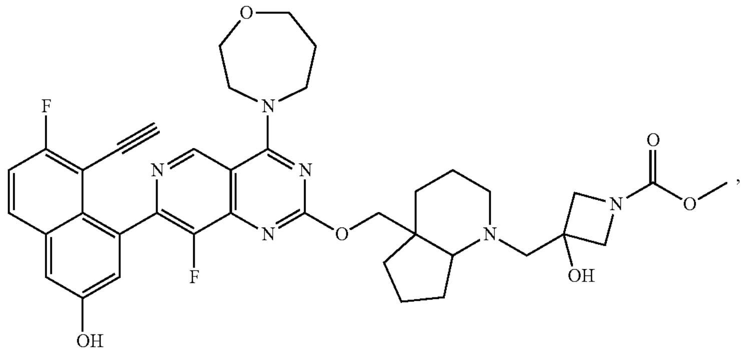
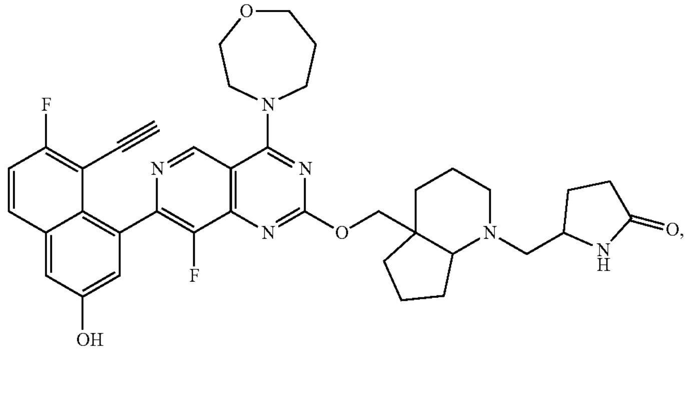

-continued
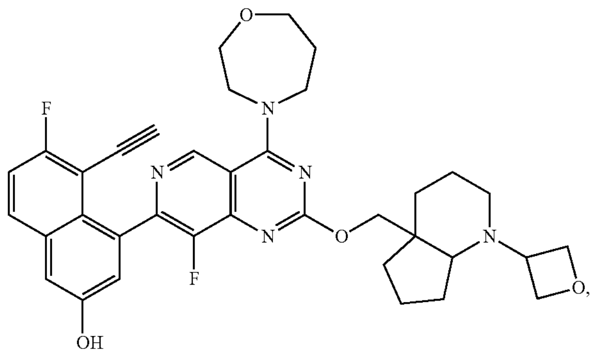
,
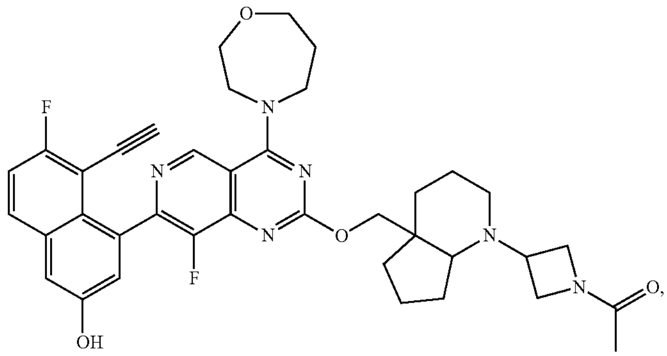
,
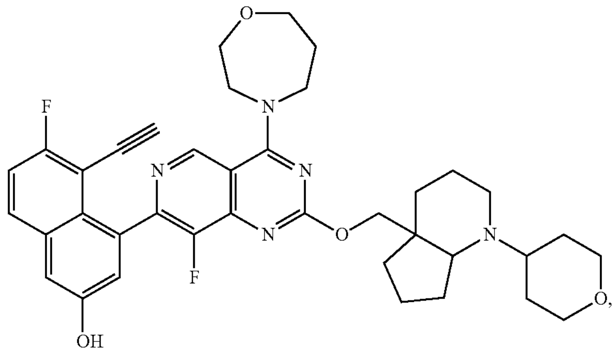
,
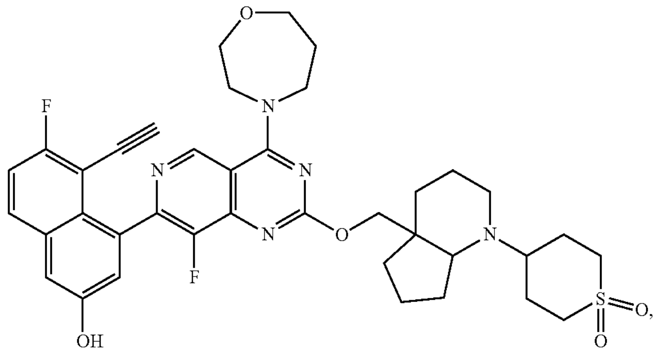
,

-continued
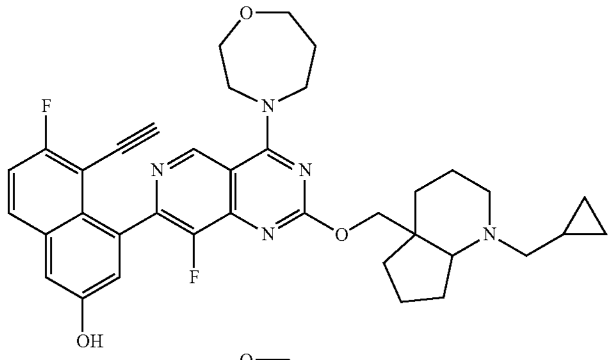
,
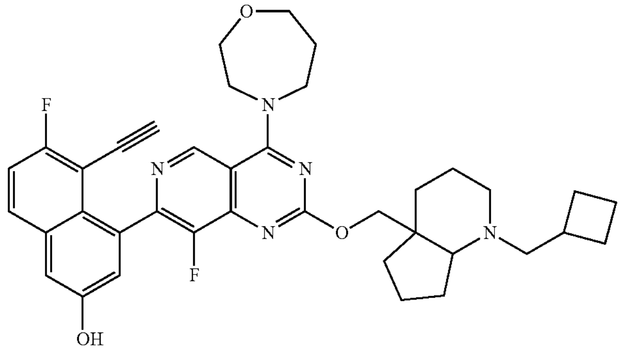
,
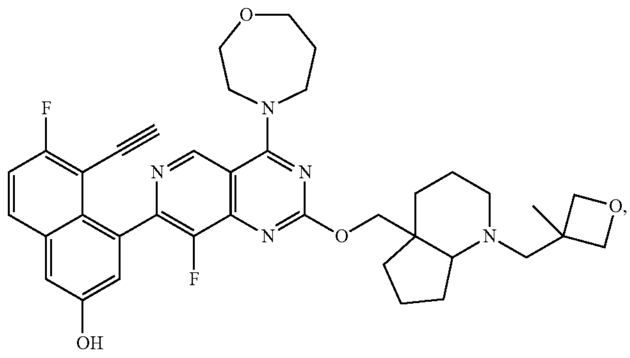
,
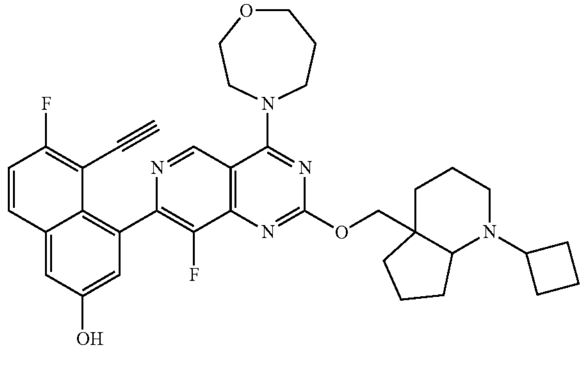
,

-continued
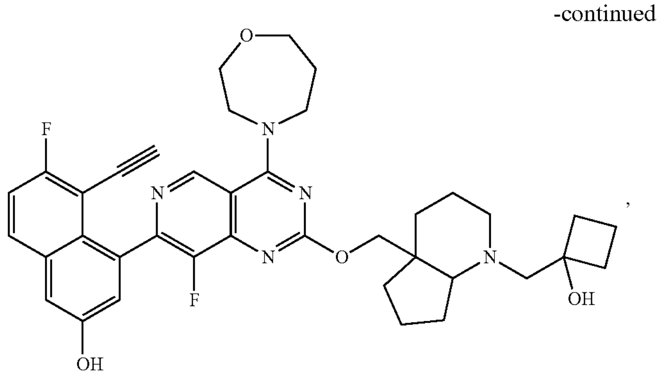
,
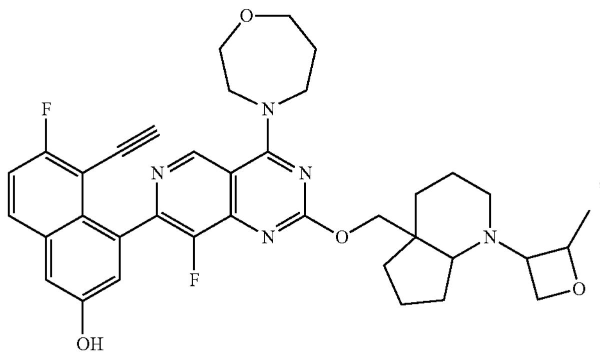
,
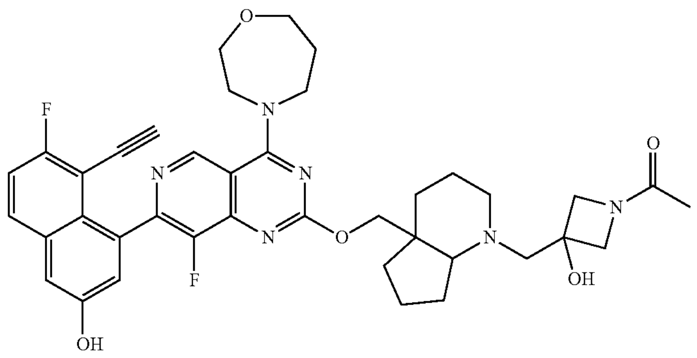
,
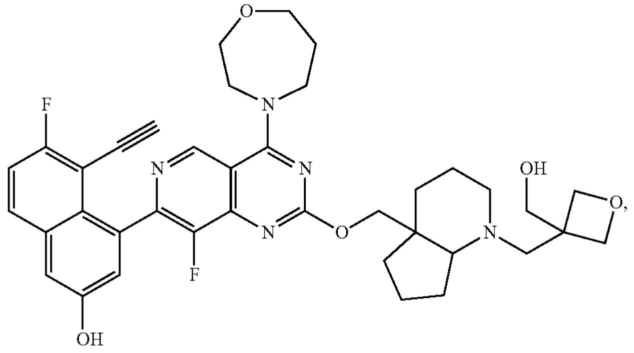
,

-continued
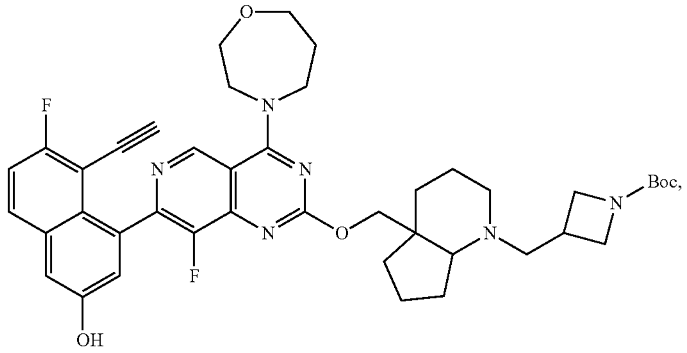
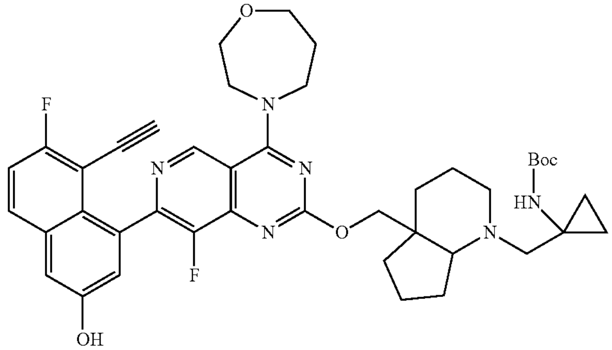
,
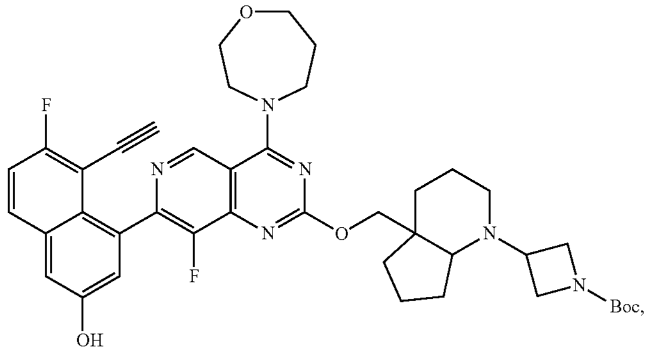
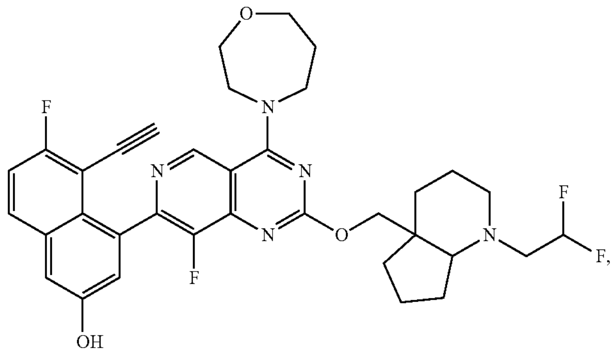

-continued
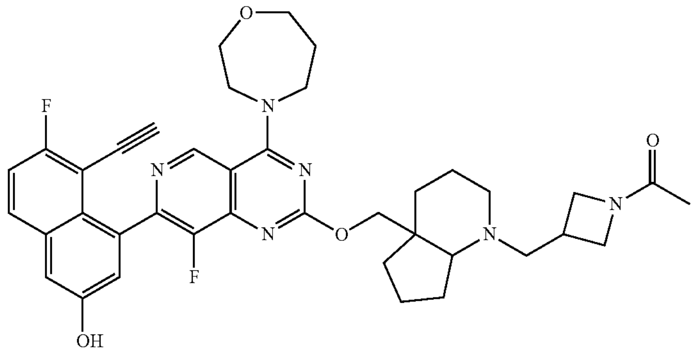
,
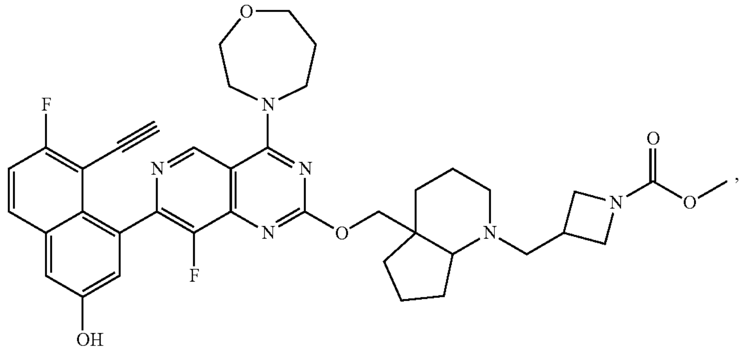
,
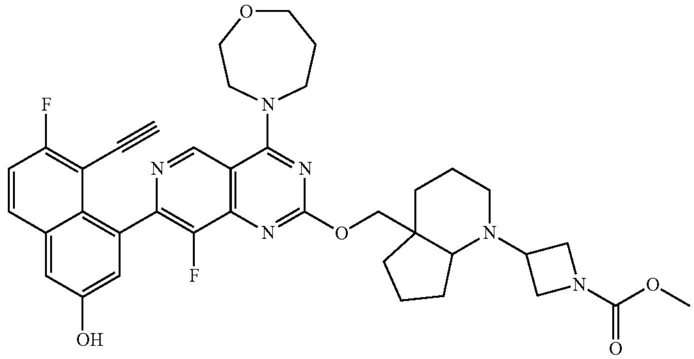
,
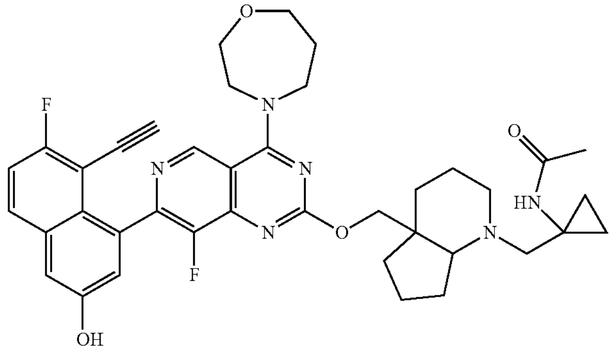
,

-continued
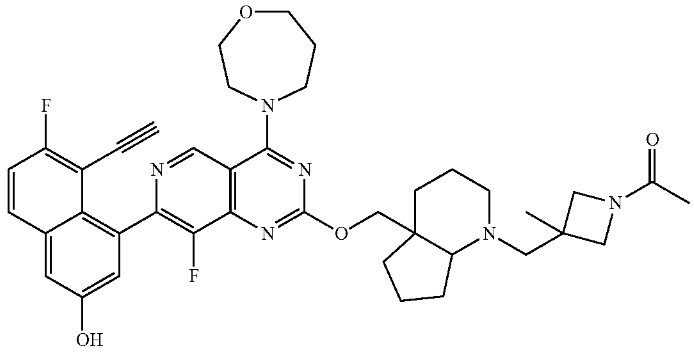
,
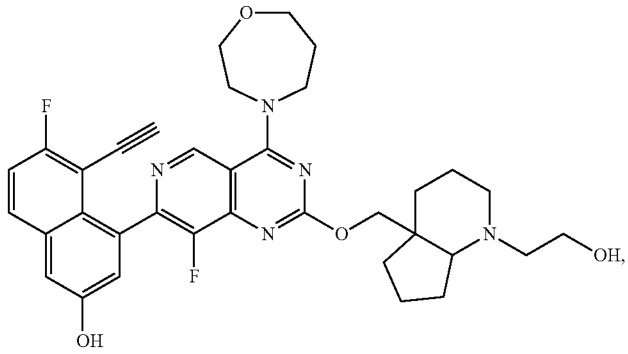
OH,
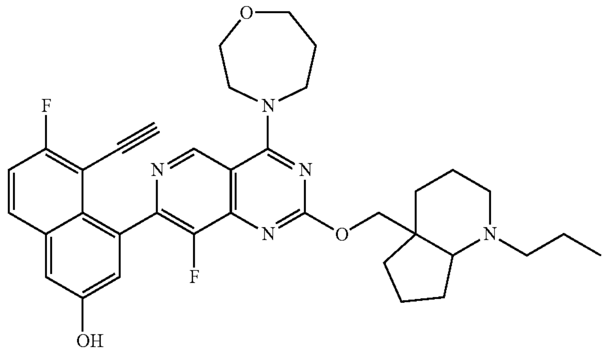
,
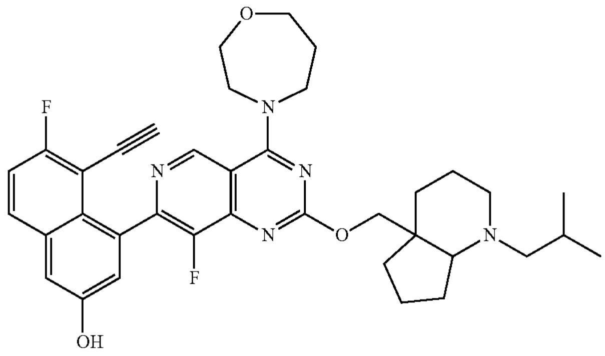
,

-continued
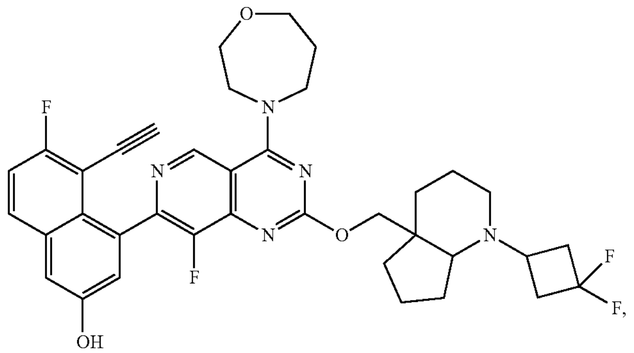
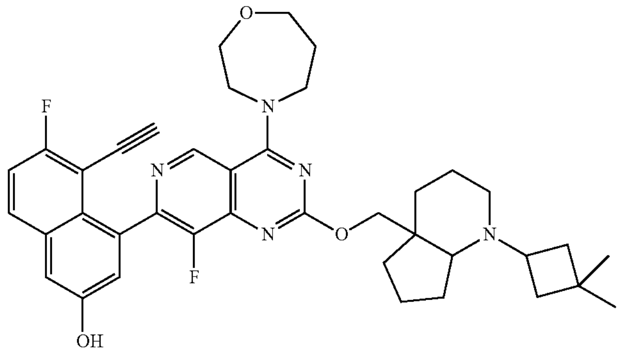
,
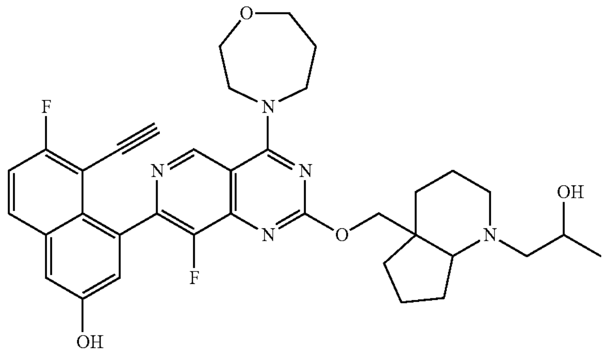
,
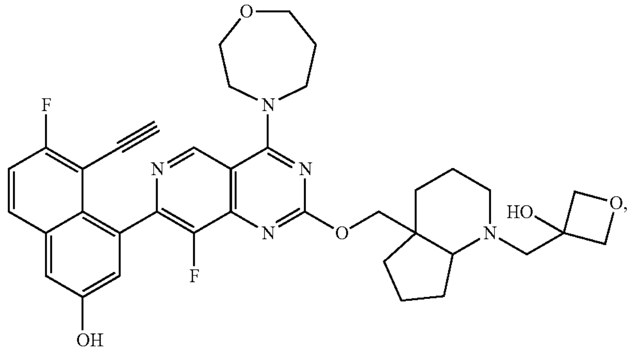

-continued
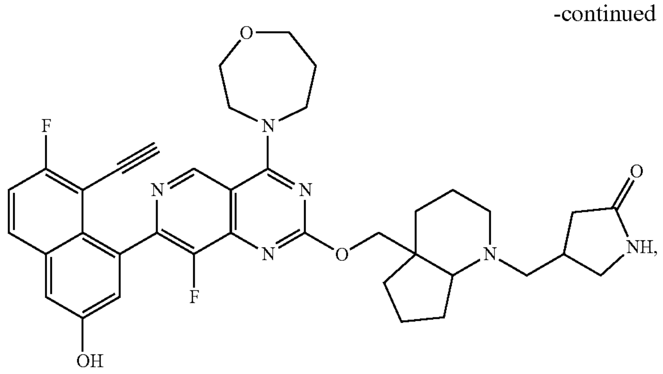
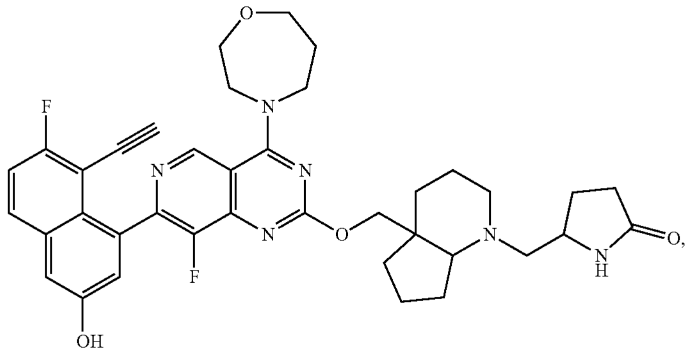
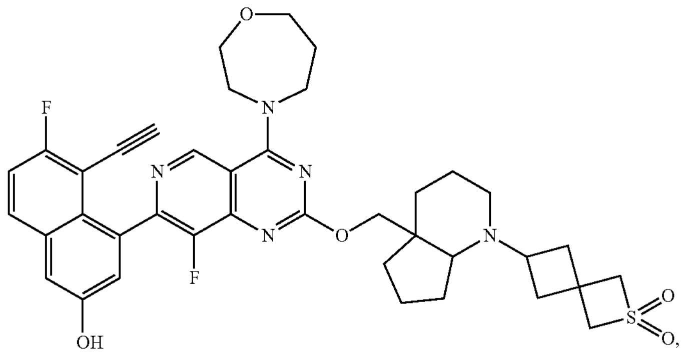
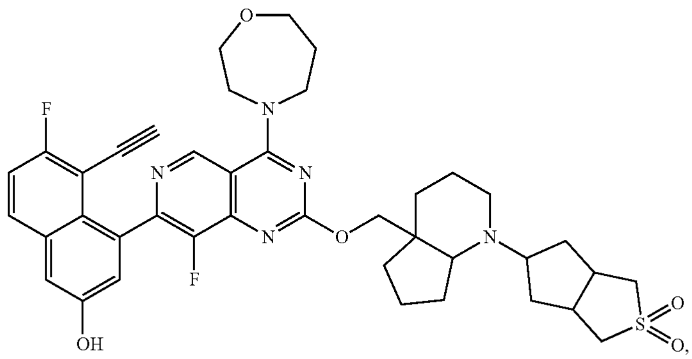

-continued
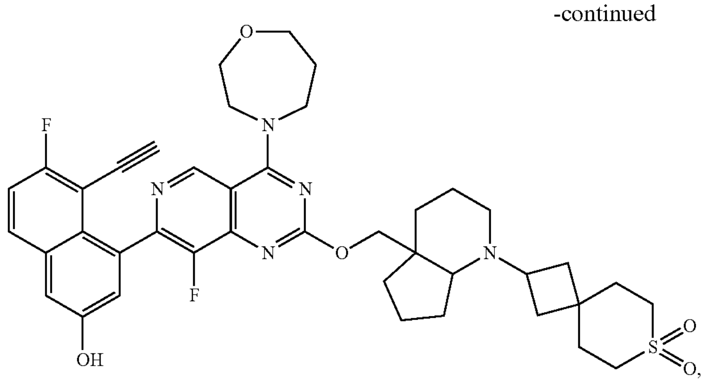
,
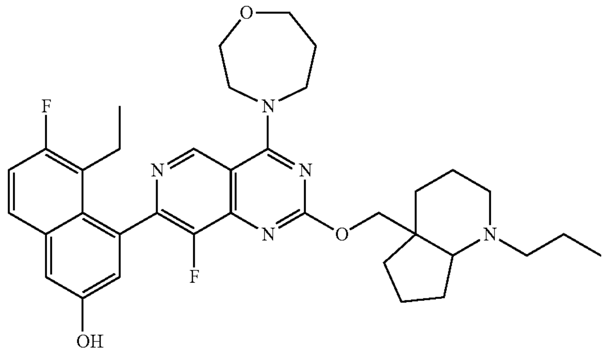
,
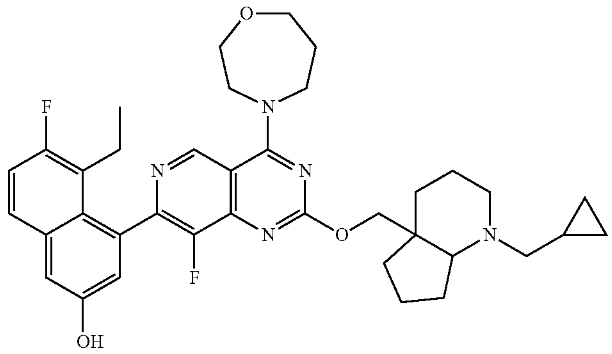
,
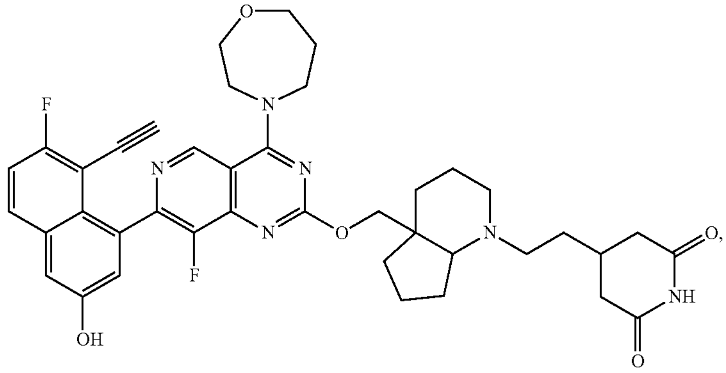
,

-continued
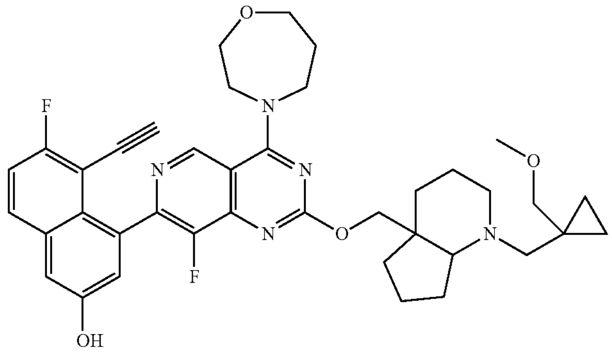
,
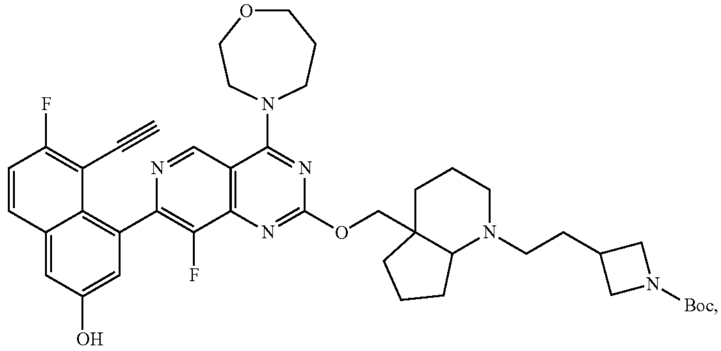
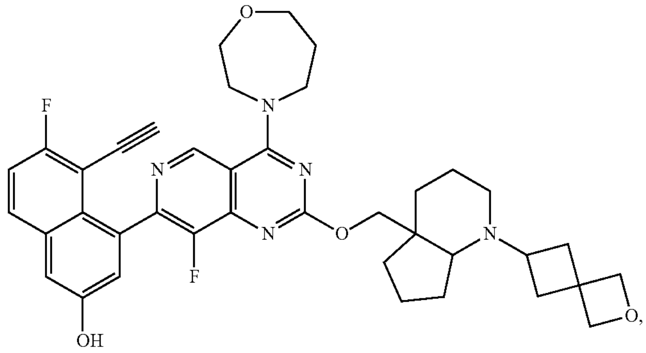
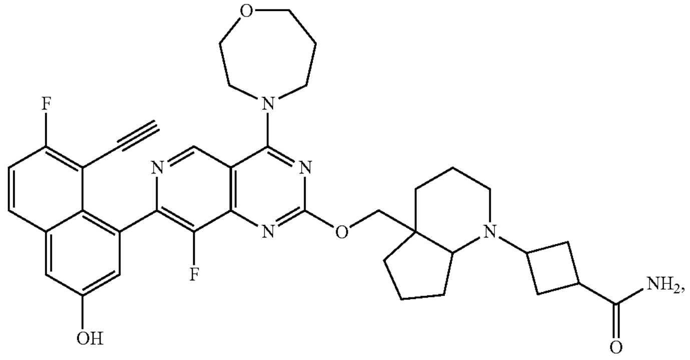

-continued
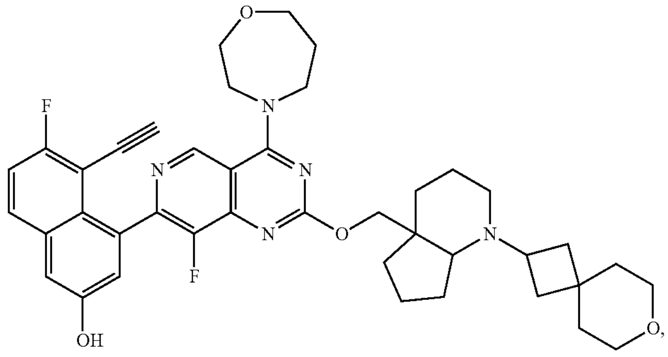
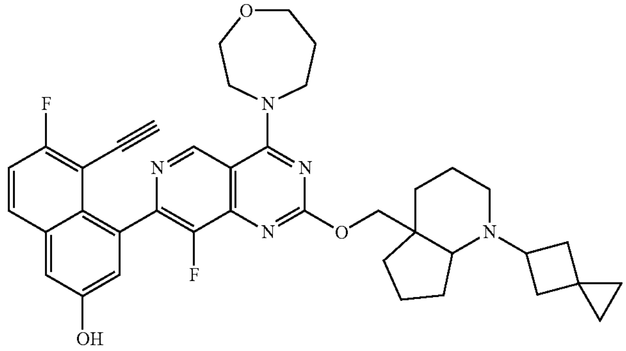
,
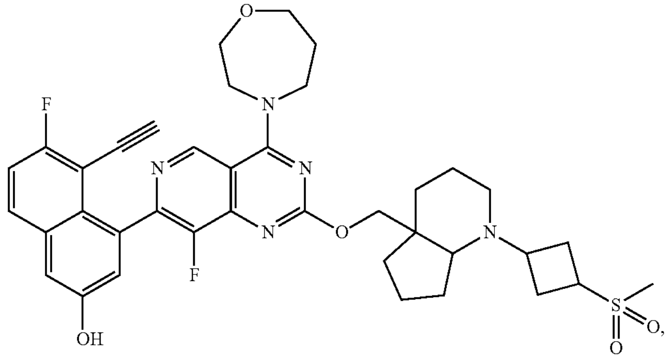
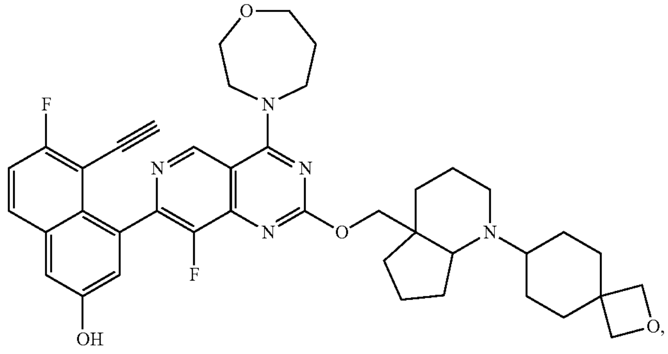

-continued
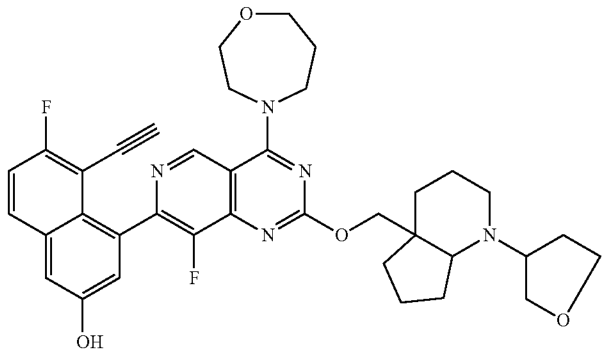
,
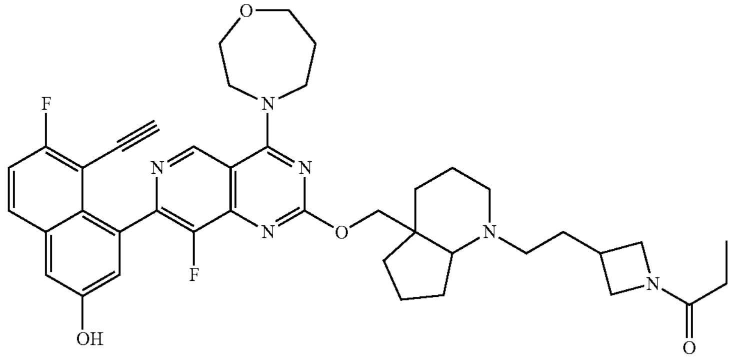
,
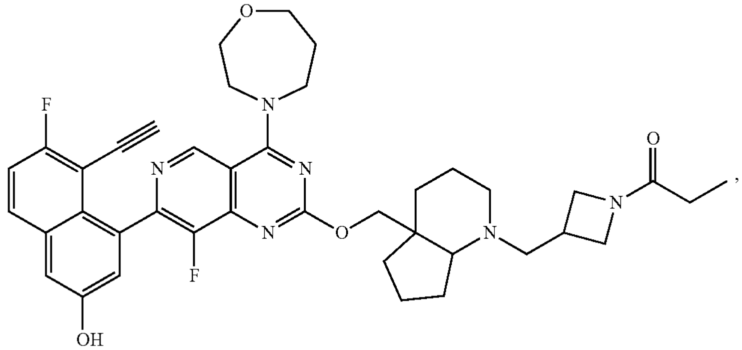
,
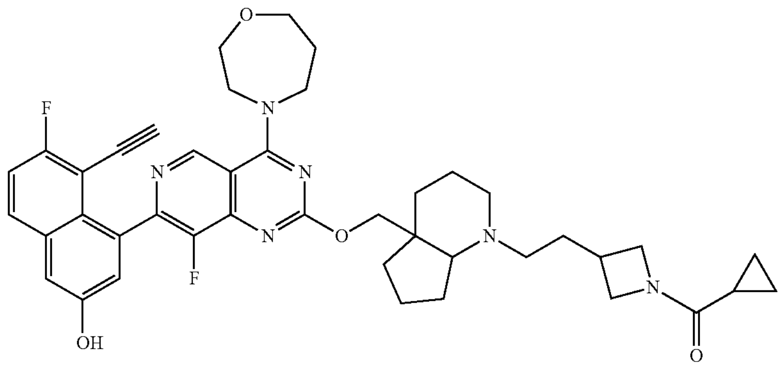
,

-continued
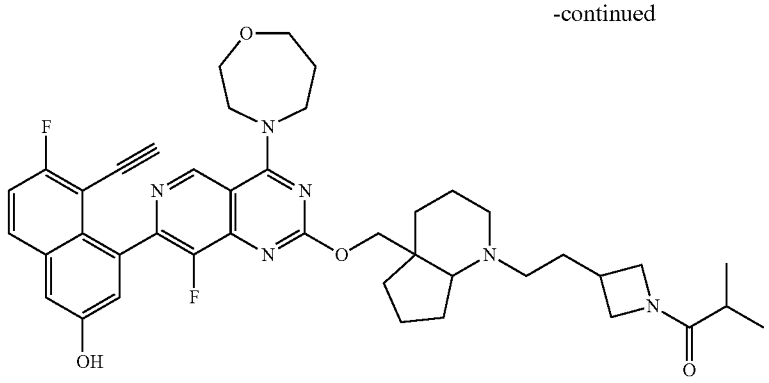
,
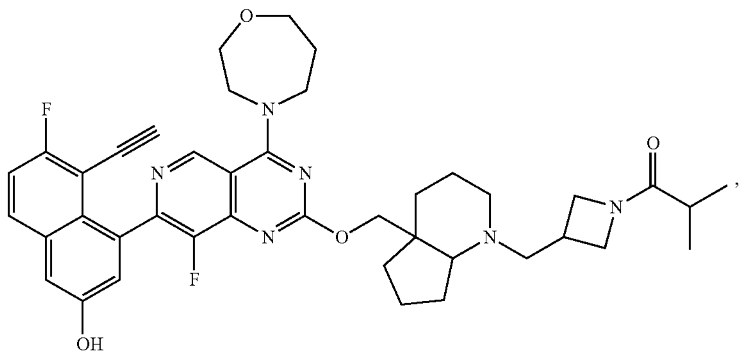
,
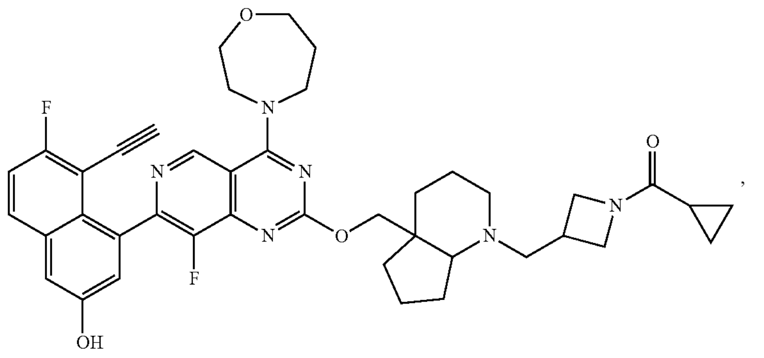
,
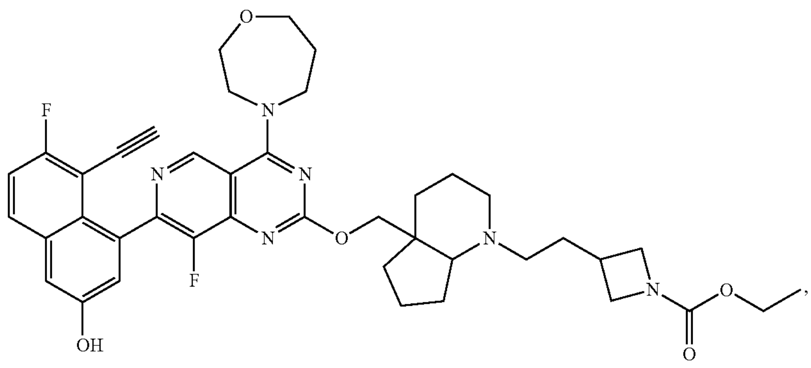
,

-continued
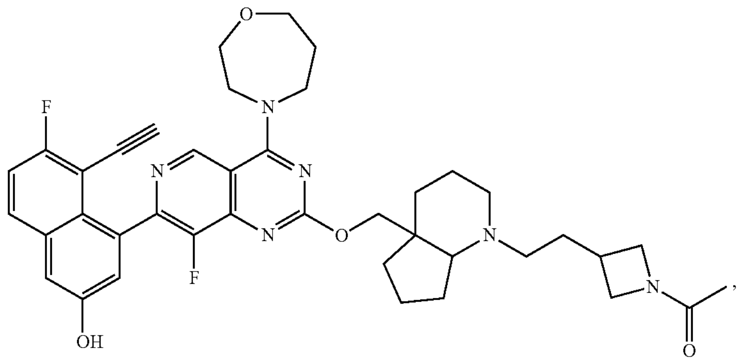
,
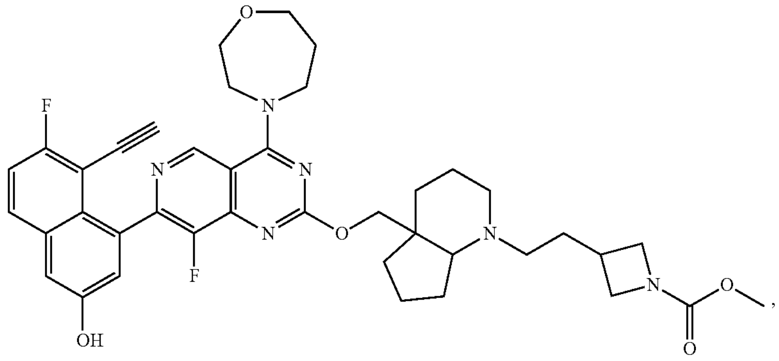
,
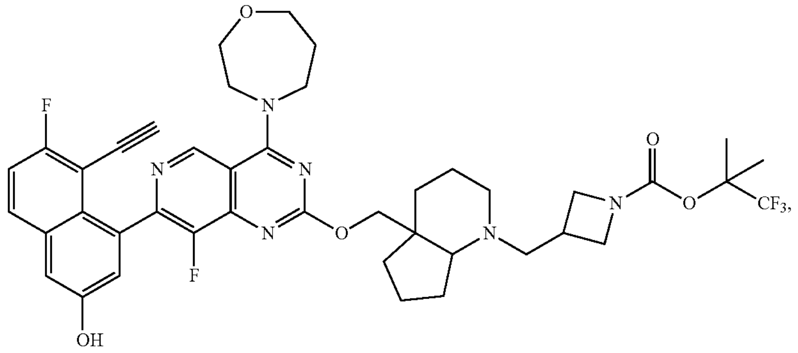
,
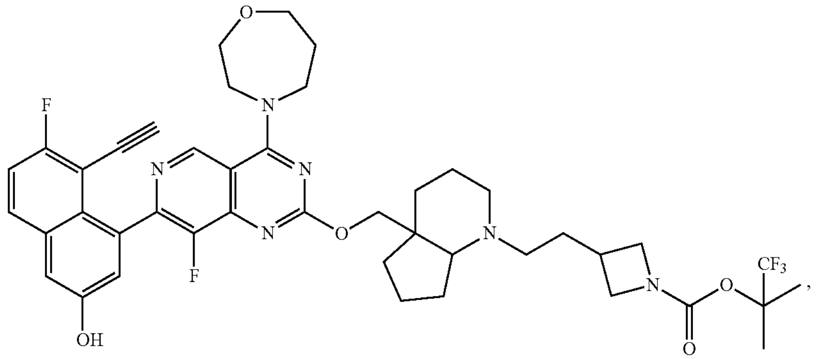
,

-continued
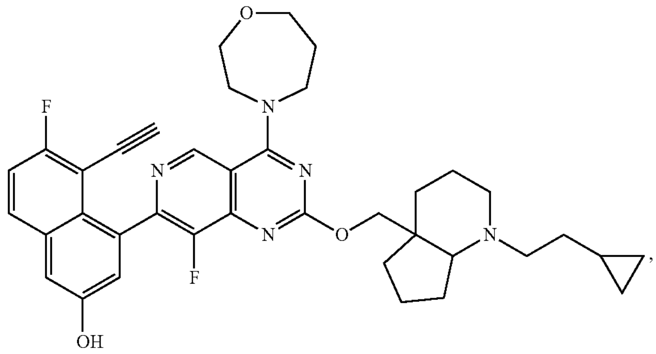
,
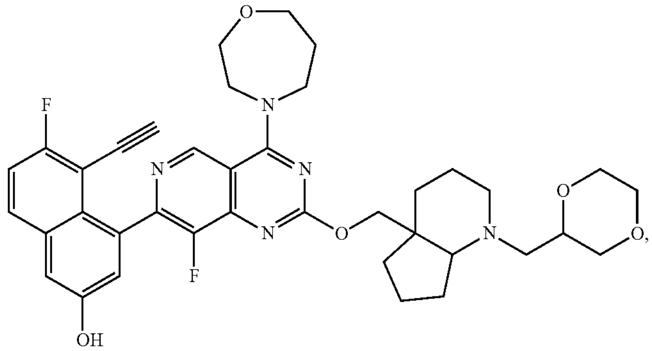
,
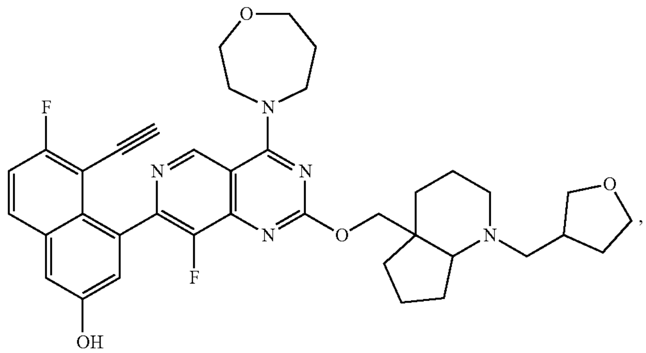
,
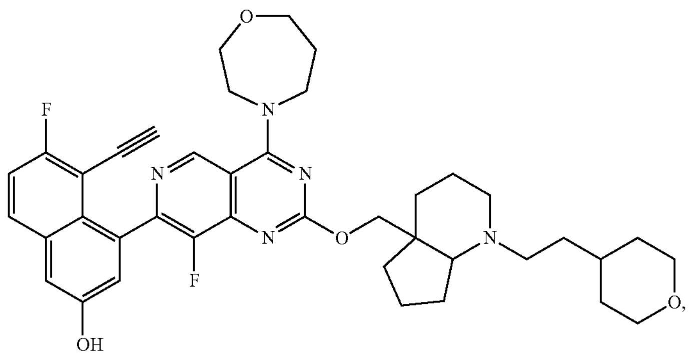
,

-continued
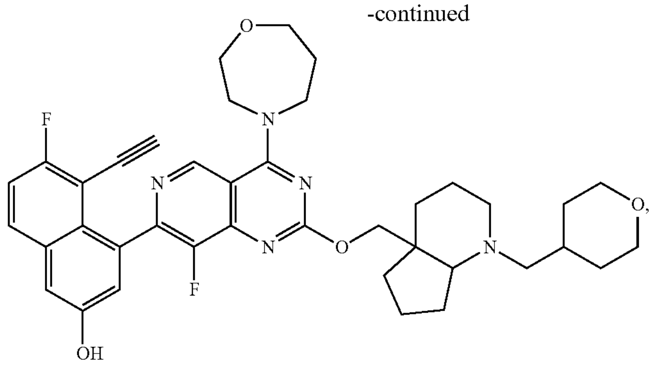
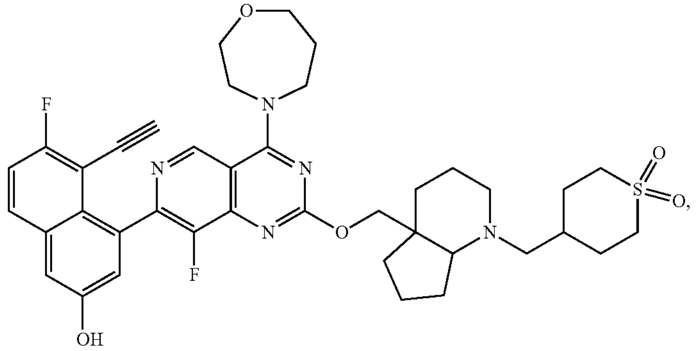
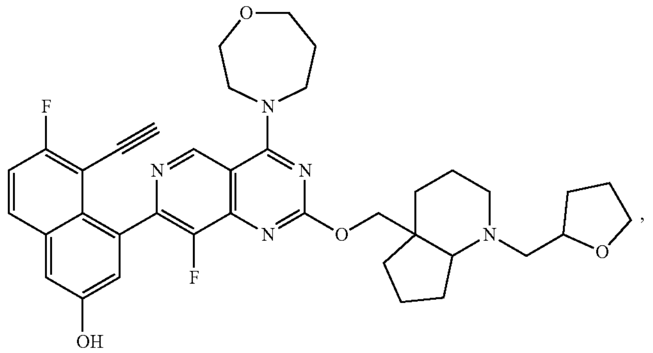
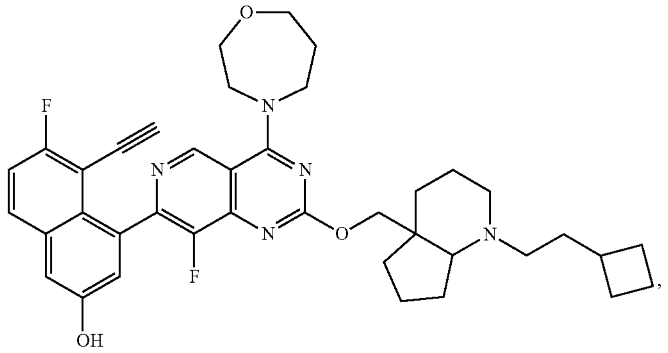

-continued
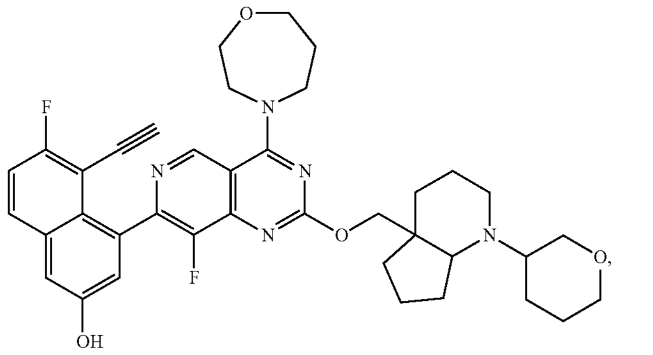
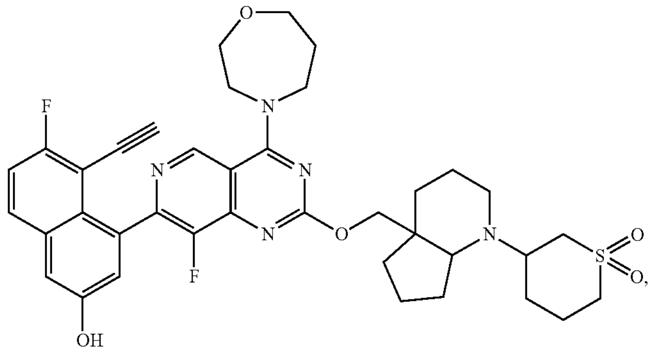
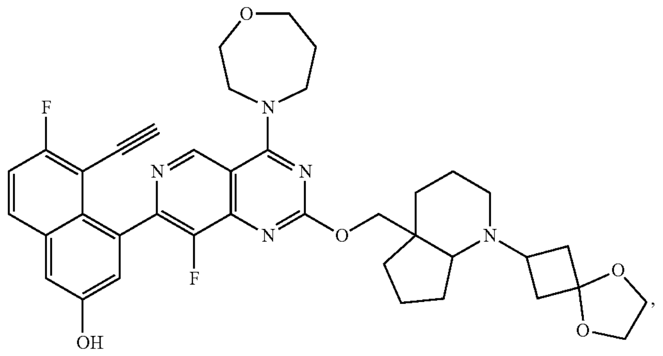
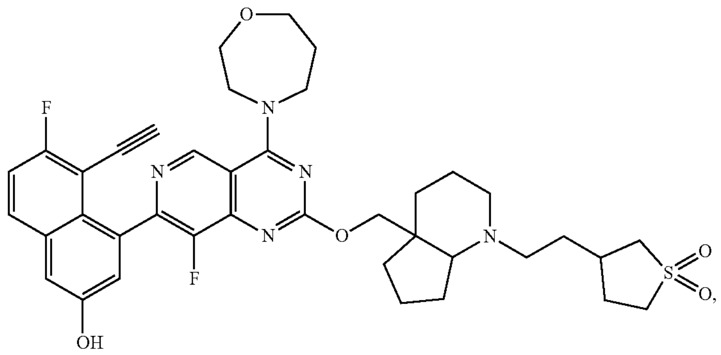

-continued
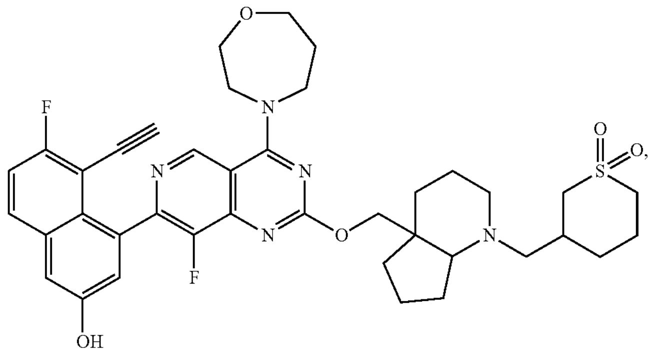
,
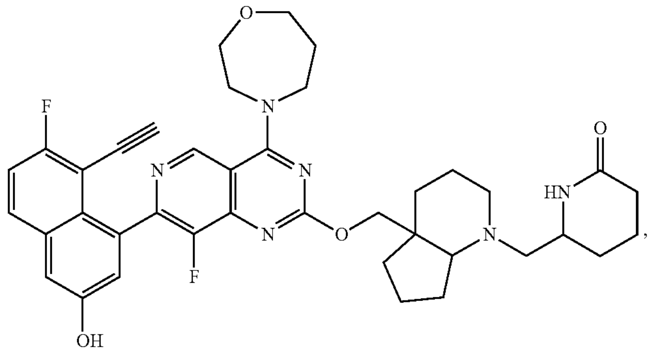
,
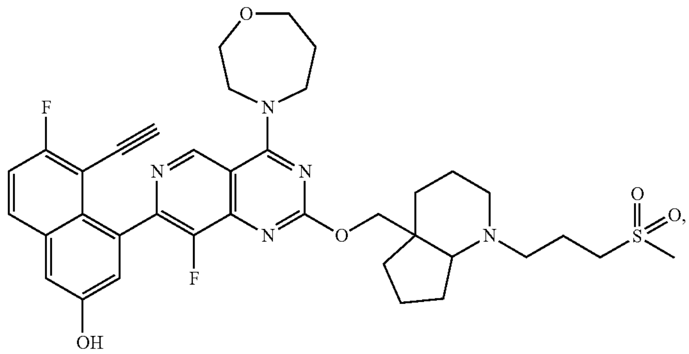
,
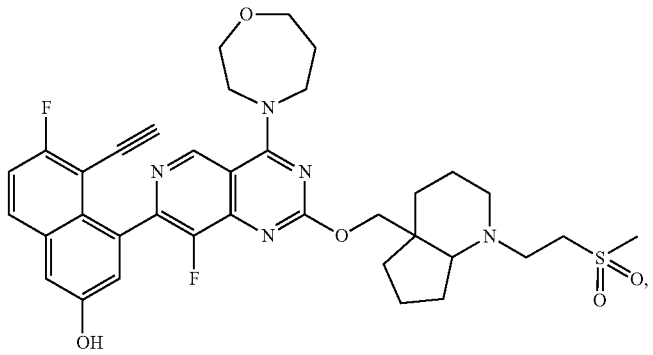
,

-continued
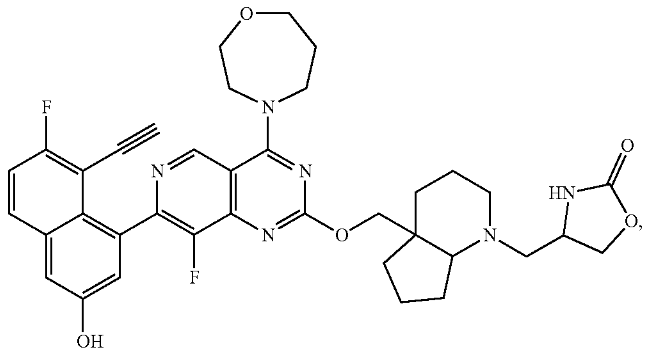
,
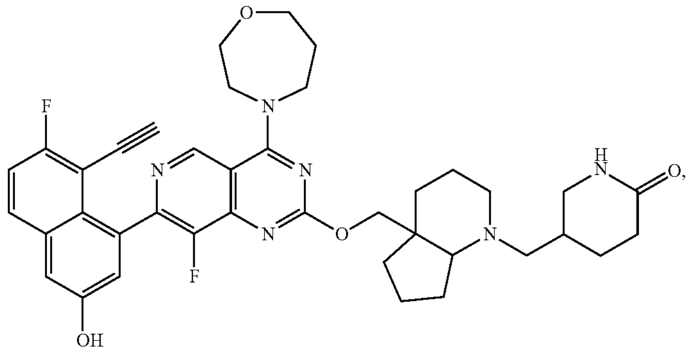
,
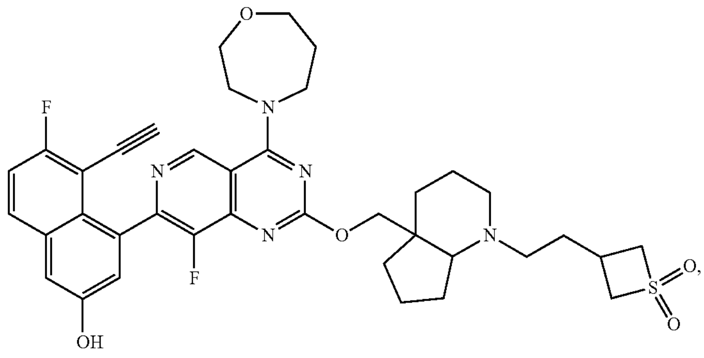
,
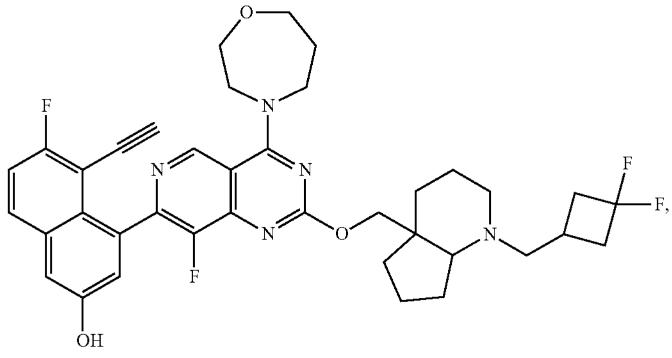
,

-continued
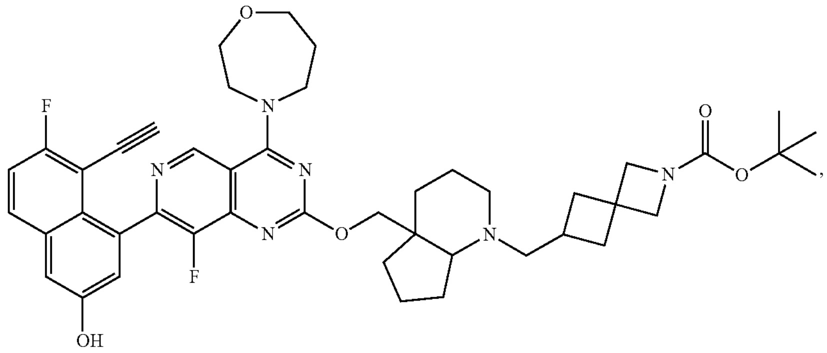
,
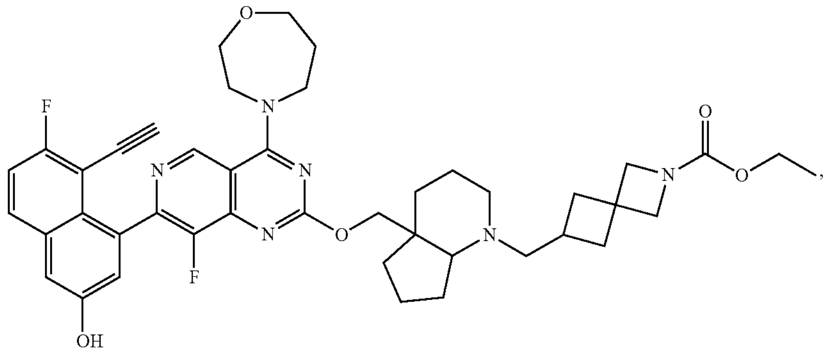
,
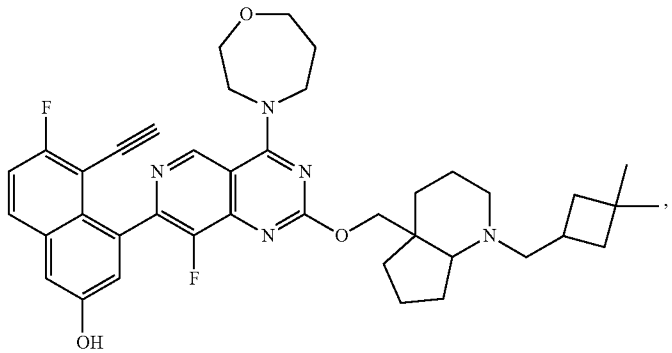
,
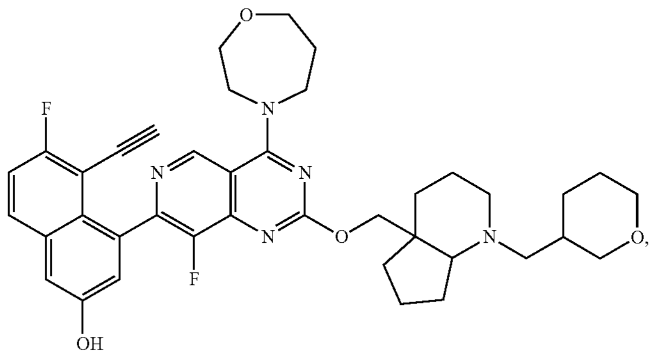
,

-continued
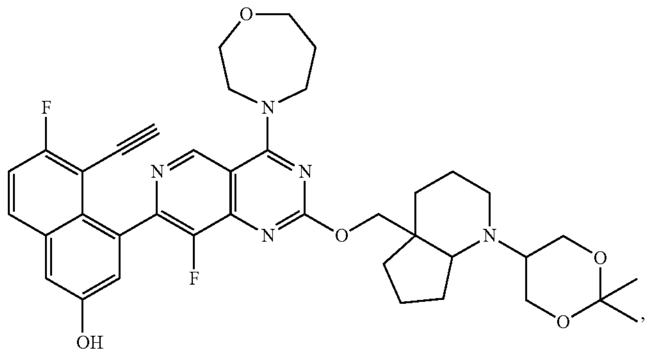
,
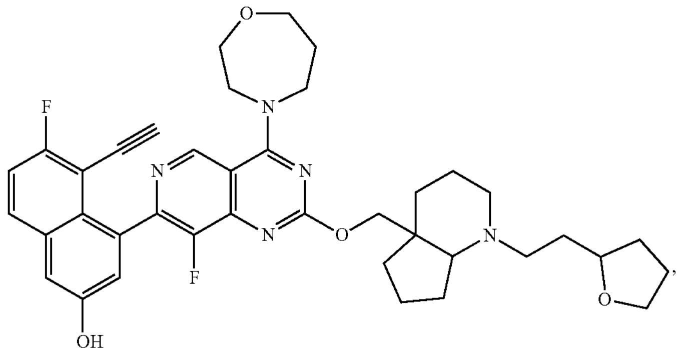
,
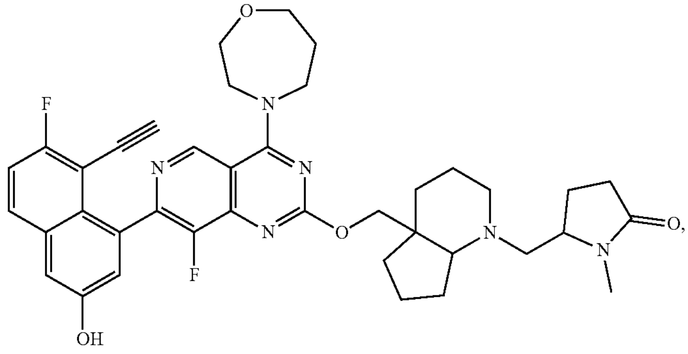
,
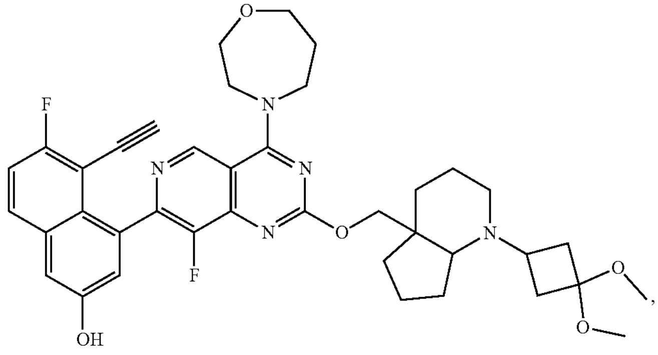
,

-continued
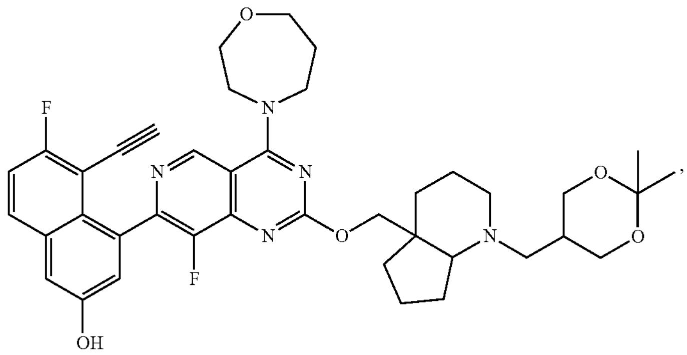
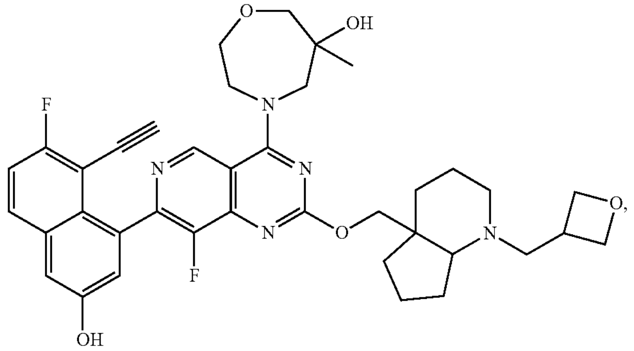
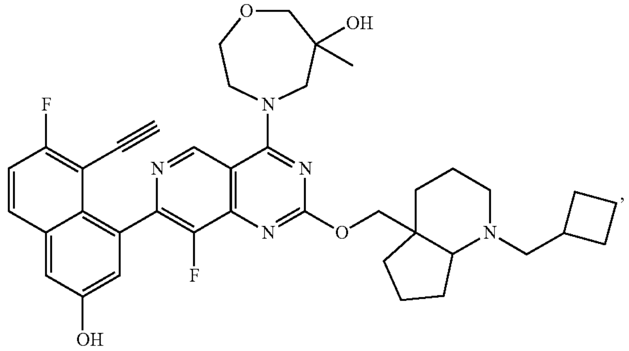
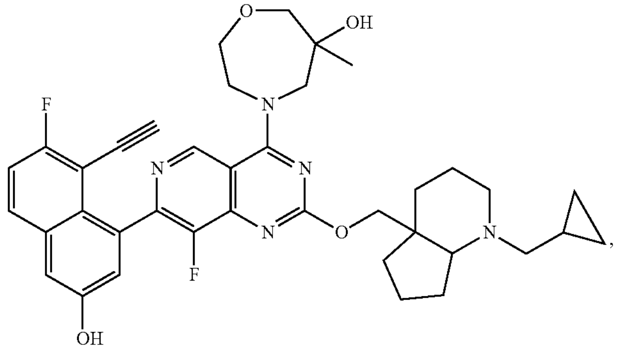

-continued
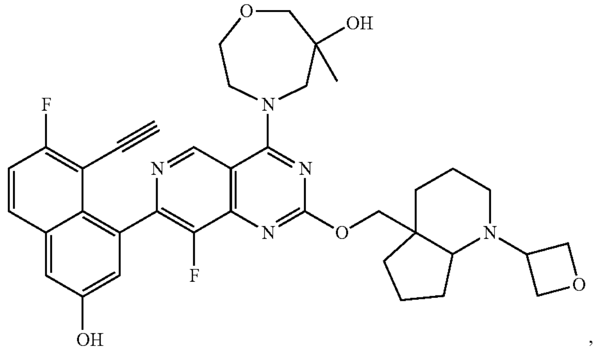
,
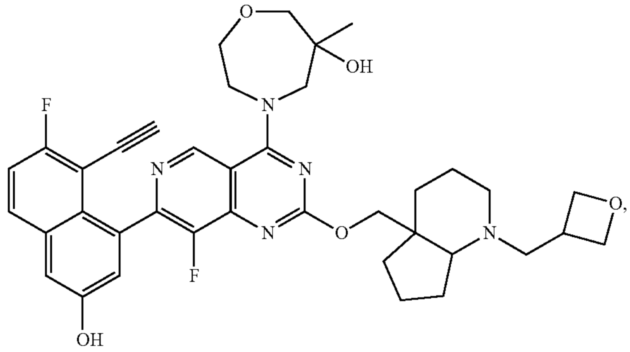
,
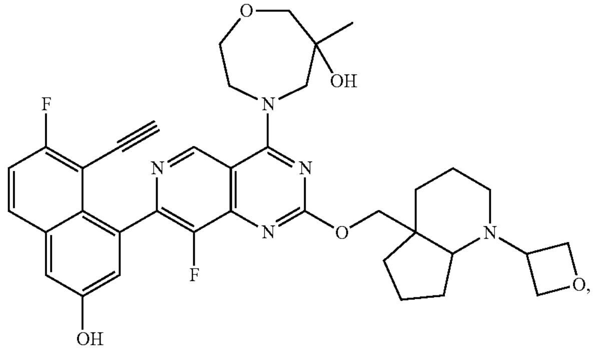
,
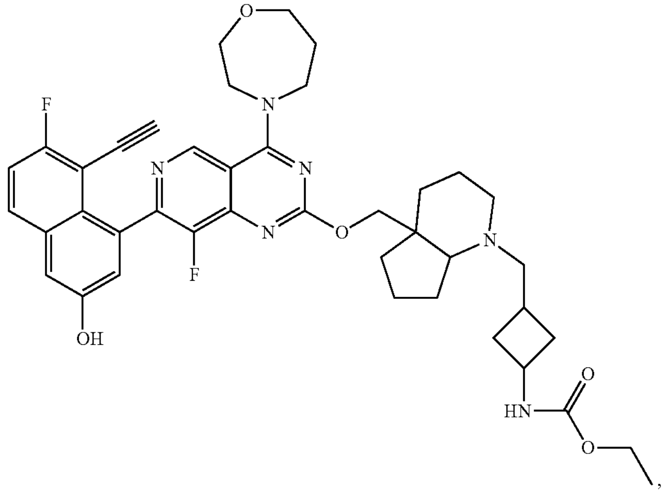
,
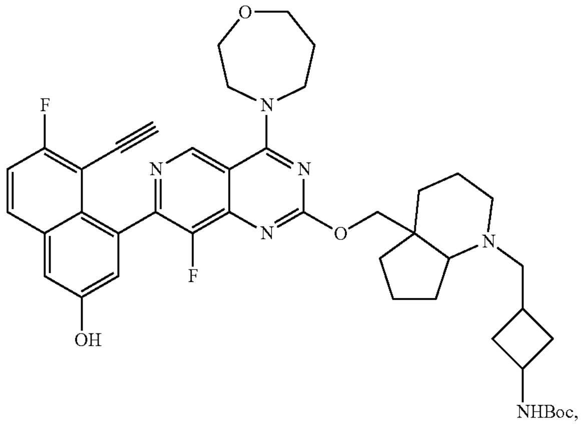
, -continued
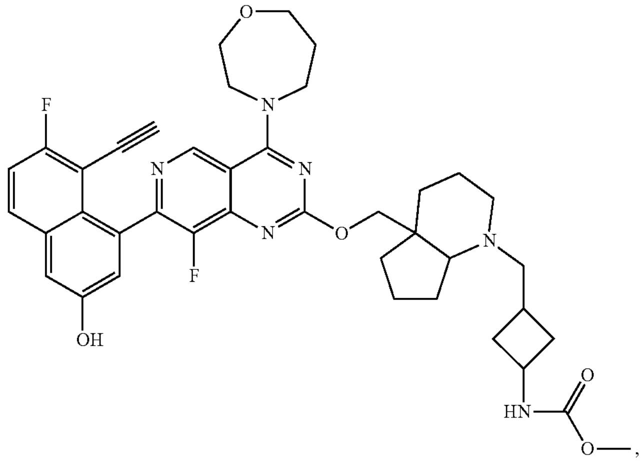
,
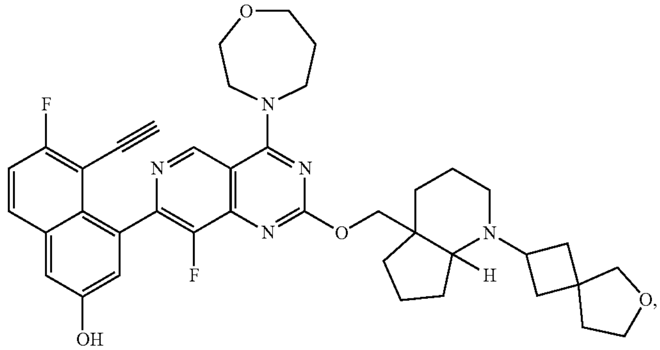
,
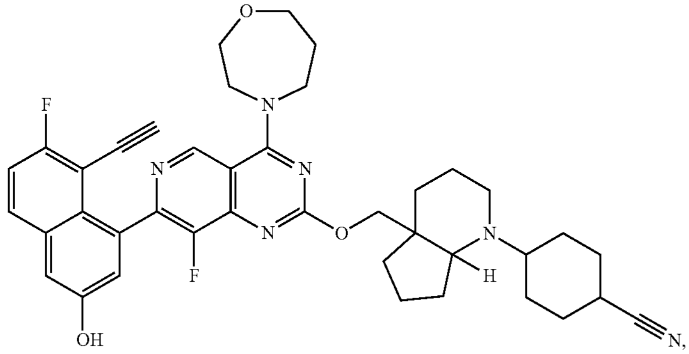
,
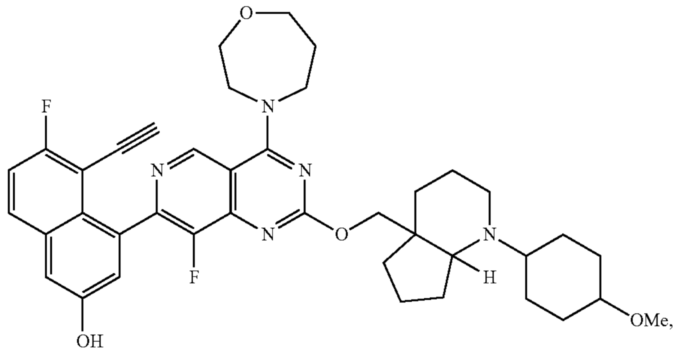
, -continued
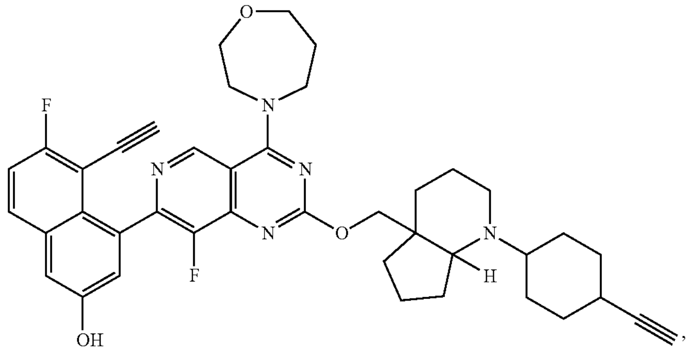
,
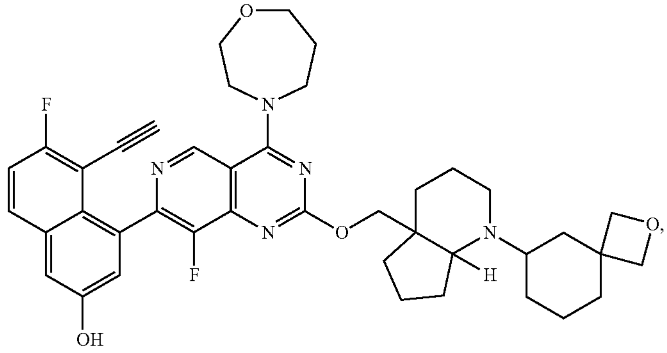
,
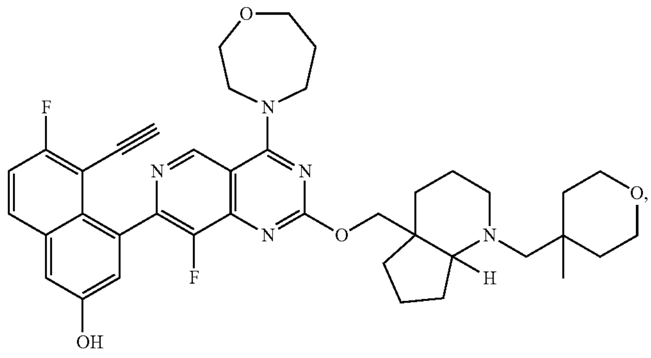
,
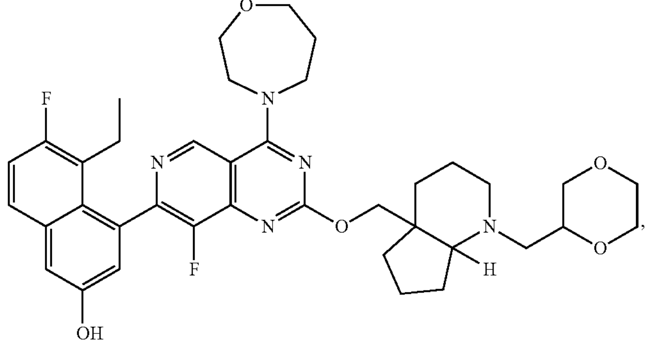
, -continued
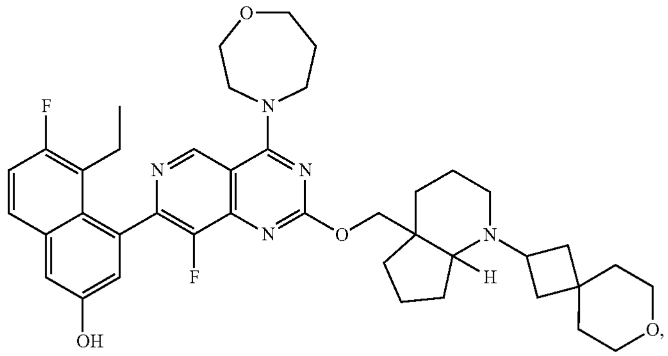
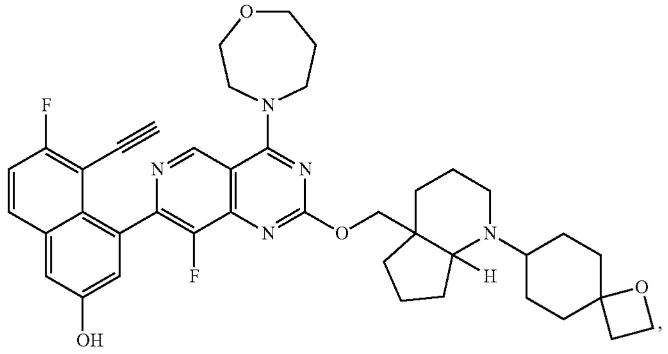
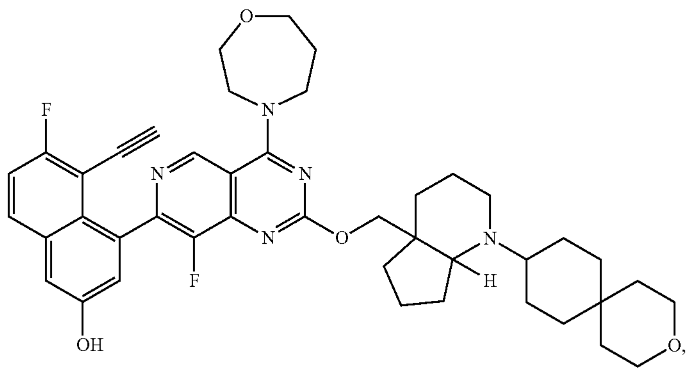
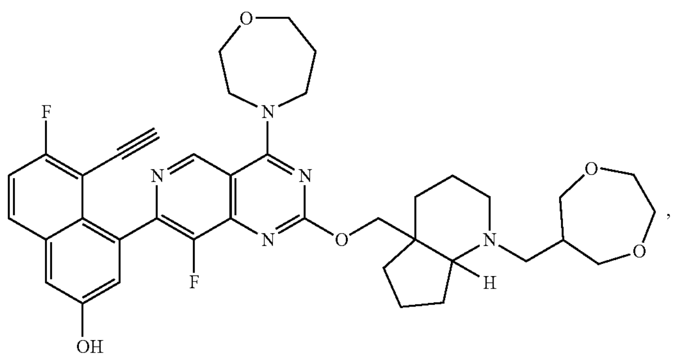

-continued
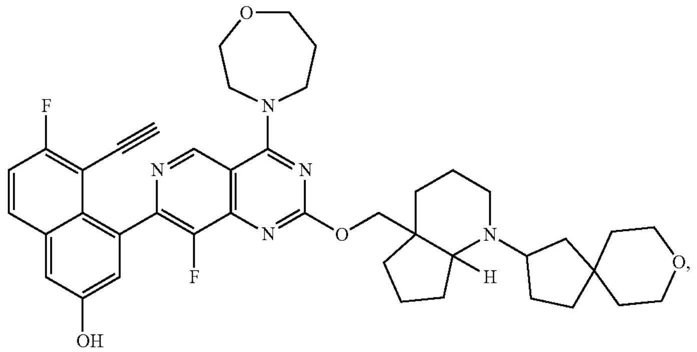
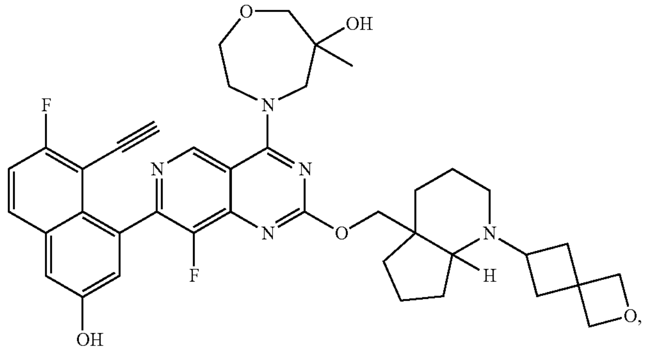
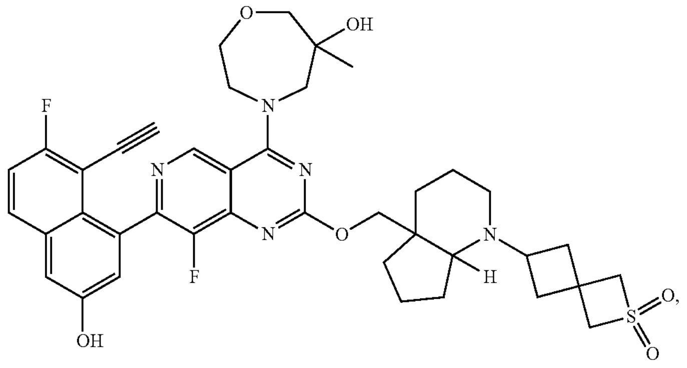
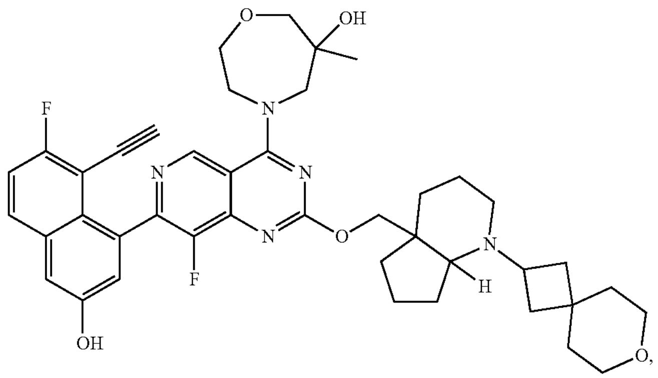

-continued
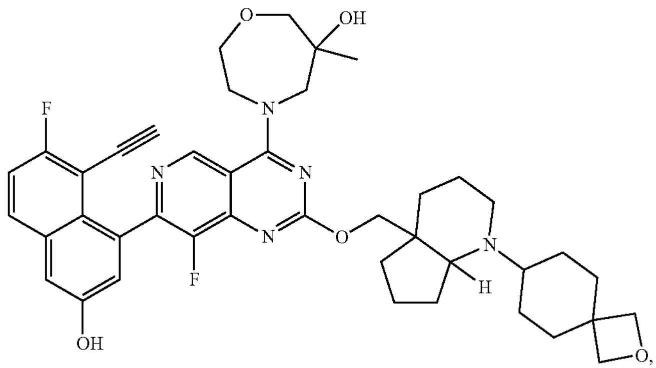
,
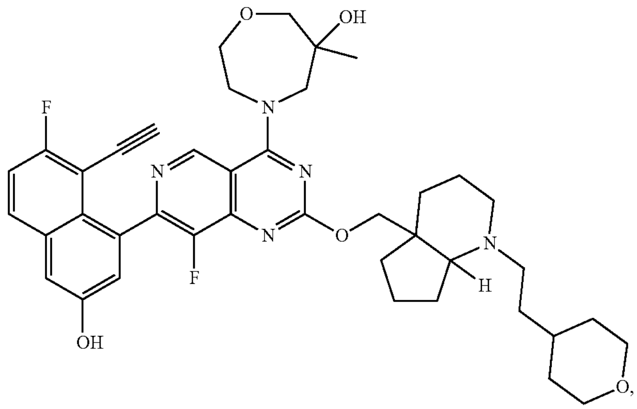
,
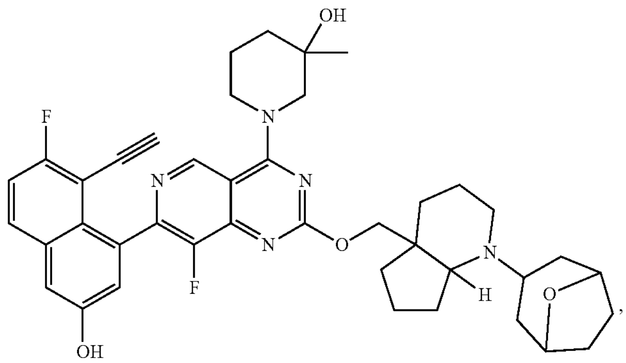
,
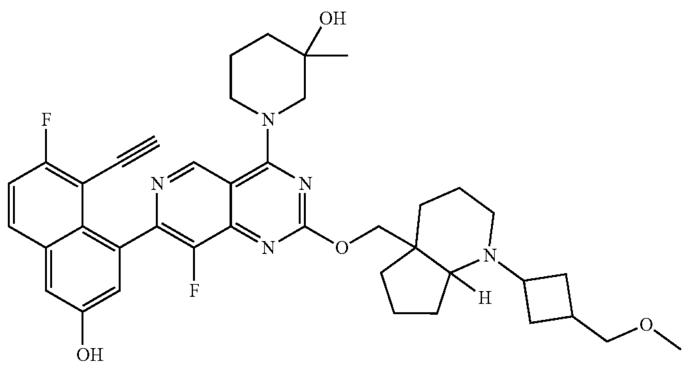
,

-continued
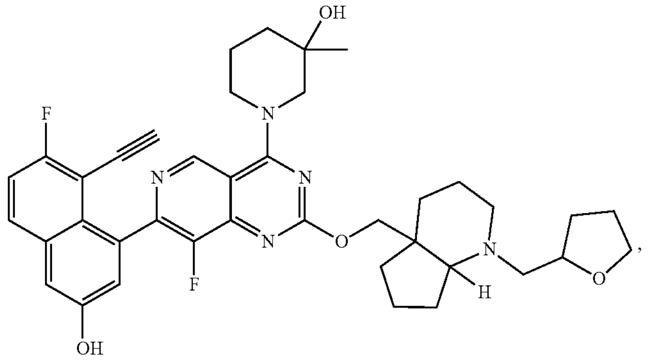
,
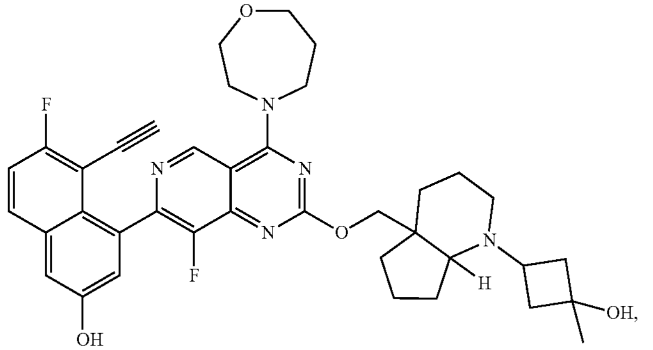
,
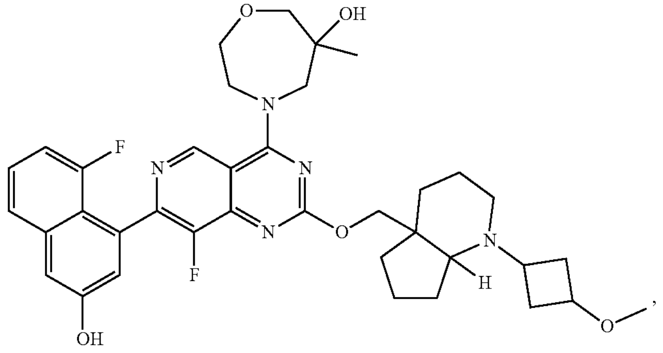
,
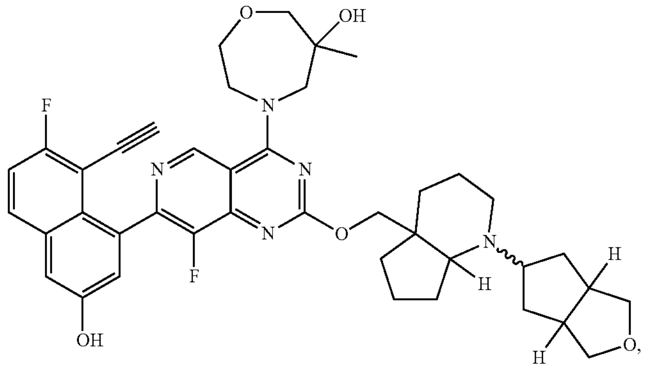
,

-continued
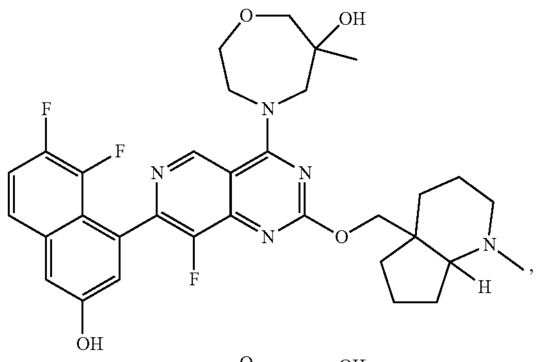
,
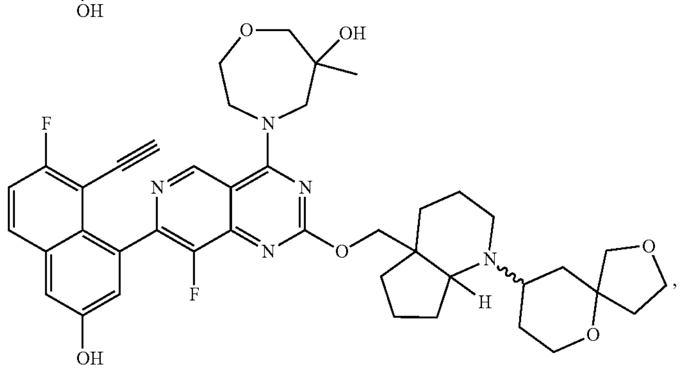
,
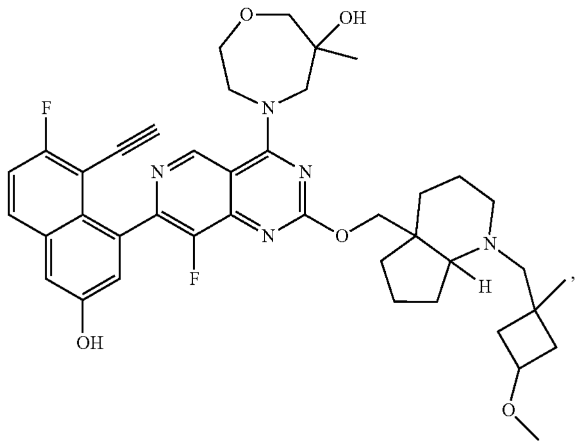
,
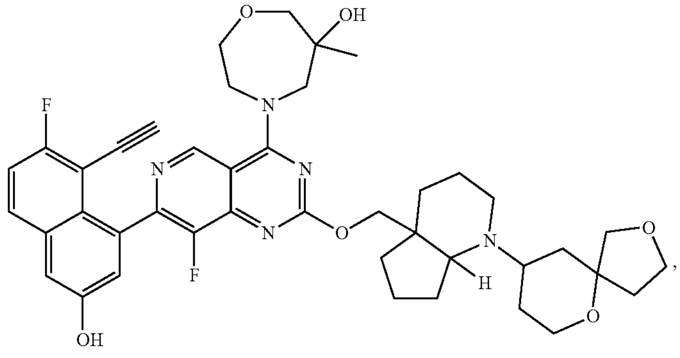
,

-continued
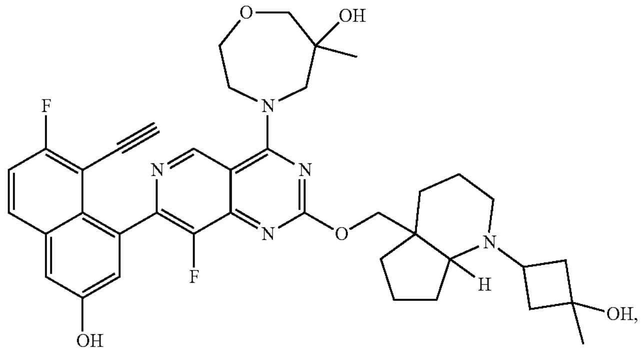
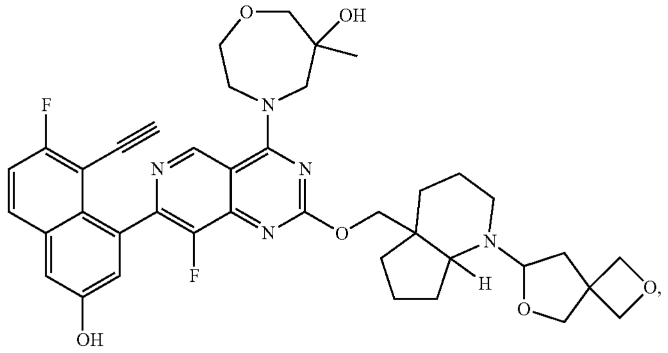
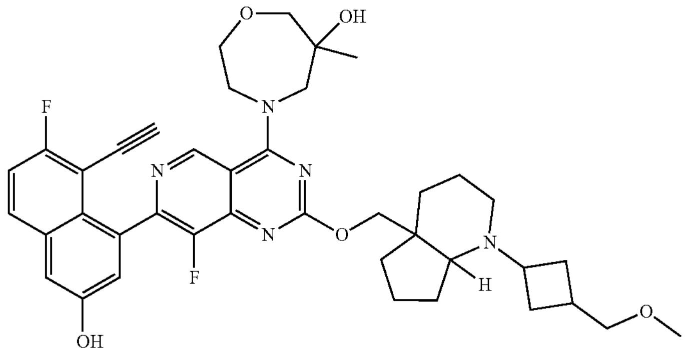
,
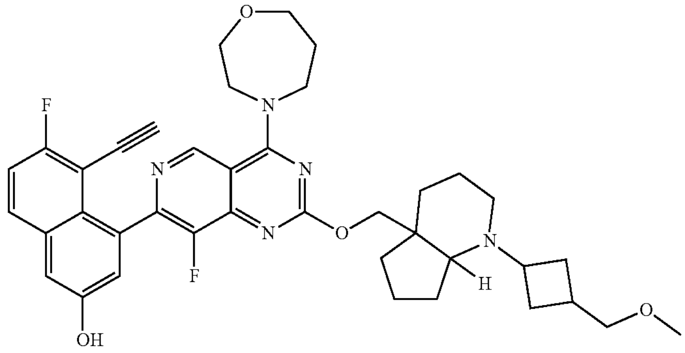
,

-continued
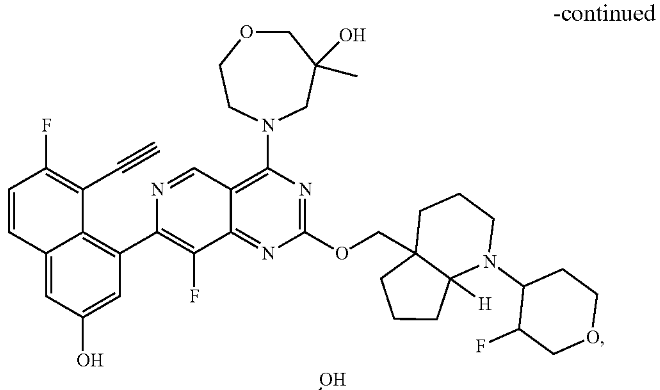
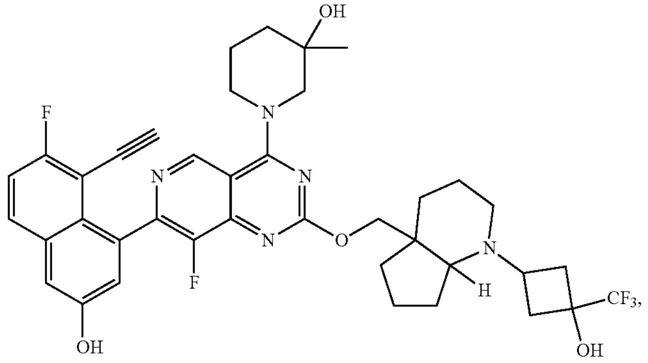
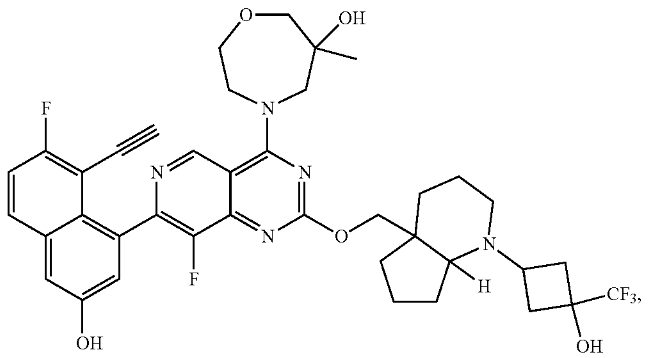
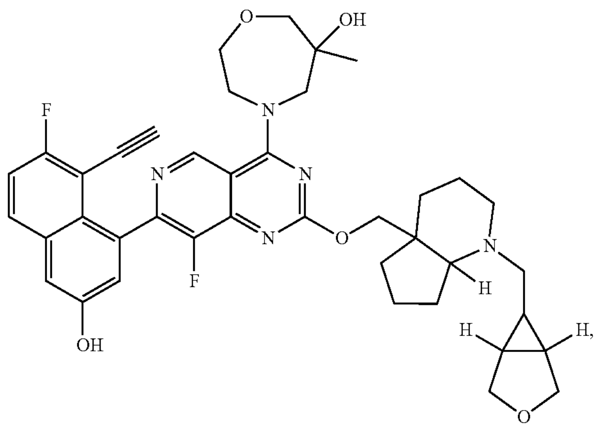

-continued
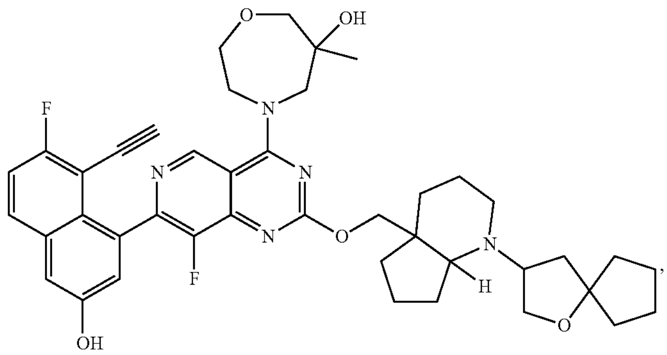
,
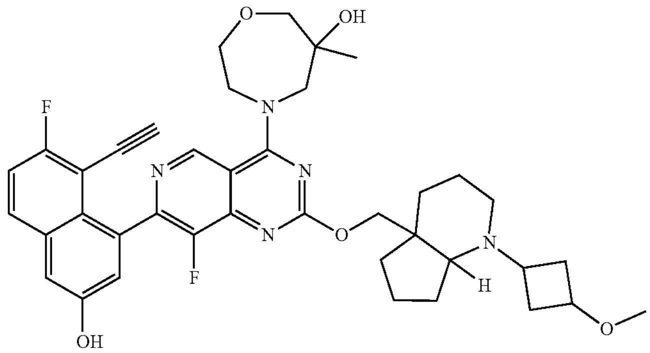
,
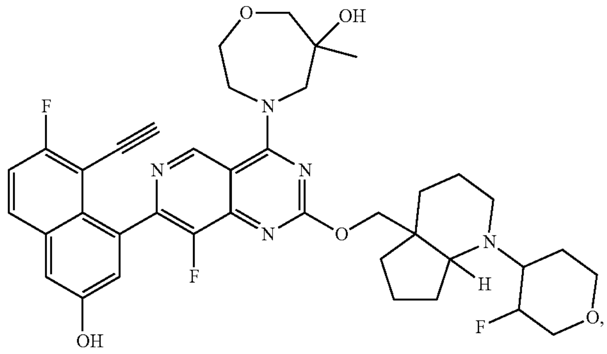
,
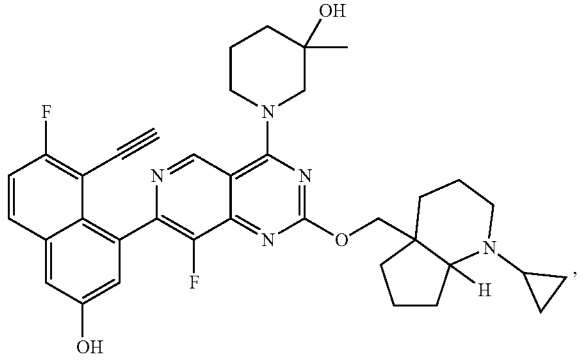
,
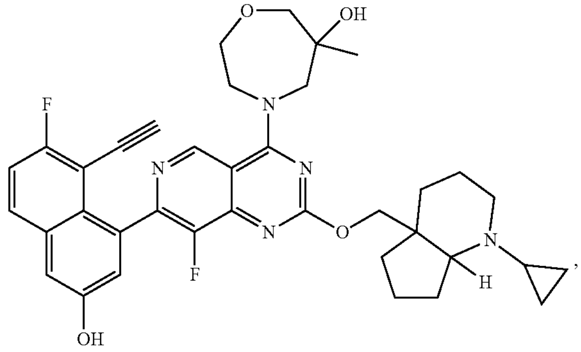
, -continued
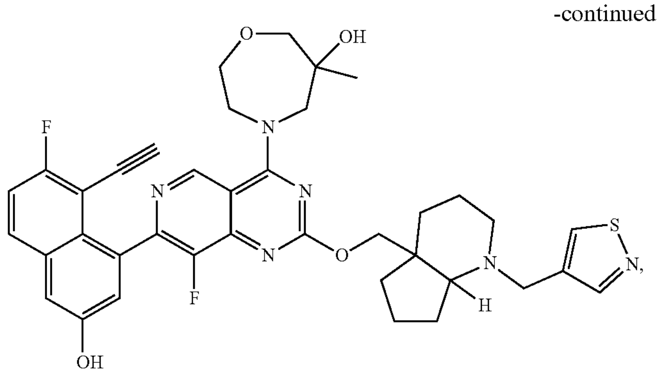
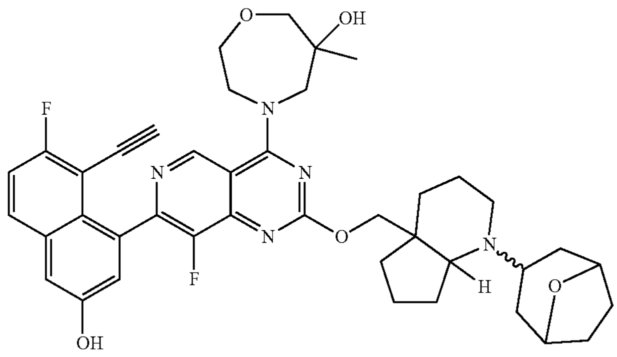
,
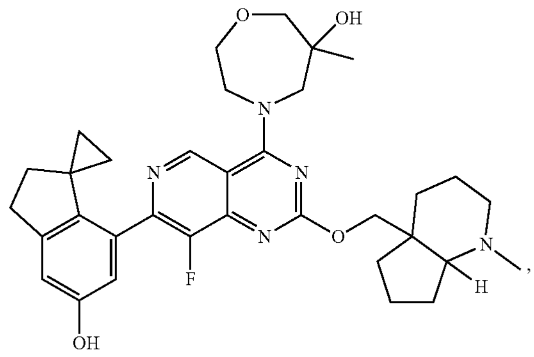
,
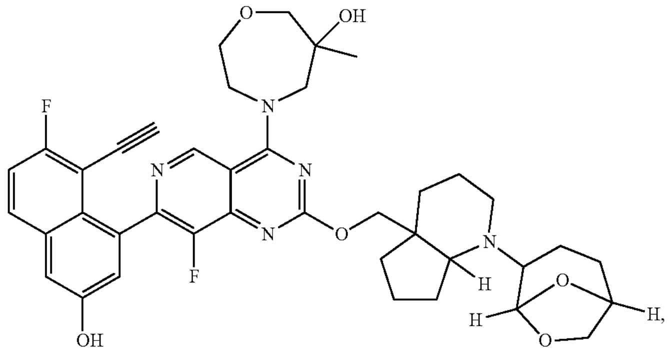
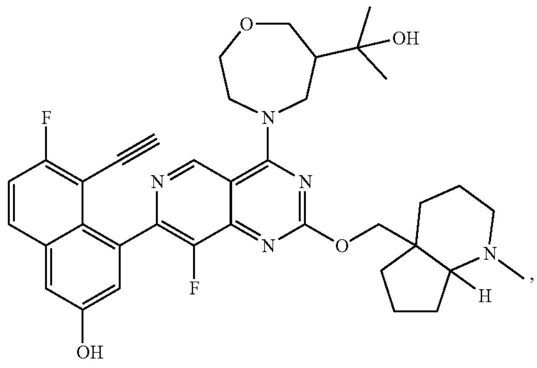
, -continued
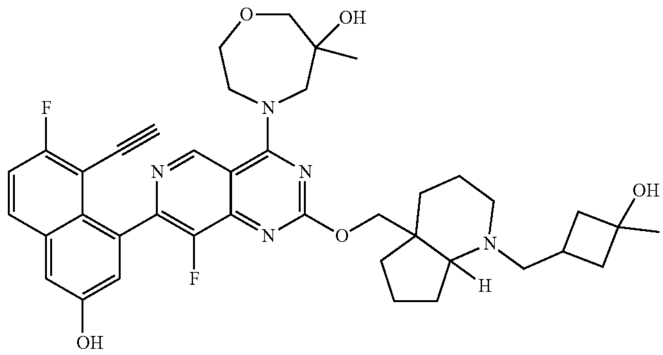
,
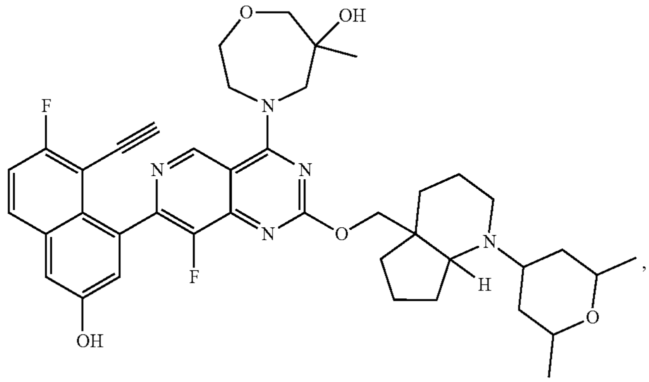
,
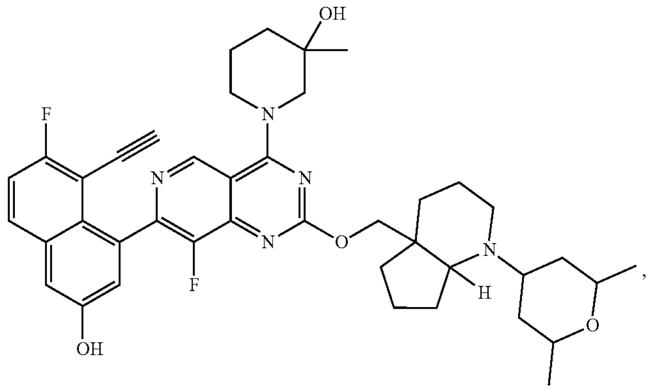
,
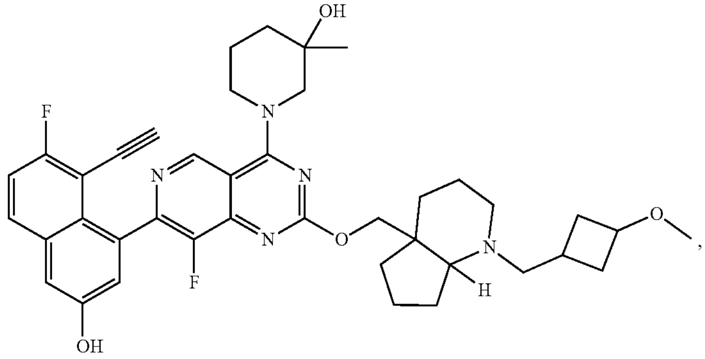
, -continued
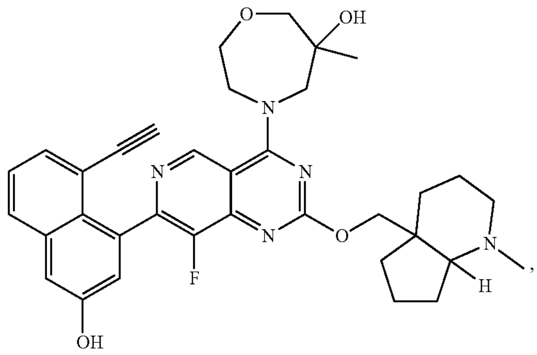
,
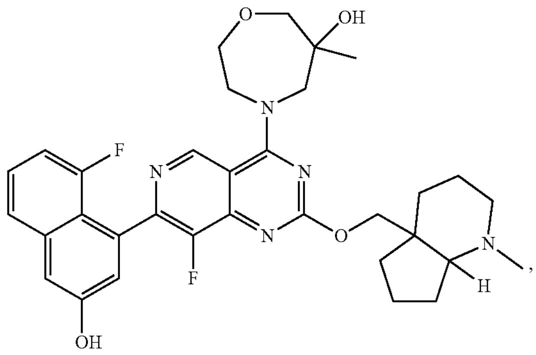
,
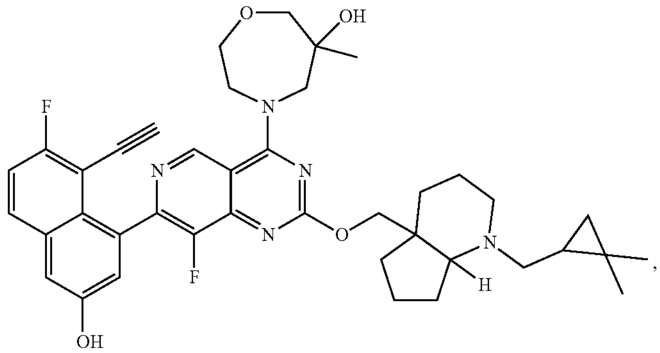
,
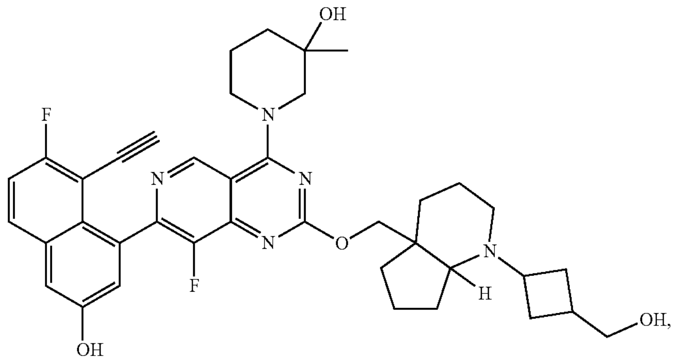
, -continued
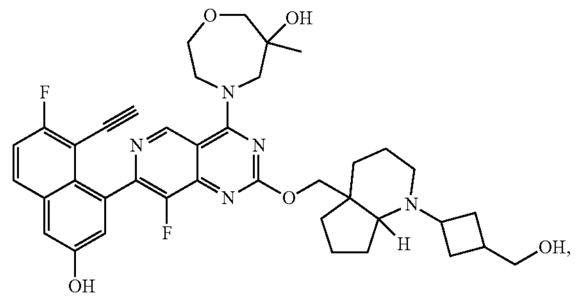 [SMILES: C#Cc1c(F)ccc2cc(O)cc(-c3ncc4c(N5CCOCC(C)(O)C5)nc(OCC56CCCC5N(C5CC(CO)C5)CCC6)nc4c3F)c12]
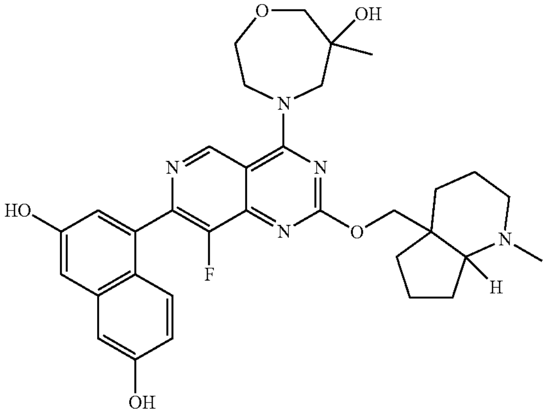
,
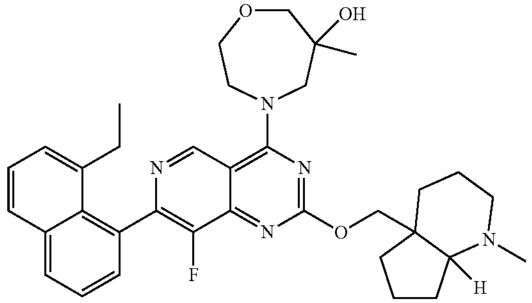
,
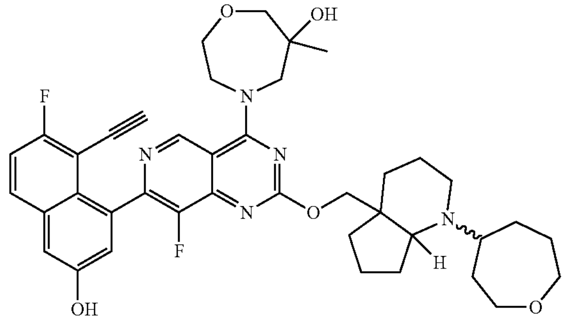
,
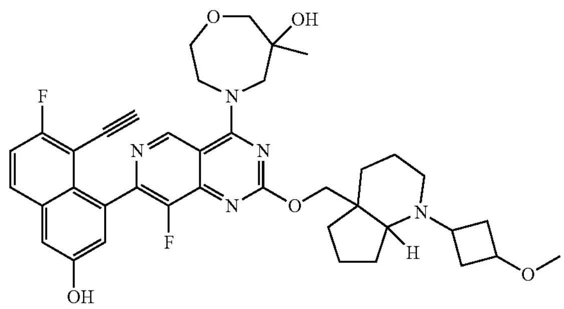
,
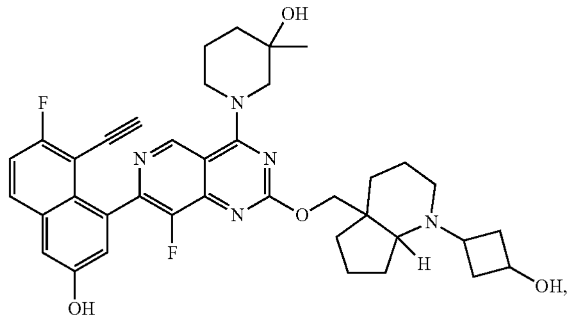
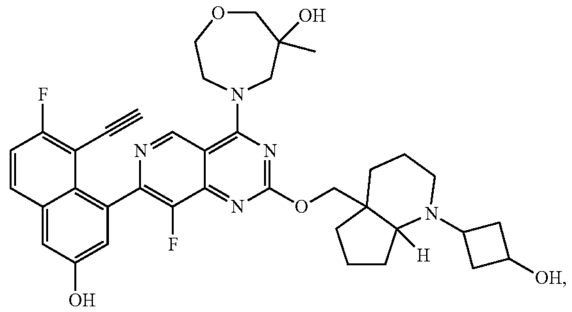
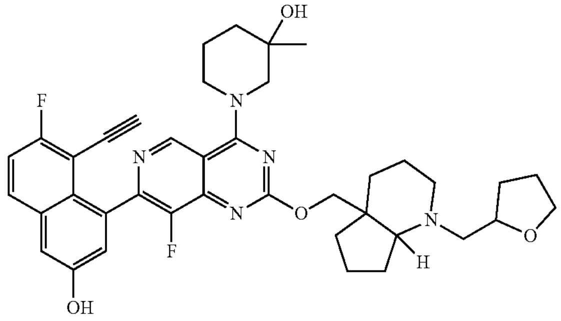
,
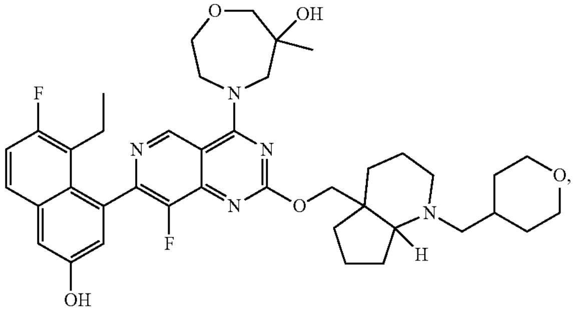
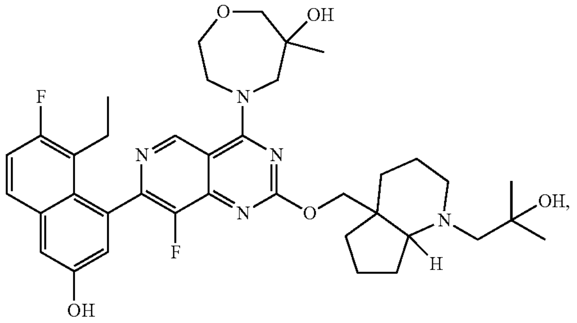

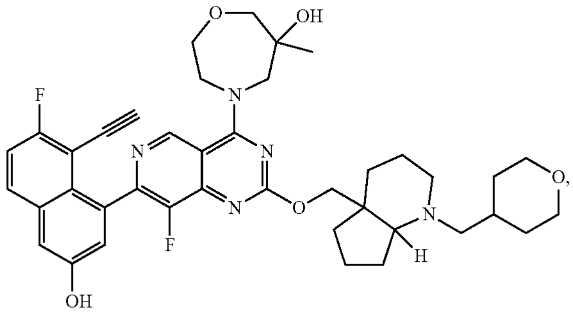
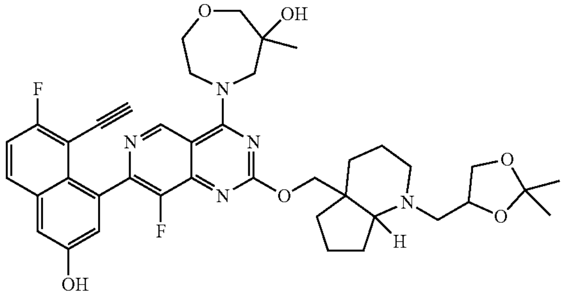
,
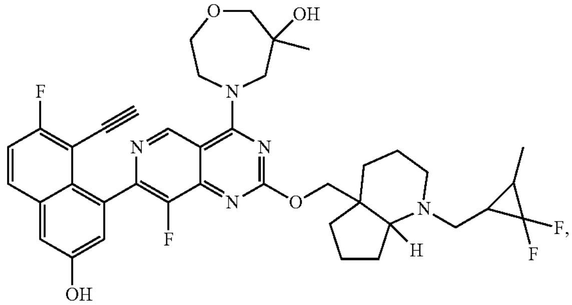
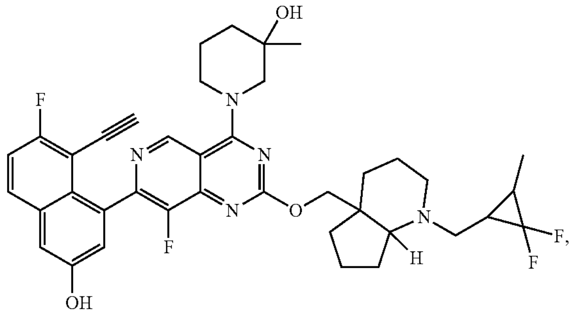
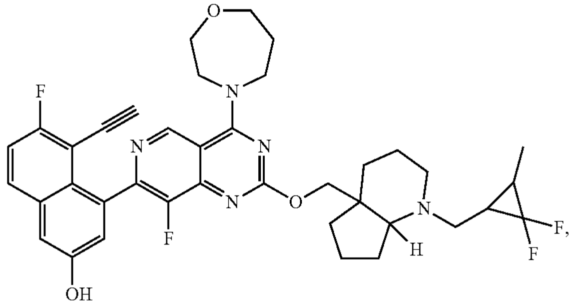
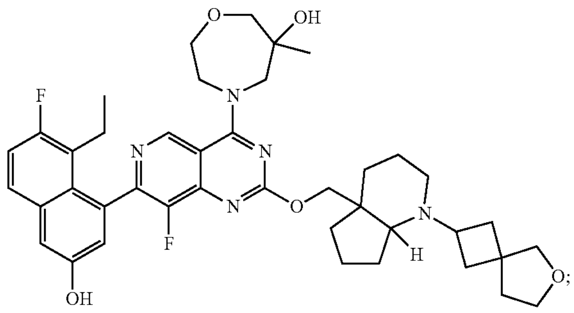
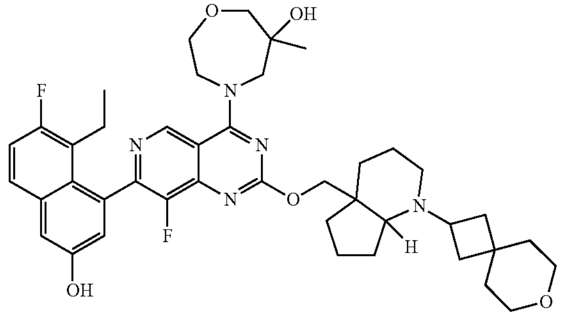
;
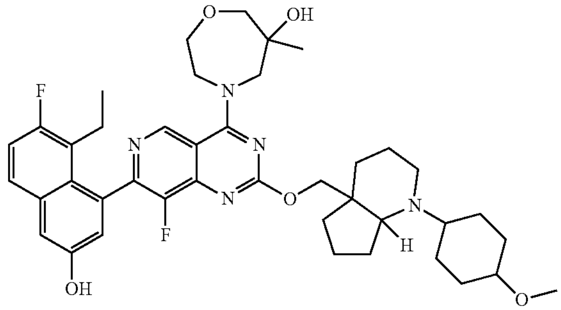
;
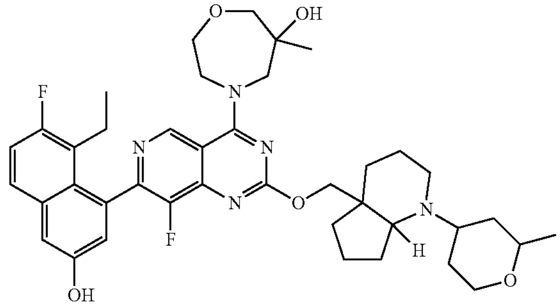
;
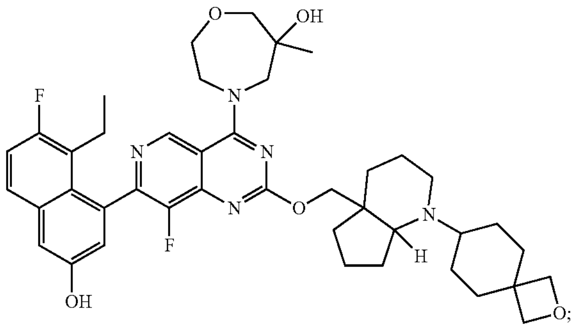

-continued
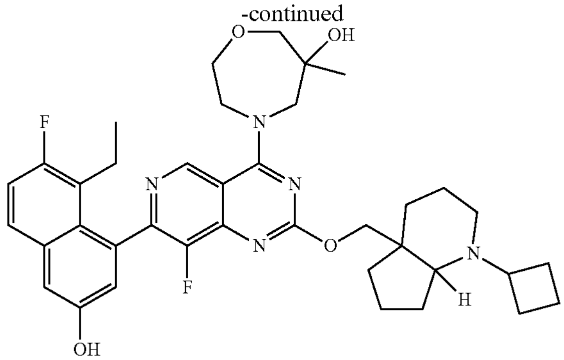
;
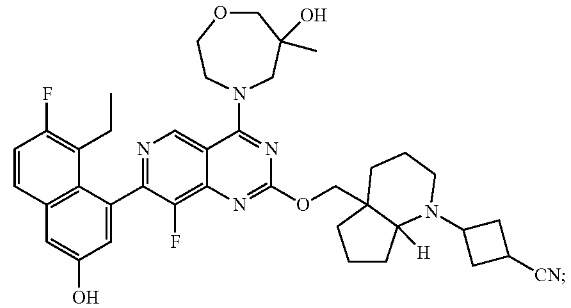
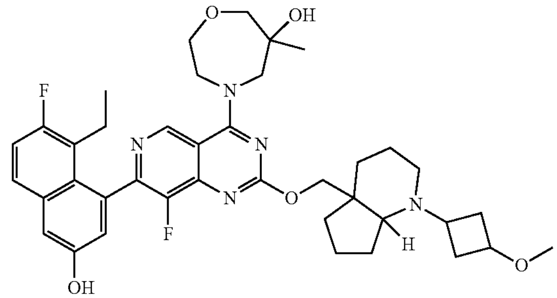
;
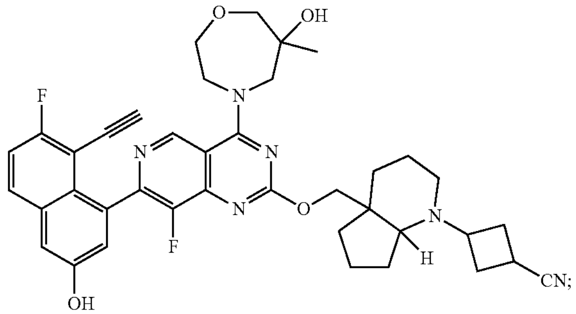
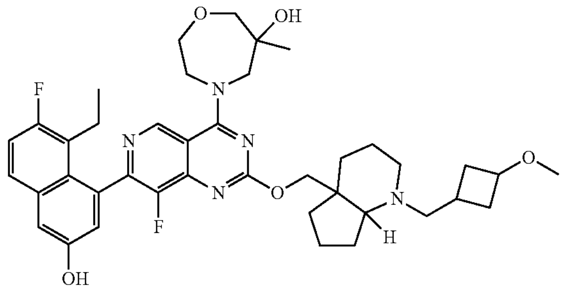
;
-continued
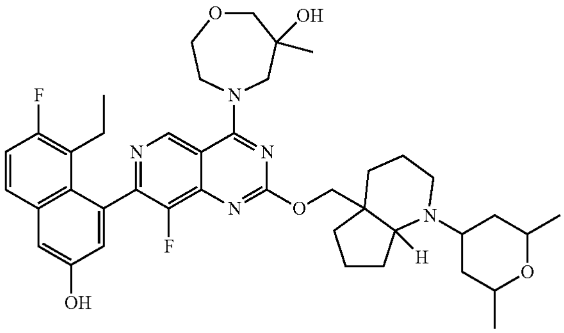
;
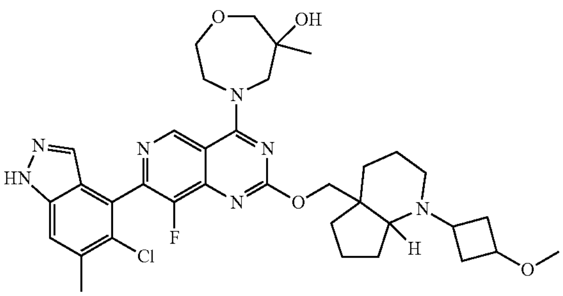
;
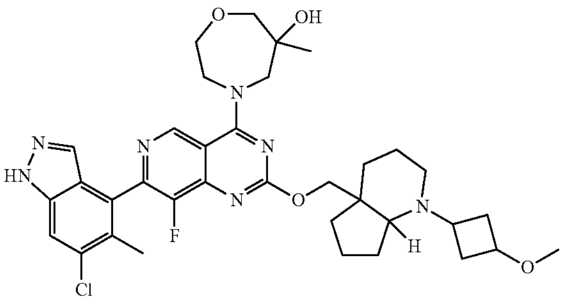
;
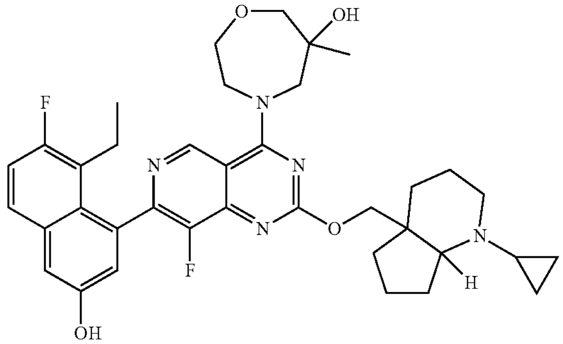
;
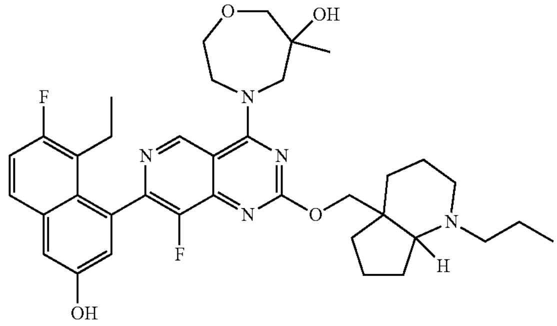
;

-continued
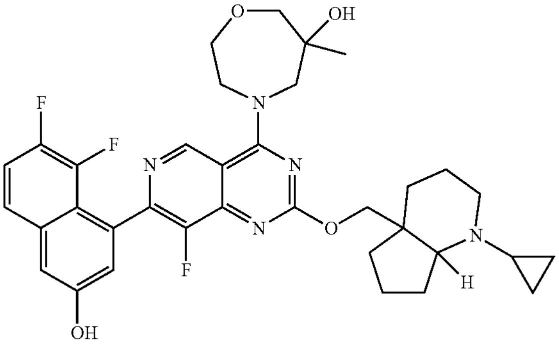
;
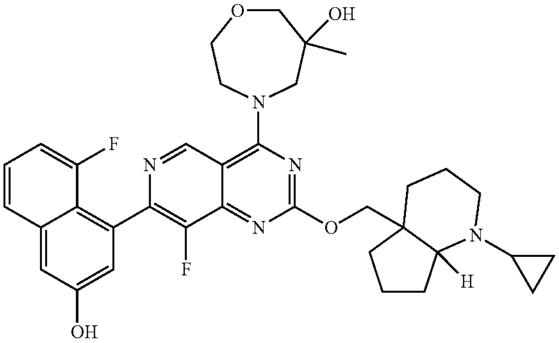
;
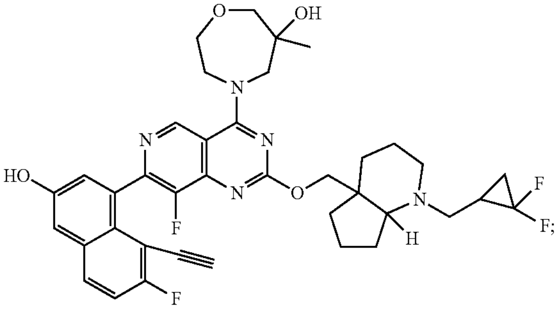
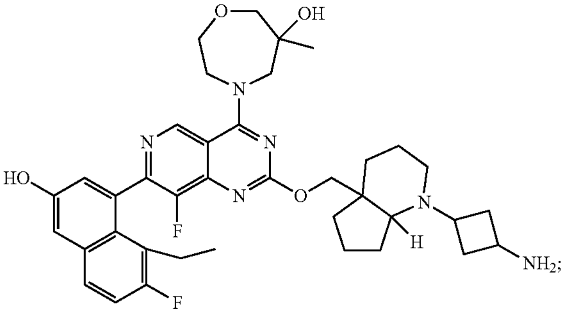
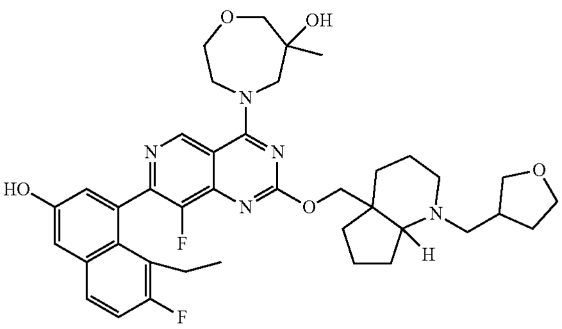
;
-continued
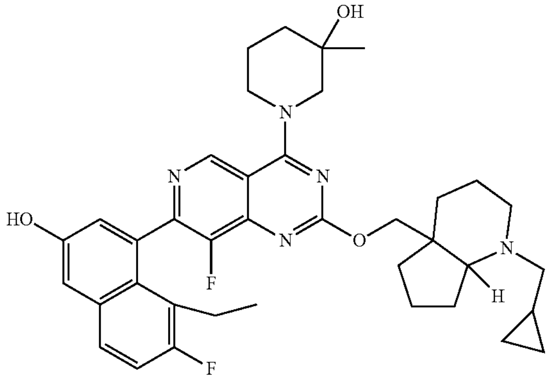
;
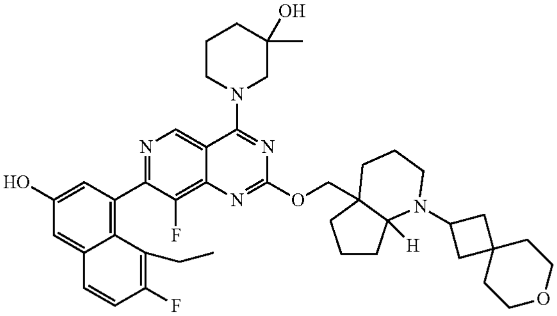
;
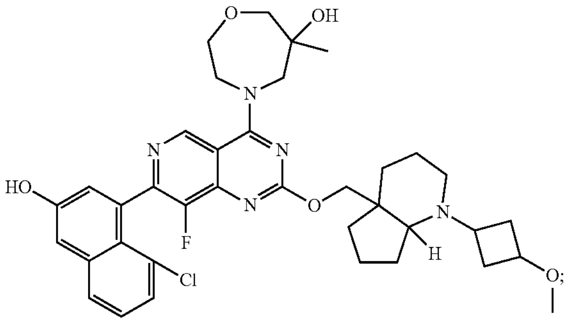
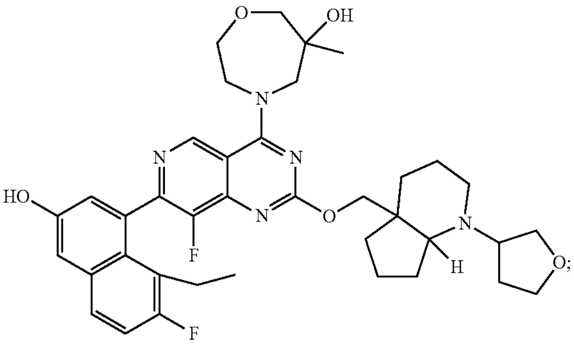
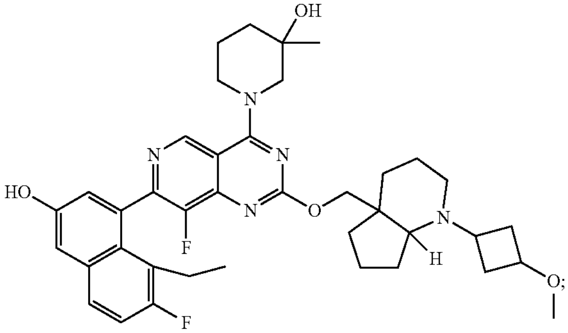

-continued
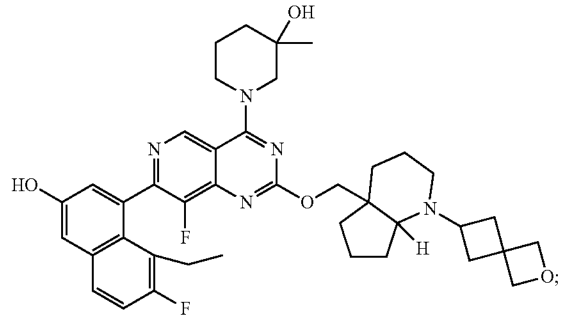
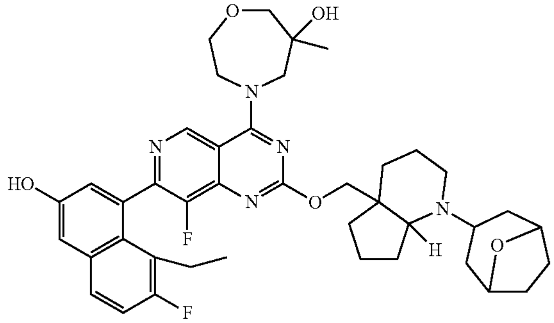
;
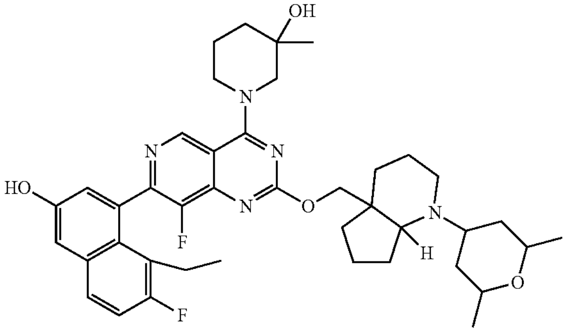
;
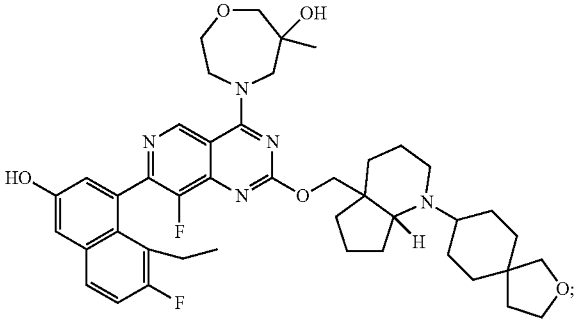
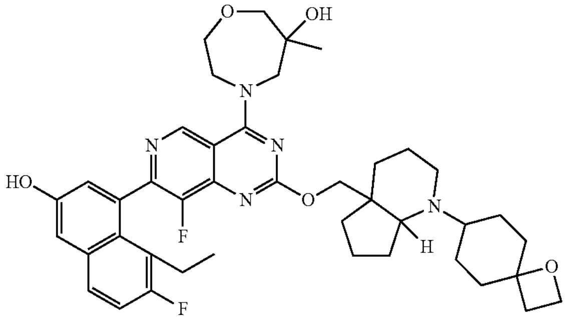
;
-continued
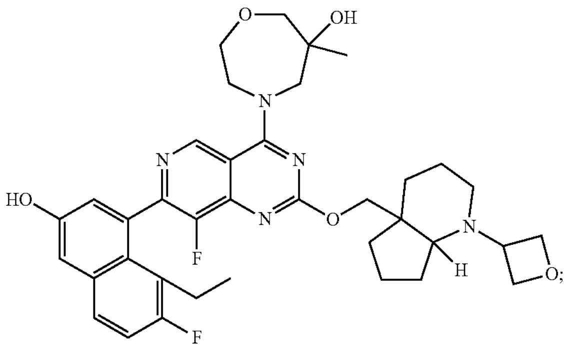
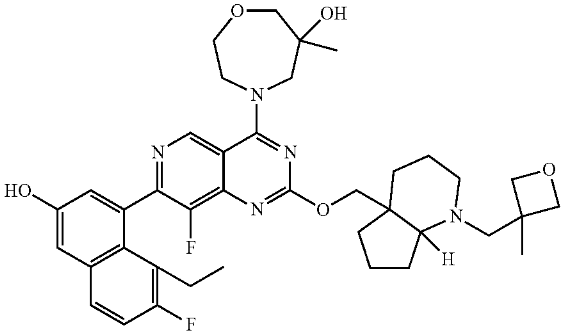
;
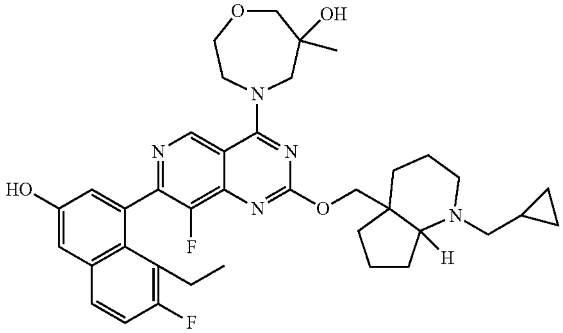
;
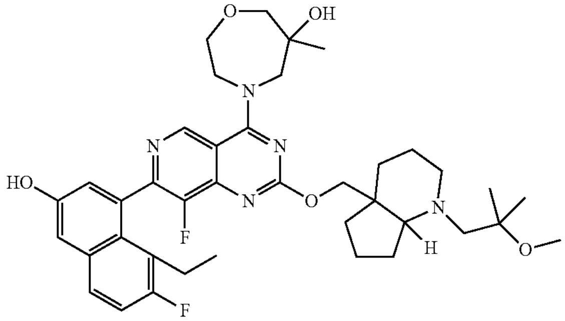
;
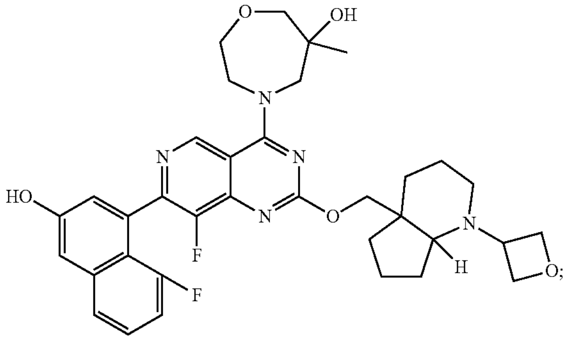

-continued
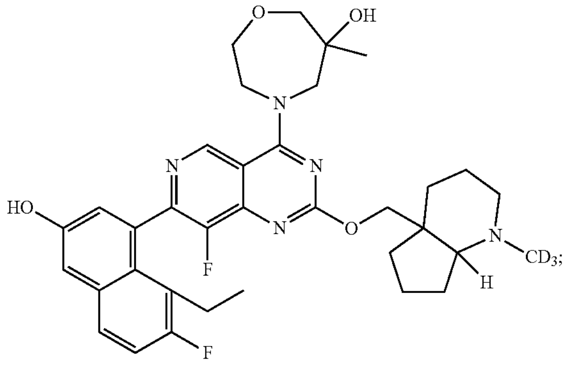
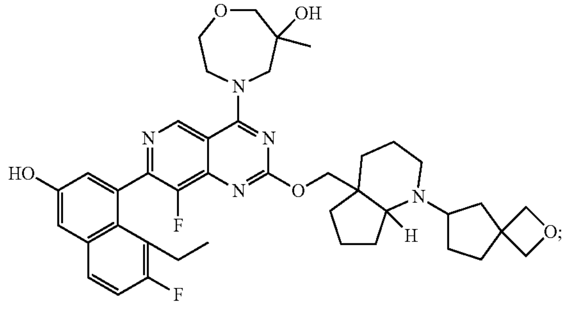
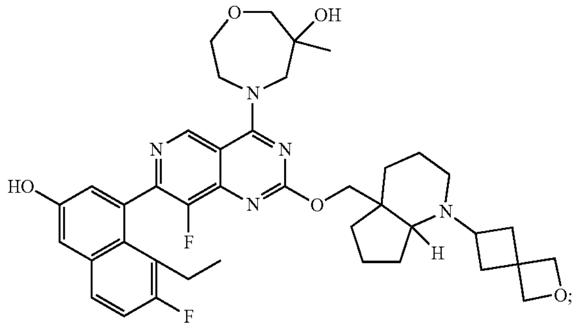
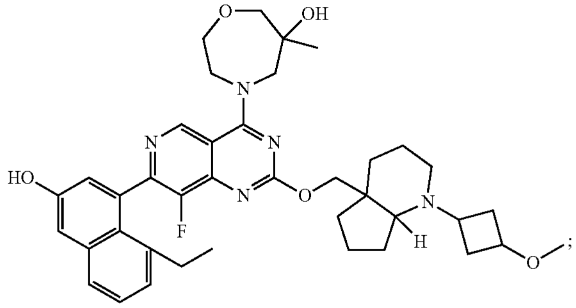
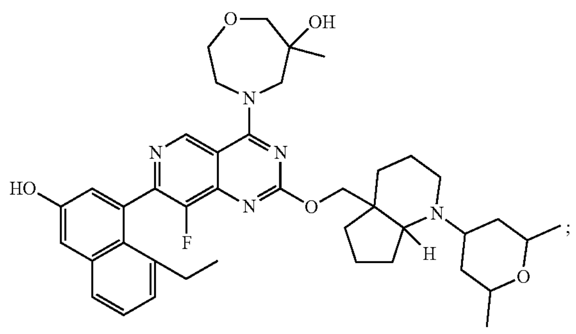
-continued
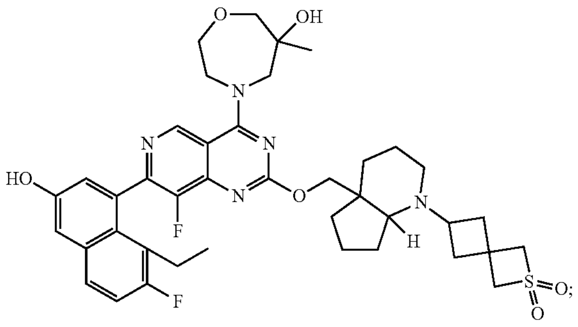
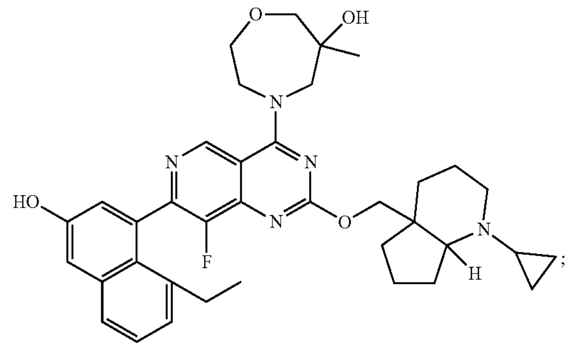
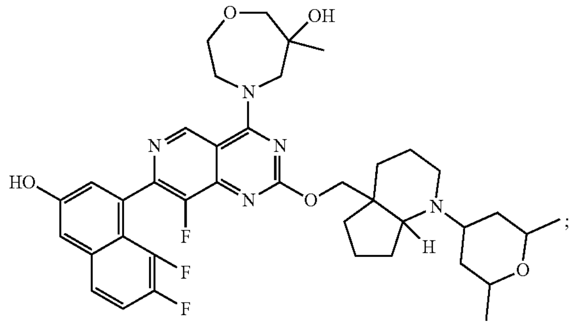
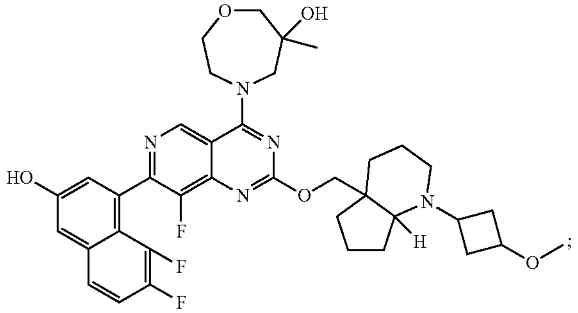
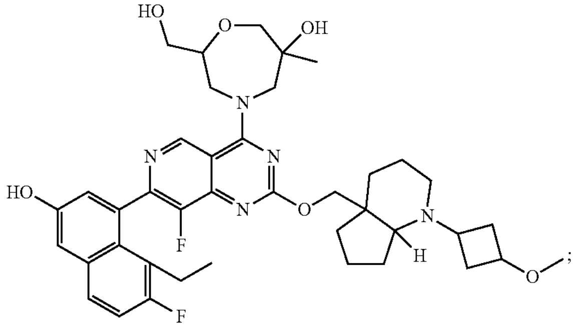

-continued
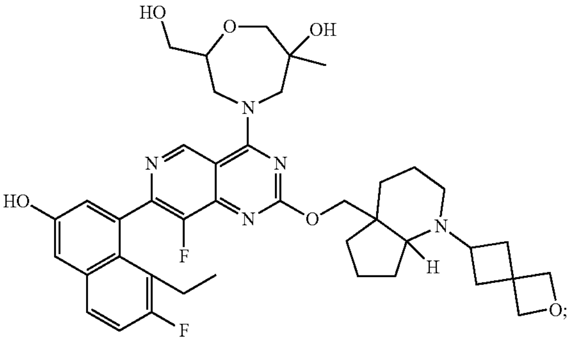
;
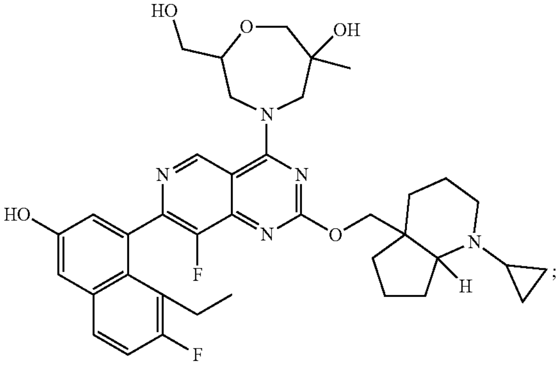
;
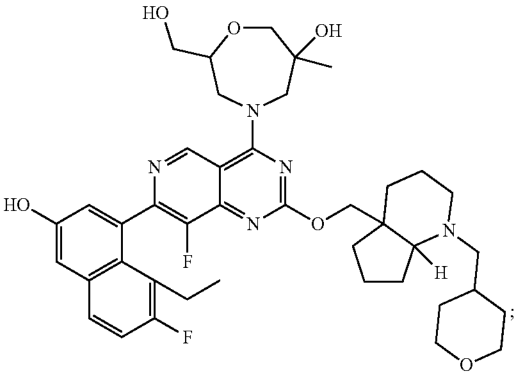
; and
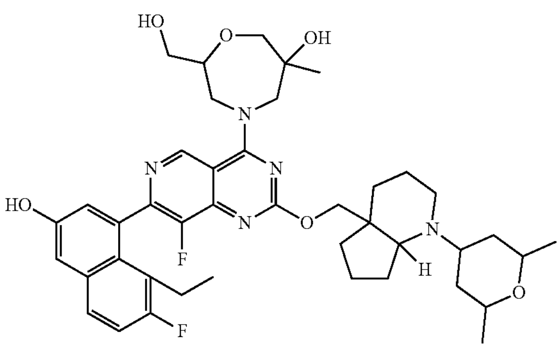
;
or a pharmaceutically acceptable salt thereof.
In some aspects, the present disclosure provides a compound selected from the group consisting of:
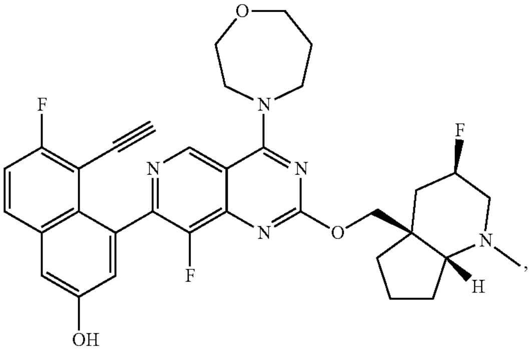
,
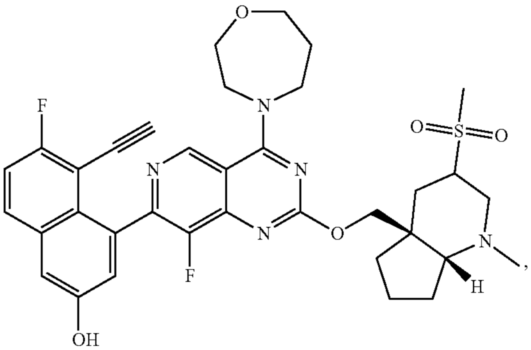
,
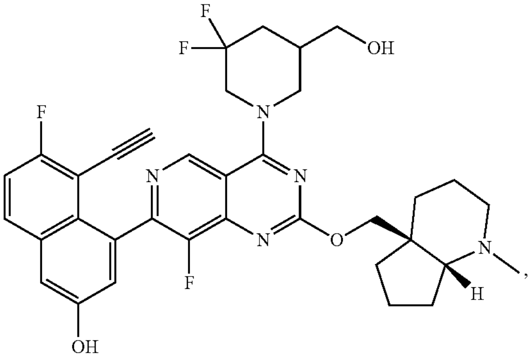
,
single diastereomer
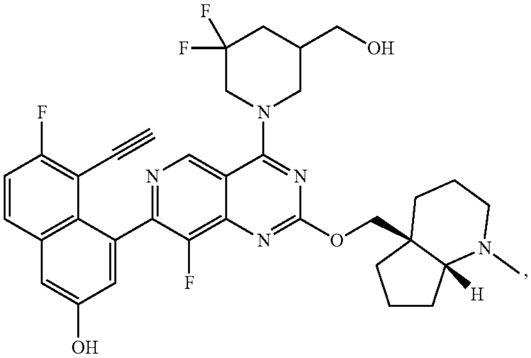
,
single diastereomer -continued
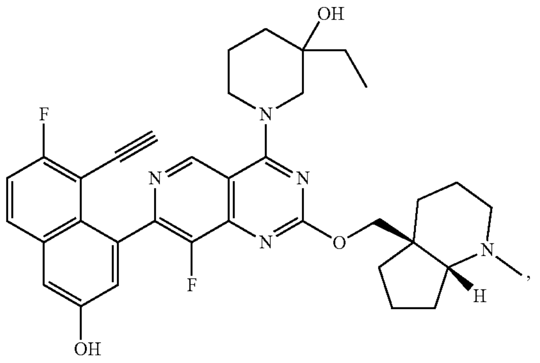
single diastereomer
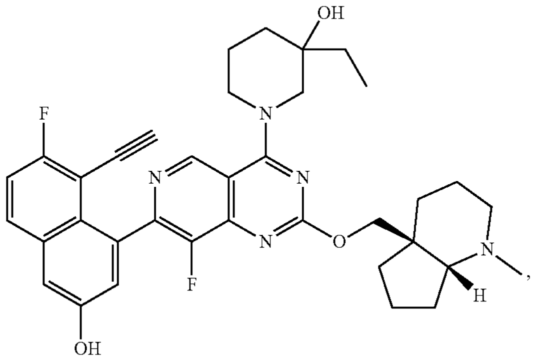
single diastereomer
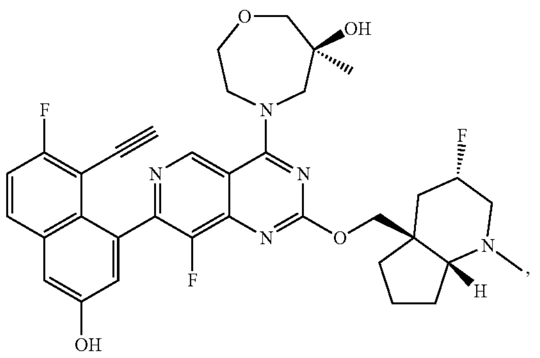
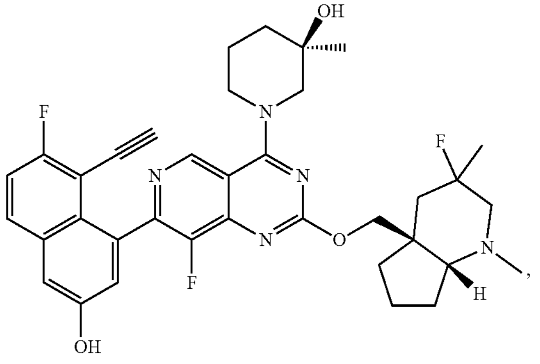
-continued
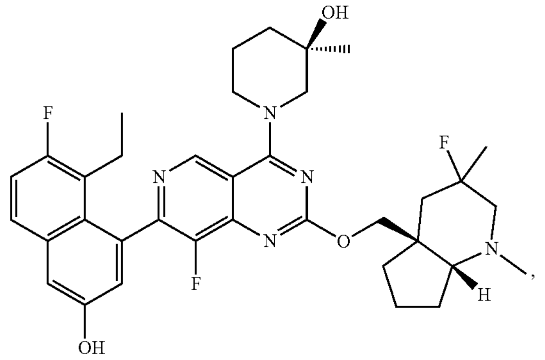
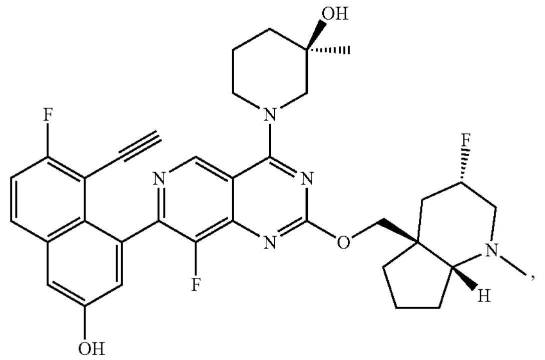
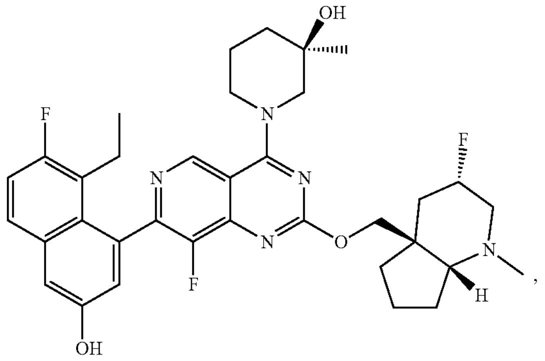
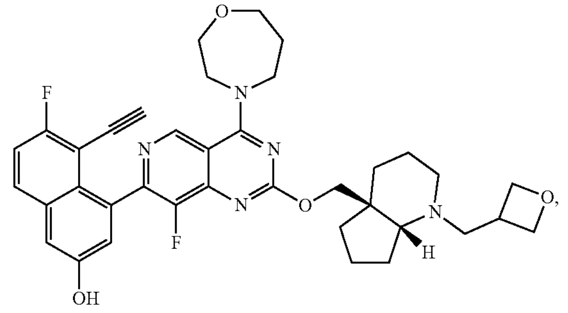
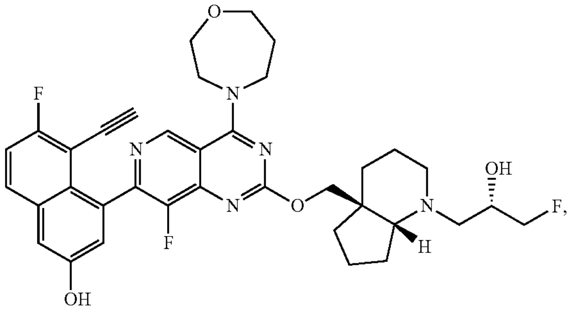

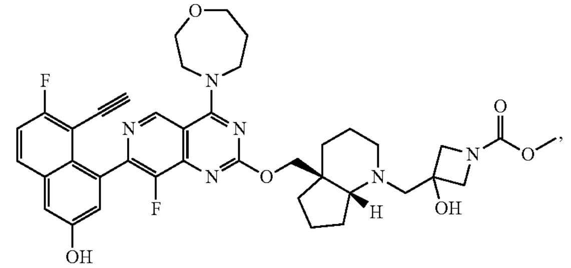
,
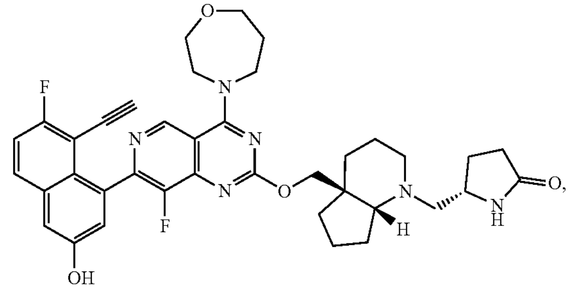
,
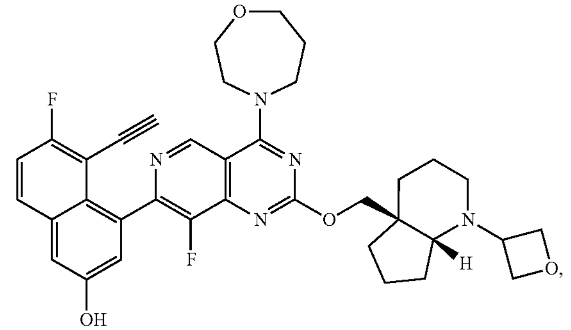
,
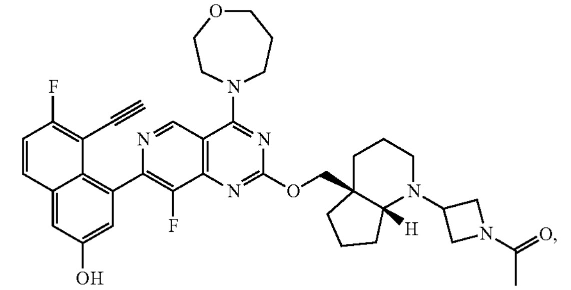
,
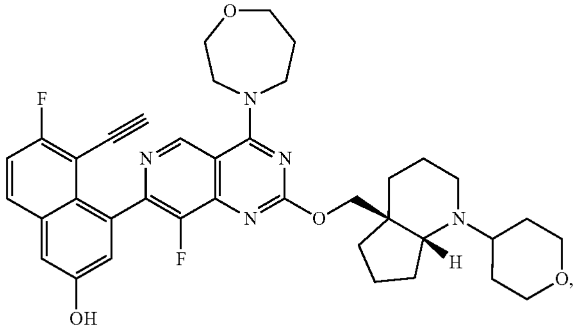
,
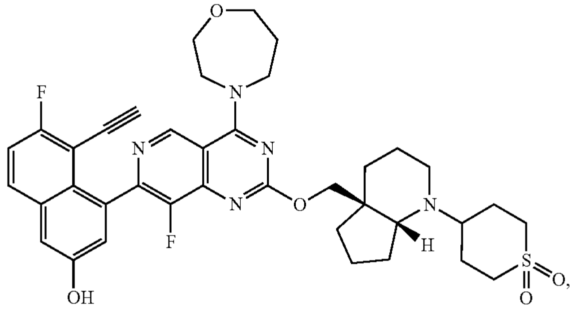
,
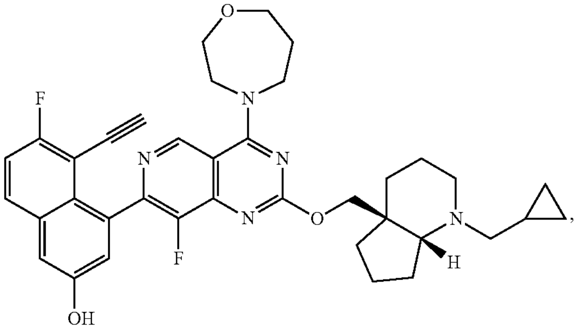
,
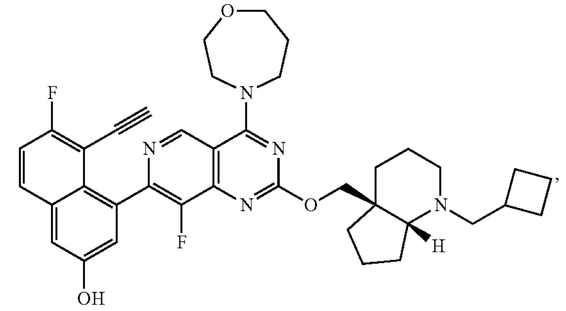
,
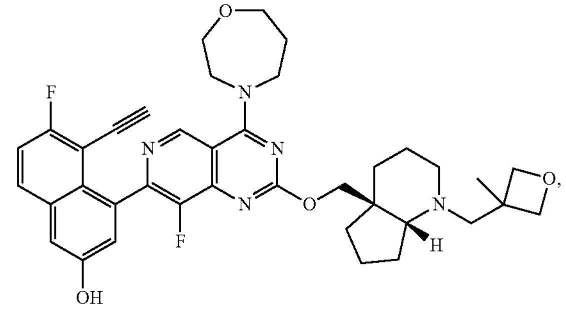
,
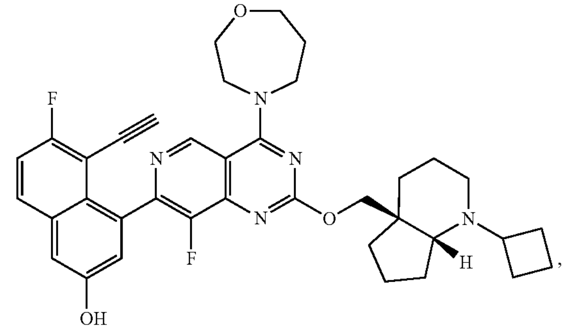
, -continued
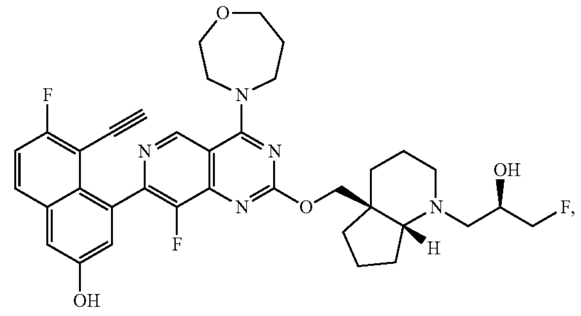
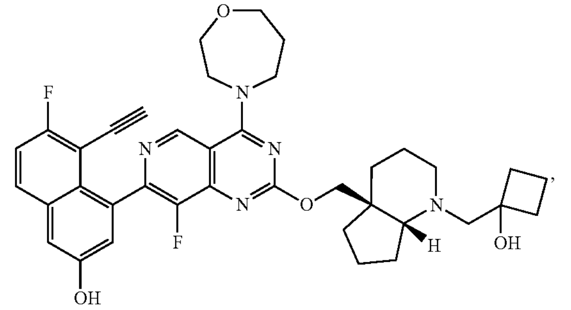
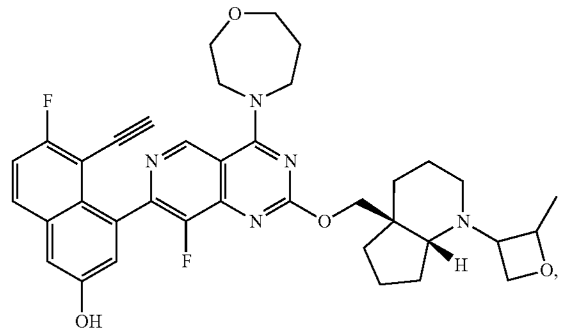
two diastereomers
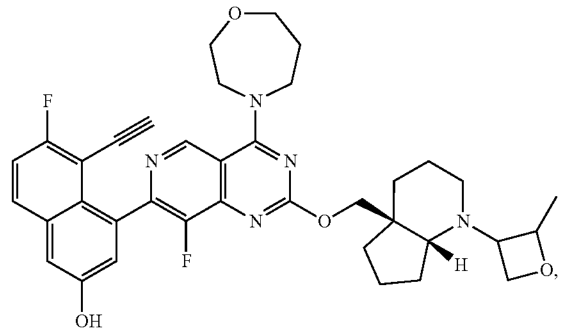
single diastereomers
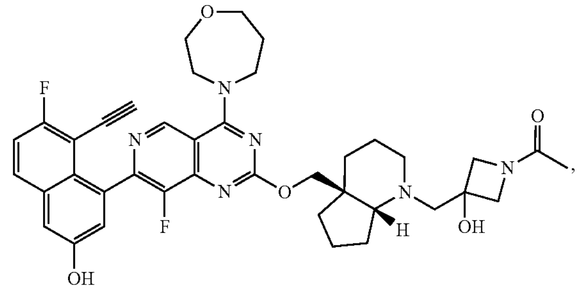
-continued
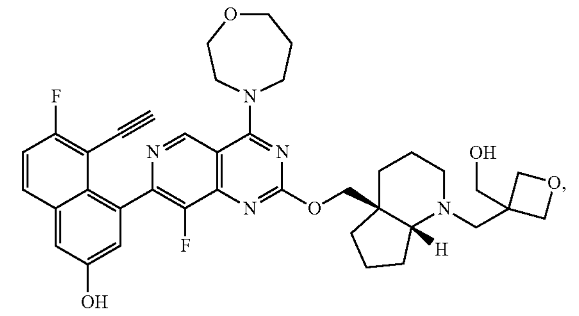
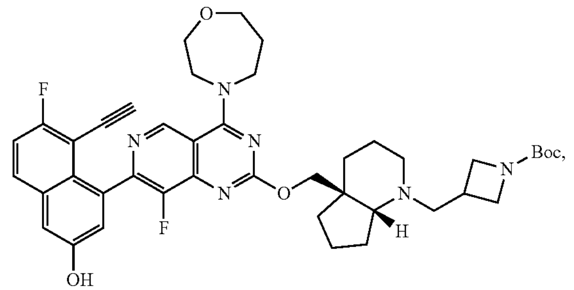
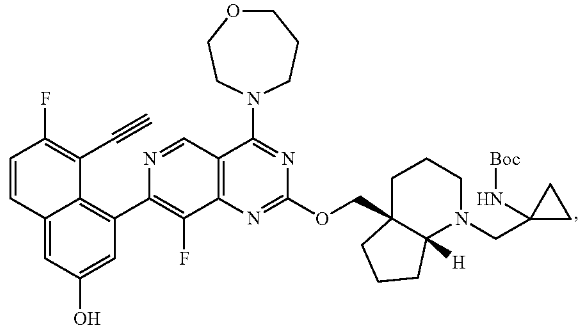
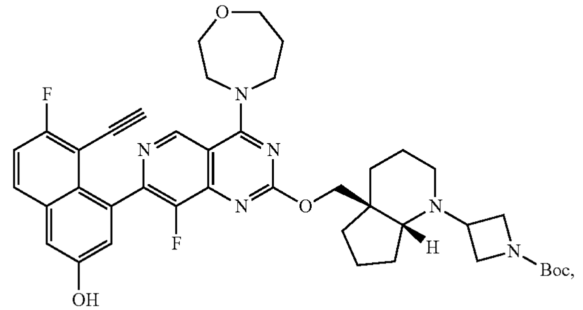
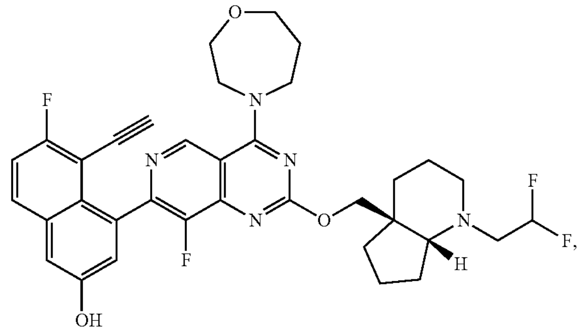

-continued
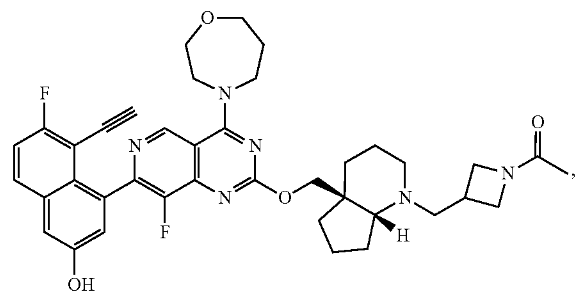
,
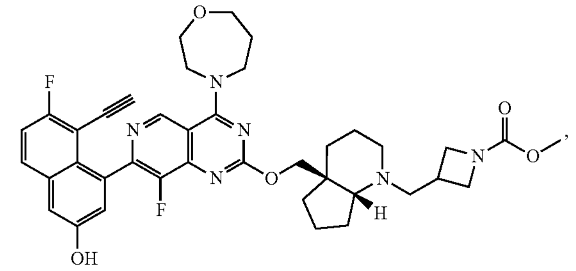
,
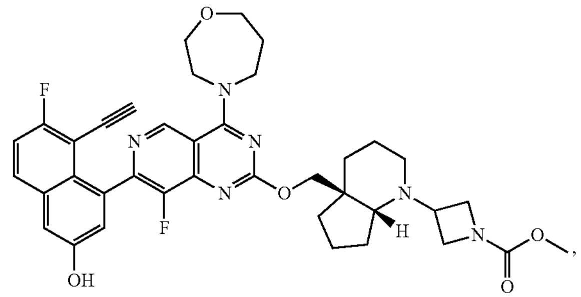
,
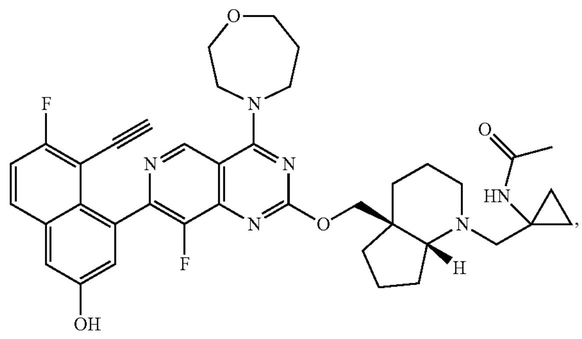
,
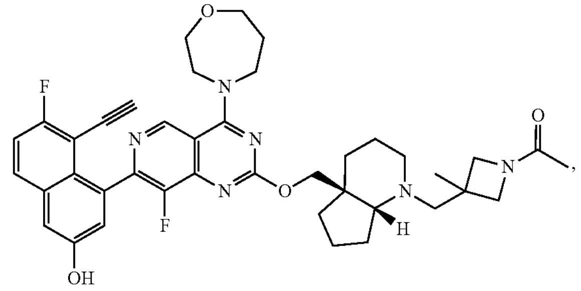
,
-continued
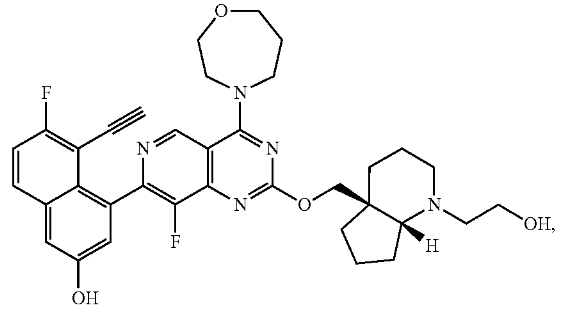
,
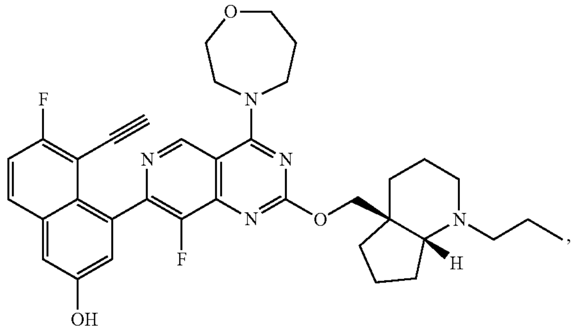
,
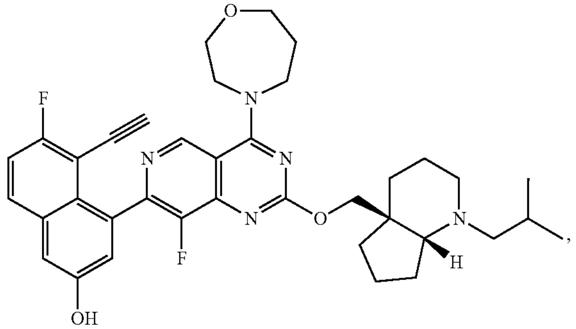
,
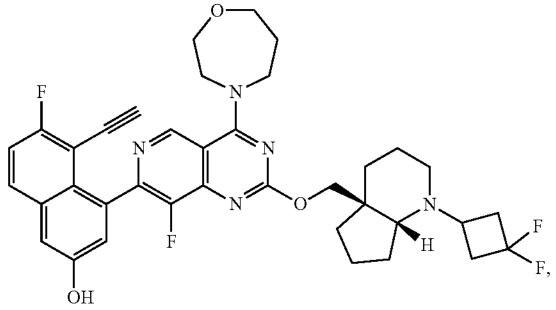
,
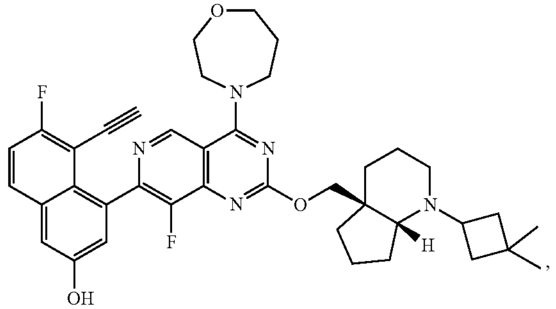
, -continued
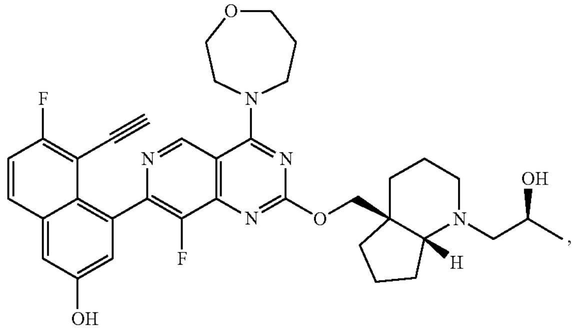
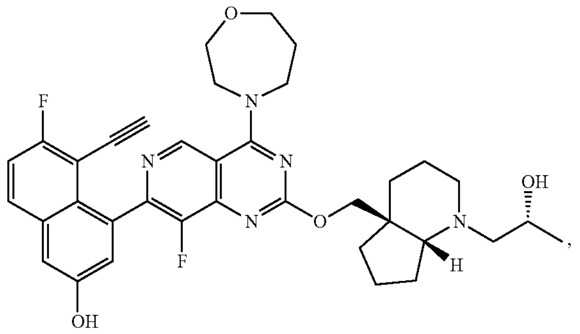
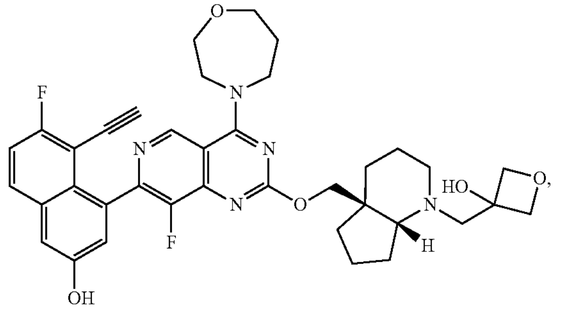
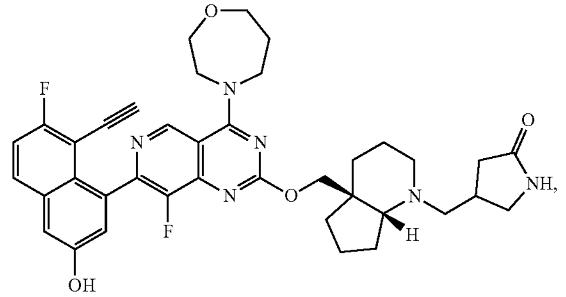
diastereomeric mixture
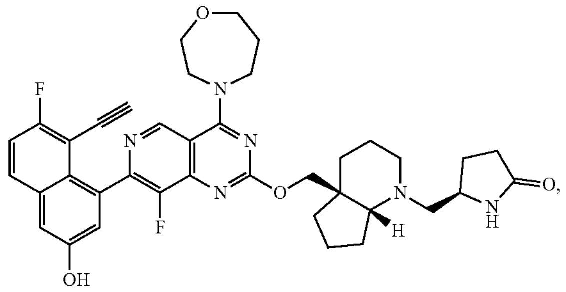
-continued
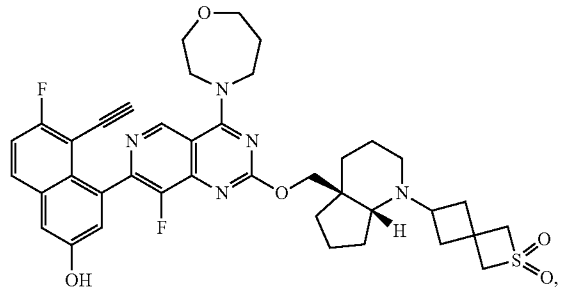
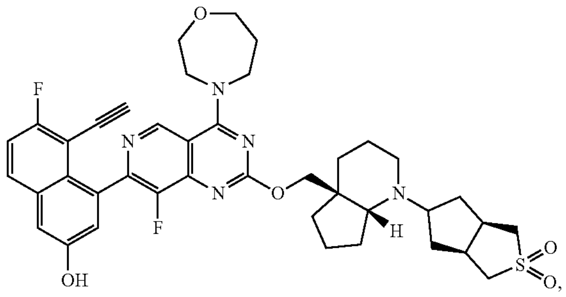
diastereomeric mixture
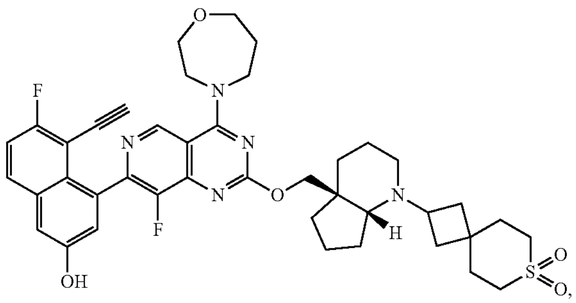
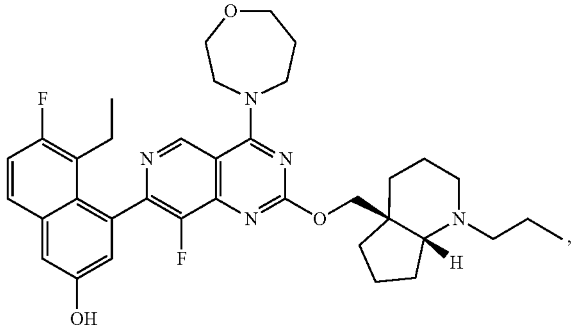
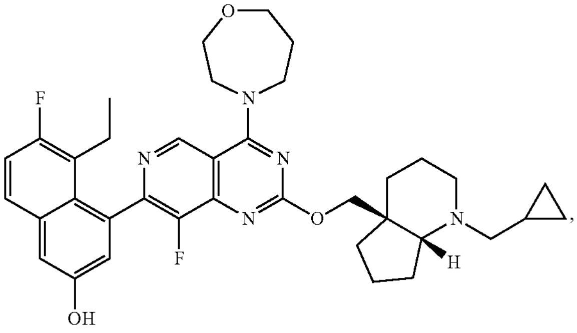

-continued
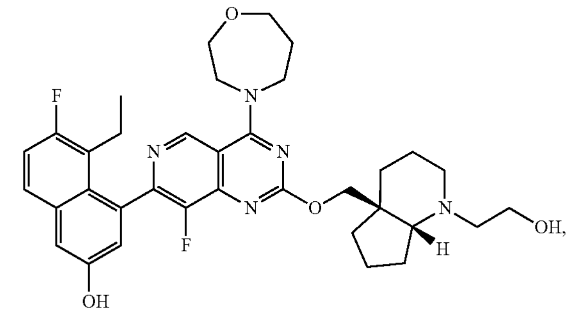
,
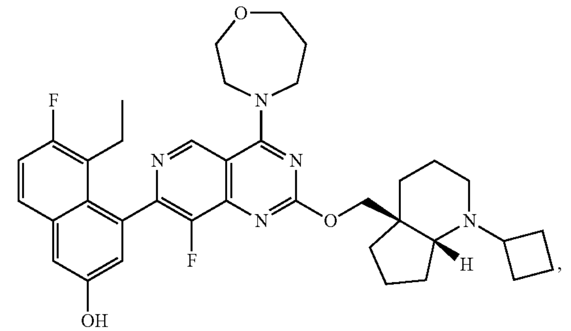
,
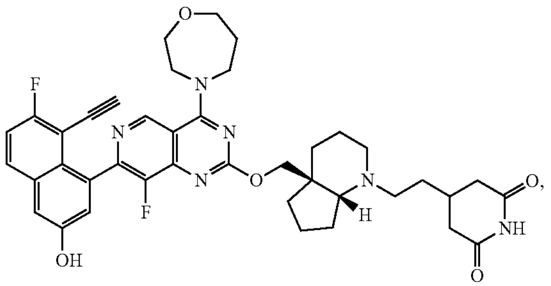
,
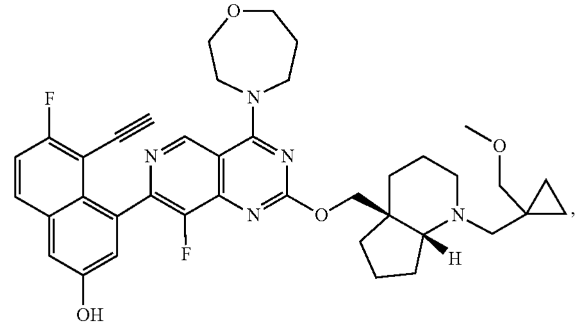
,
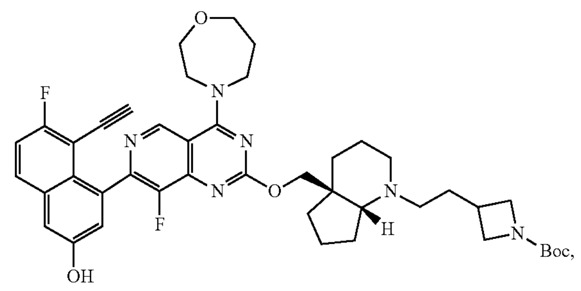
,
-continued
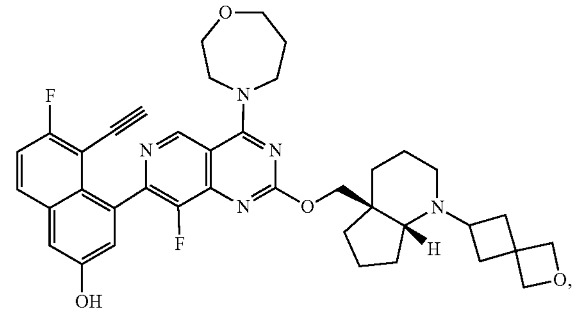
,
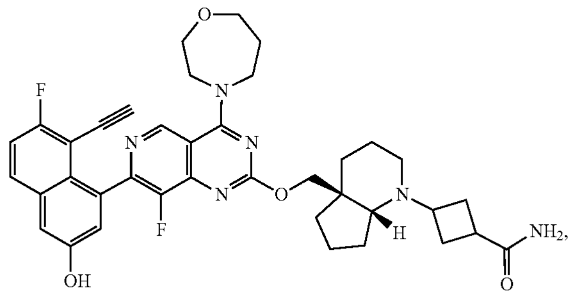
,
diasteromeric mixture
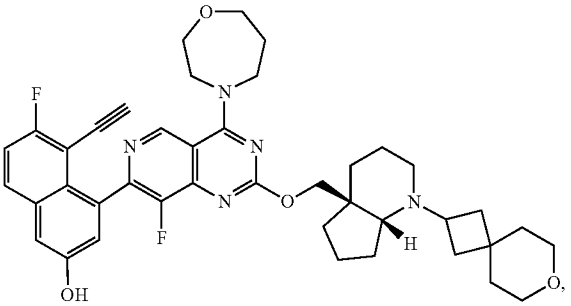
,
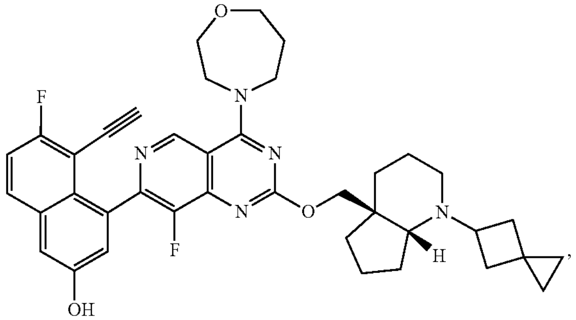
,
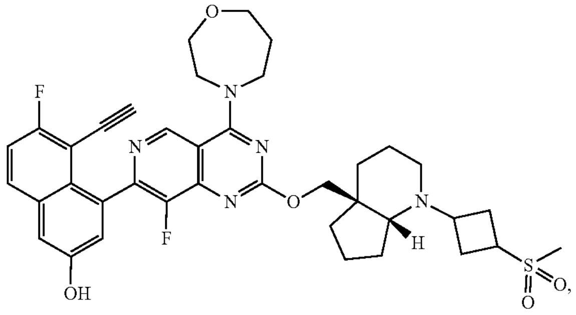
,
diasteromeric mixture -continued
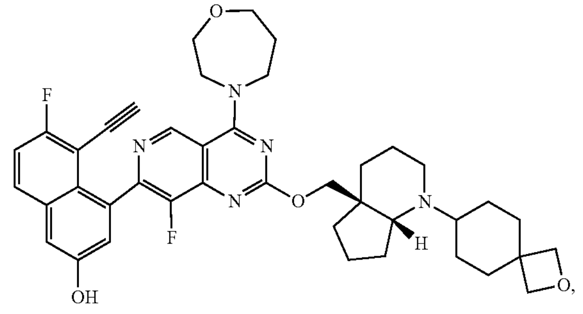
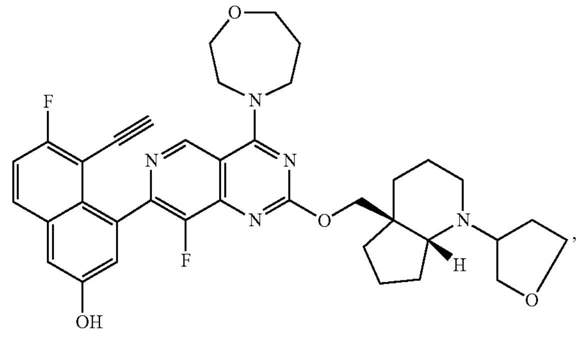
diastereomeric mixture
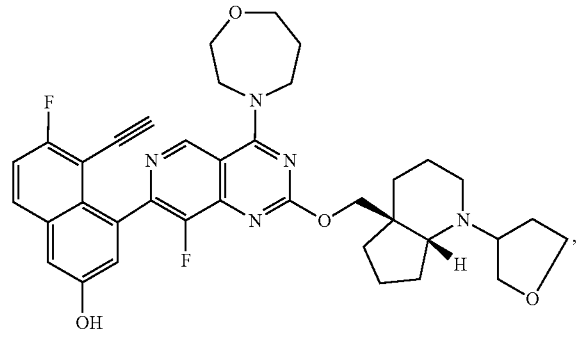
diastereomer 1
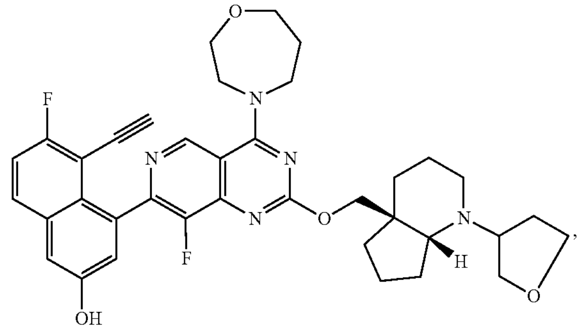
diastereomer 2
-continued
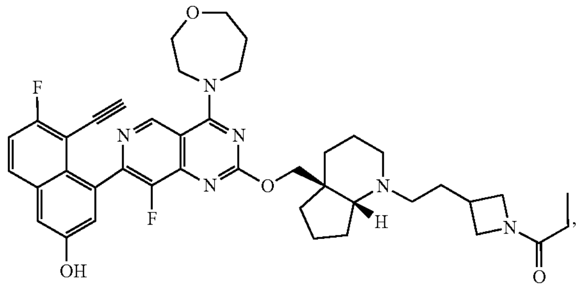
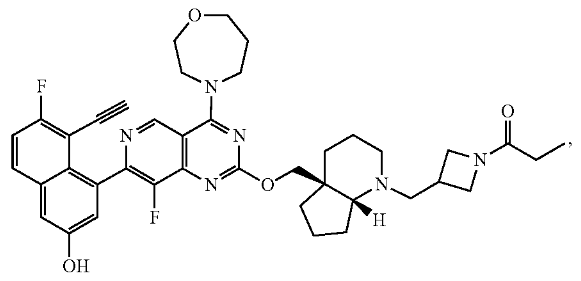
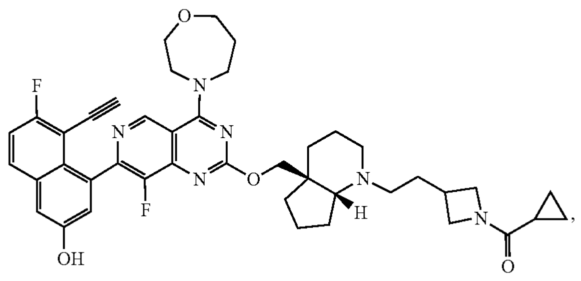

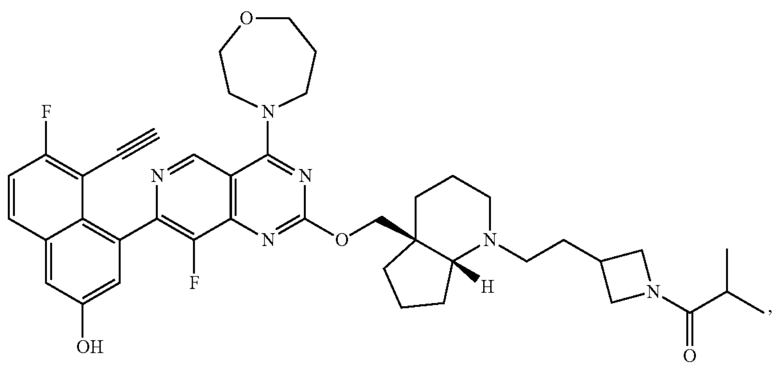
,
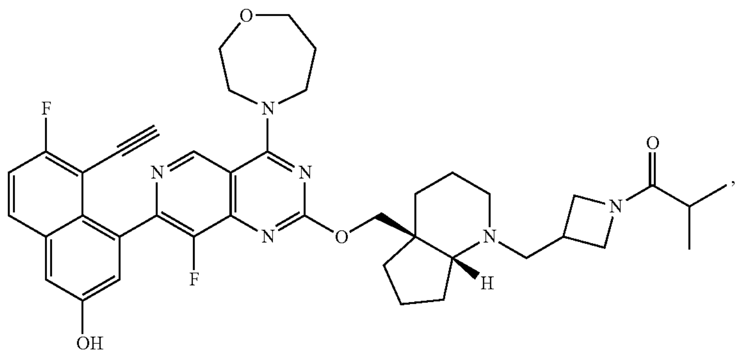
,
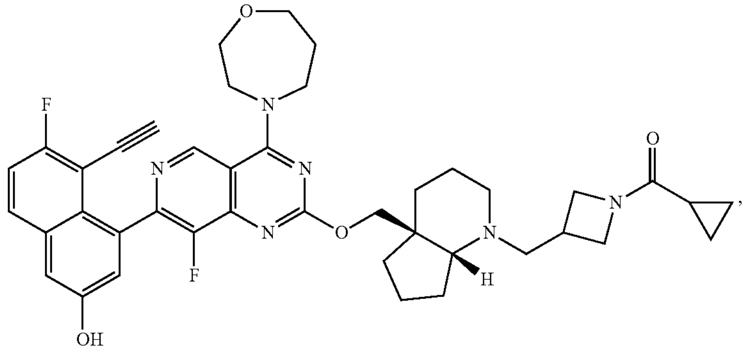
,
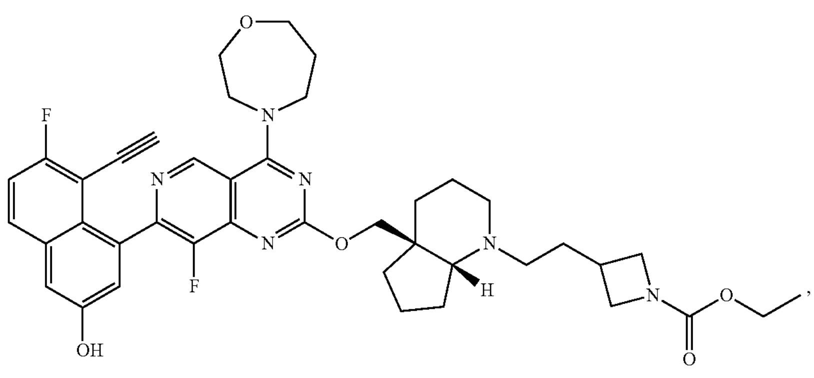
,

-continued
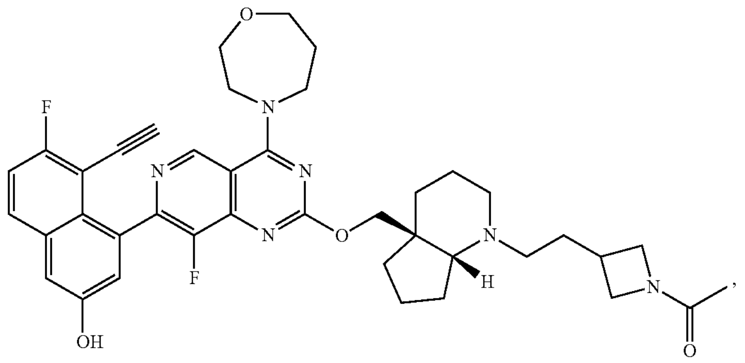
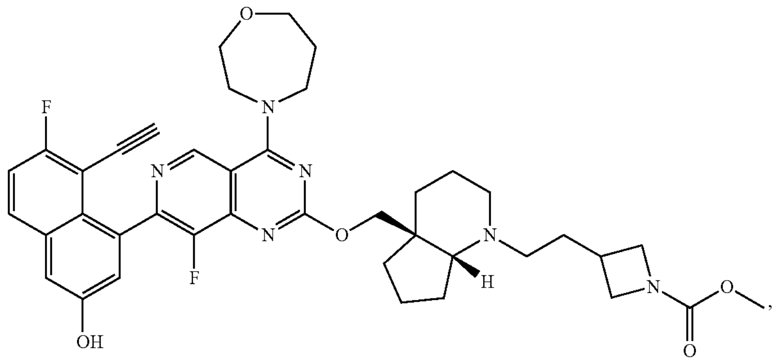
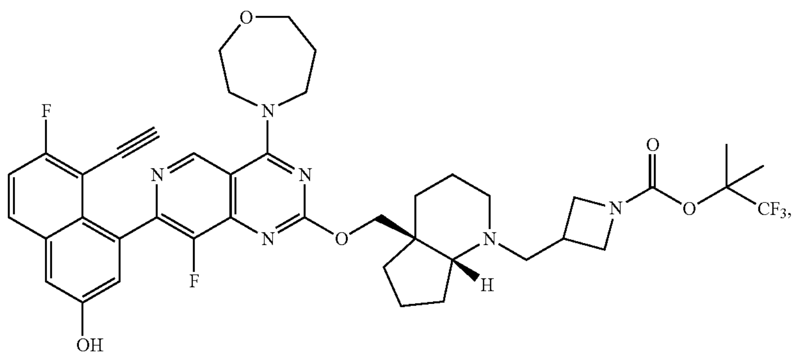
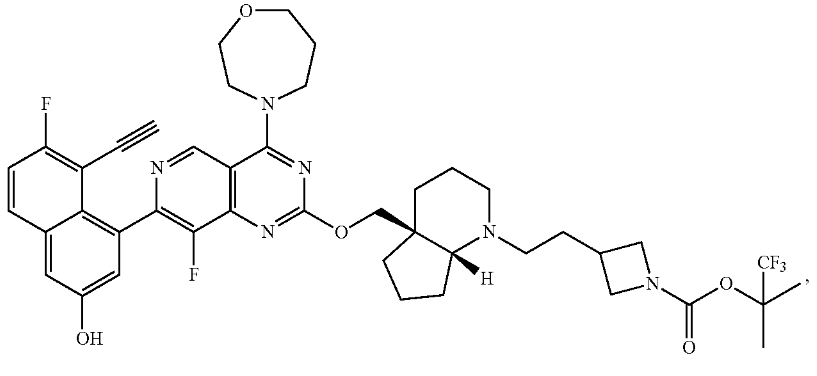

-continued
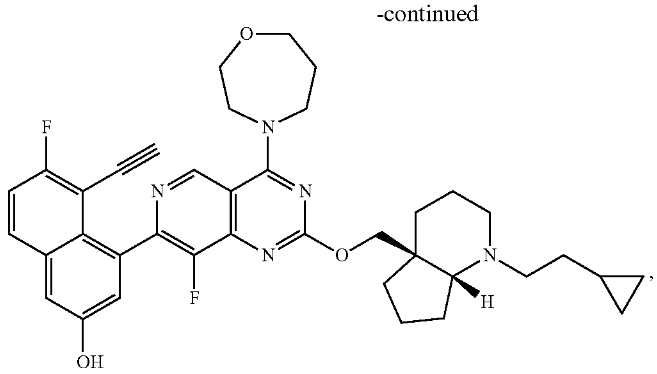
,
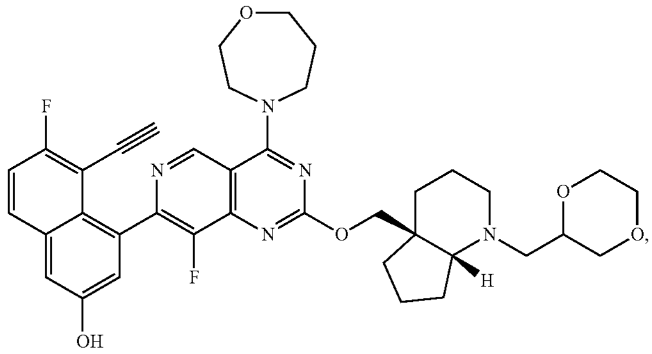
,
diasteromeric mixture
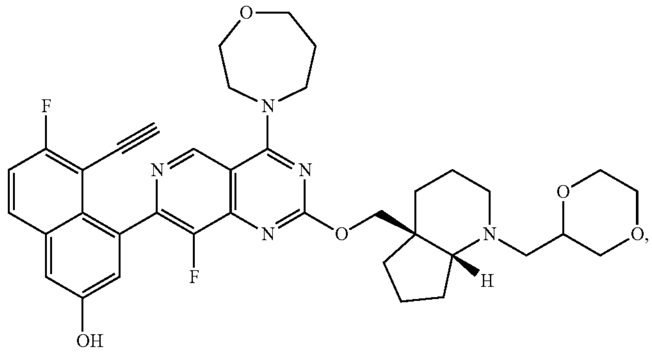
,
diasteromeric 1
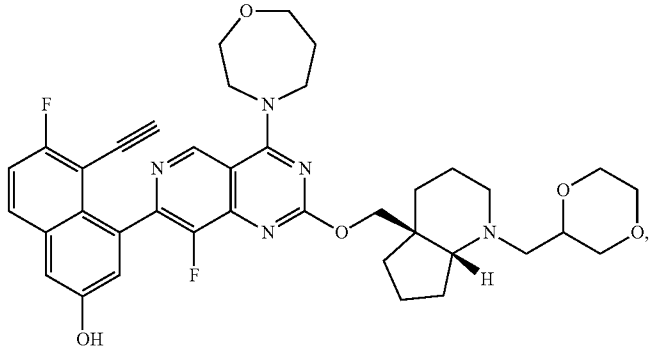
,
diasteromeric 2

-continued
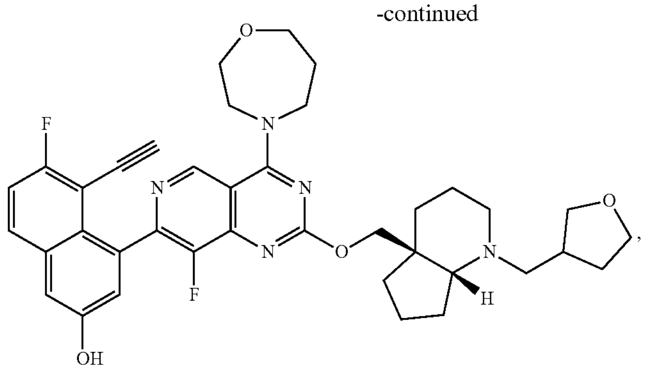
diasteromeric mixture
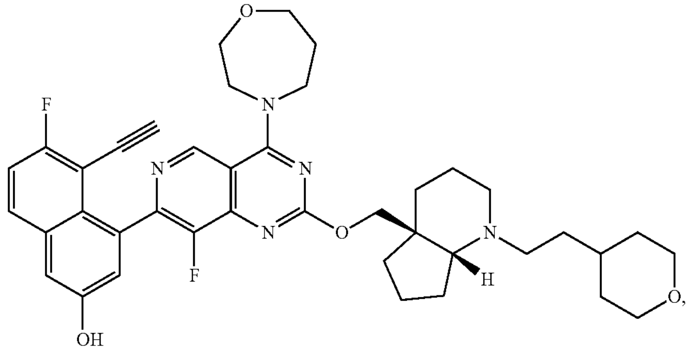
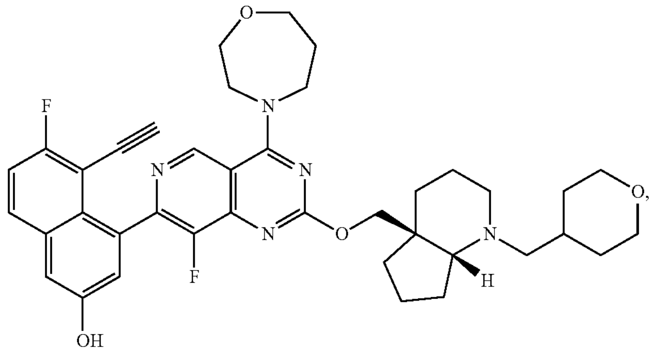
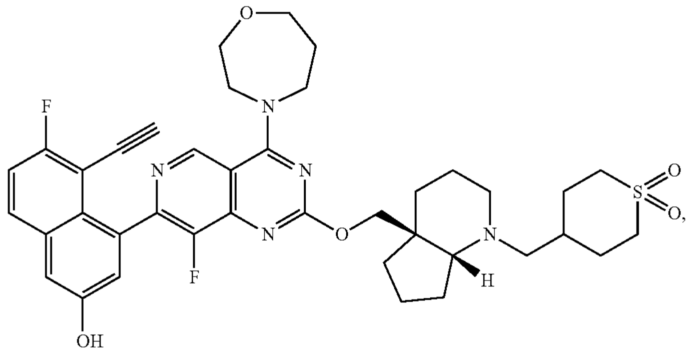

-continued
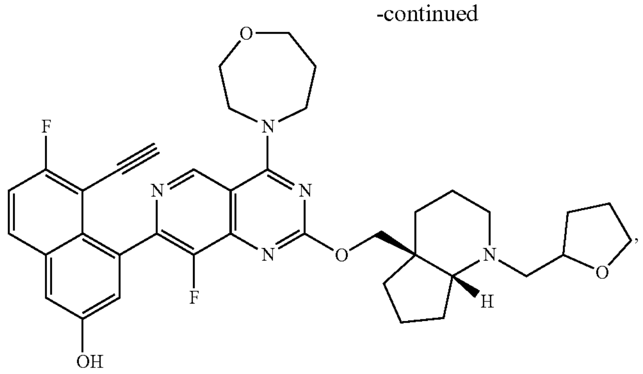
Diasteromeric 1
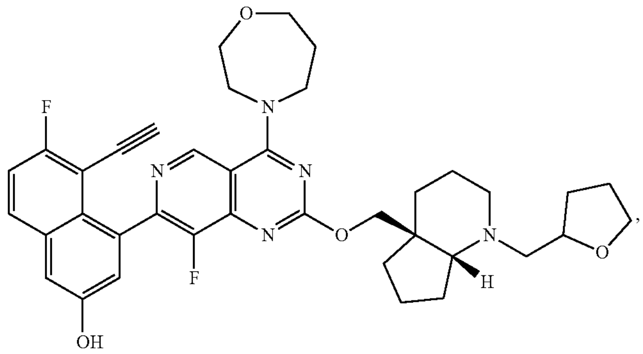
Diasteromeric 2
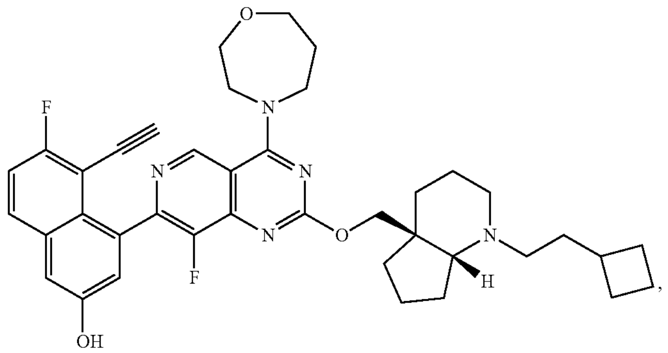
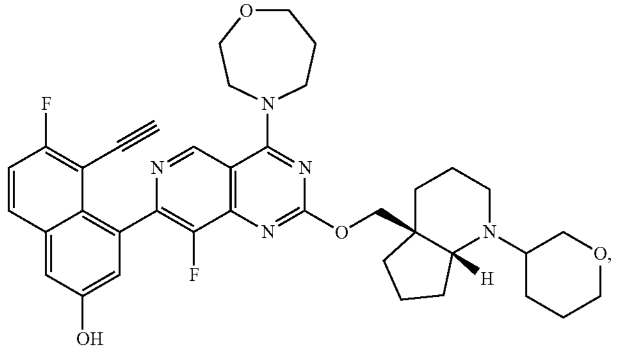
diasteromeric 1

-continued
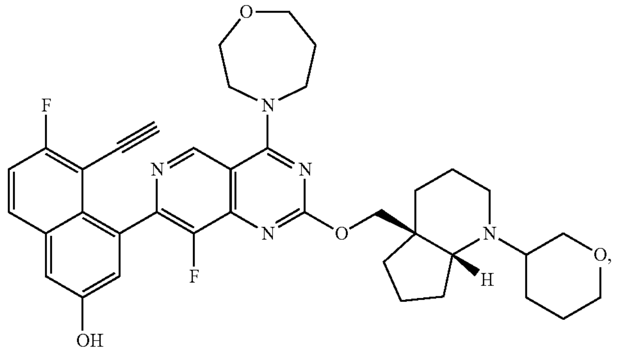
diasteromeric 2
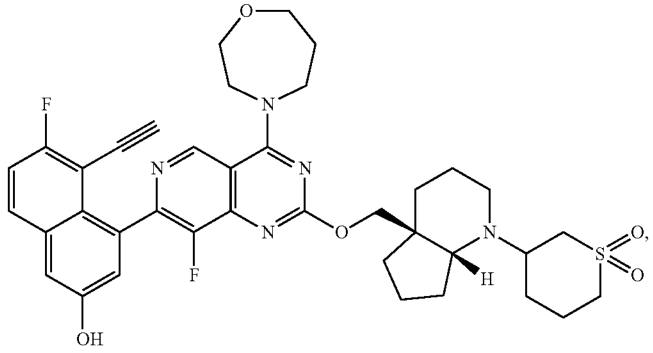
diasteromeric mixture
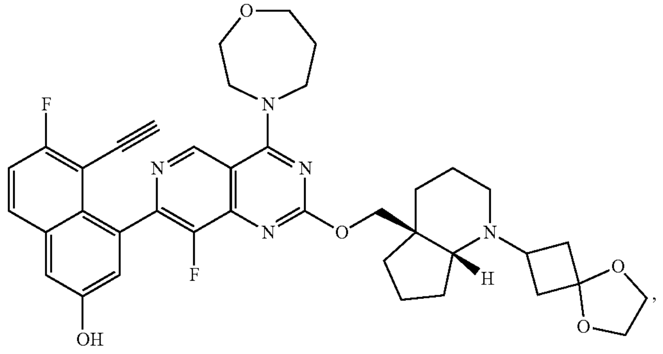
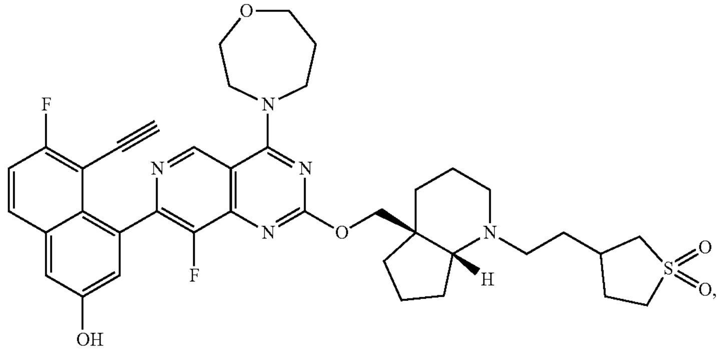
diasteromeric mixture -continued
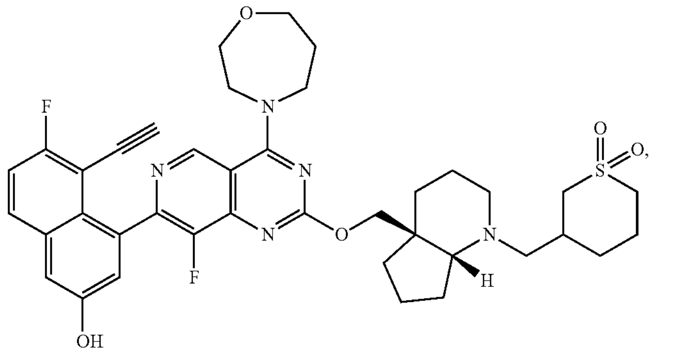
diasteromeric mixture
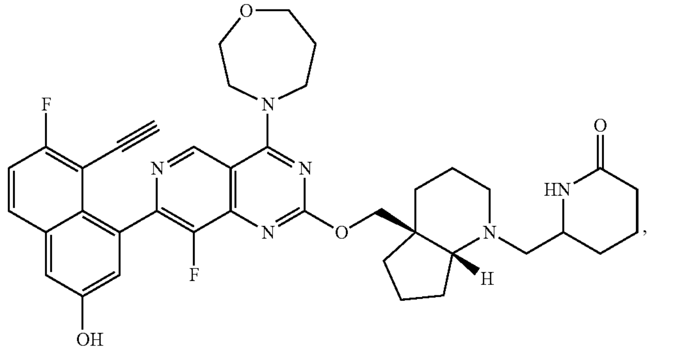
diasteromeric mixture
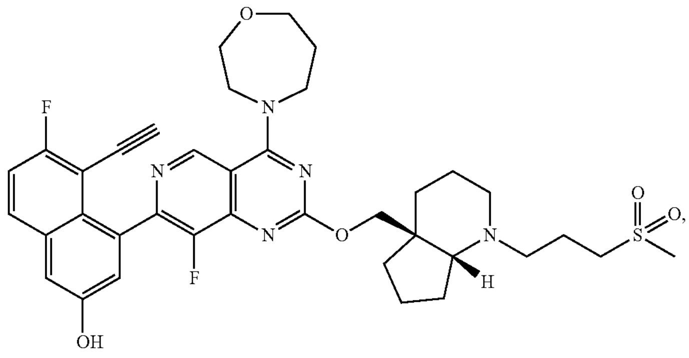
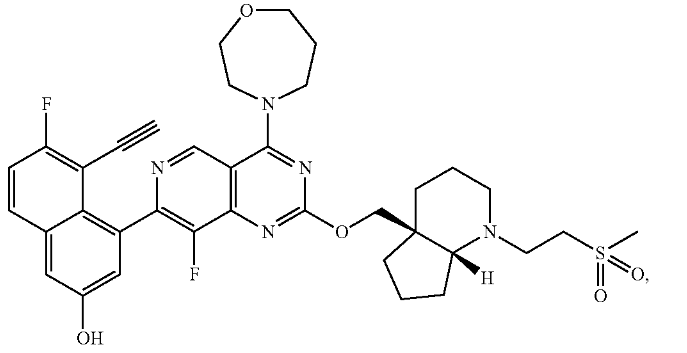

-continued
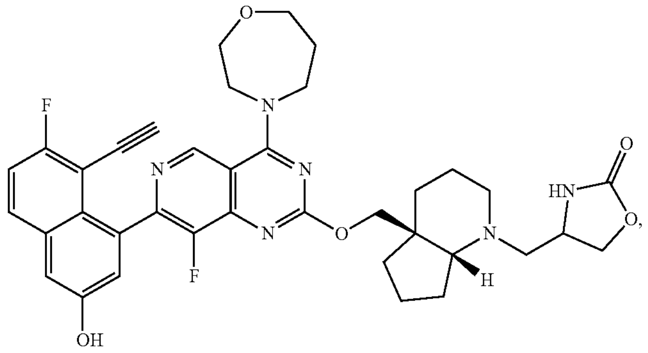
diasteromeric mixture
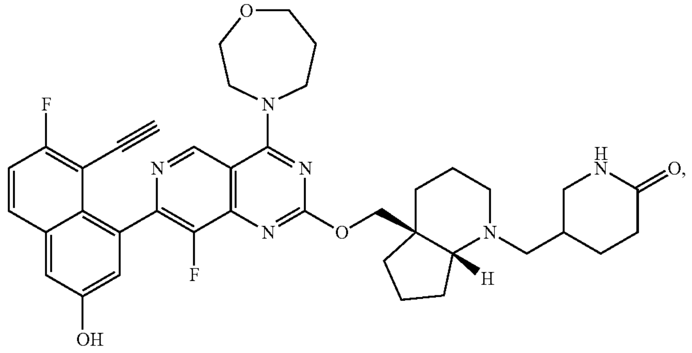
diasteromeric mixture
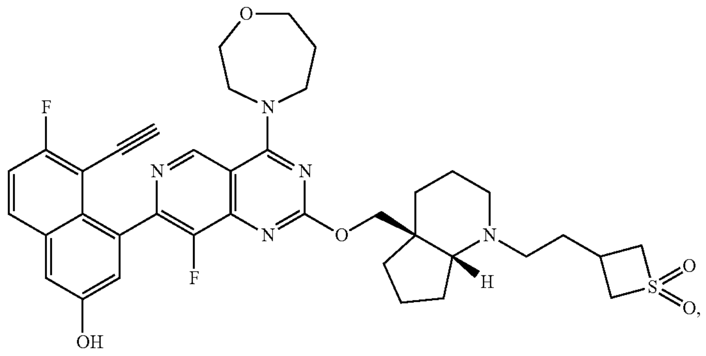
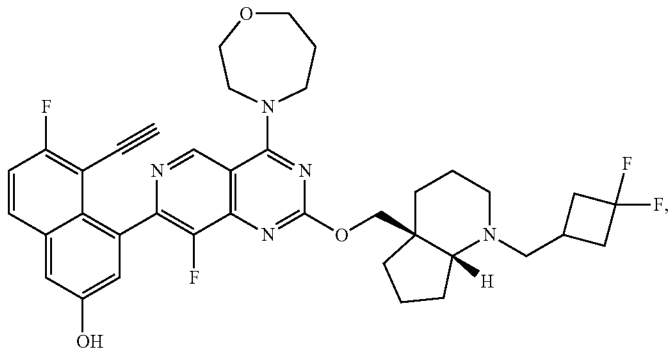

-continued
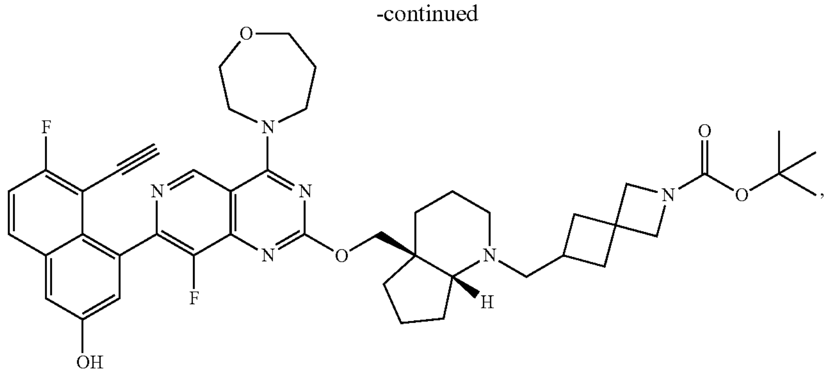
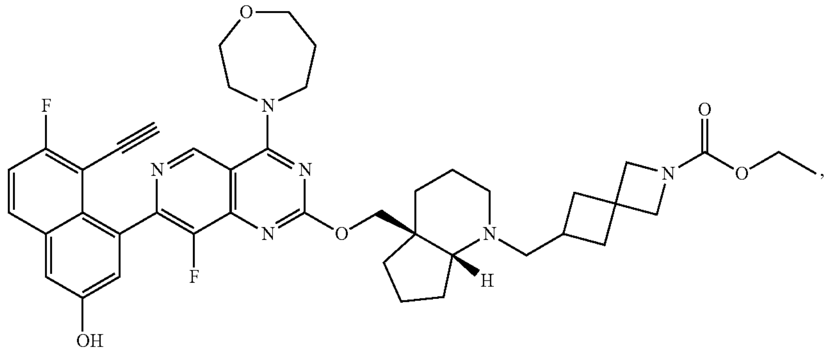
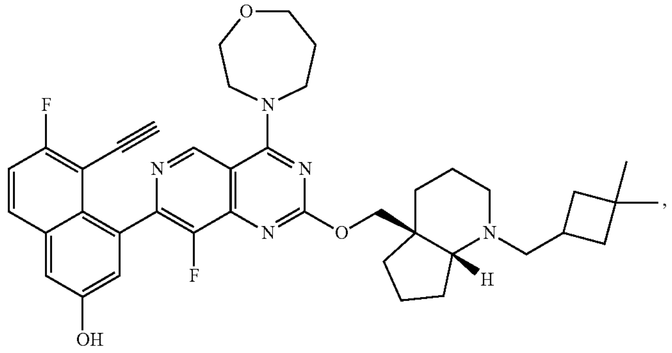
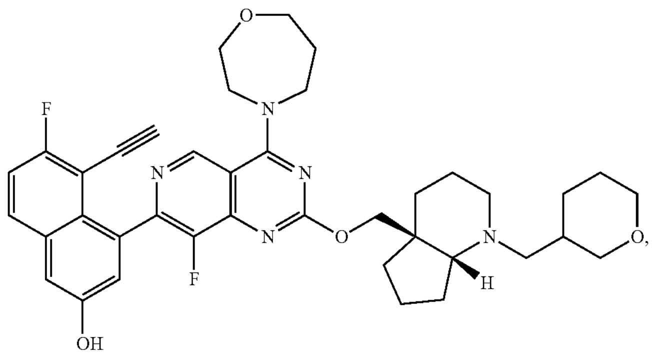
diastereomer 1

-continued
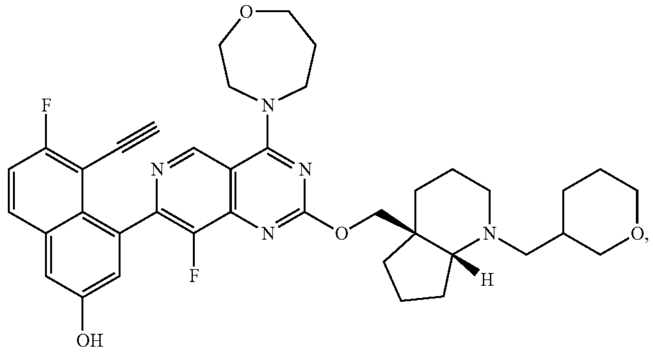
diastereomer 2
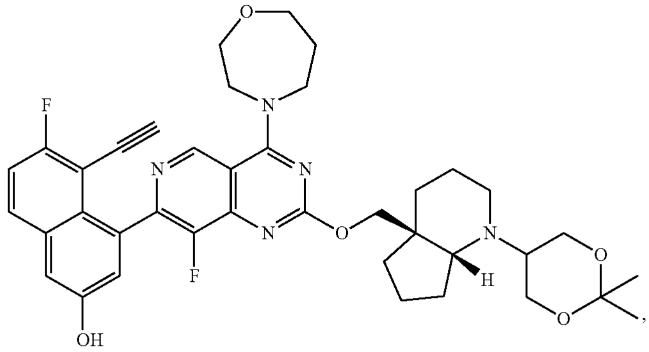
,
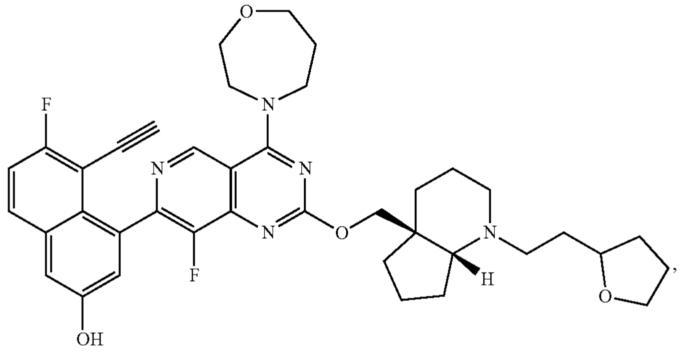
,
diasteromeric mixture
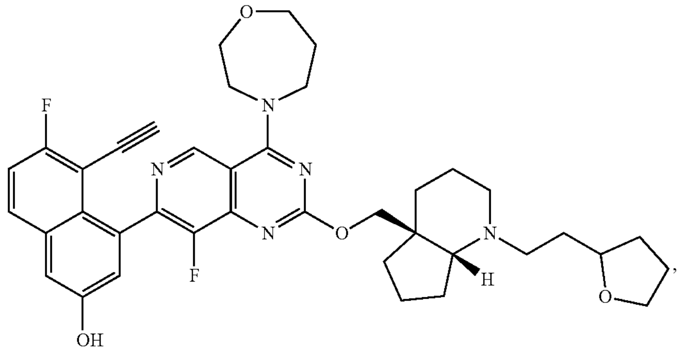
,
diasteromeric 2

-continued
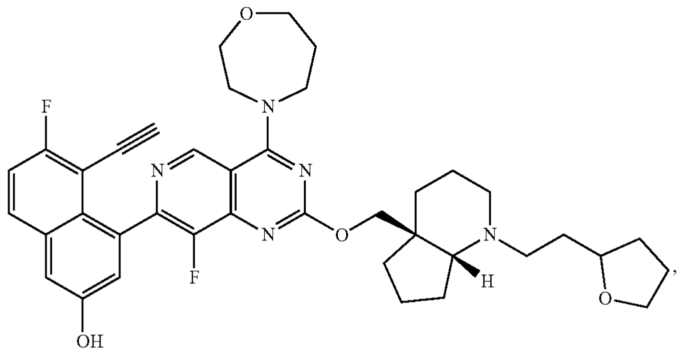
diasteromeric 1
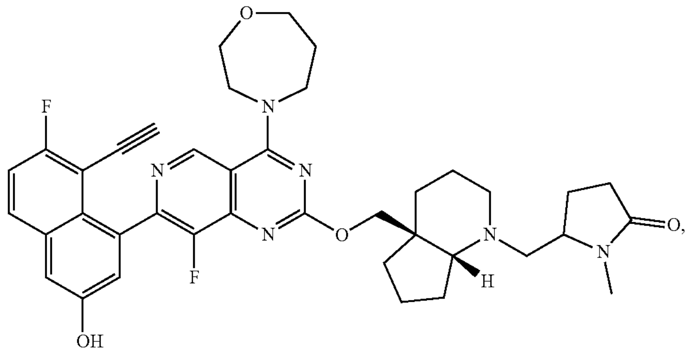
diasteromeric mixture
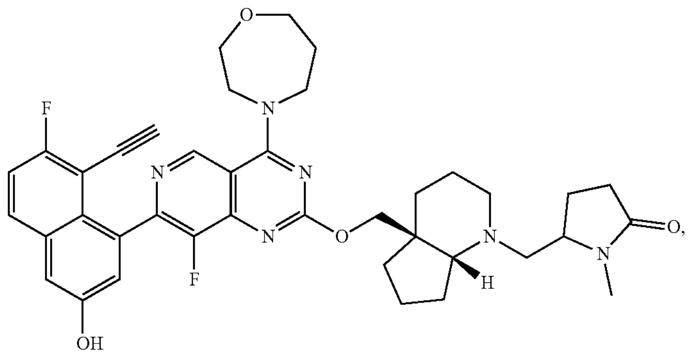
diasteromeric 1
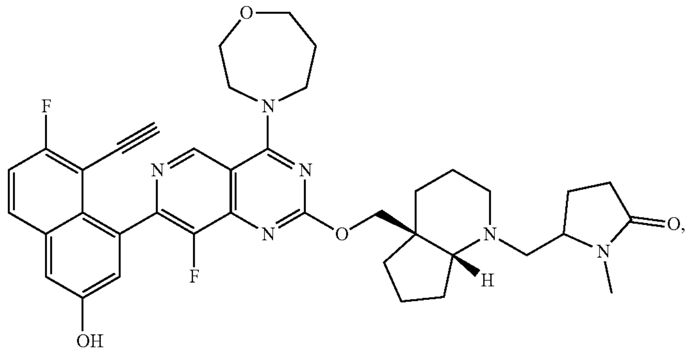
diasteromeric 2

-continued
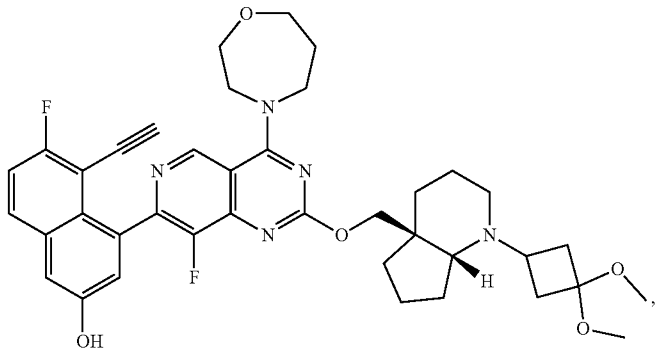
,
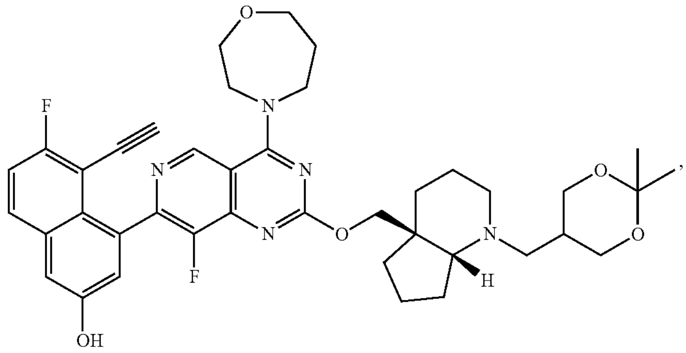
,
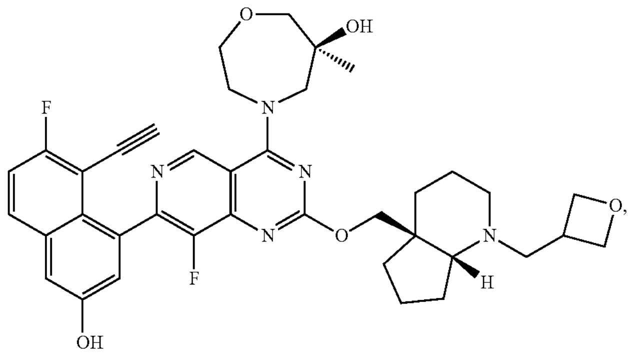
,
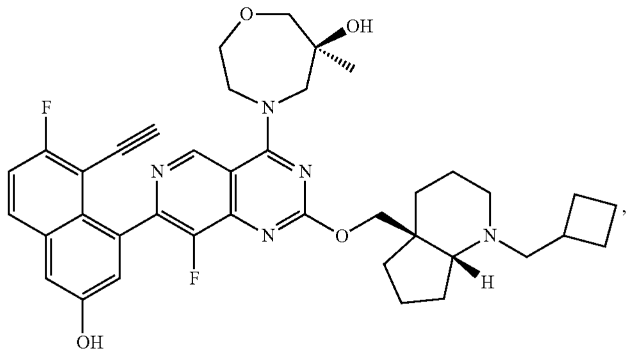
,

-continued
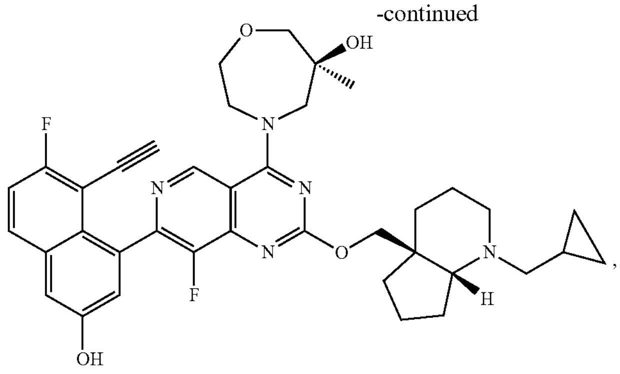
,
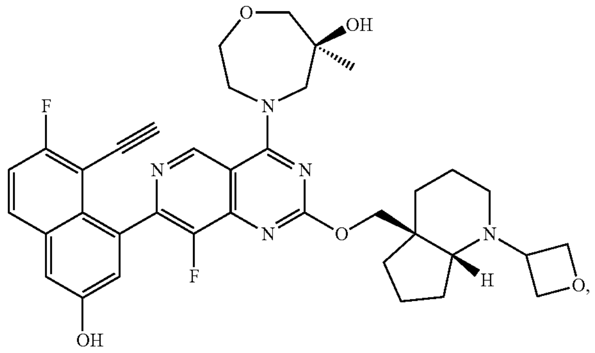
,
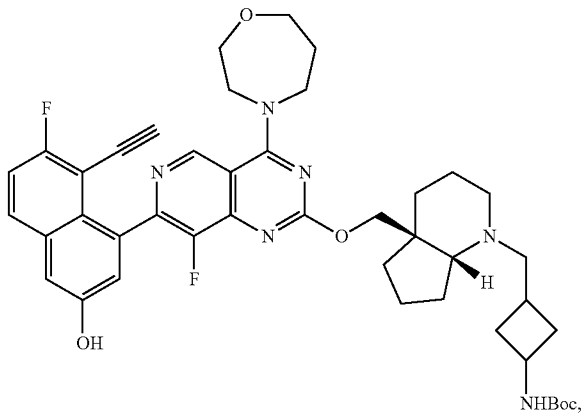
,
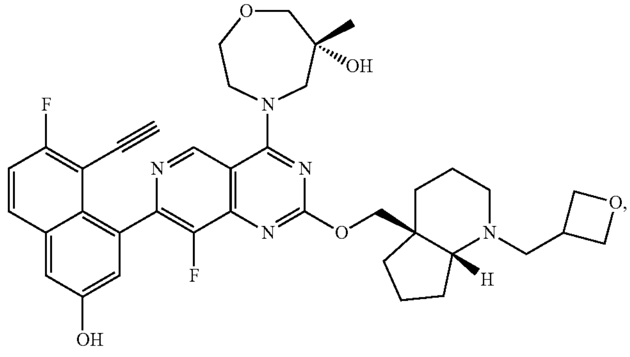
,

-continued
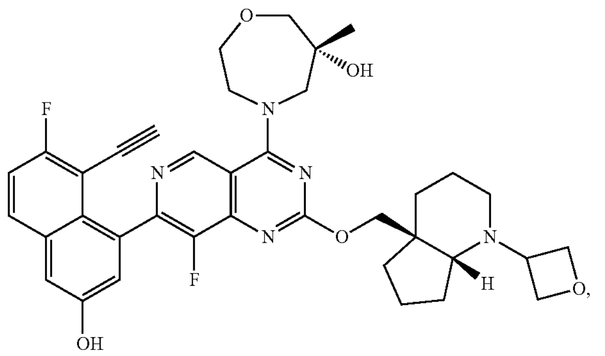
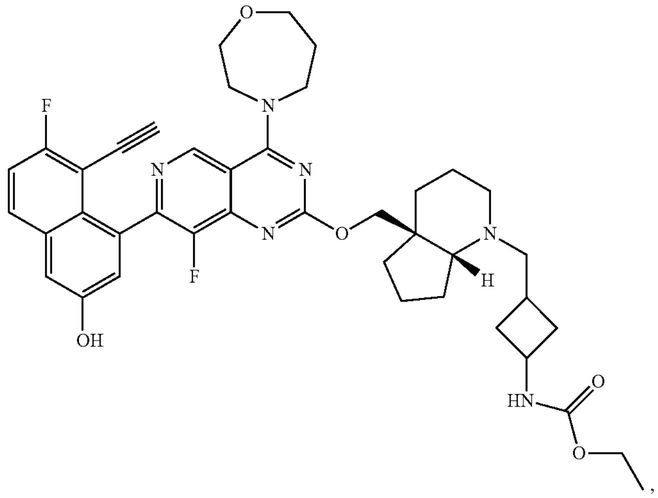
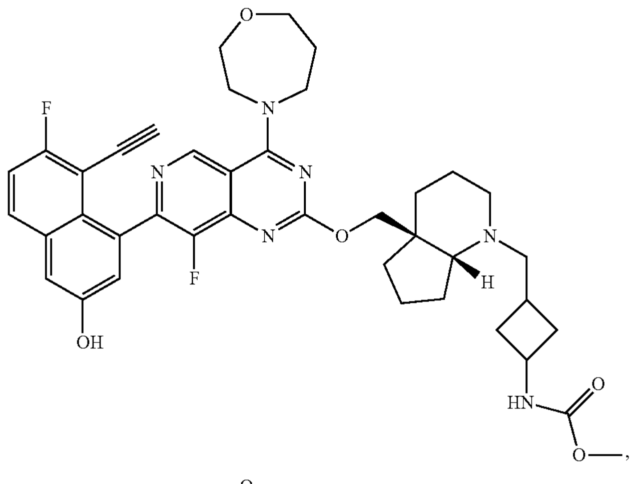
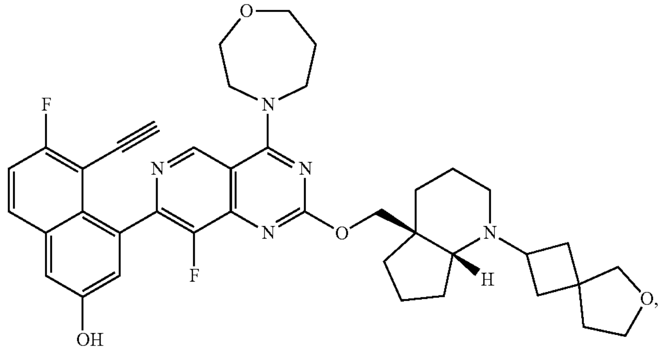
diastereomeric mixture -continued
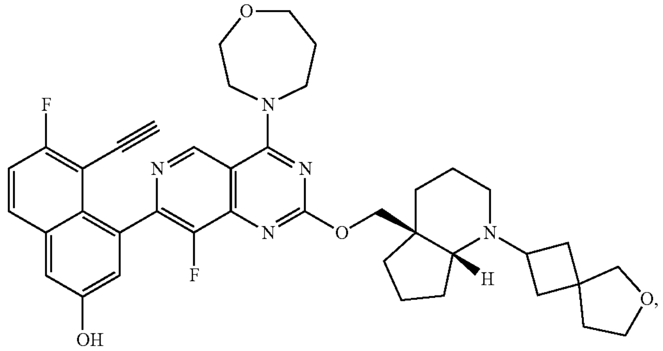
diastereomer 1
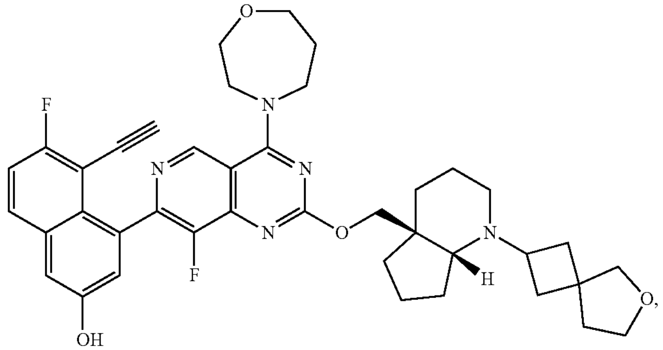
diastereomer 2
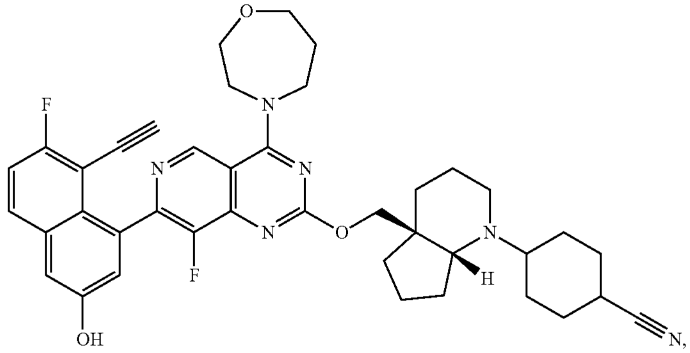
diastereomer 1
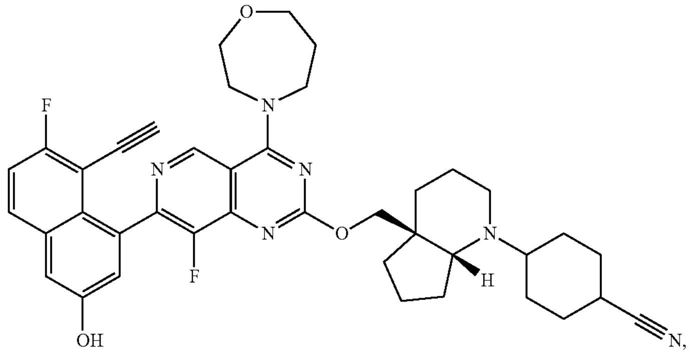
diastereomer 2

-continued
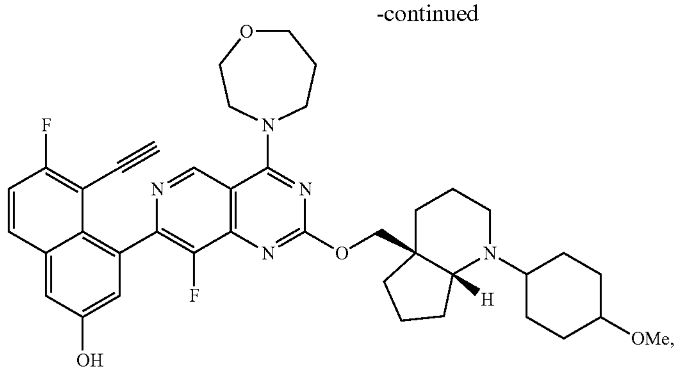
diastereomer 1
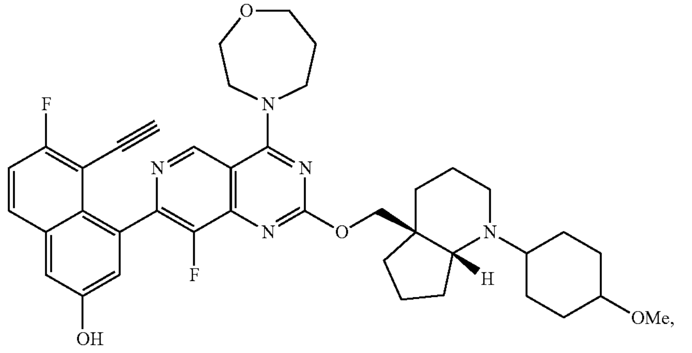
diastereomer 2
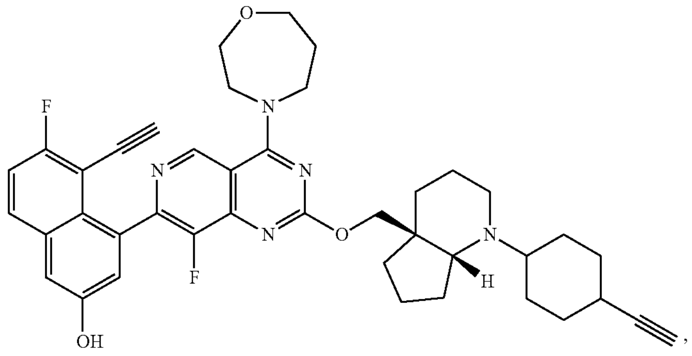
diastereomeric mixture
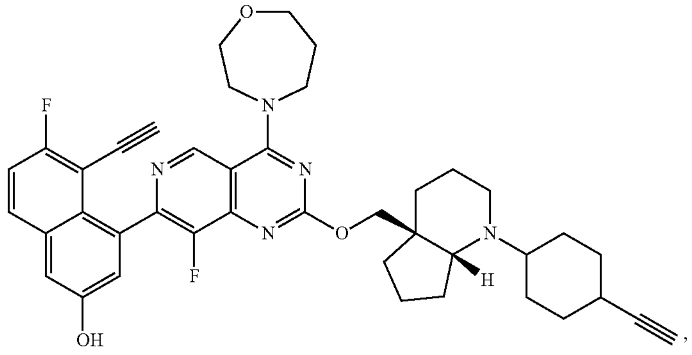
diastereomer 2

-continued
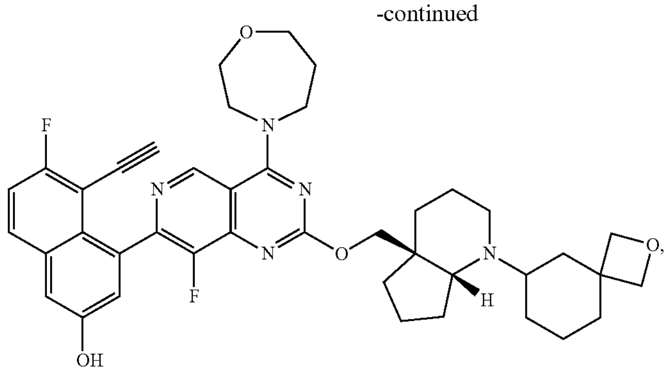
diastereomer 2
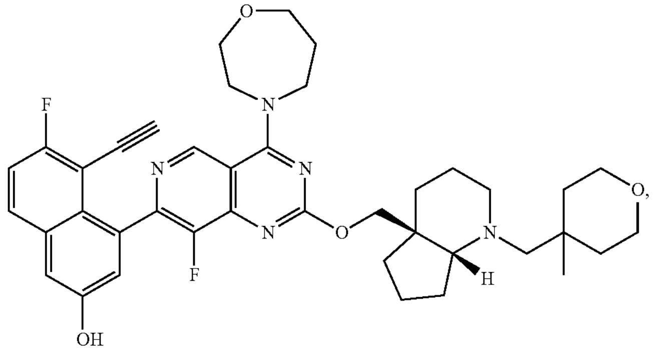
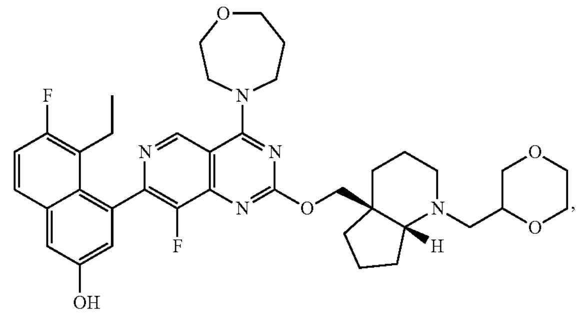
diastereomer 1
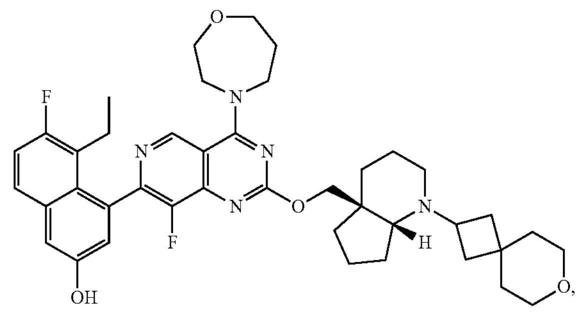
-continued
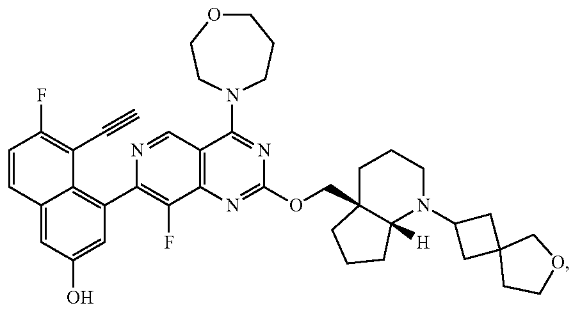
diastereomeric mixture
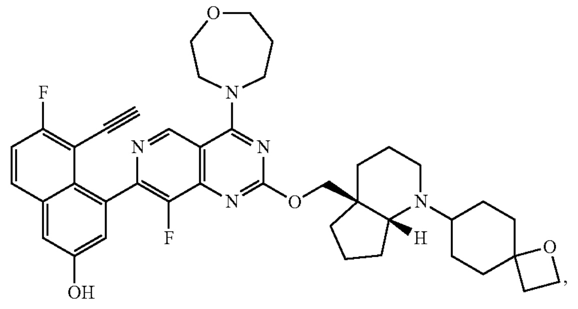
diastereomer mixture -continued
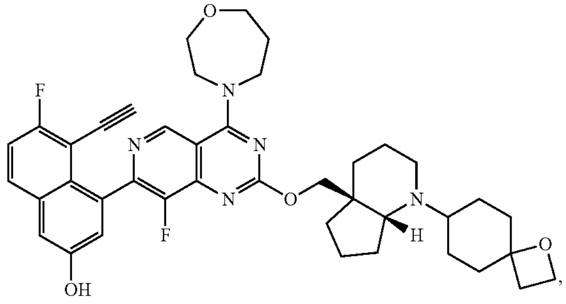
diastereomer 1
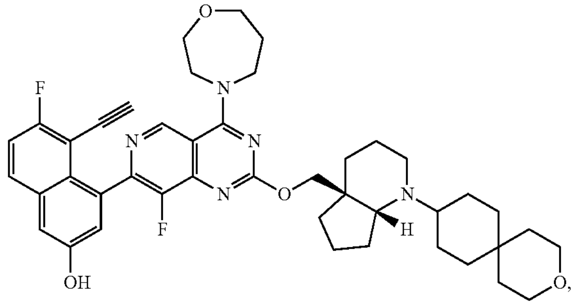
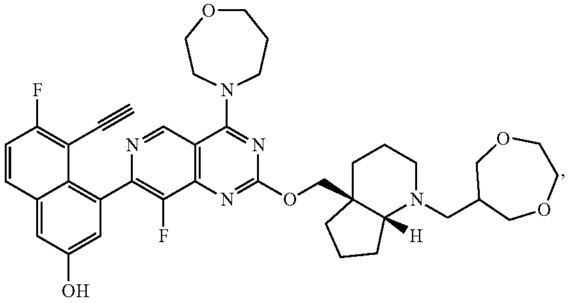
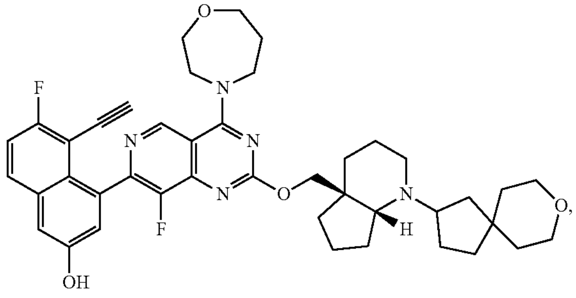
diastereomeric mixture
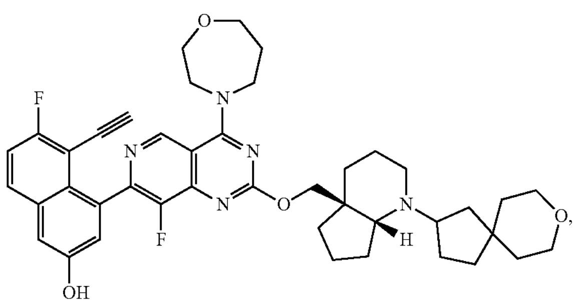
diastereomer 1
-continued
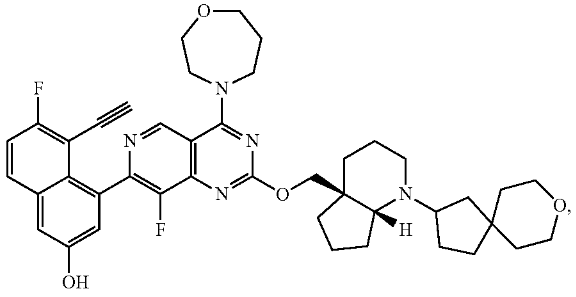
diastereomer 2
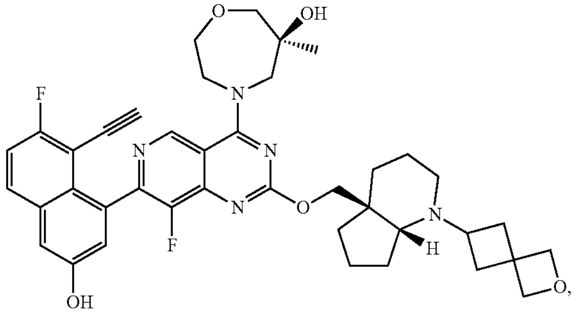
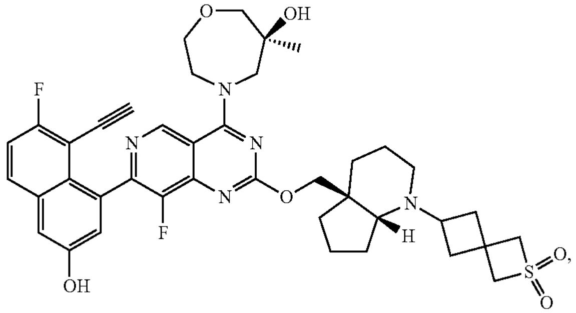
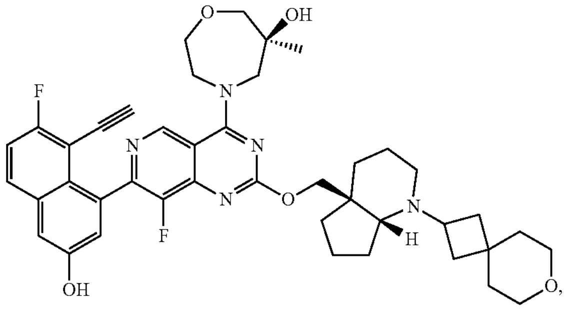
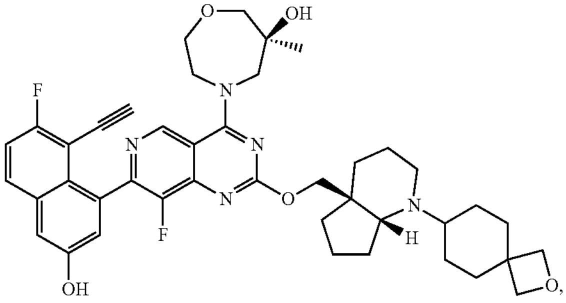

-continued
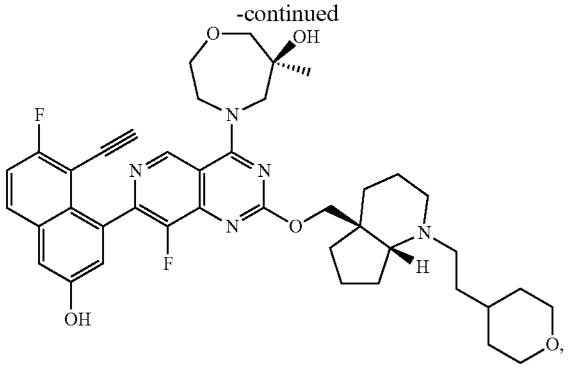
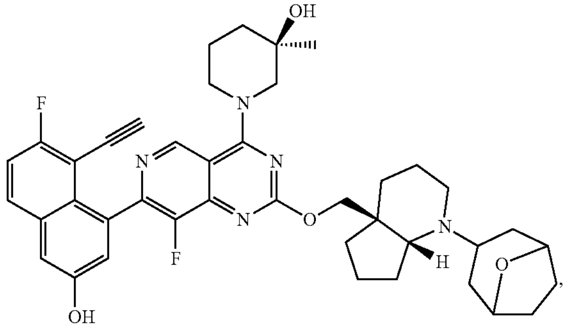
Diastereomer 1
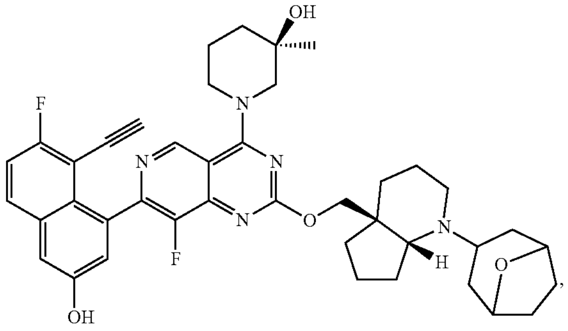
Diastereomer 2
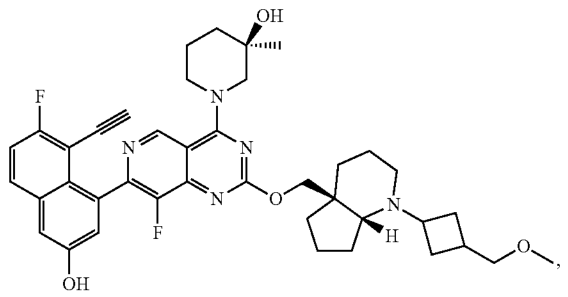
Diastereomer 1
-continued
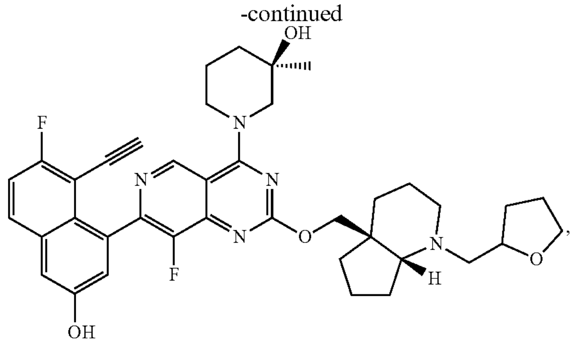
Diastereomer 1
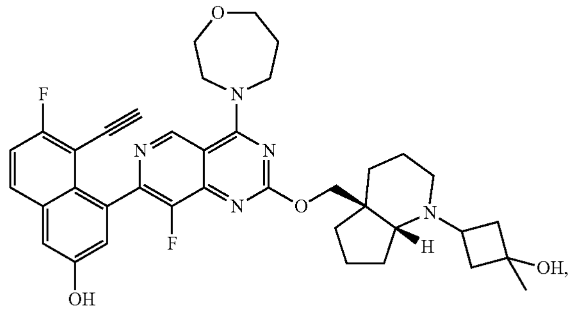
Diastereomer 1
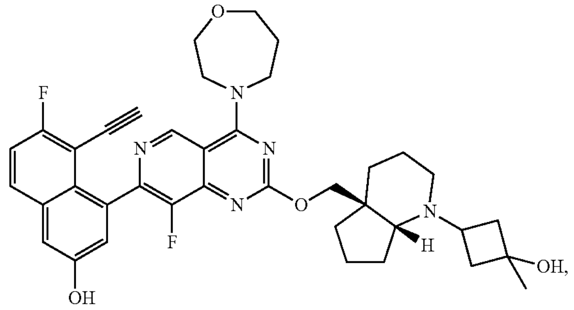
Diastereomer 2
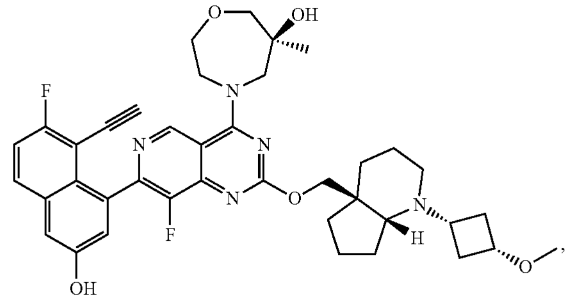
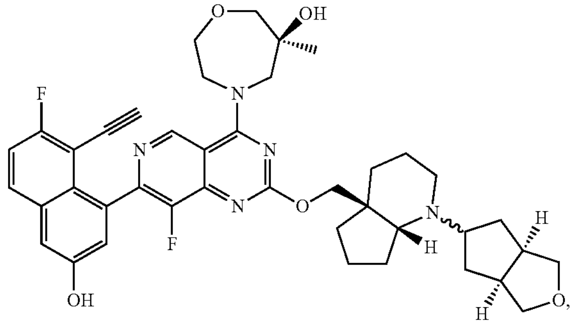
Diastereomer 1

-continued
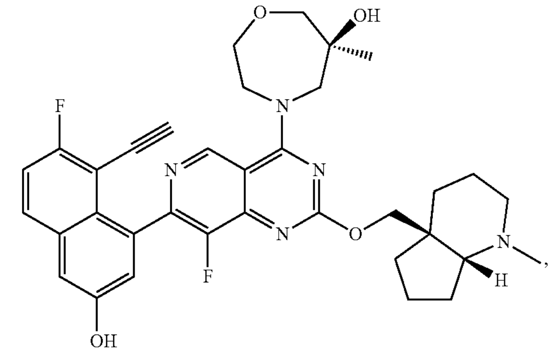
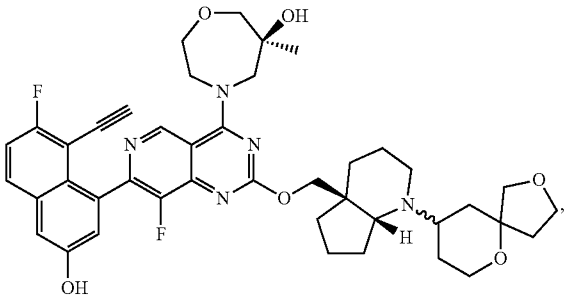
diastereomeric mixture
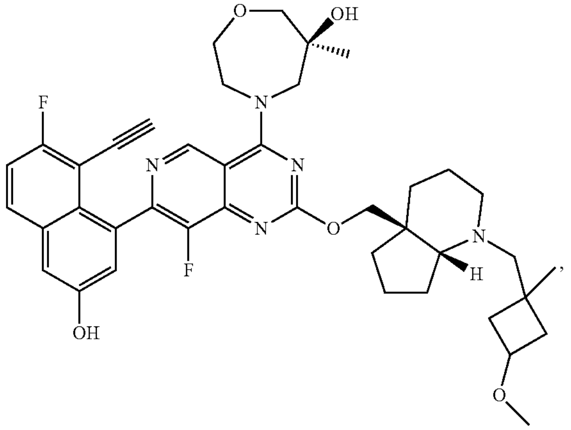
Diastereomer 1
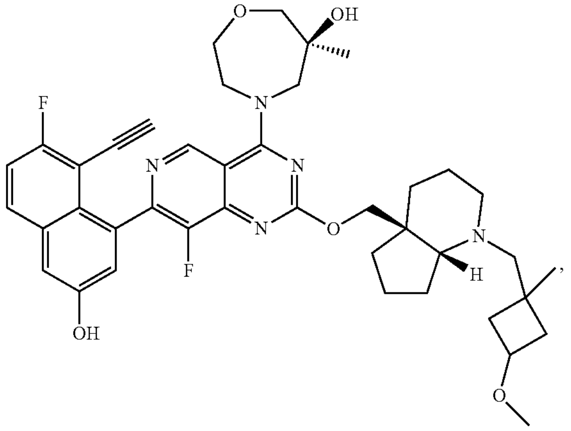
Diastereomer2
-continued
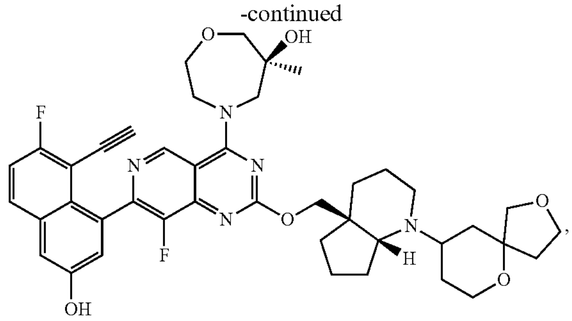
diastereomer 1
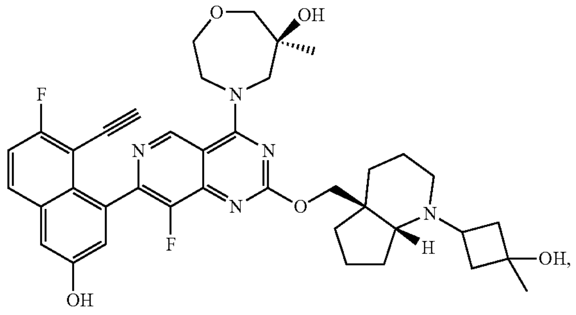
Diastereomer 1
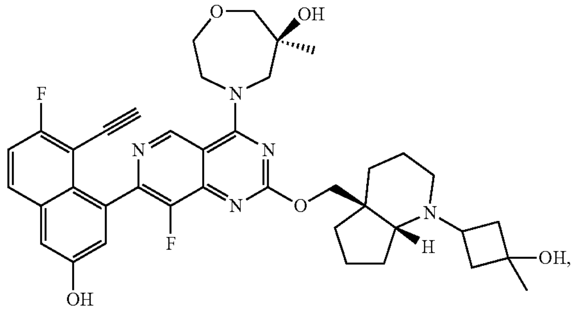
Diastereomer 2
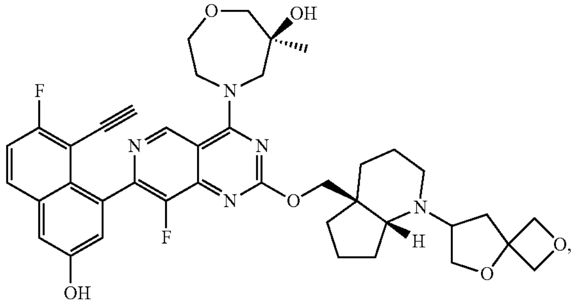
Diastereomer 1
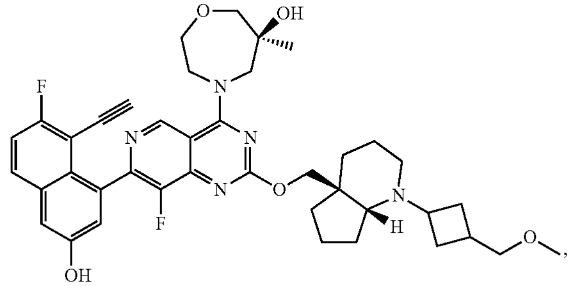
Diastereomer 1

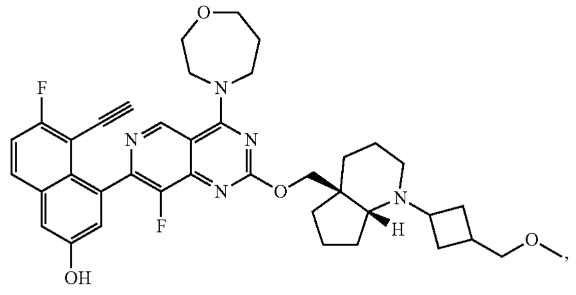
Diastereomer 1
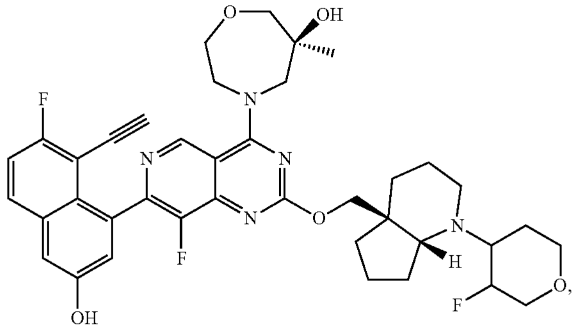
Diastereomer 4
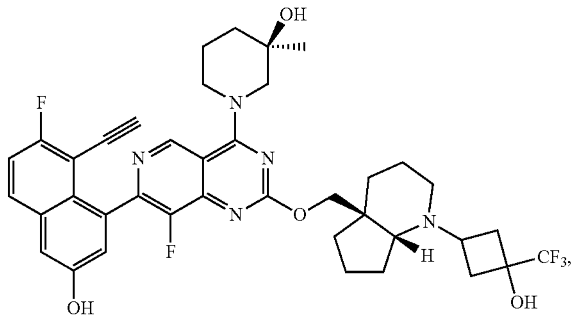
Diastereomer 1
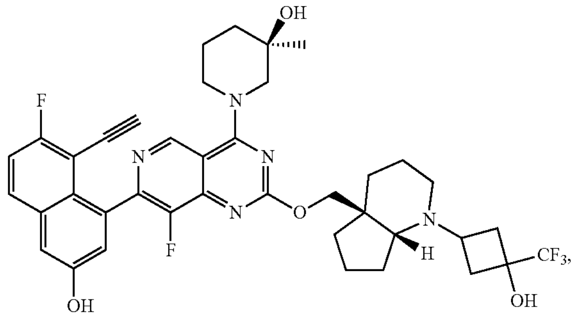
Diastereomer 2
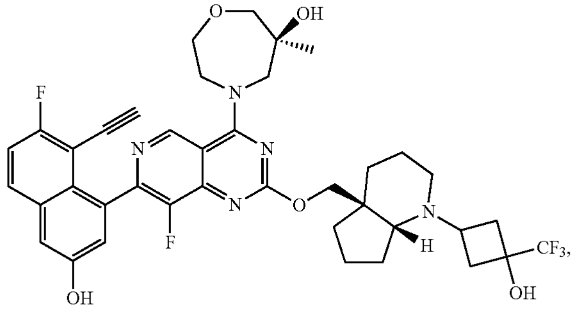
Diastereomer 1
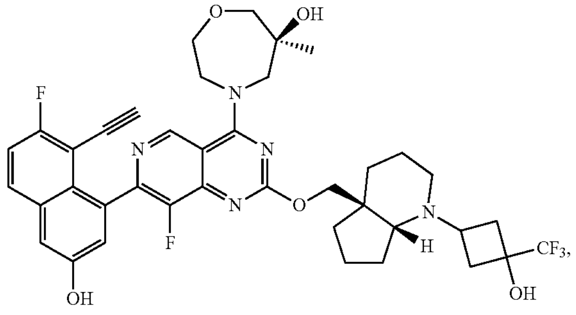
Diastereomer 2
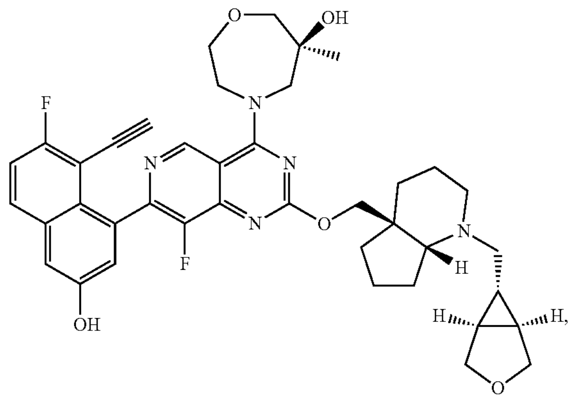
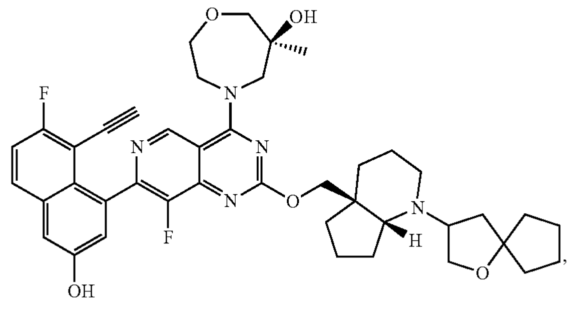
Diastereomer 1

-continued
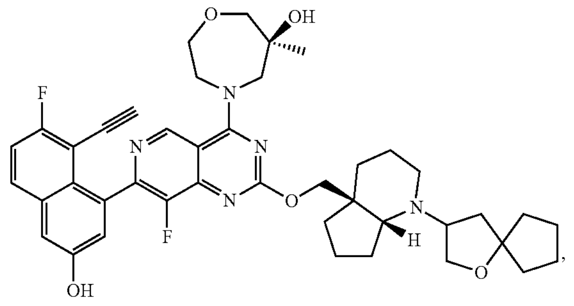
Diastereomer 2
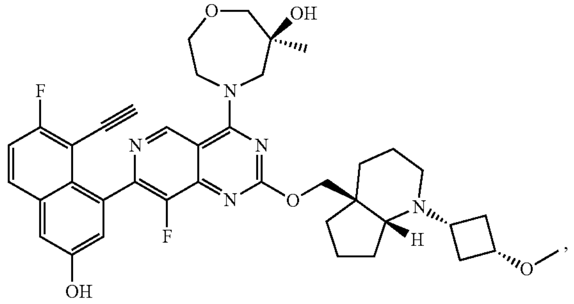
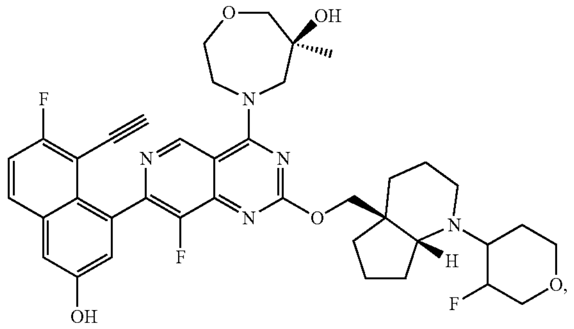
Diastereomer 3
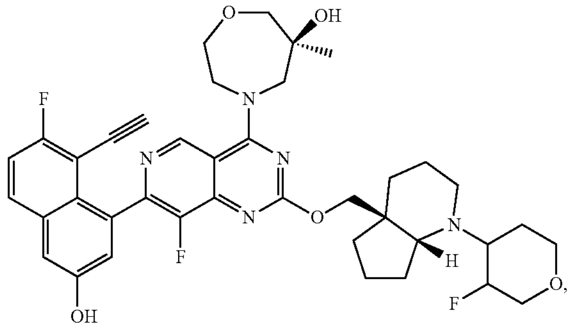
Diastereomer 2
-continued
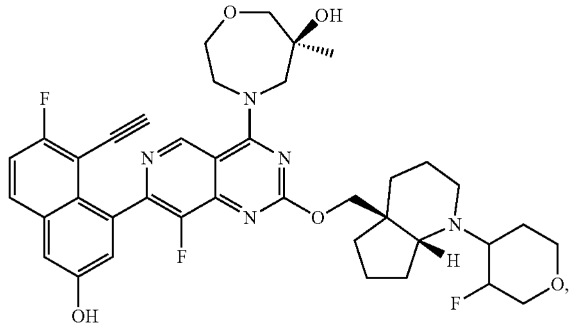
Diastereomer 1
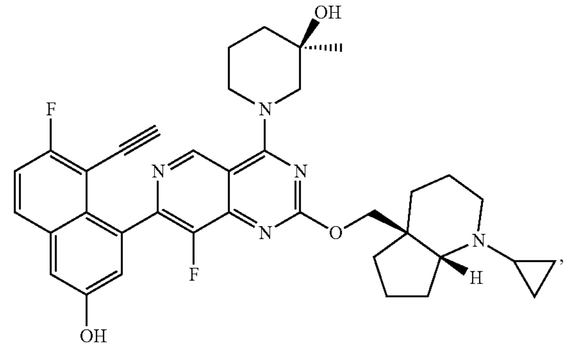
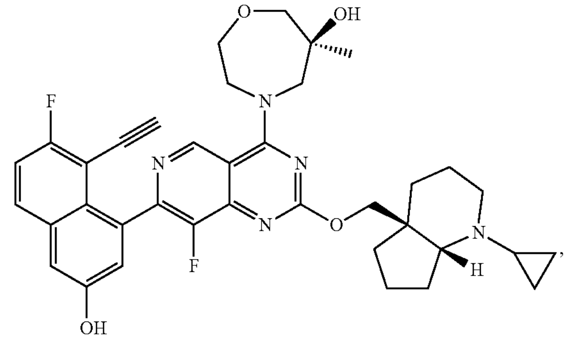
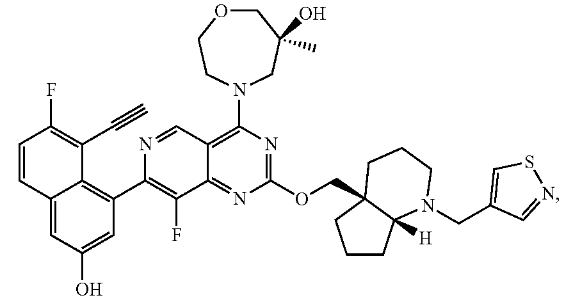
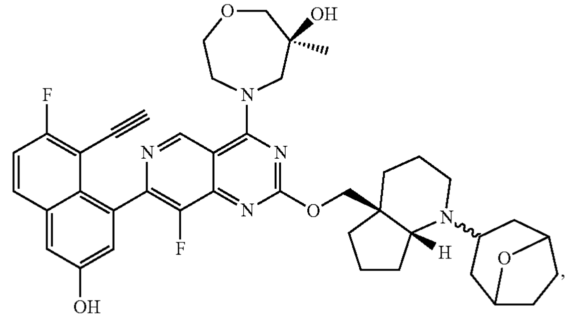
diastereomeric mixture -continued
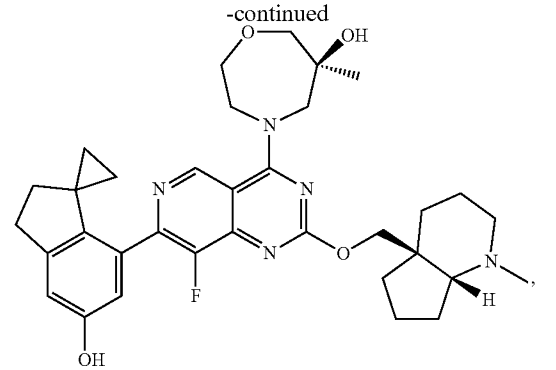
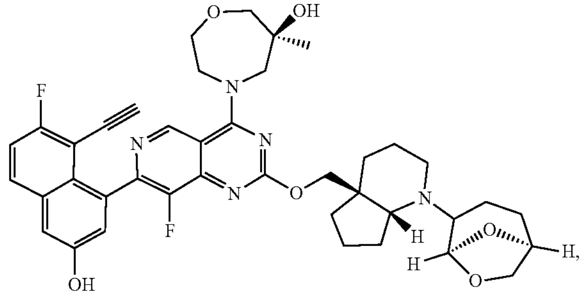
Diastereomer 2
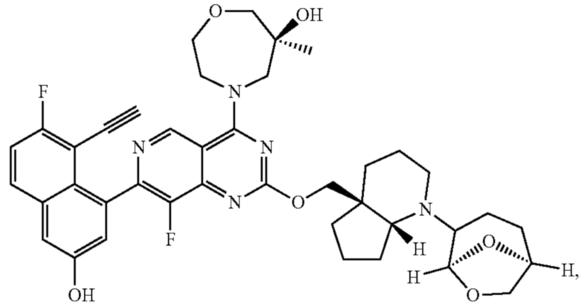
Diastereomer 1
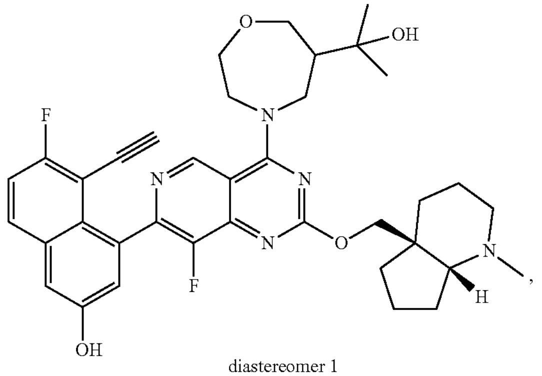
diastereomer 1
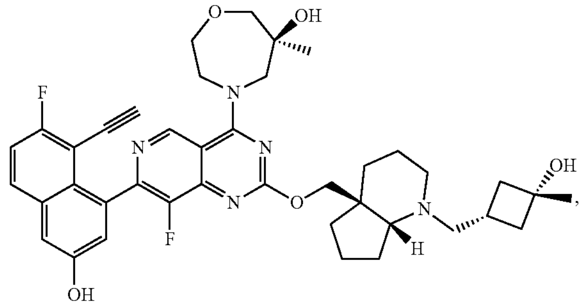
-continued
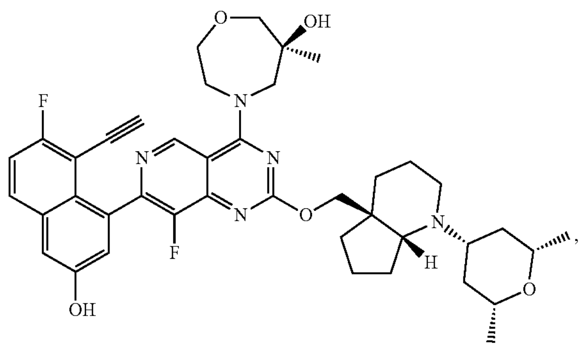
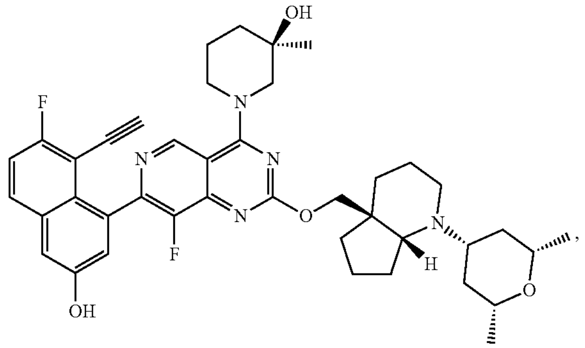
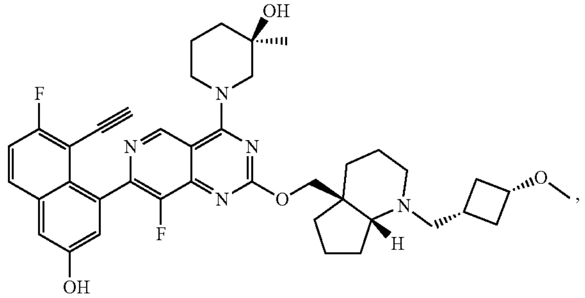
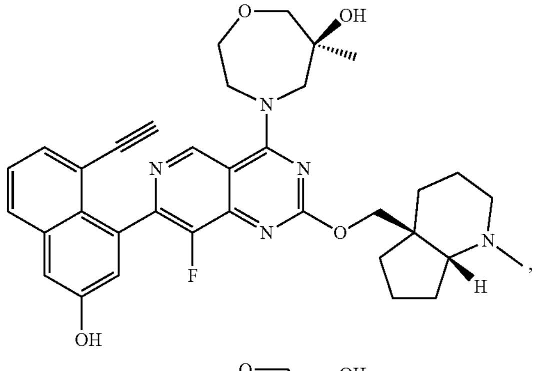
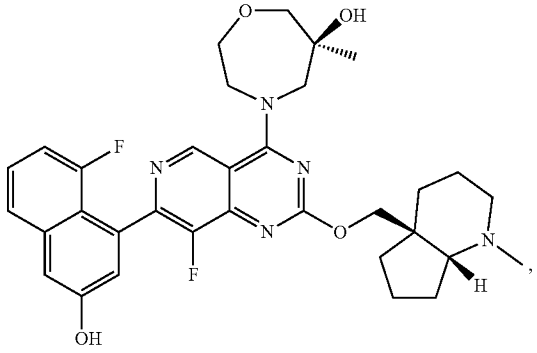

-continued
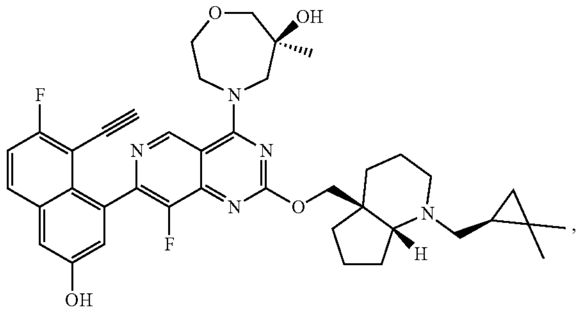
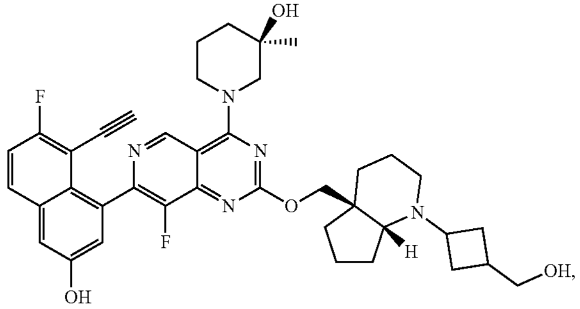
diastereomer 1
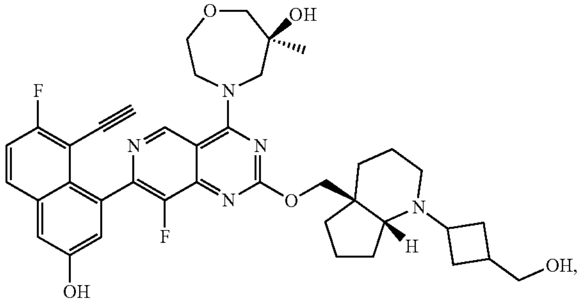
diastereomer 1
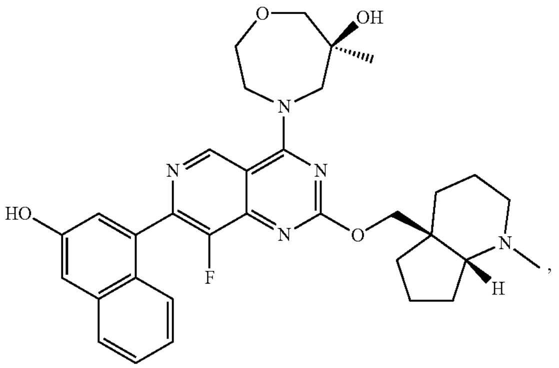
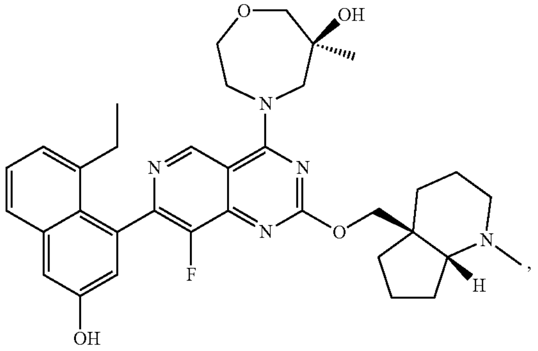
-continued
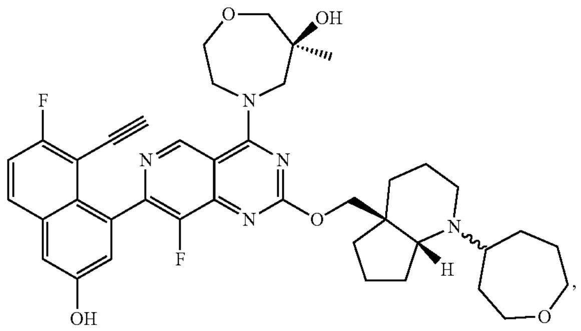
Diastereomer Mixture
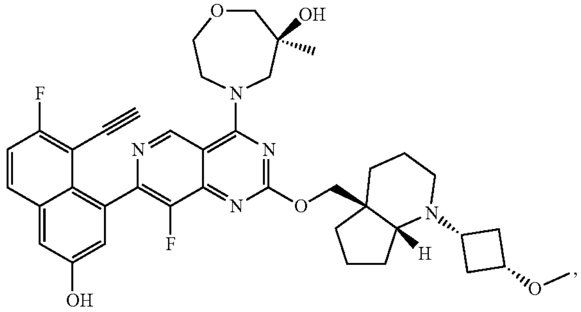
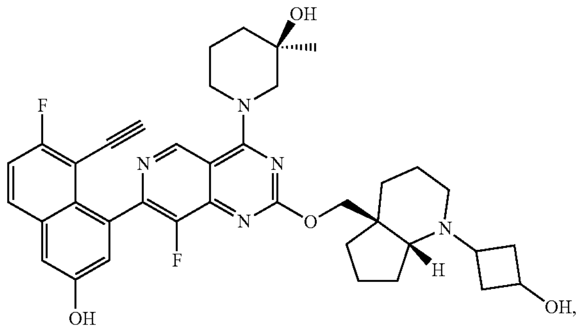
diastereomer 1
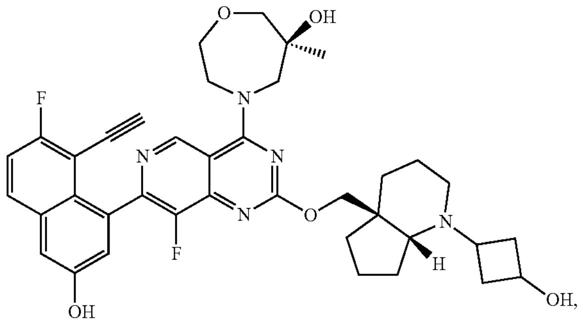
diastereomer 1

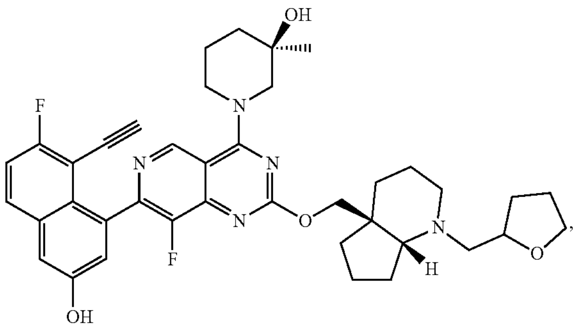
Diastereomer 2
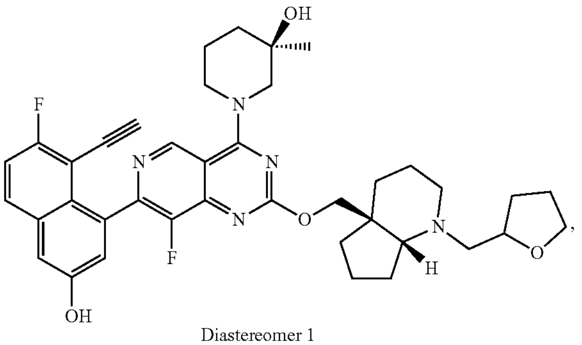
Diastereomer 1
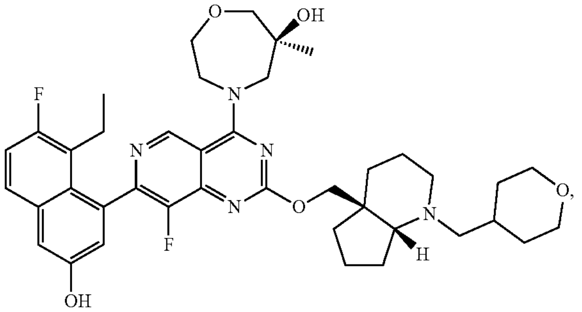
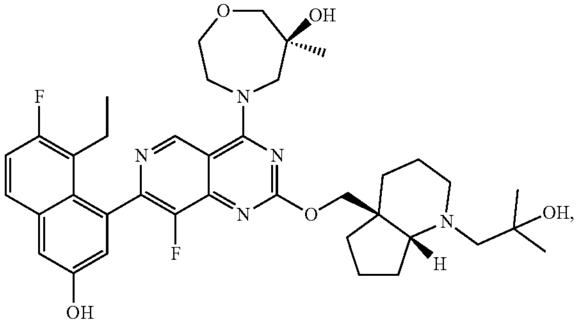
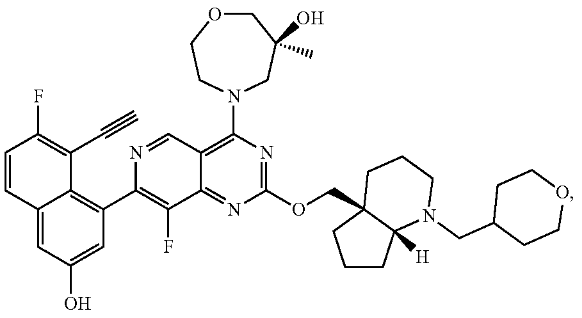
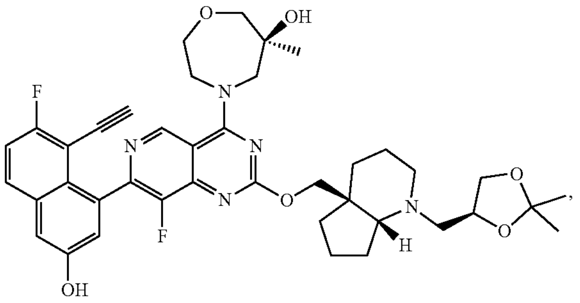
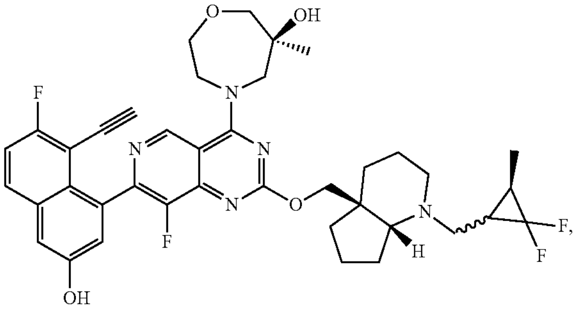
diastereomeric mixture
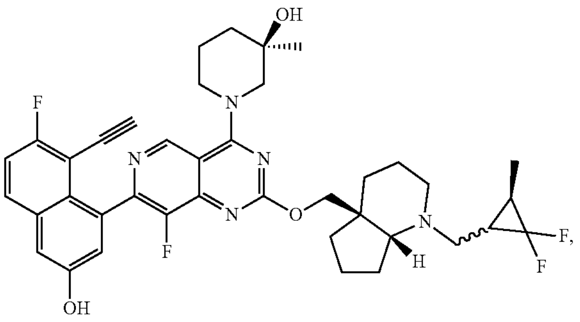
diastereomeric mixture
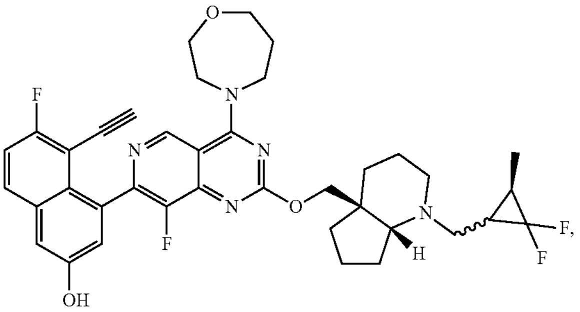
diastereomeric mixture
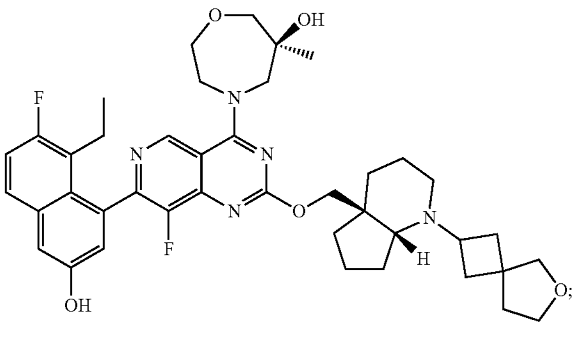
diastereomeric mixture -continued
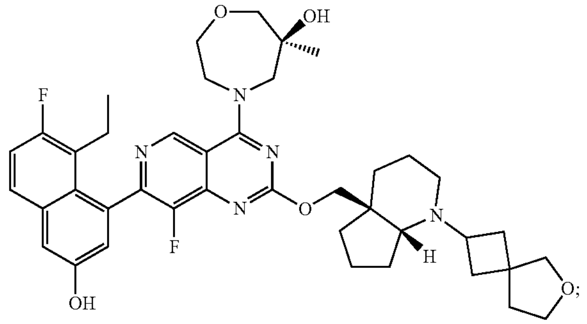
diastereomer 1
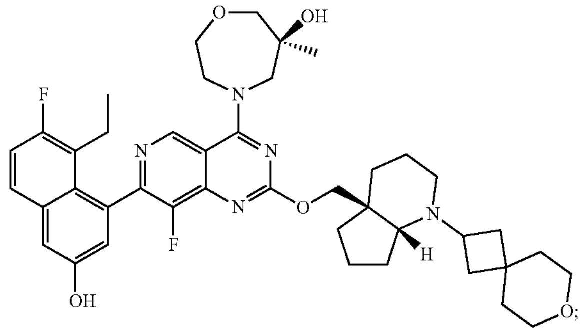
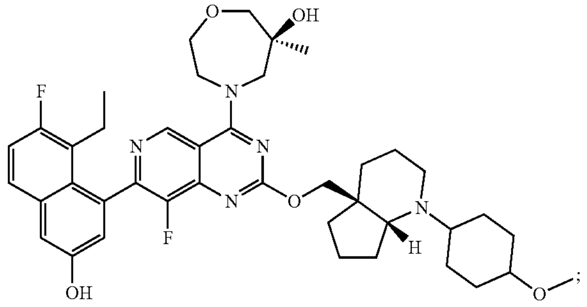
diastereomeric mixture
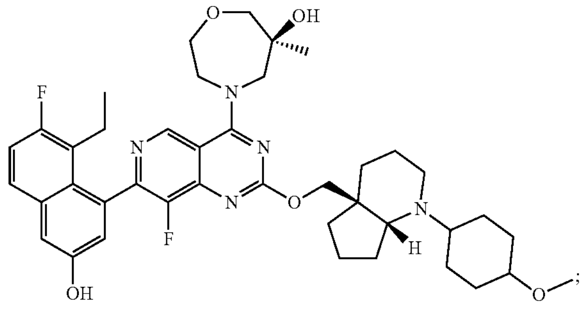
diastereomer 2
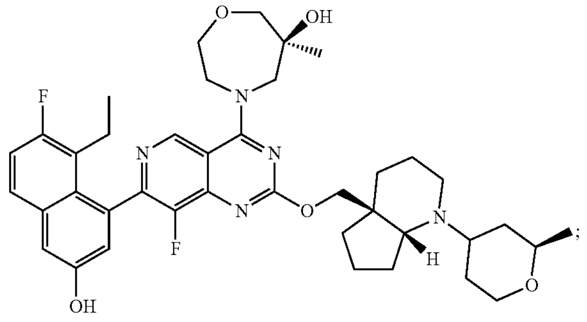
diastereomer 1
-continued
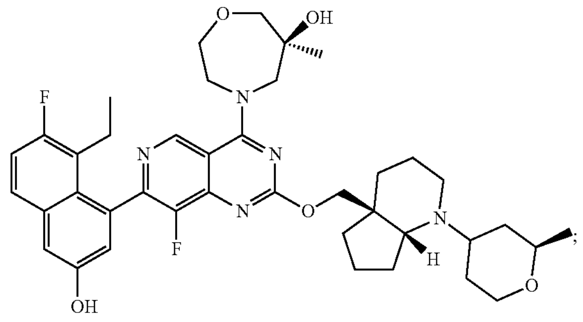
diastereomer 2
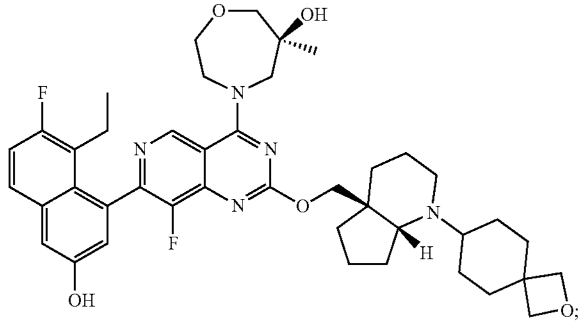
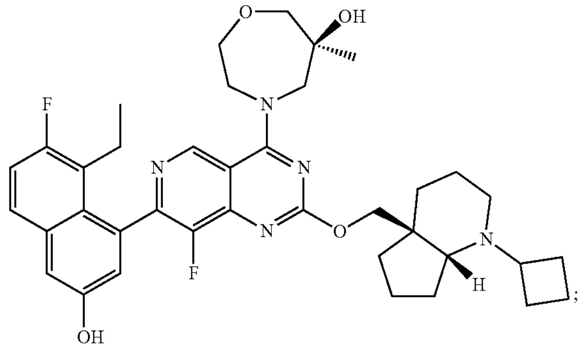
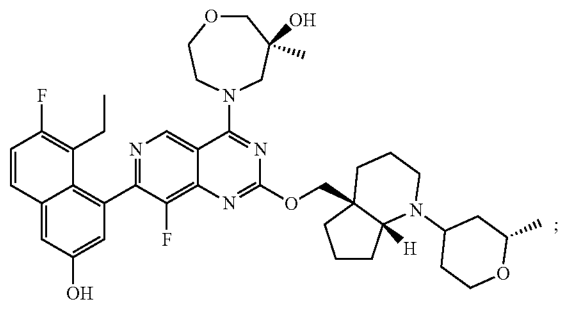
diastereomer 1

-continued
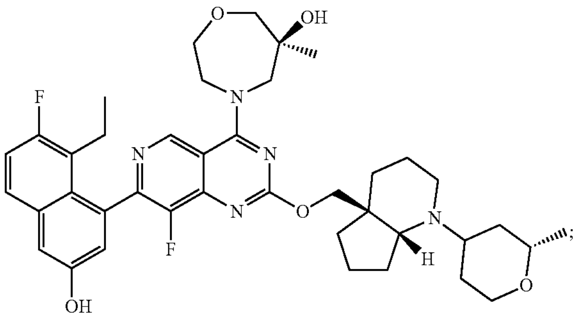
diastereomer 2
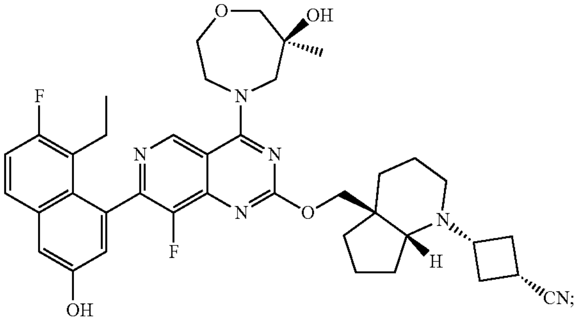
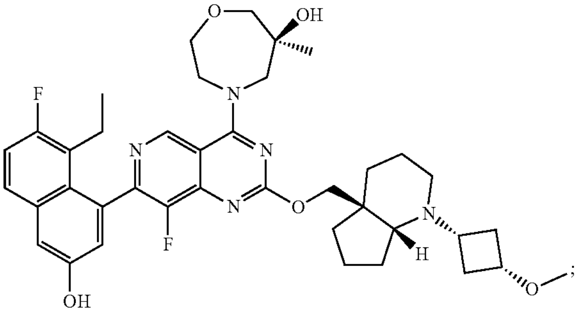
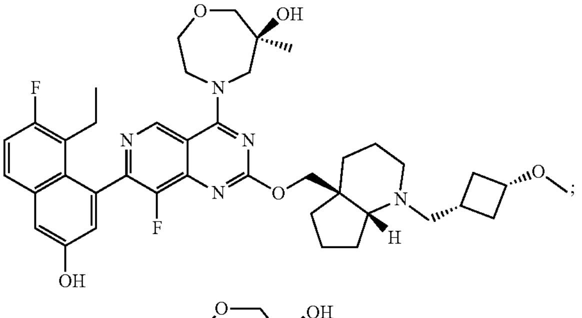
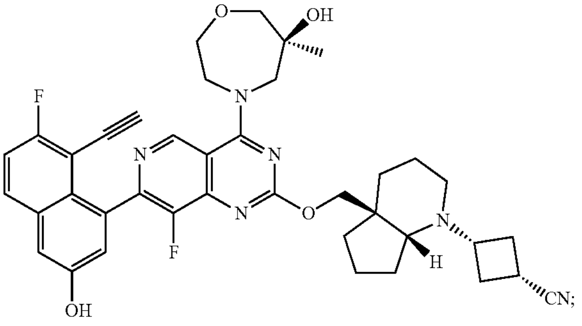
-continued
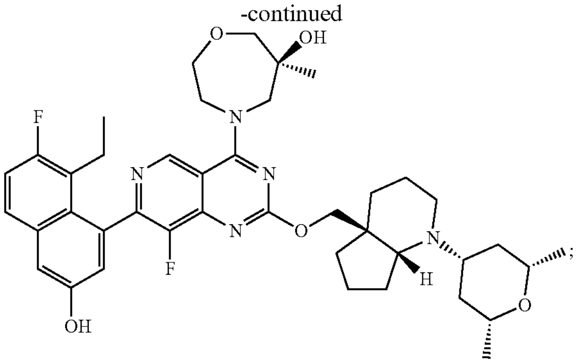
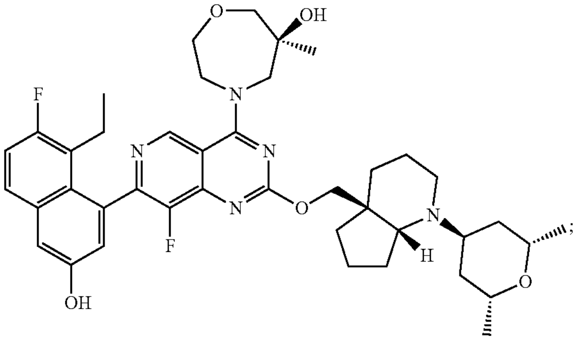
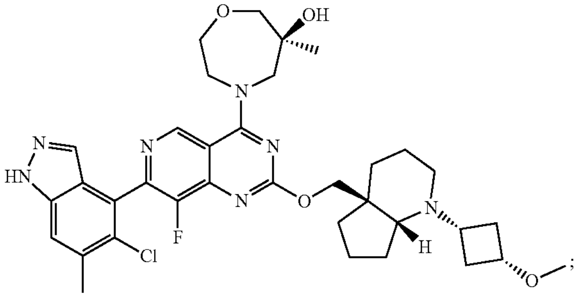
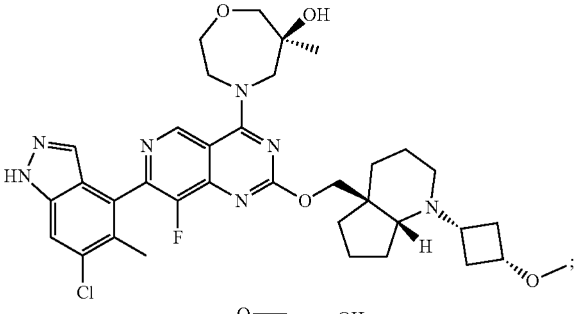
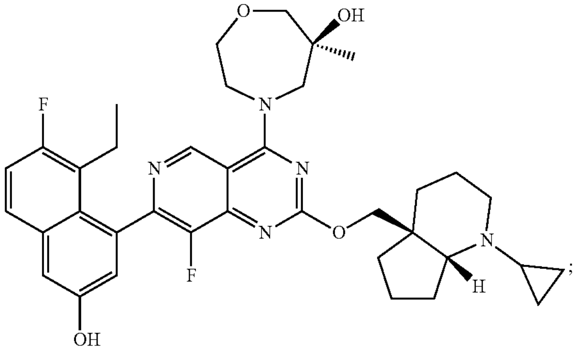

-continued
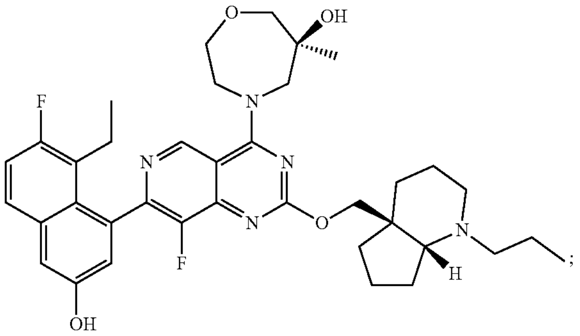
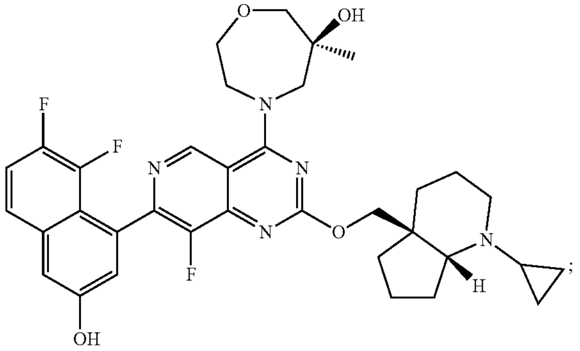
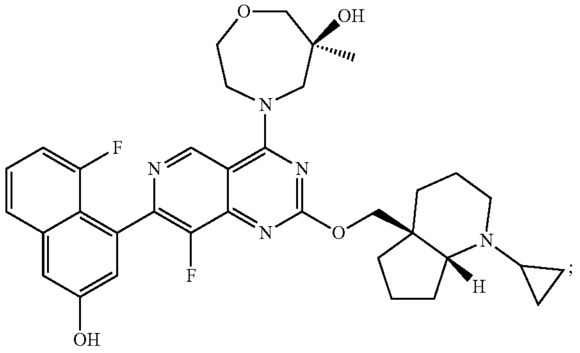
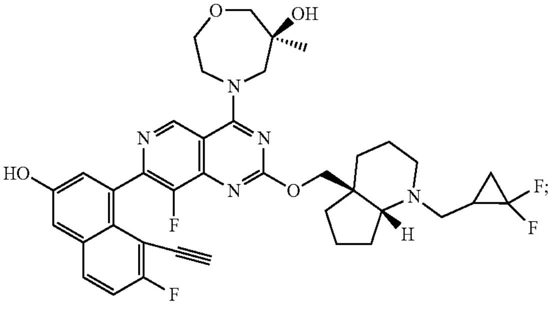
diastereomer 1
-continued
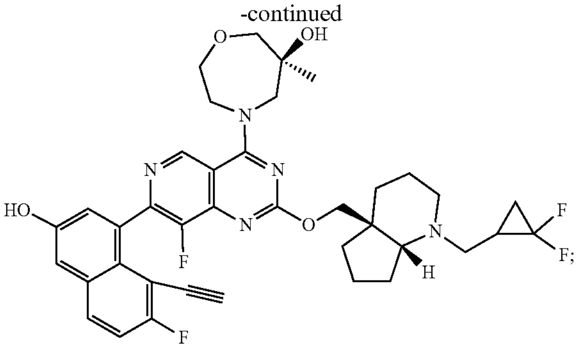
diastereomer 2
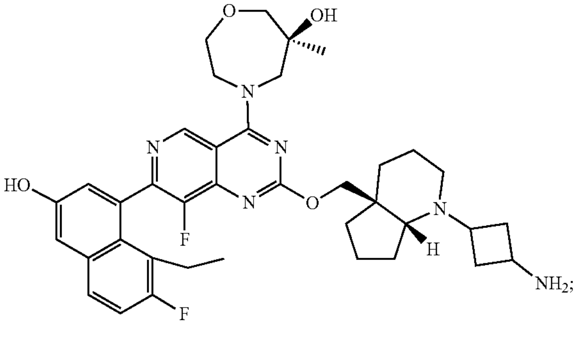
diastereomer 1
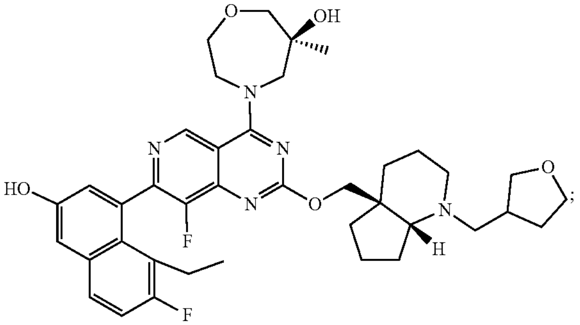
diastereomer 2
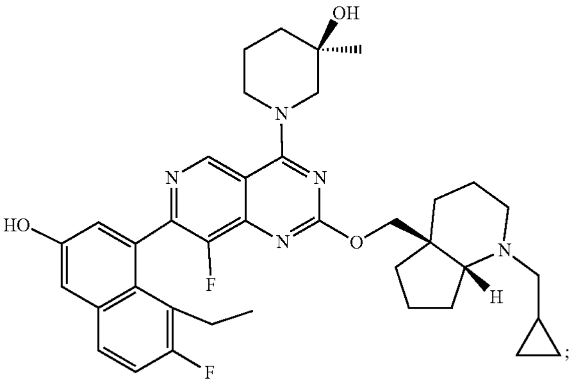

-continued
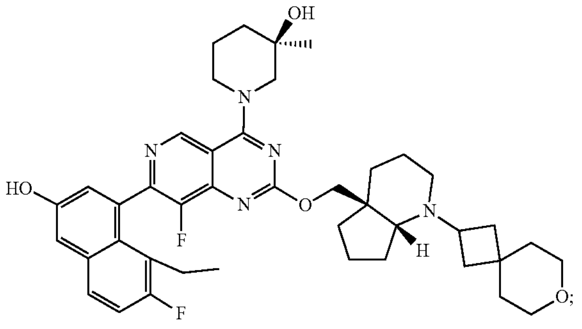
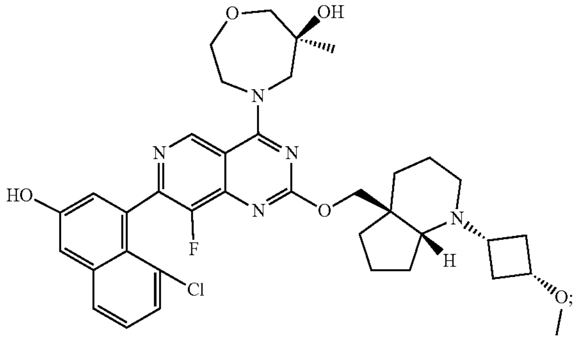
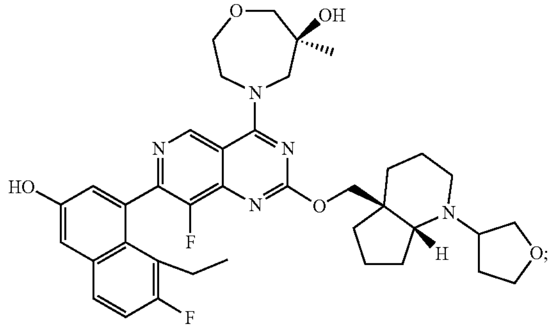
Diastereomer 1
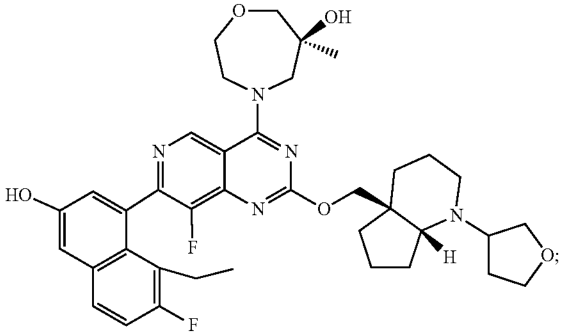
Diastereomer 2
-continued
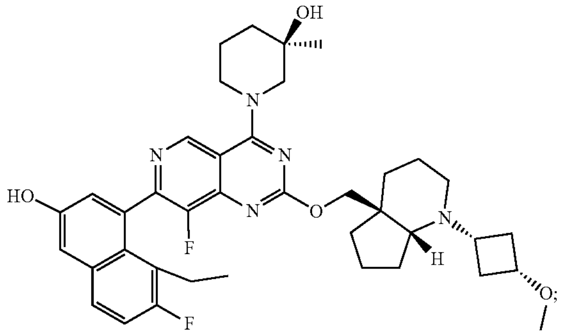
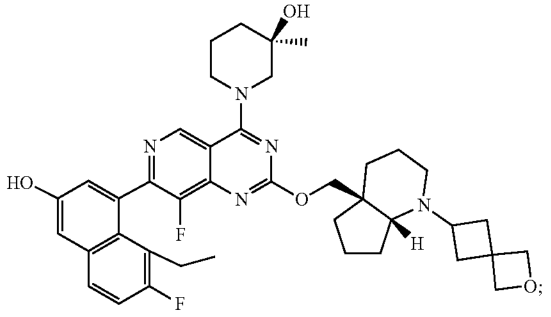
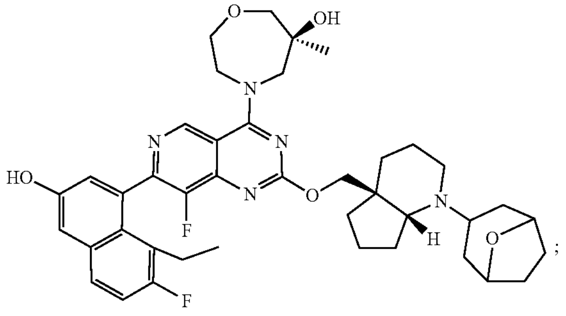
Diastereomer 1
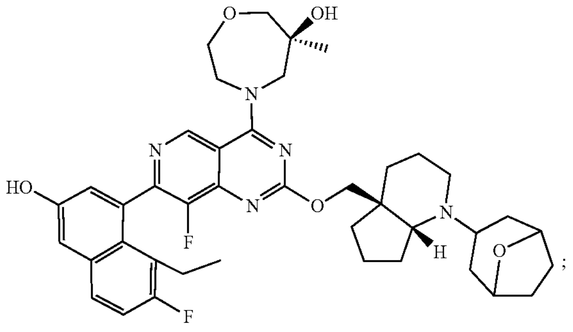
Diastereomer 2
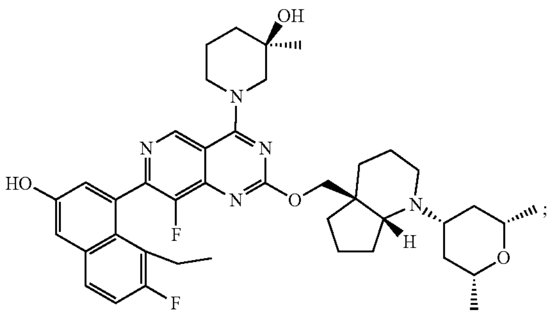

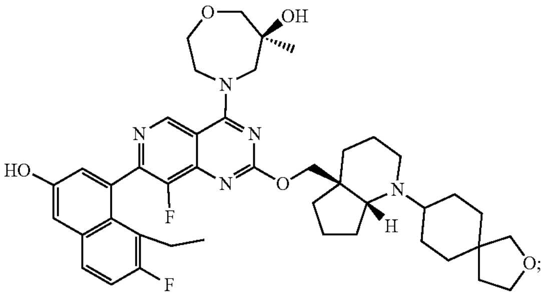
Diastereomer 1
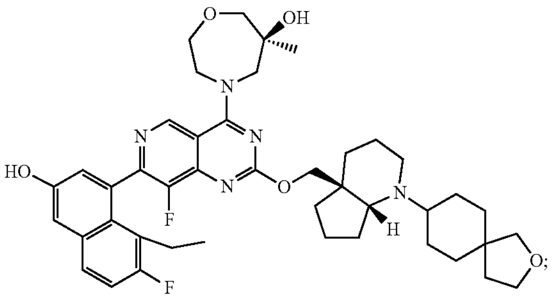
Diastereomer 2
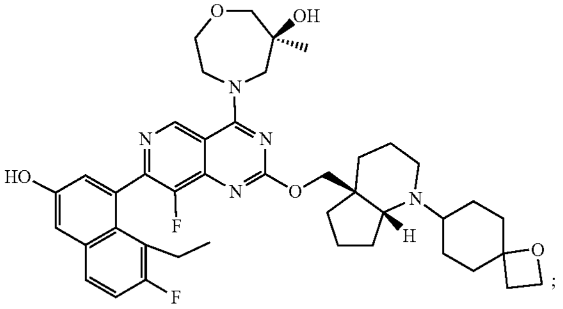
Diastereomer 1
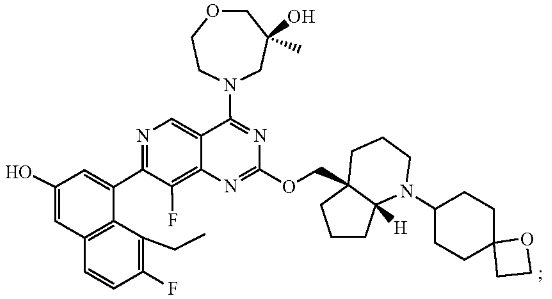
Diastereomer 2
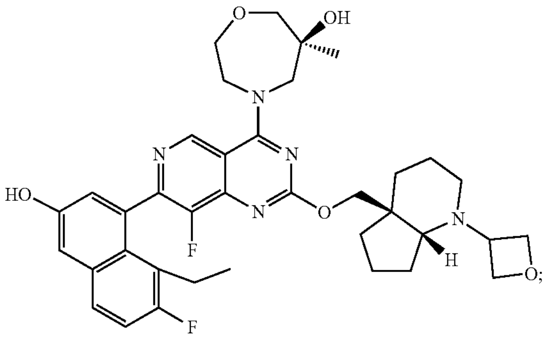
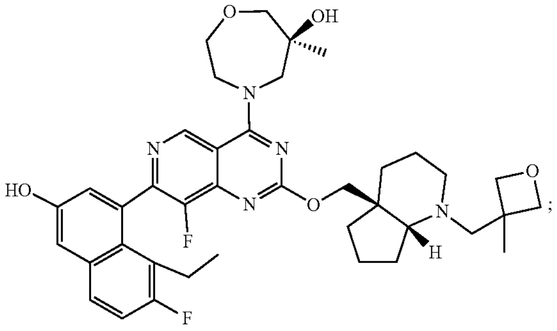
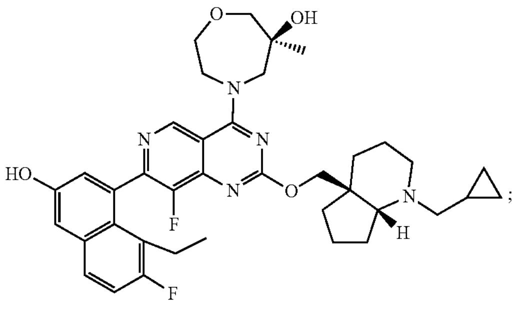
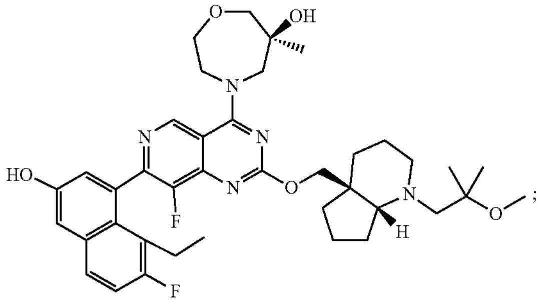
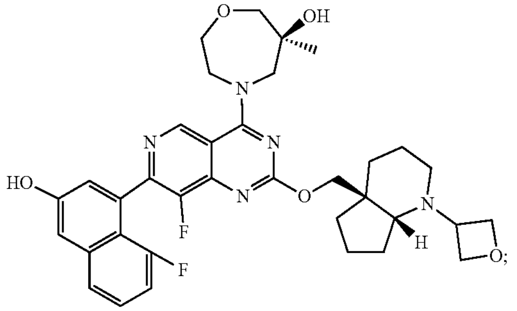
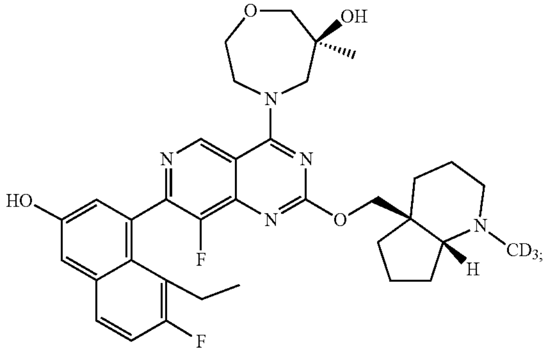

-continued
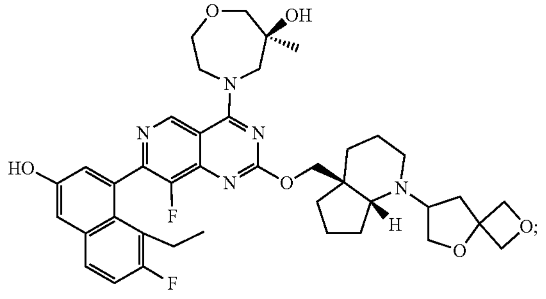
Diastereomer 1
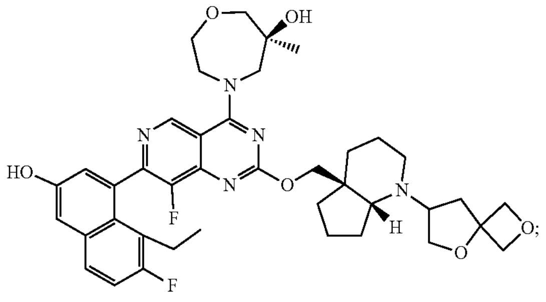
Diastereomer 2
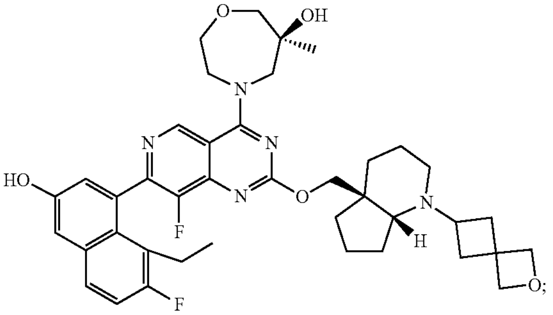
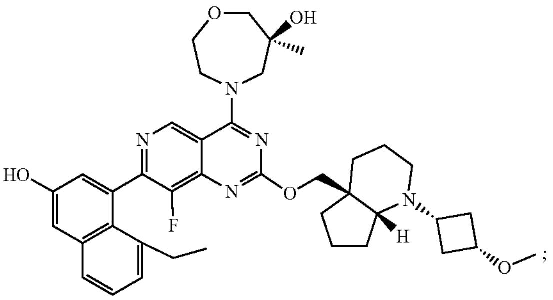
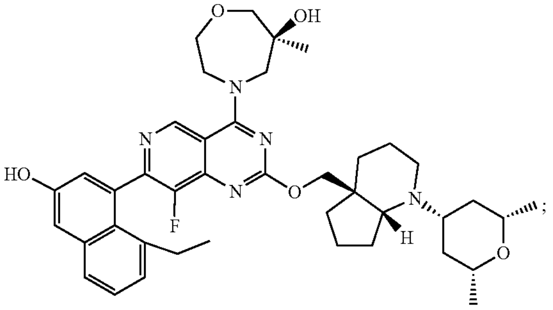
-continued
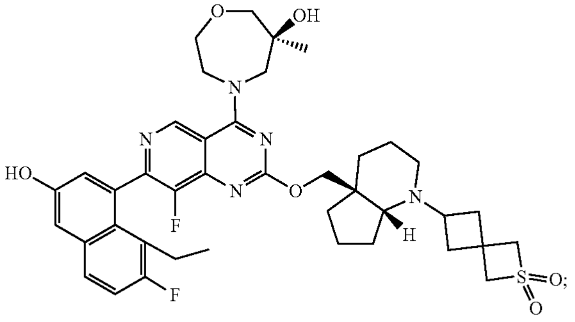
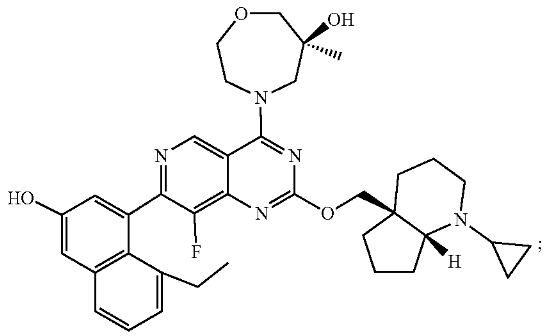
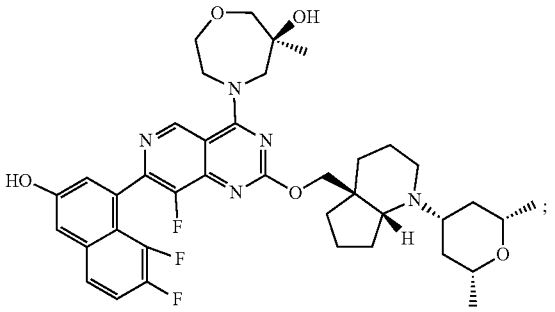
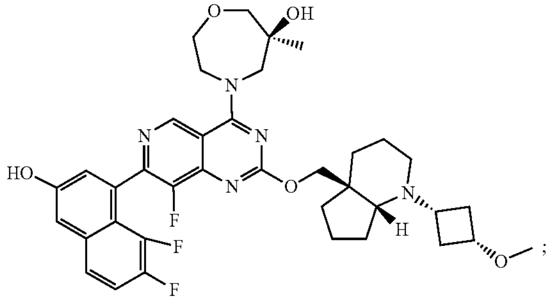
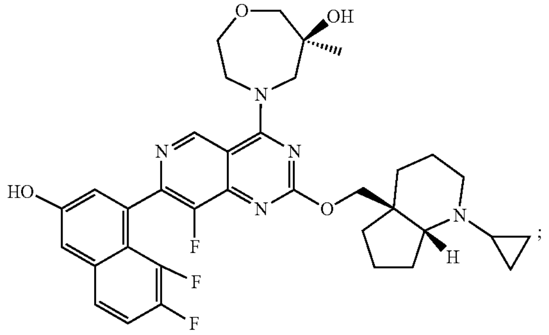

-continued
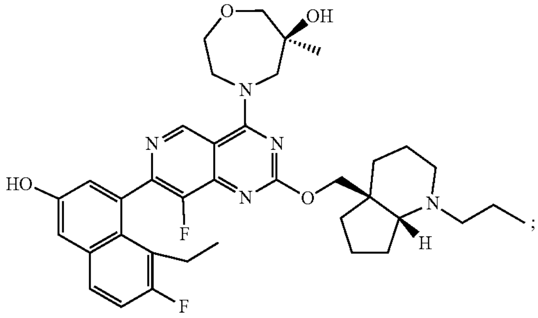
;
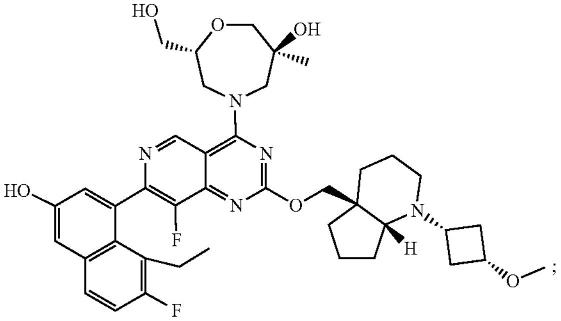
;
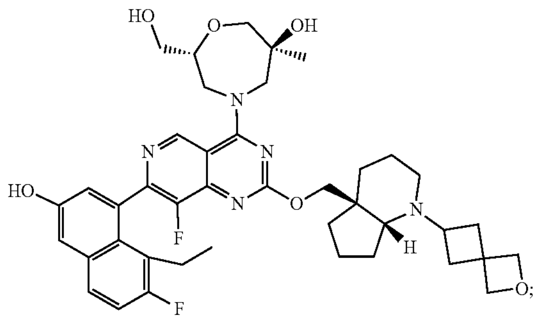
;
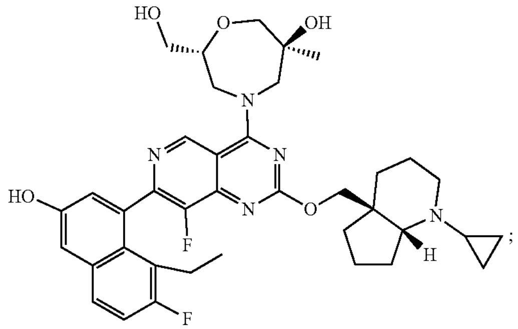
;
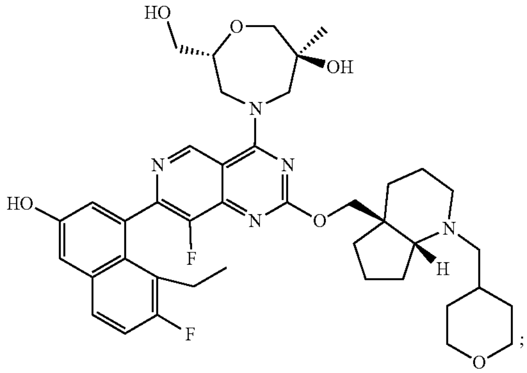
;
-continued
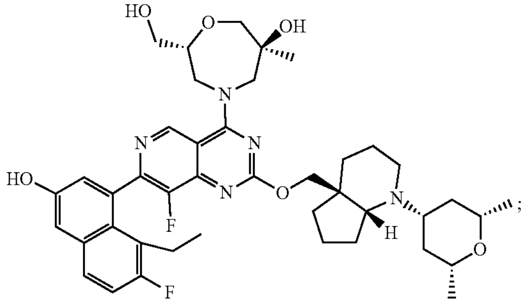
; and
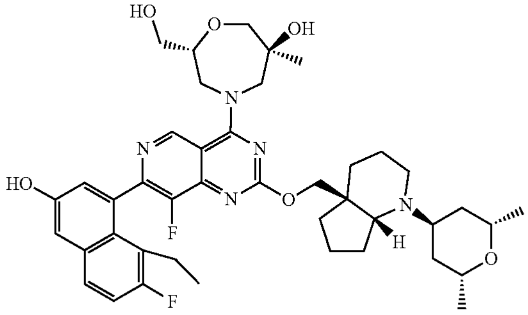
;
or a pharmaceutically acceptable salt thereof.
In some aspects, the present disclosure provides a compound selected from the group consisting of:
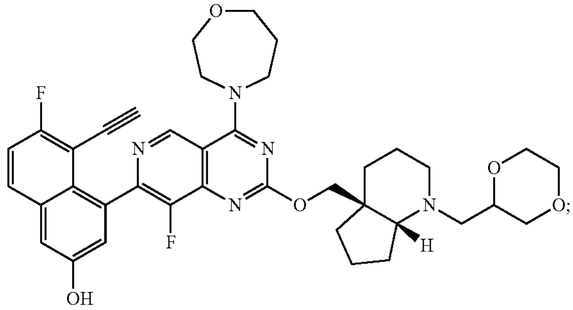
;
diastereomer 2
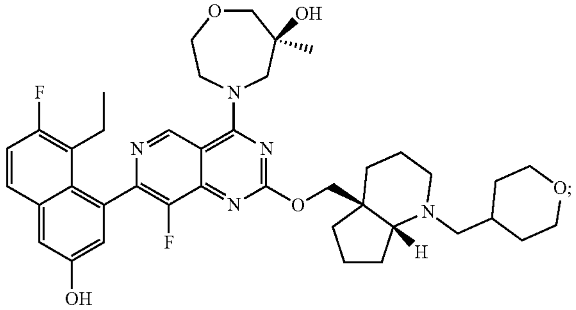
;

-continued
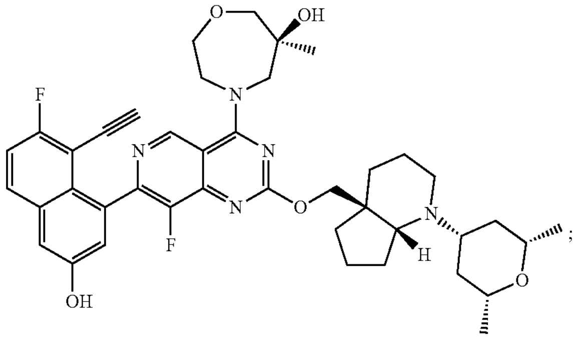
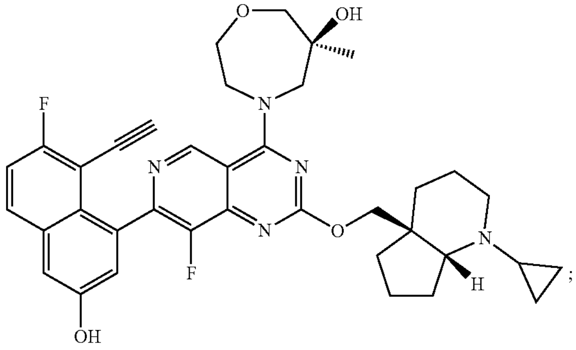
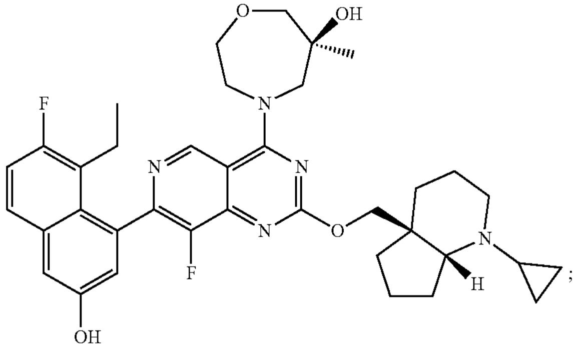
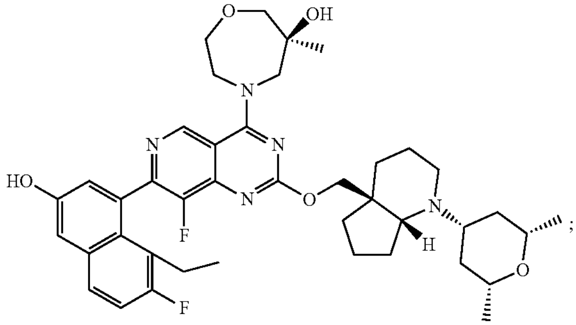
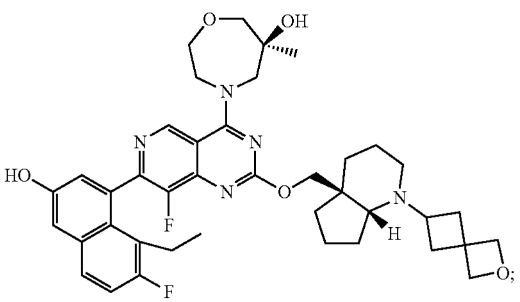
and
-continued
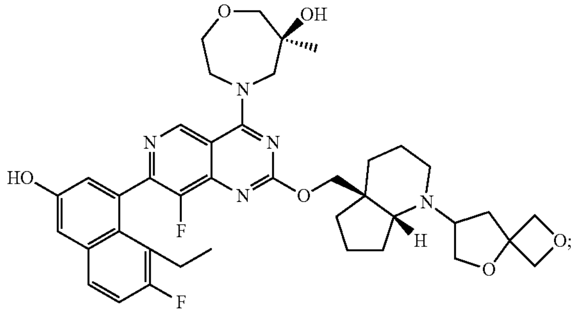
diastereomer 2
or a pharmaceutically acceptable salt thereof.
In some aspects, the present disclosure provides a compound selected from the group consisting of:
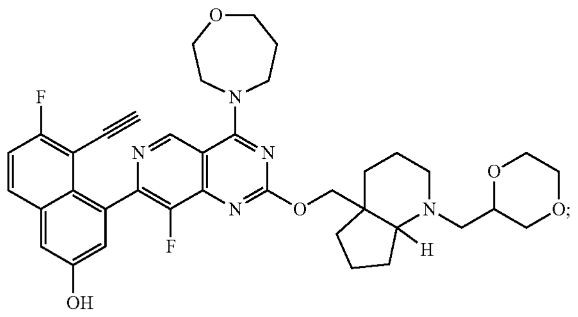
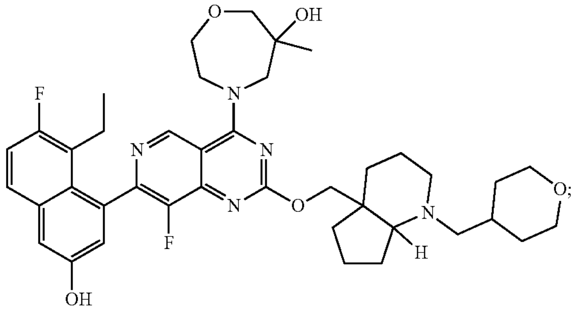
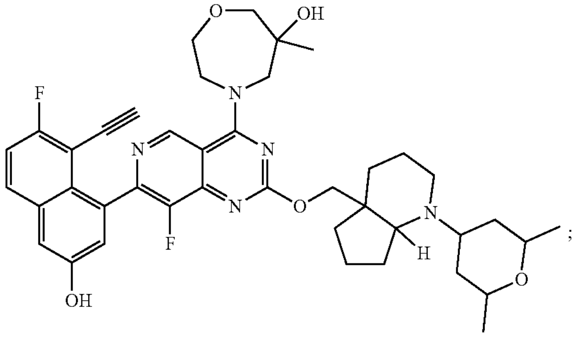

-continued

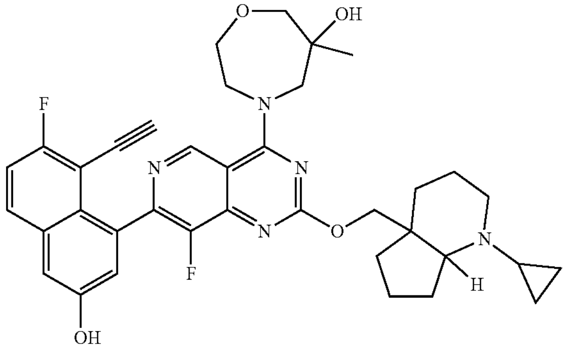

;

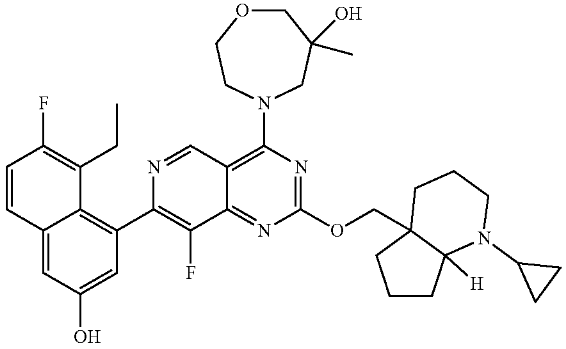

;

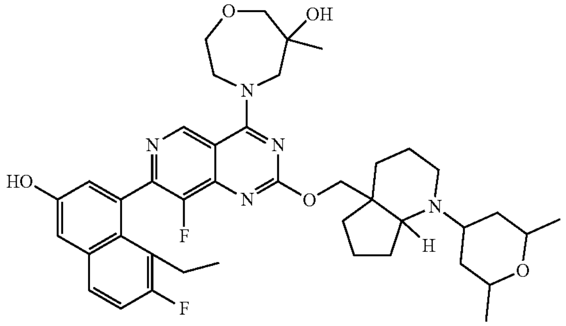

;

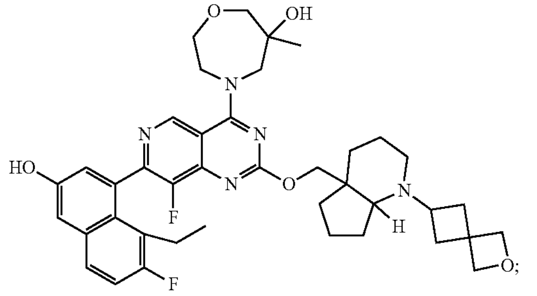

and

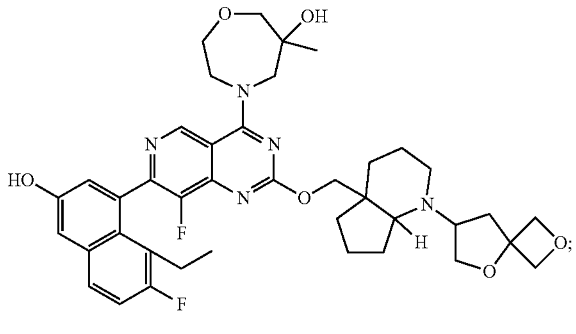

or a pharmaceutically acceptable salt thereof.

In some aspects, the present disclosure provides a compound selected from the group consisting of:

5-ethynyl-6-fluoro-4-(8-fluoro-2-(((3R,4aS,7aR)-3-fluoro-1-methyloctahydro-4aH-cyclopenta[b]pyridin-4a-yl)methoxy)-4-(1,4-oxazepan-4-yl)pyrido[4,3-d]pyrimidin-7-yl)naphthalen-2-ol;

5-ethynyl-6-fluoro-4-(8-fluoro-2-(((4aS,7aR)-1-methyl-3-(methylsulfonyl) octahydro-4aH-cyclopenta[b]pyridin-4a-yl)methoxy)-4-(1,4-oxazepan-4-yl)pyrido[4,3-d]pyrimidin-7-yl)naphthalen-2-ol;

3-ethyl-1-(7-(8-ethynyl-7-fluoro-3-hydroxynaphthalen-1-yl)-8-fluoro-2-(((4aS,7aR)-1-methyloctahydro-4aH-cyclopenta[b]pyridin-4a-yl)methoxy)pyrido[4,3-d]pyrimidin-4-yl)piperidin-3-ol;

3-ethyl-1-(7-(8-ethynyl-7-fluoro-3-hydroxynaphthalen-1-yl)-8-fluoro-2-(((4aS,7aR)-1-methyloctahydro-4aH-cyclopenta[b]pyridin-4a-yl)methoxy)pyrido[4,3-d]pyrimidin-4-yl)piperidin-3-ol;

4-(4-(3,3-difluoro-5-(hydroxymethyl)piperidin-1-yl)-8-fluoro-2-(((4aS,7aR)-1-methyloctahydro-4aH-cyclopenta[b]pyridin-4a-yl)methoxy)pyrido[4,3-d]pyrimidin-7-yl)-5-ethynyl-6-fluoronaphthalen-2-ol;

4-(4-(3,3-difluoro-5-(hydroxymethyl)piperidin-1-yl)-8-fluoro-2-(((4aS,7aR)-1-methyloctahydro-4aH-cyclopenta[b]pyridin-4a-yl)methoxy)pyrido[4,3-d]pyrimidin-7-yl)-5-ethynyl-6-fluoronaphthalen-2-ol;

(S)-4-(7-(8-ethynyl-7-fluoro-3-hydroxynaphthalen-1-yl)-8-fluoro-2-(((3S,4aS,7aR)-3-fluoro-1-methyloctahydro-4aH-cyclopenta[b]pyridin-4a-yl)methoxy)pyrido[4,3-d]pyrimidin-4-yl)-6-methyl-1,4-oxazepan-6-ol;

(3R)-1-(7-(8-ethynyl-7-fluoro-3-hydroxynaphthalen-1-yl)-8-fluoro-2-(((4aS,7aR)-3-fluoro-1,3-dimethyloctahydro-4aH-cyclopenta[b]pyridin-4a-yl)methoxy)pyrido[4,3-d]pyrimidin-4-yl)-3-methylpiperidin-3-ol;

(3R)-1-(7-(8-ethyl-7-fluoro-3-hydroxynaphthalen-1-yl)-8-fluoro-2-(((4aS,7aR)-3-fluoro-1,3-dimethyloctahydro-4aH-cyclopenta[b]pyridin-4a-yl)methoxy)pyrido[4,3-d]pyrimidin-4-yl)-3-methylpiperidin-3-ol;

(R)-1-(7-(8-ethynyl-7-fluoro-3-hydroxynaphthalen-1-yl)-8-fluoro-2-(((3S,4aS,7aR)-3-fluoro-1-methyloctahydro-4aH-cyclopenta[b]pyridin-4a-yl)methoxy)pyrido[4,3-d]pyrimidin-4-yl)-3-methylpiperidin-3-ol;

(R)-1-(7-(8-ethyl-7-fluoro-3-hydroxynaphthalen-1-yl)-8-fluoro-2-(((3S,4aS,7aR)-3-fluoro-1-methyloctahydro-4aH-cyclopenta[b]pyridin-4a-yl)methoxy)pyrido[4,3-d]pyrimidin-4-yl)-3-methylpiperidin-3-ol;

4-(2-{[(4aS,7aR)-1-[(oxetan-3-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(2S)-3-fluoro-2-hydroxypropyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

methyl 3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-

(5S)-5-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}pyrrolidin-2-one cyclopenta[b]pyridin-1-yl]methyl}-3-hydroxyazetidine-1-carboxylate;

4-(2-{[(4aS,7aR)-1-(oxetan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

1-{3-[(4aS,7aR)-4a-({[7-(8-ethynyl-7-fluoro-3-hydroxynaphthalen-1-yl)-8-fluoro-4-(1,4-oxazepan-4-yl)

pyrido[4,3-d]pyrimidin-2-yl]oxy}methyl)-octahydro-1H-cyclopenta[b]pyridin-1-yl]azetidin-1-yl}ethan-1-one;

5-ethynyl-6-fluoro-4-(8-fluoro-4-(1,4-oxazepan-4-yl)-2-(((4aS,7aR)-1-(tetrahydro-2H-pyran-4-yl) octahydro-4aH-cyclopenta[b]pyridin-4a-yl)methoxy)pyrido[4,3-d]pyrimidin-7-yl)naphthalen-2-ol;

4-((4aS,7aR)-4a-(((7-(8-ethynyl-7-fluoro-3-hydroxynaphthalen-1-yl)-8-fluoro-4-(1,4-oxazepan-4-yl)pyrido[4,3-d]pyrimidin-2-yl)oxy)methyl) octahydro-1H-cyclopenta[b]pyridin-1-yl)tetrahydro-2H-thiopyran 1,1-dioxide 4-(2-{[(4aS,7aR)-1-(cyclopropylmethyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(cyclobutylmethyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(3-methyloxetan-3-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-cyclobutyl-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(2R)-3-fluoro-2-hydroxypropyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(1-hydroxycyclobutyl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(2-methyloxetan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(2-methyloxetan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

1-(3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-3-hydroxyazetidin-1-yl) ethan-1-one;

4-(2-{[(4aS,7aR)-1-{[3-(hydroxymethyl) oxetan-3-yl]methyl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

tert-butyl 3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}azetidine-1-carboxylate;

tert-butyl N-(1-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}cyclopropyl)carbamate;

tert-butyl 3-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]azetidine-1-carboxylate;

4-(2-{[(4aS,7aR)-1-(2,2-difluoroethyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

1-(3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}azetidin-1-yl) ethan-1-one;

methyl 3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}azetidine-1-carboxylate;

methyl 3-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]azetidine-1-carboxylate;

N-(1-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}cyclopropyl)acetamide 1-(3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-3-methylazetidin-1-yl) ethan-1-one;

4-(2-{[(4aS,7aR)-1-(2-hydroxyethyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-propyl-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(2-methylpropyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(3,3-difluorocyclobutyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(3,3-dimethylcyclobutyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(2S)-2-hydroxypropyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(2R)-2-hydroxypropyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}oxetan-3-ol;

4-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}pyrrolidin-2-one;

(5R)-5-{[(4aS,7aR)-4a-({[7-(8-ethynyl-7-fluoro-3-hydroxynaphthalen-1-yl)-8-fluoro-4-(1,4-oxazepan-4-yl)

pyrido[4,3-d]pyrimidin-2-yl]oxy}methyl)-octahydro-1H-cyclopenta[b]pyridin-1-yl]methyl}pyrrolidin-2-one;

6-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]-2,6-thiaspiro[3.3]heptane-2,2-dione (3aR,6aS)-5-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]-hexahydro-1H-2,6-cyclopenta[c]thiophene-2,2-dione 2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]-7,6-thiaspiro[3.5]nonane-7,7-dione 4-(2-{[(4aS,7aR)-1-propyl-octahydro-1H-cyclopenta[b]pyridin-4a-yl]methoxy}-8-fluoro-4-(1,4-oxazepan-4-yl)pyrido[4,3-d]pyrimidin-7-yl)-5-ethyl-6-fluoronaphthalen-2-ol;

4-(2-{[(4aS,7aR)-1-(cyclopropylmethyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethyl-6-fluoronaphthalen-2-ol;

4-(2-{[(4aS,7aR)-1-(2-hydroxyethyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethyl-6-fluoronaphthalen-2-ol;

4-(2-{[(4aS,7aR)-1-cyclobutyl-octahydro-1H-cyclopenta[b]pyridin-4a-yl]methoxy}-8-fluoro-4-(1,4-oxazepan-4-yl)pyrido[4,3-d]pyrimidin-7-yl)-5-ethyl-6-fluoronaphthalen-2-ol;

4-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}piperidine-2,6-dione 4-(2-{[(4aS,7aR)-1-{[1-(methoxymethyl)cyclopropyl]methyl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

tert-butyl 3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}azetidine-1-carboxylate;

4-(2-{[(4aS,7aR)-1-{2-oxaspiro[3.3]heptan-6-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

3-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]cyclobutane-1-carboxamide 4-(2-{[(4aS,7aR)-1-{7-oxaspiro[3.5]nonan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-{spiro[2.3]hexan-5-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(3-methanesulfonylcyclobutyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-{2-oxaspiro[3.5]nonan-7-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(oxolan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(oxolan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(oxolan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

1-(3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}azetidin-1-yl) propan-1-one;

1-(3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}azetidin-1-yl) propan-1-one;

4-(2-{[(4aS,7aR)-1-[2-(1-cyclopropanecarbonylazetidin-3-yl)ethyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

1-(3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}azetidin-1-yl)-2-methylpropan-1-one;

1-(3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}azetidin-1-yl)-2-methylpropan-1-one;

4-(2-{[(4aS,7aR)-1-[(1-cyclopropanecarbonylazetidin-3-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

ethyl 3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}azetidine-1-carboxylate;

1-(3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}azetidin-1-yl) ethan-1-one;

methyl 3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}azetidine-1-carboxylate;

1,1,1-trifluoro-2-methylpropan-2-yl 3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}azetidine-1-carboxylate;

1,1,1-trifluoro-2-methylpropan-2-yl 3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}azetidine-1-carboxylate;

4-(2-{[(4aS,7aR)-1-(2-cyclopropylethyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(1,4-dioxan-2-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(1,4-dioxan-2-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(1,4-dioxan-2-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(oxolan-3-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[2-(oxan-4-yl)ethyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(oxan-4-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-1,6-thiane-1,1-dione 4-(2-{[(4aS,7aR)-1-[(oxolan-2-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(oxolan-2-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(2-cyclobutylethyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(oxan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(oxan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

3-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]-1,6-thiane-1,1-dione 4-(2-{[(4aS,7aR)-1-{5,8-dioxaspiro[3.4]octan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}-1,6-thiolane-1,1-dione 3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-1,6-thiane-1,1-dione 6-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}piperidin-2-one;

4-(2-{[(4aS,7aR)-1-(3-methanesulfonylpropyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(2-methanesulfonylethyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-1,3-oxazolidin-2-one;

5-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}piperidin-2-one;

3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}-1,6-thietane-1,1-dione 4-(2-{[(4aS,7aR)-1-[(3,3-difluorocyclobutyl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

tert-butyl 6-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-2-azaspiro[3.3]heptane-2-carboxylate;

ethyl 6-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-2-azaspiro[3.3]heptane-2-carboxylate;

4-(2-{[(4aS,7aR)-1-[(3,3-dimethylcyclobutyl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(oxan-3-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(oxan-3-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(2,2-dimethyl-1,3-dioxan-5-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[2-(oxolan-2-yl)ethyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[2-(oxolan-2-yl)ethyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[2-(oxolan-2-yl)ethyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

5-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]

pyrimidin-2-yl]oxy}methyl)-octahydro-1H-cyclopenta[b]pyridin-1-yl]methyl}-1-methylpyrrolidin-2-one;

5-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-1-methylpyrrolidin-2-one;

5-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-1-methylpyrrolidin-2-one;

4-(2-{[(4aS,7aR)-1-(3,3-dimethoxycyclobutyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(2,2-dimethyl-1,3-dioxan-5-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

(6S)-4-(2-{[(4aS,7aR)-1-[(oxetan-3-yl)methyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(cyclobutylmethyl)-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(cyclopropylmethyl)-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(oxetan-3-yl)-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

tert-butyl N-(3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}cyclobutyl)carbamate;

(6R)-4-(2-{[(4aS,7aR)-1-[(oxetan-3-yl)methyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6R)-4-(2-{[(4aS,7aR)-1-(oxetan-3-yl)-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

ethyl N-(3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}cyclobutyl)carbamate;

methyl N-(3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}cyclobutyl)carbamate;

(3R)-1-(2-{[(4aS,7aR)-1-{8-oxabicyclo[3.2.1]octan-3-yl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-3-methylpiperidin-3-ol;

(3R)-1-(2-{[(4aS,7aR)-1-{8-oxabicyclo[3.2.1]octan-3-yl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-3-methylpiperidin-3-ol;

(3R)-1-(2-{[(4aS,7aR)-1-[3-(methoxymethyl)cyclobutyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-3-methylpiperidin-3-ol;

(3R)-1-(2-{[(4aS,7aR)-1-[(oxolan-2-yl)methyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-3-methylpiperidin-3-ol;

4-(2-{[(4aS,7aR)-1-(3-hydroxy-3-methylcyclobutyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(3-hydroxy-3-methylcyclobutyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

(6S)-4-(2-{[(4aS,7aR)-1-[(1s,3s)-3-methoxycyclobutyl]-octahydro-1H-cyclopenta[b]pyridin-4a-yl]methoxy}-8-fluoro-7-(8-fluoro-3-hydroxynaphthalen-1-yl)pyrido[4,3-d]pyrimidin-4-yl)-6-methyl-1,4-oxazepan-6-ol;

(6S)-4-(2-{[(4aS,7aR)-1-[(3aR,6aS)-hexahydro-1H-cyclopenta[c]furan-5-yl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-methyl-octahydro-1H-cyclopenta[b]pyridin-4a-yl]methoxy}-7-(7,8-difluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-{2,6-dioxaspiro[4.5]decan-9-yl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(3-methoxy-1-methylcyclobutyl)methyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(3-methoxy-1-methylcyclobutyl)methyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-{2,6-dioxaspiro[4.5]decan-9-yl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(3-hydroxy-3-methylcyclobutyl)-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(3-hydroxy-3-methylcyclobutyl)-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-{2,5-dioxaspiro[3.4]octan-7-yl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[3-(methoxymethyl)cyclobutyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

4-(2-{[(4aS,7aR)-1-[3-(methoxymethyl)cyclobutyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

(6S)-4-(2-{[(4aS,7aR)-1-(3-fluorooxan-4-yl)-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(3R)-1-(2-{[(4aS,7aR)-1-[3-hydroxy-3-(trifluoromethyl)cyclobutyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-3-methylpiperidin-3-ol;

(3R)-1-(2-{[(4aS,7aR)-1-[3-hydroxy-3-(trifluoromethyl)cyclobutyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-3-methylpiperidin-3-ol;

(6S)-4-(2-{[(4aS,7aR)-1-[3-hydroxy-3-(trifluoromethyl)cyclobutyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[3-hydroxy-3-(trifluoromethyl)cyclobutyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-{[(1R,5S,6R)-3-oxabicyclo[3.1.0]hexan-6-yl]methyl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-{1-oxaspiro[4.4]nonan-3-yl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-{1-oxaspiro[4.4]nonan-3-yl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(1s,3s)-3-methoxycyclobutyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(3-fluorooxan-4-yl)-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(3-fluorooxan-4-yl)-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(3-fluorooxan-4-yl)-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(3R)-1-(2-{[(4aS,7aR)-1-cyclopropyl-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-3-methylpiperidin-3-ol;

(6S)-4-(2-{[(4aS,7aR)-1-cyclopropyl-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(1,2-thiazol-4-yl)methyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-{8-oxabicyclo[3.2.1]octan-3-yl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-methyl-octahydro-1H-cyclopenta[b]pyridin-4a-yl]methoxy}-8-fluoro-7-{5'-hydroxy-2',3'-dihydrospiro[cyclopropane-1,1'-inden]-7'-yl}pyrido[4,3-d]pyrimidin-4-yl)-6-methyl-1,4-oxazepan-6-ol;

(6S)-4-(2-{[(4aS,7aR)-1-[(1S,5R)-6,8-dioxabicyclo[3.2.1]octan-4-yl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(1S,5R)-6,8-dioxabicyclo[3.2.1]octan-4-yl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

4-(2-{[(4aS,7aR)-1-methyl-octahydro-1H-cyclopenta[b]pyridin-4a-yl]methoxy}-8-fluoro-4-[6-(2-hydroxypropan-2-yl)-1,4-oxazepan-4-yl]pyrido[4,3-d]pyrimidin-7-yl)-5-ethynyl-6-fluoronaphthalen-2-ol;

(6S)-4-(2-{[(4aS,7aR)-1-{[(1r,3s)-3-hydroxy-3-methylcyclobutyl]methyl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(2R,4r,6S)-2,6-dimethyloxan-4-yl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(3R)-1-(2-{[(4aS,7aR)-1-[(2R,4r,6S)-2,6-dimethyloxan-4-yl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-3-methylpiperidin-3-ol;

(3R)-1-(2-{[(4aS,7aR)-1-{[(1s,3s)-3-methoxycyclobutyl]methyl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-3-methylpiperidin-3-ol;

(6S)-4-(2-{[(4aS,7aR)-1-methyl-octahydro-1H-cyclopenta[b]pyridin-4a-yl]methoxy}-7-(8-ethynyl-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-methyl-octahydro-1H-cyclopenta[b]pyridin-4a-yl]methoxy}-8-fluoro-7-(8-fluoro-3-hydroxynaphthalen-1-yl)pyrido[4,3-d]pyrimidin-4-yl)-6-methyl-1,4-oxazepan-6-ol;

(6S)-4-(2-{[(4aS,7aR)-1-{[(1S)-2,2-dimethylcyclopropyl]methyl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(3R)-1-(2-{[(4aS,7aR)-1-[3-(hydroxymethyl)cyclobutyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-3-methylpiperidin-3-ol;

(6S)-4-(2-{[(4aS,7aR)-1-[3-(hydroxymethyl)cyclobutyl]-octahydro-1H-cyclopenta[b]pyridin-4a-yl]methoxy}-7-(8-ethynyl-7-fluoro-3-hydroxynaphthalen-1-yl)-8-fluoro-pyrido[4,3-d]pyrimidin-4-yl)-6-methyl-1,4-oxazepan-6-ol;

(6S)-4-(2-{[(4aS,7aR)-1-methyl-octahydro-1H-cyclopenta[b]pyridin-4a-yl]methoxy}-8-fluoro-7-(3-hydroxynaphthalen-1-yl)pyrido[4,3-d]pyrimidin-4-yl)-6-methyl-1,4-oxazepan-6-ol;

(6S)-4-(2-{[(4aS,7aR)-1-methyl-octahydro-1H-cyclopenta[b]pyridin-4a-yl]methoxy}-7-(8-ethyl-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(oxepan-4-yl)-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(1s,3s)-3-methoxycyclobutyl]-octahydro-1H-cyclopenta[b]pyridin-4a-yl]methoxy}-7-(8-ethynyl-7-fluoro-3-hydroxynaphthalen-1-yl)-8-fluoro-pyrido[4,3-d]pyrimidin-4-yl)-6-methyl-1,4-oxazepan-6-ol;

(3R)-1-(2-{[(4aS,7aR)-1-(3-hydroxycyclobutyl)-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-3-methylpiperidin-3-ol;

(6S)-4-(2-{[(4aS,7aR)-1-(3-hydroxycyclobutyl)-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(3R)-1-(2-{[(4aS,7aR)-1-[(oxolan-2-yl)methyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-3-methylpiperidin-3-ol;

(3R)-1-(2-{[(4aS,7aR)-1-[(oxolan-2-yl)methyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-3-methylpiperidin-3-ol;

(6S)-4-(2-{[(4aS,7aR)-1-[(oxan-4-yl)methyl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(2-hydroxy-2-methylpropyl)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(oxan-4-yl)methyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-{[(4S)-2,2-dimethyl-1,3-dioxolan-4-yl]methyl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-{[(3R)-2,2-difluoro-3-methylcyclopropyl]methyl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(3R)-1-(2-{[(4aS,7aR)-1-{[(3R)-2,2-difluoro-3-methylcyclopropyl]methyl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-3-methylpiperidin-3-ol;

4-(2-{[(4aS,7aR)-1-{6-oxaspiro[3.4]octan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-{6-oxaspiro[3.4]octan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-{6-oxaspiro[3.4]octan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]cyclohexane-1-carbonitrile;

4-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]cyclohexane-1-carbonitrile;

4-(2-{[(4aS,7aR)-1-(4-methoxycyclohexyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(4-methoxycyclohexyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-(4-ethynylcyclohexyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(1,4-dioxan-2-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethyl-6-fluoronaphthalen-2-ol;

4-(2-{[(4aS,7aR)-1-{7-oxaspiro[3.5]nonan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethyl-6-fluoronaphthalen-2-ol;

4-(2-{[(4aS,7aR)-1-{1-oxaspiro[3.5]nonan-7-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-{1-oxaspiro[3.5]nonan-7-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-{3-oxaspiro[5.5]undecan-9-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-[(1,4-dioxepan-6-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-{8-oxaspiro[4.5]decan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-{8-oxaspiro[4.5]decan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

4-(2-{[(4aS,7aR)-1-{8-oxaspiro[4.5]decan-2-yl}-octahydro-1H-cyclopenta[b]pyridin-4a-yl]methoxy}-8- fluoro-4-(1,4-oxazepan-4-yl)pyrido[4,3-d]pyrimidin-7-yl)-5-ethynyl-6-fluoronaphthalen-2-ol;

(6S)-4-(2-{[(4aS,7aR)-1-{2-oxaspiro[3.3]heptan-6-yl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

6-[(4aS,7aR)-4a-({[7-(8-ethynyl-7-fluoro-3-hydroxynaphthalen-1-yl)-8-fluoro-4-[(6S)-6-hydroxy-6-methyl-1,4-oxazepan-4-yl]pyrido[4,3-d]pyrimidin-2-yl]oxy}methyl)-octahydro-1H-cyclopenta[b]pyridin-1-yl]-2¿6-thiaspiro[3.3]heptane-2,2-dione;

(6S)-4-(2-{[(4aS,7aR)-1-{7-oxaspiro[3.5]nonan-2-yl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-{2-oxaspiro[3.5]nonan-7-yl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol;

4-(2-{[(4aS,7aR)-1-{[(3R)-2,2-difluoro-3-methylcyclopropyl]methyl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol;

(6S)-4-(2-{[(4aS,7aR)-1-{6-oxaspiro[3.4]octan-2-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-{7-oxaspiro[3.5]nonan-2-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(4-methoxycyclohexyl)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(2R)-2-methyloxan-4-yl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-{2-oxaspiro[3.5]nonan-7-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-cyclobutyl-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(2S)-2-methyloxan-4-yl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(1s,3s)-3-[(4aS,7aR)-4a-({[7-(8-ethyl-7-fluoro-3-hydroxynaphthalen-1-yl)-8-fluoro-4-[(6S)-6-hydroxy-6-methyl-1,4-oxazepan-4-yl]pyrido[4,3-d]pyrimidin-2-yl]oxy}methyl)-octahydro-1H-cyclopenta[b]pyridin-1-yl]cyclobutane-1-carbonitrile;

(6S)-4-(2-{[(4aS,7aR)-1-[(1s,3s)-3-methoxycyclobutyl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(1s,3s)-3-[(4aS,7aR)-4a-({[7-(8-ethynyl-7-fluoro-3-hydroxynaphthalen-1-yl)-8-fluoro-4-[(6S)-6-hydroxy-6-methyl-1,4-oxazepan-4-yl]pyrido[4,3-d]pyrimidin-2-yl]oxy}methyl)-octahydro-1H-cyclopenta[b]pyridin-1-yl]cyclobutane-1-carbonitrile;

6S)-4-(2-{[(4aS,7aR)-1-{[(1s,3s)-3-methoxycyclobutyl]methyl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(2R,4r,6S)-2,6-dimethyloxan-4-yl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(1s,3s)-3-methoxycyclobutyl]-octahydro-1H-cyclopenta[b]pyridin-4a-yl]methoxy}-7-(5-chloro-6-methyl-1H-indazol-4-yl)-8-fluoropyrido[4,3-d]pyrimidin-4-yl)-6-methyl-1,4-oxazepan-6-ol;

(6S)-4-(2-{[(4aS,7aR)-1-[(1s,3s)-3-methoxycyclobutyl]-octahydro-1H-cyclopenta[b]pyridin-4a-yl]methoxy}-7-(6-chloro-5-methyl-1H-indazol-4-yl)-8-fluoropyrido[4,3-d]pyrimidin-4-yl)-6-methyl-1,4-oxazepan-6-ol;

(6S)-4-(2-{[(4aS,7aR)-1-cyclopropyl-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-propyl-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-cyclopropyl-octahydro-1H-cyclopenta[b]pyridin-4a-yl]methoxy}-7-(7,8-difluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-cyclopropyl-octahydro-1H-cyclopenta[b]pyridin-4a-yl]methoxy}-8-fluoro-7-(8-fluoro-3-hydroxynaphthalen-1-yl)pyrido[4,3-d]pyrimidin-4-yl)-6-methyl-1,4-oxazepan-6-ol;

(6S)-4-(2-{[(4aS,7aR)-1-[(2,2-difluorocyclopropyl)methyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol (diastereomer 1);

(6S)-4-(2-{[(4aS,7aR)-1-[(2,2-difluorocyclopropyl)methyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol (diastereomer 2);

(6S)-4-(2-{[(4aS,7aR)-1-(3-aminocyclobutyl)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(oxolan-3-yl)methyl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(3R)-1-(2-{[(4aS,7aR)-1-(cyclopropylmethyl)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-3-methylpiperidin-3-ol;

(3R)-1-(2-{[(4aS,7aR)-1-{7-oxaspiro[3.5]nonan-2-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-3-methylpiperidin-3-ol;

(6S)-4-(2-{[(4aS,7aR)-1-[(1s,3s)-3-methoxycyclobutyl]-octahydro-1H-cyclopenta[b]pyridin-4a-yl]methoxy}-7-(8-chloro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(oxolan-3-yl)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (diastereomer 1);

(6S)-4-(2-{[(4aS,7aR)-1-(oxolan-3-yl)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (diastereomer 2);

(3R)-1-(2-{[(4aS,7aR)-1-[(1s,3s)-3-methoxycyclobutyl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-3-methylpiperidin-3-ol;

(3R)-1-(2-{[(4aS,7aR)-1-{2-oxaspiro[3.3]heptan-6-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-3-methylpiperidin-3-ol;

(6S)-4-(2-{[(4aS,7aR)-1-{8-oxabicyclo[3.2.1]octan-3-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (diastereomer 1);

(6S)-4-(2-{[(4aS,7aR)-1-{8-oxabicyclo[3.2.1]octan-3-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (diastereomer 2);

(3R)-1-(2-{[(4aS,7aR)-1-[(2R,4r,6S)-2,6-dimethyloxan-4-yl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-3-methylpiperidin-3-ol;

(6S)-4-(2-{[(4aS,7aR)-1-{2-oxaspiro[4.5]decan-8-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (diastereomer 1);

(6S)-4-(2-{[(4aS,7aR)-1-{2-oxaspiro[4.5]decan-8-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (diastereomer 2);

(6S)-4-(2-{[(4aS,7aR)-1-{1-oxaspiro[3.5]nonan-7-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (diastereomer 1);

(6S)-4-(2-{[(4aS,7aR)-1-{1-oxaspiro[3.5]nonan-7-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (diastereomer 2);

(6S)-4-(2-{[(4aS,7aR)-1-(oxetan-3-yl)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(3-methyloxetan-3-yl)methyl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(cyclopropylmethyl)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(2-methoxy-2-methylpropyl)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-(oxetan-3-yl)-octahydro-1H-cyclopenta[b]pyridin-4a-yl]methoxy}-8-fluoro-7-(8-fluoro-3-hydroxynaphthalen-1-yl)pyrido[4,3-d]pyrimidin-4-yl)-6-methyl-1,4-oxazepan-6-ol;

(6S)-4-(2-{[(4aS,7aR)-1-(2H3)methyl-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-{2,5-dioxaspiro[3.4]octan-7-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (diastereomer 1);

(6S)-4-(2-{[(4aS,7aR)-1-{2,5-dioxaspiro[3.4]octan-7-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (diastereomer 2);

(6S)-4-(2-{[(4aS,7aR)-1-{2-oxaspiro[3.3]heptan-6-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(1s,3s)-3-methoxycyclobutyl]-octahydro-1H-cyclopenta[b]pyridin-4a-yl]methoxy}-7-(8-ethyl-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(2R,4r,6S)-2,6-dimethyloxan-4-yl]-octahydro-1H-cyclopenta[b]pyridin-4a-yl]methoxy}-7-(8-ethyl-3-hydroxynaphthalen-1-yl)-8-fluoropyrido[4,3-d]pyrimidin-4-yl)-6-methyl-1,4-oxazepan-6-ol;

6-[(4aS,7aR)-4a-({[7-(8-ethyl-7-fluoro-3-hydroxynaphthalen-1-yl)-8-fluoro-4-[(6S)-6-hydroxy-6-methyl-1,4-oxazepan-4-yl]pyrido[4,3-d]pyrimidin-2-yl]oxy}methyl)-octahydro-1H-cyclopenta[b]pyridin-1-yl]-2lambda6-thiaspiro[3.3]heptane-2,2-dione;

(6S)-4-(2-{[(4aS,7aR)-1-cyclopropyl-octahydro-1H-cyclopenta[b]pyridin-4a-yl]methoxy}-7-(8-ethyl-3-hydroxynaphthalen-1-yl)-8-fluoropyrido[4,3-d]pyrimidin-4-yl)-6-methyl-1,4-oxazepan-6-ol;

(6S)-4-(2-{[(6'R,7'aS)-6'-fluoro-hexahydrospiro[cyclopropane-1,2'-pyrrolizin]-7'a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(6'R,7'aR)-6'-fluoro-hexahydrospiro[cyclopropane-1,2'-pyrrolizin]-7'a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(2R,4r,6S)-2,6-dimethyloxan-4-yl]-octahydro-1H-cyclopenta[b]pyridin-4a-yl]methoxy}-7-(7,8-difluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-[(1s,3s)-3-methoxycyclobutyl]-octahydro-1H-cyclopenta[b]pyridin-4a-yl]methoxy}-7-(7,8-difluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-cyclopropyl-octahydro-1H-cyclopenta[b]pyridin-4a-yl]methoxy}-7-(7,8-difluoro-3-hydroxynaphthalen-1-yl)-8-fluoropyrido[4,3-d]pyrimidin-4-yl)-6-methyl-1,4-oxazepan-6-ol;

(6S)-4-(2-{[(4aS,7aR)-1-propyl-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol;

(2R,6S)-4-(2-{[(4aS,7aR)-1-[(1s,3s)-3-methoxycyclobutyl]-octahydro-1H-cyclopenta[b]pyridin-4a-yl]methoxy}-7-(8-ethyl-7-fluoro-3-hydroxynaphthalen-1- yl)-8-fluoropyrido[4,3-d]pyrimidin-4-yl)-2-(hydroxymethyl)-6-methyl-1,4-oxazepan-6-ol;
(2R,6S)-4-(2-{[(4aS,7aR)-1-{2-oxaspiro[3.3]heptan-6-yl}-octahydro-1H-cyclopenta[b]pyridin-4a-yl]methoxy}-7-(8-ethyl-7-fluoro-3-hydroxynaphthalen-1-yl)-8-fluoro-pyrido[4,3-d]pyrimidin-4-yl)-2-(hydroxymethyl)-6-methyl-1,4-oxazepan-6-ol;
(2R,6S)-4-(2-{[(4aS,7aR)-1-cyclopropyl-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-2-(hydroxymethyl)-6-methyl-1,4-oxazepan-6-ol;
(2R,6S)-4-(2-{[(4aS,7aR)-1-[(oxan-4-yl)methyl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-2-(hydroxymethyl)-6-methyl-1,4-oxazepan-6-ol;
(2R,6S)-4-(2-{[(4aS,7aR)-1-[(2R,4r,6S)-2,6-dimethyloxan-4-yl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-2-(hydroxymethyl)-6-methyl-1,4-oxazepan-6-ol;
(2R,6S)-4-(2-{[(4aS,7aR)-1-[(2R,4s,6S)-2,6-dimethyloxan-4-yl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-2-(hydroxymethyl)-6-methyl-1,4-oxazepan-6-ol;
(6S)-4-(2-{[(4aS,7aR)-1-[(2R,4s,6S)-2,6-dimethyloxan-4-yl]-octahydro-1H-cyclopenta[b]pyridin-4a-yl]methoxy}-7-(8-ethyl-7-fluoro-3-hydroxynaphthalen-1-yl)-8-fluoro-pyrido[4,3-d]pyrimidin-4-yl)-6-methyl-1,4-oxazepan-6-ol (diastereomer 1); and
(6S)-4-(2-{[(4aS,7aR)-1-[(2R,4s,6S)-2,6-dimethyloxan-4-yl]-octahydro-1H-cyclopenta[b]pyridin-4a-yl]methoxy}-7-(8-ethyl-7-fluoro-3-hydroxynaphthalen-1-yl)-8-fluoro-pyrido[4,3-d]pyrimidin-4-yl)-6-methyl-1,4-oxazepan-6-ol (diastereomer 2);

or a pharmaceutically acceptable salt thereof.

In some aspects, the present disclosure provides a pharmaceutical composition comprising a compound described herein, or a pharmaceutically acceptable salt thereof, and one or more pharmaceutically acceptable excipients.

In some aspects, the present disclosure provides an oral dosage form comprising a compound described herein, or a pharmaceutically acceptable salt thereof, and one or more pharmaceutically acceptable excipients.

In some aspects, the compound is an atropisomer of a compound of any of the prior aspects. In certain aspects, the compound is a stable atropisomer as described herein. In some aspects, the compound is a particular diastereomer, when a chiral center carbon atom in the structure does not have the stereochemistry indicated by hashed wedged and solid wedged bonds.

In another aspect, the present disclosure provides a method of treating a KRAS G12D-associated disease or disorder associated with KRAS G12A, KRAS G12C, KRAS G12D, KRAS G12R, KRAS G12S, KRAS G12V, KRAS G13D and/or KRAS Q61H in a subject in need of such treatment, the method comprising administering to the subject a therapeutically effective amount of a compound described herein, or a pharmaceutically acceptable salt thereof, or a pharmaceutical composition thereof as defined herein.

In another aspect, the present disclosure provides a method for treating a cancer susceptible to KRAS G12A, KRAS G12C, KRAS G12D, KRAS G12R, KRAS G12S, KRAS G12V, KRAS G13D and/or KRAS Q61H inhibition in a subject in need thereof, the method comprising administering to the subject a compound described herein, or a pharmaceutically acceptable salt thereof.

In some aspects, the present disclosure provides a method for treating a cancer expressing a KRAS mutation and/or a KRAS copy number amplification in a subject in need thereof, the method comprising administering to the subject a compound described herein, or a pharmaceutically acceptable salt thereof.

In some aspects, the present disclosure provides a method for treating a cancer expressing a KRAS G13R, Q61R, A146T, A146V, A59G, G12A, G12C, G12D, G12R, G12S, G12V, G13C, G13D, Q61H, Q61K, and/or a KRAS Q61L mutation, and/or a KRAS copy number amplification, in a subject in need thereof, the method comprising administering to the subject a compound described herein, or a pharmaceutically acceptable salt thereof.

In some aspects, the present disclosure provides a method for treating a cancer expressing KRAS G12A, KRAS G12C, KRAS G12D, KRAS G12R, KRAS G12S, KRAS G12V, KRAS G13D, KRAS A146T, and/or KRAS Q61H mutation in a subject in need thereof, the method comprising administering to the subject a compound, a pharmaceutically acceptable salt of a compound, a composition, or a dosage form described herein.

In some aspects, the present disclosure provides a method for treating a cancer expressing KRAS G12A, KRAS G12C, KRAS G12D, KRAS G12R, KRAS G12S, KRAS G12V, KRAS G13D, and/or KRAS Q61H mutation in a subject in need thereof, the method comprising administering to the subject a compound described herein, or a pharmaceutically acceptable salt thereof.

In another aspect, the present disclosure provides a method of inhibiting cell proliferation, in vitro or in vivo, the method comprising contacting a cell with a therapeutically effective amount of a compound described herein, or a pharmaceutically acceptable salt thereof, or a pharmaceutical composition thereof as defined herein.

In another aspect, the present disclosure provides a method for treating a cancer in a subject in need thereof, the method comprising administering to the subject a compound described herein, or a pharmaceutically acceptable salt thereof. In some aspects, the cancer is pancreatic cancer, colorectal cancer, lung cancer, gastric cancer, breast cancer, bladder cancer, cervical cancer, ovarian cancer, cancer of the uterus, or a combination thereof. In some aspects, the cancer is non-small cell lung cancer.

In another aspect, the present disclosure provides a compound described herein, or a pharmaceutically acceptable salt thereof, or a pharmaceutical composition thereof as defined herein, for use in the treatment of a disease or disorder associated with KRAS G12A, KRAS G12C, KRAS G12D, KRAS G12R, KRAS G12S, KRAS G12V, KRAS G13D and/or KRAS Q61H.

In another aspect, the present disclosure provides a use of a compound described herein, or a pharmaceutically acceptable salt thereof, as defined herein in the manufacture of a medicament for the treatment of cancer.

In another aspect, the present disclosure provides the use of a compound described herein, or a pharmaceutically acceptable salt thereof, as defined herein in the manufacture of a medicament for the inhibition of activity of inhibiting KRAS G12A, KRAS G12C, KRAS G12D, KRAS G12R, KRAS G12S, KRAS G12V, KRAS G13D and/or KRAS Q61H.

In another aspect, the present disclosure provides the use of a compound described herein, or a pharmaceutically acceptable salt thereof, as defined herein, in the manufacture of a medicament for the treatment of a disease or disorder associated with KRAS G12A, KRAS G12C, KRAS G12D, KRAS G12R, KRAS G12S, KRAS G12V, KRAS G13D and/or KRAS Q61H.

In some aspects, the present disclosure provides an atropisomer of a compound of any of the prior aspects. In certain embodiments, the compound is a stable atropisomer as described herein.

DETAILED DESCRIPTION

The issued U.S. patents, published U.S., international, and foreign patent applications, and references that are cited herein are hereby incorporated by reference to the same extent as if each was specifically and individually indicated to be incorporated by reference.

Unless otherwise indicated, any atom with unsatisfied valences is assumed to have hydrogen atoms sufficient to satisfy the valences.

The singular forms "a," "an," and "the" include plural referents unless the context dictates otherwise.

As used herein, the term "or" is a logical disjunction (i.e., and/or) and does not indicate an exclusive disjunction unless expressly indicated such as with the terms "either," "unless," "alternatively," and words of similar effect.

As used herein, the phrase "or a pharmaceutically acceptable salt thereof" refers to at least one compound, or at least one salt of the compound, or a combination thereof.

The term "$C_2$-$C_4$alkenyl," as used herein, refers to a group derived from a straight or branched chain hydrocarbon containing from two to four carbon atoms and at least one double bond.

The term "$C_1$-$C_3$alkoxy," as used herein, refers to a $C_{1-3}$alkyl group attached to the parent molecular moiety through an oxygen atom.

The terms "$C_1$-$C_4$alkoxy," and "$C_{1-4}$ alkoxy," as used herein, refers to a $C_1$-$C_4$alkyl group attached to the parent molecular moiety through an oxygen atom.

The terms "$C_1$-$C_4$alkoxy$C_1$-$C_4$alkyl," and "$C_{1-4}$alkoxy $C_{1-4}$alkyl," as used herein, refer to a $C_1$-$C_4$alkoxy group attached to the parent molecular moiety through a $C_1$-$C_4$alkyl group.

The terms "$C_1$-$C_4$alkoxycarbonyl," and "$C_{1-4}$alkoxycarbonyl," as used herein, refer to a $C_1$-$C_4$alkoxy group attached to the parent molecular moiety through a carbonyl group.

The term "$C_{1-3}$ alkyl," as used herein, refers to a group derived from a straight or branched chain saturated hydrocarbon containing from one to three carbon atoms.

The terms "$C_1$-$C_4$alkyl," and "$C_{1-4}$ alkyl," as used herein, refer to a group derived from a straight or branched chain saturated hydrocarbon containing from one to four carbon atoms.

The term "$C_{1-6}$alkyl," as used herein, refer to a group derived from a straight or branched chain saturated hydrocarbon containing from one to six carbon atoms.

The term "$C_2$-$C_6$alkyl," as used herein, refers to a group derived from a straight or branched chain saturated hydrocarbon containing from two to six carbon atoms.

The term "$C_{1-4}$ alkylamido," as used herein, refers to a $C_1$-$C_4$alkyl group attached to the parent molecular moiety through an amide (—NHC(O)—) group.

The term "$C_{1-4}$ alkylcarbamato," as used herein, refers to a $C_1$-$C_4$alkyl group attached to the parent molecular moiety through a carbamate (—NHC(O)O—) group.

The terms "$C_1$-$C_4$alkylcarbonyl," and "$C_{1-4}$alkylcarbonyl," as used herein, refer to a $C_1$-$C_4$alkyl group attached to the parent molecular moiety through a carbonyl group.

The term "$C_{1-6}$ alkylsulfonyl," as used herein, refers to —$S(O)_2C_{1-6}$alkyl.

The term "cyano," as used herein, refers to —CN.

The terms "$C_3$-$C_6$cycloalkyl," and "$C_{3-6}$ cycloalkyl," as used herein, refers to a saturated monocyclic ring system having three to six carbon atoms and zero heteroatoms (e.g., cyclopropyl, cyclobutyl, cyclopentyl, or cyclohexyl). The term "cycloalkyl" also includes groups in which the cycloalkyl ring is fused to a three, four, five-, or six-membered carbocyclic ring. The term "cycloalkyl" also includes a cycloalkyl group further substituted with one or more spirocyclic groups that are attached to the cycloalkyl group through a spiro carbon.

The terms "$C_3$-$C_6$cycloalkylcarbonyl," and "$C_{3-6}$cycloalkylcarbonyl," as used herein, refer to a $C_3$-$C_6$ cycloalkyl group (e.g., cyclopropyl, cyclobutyl, cyclopentyl, cyclohexyl) attached to the parent molecular moiety through a carbonyl group.

The term "cyclopropylsulfonyl," as used herein, refers —$SO_2$-cyclopropyl.

The term "ethylsulfonyl," as used herein, refers to —$S(O)_2CH_2CH_3$.

The term "$C_{3-6}$ heterocycloalkyl," as used herein, refers to a three, four-, five-, or six-membered saturated ring containing one or two, heteroatoms independently selected from nitrogen, oxygen, and sulfonyl (—$SO_2$). The term "heterocycloalkyl" also includes groups in which the heterocycloalkyl ring is fused to a three, four, five-, or six-membered carbocyclic ring as well as fused bicyclic structures. The term "heterocycloalkyl" also includes a heterocycloalkyl group further substituted with one or more spirocyclic groups that are attached to the heterocycloalkyl group through a spiro carbon. Examples of heterocyclyl groups include, but are not limited to, dihydro-1'H,3'H,5'H-dispiro[cyclopropane-1,2'-pyrrolizine-6',1"-cyclopropane], hexahydro-2H-1,4-dioxa-2a1-azacyclopenta[cd]pentalenyl, hexahydropyrrolizinyl, indolinyl, morpholinyl, octahydroindolizinyl, octahydroquinolizinyl, piperazinyl, piperidinyl, pyrrolidinyl, tetrahydrofuranyl, tetrahydropyranyl, oxetanyl, azetidinyl, 1,2-dioxanyl, 1,3-dioxanyl, 1,4-dioxanyl, triemethylenyl oxide, imidazolidinyl, homopiperazinyl, pyrrolinyl, tetrahydrothiofuranyl, and pyranyl.

The term "$C_{3-7}$ heterocycloalkyl," as used herein, refers to a three, four-, five-, six, or seven-membered saturated ring containing one or two, heteroatoms independently selected from nitrogen, oxygen, and sulfonyl (—$SO_2$). The term "heterocycloalkyl" also includes groups in which the heterocycloalkyl ring is fused to a three, four, five-, or six-membered carbocyclic ring. The term "heterocycloalkyl" also includes a heterocycloalkyl group further substituted with one or more spirocyclic groups that are attached to the heterocycloalkyl group through a spiro carbon.

The term "amido," as used herein, refers to —$C(O)NH_2$.

The term "halo," as used herein, refers to F, Cl, Br, or I.

The term "$C_{1-4}$ haloalkoxy," as used herein, refers to a $C_1$-$C_4$ alkoxy group substituted by one, two, or three halogen atoms.

The term "halo $C_{1-4}$ alkoxycarbonyl," as used herein, refers to a $C_{1-4}$ haloalkoxy group attached to the parent molecular moiety through a carbonyl group.

The terms "$C_{1-4}$ haloalkyl," and "halo$C_{1-4}$ alkyl," as used herein, refer to a $C_1$-$C_4$ alkyl group substituted with one, two, or three halogen atoms.

The terms "halo$C_1$-$C_6$alkyl," and "halo$C_{1-6}$ alkyl," as used herein, refers to a $C_1$-$C_6$alkyl group substituted with one, two, or three halogen atoms.

The term "halo$C_1$-$C_4$alkylcarbonyl," as used herein, refers to a halo$C_1$-$C_4$alkyl group attached to the parent molecular moiety through a carbonyl group.

The term "hydroxy," as used herein, refers to —OH.

The terms "$C_{1-4}$ hydroxyalkyl," "$C_1$-$C_4$hydroxyalkyl," and "hydroxy$C_1$-$C_4$alkyl," as used herein, refer to a hydroxy group attached to the parent molecular moiety through a $C_1$-$C_4$alkyl group.

The terms "hydroxy$C_1$-$C_6$alkyl," and "hydroxy$C_{1-6}$alkyl," as used herein, refer to a hydroxy group attached to the parent molecular moiety through a $C_1$-$C_6$alkyl group.

The terms "hydroxy-halo$C_1$-$C_6$alkyl," and "hydroxy-halo$C_{1-6}$alkyl," as used herein, refer to a $C_1$-$C_6$alkyl group substituted with one, two, or three halogen atoms and at least one hydroxy.

The term "methylsulfonyl," as used herein, refers to —$S(O)_2CH_3$.

The term "methylsulfonyl$C_1$-$C_6$alkyl," as used herein, refers to a methylsulfonyl group attached to the parent molecular moiety through a $C_{1-6}$ alkyl group.

The term "oxo," as used herein, refers to =O.

An additional aspect of the subject matter described herein is the use of the disclosed compounds as radiolabeled ligands for development of ligand binding assays or for monitoring of in vivo adsorption, metabolism, distribution, receptor binding or occupancy, or compound disposition. For example, a compound described herein can be prepared using a radioactive isotope and the resulting radiolabeled compound can be used to develop a binding assay or for metabolism studies. Alternatively, and for the same purpose, a compound described herein can be converted to a radiolabeled form by catalytic tritiation using methods known to those skilled in the art.

Certain compounds of the present disclosure exist as stereoisomers. It should be understood that when stereochemistry is not specified, the present disclosure encompasses all stereochemical isomeric forms, or mixtures thereof, which possess the ability inhibit mutant KRAS. Therefore, unless otherwise indicated, single stereochemical isomers as well as enantiomeric, racemic and diastereomeric mixtures of the present chemical entities are within the scope of the invention. When a stereochemical configuration is denoted for a compound, the diastereoisomeric or enantiomeric excess of the compound is at least 90%.

Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure exist as atropisomers. The term "atropisomers" refers to conformational stereoisomers which occur when rotation about a single bond in the molecule is prevented, or greatly slowed, as a result of steric interactions with other parts of the molecule and the substituents at both ends of the single bond are asymmetrical (i.e., optical activity arises without requiring an asymmetric carbon center or stereocenter). Where the rotational barrier about the single bond is high enough, and interconversion between conformations is slow enough, separation and isolation of the isomeric species may be permitted. Atropisomers are enantiomers (or epimers) without a single asymmetric atom.

The atropisomers can be considered stable if the barrier to interconversion is high enough to permit the atropisomers to undergo little or no interconversion at room temperature for at least a week. In some aspects the atropisomers undergo little or no interconversion at room temperature for at least a year. In some aspects, an atropisomeric compound of the disclosure does not undergo more than about 5% interconversion to its opposite atropisomer at room temperature during one week when the atropisomeric compound is in substantially pure form, which is generally a solid state. In some aspects, an atropisomeric compound of the disclosure does not undergo more than about 5% interconversion to its opposite atropisomer at room temperature (approximately 25° C.) during one year. In some aspects, the atropisomeric compounds of the disclosure are stable enough to undergo no more than about 5% interconversion in an aqueous pharmaceutical formulation held at 0° C. for at least one week. The present chemical entities, pharmaceutical compositions and methods are meant to include all such possible atropisomers, including racemic mixtures, diastereomeric mixtures, epimeric mixtures, optically pure forms of single atropisomers, and intermediate mixtures.

The energy barrier to thermal racemization of atropisomers may be determined by the steric hindrance to free rotation of one or more bonds forming a chiral axis. Certain biaryl compounds exhibit atropisomerism where rotation around an interannular bond lacking C2 symmetry is restricted. The free energy barrier for isomerization (enantiomerization) is a measure of the stability of the interannular bond with respect to rotation. Optical and thermal excitation can promote racemization of such isomers, dependent on electronic and steric factors.

Ortho-substituted biaryl compounds may exhibit this type of conformational, rotational isomerism. Such biaryls are enantiomeric, chiral atropisomers where the $sp^2$-$sp^2$ carbon-carbon, interannular bond between the aryl rings has a sufficiently high energy barrier to prevent free rotation, and where substituents $W^1 \neq W^2$ and $W^3 \neq W^4$ render the molecule asymmetric.

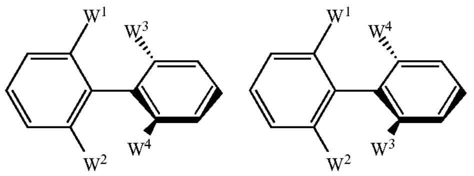

The steric interaction between $W^1$:$W^3$, $W^1$:$W^4$, and/or $W^2$:$W^4$, $W^2$:$W^3$ is large enough to make the planar conformation an energy maximum. Two non-planar, axially chiral enantiomers then exist as atropisomers when their interconversion is slow enough such that they can be isolated free of each other. Bold lines and dashed lines in the figures shown above indicate those moieties, or portions of the molecule, which are sterically restricted due to a rotational energy barrier. Balded moieties exist orthogonally above the plane of the page, and dashed moieties exist orthogonally below the plane of the page. The 'flat' part of the molecule (the left ring in each of the two depicted biaryls) is in the plane of the page.

The pharmaceutical compositions of the disclosure can include one or more pharmaceutically acceptable salts. A "pharmaceutically acceptable salt" refers to a salt that retains the desired biological activity of the parent compound and does not impart any undesired toxicological effects (see e.g., Berge, S. M. et al., *J. Pharm. Sci.,* 66:1-19 (1977)). The salts can be obtained during the final isolation and purification of the compounds described herein, or separately be reacting a free base function of the compound with a suitable acid or by reacting an acidic group of the compound with a suitable base. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutical Compositions

In another aspect, the present disclosure provides a composition, e.g., a pharmaceutical composition, containing one or a combination of the compounds described within the present disclosure, formulated together with a pharmaceutically acceptable carrier. Pharmaceutical compositions of the disclosure also can be administered in combination therapy, i.e., combined with other agents, as described herein.

As used herein, "pharmaceutically acceptable carrier" includes any and all solvents, dispersion media, coatings, antibacterial and antifungal agents, isotonic and absorption delaying agents, and the like that are physiologically compatible. In some aspects, the carrier is suitable for intravenous, intramuscular, subcutaneous, parenteral, spinal or epidermal administration (e.g., by injection or infusion). Depending on the route of administration, the active compound can be coated in a material to protect the compound from the action of acids and other natural conditions that can inactivate the compound.

The pharmaceutical compositions of the present disclosure can be administered via one or more routes of administration using one or more of a variety of methods known in the art. As will be appreciated by the skilled artisan, the route and/or mode of administration will vary depending upon the desired results. In some aspects, the routes of administration for compounds of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, some methods of preparation are reduced pressure drying and freeze-drying (lyophilization) that yield a powder of the active ingredient plus any additional desired ingredient from a previously sterile-filtered solution thereof.

Examples of suitable aqueous and non-aqueous carriers that can be employed in the pharmaceutical compositions of the disclosure include water, ethanol, polyols (such as glycerol, propylene glycol, polyethylene glycol, and the like), and suitable mixtures thereof, vegetable oils, and injectable organic esters. Proper fluidity can be maintained, for example, by the use of coating materials, such as lecithin, by the maintenance of the required particle size in the case of dispersions, and by the use of surfactants.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution or as a liquid with ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be desirable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Alternatively, the compounds of the disclosure can be administered via a non-parenteral route, such as a topical, epidermal or mucosal route of administration, for example, intranasally, orally, vaginally, rectally, sublingually or topically.

Any pharmaceutical composition contemplated herein can, for example, be delivered orally via any acceptable and suitable oral preparation. Exemplary oral preparations include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the disclosure can contain at least one agent selected from the group consisting of sweetening agents, flavoring agents, coloring agents, demulcents, antioxidants, and preserving agents.

A tablet can, for example, be prepared by admixing at least one compound described herein and/or at least one pharmaceutically acceptable salt thereof with at least one non-toxic pharmaceutically acceptable excipient suitable for the manufacture of tablets.

An aqueous suspension can be prepared, for example, by admixing at least one compound described herein and/or at least one pharmaceutically acceptable salt thereof with at least one excipient suitable for the manufacture of an aqueous suspension, including, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example, heptadecathylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound described herein and/or at least one pharmaceutically acceptable salt thereof in either a vegetable oil, such as, for example, *arachis* oil, sesame oil, and coconut oil; or in mineral oil, such as, for example, liquid paraffin. An oily suspension can also contain at least one thickening agent, such as, for example, beeswax, hard paraffin, and cetyl alcohol. In order to provide a palatable oily suspension, at least one of the sweetening agents already described herein above, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound described herein and/or at least one pharmaceutically acceptable salt thereof with at least one dispersing and/or wetting agent, at least one suspending agent, and/or at least one preservative. Suitable dispersing agents, wetting agents, and suspending agents are already described above. Exemplary preservatives include, but are not limited to, for example, anti-oxidants, e.g., ascorbic acid. In addition, dispersible powders and granules can also contain at least one excipient, including, but not limited to, for example, sweetening agents, flavoring agents, and coloring agents.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Robinson, J. R., ed., Sustained and Controlled Release Drug Delivery Systems, Marcel Dekker, Inc., New York (1978).

Therapeutic compositions can be administered with medical devices known in the art. For example, in one aspect, a therapeutic composition of the disclosure can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medication through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain aspects, the compounds of the present disclosure can be administered parenterally, i.e., by injection, including, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and/or infusion.

In some aspects, the compounds of the present disclosure can be administered orally, i.e, via a gelatin capsule, tablet, hard or soft capsule, or a liquid capsule.

Use of KRAS Inhibitors/Methods of Treating

Administration of a therapeutic agent described herein may include administration of a therapeutically effective amount of therapeutic agent. The term "therapeutically effective amount" as used herein refers, without limitation, to an amount of a therapeutic agent to treat a condition treatable by administration of a composition comprising the KRAS inhibitors described herein. That amount is the amount sufficient to exhibit a detectable therapeutic or ameliorative effect. The effect can include, for example and without limitation, treatment of the conditions listed herein. The precise effective amount for a subject will depend upon the subject's size and health, the nature and extent of the condition being treated, recommendations of the treating physician, and therapeutics or combination of therapeutics selected for administration.

The disclosed compounds strongly inhibit anchorage-independent cell growth and therefore have the potential to inhibit tumor metastasis. Accordingly, in another aspect the disclosure provides a method for inhibiting tumor metastasis, the method comprising administering an effective amount a pharmaceutical composition of comprising any of the compounds disclosed herein and a pharmaceutically acceptable carrier to a subject in need thereof.

Ras mutations including but not limited to KRAS mutations have also been identified in hematological malignancies (e.g., cancers that affect blood, bone marrow and/or lymph nodes). Accordingly, certain aspects are directed to administration of a disclosed compounds (e.g., in the form of a pharmaceutical composition) to a patient in need of treatment of a hematological malignancy. Such malignancies include, but are not limited to, leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMOL) and/or other leukemias. In other aspects, the compounds are useful for treatment of lymphomas such as all subtypes of Hodgkins lymphoma or non-Hodgkins lymphoma.

Determining whether a tumor or cancer comprises a KRAS mutation can be undertaken by assessing the nucleotide sequence encoding the KRAS protein, by assessing the amino acid sequence of KRAS protein, or by assessing the characteristics of a putative KRAS mutant protein. The sequence of wild-type human KRAS proteins is known in the art.

Methods for detecting a KRAS mutation are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some aspects, samples are evaluated for KRAS mutations including by real-time PCR. In real-time PCR, fluorescent probes specific for the KRAS mutation are used. When a mutation is present, the probe binds and fluorescence is detected. In some aspects, the KRAS mutation is identified using a direct sequencing method of specific regions (e.g., exon 2 and/or exon 3) in the KRAS gene, for example. This technique will identify all possible mutations in the region sequenced.

Methods for detecting a mutation in a KRAS protein are known by those of skill in the art. These methods include, but are not limited to, detection of a KRAS mutant using a binding agent (e.g., an antibody) specific for the mutant protein, protein electrophoresis and Western blotting, and direct peptide sequencing.

Methods for determining whether a tumor or cancer comprises a KRAS mutation can use a variety of samples. In some aspects, the sample is taken from a subject having a tumor or cancer. In some aspects, the sample is taken from a subject having a cancer or tumor. In some aspects, the sample is a fresh tumor/cancer sample. In some aspects, the sample is a frozen tumor/cancer sample. In some aspects, the sample is a formalin-fixed paraffin-embedded sample. In some aspects, the sample is processed to a cell lysate. In some aspects, the sample is processed to DNA or RNA. The disclosure also relates to a method of treating a hyperproliferative disorder in a mammal that comprises administering to said mammal a therapeutically effective amount of a compound of the present disclosure, or a pharmaceutically acceptable salt, ester, prodrug, solvate, hydrate or derivative thereof. In some aspects, said method relates to the treatment of cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip; and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some aspects, said method relates to the treatment of a non-cancerous hyperproliferative disorder such as benign hyperplasia of the skin (e.g., psoriasis), restenosis, or prostate (e.g., benign prostatic hypertrophy (BPH)).

In certain aspects, the disclosure relates to methods for treatment of lung cancers, the methods comprise administering an effective amount of any of the above-described compound (or a pharmaceutical composition comprising the same) to a subject in need thereof. In certain aspects the lung cancer is a non-small cell lung carcinoma (NSCLC), for example adenocarcinoma, squamous-cell lung carcinoma or large-cell lung carcinoma. In other aspects, the lung cancer is a small cell lung carcinoma. Other lung cancers treatable with the disclosed compounds include, but are not limited to, glandular tumors, carcinoid tumors and undifferentiated carcinomas. Subjects that can be treated with compounds of the disclosure, or pharmaceutically acceptable salt, ester, prodrug, solvate, tautomer, hydrate or derivative of said compounds, according to the methods of this disclosure include, for example, subjects that have been diagnosed as having acute myeloid leukemia, acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis; paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some aspects subjects that are treated with the compounds of the disclosure include subjects that have been diagnosed as having a non-cancerous hyperproliferative disorder such as benign hyperplasia of the skin (e.g., psoriasis), restenosis, or prostate (e.g., benign pro static hypertrophy (BPH)). The disclosure further provides methods of modulating a mutant KRAS protein activity by contacting the protein with an effective amount of a compound of the disclosure. Modulation can be inhibiting or activating protein activity. In some aspects, the disclosure provides methods of inhibiting protein activity by contacting the mutant KRAS protein with an effective amount of a compound of the disclosure in solution. In some aspects, the disclosure provides methods of inhibiting the mutant KRAS protein activity by contacting a cell, tissue, organ that express the protein of interest. In some aspects, the disclosure provides methods of inhibiting protein activity in a subject including but not limited to rodents and mammal (e.g., human) by administering into the subject an effective amount of a compound of the disclosure. In some aspects, the percentage modulation exceeds 25%, 30%, 40%, 50%, 60%, 70%, 80%, or 90%. In some aspects, the percentage of inhibiting exceeds 25%, 30%, 40%, 50%, 60%, 70%, 80%, or 90%. In some aspects, the disclosure provides methods of inhibiting KRAS activity in a cell by contacting said cell with an amount of a compound of the disclosure sufficient to inhibit the activity of a KRAS mutant in said cell. In some aspects, the disclosure provides methods of inhibiting mutant KRAS in a tissue by contacting said tissue with an amount of a compound of the disclosure sufficient to inhibit the activity of mutant KRAS in said tissue. In some aspects, the disclosure provides methods of inhibiting KRAS in an organism by contacting said organism with an amount of a compound of the disclosure sufficient to inhibit the activity of KRAS in said organism. In some aspects, the disclosure provides methods of inhibiting KRAS activity in an animal by contacting said animal with an amount of a compound of the disclosure sufficient to inhibit the activity of KRAS in said animal. In some aspects, the disclosure provides methods of inhibiting KRAS including in a mammal by contacting said mammal with an amount of a compound of the disclosure sufficient to inhibit the activity of KRAS in said mammal. In some aspects, the disclosure provides methods of inhibiting KRAS activity in a human by contacting said human with an amount of a compound of the disclosure sufficient to inhibit the activity of KRAS in said human. The present disclosure provides methods of treating a disease mediated by KRAS activity in a subject in need of such treatment. The present disclosure also provides methods for combination therapies in which an agent known to modulate other pathways, or other components of the same pathway, or even overlapping sets of target enzymes are used in combination with a compound of the present disclosure, or a pharmaceutically acceptable salt, ester, prodrug, solvate, tautomer, hydrate or derivative thereof.

The compounds can be made by methods known in the art including those described below and including variations within the skill of the art. Some reagents and intermediates are known in the art. Other reagents and intermediates can be made by methods known in the art using readily available materials. Any variables (e.g., numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the disclosure.

Synthesis

Abbreviations used herein include: AA for ammonium acetate; ACN or MeCN for acetonitrile; BOC or Boc for tert-butoxycarbonyl; BOP for (benzotriazol-1-yloxytris(dimethylamino)phosphonium hexafluorophosphate); t-Bu or tBu for tert-butyl; CDI for Carbonyldiimidazole; DAST for diethylaminosulfur trifluoride; DCM for dichloromethane; DEA for diethanolamine; dF(CF3)ppy for 2-(2,4-Difluorophenyl)-5-(trifluoromethyl)pyridine; DIBAL-H for diisobutylaluminum hydride; DIEA or DIPEA for diisopropylethylamine; DMA for dimethylacetamide; DMAP for N,N-dimethylaminopyridine; DMF for dimethylformamide; DMSO for dimethylsulfoxide; dppf for 1,1□-bis(diphenylphosphino) ferrocene; dtbbpy for 4,4'-Di-tert-butyl-2,2'-bipyridine; EtOAc for ethyl acetate; EtOH for ethanol; h for hours; IPA for isopropanol; LAH for lithium aluminum hydride; LCMS for liquid chromatography-mass spectrometry; LDA for Lithium diisopropylamide; LiHMDS for lithium bis(trimethylsilyl)amide; MeOH for methanol; min for minutes; MOM for methoxymethyl; $NaCNBD_3$ for Deuterated sodium cyanoborohydride; PCC for Pyridinium chlorochromate; NMP: N-methyl pyrrolidone; Piv for pivaloyl; SNAr for nucleophilic aromatic substitution; PyBOP for (Benzotriazol-1-yloxy)tripyrrolidinophosphonium hexafluorophosphateSELECTFLUOR for 1-(Chloromethyl)-4-fluoro-1,4-diazabicyclo[2.2.2]octane-1,4-diium ditetrafluoroborate; TBAF for tetrabutylammonium fluoride; TEA for trimethylamine; TFA for trifluoroacetic acid; $Tf_2O$ for Trifluoromethanesulfonic anhydride; and THF for tetrahydrofuran.

The compounds described herein can be prepared according to the methodology described in the Examples shown below.

Preparation of Intermediate 1: ethyl (S)-2-((1-phenylethyl)amino)cyclopent-1-ene-1-carboxylate

I

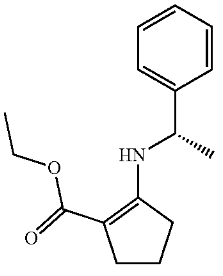

To a stirred solution of ethyl 2-oxocyclopentane-1-carboxylate (140.5 g, 900 mmol) and 4 Å molecular sieves in DCM (500 mL) was added (S)-1-phenylethan-1-amine (109 g, 900 mmol) at room temperature. The reaction mixture was stirred under reflux for 1 day. The reaction mixture was cooled to room temperature, filtered through a diatomaceous earth pad (CELITE™", Sigma Aldrich, St. Louis, MO) and the filtrate was concentrated under reduced pressure to provide a crude residue which was purified by COMBIFLASH™ chromatography (Teledyne ISO, Lincoln, NE) (using 4-5% ethyl acetate/petroleum ether) to provide ethyl (S)-2-((1-phenylethyl)amino)cyclopent-1-ene-1-carboxylate (233 g, 898 mmol, 100% yield). MS (ESI) m/z: 259.8 $[M+H]^+$.

Preparation of Intermediate 2: ethyl (S,E)-1-(3-ethoxy-3-oxopropyl)-2-(((S)-1-phenylethyl)imino)cyclopentane-1-carboxylate

2

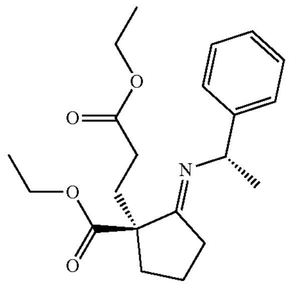

To a mixture of zinc (II) chloride in 2-MeTHF (473 mL, 898 mmol) and ethyl acrylate (90 g, 898 mmol) at 0° C. was added, dropwise, ethyl (S)-2-((1-phenylethyl)amino)cyclopent-1-ene-1-carboxylate (Intermediate 1, 233 g, 898 mmol) in THF (233 mL) and the mixture was stirred at 0° C. for 16 h. The reaction mixture was neutralized with saturated NaOH solution and extracted with EtOAc (3×500 mL). The combined extracts were dried over anhydrous $Na_2SO_4$, filtered, and concentrated in vacuo to provide ethyl (S,E)-1-(3-ethoxy-3-oxopropyl)-2-(((S)-1-phenylethyl)imino)cyclopentane-1-carboxylate (300 g, 835 mmol, 93% yield)) as a colorless oil which was taken for the next step without further purification. MS (ESI) m/z: 360.1 $[M+H]^+$.

Preparation of Intermediate 3: ethyl (4aS,7aR)-2-oxooctahydro-4aH-cyclopenta[b]pyridine-4a-carboxylate

3

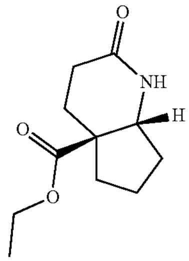

A mixture of ethyl (S,E)-1-(3-ethoxy-3-oxopropyl)-2-(((S)-1-phenylethyl)imino)-cyclopentane-1-carboxylate (145 g, 403 mmol) and 10% palladium on carbon (35 g, 10% w/w) in ethanol (336 mL) was hydrogenated under 50 PSI of hydrogen for 18 h at room temperature. The reaction mixture was filtered through a diatomaceous earth pad (CELITE™, Sigma Aldrich, St. Louis, MO) and the filtrate was concentrated under reduced pressure to provide a crude residue, which was purified by COMBIFLASH™ chromatography (Teledyne ISO, Lincoln, NE) (using 4-5% ethyl acetate/petroleum ether) to obtain the set of diastereomers which were further submitted for SFC purification to provide ethyl (4aS,7aR)-2-oxooctahydro-4aH-cyclopenta[b]pyridine-4a-carboxylate, a desired isomer (36 g, 170 mmol, 42.2% yield) as a colorless oil. MS (ESI) m/z: 211.6 [M+H]+. Prep SFC Condition: Column: Lux i-Amylose-3 (5 µm, 250×50 mm); Flow rate: 300 g/min; Eluent: 25% of 0.1% $NH_4OH$ in Methanol, 75% $CO_2$; Back Pressure: 120 bar, Temp: 40° C.

Preparation of Intermediate 4: ((4aS,7aR)-octahydro-4aH-cyclopenta[b]pyridin-4a-yl)methanol

4

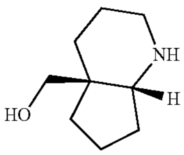

A solution of ethyl (4aS)-2-oxooctahydro-4aH-cyclopenta[b]pyridine-4a-carboxylate (23.7 g, 112 mmol), in THF (415 mL) was added drop wise to an ice-cold solution of 1M LAH (258 mL, 258 mmol) in THF. The reaction mixture was heated to 70° C. for 4 hours. The reaction mixture was cooled to 0° C., quenched with water (9.8 mL), 10% NaOH (9 mL) and additional water (27 mL). Then, the reaction mixture was allowed to warm to room temperature and stirred for 20 minutes. The reaction mixture was filtered through a diatomaceous earth pad (CELITE™, Sigma Aldrich, St. Louis, MO) and washed with excess EtOAc. The filtrate was dried over $Na_2SO_4$, filtered, and concentrated under reduced pressure to provide ((4aS,7aR)-octahydro-4aH-cyclopenta[b]pyridin-4a-yl)methanol (17.3 g, 111 mmol, 99% yield) as a white solid which was taken as such for next step without further purification. MS (ESI) m/z: 156.0 $[M+H]^+$.

Preparation of Intermediate 5: tert-butyl (4aS,7aR)-4a-(hydroxymethyl) octahydro-1H-cyclopenta[b] pyridine-1-carboxylate

5

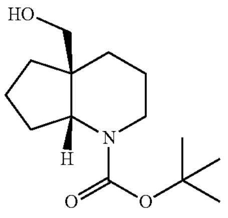

A mixture of ((4aS,7aR)-octahydro-4aH-cyclopenta[b] pyridin-4a-yl)methanol (6.21 g, 40.0 mmol) and di-tert-butyl dicarbonate (8.73 g, 40.0 mmol) in THF (100 mL) was stirred at room temperature for 18 hours. The mixture was concentrated. The crude product was subjected to silica gel chromatography eluting with 20-40% ethyl acetate in hexane to yield tert-butyl (4aS,7aR)-4a-(hydroxymethyl) octahydro-1H-cyclopenta[b]pyridine-1-carboxylate (8.1 g, 31.7 mmol, 79% yield) as clear oil. MS (ESI) m/z: 255.9 $[M+H]^+$.

Preparation of Intermediate 6: 4-{2,7-dichloro-8-fluoropyrido[4,3-d]pyrimidin-4-yl}-1,4-oxazepane

6

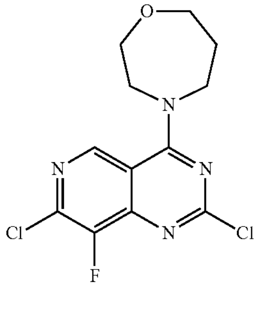

To a stirred solution of commercially available 2,4,7-trichloro-8-fluoropyrido[4,3-d]pyrimidine (1 g, 3.96 mmol) in DCM (10 mL) at −40° C. was added DIPEA (1.38 mL, 7.92 mmol) followed by 1,4-oxazepane (0.401 g, 3.96 mmol). The reaction mixture was stirred at −40° C. for 30 minutes. The reaction mixture was quenched with water and extracted with DCM. The combined organic layers were washed with brine, dried over anhydrous sodium sulfate, filtered, and evaporated under reduced pressure to provide the crude product. The crude compound was purified by COMBIFLASH™ chromatography (Teledyne ISO, Lincoln, NE) (40 g silica gel column, using 50 to 80% ethyl acetate/petroleum ether) to provide tert-butyl 3-{2,7-dichloro-8-fluoropyrido[4,3-d]pyrimidin-4-yl}-3,8-diazabicyclo[3.2.1] octane-8-carboxylate (0.85 g, 2.68 mmol, 68% yield) as a pale-yellow solid. MS (ESI) m/z: 317.2 $[M+H]^+$.

Preparation of Intermediate 7: tert-butyl (4aS,7aR)-4a-(((7-chloro-8-fluoro-4-(1,4-oxazepan-4-yl)pyrido [4,3-d]pyrimidin-2-yl)oxy)methyl) octahydro-1H-cyclopenta[b]pyridine-1-carboxylate

7

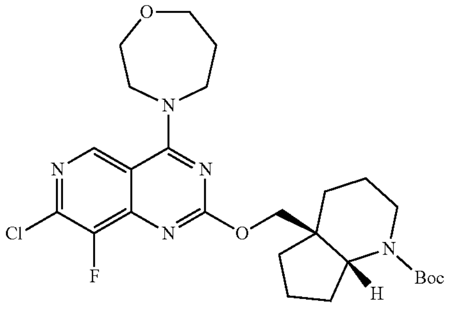

To a solution of 4-(2,7-dichloro-8-fluoropyrido[4,3-d]pyrimidin-4-yl)-1,4-oxazepane (2000 mg, 6.31 mmol) and tert-butyl (4aS,7aR)-4a-(hydroxymethyl) octahydro-1H-cyclopenta[b]pyridine-1-carboxylate (1771 mg, 6.94 mmol) in anhydrous THF (50 mL) was added lithium bis(trimethylsilyl)amide (8.20 mL, 8.20 mmol), and the mixture was stirred at room temperature for 6 hours. After concentration, the residue was purified on silica gel, eluting with 50%-80% ethyl acetate in hexanes to afford tert-butyl (4aS,7aR)-4a-(((7-chloro-8-fluoro-4-(1,4-oxazepan-4-yl)pyrido[4,3-d]pyrimidin-2-yl)oxy)methyl) octahydro-1H-cyclopenta[b]pyridine-1-carboxylate (2.8 g, 5.22 mmol, 83% yield). MS (ESI) m/z: 536.3 $[M+H]^+$. $^1H$ NMR (499 MHz, DMSO-$d_6$) δ 8.97-8.90 (m, 1H), 4.44-4.21 (m, 3H), 4.14-4.06 (m, 4H), 3.92-3.78 (m, 3H), 3.73-3.67 (m, 2H), 2.89-2.73 (m, 1H), 2.04 (quin, J=5.4 Hz, 2H), 1.87 (br d, J=4.2 Hz, 1H), 1.80-1.68 (m, 3H), 1.67-1.57 (m, 2H), 1.47 (br d, J=6.8 Hz, 4H), 1.34 (br s, 9H).

Preparation of Intermediate 8: tert-butyl (4aS,7aR)-4a-(((8-fluoro-7-(7-fluoro-3-(methoxymethoxy)-8-((triisopropylsilyl) ethynyl)naphthalen-1-yl)-4-(1,4-oxazepan-4-yl)pyrido[4,3-d]pyrimidin-2-yl)oxy) methyl) octahydro-1H-cyclopenta[b]pyridine-1-carboxylate

8

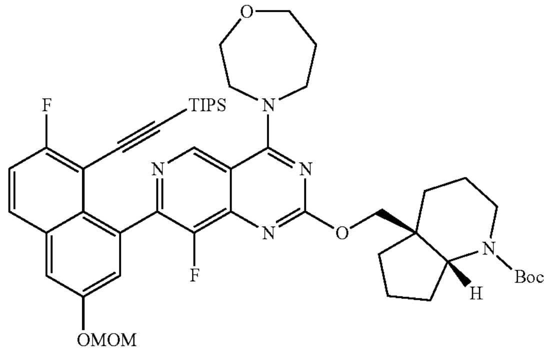

To a solution of tert-butyl (4aS,7aR)-4a-(((7-chloro-8-fluoro-4-(1,4-oxazepan-4-yl)pyrido[4,3-d]pyrimidin-2-yl) oxy)methyl) octahydro-1H-cyclopenta[b]pyridine-1-carboxylate (1400 mg, 2.61 mmol) in THF (20 mL) was added potassium phosphate, tribasic (3.92 mL, 7.84 mmol) and commercially available ((2-fluoro-6-(methoxymethoxy)-8-(4,4,5,5-tetramethyl-1,3,2-dioxaborolan-2-yl)naphthalen-1-yl) ethynyl)triisopropylsilane (2008 mg, 3.92 mmol), and the mixture was degassed for 10 min, then methanesulfonato (diadamantyl-n-butylphosphino)-2'-amino-1,1'-biphenyl-2-yl)palladium (II) dichloromethane adduct was added (190 mg, 0.261 mmol). The mixture was degassed for 10 min and the resulting solution was heated at 65° C. for 16 h. The reaction was diluted with ethyl acetate. The organic layer was washed with brine, dried over $MgSO_4$, filtered and then concentrated, and the residue was purified by silica gel column, eluting with 40-80% ethyl acetate in hexanes to afford tert-butyl (4aS,7aR)-4a-(((8-fluoro-7-(7-fluoro-3-(methoxymethoxy)-8-((triisopropylsilyl) ethynyl)naphthalen-1-yl)-4-(1,4-oxazepan-4-yl)pyrido[4,3-d]pyrimidin-2-yl)oxy)methyl) octahydro-1H-cyclopenta[b]pyridine-1-carboxylate (2.1 g, 2.370 mmol, 91% yield). MS (ESI) m/z: 886.9 $[M+H]^+$. $^1H$ NMR (499 MHz, DMSO-$d_6$) δ 9.17 (d, J=2.5 Hz, 1H), 8.11 (dd, J=8.8, 5.5 Hz, 1H), 7.75 (d, J=2.5 Hz, 1H), 7.57 (t, J=8.9 Hz, 1H), 7.34 (t, J=2.4 Hz, 1H), 5.37 (s, 2H), 4.51-4.34 (m, 1H), 4.29-4.22 (m, 1H), 4.21-4.06 (m, 5H), 3.94 (br s, 2H), 3.88-3.70 (m, 3H), 3.44 (s, 3H), 2.93-2.74 (m, 1H), 2.16-2.02 (m, 2H), 1.93-1.83 (m, 1H), 1.82-1.60 (m, 5H), 1.59-1.52 (m, 1H), 1.46 (br s, 2H), 1.35 (br d, J=4.3 Hz, 9H), 0.87-0.80 (m, 18H), 0.52 (quin, J=7.4 Hz, 3H).

Preparation of Intermediate 9: tert-butyl (4aS,7aR)-4a-(((7-(8-ethynyl-7-fluoro-3-(methoxymethoxy) naphthalen-1-yl)-8-fluoro-4-(1,4-oxazepan-4-yl) pyrido[4,3-d]pyrimidin-2-yl)oxy)methyl) octahydro-1H-cyclopenta[b]pyridine-1-carboxylate

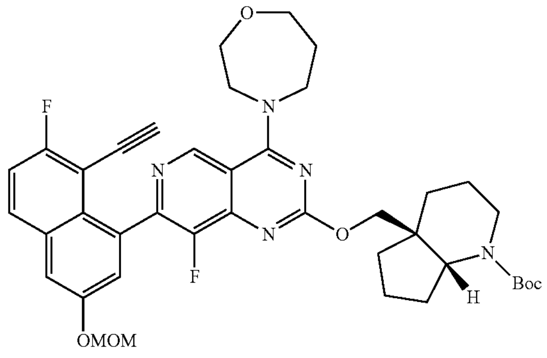

9

To a solution of tert-butyl (4aS,7aR)-4a-(((8-fluoro-7-(7-fluoro-3-(methoxymethoxy)-8-((triisopropylsilyl) ethynyl) naphthalen-1-yl)-4-(1,4-oxazepan-4-yl)pyrido[4,3-d]pyrimidin-2-yl)oxy)methyl) octahydro-1H-cyclopenta[b] pyridine-1-carboxylate (2.1 g, 2.370 mmol) in THF (20 mL) was added TBAF (7.11 mL, 7.11 mmol) and the reaction mixture was heated at 60° C. for 0.7 h. The reaction mixture was diluted with ethyl acetate, washed with brine, dried over $Na_2SO_4$, filtered, and concentrated in vacuo. The residue was purified by silica gel column eluting with 50-80% ethyl acetate in hexanes to afford tert-butyl (4aS,7aR)-4a-(((7-(8-ethynyl-7-fluoro-3-(methoxymethoxy) naphthalen-1-yl)-8-fluoro-4-(1,4-oxazepan-4-yl)pyrido[4,3-d]pyrimidin-2-yl) oxy)methyl) octahydro-1H-cyclopenta[b]pyridine-1-carboxylate (1.65 g, 2.261 mmol, 95% yield). MS (ESI) m/z: 730.5 $[M+H]^+$. $^1H$ NMR (499 MHz, DMSO-$d_6$) δ 9.13-9.08 (m, 1H), 8.10 (dd, J=9.2, 6.0 Hz, 1H), 7.75 (d, J=2.5 Hz, 1H), 7.55 (t, J=9.0 Hz, 1H), 7.36 (d, J=2.1 Hz, 1H), 5.38 (s, 2H), 4.43-4.35 (m, 1H), 4.33-4.21 (m, 2H), 4.19-4.10 (m, 4H), 4.06-4.02 (m, 1H), 3.94 (t, J=4.4 Hz, 2H), 3.88-3.79 (m, 1H), 3.76 (br t, J=5.0 Hz, 2H), 3.45 (s, 3H), 2.89-2.74 (m, 1H), 2.14-2.07 (m, 2H), 1.91-1.82 (m, 1H), 1.81-1.68 (m, 3H), 1.67-1.59 (m, 2H), 1.57-1.41 (m, 4H), 1.32 (br s, 9H).

Preparation of Intermediate 10:5-ethynyl-6-fluoro-4-(8-fluoro-2-(((4aS,7aR)-octahydro-4aH-cyclopenta [b]pyridin-4a-yl)methoxy)-4-(1,4-oxazepan-4-yl) pyrido[4,3-d]pyrimidin-7-yl)naphthalen-2-ol, HCl

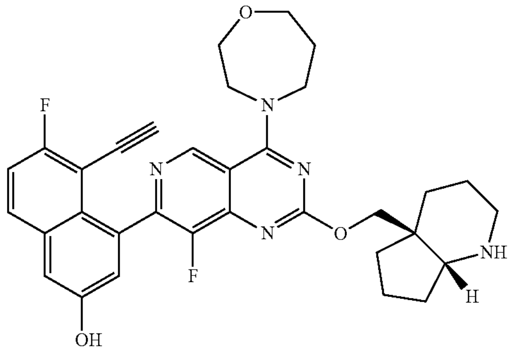

10

To a solution of tert-butyl (4aS,7aR)-4a-(((7-(8-ethynyl-7-fluoro-3-(methoxymethoxy) naphthalen-1-yl)-8-fluoro-4-(1,4-oxazepan-4-yl)pyrido[4,3-d]pyrimidin-2-yl)oxy) methyl) octahydro-1H-cyclopenta[b]pyridine-1-carboxylate (1.4 g, 1.918 mmol) in MeCN (20 ml) at room temperature was added 4 N HCl in dioxane (5 ml, 10.00 mmol). After stirring for 45 min, the reaction mixture was concentrated to afford 5-ethynyl-6-fluoro-4-(8-fluoro-2-(((4aS,7aR)-octahydro-4aH-cyclopenta[b]pyridin-4a-yl)methoxy)-4-(1,4-oxazepan-4-yl)pyrido[4,3-d]pyrimidin-7-yl)naphthalen-2-ol, HCl (1.19 g, 1.913 mmol, 100% yield), which was used without further purification. MS (ESI) m/z: 586.3 $[M+H]^+$. $^1H$ NMR (499 MHz, DMSO-$d_6$) δ 9.66 (br d, J=2.9 Hz, 1H), 9.18 (s, 1H), 8.85 (br d, J=5.8 Hz, 1H), 8.00 (dd, J=9.2, 5.9 Hz, 1H), 7.53-7.44 (m, 2H), 7.29 (d, J=2.2 Hz, 1H), 4.48 (br d, J=11.0 Hz, 1H), 4.29-4.17 (m, 5H), 4.10 (d, J=4.4 Hz, 1H), 3.97 (br t, J=4.4 Hz, 2H), 3.78 (br t, J=4.6 Hz, 2H), 3.74-3.65 (m, 1H), 3.49-3.43 (m, 1H), 3.09 (br d, J=6.1 Hz, 1H), 2.82 (br d, J=5.0 Hz, 1H), 2.13 (br s, 3H), 2.00-1.58 (m, 9H).

Example 1-1: 4-(2-{[(4aS,7aR)-1-[(oxetan-3-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol 1-1

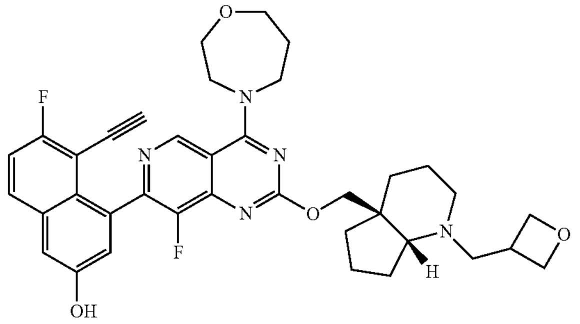

A solution of 5-ethynyl-6-fluoro-4-(8-fluoro-2-(((4aS,7aR)-octahydro-4aH-cyclopenta[b]pyridin-4a-yl)methoxy)-4-(1,4-oxazepan-4-yl)pyrido[4,3-d]pyrimidin-7-yl)naphthalen-2-ol HCl (20 mg, 0.034 mmol), acetic acid (9.77 µl, 0.171 mmol) and oxetane-3-carbaldehyde (2.94 mg, 0.034 mmol) and sodium triacetoxyborohydride (21.71 mg, 0.102 mmol) in DMSO (2 mL) was stirred at room temperature for 3 h. The crude material was purified via preparative reverse phase chromatography with the following conditions: Column: XBridge C18, 19 mm×200 mm, 5 µm particles; Flow Rate: 20 mL/min; Column Temperature: 25° C. Mobile phase A: acetonitrile/water (5:95) with 10 mM ammonium acetate; Mobile phase B: acetonitrile/water (95:5) with 10 mM ammonium acetate; Gradient=0 (min)-24% B, 20-64% B, 20.1-100% B, 24-100% B. Fraction collection was triggered by MS (ESI +). Fractions containing the desired product were combined and dried via centrifugal evaporation to isolate 5-ethynyl-6-fluoro-4-(8-fluoro-4-(1,4-oxazepan-4-yl)-2-(((4aS,7aR)-1-(oxetan-3-ylmethyl) octahydro-4aH-cyclopenta[b]pyridin-4a-yl)methoxy)pyrido[4,3-d]pyrimidin-7-yl)naphthalen-2-ol (13 mg, 0.020 mmol, 57.2% yield). MS (ESI) m/z: 656 $[M+H]^+$. $^1H$ NMR (500 MHz, DMSO-$d_6$) δ 9.10 (s, 1H), 7.97 (dd, J=9.1, 6.0 Hz, 1H), 7.46 (t, J=9.0 Hz, 1H), 7.39 (d, J=2.3 Hz, 1H), 7.19 (s, 1H), 4.62-4.47 (m, 3H), 4.28-4.07 (m, 8H), 4.00-3.92 (m, 3H), 3.77 (br t, J=4.8 Hz, 2H), 3.15-3.07 (m, 1H), 2.83 (br t, J=7.6 Hz, 1H), 2.72-2.58 (m, 2H), 2.44-2.37 (m, 1H), 2.30 (br dd, J=9.4, 1.7 Hz, 1H), 2.11 (br s, 2H), 1.91-1.81 (m, 1H), 1.75-1.67 (m, 1H), 1.64-1.48 (m, 6H), 1.47-1.39 (m, 1H), 1.37-1.29 (m, 1H).

Example 1-2: 4-(2-{[(4aS,7aR)-1-[(2S)-3-fluoro-2-hydroxypropyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol 1-2

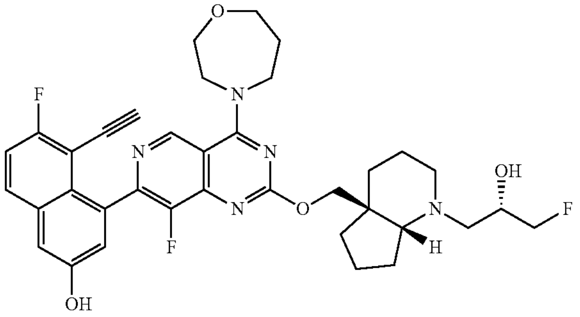

A solution of 5-ethynyl-6-fluoro-4-(8-fluoro-2-(((4aS,7aR)-octahydro-4aH-cyclopenta[b]pyridin-4a-yl)methoxy)-4-(1,4-oxazepan-4-yl)pyrido[4,3-d]pyrimidin-7-yl)naphthalen-2-ol, HCl (20 mg, 0.032 mmol), (S)-2-(fluoromethyl) oxirane (4.89 mg, 0.064 mmol) and DIPEA (0.022 mL, 0.129 mmol) in DMSO (2 mL) was stirred at 80° C. for 16 h. The crude material was purified via preparative reverse phase chromatography with the following conditions: Column: XBridge C18, 19 mm×200 mm, 5 µm particles; Flow Rate: 20 mL/min; Column Temperature: 25° C. Mobile phase A: acetonitrile/water (5:95) with 10 mM ammonium acetate; Mobile phase B: acetonitrile/water (95:5) with 10 mM ammonium acetate; Gradient=0 (min)-22% B, 20-62% B, 20.1-100% B, 24-100% B. Fraction collection was triggered by MS (ESI +). Fractions containing the desired product were combined and dried via centrifugal evaporation to isolate 4-(2-{[(4aS,7aR)-1-[(2S)-3-fluoro-2-hydroxypropyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol (11.3 mg, 0.017 mmol, 51.7% yield). MS (ESI) m/z: 662.6 $[M+H]^+$. $^1H$ NMR (500 MHz, DMSO-$d_6$) δ 9.10 (s, 1H), 7.98 (br dd, J=8.6, 6.5 Hz, 1H), 7.47 (t, J=9.2 Hz, 1H), 7.40 (s, 1H), 7.19 (br s, 1H), 4.61 (br d, J=10.7 Hz, 1H), 4.49-4.39 (m, 1H), 4.34 (br dd, J=10.1, 4.8 Hz, 1H), 4.27-4.10 (m, 6H), 4.02-3.92 (m, 3H), 3.81-3.69 (m, 4H), 2.89 (br t, J=7.5 Hz, 1H), 2.36 (br s, 2H), 2.11 (br s, 2H), 1.93-1.83 (m, 2H), 1.77-1.65 (m, 1H), 1.63-1.49 (m, 7H), 1.49-1.41 (m, 1H), 1.36-1.25 (m, 1H).

Preparation of Intermediate 11: tert-butyl 3-(((4aS,7aR)-4a-(((7-(8-ethynyl-7-fluoro-3-hydroxynaphthalen-1-yl)-8-fluoro-4-(1,4-oxazepan-4-yl)pyrido[4,3-d]pyrimidin-2-yl)oxy)methyl) octahydro-1H-cyclopenta[b]pyridin-1-yl)methyl)-3-hydroxyazetidine-1-carboxylate

11

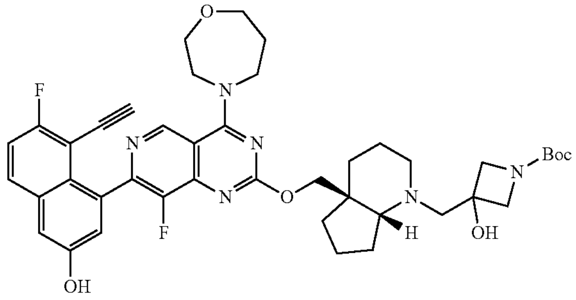

A solution of 5-ethynyl-6-fluoro-4-(8-fluoro-2-(((4aS,7aR)-octahydro-4aH-cyclopenta[b]pyridin-4a-yl)methoxy)-4-(1,4-oxazepan-4-yl)pyrido[4,3-d]pyrimidin-7-yl)naphthalen-2-ol, HCl (6 mg, 9.64 μmol), tert-butyl 1-oxa-5-azaspiro[2.3]hexane-5-carboxylate (3.57 mg, 0.019 mmol) and DIPEA (6.74 μl, 0.039 mmol) in DMSO (2 mL) was stirred at 80° C. for 3 h. The crude material was purified via preparative reverse phase chromatography with the following conditions: Column: XBridge C18, 19 mm×200 mm, 5 μm particles; Flow Rate: 20 mL/min; Column Temperature: 25° C. Mobile phase A: acetonitrile/water (5:95) with 10 mM ammonium acetate; Mobile phase B: acetonitrile/water (95:5) with 10 mM ammonium acetate; Gradient=0 (min)-39% B, 20-79% B, 20.1-100% B, 24-100% B. Fraction collection was triggered by MS (ESI +). Fractions containing the desired product were combined and dried via centrifugal evaporation to afford tert-butyl 3-(((4aS,7aR)-4a-(((7-(8-ethynyl-7-fluoro-3-hydroxynaphthalen-1-yl)-8-fluoro-4-(1,4-oxazepan-4-yl)pyrido[4,3-d]pyrimidin-2-yl)oxy)methyl) octahydro-1H-cyclopenta[b]pyridin-1-yl)methyl)-3-hydroxyazetidine-1-carboxylate (5.9 mg, 7.43 μmol, 77% yield). MS (ESI) m/z: 771.1 $[M+H]^+$. $^1H$ NMR (500 MHz, DMSO-$d_6$) δ 9.10 (s, 1H), 7.98 (dd, J=8.9, 6.1 Hz, 1H), 7.47 (t, J=9.0 Hz, 1H), 7.40 (s, 1H), 7.18 (s, 1H), 5.51-5.33 (m, 1H), 4.61 (br d, J=10.6 Hz, 1H), 4.28-4.09 (m, 6H), 4.01-3.93 (m, 3H), 3.82-3.69 (m, 5H), 3.63-3.52 (m, 4H), 3.04-2.95 (m, 1H), 2.12 (br s, 2H), 1.93-1.82 (m, 2H), 1.78-1.68 (m, 1H), 1.62-1.26 (m, 17H).

Example 1-3: methyl 3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-3-hydroxyazetidine-1-carboxylate 1-3

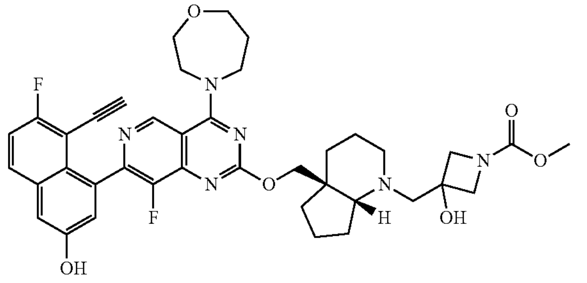

To a solution of tert-butyl 3-(((4aS,7aR)-4a-(((7-(8-ethynyl-7-fluoro-3-hydroxynaphthalen-1-yl)-8-fluoro-4-(1,4-oxazepan-4-yl)pyrido[4,3-d]pyrimidin-2-yl)oxy)methyl) octahydro-1H-cyclopenta[b]pyridin-1-yl)methyl)-3-hydroxyazetidine-1-carboxylate (20 mg, 0.026 mmol) in MeCN (2 mL) at room temperature was added HCl in dioxane (0.5 mL, 2.000 mmol). After stirring for 10 min, the reaction mixture was concentrated to afford 3-(((4aS,7aR)-4a-(((7-(8-ethynyl-7-fluoro-3-hydroxynaphthalen-1-yl)-8-fluoro-4-(1,4-oxazepan-4-yl)pyrido[4,3-d]pyrimidin-2-yl)oxy)methyl) octahydro-1H-cyclopenta[b]pyridin-1-yl)methyl) azetidin-3-ol, HCl, which was used without further purification. To a solution of the crude product above in DMSO (1 mL) was added DIPEA (0.018 mL, 0.104 mmol) and methyl chloroformate (4.02 μl, 0.052 mmol). After stirring for 10 min, the reaction was quenched with 0.1 mL of MeOH. The crude material was purified via preparative reverse phase chromatography with the following conditions: Column: XBridge C18, 19 mm×200 mm, 5 μm particles; Flow Rate: 20 mL/min; Column Temperature: 25° C. Mobile phase A: acetonitrile/water (5:95) with 10 mM ammonium acetate; Mobile phase B: acetonitrile/water (95:5) with 10 mM ammonium acetate; Gradient=0 (min)-34% B, 20-64% B, 20.1-100% B, 24-100% B. Fraction collection was triggered by MS (ESI +). Fractions containing the desired product were combined and dried via centrifugal evaporation to isolate methyl 3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-3-hydroxyazetidine-1-carboxylate (3.3 mg, 4.22 μmol, 16.27% yield). MS (ESI) m/z: 728.9 $[M+H]^+$.

Example 1-4: (5S)-5-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}pyrrolidin-2-one 1-4

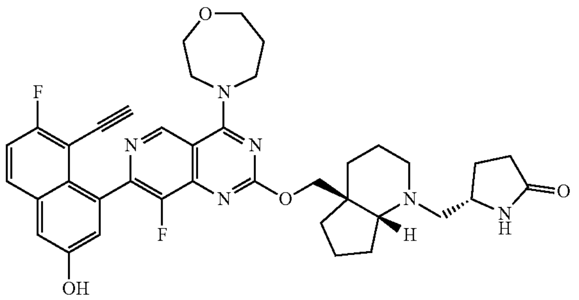

A solution of 5-ethynyl-6-fluoro-4-(8-fluoro-2-(((4aS,7aR)-octahydro-4aH-cyclopenta[b]pyridin-4a-yl)methoxy)-4-(1,4-oxazepan-4-yl)pyrido[4,3-d]pyrimidin-7-yl)naphthalen-2-ol (10 mg, 0.017 mmol), (S)-5-(bromomethyl)pyrrolidin-2-one (4.56 mg, 0.026 mmol) and DIPEA (8.95 μl, 0.051 mmol) in DMSO (1 mL) was stirred at 80° C. for 3 days. The crude material was purified via preparative reverse phase chromatography with the following conditions: Column: XBridge C18, 19 mm×200 mm, 5 μm particles; Flow Rate: 20 mL/min; Column Temperature: 25° C. Mobile phase A: acetonitrile/water (5:95) with 10 mM ammonium acetate; Mobile phase B: acetonitrile/water (95:5) with 10 mM ammonium acetate; Gradient=0 (min)-36% B, 20-76% B, 20.1-100% B, 24-100% B. Fraction collection was triggered by MS (ESI+). Fractions containing the desired product were combined and dried via centrifugal evaporation to afford (5S)-5-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}pyrrolidin-2-one (1.8 mg, 2.497 μmol, 14.62% yield). MS (ESI) m/z: 683.2 $[M+H]^+$. $^1H$ NMR (500 MHz, DMSO-$d_6$) δ 9.09 (s, 1H), 8.01-7.93 (m, 1H), 7.51-7.42 (m, 1H), 7.40 (d, J=2.5 Hz, 1H), 7.19 (d, J=2.3 Hz, 1H), 4.63-4.51 (m, 1H), 4.33-4.23 (m, 1H), 4.21-4.07 (m, 4H), 4.00-3.88 (m, 4H), 3.80-3.73 (m, 2H), 3.70-3.58 (m, 3H), 2.95-2.84 (m, 1H), 2.48-2.36 (m, 3H), 2.35-2.25 (m, 1H), 2.18-1.97 (m, 5H), 1.78-1.49 (m, 7H), 1.47-1.39 (m, 1H), 1.38-1.26 (m, 1H).

Preparation of Intermediate 12: tert-butyl (4aS,7aR)-4a-(((7-(8-ethyl-7-fluoro-3-(methoxymethoxy)naphthalen-1-yl)-8-fluoro-4-(1,4-oxazepan-4-yl)pyrido[4,3-d]pyrimidin-2-yl)oxy)methyl) octahydro-1H-cyclopenta[b]pyridine-1-carboxylate

12

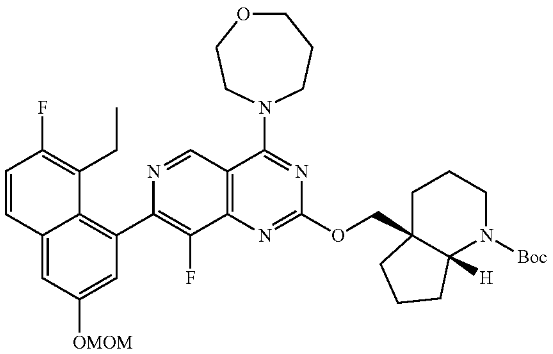

The mixture of tert-butyl (4aS,7aR)-4a-(((7-(8-ethynyl-7-fluoro-3-(methoxymethoxy) naphthalen-1-yl)-8-fluoro-4-(1,4-oxazepan-4-yl)pyrido[4,3-d]pyrimidin-2-yl)oxy)methyl) octahydro-1H-cyclopenta[b]pyridine-1-carboxylate (500 mg, 0.685 mmol) and palladium on carbon (10%) (100 mg, 0.094 mmol) in MeOH was charged with a $H_2$ balloon. The reaction was stirred at room temperature for 3 h. The mixture was filtered and concentrated to afford tert-butyl (4aS,7aR)-4a-(((7-(8-ethyl-7-fluoro-3-(methoxymethoxy) naphthalen-1-yl)-8-fluoro-4-(1,4-oxazepan-4-yl)pyrido[4,3-d]pyrimidin-2-yl)oxy)methyl) octahydro-1H-cyclopenta[b]pyridine-1-carboxylate (500 mg, 0.681 mmol, 99% yield), which was used in the next step. MS (ESI) m/z: 734.5 $[M+H]^+$. $^1H$ NMR (499 MHz, DMSO-$d_6$) δ 9.18 (s, 1H), 7.90 (dd, J=9.2, 6.0 Hz, 1H), 7.68 (d, J=2.8 Hz, 1H), 7.44 (t, J=9.4 Hz, 1H), 7.20 (d, J=2.6 Hz, 1H), 5.35 (s, 2H), 4.52-4.22 (m, 3H), 4.20-4.11 (m, 4H), 3.94 (t, J=4.6 Hz, 2H), 3.89-3.80 (m, 1H), 3.75 (br t, J=5.0 Hz, 2H), 3.44 (s, 3H), 2.91-2.73 (m, 1H), 2.44-2.35 (m, 1H), 2.19 (ddd, J=14.0, 7.1, 3.0 Hz, 1H), 2.12-2.04 (m, 2H), 1.93-1.67 (m, 4H), 1.67-1.56 (m, 2H), 1.48 (br d, J=10.3 Hz, 4H), 1.29 (br s, 9H), 0.75 (t, J=7.4 Hz, 3H).

Preparation of Intermediate 13: 5-ethyl-6-fluoro-4-(8-fluoro-2-(((4aS,7aR)-octahydro-4aH-cyclopenta[b]pyridin-4a-yl)methoxy)-4-(1,4-oxazepan-4-yl)pyrido[4,3-d]pyrimidin-7-yl)naphthalen-2-ol

13

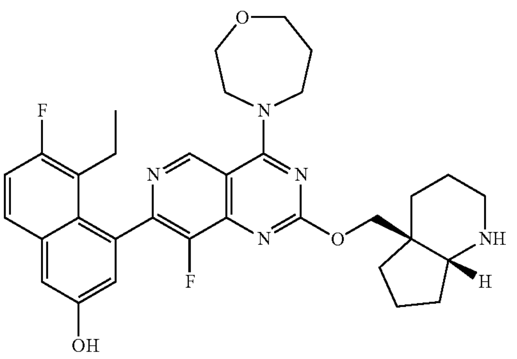

To a solution of tert-butyl (4aS,7aR)-4a-(((7-(8-ethyl-7-fluoro-3-(methoxymethoxy) naphthalen-1-yl)-8-fluoro-4-(1,4-oxazepan-4-yl)pyrido[4,3-d]pyrimidin-2-yl)oxy)methyl) octahydro-1H-cyclopenta[b]pyridine-1-carboxylate (10 mg, 0.014 mmol) in MeCN (2 ml) at room temperature was added 4 N HCl in dioxane (0.5 ml, 0.014 mmol). After stirring for 10 min, the reaction mixture was concentrated to afford 5-ethyl-6-fluoro-4-(8-fluoro-2-(((4aS,7aR)-octahydro-4aH-cyclopenta[b]pyridin-4a-yl)methoxy)-4-(1,4-oxazepan-4-yl)pyrido[4,3-d]pyrimidin-7-yl)naphthalen-2-ol (8 mg, 0.014 mmol, 100% yield) after removal of HCl, which was used without further purification. MS (ESI) m/z: 590.2 $[M+H]^+$. $^1$H NMR (500 MHz, DMSO-$d_6$) δ 9.16 (s, 1H), 7.95 (s, 1H), 7.76 (dd, J=8.8, 6.1 Hz, 1H), 7.37-7.30 (m, 2H), 7.03 (d, J=2.4 Hz, 1H), 4.33 (br dd, J=10.7, 7.2 Hz, 1H), 4.20-4.11 (m, 5H), 3.94 (br t, J=4.3 Hz, 3H), 3.75 (br d, J=5.0 Hz, 2H), 3.11 (br d, J=2.6 Hz, 1H), 2.61-2.56 (m, 1H), 2.41-2.33 (m, 1H), 2.18-2.05 (m, 3H), 1.96-1.89 (m, 1H), 1.83-1.72 (m, 2H), 1.71-1.57 (m, 4H), 1.56-1.46 (m, 3H), 0.73 (br t, J=7.4 Hz, 3H).

Preparation of Intermediate 24: 4-(2,7-dichloro-8-fluoropyrido[4,3-d]pyrimidin-4-yl)-6-methyl-1,4-oxazepan-6-ol

24

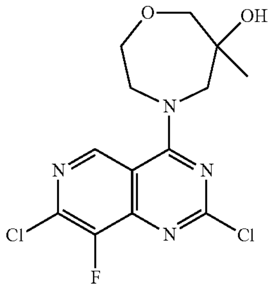

To a stirring solution of 2,4,7-trichloro-8-fluoropyrido[4,3-d]pyrimidine (3.03 g, 12 mmol) and N-ethyl-N-isopropylpropan-2-amine (6.29 mL, 36.0 mmol) in DCM (24 mL) was added 6-methyl-1,4-oxazepan-6-ol, HCl (2.012 g, 12.00 mmol) at −40° C. The reaction was allowed to warm to room temperature. After stirring for 1 h, the reaction mixture was quenched with water and diluted with $CHCl_3$. The organics were dried over $MgSO_4$, filtered and concentrated to afford a solid. The solid was taken into ethyl acetate and stirred for 10 min. The solid was collected, washing with ethyl acetate to afford 4-(2,7-dichloro-8-fluoropyrido[4,3-d]pyrimidin-4-yl)-6-methyl-1,4-oxazepan-6-ol (3.1 g, 8.93 mmol, 74.4% yield) as an orange solid. $^1$H NMR (499 MHz, DMSO-$d_6$) δ 9.49 (br s, 1H), 5.20 (s, 1H), 4.44-4.32 (m, 1H), 4.25 (br d, J=14.8 Hz, 1H), 4.07-3.75 (m, 4H), 3.64-3.48 (m, 2H), 1.16 (s, 3H). MS (ESI) m/z: 348.7 $[M+H]^+$.

Preparation of Intermediate 25 and 26: tert-butyl (4aS,7aR)-4a-(((7-chloro-8-fluoro-4-((S)-6-hydroxy-6-methyl-1,4-oxazepan-4-yl)pyrido[4,3-d]pyrimidin-2-yl)oxy)methyl) octahydro-1H-cyclopenta[b]pyridine-1-carboxylate and tert-butyl (4aS,7aR)-4a-(((7-chloro-8-fluoro-4-((R)-6-hydroxy-6-methyl-1,4-oxazepan-4-yl)pyrido[4,3-d]pyrimidin-2-yl)oxy)methyl) octahydro-1H-cyclopenta[b]pyridine-1-carboxylate

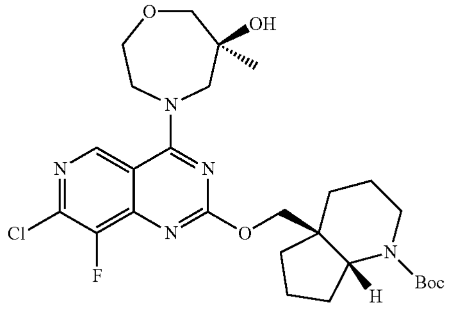
25

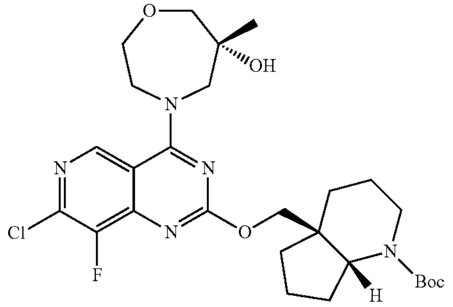
26

To a stirred solution of 4-(2,7-dichloro-8-fluoropyrido[4,3-d]pyrimidin-4-yl)-6-methyl-1,4-oxazepan-6-ol (1.5 g, 4.32 mmol) in tetrahydrofuran (20 mL) was added tert-butyl (4aS,7aR)-4a-(hydroxymethyl) octahydro-1H-cyclopenta[b]pyridine-1-carboxylate (1.214 g, 4.75 mmol) and lithium bis(trimethylsilyl)amide solution in THF (10.80 mL, 10.80 mmol) dropwise at 0° C. The resulting reaction was allowed to stir for 16 h at room temperature. The reaction mixture was quenched with sat. aq. NaCl solution and extracted with ethyl acetate (50 mL×2). The organic layer was dried over sodium sulphate, filtered and concentrated under reduced pressure to afford a crude material. The residue was then purified by a silica gel column, eluting with EtOAc to isolate 1.5 g of the desired product. The material was then purified by a SFC column, using a Chiralpak IG column (5×25 cm, 5um), eluted with 45% MeOH w 0.1% $NH_4OH$ in $CO_2$; flow rate=300 ml/min; detector wavelength=220 nm; temperature=45° C., pressure=100 bars to isolate intermediate 25, tert-butyl (4aS,7aR)-4a-(((7-chloro-8-fluoro-4-((S)-6-hydroxy-6-methyl-1,4-oxazepan-4-yl)pyrido[4,3-d]pyrimidin-2-yl)oxy)methyl) octahydro-1H-cyclopenta[b]pyridine-1-carboxylate (0.69 g, 1.219 mmol, 28.2% yield), MS (ESI) m/z: 566.3 $[M+H]^+$; and intermediate 26, tert-butyl (4aS,7aR)-4a-(((7-chloro-8-fluoro-4-((R)-6-hydroxy-6-methyl-1,4-oxazepan-4-yl)pyrido[4,3-d]pyrimidin-2-yl)oxy)methyl) octahydro-1H-cyclopenta[b]pyridine-1-carboxylate (0.57 g, 1.007 mmol, 23.31% yield), MS (ESI) m/z: 566.3 $[M+H]^+$.

Preparation of Intermediate 27: tert-butyl (4aS,7aR)-4a-(((8-fluoro-7-(7-fluoro-3-(methoxymethoxy)-8-((triisopropylsilyl) ethynyl) naphthalen-1-yl)-4-((S)-6-hydroxy-6-methyl-1,4-oxazepan-4-yl)pyrido[4,3-d]pyrimidin-2-yl)oxy) methyl) octahydro-1H-cyclopenta[b]pyridine-1-carboxylate

27

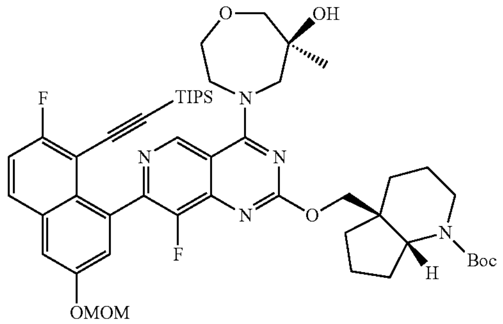

To a $N_2$ purged solution of ((2-fluoro-6-(methoxymethoxy)-8-(4,4,5,5-tetramethyl-1,3,2-dioxaborolan-2-yl)naphthalen-1-yl) ethynyl)triisopropylsilane (0.910 g, 1.775 mmol), tert-butyl (4aS,7aR)-4a-(((7-chloro-8-fluoro-4-((S)-6-hydroxy-6-methyl-1,4-oxazepan-4-yl) pyrido[4,3-d]pyrimidin-2-yl)oxy)methyl) octahydro-1H-cyclopenta[b]pyridine-1-carboxylate (Intermediate 25, 0.67 g, 1.184 mmol) and potassium phosphate (1.775 mL, 3.55 mmol) in THF (10 mL) was added cataCXiumR™ A Palladacycle Gen. 3 (0.086 g, 0.118 mmol). The reaction mixture was degassed with $N_2$ for 10 min. and the resulting solution was heated at 65° C. for 24 h. The reaction mixture was cooled, filtered through a CELITE™ (Sigma Aldrich, St. Louis, MO) pad and the filtrate was concentrated under reduced pressure to afford the crude compound which was purified by silica gel chromatography, eluted with EtOAc to isolate tert-butyl (4aS,7aR)-4a-(((8-fluoro-7-(7-fluoro-3-(methoxymethoxy)-8-((triisopropylsilyl) ethynyl)naphthalen-1-yl)-4-((S)-6-hydroxy-6-methyl-1,4-oxazepan-4-yl) pyrido[4,3-d]pyrimidin-2-yl)oxy)methyl) octahydro-1H-cyclopenta[b]pyridine-1-carboxylate (1 g, 1.091 mmol, 92% yield). MS (ESI) m/z 917.0. $[M+H]^+$.

Preparation of Intermediate 28: tert-butyl (4aS,7aR)-4a-(((7-(8-ethynyl-7-fluoro-3-(methoxymethoxy) naphthalen-1-yl)-8-fluoro-4-((S)-6-hydroxy-6-methyl-1,4-oxazepan-4-yl)pyrido[4,3-d]pyrimidin-2-yl)oxy)methyl) octahydro-1H-cyclopenta[b]pyridine-1-carboxylate

28

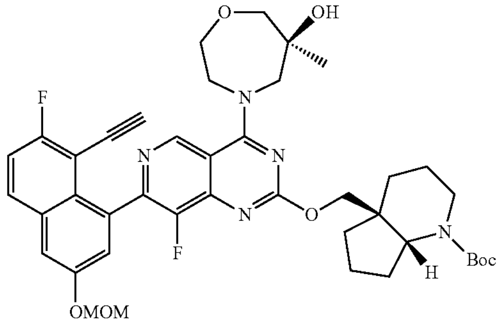

A mixture of tert-butyl (4aS,7aR)-4a-(((8-fluoro-7-(7-fluoro-3-(methoxymethoxy)-8-((triisopropylsilyl) ethynyl) naphthalen-1-yl)-4-((S)-6-hydroxy-6-methyl-1,4-oxazepan-4-yl)pyrido[4,3-d]pyrimidin-2-yl)oxy)methyl) octahydro-1H-cyclopenta[b]pyridine-1-carboxylate (1 g, 1.091 mmol) and CsF (1.658 g, 10.91 mmol) in acetonitrile (5 mL) was heated at 65° C. for 3 h. The mixture was then concentrated and then EtOAc was added. The mixture was filtered. The filtrate was washed with water. The organic layer was dried over $MgSO_4$, filtered and concentrated to obtain tert-butyl (4aS,7aR)-4a-(((7-(8-ethynyl-7-fluoro-3-(methoxymethoxy) naphthalen-1-yl)-8-fluoro-4-((S)-6-hydroxy-6-methyl-1,4-oxazepan-4-yl)pyrido[4,3-d]pyrimidin-2-yl)oxy)methyl) octahydro-1H-cyclopenta[b]pyridine-1-carboxylate (0.65 g, 0.855 mmol, 78% yield). MS (ESI) m/z: 760.5 $[M+H]^+$.

Preparation of Intermediate 29: (S)-4-(7-(8-ethynyl-7-fluoro-3-hydroxynaphthalen-1-yl)-8-fluoro-2-(((4aS,7aR)-octahydro-4aH-cyclopenta[b]pyridin-4a-yl)methoxy)pyrido[4,3-d]pyrimidin-4-yl)-6-methyl-1,4-oxazepan-6-ol, HCl

29

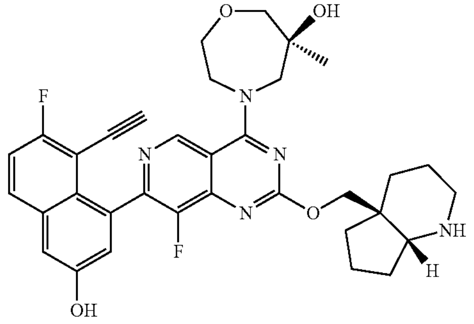

A mixture of tert-butyl (4aS,7aR)-4a-(((7-(8-ethynyl-7-fluoro-3-(methoxymethoxy) naphthalen-1-yl)-8-fluoro-4-((S)-6-hydroxy-6-methyl-1,4-oxazepan-4-yl)pyrido[4,3-d] pyrimidin-2-yl)oxy)methyl) octahydro-1H-cyclopenta[b]

pyridine-1-carboxylate (0.65 g, 0.855 mmol) and 4M HCl (1 mL, 4.00 mmol)/dioxane in acetonitrile (4 mL) was stirred at room temperature for 1 h. The mixture was then concentrated to obtain (S)-4-(7-(8-ethynyl-7-fluoro-3-hydroxynaphthalen-1-yl)-8-fluoro-2-(((4aS,7aR)-octahydro-4aH-cyclopenta[b]pyridin-4a-yl)methoxy)pyrido[4,3-d]pyrimidin-4-yl)-6-methyl-1,4-oxazepan-6-ol, HCl (0.56 g, 0.859 mmol, 100% yield). MS (ESI) m/z: 616.3 $[M+H]^+$.

Example 1-17: 1-(3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-3-hydroxyazetidin-1-yl) ethan-1-one 1-17

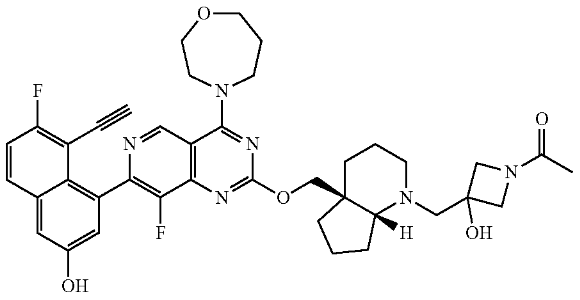

To a solution of tert-butyl 3-(((4aS,7aR)-4a-(((7-(8-ethynyl-7-fluoro-3-hydroxynaphthalen-1-yl)-8-fluoro-4-(1,4-oxazepan-4-yl)pyrido[4,3-d]pyrimidin-2-yl)oxy)methyl) octahydro-1H-cyclopenta[b]pyridin-1-yl)methyl)-3-hydroxyazetidine-1-carboxylate (20 mg, 0.026 mmol) in MeCN (2 mL) at room temperature was added HCl in dioxane (0.5 mL, 2.0 mmol). After stirring for 10 minutes, the reaction mixture was concentrated to give crude 3-(((4aS,7aR)-4a-(((7-(8-ethynyl-7-fluoro-3-hydroxynaphthalen-1-yl)-8-fluoro-4-(1,4-oxazepan-4-yl)pyrido[4,3-d]pyrimidin-2-yl)oxy)methyl) octahydro-1H-cyclopenta[b]pyridin-1-yl)methyl) azetidin-3-ol (17 mg, 0.025 mmol, 98% yield), which was used without further purification. To a solution of the crude product above in DMSO (1 mL) was added DIEA (0.018 mL, 0.104 mmol) and acetic anhydride (4.90 µl, 0.052 mmol). After stirring for 10 minutes, the reaction was quenched with 0.1 mL of MeOH and was purified via preparative reverse phase chromatography with the following conditions: Column: XBridge C18, 19 mm×200 mm, 5 µm particles; Flow Rate: 20 mL/min; Column Temperature: 25° C. Fraction collection was triggered by MS (ESI +). Fractions containing the desired product were combined and dried via centrifugal evaporation. to isolate 1-(3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-3-hydroxyazetidin-1-yl) ethan-1-one (5.6 mg, 7.68 µmol, 29.6% yield). MS (ESI) m/z: 713.8. $[M+H]^+$. $^1H$ NMR (500 MHz, DMSO-$d_6$) δ 9.10 (s, 1H), 7.97 (dd, J=9.1, 6.0 Hz, 1H), 7.46 (t, J=9.0 Hz, 1H), 7.40 (d, J=2.4 Hz, 1H), 7.19 (br d, J=1.7 Hz, 1H), 4.60-4.49 (m, 1H), 4.33-4.25 (m, 1H), 4.15 (br d, J=2.1 Hz, 4H), 4.03-3.93 (m, 4H), 3.83-3.70 (m, 5H), 3.55-3.47 (m, 2H), 3.07-2.97 (m, 1H), 2.64-2.57 (m, 2H), 2.11 (br d, J=4.7 Hz, 2H), 1.93-1.83 (m, 1H), 1.76-1.45 (m, 11H), 1.45-1.38 (m, 1H), 1.37-1.28 (m, 1H).

The compounds in Table 1 were prepared according to procedures described for Examples 1-1, 1-2, 1-3, 1-4 and 1-17 from appropriate starting material's.

Examples 1-16, 1-55, 1-56, 1-70, 1-71, 1-76, 1-77, 1-79, 1-80, 1-95, 1-96, 1-99, 1-100, 1-102, 1-103, 1-131, 1-132, 1-134, 1-135, 1-136, 1-137, 1-141, 1-144, 1-205, 1-214, 1-220, 1-221, 1-323, 1-327, 1-331, 1-332, 1-333, and 1-334 were synthesized as diastereomeric mixtures. They were purified by prep-HPLC to provide pure diastereomeric mixtures which were further purified by either chiral HPLC or SFC as noted to provide single diastereomers. Superscripts appearing after the example number in the table designate which of the following chiral separation conditions were used:

A. CHIRALPAK™ IC (5×25 cm, 5 µm, #406191); BPR pressure: 100 bars; Temperature: 35° C.; Flow rate: 333 mL/min; Mobile Phase: $CO_2$/MeOH:MeCN(1:1) with 0.1% $NH_4OH$ (55/45); Detector Wavelength: 220 nm.

B. CHIRALPAK™ IC (5×25 cm, 5 µm, #123253); BPR pressure: 100 bars; Temperature: 35° C.; Flow rate: 180 mL/min; Mobile Phase: $CO_2$/MeOH:MeCN(1:1) w 0.1% $NH_4OH$ (68/32); Detector Wavelength: 220 nm.

C. Cellulose-2 (3×25 cm, 5 µm, #471467); BPR pressure: 100 bars; Temperature: 35° C.; Flow rate: 160 mL/min; Mobile Phase: $CO_2$/MeOH:MeCN(1:1) w 0.1% $NH_4OH$ (55/45); Detector Wavelength: 220 nm.

D. Chiralcel IA, 30 mm×250 mm, 5 µm particles; Flow Rate: 100.00 mL/min; Column Temperature: 50° C. Mobile Phase A ($CO_2$) (60%), Mobile Phase B (MeOH with 0.1% $NH_4OH$) (40%). Fraction collection was triggered by UV (220 nm)

E. Chiralpak AD-H, 30 mm×250 mm, 5 µm particles; Flow Rate: 100.00 mL/min; Column Temperature: 50° C. Mobile Phase A ($CO_2$) Mobile (70%), Phase B (MeOH/ACN (50:50)) (30%). Fraction collection was triggered by UV (220 nm).

G. Chiralpak AS-H, 30 mm×250 mm, 5 µm particles; Flow Rate: 100.00 mL/min; Column Temperature: 50° C. Mobile Phase A ($CO_2$) Mobile (80%), Phase B (MeOH with 0.1% DEA) (20%). Fraction collection was triggered by UV (220 nm).

J. Chiralpak IG-H, 19 mm×200 mm, 5 µm particles; Flow Rate: 100.00 mL/min; Column Temperature: 50° C. Mobile Phase A ($CO_2$) Mobile (60%), Phase B (MeOH with 0.1% DEA) (40%). Fraction collection was triggered by UV (220 nm).

K. Chiralpak OJ, 30 mm×250 mm, 5 µm particles; Flow Rate: 100.00 mL/min; Column Temperature: 35° C. Mobile Phase A ($CO_2$) Mobile (75%), Phase B (IPA with 0.1% DEA) (40%). Fraction collection was triggered by UV (220 nm).

O. Chiralpak AD-H, 30 mm×250 mm, 5 µm particles; Flow Rate: 100.00 mL/min; Column Temperature: 50° C. Mobile Phase A ($CO_2$) Mobile (60%), Phase B (EtOH with 0.1% DEA) (40%). Fraction collection was triggered by UV (220 nm).

P. Chiralpak IG-H, 30 mm×250 mm, 5 µm particles; Flow Rate: 100.00 mL/min; Column Temperature: 50° C. Mobile Phase A ($CO_2$) Mobile (65%), Phase B (MeOH with 0.1% DEA) (35%). Fraction collection was triggered by UV (220 nm).

V. XBridge C18, 19 mm×200 mm, 5 µm particles; Flow Rate: 20.00 mL/min; Column Temperature: 25° C. Mobile A: acetonitrile/water (5:95) with 10 mM ammonium acetate; Mobile phase B: acetonitrile/water (95:5) with 10 mM ammonium acetate; Gradient=0 (min)-

21% B, 21-61% B, 100-100% B. Fraction collection was triggered by UV (220 nm).

W. XBridge C18, 19 mm×200 mm, 5 μm particles; Flow Rate: 20.00 mL/min; Column Temperature: 25° C. Mobile A: acetonitrile/water (5:95) with 10 mM ammonium acetate; Mobile phase B: acetonitrile/water (95:5) with 10 mM ammonium acetate; Gradient=0 (min)-30% B, 30-70% B, 100-100% B. Fraction collection was triggered by UV (220 nm).

Y. XBridge C18, 30 mm×200 mm, 5 μm particles; Flow Rate: 50.00 mL/min; Column Temperature: 25° C. Mobile A: acetonitrile/water (5:95) with 10 mM ammonium acetate; Mobile phase B: acetonitrile/water (95:5) with 10 mM ammonium acetate; Gradient=0 (min)-25% B, 25-55% B, 100-100% B. Fraction collection was triggered by UV (220 nm).

Z. XBridge C18, 30 mm×200 mm, 5 μm particles; Flow Rate: 50.00 mL/min; Column Temperature: 25° C. Mobile A: acetonitrile/water (5:95) with 10 mM ammonium acetate; Mobile phase B: acetonitrile/water (95:5) with 10 mM ammonium acetate; Gradient=0 (min)-33% B, 33-63% B, 100-100% B. Fraction collection was triggered by UV (220 nm).

AB. XBridge C18, 19 mm×200 mm, 5 μm particles; Flow Rate: 20.00 mL/min; Column Temperature: 25° C. Mobile A: acetonitrile/water (5:95) with 10 mM ammonium acetate; Mobile phase B: acetonitrile/water (95:5) with 10 mM ammonium acetate; Gradient=0 (min)-20% B, 20-60% B, 100-100% B. Fraction collection was triggered by UV (220 nm).

AC. XBridge C18, 19 mm×200 mm, 5 μm particles; Flow Rate: 20.00 mL/min; Column Temperature: 25° C. Mobile A: acetonitrile/water (5:95) with 10 mM ammonium acetate; Mobile phase B: acetonitrile/water (95:5) with 10 mM ammonium acetate; Gradient=0 (min)-37% B, 37-75% B, 100-100% B. Fraction collection was triggered by UV (220 nm).

AJ. XBridge C18, 19 mm×200 mm, 5 μm particles; Flow Rate: 20.00 mL/min; Column Temperature: 25° C. Mobile A: acetonitrile/water (5:95) with 10 mM ammonium acetate; Mobile phase B: acetonitrile/water (95:5) with 10 mM ammonium acetate; Gradient=0 (min)-41% B, 41-76% B, 100-100% B. Fraction collection was triggered by UV (220 nm).

AK. Chiralpak IG-H, 30 mm×250 mm, 5 μm particles; Flow Rate: 100.00 mL/min; Column Temperature: 50° C. Mobile Phase A ($CO_2$) Mobile (60%), Phase B (MeOH with 0.1% DEA) (40%). Fraction collection was triggered by UV (220 nm).

AL. XBridge C18, 19 mm×200 mm, 5 μm particles; Flow Rate: 20.00 mL/min; Column Temperature: 25° C. Mobile A: acetonitrile/water (5:95) with 10 mM ammonium acetate; Mobile phase B: acetonitrile/water (95:5) with 10 mM ammonium acetate; Gradient=0 (min)-41% B, 41-71% B, 100-100% B. Fraction collection was triggered by UV (220 nm).

AM. XBridge C18, 19 mm×200 mm, 5 μm particles; Flow Rate: 20.00 mL/min; Column Temperature: 25° C. Mobile A: acetonitrile/water (5:95) with 10 mM ammonium acetate; Mobile phase B: acetonitrile/water (95:5) with 10 mM ammonium acetate; Gradient=0 (min)-32% B, 32-72% B, 100-100% B. Fraction collection was triggered by UV (220 nm).

TABLE 1

| # | Structure | IUPAC | LCMS (M + H)+ | $^1$H NMR |
|---|---|---|---|---|
| 1-5 | 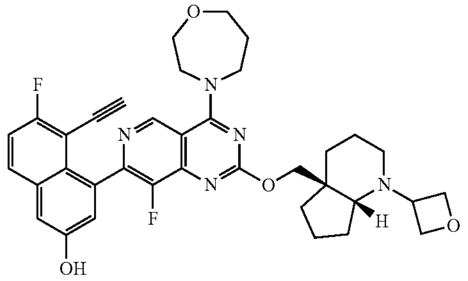 [SMILES: C#Cc1c(F)ccc2cc(O)cc(-c3ncc4c(N5CCCOCC5)nc(OC[C@]56CCC[C@H]5N(C5COC5)CCC6)nc4c3F)c12] | 4-(2-{[(4aS,7aR)-1-(oxetan-3-yl)-octahydro-1H-cyclopenta[b]pyridin-4a-yl]methoxy}-8-fluoro-4-(1,4-oxazepan-4-yl)pyrido[4,3-d]-pyrimidin-7-yl)-5-ethynyl-6-fluoronaphthalen-2-ol | 642.4 | $^1$H NMR (500 MHz, DMSO-$d_6$) δ 9.10 (s, 1H), 7.98 (dd, J = 9.0, 5.6 Hz, 1H), 7.47 (br t, J = 8.9 Hz, 1H), 7.40 (d, J = 2.4 Hz, 1H), 7.19 (d, J = 2.3 Hz, 1H), 4.60 (br d, J = 10.6 Hz, 1H), 4.53-4.47 (m, 1H), 4.46-4.39 (m, 3H), 4.28 (br dd, J = 10.7, 5.7 Hz, 1H), 4.15 (br s, 4H), 4.03-3.93 (m, 3H), 3.77 (br d, J = 4.8 Hz, 2H), 3.74-3.68 (m, 1H), 2.96-2.85 (m, 1H), 2.47-2.38 (m, 1H), 2.34-2.24 (m, 1H), 2.11 (br s, 2H), 1.86-1.76 (m, 1H), 1.73-1.54 (m, 5H), 1.50-1.41 (m, 2H), 1.37-1.28 (m, 2H). |

TABLE 1-continued

| # | Structure | IUPAC | LCMS (M + H)+ | $^1$H NMR |
|---|---|---|---|---|
| 1-6 | 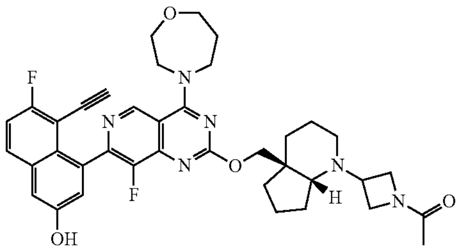 [SMILES: C#Cc1c(F)ccc2cc(O)cc(-c3ncc4c(N5CCCOCC5)nc(OC[C@]56CCC[C@H]5N(C5CN(C(C)=O)C5)CCC6)nc4c3F)c12] | 1-{3-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}-methyl)-octahydro-1H-cyclopenta[b]pyridin-1-yl]azetidin-1-yl}ethan-1-one | 683.5 | $^1$H NMR (500 MHz, DMSO-$d_6$) δ 9.09 (d, J = 1.8 Hz, 1H), 7.95 (dd, J = 9.2, 6.0 Hz, 1H), 7.45 (t, J = 8.9 Hz, 1H), 7.38 (d, J = 2.4 Hz, 1H), 7.20-7.16 (m, 1H), 4.61-4.53 (m, 1H), 4.50-4.41 (m, 1H), 4.35-4.23 (m, 1H), 4.21-4.05 (m, 6H), 4.01-3.84 (m, 5H), 3.80-3.73 (m, 3H), 3.05-2.97 (m, 1H), 2.49-2.43 (m, 1H), 2.34-2.24 (m, 1H), 2.15-2.06 (m, 2H), 1.92-1.80 (m, 1H), 1.74-1.65 (m, 5H), 1.61-1.52 (m, 3H), 1.50-1.42 (m, 2H), 1.42-1.29 (m, 2H) |
| 1-7 | 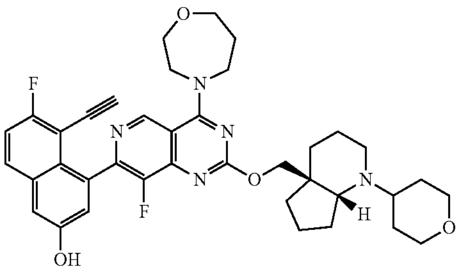 [SMILES: C#Cc1c(F)ccc2cc(O)cc(-c3ncc4c(N5CCCOCC5)nc(OC[C@]56CCC[C@H]5N(C5CCOCC5)CCC6)nc4c3F)c12] | 5-ethynyl-6-fluoro-4-(8-fluoro-4-(1,4-oxazepan-4-yl)-2-(((4aS,7aR)-1-(tetrahydro-2H-pyran-4-yl)octahydro-4aH-cyclopenta[b]pyridin-4a-yl)-methoxy)pyrido[4,3-d]pyrimidin-7-yl)-naphthalen-2-ol | 670 | $^1$H NMR (500 MHz, DMSO-$d_6$) δ 9.10 (s, 1H), 7.97 (dd, J = 9.2, 5.9 Hz, 1H), 7.47 (t, J = 8.9 Hz, 1H), 7.40 (d, J = 2.1 Hz, 1H), 7.19 (s, 1H), 4.61 (br d, J = 10.7 Hz, 1H), 4.24-4.09 (m, 5H), 4.04-3.92 (m, 3H), 3.87-3.73 (m, 5H), 3.28-3.21 (m, 3H), 3.13 (br t, J = 8.3 Hz, 1H), 2.65-2.58 (m, 1H), 2.48-2.36 (m, 2H), 2.11 (br s, 2H), 1.97-1.86 (m, 1H), 1.76-1.28 (m, 13H). |
| 1-8 | 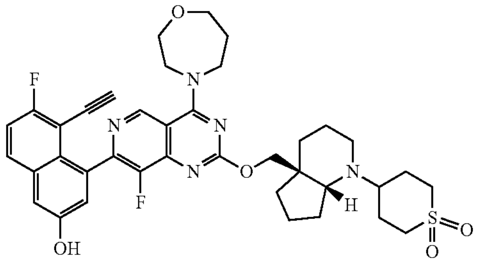 [SMILES: C#Cc1c(F)ccc2cc(O)cc(-c3ncc4c(N5CCCOCC5)nc(OC[C@]56CCC[C@H]5N(C5CCS(=O)(=O)CC5)CCC6)nc4c3F)c12] | 4-((4aS,7aR)-4a-(((7-(8-ethynyl-7-fluoro-3-hydroxynaphthalen-1-yl)-8-fluoro-4-(1,4-oxazepan-4-yl)pyrido[4,3-d]pyrimidin-2-yl)oxy)methyl) octahydro-1H-cyclopenta[b] pyridin-1-yl)-tetrahydro-2H-thiopyran 1,1-dioxide | 718.4 | $^1$H NMR (500 MHz, DMSO-$d_6$) δ 9.09 (s, 1H), 8.00-7.94 (m, 2H), 7.46 (t, J = 9.0 Hz, 1H), 7.40 (d, J = 2.4 Hz, 1H), 7.19 (d, J = 2.3 Hz, 1H), 4.27 (br dd, J = 10.1, 8.0 Hz, 1H), 4.21-4.08 (m, 5H), 4.00-3.93 (m, 3H), 3.76 (br t, J = 5.0 Hz, 2H), 3.12-2.95 (m, 5H), 2.68-2.61 (m, 1H), 2.45-2.36 (m, 1H), 2.19-2.06 (m, 4H), 1.98-1.84 (m, 5H), 1.80-1.69 (m, 1H), 1.66-1.44 (m, 7H), 1.38-1.29 (m, 1H) |

TABLE 1-continued

| # | Structure | IUPAC | LCMS (M + H)+ | 1H NMR |
|---|---|---|---|---|
| 1-9 | 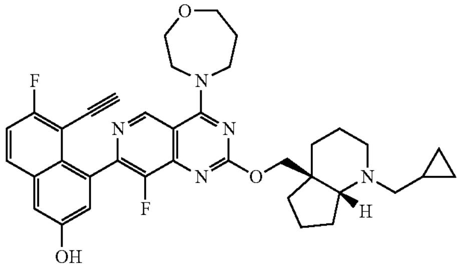 [SMILES: C#Cc1c(F)ccc2cc(O)cc(-c3ncc4c(N5CCCOCC5)nc(OC[C@]56CCC[C@H]5N(CC5CC5)CCC6)nc4c3F)c12] | 4-(2-{[(4aS,7aR)-1-(cyclopropyl-methyl)-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaph-thalen-2-ol | 640.1 | $^1$H NMR (500 MHz, DMSO-$d_6$) δ 9.07 (s, 1H), 7.94 (dd, J = 9.1, 6.0 Hz, 1H), 7.43 (t, J = 9.0 Hz, 1H), 7.37 (d, J = 2.3 Hz, 1H), 7.17 (d, J = 2.0 Hz, 1H), 4.56 (br d, J = 10.5 Hz, 1H), 4.20-4.05 (m, 5H), 3.97 (br d, J = 7.5 Hz, 1H), 3.92 (br t, J = 4.1 Hz, 2H), 3.77-3.71 (m, 2H), 2.98 (br t, J = 7.5 Hz, 1H), 2.44-2.36 (m, 1H), 2.30 (dt, J = 12.7, 6.3 Hz, 1H), 2.18-2.04 (m, 3H), 1.80-1.75 (m, 1H), 1.72-1.64 (m, 1H), 1.60-1.40 (m, 7H), 1.37-1.27 (m, 1H), 0.79-0.71 (m, 1H), 0.38 (br d, J = 7.7 Hz, 2H), 0.07--0.03 (m, 2H) |
| 1-10 | 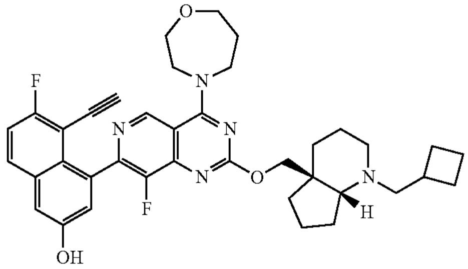 [SMILES: C#Cc1c(F)ccc2cc(O)cc(-c3ncc4c(N5CCCOCC5)nc(OC[C@]56CCC[C@H]5N(CC5CCC5)CCC6)nc4c3F)c12] | 4-(2-{[(4aS,7aR)-1-(cyclobut-ylmethyl)-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaph-thalen-2-ol | 654.2 | $^1$H NMR (500 MHz, DMSO-$d_6$) δ 8.88 (s, 1H), 7.75 (dd, J = 9.0, 6.0 Hz, 1H), 7.25 (t, J = 8.9 Hz, 1H), 7.18 (d, J = 2.2 Hz, 1H), 6.98 (d, J = 2.1 Hz, 1H), 4.39-4.31 (m, 1H), 4.01-3.85 (m, 5H), 3.79-3.70 (m, 3H), 3.55 (br t, J = 4.8 Hz, 2H), 2.63 (br t, J = 8.0 Hz, 1H), 2.25-2.08 (m, 5H), 1.89 (br d, J = 3.6 Hz, 2H), 1.78-1.67 (m, 2H), 1.66-1.44 (m, 5H), 1.43-1.26 (m, 8H), 1.25-1.16 (m, 1H), 1.15-1.05 (m, 1H) |
| 1-11 | 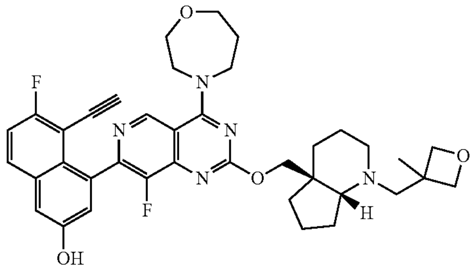 [SMILES: C#Cc1c(F)ccc2cc(O)cc(-c3ncc4c(N5CCCOCC5)nc(OC[C@]56CCC[C@H]5N(CC5(C)COC5)CCC6)nc4c3F)c12] | 4-(2-{[(4aS,7aR)-1-[(3-methylox-eoxetan-3-yl)-methyl]-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethyn-yl-6-fluoro-naphthalen-2-ol | 670.5 | $^1$H NMR (500 MHz, DMSO-$d_6$) δ 9.09 (s, 1H), 8.00-7.91 (m, 2H), 7.46 (t, J = 9.0 Hz, 1H), 7.39 (d, J = 2.4 Hz, 1H), 7.18 (s, 1H), 4.63 (d, J = 10.6 Hz, 1H), 4.39-4.29 (m, 2H), 4.23-4.08 (m, 7H), 3.98-3.91 (m, 3H), 3.76 (br t, J = 4.8 Hz, 2H), 2.49-2.41 (m, 3H), 2.18 (br d, J = 11.6 Hz, 1H), 2.13-2.04 (m, 2H), 1.87 (s, 3H), 1.75-1.68 (m, 1H), 1.63-1.47 (m, 7H), 1.44-1.38 (m, 1H), 1.34-1.29 (m, 1H), 1.23 (d, J = 3.5 Hz, 3H) |

TABLE 1-continued

| # | Structure | IUPAC | LCMS (M + H)+ | 1H NMR |
|---|---|---|---|---|
| 1-12 | 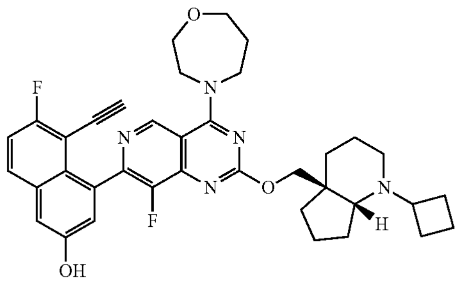 [SMILES: C#Cc1c(F)ccc2cc(O)cc(-c3ncc4c(N5CCCOCC5)nc(OC[C@]56CCC[C@H]5N(C5CCC5)CCC6)nc4c3F)c12] | 4-(2-{[(4aS,7aR)-1-cyclobutyl-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 640.4 | $^1$H NMR (500 MHz, DMSO-$d_6$) δ 9.10 (s, 1H), 7.98 (dd, J = 9.1, 6.0 Hz, 1H), 7.47 (br t, J = 9.0 Hz, 1H), 7.40 (d, J = 2.3 Hz, 1H), 7.19 (s, 1H), 4.60 (dd, J = 10.5, 2.8 Hz, 1H), 4.27-4.07 (m, 6H), 4.03-3.92 (m, 3H), 3.77 (br t, J = 4.8 Hz, 2H), 3.02-2.96 (m, 1H), 2.95-2.88 (m, 1H), 2.45 (br d, J = 10.9 Hz, 1H), 2.18-2.08 (m, 3H), 1.97-1.80 (m, 4H), 1.75-1.64 (m, 3H), 1.63-1.51 (m, 6H), 1.49-1.33 (m, 3H), 1.32-1.22 (m, 1H) |
| 1-13 | 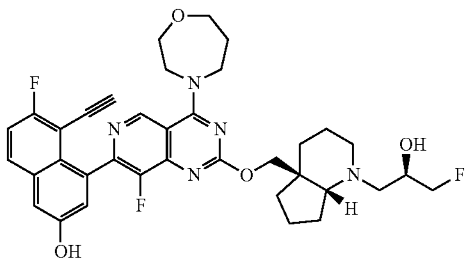 [SMILES: C#Cc1c(F)ccc2cc(O)cc(-c3ncc4c(N5CCCOCC5)nc(OC[C@]56CCC[C@H]5N(C[C@@H](O)CF)CCC6)nc4c3F)c12] | 4-(2-{[(4aS,7aR)-1-[(2R)-3-fluoro-2-hydroxy-propyl]-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaph-thalen-2-ol | 661.8 | $^1$H NMR (500 MHz, DMSO-$d_6$) δ 9.10 (s, 1H), 8.00-7.94 (m, 1H), 7.49-7.44 (m, 1H), 7.40 (d, J = 2.2 Hz, 1H), 7.19 (br s, 1H), 4.53 (br dd, J = 10.6, 7.9 Hz, 1H), 4.46-4.39 (m, 1H), 4.37-4.30 (m, 1H), 4.27-4.11 (m, 6H), 4.01-3.93 (m, 3H), 3.84-3.73 (m, 4H), 2.88 (br t, J = 6.6 Hz, 1H), 2.42-2.34 (m, 3H), 2.11 (br d, J = 3.7 Hz, 2H), 1.90-1.81 (m, 1H), 1.76-1.69 (m, 1H), 1.65-1.51 (m, 7H), 1.48-1.40 (m, 1H), 1.40-1.30 (m, 1H) |
| 1-14 | 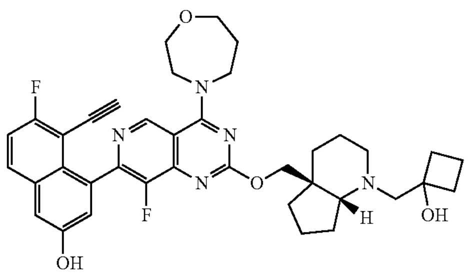 [SMILES: C#Cc1c(F)ccc2cc(O)cc(-c3ncc4c(N5CCCOCC5)nc(OC[C@]56CCC[C@H]5N(CC5(O)CCC5)CCC6)nc4c3F)c12] | 4-(2-{[(4aS,7aR)-1-[(1-hydroxy-cyclobutyl)-methyl]-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 670.2 | $^1$H NMR (500 MHz, DMSO-$d_6$) δ 9.09 (s, 1H), 7.99-7.94 (m, 1H), 7.46 (t, J = 9.0 Hz, 1H), 7.39 (d, J = 2.2 Hz, 1H), 7.18 (d, J = 2.3 Hz, 1H), 4.66 (br d, J = 10.9 Hz, 1H), 4.24-4.09 (m, 5H), 4.00-3.89 (m, 4H), 3.76 (br s, 2H), 3.00-2.92 (m, 1H), 2.89 (s, 1H), 2.73 (s, 1H), 2.46-2.36 (m, 2H), 2.10 (br s, 2H), 2.04-1.94 (m, 2H), 1.91-1.80 (m, 4H), 1.75-1.66 (m, 1H), 1.64-1.50 (m, 8H), 1.45-1.37 (m, 2H), 1.35-1.26 (m, 1H) |

TABLE 1-continued

| # | Structure | IUPAC | LCMS (M + H)+ | 1H NMR |
|---|---|---|---|---|
| 1-15 | 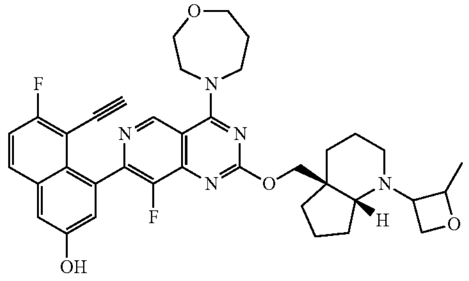 Diastereomer Mixture | 4-(2-{[(4aS,7aR)-1-(2-methyloxetan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 656 | |
| 1-16[4M] | 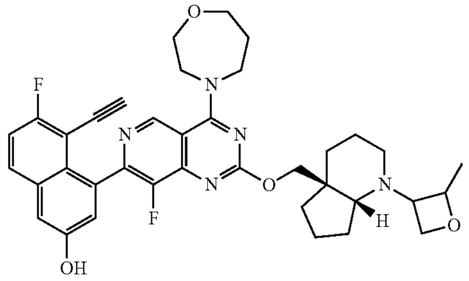 Diastereomer 2 | 4-(2-{[(4aS,7aR)-1-(2-methyl-oxetan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 656.2 | |
| 1-18 | 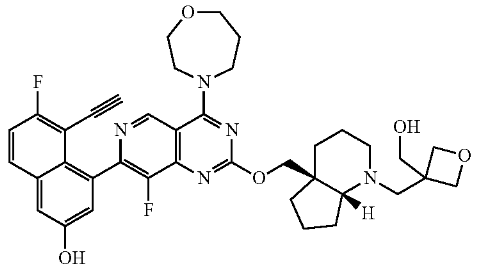 [SMILES: C#Cc1c(F)ccc2cc(O)cc(-c3ncc4c(N5CCCOCC5)nc(OC[C@]56CCC[C@H]5N(CC5(CO)COC5)CCC6)nc4c3F)c12] | 4-(2-{[(4aS,7aR)-1-{[3-(hydroxymethyl)-oxetan-3-yl]methyl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 685.9 | $^1$H NMR (500 MHz, DMSO-$d_6$) δ 9.09 (s, 1H), 8.00-7.92 (m, 1H), 7.46 (t, J = 9.0 Hz, 1H), 7.39 (d, J = 2.5 Hz, 1H), 7.18 (d, J = 2.4 Hz, 1H), 4.61 (br dd, J = 10.6, 4.9 Hz, 1H), 4.32-4.22 (m, 3H), 4.20-4.08 (m, 4H), 4.00-3.88 (m, 3H), 3.76 (br t, J = 4.7 Hz, 2H), 3.59 (br d, J = 3.2 Hz, 2H), 2.89 (s, 1H), 2.83-2.76 (m, 1H), 2.73 (s, 1H), 2.69-2.57 (m, 2H), 2.46 (br dd, J = 10.8, 2.2 Hz, 1H), 2.28-2.20 (m, 1H), 2.15-2.05 (m, 2H), 1.94-1.84 (m, 1H), 1.77-1.67 (m, 1H), 1.66-1.46 (m, 5H), 1.44-1.38 (m, 1H), 1.35-1.20 (m, 2H) |
| 1-19 | 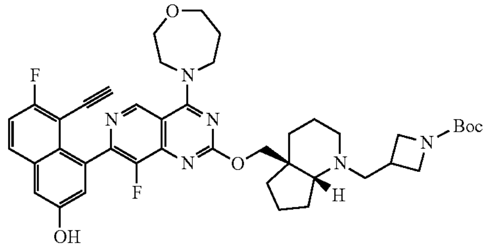 [SMILES: C#Cc1c(F)ccc2cc(O)cc(-c3ncc4c(N5CCCOCC5)nc(OC[C@]56CCC[C@H]5N(CC5CN(C(=O)OC(C)(C)C)C5)CCC6)nc4c3F)c12] | tert-butyl 3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta | 755.2 | $^1$H NMR (500 MHz, DMSO-$d_6$) δ 9.10 (s, 1H), 7.96 (dd, J = 9.0, 5.8 Hz, 1H), 7.46 (t, J = 9.0 Hz, 1H), 7.39 (d, J = 2.4 Hz, 1H), 7.18 (d, J = 2.4 Hz, 1H), 4.57-4.49 (m, 1H), 4.27-4.12 (m, 5H), 4.00-3.89 (m, 4H), 3.85-3.74 (m, 5H), 2.89 (s, 1H), 2.88-2.83 (m, 1H), 2.73 |

TABLE 1-continued

| # | Structure | IUPAC | LCMS (M + H)+ | $^1$H NMR |
|---|---|---|---|---|
| | | [b]pyridin-1-yl]methyl}-azetidine-1-carboxylate | | (s, 1H), 2.71-2.63 (m, 1H), 2.46-2.33 (m, 2H), 2.15-2.07 (m, 2H), 1.87-1.80 (m, 4H), 1.75-1.65 (m, 1H), 1.62-1.49 (m, 5H), 1.46-1.39 (m, 1H), 1.38-1.26 (m, 10H) |
| 1-20 | 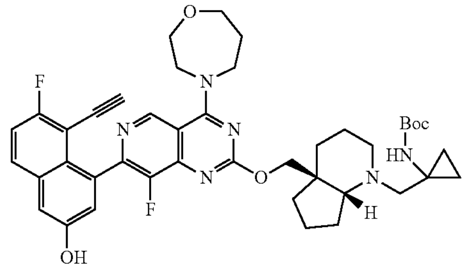 [SMILES: C#Cc1c(F)ccc2cc(O)cc(-c3ncc4c(N5CCCOCC5)nc(OC[C@]56CCC[C@H]5N(CC5(NC(=O)OC(C)(C)C)CC5)CCC6)nc4c3F)c12] | tert-butyl N-(1-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-cyclopropyl)-carbamate | 754.9 | $^1$H NMR (500 MHz, DMSO-$d_6$) δ 9.09 (s, 1H), 7.95 (dd, J = 9.2, 6.2 Hz, 1H), 7.45 (t, J = 9.0 Hz, 1H), 7.38 (d, J = 2.4 Hz, 1H), 7.17 (s, 1H), 4.59-4.50 (m, 1H), 4.23-4.08 (m, 5H), 3.98-3.92 (m, 3H), 3.77 (br t, J = 5.1 Hz, 2H), 3.62-3.52 (m, 5H), 2.89-2.80 (m, 1H), 2.49-2.28 (m, 3H), 2.15-2.05 (m, 2H), 1.86-1.78 (m, 1H), 1.75-1.67 (m, 1H), 1.66 (s, 1H), 1.61-1.51 (m, 5H), 1.47-1.40 (m, 1H), 1.39-1.20 (m, 10H), 0.64-0.43 (m, 4H) |
| 1-21 | 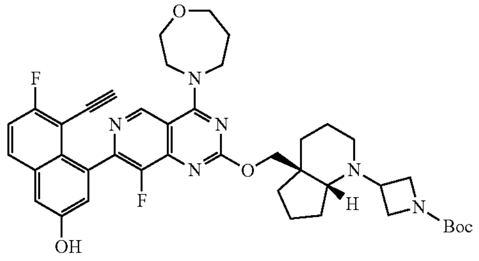 [SMILES: C#Cc1c(F)ccc2cc(O)cc(-c3ncc4c(N5CCCOCC5)nc(OC[C@]56CCC[C@H]5N(C5CN(C(=O)OC(C)(C)C)C5)CCC6)nc4c3F)c12] | tert-butyl 3-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]azetidine-1-carboxylate | 741 | $^1$H NMR (500 MHz, DMSO-$d_6$) δ 9.10 (s, 1H), 8.01-7.94 (m, 2H), 7.46 (t, J = 9.0 Hz, 1H), 7.39 (s, 1H), 7.19 (br s, 1H), 4.56 (br d, J = 10.8 Hz, 1H), 4.34-4.23 (m, 1H), 4.20-4.10 (m, 4H), 4.01-3.94 (m, 3H), 3.77 (br d, J = 4.1 Hz, 3H), 3.68-3.60 (m, 2H), 3.05-2.96 (m, 1H), 2.90 (s, 2H), 2.74 (s, 2H), 2.49-2.41 (m, 1H), 2.27 (br t, J = 11.1 Hz, 1H), 2.12 (br d, J = 5.5 Hz, 2H), 1.89-1.81 (m, 2H), 1.76-1.64 (m, 2H), 1.61-1.52 (m, 3H), 1.49-1.38 (m, 3H), 1.34 (br s, 9H). |
| 1-22 | 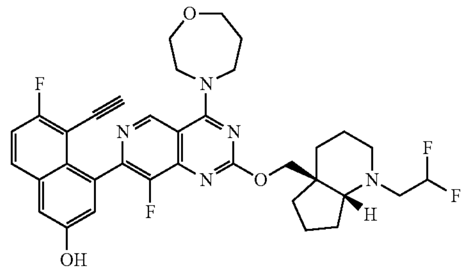 [SMILES: C#Cc1c(F)ccc2cc(O)cc(-c3ncc4c(N5CCCOCC5)nc(OC[C@]56CCC[C@H]5N(CC(F)F)CCC6)nc4c3F)c12] | 4-(2-{[(4aS,7aR)-1-(2,2-difluoroethyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 450.1 | $^1$H NMR (500 MHz, DMSO-$d_6$) δ 9.09 (s, 1H), 7.97 (dd, J = 9.2, 6.0 Hz, 1H), 7.46 (t, J = 9.0 Hz, 1H), 7.39 (d, J = 2.4 Hz, 1H), 7.19 (s, 1H), 6.15-5.87 (m, 1H), 4.56 (dd, J = 10.8, 5.3 Hz, 1H), 4.21-4.07 (m, 5H), 4.00-3.89 (m, 3H), 3.76 (br t, J = 5.1 Hz, 2H), 2.96-2.91 (m, 1H), 2.83-2.68 (m, 2H), 2.63-2.56 (m, 1H), 2.49 (br s, 2H), 2.15-2.05 (m, |

TABLE 1-continued

| # | Structure | IUPAC | LCMS (M + H)+ | $^1$H NMR |
|---|---|---|---|---|
| | | | | 2H), 1.88-1.79 (m, 1H), 1.76-1.68 (m, 1H), 1.65-1.52 (m, 6H), 1.49-1.42 (m, 1H), 1.39-1.30 (m, 1H). |
| 1-23 | 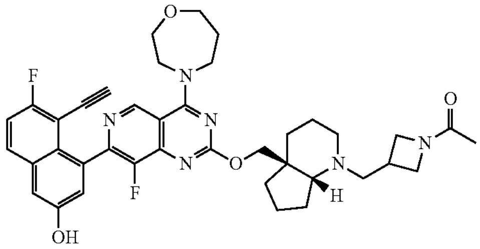 [SMILES: C#Cc1c(F)ccc2cc(O)cc(-c3ncc4c(N5CCCOCC5)nc(OC[C@]56CCC[C@H]5N(CC5CN(C(C)=O)C5)CCC6)nc4c3F)c12] | 1-(3-{[(4aS,7aR)-4a-({[7-(8-ethynyl-7-fluoro-3-hydroxy-naphthalen-1-yl)-8-fluoro-4-(1,4-oxazepan-4-yl)pyrido[4,3-d]pyrimidin-2-yl]oxy}-methyl)-octa-hydro-1H-cyclopenta[b]pyridin-1-yl]methyl}azetidin-1-yl)ethan-1-one | 697.2 | $^1$H NMR (500 MHz, DMSO-$d_6$) δ 9.12-9.05 (m, 1H), 8.00-7.94 (m, 2H), 7.47 (t, J = 9.0 Hz, 1H), 7.40 (d, J = 2.5 Hz, 1H), 7.19 (d, J = 2.0 Hz, 1H), 4.57-4.45 (m, 1H), 4.32-4.21 (m, 1H), 4.20-4.11 (m, 4H), 4.09-3.94 (m, 4H), 3.84-3.62 (m, 5H), 2.87 (br d, J = 2.0 Hz, 2H), 2.74-2.67 (m, 2H), 2.48-2.33 (m, 2H), 2.16-2.06 (m, 2H), 1.91 (s, 1H), 1.88-1.81 (m, 1H), 1.78-1.68 (m, 1H), 1.68-1.63 (m, 3H), 1.62-1.44 (m, 6H), 1.43 (br s, 1H), 1.39-1.30 (m, 1H) |
| 1-24 | 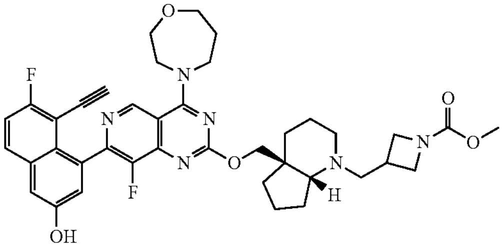 [SMILES: C#Cc1c(F)ccc2cc(O)cc(-c3ncc4c(N5CCCOCC5)nc(OC[C@]56CCC[C@H]5N(CC5CN(C(=O)OC)C5)CCC6)nc4c3F)c12] | methyl 3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}azetidine-1-carboxylate | 713.8 | |
| 1-25 | 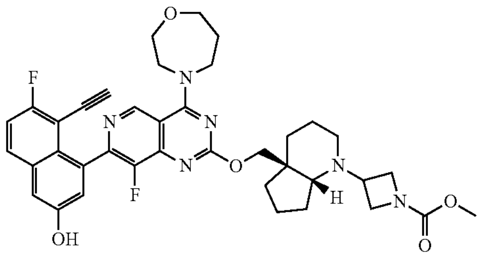 [SMILES: C#Cc1c(F)ccc2cc(O)cc(-c3ncc4c(N5CCCOCC5)nc(OC[C@]56CCC[C@H]5N(C5CN(C(=O)OC)C5)CCC6)nc4c3F)c12] | methyl 3-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}-methyl)-octa-hydro-1H-cyclopenta[b]pyridin-1-yl]azetidine-1-carboxylate | 699.3 | |

TABLE 1-continued

| # | Structure | IUPAC | LCMS (M + H)+ | $^1$H NMR |
|---|---|---|---|---|
| 1-26 | 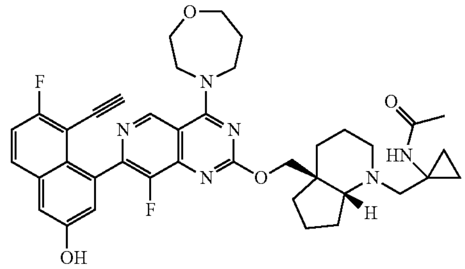 [SMILES: C#Cc1c(F)ccc2cc(O)cc(-c3ncc4c(N5CCCOCC5)nc(OC[C@]56CCC[C@H]5N(CC5(NC(C)=O)CC5)CCC6)nc4c3F)c12] | N-(1-{[(4aS,7aR)-4a-({[7-(8-ethynyl-7-fluoro-3-hydroxy-naphthalen-1-yl)-8-fluoro-4-(1,4-oxazepan-4-yl)pyrido[4,3-d]pyrimi-din-2-yl]oxy}-methyl)-octa-hydro-1H-cyclopenta[b]pyridin-1-yl]methyl}cyclo-propyl)acet-amide | 697.1 | $^1$H NMR (500 MHz, DMSO-$d_6$) δ 9.09 (s, 1H), 8.00-7.94 (m, 2H), 7.87 (s, 1H), 7.47 (t, J = 9.0 Hz, 1H), 7.40 (d, J = 2.4 Hz, 1H), 7.18 (s, 1H), 4.58 (br dd, J = 10.7, 5.0 Hz, 1H), 4.20-4.11 (m, 5H), 4.00-3.93 (m, 3H), 3.82-3.73 (m, 3H), 2.94-2.82 (m, 4H), 2.45-2.36 (m, 1H), 2.11 (br s, 2H), 1.93-1.89 (m, 2H), 1.86-1.76 (m, 1H) 1.72-1.68 (m, 3H), 1.63-1.42 (m, 7H), 1.38-1.27 (m, 1H), 0.58-0.45 (m, 4H) |
| 1-27 | 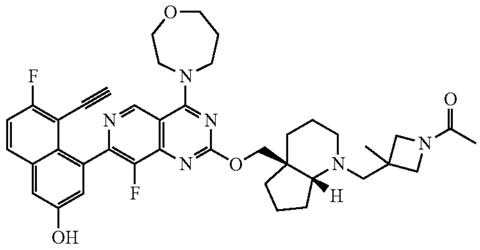 [SMILES: C#Cc1c(F)ccc2cc(O)cc(-c3ncc4c(N5CCCOCC5)nc(OC[C@]56CCC[C@H]5N(CC5(C)CN(C(C)=O)C5)CCC6)nc4c3F)c12] | 1-(3-{[(4aS,7aR)-4a-({[7-(8-ethynyl-7-fluoro-3-hydroxynaph-thalen-1-yl)-8-fluoro-4-(1,4-oxazepan-4-yl)pyrido[4,3-d]pyrimidin-2-yl]oxy}meth-yl)-octahydro-1H-cyclopenta[b]pyridin-1-yl]methyl}-3-methylazeti-din-1-yl)ethan-1-one | 771.4 | H NMR (500 MHz, DMSO-$d_6$) δ 10.17 (s, 1H), 9.10 (s, 1H), 7.98 (dd, J = 8.9, 6.0 Hz, 1H), 7.47 (t, J = 9.0 Hz, 1H), 7.40 (d, J = 2.4 Hz, 1H), 7.19 (br s, 1H), 4.66-4.53 (m, 1H), 4.30-4.21 (m, 1H), 4.15 (br s, 5H), 4.04-3.90 (m, 4H), 3.87-3.73 (m, 4H), 3.67-3.51 (m, 2H), 2.88 (br dd, J = 5.6, 1.5 Hz, 1H), 2.44-2.28 (m, 2H), 2.11 (br s, 2H), 1.94-1.84 (m, 1H), 1.77-1.40 (m, 10H), 1.37-1.22 (m, 2H), 1.18 (br d, J = 3.7 Hz, 3H) |
| 1-28 | 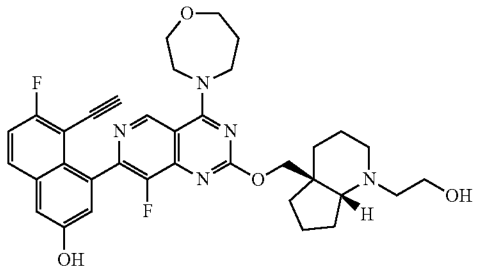 [SMILES: C#Cc1c(F)ccc2cc(O)cc(-c3ncc4c(N5CCCOCC5)nc(OC[C@]56CCC[C@H]5N(CCO)CCC6)nc4c3F)c12] | 4-(2-{[(4aS,7aR)-1-(2-hydroxy-ethyl)-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaph-thalen-2-ol | 630.1 | $^1$H NMR (500 MHz, DMSO-$d_6$) δ 9.09 (s, 1H), 8.01-7.92 (m, 2H), 7.47 (t, J = 9.0 Hz, 1H), 7.40 (d, J = 2.3 Hz, 1H), 7.19 (s, 1H), 4.55 (dd, J = 10.9, 3.4 Hz, 1H), 4.25-4.07 (m, 6H), 4.03-3.89 (m, 4H), 3.77 (br t, J = 4.8 Hz, 3H), 2.91 (br s, 1H), 2.45 (br t, J = 6.2 Hz, 4H), 2.14-2.08 (m, 2H), 1.88-1.82 (m, 1H), 1.77-1.68 (m, 1H), 1.63-1.52 (m, 6H), 1.49-1.42 (m, 1H), 1.40-1.32 (m, 1H) |

TABLE 1-continued

| # | Structure | IUPAC | LCMS (M + H)+ | $^1$H NMR |
|---|---|---|---|---|
| 1-29 | 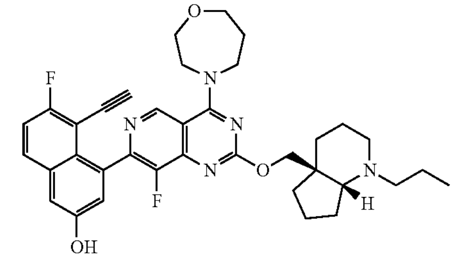 [SMILES: C#Cc1c(F)ccc2cc(O)cc(-c3ncc4c(N5CCCOCC5)nc(OC[C@]56CCC[C@H]5N(CCC)CCC6)nc4c3F)c12] | 4-(2-{[(4aS,7aR)-1-propyl-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 628.5 | $^1$H NMR (500 MHz, DMSO-$d_6$) δ 9.10 (s, 1H), 8.03-7.94 (m, 2H), 7.47 (t, J = 9.0 Hz, 1H), 7.40 (d, J = 2.5 Hz, 1H), 7.19 (br s, 1H), 4.64-4.55 (m, 1H), 4.22-4.11 (m, 5H), 4.00 (br d, J = 6.1 Hz, 1H), 3.95 (br t, J = 4.3 Hz, 2H), 3.81-3.76 (m, 2H), 2.94-2.91 (m, 1H), 2.43-2.36 (m, 2H), 2.30 (br t, J = 6.6 Hz, 2H), 2.11 (br s, 2H), 1.87-1.80 (m, 1H), 1.75-1.67 (m, 1H), 1.65-1.51 (m, 6H), 1.47-1.37 (m, 3H), 0.82 (br t, J = 7.3 Hz, 3H) |
| 1-30 | 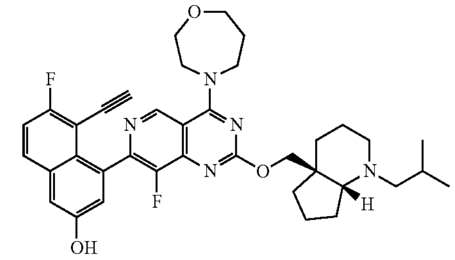 [SMILES: C#Cc1c(F)ccc2cc(O)cc(-c3ncc4c(N5CCCOCC5)nc(OC[C@]56CCC[C@H]5N(CC(C)C)CCC6)nc4c3F)c12] | 4-(2-{[(4aS,7aR)-1-(2-methyl-propyl)-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 642.5 | $^1$H NMR (500 MHz, DMSO-$d_6$) δ 9.10 (s, 1H), 8.01-7.93 (m, 2H), 7.47 (t, J = 8.9 Hz, 1H), 7.40 (d, J = 2.4 Hz, 1H), 7.19 (br s, 1H), 4.65 (br dd, J = 10.6, 4.1 Hz, 1H), 4.24-4.07 (m, 5H), 4.02-3.88 (m, 3H), 3.76 (br d, J = 4.4 Hz, 2H), 2.88-2.81 (m, 1H), 2.47-2.32 (m, 2H), 2.10 (br s, 4H), 1.84 (br dd, J = 9.8, 3.2 Hz, 1H), 1.72 (br dd, J = 13.4, 6.6 Hz, 2H), 1.63-1.39 (m, 8H), 1.38-1.28 (m, 1H), 0.85-0.78 (m, 6H) |
| 1-31 | 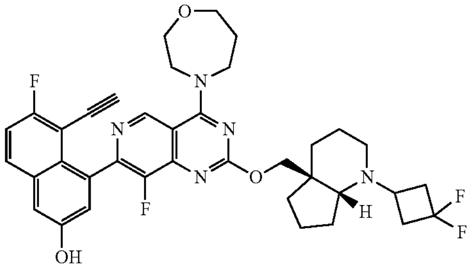 [SMILES: C#Cc1c(F)ccc2cc(O)cc(-c3ncc4c(N5CCCOCC5)nc(OC[C@]56CCC[C@H]5N(C5CC(F)(F)C5)CCC6)nc4c3F)c12] | 4-(2-{[(4aS,7aR)-1-(3,3-difluoro-cyclobutyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 676.2 | |
| 1-32 | 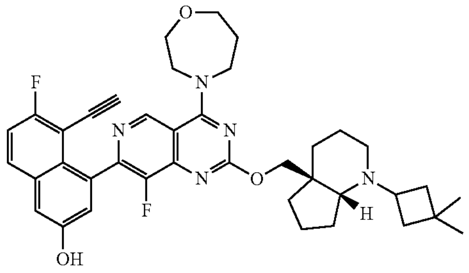 [SMILES: C#Cc1c(F)ccc2cc(O)cc(-c3ncc4c(N5CCCOCC5)nc(OC[C@]56CCC[C@H]5N(C5CC(C)(C)C5)CCC6)nc4c3F)c12] | 4-(2-{[(4aS,7aR)-1-(3,3-dimethylcyclobutyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl- | 668.5 | $^1$H NMR (500 MHz, DMSO-$d_6$) δ 9.10 (s, 1H), 8.01-7.92 (m, 2H), 7.47 (t, J = 9.0 Hz, 1H), 7.40 (d, J = 2.4 Hz, 1H), 7.19 (br d, J = 2.0 Hz, 1H), 4.61 (br d, J = 10.8 Hz, 1H), 4.24 (br t, J = 10.6 Hz, 1H), 4.15 (br s, 4H), 4.03-3.93 (m, 3H), 3.77 (br s, 2H), |

TABLE 1-continued

| # | Structure | IUPAC | LCMS (M + H)+ | $^1$H NMR |
|---|---|---|---|---|
| | | 6-fluoronaphthalen-2-ol | | 3.01-2.93 (m, 2H), 2.46-2.39 (m, 1H), 2.11 (br s, 3H), 1.86-1.74 (m, 3H), 1.71-1.22 (m, 11H), 1.07 (s, 3H), 0.98 (d, J = 2.1 Hz, 3H) |
| 1-33 | 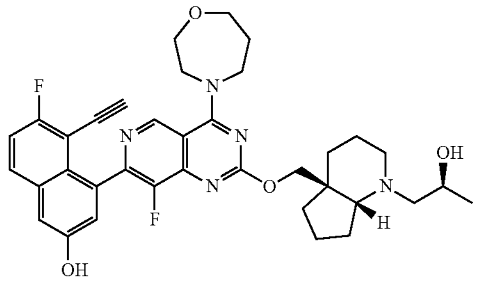 [SMILES: C#Cc1c(F)ccc2cc(O)cc(-c3ncc4c(N5CCCOCC5)nc(OC[C@]56CCC[C@H]5N(C[C@H](C)O)CCC6)nc4c3F)c12] | 4-(2-{[(4aS,7aR)-1-[(2S)-2-hydroxypropyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 644.5 | $^1$H NMR (500 MHz, DMSO-$d_6$) δ 9.09 (s, 1H), 8.01-7.91 (m, 2H), 7.47 (br t, J = 9.0 Hz, 1H), 7.40 (br d, J = 2.3 Hz, 1H), 7.19 (br s, 1H), 4.58 (br dd, J = 10.6, 3.8 Hz, 1H), 4.23 (br t, J = 11.3 Hz, 1H), 4.18-4.07 (m, 4H), 4.00-3.92 (m, 3H), 3.79-3.69 (m, 3H), 2.47-2.41 (m, 1H), 2.34-2.28 (m, 1H), 2.21 (br dd, J = 11.0, 5.1 Hz, 1H), 2.10 (br s, 2H), 1.88-1.82 (m, 1H), 1.74-1.68 (m, 1H), 1.62-1.27 (m, 8H), 1.04-0.96 (m, 3H) |
| 1-34 | 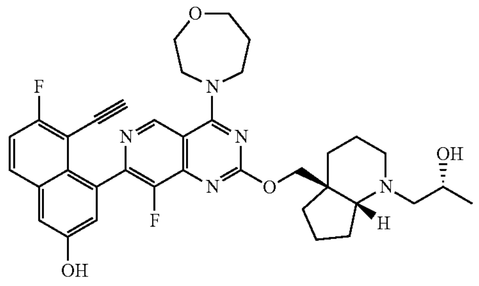 [SMILES: C#Cc1c(F)ccc2cc(O)cc(-c3ncc4c(N5CCCOCC5)nc(OC[C@]56CCC[C@H]5N(C[C@@H](C)O)CCC6)nc4c3F)c12] | 4-(2-{[(4aS,7aR)-1-[(2R)-2-hydroxypropyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 644.4 | $^1$H NMR (500 MHz, DMSO-$d_6$) δ 9.10 (s, 1H), 8.01-7.94 (m, 1H), 7.47 (br t, J = 8.9 Hz, 1H), 7.40 (d, J = 2.2 Hz, 1H), 7.19 (s, 1H), 4.61 (br d, J = 10.4 Hz, 1H), 4.23-4.10 (m, 5H), 4.01-3.92 (m, 3H), 3.76 (br d, J = 4.7 Hz, 2H), 3.71-3.65 (m, 1H), 2.47-2.42 (m, 1H), 2.36-2.28 (m, 1H), 2.24-2.18 (m, 1H), 2.11 (br d, J = 1.1 Hz, 2H), 1.89-1.83 (m, 1H), 1.79-1.69 (m, 1H), 1.63-1.18 (m, 10H), 1.01 (dd, J = 5.8, 3.7 Hz, 3H). |
| 1-35 | 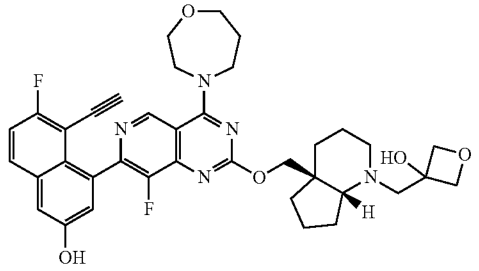 [SMILES: C#Cc1c(F)ccc2cc(O)cc(-c3ncc4c(N5CCCOCC5)nc(OC[C@]56CCC[C@H]5N(CC5(O)COC5)CCC6)nc4c3F)c12] | 3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}-methyl)-octahydro-1H-cyclopenta[b]pyridin-1-yl]methyl}oxetan-3-ol | 672.4 | |

TABLE 1-continued

| # | Structure | IUPAC | LCMS $(M + H)^+$ | $^1$H NMR |
|---|---|---|---|---|
| 1-36 | 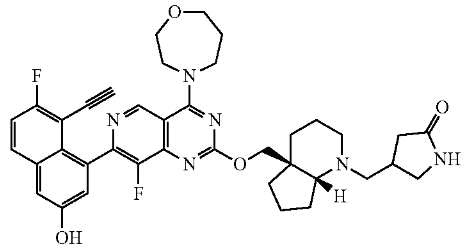 Diastereomer Mixture | 4-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}pyrrolidin-2-one | 683.2 | |
| 1-37 | 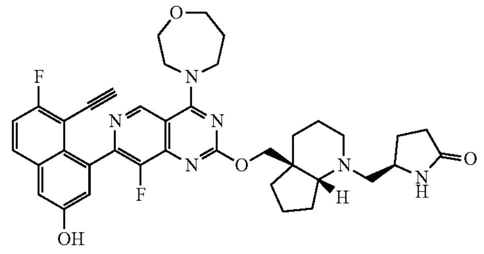 [SMILES: C#Cc1c(F)ccc2cc(O)cc(-c3ncc4c(N5CCCOCC5)nc(OC[C@]56CCC[C@H]5N(C[C@H]5CCC(=O)N5)CCC6)nc4c3F)c12] | (5R)-5-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}pyrrolidin-2-one | 683.3 | $^1$H NMR (500 MHz, DMSO-$d_6$) δ 10.19 (s, 1H), 9.10 (s, 1H), 7.98 (dd, J = 9.0, 5.8 Hz, 1H), 7.47 (t, J = 9.1 Hz, 1H), 7.40 (d, J = 2.4 Hz, 1H), 7.33 (br s, 1H), 7.19 (d, J = 2.4 Hz, 1H), 4.60 (br dd, J = 10.5, 1.3 Hz, 1H), 4.29-4.21 (m, 1H), 4.20-4.08 (m, 4H), 4.02-3.92 (m, 3H), 3.77 (br t, J = 5.1 Hz, 2H), 3.64-3.56 (m, 1H), 2.96-2.87 (m, 1H), 2.45-2.27 (m, 3H), 2.16-1.98 (m, 5H), 1.89-1.80 (m, 1H), 1.77-1.65 (m, 2H), 1.56 (br d, J = 2.8 Hz, 5H), 1.49-1.40 (m, 1H), 1.38-1.27 (m, 2H) |
| 1-38 | 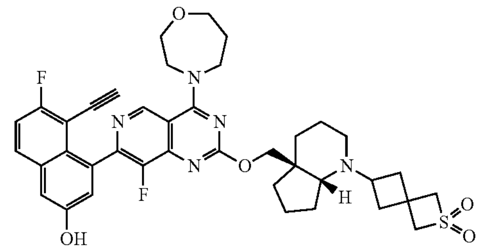 [SMILES: C#Cc1c(F)ccc2cc(O)cc(-c3ncc4c(N5CCCOCC5)nc(OC[C@]56CCC[C@H]5N(C5CC7(C5)CS(=O)(=O)C7)CCC6)nc4c3F)c12] | 6-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]-2,6-thiaspiro[3.3]heptane-2,2-dione | 730.2 | $^1$H NMR (500 MHz, DMSO-$d_6$) δ 9.05 (s, 1H), 7.95-7.88 (m, 2H), 7.42 (br t, J = 8.9 Hz, 1H), 7.35 (d, J = 2.4 Hz, 1H), 7.14 (br s, 1H), 4.56-4.50 (m, 1H), 4.22-4.00 (m, 9H), 3.96-3.87 (m, 3H), 3.72 (br t, J = 4.8 Hz, 2H), 2.94-2.88 (m, 1H), 2.38 (br dd, J = 8.9, 1.3 Hz, 1H), 2.32-2.22 (m, 2H), 2.14-2.03 (m, 3H), 2.02-1.93 (m, 2H), 1.80-1.72 (m, 1H), 1.68-1.47 (m, 5H), 1.44-1.32 (m, 3H), 1.29-1.18 (m, 1H) |

TABLE 1-continued

| # | Structure | IUPAC | LCMS (M + H)+ | $^1$H NMR |
|---|---|---|---|---|
| 1-39 | 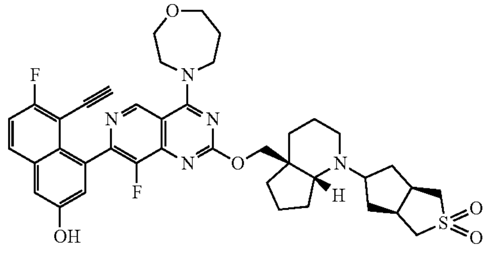 Diastereomer Mixture | (3aR,6aS)-5-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]-hexahydro-1H-2,6-cyclopenta[c]thiophene-2,2-dione | 744.2 | $^1$H NMR (500 MHz, DMSO-$d_6$) δ 10.19 (s, 1H), 9.10 (s, 1H), 7.98 (dd, J = 9.2, 5.8 Hz, 1H), 7.47 (t, J = 9.0 Hz, 1H), 7.40 (d, J = 2.4 Hz, 1H), 7.19 (d, J = 2.1 Hz, 1H), 4.67-4.53 (m, 1H), 4.31 (br dd, J = 10.3, 6.2 Hz, 1H), 4.26-4.07 (m, 5H), 4.03-3.90 (m, 4H), 3.77 (br t, J = 5.0 Hz, 2H), 3.34-3.23 (m, 4H), 2.88-2.78 (m, 1H), 2.77-2.67 (m, 1H), 2.44-2.30 (m, 1H), 2.11 (br s, 2H), 1.89-1.24 (m, 16H) |
| 1-40 | 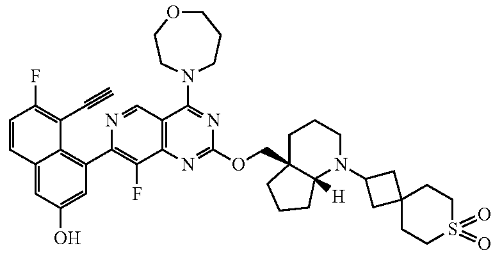 [SMILES: C#Cc1c(F)ccc2cc(O)cc(-c3ncc4c(N5CCCOCC5)nc(OC[C@]56CCC[C@H]5N(C5CC7(CCS(=O)(=O)CC7)C5)CCC6)nc4c3F)c12] | 2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]-7,6-thiaspiro[3.5]nonane-7,7-dione | 758.2 | $^1$H NMR (500 MHz, DMSO-$d_6$) δ 9.10 (s, 1H), 8.02-7.92 (m, 2H), 7.47 (t, J = 9.0 Hz, 1H), 7.40 (d, J = 2.3 Hz, 1H), 7.19 (br s, 1H), 4.60 (br d, J = 10.5 Hz, 1H), 4.24-4.08 (m, 6H), 4.02-3.93 (m, 3H), 3.88-3.75 (m, 7H), 3.12-3.07 (m, 1H), 2.49-2.40 (m, 1H), 2.36-2.28 (m, 1H), 2.10 (br d, J = 4.9 Hz, 2H), 1.89-1.83 (m, 2H), 1.77-1.64 (m, 2H), 1.63-1.40 (m, 11H), 1.39-1.18 (m, 3H) |
| 1-41 | 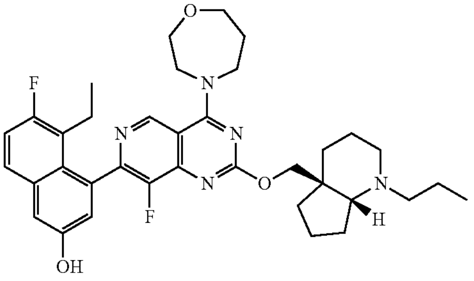 [SMILES: CCCN1CCC[C@@]2(COc3nc(N4CCCOCC4)c4cnc(-c5cc(O)cc6ccc(F)c(CC)c56)c(F)c4n3)CCC[C@@H]12] | 4-(2-{[(4aS,7aR)-1-propyl-octahydrocyclopenta[b]pyridin-4a-yl]methoxy}-8-fluoro-4-(1,4-oxazepan-4-yl)pyrido[4,3-d]pyrimidin-7-yl)-5-ethyl-6-fluoronaphthalen-2-ol | 632.8 | $^1$H NMR (500 MHz, DMSO-$d_6$) δ 9.16 (s, 1H), 7.95 (s, 1H), 7.76 (dd, J = 8.9, 6.0 Hz, 1H), 7.38-7.31 (m, 2H), 7.03 (d, J = 2.5 Hz, 1H), 4.61 (br dd, J = 10.5, 7.3 Hz, 1H), 4.25-4.12 (m, 5H), 3.94 (br s, 2H), 3.75 (br t, J = 5.1 Hz, 3H), 3.31-3.22 (m, 1H), 2.43-2.33 (m, 3H), 2.28 (br s, 2H), 2.21-2.04 (m, 3H), 1.86-1.78 (m, 1H), 1.74-1.66 (m, 1H), 1.64-1.48 (m, 6H), 1.47-1.29 (m, 4H), 0.83-0.77 (m, 3H), 0.76-0.70 (m, 3H) |

TABLE 1-continued

| # | Structure | IUPAC | LCMS (M + H)+ | 1H NMR |
|---|---|---|---|---|
| 1-42 | 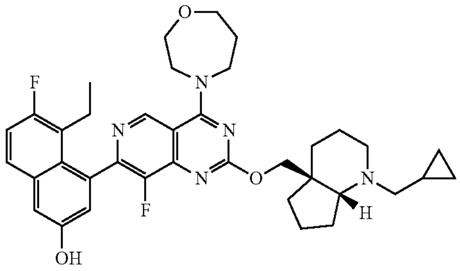 [SMILES: CCc1c(F)ccc2cc(O)cc(-c3ncc4c(N5CCCOCC5)nc(OC[C@]56CCC[C@H]5N(CC5CC5)CCC6)nc4c3F)c12] | 4-(2-{[(4aS,7aR)-1-(cyclopropyl-methyl)-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethyl-6-fluoronaphthalen-2-ol | 644.2 | $^1H$ NMR (500 MHz, DMSO-$d_6$) δ 9.11 (s, 1H), 7.90 (s, 1H), 7.72 (dd, J = 8.9, 5.9 Hz, 1H), 7.33-7.25 (m, 2H), 6.98 (d, J = 2.0 Hz, 1H), 4.54 (br d, J = 10.9 Hz, 1H), 4.21 (br dd, J = 9.9, 7.7 Hz, 1H), 4.15-4.07 (m, 4H), 3.90 (br t, J = 3.9 Hz, 2H), 3.70 (br t, J = 5.0 Hz, 2H), 2.96 (br t, J = 8.0 Hz, 1H), 2.43-2.22 (m, 3H), 2.15-2.01 (m, 4H), 1.81-1.73 (m, 1H), 1.70-1.61 (m, 1H), 1.59-1.37 (m, 7H), 1.35-1.25 (m, 1H), 0.74-0.66 (m, 4H), 0.34 (br t, J = 8.2 Hz, 2H), 0.04--0.07 (m, 2H). |
| 1-43 | 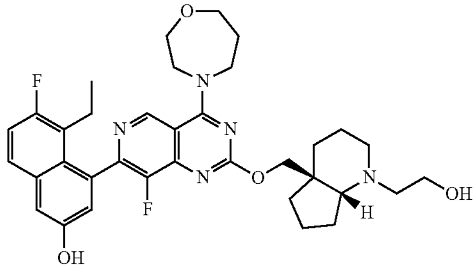 [SMILES: CCc1c(F)ccc2cc(O)cc(-c3ncc4c(N5CCCOCC5)nc(OC[C@]56CCC[C@H]5N(CCO)CCC6)nc4c3F)c12] | 4-(2-{[(4aS,7aR)-1-(2-hydroxy-ethyl)-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethyl-6-fluoronaphthalen-2-ol | 634.2 | $^1H$ NMR (500 MHz, DMSO-$d_6$) δ 8.96 (s, 1H), 7.75 (s, 1H), 7.56 (dd, J = 8.9, 6.1 Hz, 1H), 7.18-7.10 (m, 2H), 6.83 (d, J = 2.2 Hz, 1H), 4.38 (br t, J = 11.4 Hz, 1H), 4.05-3.88 (m, 7H), 3.77-3.68 (m, 3H), 3.59-3.50 (m, 2H), 2.27-2.12 (m, 5H), 1.99-1.84 (m, 3H), 1.66-1.59 (m, 1H), 1.57-1.45 (m, 1H), 1.43-1.29 (m, 6H), 1.28-1.19 (m, 1H), 1.19-1.09 (m, 1H), 0.53 (br t, J = 7.1 Hz, 3H). |
| 1-44 | 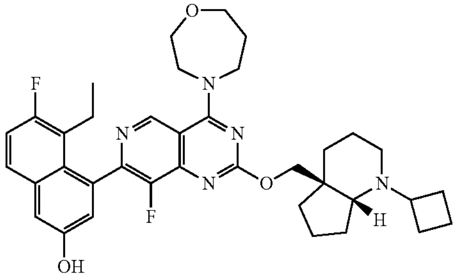 [SMILES: CCc1c(F)ccc2cc(O)cc(-c3ncc4c(N5CCCOCC5)nc(OC[C@]56CCC[C@H]5N(C5CCC5)CCC6)nc4c3F)c12] | 4-(2-{[(4aS,7aR)-1-cyclobutyl-octahydro-1H-cyclopenta[b]pyridin-4a-yl]methoxy}-8-fluoro-4-(1,4-oxazepan-4-yl)pyrido[4,3-d]pyrimidin-7-yl)-5-ethyl-6-fluoronaphthalen-2-ol | 644.3 | $^1H$ NMR (500 MHz, DMSO-$d_6$) δ 9.16 (s, 1H), 7.95 (s, 1H), 7.76 (dd, J = 9.3, 6.0 Hz, 1H), 7.41-7.26 (m, 2H), 7.03 (d, J = 2.3 Hz, 1H), 4.60 (br dd, J = 10.9, 5.5 Hz, 1H), 4.29 (br dd, J = 15.1, 10.6 Hz, 2H), 4.20-4.11 (m, 5H), 3.95 (br s, 3H), 3.80-3.71 (m, 2H), 3.02-2.93 (m, 1H), 2.48-2.42 (m, 1H), 2.40-2.30 (m, 1H), 2.19-2.05 (m, 4H), 1.86-1.76 (m, 2H), 1.74-1.49 (m, 10H), 1.47-1.34 (m, 3H), 1.32-1.23 (m, 1H), 0.77-0.68 (m, 3H) |

TABLE 1-continued

| # | Structure | IUPAC | LCMS (M + H)+ | $^1$H NMR |
|---|---|---|---|---|
| 1-45 | 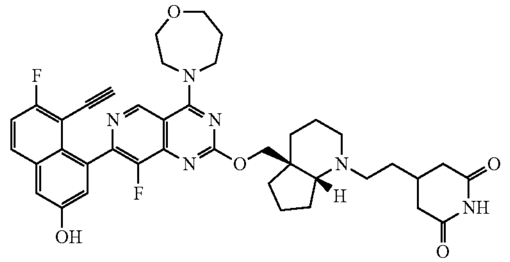 [SMILES: C#Cc1c(F)ccc2cc(O)cc(-c3ncc4c(N5CCCOCC5)nc(OC[C@]56CCC[C@H]5N(CCC5CC(=O)NC(=O)C5)CCC6)nc4c3F)c12] | 4-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}piperidine-2,6-dione | 725.1 | $^1$H NMR (500 MHz, DMSO-$d_6$) δ 10.57 (br d, J = 2.1 Hz, 1H), 9.09 (s, 1H), 7.97 (dd, J = 9.0, 5.9 Hz, 1H), 7.46 (t, J = 9.0 Hz, 1H), 7.40 (d, J = 2.2 Hz, 1H), 7.20 (br s, 1H), 4.54-4.43 (m, 1H), 4.29-4.20 (m, 1H), 4.18-4.06 (m, 5H), 3.96 (br d, J = 18.7 Hz, 3H), 3.77 (br t, J = 4.8 Hz, 2H), 3.00-2.91 (m, 1H), 2.44-2.30 (m, 5H), 2.30-2.19 (m, 2H), 2.13-2.03 (m, 3H), 1.90-1.77 (m, 1H), 1.76-1.68 (m, 1H), 1.66-1.34 (m, 11H) |
| 1-46 | 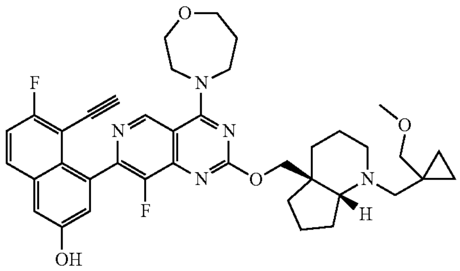 [SMILES: C#Cc1c(F)ccc2cc(O)cc(-c3ncc4c(N5CCCOCC5)nc(OC[C@]56CCC[C@H]5N(CC5(COC)CC5)CCC6)nc4c3F)c12] | 4-(2-{[(4aS,7aR)-1-{[1-(methoxymethyl)cyclopropyl]methyl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 684.3 | $^1$H NMR (500 MHz, DMSO-$d_6$) δ 8.87 (s, 1H), 7.74 (dd, J = 9.0, 5.8 Hz, 1H), 7.24 (t, J = 9.0 Hz, 1H), 7.17 (d, J = 2.4 Hz, 1H), 6.98-6.94 (m, 1H), 4.43 (br d, J = 10.5 Hz, 1H), 4.02-3.88 (m, 5H), 3.78-3.70 (m, 3H), 3.57-3.52 (m, 2H), 2.97-2.90 (m, 6H), 2.76-2.67 (m, 1H), 2.26-2.17 (m, 2H), 2.12-2.00 (m, 2H), 1.89 (br s, 2H), 1.65-1.55 (m, 1H), 1.54-1.45 (m, 1H), 1.42-1.21 (m, 7H), 1.16-1.07 (m, 1H), 0.16-- 0.04 (m, 4H). |
| 1-47 | 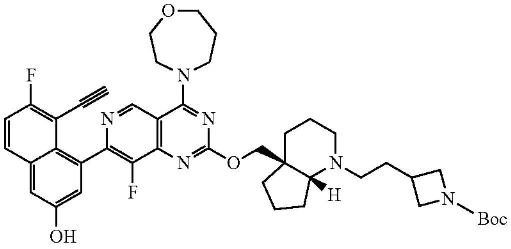 [SMILES: C#Cc1c(F)ccc2cc(O)cc(-c3ncc4c(N5CCCOCC5)nc(OC[C@]56CCC[C@H]5N(CCC5CN(C(=O)OC(C)(C)C)C5)CCC6)nc4c3F)c12] | tert-butyl 3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}azetidine-1-carboxylate | 769.1 | $^1$H NMR (500 MHz, DMSO-$d_6$) δ 9.09 (d, J = 2.7 Hz, 1H), 7.96 (dd, J = 9.1, 6.0 Hz, 1H), 7.49-7.42 (m, 1H), 7.39 (d, J = 2.4 Hz, 1H), 7.20-7.15 (m, 1H), 4.58-4.48 (m, 1H), 4.27-4.06 (m, 6H), 4.00-3.92 (m, 3H), 3.87-3.72 (m, 4H), 3.48-3.40 (m, 1H), 2.91-2.83 (m, 1H), 2.42-2.33 (m, 2H), 2.33-2.19 (m, 2H), 2.11 (br s, 2H), 1.86-1.40 (m, 13H), 1.38-1.25 (m, 11H) |

TABLE 1-continued

| # | Structure | IUPAC | LCMS (M + H)+ | 1H NMR |
|---|---|---|---|---|
| 1-48 | 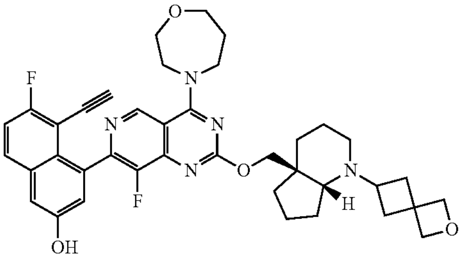 [SMILES: C#Cc1c(F)ccc2cc(O)cc(-c3ncc4c(N5CCCOCC5)nc(OC[C@]56CCC[C@H]5N(C5CC7(COC7)C5)CCC6)nc4c3F)c12] | 4-(2-{[(4aS,7aR)-1-{2-oxaspiro[3.3]heptan-6-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 682.3 | $^1$H NMR (500 MHz, DMSO-$d_6$) δ 10.20 (br s, 1H), 9.10 (s, 1H), 8.01-7.93 (m, 1H), 7.47 (br t, J = 8.5 Hz, IH), 7.40 (br s, 1H), 7.19 (br s, 1H), 4.54 (br s, 3H), 4.38 (br d, J = 14.9 Hz, 2H), 4.24 (br dd, J = 10.5, 4.9 Hz, 1H), 4.15 (br d, J = 3.1 Hz, 4H), 4.01-3.91 (m, 3H), 3.77 (br d, J = 4.5 Hz, 2H), 3.07-2.90 (m, 1H), 2.78-2.64 (m, 1H), 2.35-2.21 (m, 2H), 2.11 (br s, 3H), 1.95-1.19 (m, 14H) |
| 1-49 | 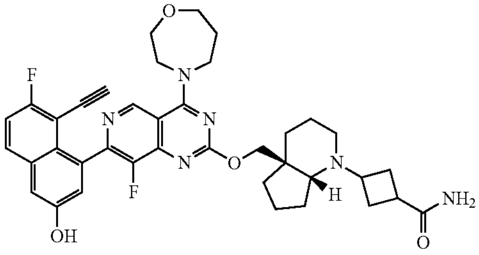<br>Diastereomer Mixture | 3-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]cyclobutane-1-carboxamide | 683.1 | $^1$H NMR (500 MHz, DMSO-$d_6$) δ 9.09 (s, 1H), 7.97 (dd, J = 9.2, 6.0 Hz, 1H), 7.46 (t, J = 9.0 Hz, 1H), 7.40 (d, J = 2.5 Hz, 1H), 7.20 (s, 1H), 7.14 (br s, 1H), 6.66 (br s, 1H), 4.53 (br dd, J = 13.8, 10.9 Hz, 1H), 4.39-4.26 (m, 1H), 4.22-4.09 (m, 4H), 4.05-3.92 (m, 3H), 3.77 (br t, J = 4.8 Hz, 2H), 3.04-2.94 (m, 1H), 2.85-2.76 (m, 1H), 2.48-2.41 (m, 1H), 2.21-2.02 (m, 4H), 1.90-1.77 (m, 4H), 1.73-1.49 (m, 5H), 1.46-1.24 (m, 4H) |
| 1-50 | 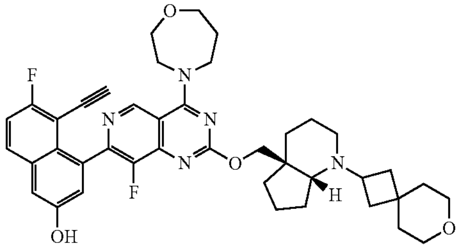 [SMILES: C#Cc1c(F)ccc2cc(O)cc(-c3ncc4c(N5CCCOCC5)nc(OC[C@]56CCC[C@H]5N(C5CC7(CCOCC7)C5)CCC6)nc4c3F)c12] | 4-(2-{[(4aS,7aR)-1-{7-oxaspiro[3.5]nonan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 710.2 | $^1$H NMR (500 MHz, DMSO-$d_6$) δ 9.09 (s, 1H), 7.97 (dd, J = 9.2, 6.0 Hz, 1H), 7.46 (t, J = 9.0 Hz, 1H), 7.40 (d, J = 2.4 Hz, 1H), 7.18 (br s, 1H), 4.57 (br dd, J = 10.6, 5.6 Hz, 1H), 4.36-4.24 (m, 1H), 4.21-4.06 (m, 4H), 4.01-3.92 (m, 3H), 3.76 (br d, J = 4.9 Hz, 2H), 3.39-3.27 (m, 4H), 3.00 (br t, J = 8.9 Hz, 1H), 2.93-2.85 (m, 1H), 2.47-2.40 (m, 1H), 2.16-2.05 (m, 3H), 1.91-1.77 (m, 3H), 1.73-1.60 (m, 2H), 1.59-1.27 (m, 13H) |

TABLE 1-continued

| # | Structure | IUPAC | LCMS $(M + H)^+$ | $^1H$ NMR |
|---|---|---|---|---|
| 1-51 | 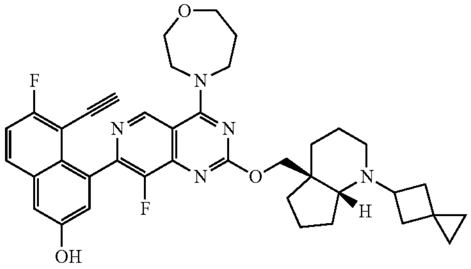 [SMILES: C#Cc1c(F)ccc2cc(O)cc(-c3ncc4c(N5CCCOCC5)nc(OC[C@]56CCC[C@H]5N(C5CC7(CC7)C5)CCC6)nc4c3F)c12] | 4-(2-{[(4aS,7aR)-1-{spiro[2.3]hexan-5-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 668.8 | $^1H$ NMR (500 MHz, DMSO-$d_6$) δ 8.86 (d, J = 1.3 Hz, 1H), 7.77-7.70 (m, 2H), 7.23 (t, J = 9.0 Hz, 1H), 7.16 (d, J = 2.3 Hz, 1H), 6.96 (d, J = 1.6 Hz, 1H), 4.36 (dd, J = 10.8, 3.1 Hz, 1H), 4.09-4.00 (m, 1H), 3.97-3.85 (m, 4H), 3.78-3.68 (m, 3H), 3.53 (br t, J = 4.7 Hz, 1H), 2.95-2.87 (m, 1H), 2.80 (br t, J = 9.2 Hz, 1H), 2.26-2.21 (m, 1H), 1.99-1.90 (m, 1H), 1.87 (br s, 2H), 1.83-1.74 (m, 2H), 1.63-1.58 (m, 2H), 1.51-1.26 (m, 5H), 1.24-1.02 (m, 5H), 0.20-0.10 (m, 2H), 0.07--0.03 (m, 2H) |
| 1-52 | 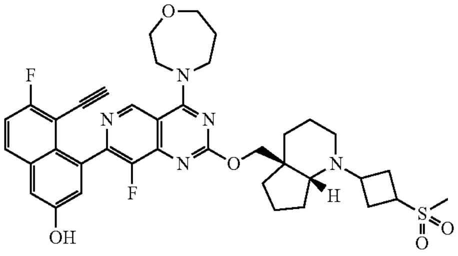 Diastereomer Mixture | 4-(2-{[(4aS,7aR)-1-(3-methanesulfonylcyclobutyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 718.7 | $^1H$ NMR (500 MHz, DMSO-$d_6$) δ 7.19 (s, 1H), 4.62-4.52 (m, 1H), 4.28-4.06 (m, 6H), 4.01-3.87 (m, 3H), 3.77 (br s, 2H), 3.04-2.93 (m, 2H), 2.81 (d, J = 4.7 Hz, 3H), 2.47 (br dd, J = 11.2, 1.5 Hz, 1H), 2.31-2.18 (m, 3H), 2.14-2.00 (m, 5H), 1.89-1.76 (m, 2H), 1.75-1.36 (m, 10H), 1.35-1.20 (m, 1H) |
| 1-53 | 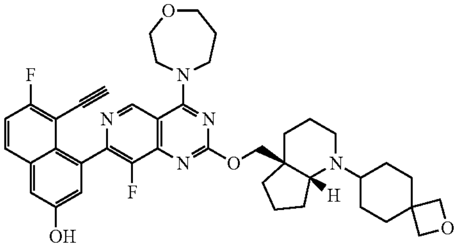 [SMILES: C#Cc1c(F)ccc2cc(O)cc(-c3ncc4c(N5CCCOCC5)nc(OC[C@]56CCC[C@H]5N(C5CCC7(CC5)COC7)CCC6)nc4c3F)c12] | 4-(2-{[(4aS,7aR)-1-{2-oxaspiro[3.5]nonan-7-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 710.8 | $^1H$ NMR (500 MHz, DMSO-$d_6$) δ 9.10 (s, 1H), 7.98 (br dd, J = 9.0, 5.9 Hz, 1H), 7.51-7.43 (m, 1H), 7.40 (d, J = 2.2 Hz, 1H), 7.19 (br s, 1H), 4.57 (br dd, J = 10.7, 5.0 Hz, 1H), 4.25-4.09 (m, 10H), 4.01-3.91 (m, 3H), 3.77 (br t, J = 4.9 Hz, 2H), 3.08 (br t, J = 8.4 Hz, 1H), 2.47-2.39 (m, 1H), 2.29-2.19 (m, 1H), 2.10 (br s, 2H), 2.01-1.85 (m, 4H), 1.76-1.12 (m, 14H) |

TABLE 1-continued

| # | Structure | IUPAC | LCMS $(M + H)^+$ | $^1H$ NMR |
|---|---|---|---|---|
| 1-54 | 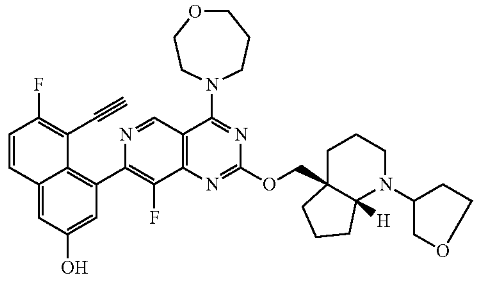 Diastereomer Mixture | 4-(2-{[(4aS,7aR)-1-(oxolan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 656.2 | $^1H$ NMR (500 MHz, DMSO-$d_6$) δ 10.21 (br s, 1H), 9.10 (s, 1H), 7.97 (dd, J = 8.9, 6.0 Hz, 1H), 7.47 (t, J = 8.9 Hz, 1H), 7.40 (d, J = 2.5 Hz, 1H), 7.19 (d, J = 2.0 Hz, 1H), 4.65-4.54 (m, 1H), 4.32-4.07 (m, 6H), 4.04-3.92 (m, 4H), 3.84-3.72 (m, 5H), 3.67-3.57 (m, 2H), 2.44-2.35 (m, 1H), 2.10 (br d, J = 4.5 Hz, 2H), 2.06-2.00 (m, 1H), 1.98-1.89 (m, 1H), 1.79-1.38 (m, 10H), 1.35-1.23 (m, 1H) |
| 1-55[A] | 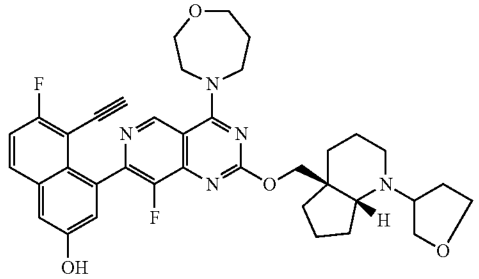 Diastereomer 1 | 4-(2-{[(4aS,7aR)-1-(oxolan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 656.3 | |
| 1-56[A] | 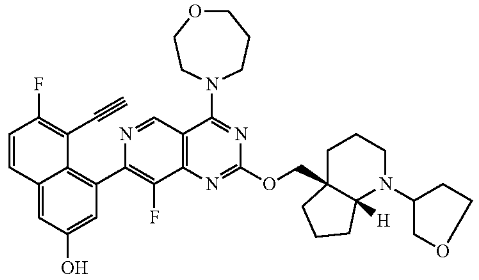 Diastereomer 2 | 4-(2-{[(4aS,7aR)-1-(oxolan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 656.3 | |
| 1-57 | 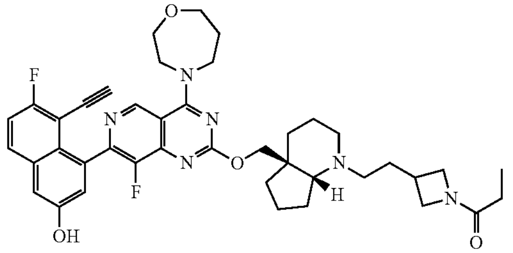 [SMILES: C#Cc1c(F)ccc2cc(O)cc(-c3ncc4c(N5CCCOCC5)nc(OC[C@]56CCC[C@H]5N(CCC5CN(C(=O)CC)C5)CCC6)nc4c3F)c12] | 1-(3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}azetidin-1-yl)propan-1-one | 725.3 | $^1H$ NMR (500 MHz, DMSO-$d_6$) δ 9.08 (s, 1H), 7.99-7.93 (m, 1H), 7.46 (br t, J = 9.0 Hz, 1H), 7.39 (d, J = 2.4 Hz, 1H), 7.18 (br d, J = 2.7 Hz, 1H), 4.56-4.46 (m, 1H), 4.27-4.03 (m, 6H), 3.98-3.92 (m, 2H), 3.86-3.74 (m, 2H), 3.71-3.64 (m, 1H), 3.57 (br d, J = 2.8 Hz, 1H), 3.45-3.36 (m, 1H), 2.95-2.84 (m, 2H), 2.39 (br d, J = 1.5 Hz, 2H), 2.34-2.23 (m, 2H), 2.10 |

TABLE 1-continued

| # | Structure | IUPAC | LCMS (M + H)+ | $^1$H NMR |
|---|---|---|---|---|
| | | | | (br s, 2H), 1.96-1.90 (m, 2H), 1.83-1.76 (m, 1H), 1.73-1.40 (m, 11H), 1.38-1.30 (m, 1H), 0.93-0.81 (m, 3H). |
| 1-58 | 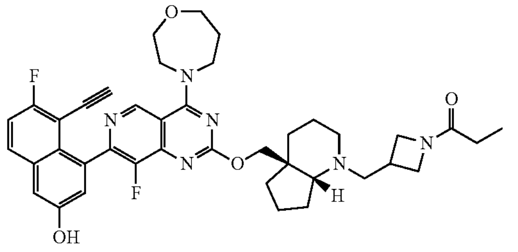 [SMILES: C#Cc1c(F)ccc2cc(O)cc(-c3ncc4c(N5CCCOCC5)nc(OC[C@]56CCC[C@H]5N(CC5CN(C(=O)CC)C5)CCC6)nc4c3F)c12] | 1-(3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yloxy}methyl)-octahydro-1H-cyclopenta[b]pyridin-1-yl]methyl}azetidin-1-yl)propan-1-one | 711 | |
| 1-59 | 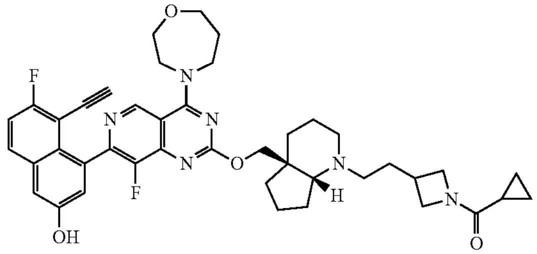 [SMILES: C#Cc1c(F)ccc2cc(O)cc(-c3ncc4c(N5CCCOCC5)nc(OC[C@]56CCC[C@H]5N(CCC5CN(C(=O)C7CC7)C5)CCC6)nc4c3F)c12] | 4-(2-{[(4aS,7aR)-1-[2-(1-cyclopropanecarbonylazetidin-3-yl)ethyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 737.4 | $^1$H NMR (500 MHz, DMSO-$d_6$) δ 8.85 (s, 1H), 7.76-7.68 (m, 1H), 7.22 (t, J = 9.0 Hz, 1H), 7.16 (d, J = 2.3 Hz, 1H), 6.95 (br s, 1H), 4.35-4.26 (m, 1H), 4.08-3.82 (m, 6H), 3.80-3.65 (m, 3H), 3.64-3.49 (m, 2H), 3.26-3.13 (m, 1H), 2.70-2.66 (m, 1H), 2.41-2.33 (m, 1H), 2.21-2.01 (m, 4H), 1.87 (br s, 2H), 1.48-1.07 (m, 13H), 0.36 (br d, J = 3.8 Hz, 4H) |
| 1-60 | 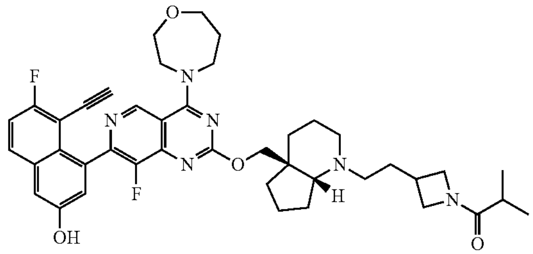 [SMILES: C#Cc1c(F)ccc2cc(O)cc(-c3ncc4c(N5CCCOCC5)nc(OC[C@]56CCC[C@H]5N(CCC5CN(C(=O)C(C)C)C5)CCC6)nc4c3F)c12] | 1-(3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}azetidin-1-yl)-2-methylpropan-1-one | 739.3 | $^1$H NMR (500 MHz, DMSO-$d_6$) δ 9.09 (s, 1H), 8.00-7.91 (m, 2H), 7.46 (t, J = 9.0 Hz, 1H), 7.39 (d, J = 2.4 Hz, 1H), 7.18 (d, J = 2.4 Hz, 1H), 4.59-4.49 (m, 1H), 4.26-4.07 (m, 6H), 4.04-3.92 (m, 3H), 3.85-3.69 (m, 4H), 2.94-2.85 (m, 2H), 2.43-2.26 (m, 5H), 2.15-2.06 (m, 2H), 1.81 (br d, J = 3.2 Hz, 1H), 1.75-1.43 (m, 11H), 1.39-1.30 (m, 1H), 0.94-0.83 (m, 6H) |

TABLE 1-continued

| # | Structure | IUPAC | LCMS (M + H)+ | 1H NMR |
|---|---|---|---|---|
| 1-61 | 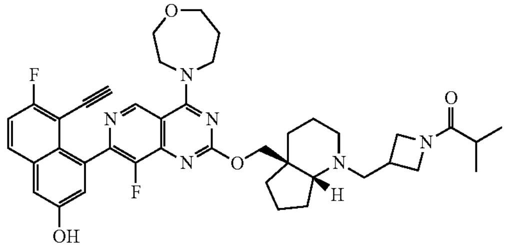 [SMILES: C#Cc1c(F)ccc2cc(O)cc(-c3ncc4c(N5CCCOCC5)nc(OC[C@]56CCC[C@H]5N(CC5CN(C(=O)C(C)C)C5)CCC6)nc4c3F)c12] | 1-(3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-azetidin-1-yl)-2-methylpropan-1-one | 725 | $^1$H NMR (500 MHz, DMSO-$d_6$) δ 8.87 (br d, J = 2.5 Hz, 1H), 7.76-7.68 (m, 1H), 7.22 (t, J = 9.0 Hz, 1H), 7.16 (d, J = 2.2 Hz, 1H), 6.95 (br s, 1H), 4.33-4.18 (m, 1H), 4.14-4.00 (m, 1H), 3.98-3.85 (m, 5H), 3.80-3.68 (m, 3H), 3.61-3.41 (m, 4H), 2.70-2.61 (m, 2H), 2.24-1.99 (m, 4H), 1.88 (br s, 2H), 1.66-1.60 (m, 1H), 1.53-1.45 (m, 1H), 1.42-1.17 (m, 8H), 1.16-1.06 (m, 1H), 0.69-0.62 (m, 6H) |
| 1-62 | 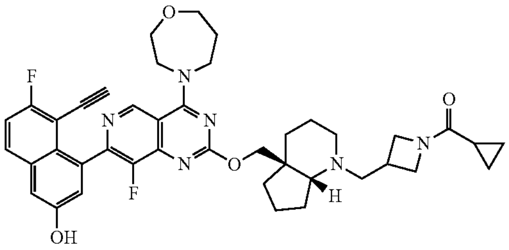 [SMILES: C#Cc1c(F)ccc2cc(O)cc(-c3ncc4c(N5CCCOCC5)nc(OC[C@]56CCC[C@H]5N(CC5CN(C(=O)C7CC7)C5)CCC6)nc4c3F)c12] | 4-(2-{[(4aS,7aR)-1-[(1-cyclopropanecarbonyl-azetidin-3-yl)-methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 723.5 | $^1$H NMR (500 MHz, DMSO-$d_6$) δ 9.09 (s, 1H), 7.99-7.93 (m, 2H), 7.46 (t, J = 9.0 Hz, 1H), 7.40 (d, J = 2.4 Hz, 1H), 7.18 (s, 1H), 4.56-4.43 (m, 1H), 4.33-4.10 (m, 6H), 4.03-3.91 (m, 3H), 3.85-3.73 (m, 3H), 3.40 (br dd, J = 9.1, 4.8 Hz, 1H), 2.77 (br d, J = 1.4 Hz, 1H), 2.57 (br d, J = 7.2 Hz, 1H), 2.48-2.36 (m, 2H), 2.10 (br s, 2H), 1.71 (br dd, J = 5.9, 1.0 Hz, 1H), 1.64-1.33 (m, 10H), 0.62 (br s, 4H) |
| 1-63 | 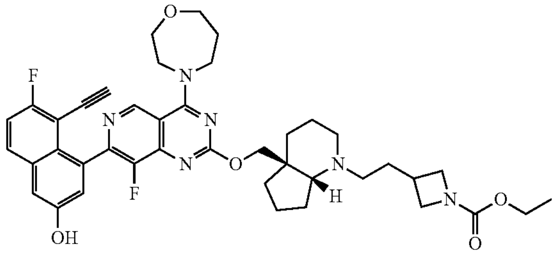 [SMILES: C#Cc1c(F)ccc2cc(O)cc(-c3ncc4c(N5CCCOCC5)nc(OC[C@]56CCC[C@H]5N(CCC5CN(C(=O)OCC)C5)CCC6)nc4c3F)c12] | ethyl 3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}azetidine-1-carboxylate | 741.4 | $^1$H NMR (500 MHz, DMSO-$d_6$) δ 9.08 (s, 1H), 7.97 (dd, J = 9.0, 5.8 Hz, 1H), 7.46 (br t, J = 9.0 Hz, 1H), 7.40 (d, J = 2.4 Hz, 1H), 7.19 (d, J = 2.3 Hz, 1H), 4.51 (br d, J = 10.4 Hz, 1H), 4.26-4.08 (m, 5H), 4.01-3.83 (m, 6H), 3.77 (br t, J = 5.1 Hz, 2H), 2.87 (br t, J = 7.8 Hz, 1H), 2.43-2.22 (m, 4H), 2.14-2.06 (m, 2H), 1.82-1.76 (m, 1H), 1.73-1.39 (m, 11H), 1.38-1.29 (m, 1H), 1.09 (td, J = 7.0, 3.5 Hz, 3H). |

TABLE 1-continued

| # | Structure | IUPAC | LCMS (M + H)$^+$ | $^1$H NMR |
|---|---|---|---|---|
| 1-64 | 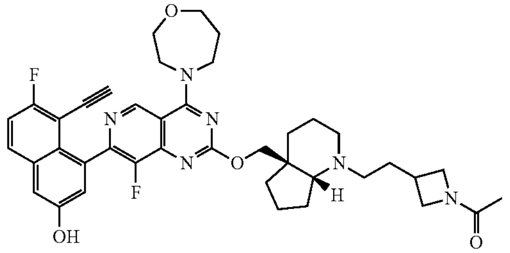 [SMILES: C#Cc1c(F)ccc2cc(O)cc(-c3ncc4c(N5CCCOCC5)nc(OC[C@]56CCC[C@H]5N(CCC5CN(C(C)=O)C5)CCC6)nc4c3F)c12] | 1-(3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}azetidin-1-yl)ethan-1-one | 711.4 | $^1$H NMR (500 MHz, DMSO-$d_6$) δ 9.09 (s, 1H), 7.98-7.91 (m, 1H), 7.45 (t, J = 9.0 Hz, 1H), 7.39 (d, J = 2.5 Hz, 1H), 7.19 (br s, 1H), 4.61-4.49 (m, 1H), 4.28-4.04 (m, 6H), 4.01-3.92 (m, 3H), 3.87-3.65 (m, 4H), 2.94-2.85 (m, 2H), 2.43-2.22 (m, 4H), 2.16-2.07 (m, 2H), 1.86-1.80 (m, 1H), 1.75-1.41 (m, 13H), 1.39-1.30 (m, 2H) |
| 1-65 | 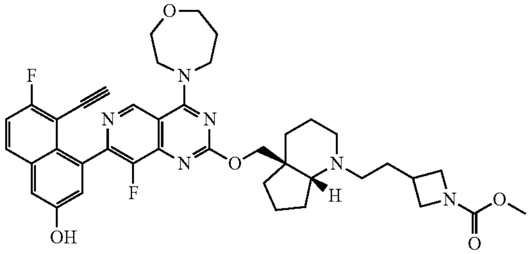 [SMILES: C#Cc1c(F)ccc2cc(O)cc(-c3ncc4c(N5CCCOCC5)nc(OC[C@]56CCC[C@H]5N(CCC5CN(C(=O)OC)C5)CCC6)nc4c3F)c12] | methyl 3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}-methyl)-octahydro-1H-cyclopenta[b]pyridin-1-yl]ethyl}azetidine-1-carboxylate | 727.4 | $^1$H NMR (500 MHz, DMSO-$d_6$) δ 8.92 (s, 1H), 7.78 (dd, J = 9.1, 6.0 Hz, 1H), 7.27 (br t, J = 9.0 Hz, 1H), 7.21 (d, J = 2.6 Hz, 1H), 7.02 (d, J = 2.0 Hz, 1H), 4.34 (br d, J = 10.4 Hz, 1H), 4.10-3.93 (m, 5H), 3.84-3.66 (m, 6H), 3.59 (br t, J = 5.1 Hz, 2H), 3.30 (d, J = 3.3 Hz, 3H), 2.70 (br t, J = 7.7 Hz, 1H), 2.36 (br d, J = 6.0 Hz, 1H), 2.25-2.05 (m, 4H), 1.93 (br d, J = 2.7 Hz, 2H), 1.69-1.59 (m, 1H), 1.53-1.11 (m, 12H) |
| 1-66 | 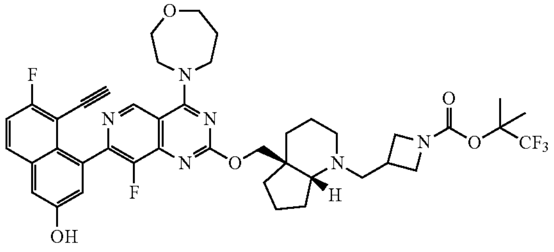 [SMILES: C#Cc1c(F)ccc2cc(O)cc(-c3ncc4c(N5CCCOCC5)nc(OC[C@]56CCC[C@H]5N(CC5CN(C(=O)OC(C)(C)C(F)(F)F)C5)CCC6)nc4c3F)c12] | 1,1,1-trifluoro-2-methylpropan-2-yl 3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yloxy}methyl)-octahydro-1H-cyclopenta[b]pyridin-1-yl]methyl}-azetidine-1-carboxylate | 809.4 | $^1$H NMR (500 MHz, DMSO-$d_6$) δ 9.10 (s, 1H), 7.97 (dd, J = 9.1, 5.9 Hz, 1H), 7.46 (br t, J = 9.1 Hz, 1H), 7.40 (d, J = 2.4 Hz, 1H), 7.19 (s, 1H), 4.60-4.50 (m, 1H), 4.27-4.07 (m, 6H), 4.00-3.85 (m, 5H), 3.76 (br d, J = 4.3 Hz, 2H), 2.92-2.83 (m, 1H), 2.79-2.70 (m, 1H), 2.46-2.31 (m, 2H), 2.11 (br s, 2H), 1.90-1.77 (m, 2H), 1.72 (td, J = 5.0, 2.5 Hz, 1H), 1.65-1.48 (m, 14H), 1.47-1.40 (m, 1H), 1.38-1.28 (m, 1H) |
| 1-67 | 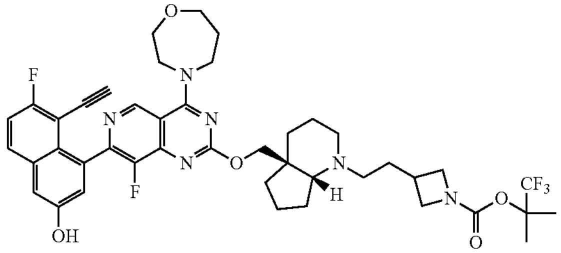 [SMILES: C#Cc1c(F)ccc2cc(O)cc(-c3ncc4c(N5CCCOCC5)nc(OC[C@]56CCC[C@H]5N(CCC5CN(C(=O)OC(C)(C)C(F)(F)F)C5)CCC6)nc4c3F)c12] | 1,1,1-trifluoro-2-methylpropan-2-yl 3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}meth- | 823.3 | $^1$H NMR (500 MHz, DMSO-$d_6$) δ 9.09 (d, J = 2.4 Hz, 1H), 8.01-7.95 (m, 2H), 7.46 (br t, J = 9.1 Hz, 1H), 7.39 (d, J = 2.5 Hz, 1H), 7.18 (s, 1H), 4.59-4.47 (m, 1H), 4.27-4.08 (m, 5H), 3.99-3.86 (m, 4H), 3.81-3.73 (m, 1H), 3.71-3.60 (m, 1H), 3.55- |

TABLE 1-continued

| # | Structure | IUPAC | LCMS (M + H)+ | $^1$H NMR |
|---|---|---|---|---|
| | | yl)-octahydro-1H-cyclopenta[b]pyridin-1-ylethyl}azetidine-1-carboxylate | | 3.46 (m, 1H), 2.86 (br s, 1H), 2.44-2.22 (m, 5H), 2.11 (br s, 2H), 1.85-1.40 (m, 18H), 1.39-1.30 (m, 1H) |
| 1-68 | 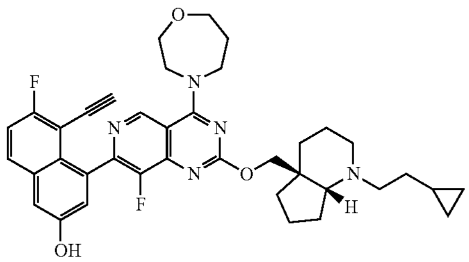 [SMILES: C#Cc1c(F)ccc2cc(O)cc(-c3ncc4c(N5CCCOCC5)nc(OC[C@]56CCC[C@H]5N(CCC5CC5)CCC6)nc4c3F)c12] | 4-(2-{[(4aS,7aR)-1-(2-cyclopropylethyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 654.4 | $^1$H NMR (500 MHz, DMSO-$d_6$) δ 9.11 (s, 1H), 7.99 (dd, J = 9.2, 6.0 Hz, 1H), 7.49 (t, J = 9.0 Hz, 1H), 7.42 (d, J = 2.4 Hz, 1H), 7.20 (d, J = 2.3 Hz, 1H), 4.63-4.54 (m, 1H), 4.25-4.10 (m, 5H), 4.04-3.93 (m, 3H), 3.78 (t, J = 5.1 Hz, 2H), 2.95 (br t, J = 7.9 Hz, 1H), 2.43 (br d, J = 3.4 Hz, 4H), 2.12 (br d, J = 4.5 Hz, 2H), 1.92-1.82 (m, 1H), 1.79-1.69 (m, 1H), 1.65-1.52 (m, 6H), 1.49-1.43 (m, 1H), 1.41-1.24 (m, 4H), 0.73-0.63 (m, 1H), 0.35 (br dd, J = 5.1, 3.2 Hz, 2H), 0.01 (br d, J = 3.2 Hz, 2H) |
| 1-69 | 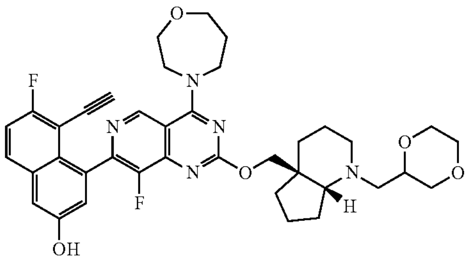 Diastereomer Mixture | 4-(2-{[(4aS,7aR)-1-[(1,4-dioxan-2-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 686.7 | $^1$H NMR (500 MHz, DMSO-$d_6$) δ 9.10 (s, 1H), 8.01-7.94 (m, 1H), 7.47 (br t, J = 9.0 Hz, 1H), 7.40 (d, J = 2.5 Hz, 1H), 7.19 (br s, 1H), 4.61-4.48 (m, 1H), 4.24-4.10 (m, 5H), 4.01-3.93 (m, 3H), 3.80-3.73 (m, 2H), 3.73-3.44 (m, 8H), 3.21-3.11 (m, 1H), 2.87 (br s, 1H), 2.46-2.27 (m, 3H), 2.12 (br s, 2H), 1.88-1.78 (m, 1H), 1.75-1.66 (m, 1H), 1.63-1.49 (m, 6H), 1.47-1.40 (m, 1H), 1.39-1.27 (m, 1H). |
| 1-70[B] | 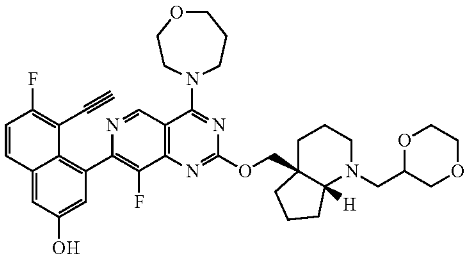 Diastereomer 1 | 4-(2-{[(4aS,7aR)-1-[(1,4-dioxan-2-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 686.5 | $^1$H NMR (499 MHz, DMSO-$d_6$) δ 10.15 (s, 1H), 9.10 (s, 1H), 8.03-7.92 (m, 1H), 7.47 (t, J = 9.0 Hz, 1H), 7.40 (d, J = 2.5 Hz, 1H), 7.18 (d, J = 2.4 Hz, 1H), 4.50 (br dd, J = 10.2, 7.0 Hz, 1H), 4.24-4.08 (m, 5H), 4.01-3.92 (m, 3H), 3.77 (br t, J = 5.0 Hz, 2H), 3.72-3.64 (m, 2H), 3.63-3.36 (m, 7H), 3.22-3.14 (m, 1H), 2.89-2.83 (m, 1H), 2.45-2.25 (m, 3H), 2.16-2.07 (m, 2H), 1.88-1.53 (m, |

TABLE 1-continued

| # | Structure | IUPAC | LCMS $(M + H)^+$ | $^1H$ NMR |
|---|---|---|---|---|
| | | | | 8H), 1.48-1.40 (m, 1H), 1.39-1.30 (m, 1H) |
| 1-71[B] | 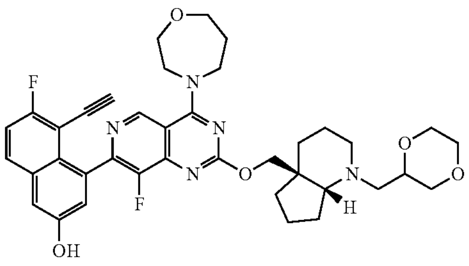 Diastereomer 2 | 4-(2-{[(4aS,7aR)-1-[(1,4-dioxan-2-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 686.5 | $^1H$ NMR (499 MHz, DMSO-$d_6$) δ 10.15 (s, 1H), 9.10 (s, 1H), 7.98 (dd, J = 9.2, 5.9 Hz, 1H), 7.47 (t, J = 8.9 Hz, 1H), 7.40 (d, J = 2.5 Hz, 1H), 7.18 (d, J = 2.5 Hz, 1H), 4.58 (d, J = 10.7 Hz, 1H), 4.25-4.08 (m, 5H), 4.02-3.93 (m, 3H), 3.80-3.75 (m, 2H), 3.73-3.40 (m, 7H), 3.17 (s, 1H), 2.90 (br s, 1H), 2.45-2.28 (m, 3H), 2.16-2.07 (m, 2H), 1.89-1.78 (m, 1H), 1.76-1.67 (m, 1H), 1.64-1.48 (m, 6H), 1.46-1.38 (m, 1H), 1.35-1.22 (m, 1H) |
| 1-72 | 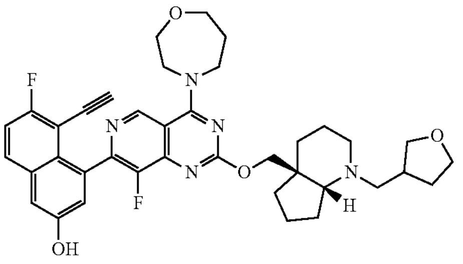 Diastereomer Mixture | 4-(2-{[(4aS,7aR)-1-[(oxolan-3-yl)-methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 670.1 | $^1H$ NMR (500 MHz, DMSO-$d_6$) δ 9.10 (s, 1H), 8.00-7.93 (m, 1H), 7.46 (t, J = 9.0 Hz, 1H), 7.39 (d, J = 2.3 Hz, 1H), 7.19 (d, J = 2.1 Hz, 1H), 4.64-4.49 (m, 1H), 4.29-4.11 (m, 5H), 4.00-3.93 (m, 3H), 3.77 (br s, 2H), 3.69-3.52 (m, 3H), 2.93 (br t, J = 8.3 Hz, 1H), 2.48-2.23 (m, 5H), 2.11 (br s, 2H), 1.91-1.80 (m, 3H), 1.76-1.67 (m, 1H), 1.64-1.43 (m, 8H), 1.38-1.28 (m, 1H) |
| 1-73 | 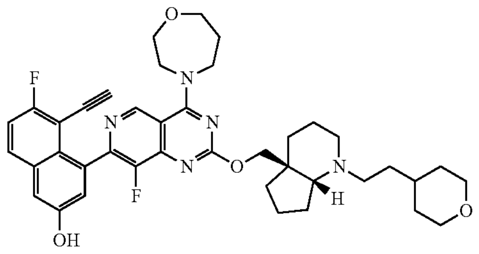 [SMILES: C#Cc1c(F)ccc2cc(O)cc(-c3ncc4c(N5CCCOCC5)nc(OC[C@]56CCC[C@H]5N(CCC5CCOCC5)CCC6)nc4c3F)c12] | 4-(2-{[(4aS,7aR)-1-[2-(oxan-4-yl)-ethyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 697.9 | $^1H$ NMR (500 MHz, DMSO-$d_6$) δ 9.10 (d, J = 2.3 Hz, 1H), 7.98 (dd, J = 9.0, 6.0 Hz, 1H), 7.47 (t, J = 9.0 Hz, 1H), 7.40 (d, J = 2.4 Hz, 1H), 7.18 (br s, 1H), 4.49 (br t, J = 11.1 Hz, 1H), 4.33-4.23 (m, 1H), 4.20-4.08 (m, 4H), 3.95 (br d, J = 4.3 Hz, 3H), 3.80-3.69 (m, 4H), 3.19-2.93 (m, 3H), 2.45-2.33 (m, 4H), 2.11 (br s, 2H), 1.89-1.45 (m, 12H), 1.41-1.29 (m, 3H), 1.17-1.03 (m, 2H). |

TABLE 1-continued

| # | Structure | IUPAC | LCMS (M + H)$^+$ | $^1$H NMR |
|---|---|---|---|---|
| 1-74 | 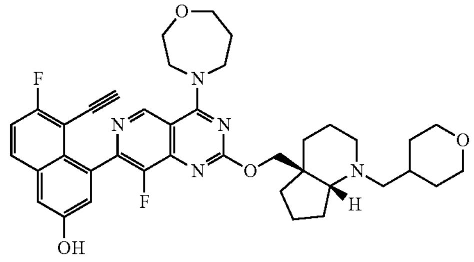 [SMILES: C#Cc1c(F)ccc2cc(O)cc(-c3ncc4c(N5CCCOCC5)nc(OC[C@]56CCC[C@H]5N(CC5CCOCC5)CCC6)nc4c3F)c12] | 4-(2-{[(4aS,7aR)-1-[(oxan-4-yl)-methyl]-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 684.5 | $^1$H NMR (500 MHz, DMSO-$d_6$) δ 9.10 (s, 1H), 7.98 (br dd, J = 9.1, 5.9 Hz, 1H), 7.47 (t, J = 9.0 Hz, 1H), 7.40 (d, J = 2.4 Hz, 1H), 7.18 (d, J = 2.1 Hz, 1H), 4.56 (br t, J = 10.9 Hz, 1H), 4.30-4.20 (m, 1H), 4.21-4.07 (m, 4H), 4.00-3.92 (m, 3H), 3.82-3.68 (m, 4H), 3.43-3.34 (m, 2H), 3.29-3.13 (m, 1H), 2.47-2.32 (m, 2H), 2.23-2.14 (m, 2H), 2.10 (br s, 2H), 1.89-1.80 (m, 1H), 1.76-1.66 (m, 2H), 1.61-1.41 (m, 9H), 1.38-1.29 (m, 1H), 1.15-1.00 (m, 2H) |
| 1-75 | 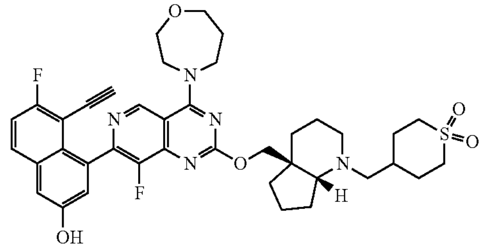 [SMILES: C#Cc1c(F)ccc2cc(O)cc(-c3ncc4c(N5CCCOCC5)nc(OC[C@]56CCC[C@H]5N(CC5CCS(=O)(=O)CC5)CCC6)nc4c3F)c12] | 4-{[(4aS,7aR)-4a-({[7-(8-ethynyl-7-fluoro-3-hydroxy-naphthalen-1-yl)-8-fluoro-4-(1,4-oxazepan-4-yl)pyrido[4,3-d]pyrimi-din-2-yl]oxy}-methyl)-octa-hydro-1H-cyclopenta[b]pyridin-1-yl]methyl}-1,6-thiane-1,1-dione | 732.3 | $^1$H NMR (500 MHz, DMSO-$d_6$) δ 9.10 (s, 1H), 8.00-7.93 (m, 2H), 7.47 (t, J = 9.0 Hz, 1H), 7.40 (d, J = 2.4 Hz, 1H), 7.19 (br s, 1H), 4.56 (br d, J = 11.3 Hz, 1H), 4.26-4.20 (m, 1H), 4.19-4.11 (m, 4H), 4.00-3.93 (m, 3H), 3.77 (br t, J = 4.5 Hz, 3H), 3.14-2.92 (m, 4H), 2.48-2.33 (m, 2H), 2.20 (br d, J = 6.7 Hz, 2H), 2.14-2.07 (m, 2H), 2.02 (br d, J = 13.4 Hz, 2H), 1.89-1.77 (m, 2H), 1.75-1.68 (m, 1H), 1.64-1.31 (m, 12H) |
| 1-76[V] | 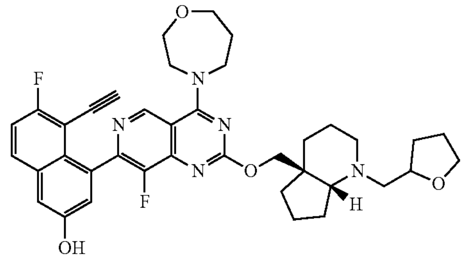 Diastereomer 1 | 4-(2-{[(4aS,7aR)-1-[(oxolan-2-yl)-methyl]-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethyn-yl-6-fluoro-naphthalen-2-ol | 670.2 | $^1$H NMR (500 MHz, DMSO-$d_6$) δ 9.10 (s, 1H), 8.01-7.92 (m, 1H), 7.47 (t, J = 9.0 Hz, 1H), 7.40 (d, J = 2.4 Hz, 1H), 7.19 (d, J = 2.1 Hz, 1H), 4.61 (br d, J = 10.6 Hz, 1H), 4.25-4.10 (m, 5H), 4.03-3.92 (m, 3H), 3.88-3.82 (m, 1H), 3.77 (br t, J = 5.1 Hz, 2H), 3.74-3.68 (m, 1H), 3.60-3.52 (m, 2H), 2.97-2.91 (m, 1H), 2.48-2.36 (m, 3H), 2.11 (br s, 2H), 1.90-1.81 (m, 2H), 1.79-1.67 (m, 3H), 1.60-1.28 (m, 9H) |

TABLE 1-continued

| # | Structure | IUPAC | LCMS $(M+H)^+$ | $^1H$ NMR |
|---|---|---|---|---|
| 1-77[V] | 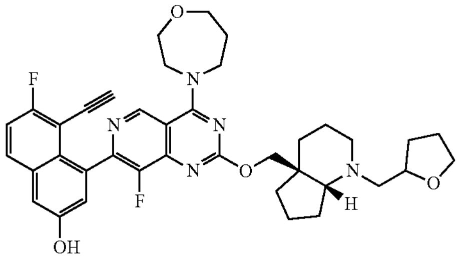 Diastereomer 2 | 4-(2-{[(4aS,7aR)-1-[(oxolan-2-yl)-methyl]-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 669.9 | $^1H$ NMR (500 MHz, DMSO-$d_6$) δ 9.10 (s, 1H), 7.99-7.92 (m, 2H), 7.47 (t, J = 9.0 Hz, 1H), 7.40 (d, J = 2.2 Hz, 1H), 7.19 (d, J = 2.2 Hz, 1H), 4.56 (dd, J = 10.5, 3.0 Hz, 1H), 4.23-4.09 (m, 5H), 4.01-3.93 (m, 3H), 3.90-3.84 (m, 1H), 3.77 (br t, J = 4.8 Hz, 2H), 3.73-3.66 (m, 1H), 3.60-3.52 (m, 2H). 2.98-2.91 (m, 1H), 2.47-2.33 (m, 3H), 2.11 (br s, 2H), 1.86-1.80 (m, 2H), 1.78-1.66 (m, 3H), 1.60-1.32 (m, 9H) |
| 1-78 | 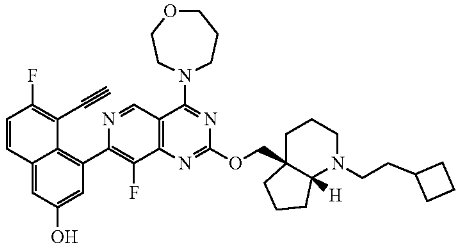 [SMILES: C#Cc1c(F)ccc2cc(O)cc(-c3ncc4c(N5CCCOCC5)nc(OC[C@]56CCC[C@H]5N(CCC5CCC5)CCC6)nc4c3F)c12] | 4-(2-{[(4aS,7aR)-1-(2-cyclobutyl-ethyl)-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 668.3 | $^1H$ NMR (500 MHz, DMSO-$d_6$) δ 9.10 (d, J = 1.7 Hz, 1H), 8.00-7.94 (m, 1H), 7.47 (t, J = 9.0 Hz, 1H), 7.40 (d, J = 2.4 Hz, 1H), 7.18 (s, 1H), 4.55 (br dd, J = 10.6, 6.2 Hz, 1H), 4.26-4.11 (m, 5H), 4.01-3.93 (m, 3H), 3.81-3.76 (m, 2H), 2.39 (br s, 2H), 2.23 (dq, J = 13.8, 6.9 Hz, 3H), 2.11 (br s, 2H), 1.94 (br d, J = 5.6 Hz, 2H), 1.86-1.79 (m, 1H), 1.76-1.68 (m, 3H), 1.62-1.42 (m, 12H), 1.38-1.29 (m, 1H) |
| 1-79[W] | 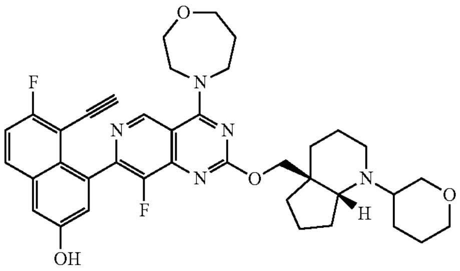 Diastereomer 1 | 4-(2-{[(4aS,7aR)-1-(oxan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 670.3 | $^1H$ NMR (500 MHz, DMSO-$d_6$) δ 9.10 (s, 1H), 8.00-7.93 (m, 2H), 7.47 (t, J = 9.0 Hz, 1H), 7.40 (d, J = 2.3 Hz, 1H), 7.19 (d, J = 2.1 Hz, 1H), 4.58 (dd, J = 10.6, 3.9 Hz, 1H), 4.25-4.09 (m, 5H), 4.01-3.92 (m, 3H), 3.91 (s, 1H), 3.83-3.74 (m, 3H), 3.67 (br d, J = 11.3 Hz, 1H), 3.17-3.06 (m, 2H), 2.59 (br d, J = 10.6 Hz, 1H), 2.48-2.42 (m, 1H), 2.40-2.32 (m, 1H), 2.11 (br s, 2H), 1.95-1.88 (m, 2H), 1.77-1.67 (m, 1H), 1.63-1.31 (m, 12H) |

TABLE 1-continued

| # | Structure | IUPAC | LCMS (M + H)+ | 1H NMR |
|---|---|---|---|---|
| 1-80[W] | 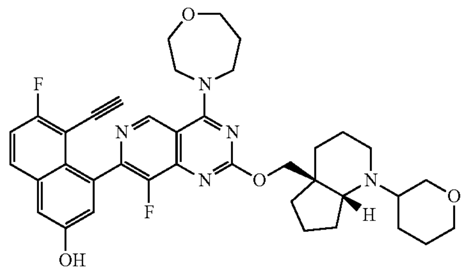 Diastereomer 2 | 4-(2-{[(4aS,7aR)-1-(oxan-3-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 670 | $^1$H NMR (500 MHz, DMSO-$d_6$) δ 9.12-9.04 (m, 1H), 8.00-7.95 (m, 2H), 7.49-7.44 (m, 1H), 7.40 (d, J = 2.4 Hz, 1H), 7.19 (br s, 1H), 4.59 (br dd, J = 13.8, 10.9 Hz, 1H), 4.29-4.09 (m, 5H), 4.01-3.92 (m, 3H), 3.91 (s, 1H), 3.81-3.71 (m, 3H), 3.71-3.65 (m, 1H), 3.18-3.01 (m, 3H), 2.47-2.39 (m, 1H), 2.11 (br d, J = 5.1 Hz, 2H), 1.83-1.77 (m, 1H), 1.75-1.68 (m, 1H), 1.65-1.38 (m, 11H), 1.35-1.23 (m, 2H) |
| 1-81 | 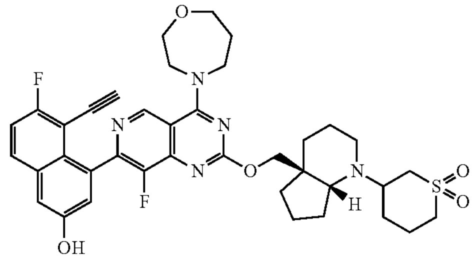 Diastereomer Mixture | 3-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]-1,6-thiane-1,1-dione | 718.2 | $^1$H NMR (500 MHz, DMSO-$d_6$) δ 9.09 (s, 1H), 7.97 (dd, J = 9.1, 6.0 Hz, 1H), 7.46 (t, J = 9.0 Hz, 1H), 7.39 (d, J = 2.4 Hz, 1H), 7.18 (d, J = 2.1 Hz, 1H), 4.59-4.47 (m, 1H), 4.29-4.22 (m, 1H), 4.20-4.08 (m, 4H), 4.01-3.92 (m, 3H), 3.76 (br t, J = 4.8 Hz, 2H), 3.63-3.54 (m, 2H), 3.30-3.17 (m, 1H), 3.12-2.89 (m, 4H), 2.83 (br d, J = 13.2 Hz, 1H), 2.15-2.05 (m, 2H), 2.01-1.86 (m, 2H), 1.78-1.49 (m, 9H), 1.46-1.38 (m, 2H), 1.37-1.24 (m, 1H) |
| 1-82 | 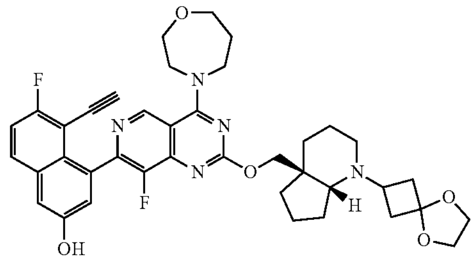 [SMILES: C#Cc1c(F)ccc2cc(O)cc(-c3ncc4c(N5CCCOCC5)nc(OC[C@]56CCC[C@H]5N(C5CC7(C5)OCCO7)CCC6)nc4c3F)c12] | 4-(2-{[(4aS,7aR)-1-{5,8-dioxaspiro[3.4]octan-2-yl}-octahydro-1H-cyclopenta[b]pyridin-4a-yl]methoxy}-8-fluoro-4-(1,4-oxazepan-4-yl)-pyrido[4,3-d]pyrimidin-7-yl)-5-ethynyl-6-fluoro-naphthalen-2-ol | 698 | $^1$H NMR (500 MHz, DMSO-$d_6$) δ 9.10 (s, 1H), 7.97 (dd, J = 9.0, 5.8 Hz, 1H), 7.46 (t, J = 8.9 Hz, 1H), 7.39 (d, J = 2.4 Hz, 1H), 7.19 (d, J = 1.6 Hz, 1H), 4.55 (dd, J = 10.4, 3.9 Hz, 1H), 4.29 (dd, J = 10.9, 5.5 Hz, 1H), 4.22-4.09 (m, 4H), 3.98-3.93 (m, 2H), 3.84-3.76 (m, 4H), 3.74-3.68 (m, 2H), 3.05-3.01 (m, 1H), 2.75-2.67 (m, 1H), 2.44 (br d, J = 10.1 Hz, 1H), 2.31-2.17 (m, 3H), 2.11 (br s, 2H), 1.99-1.90 (m, 2H), 1.89-1.81 (m, 1H), 1.74-1.50 (m, 6H), 1.47-1.26 (m, 5H) |

TABLE 1-continued

| # | Structure | IUPAC | LCMS (M + H)+ | $^1$H NMR |
|---|---|---|---|---|
| 1-83 | 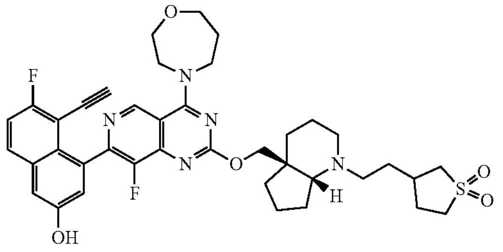 Diastereomer Mixture | 3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}-1,6-thiolane-1,1-dione | 732.2 | $^1$H NMR (500 MHz, DMSO-$d_6$) δ 10.18 (s, 1H), 9.09 (s, 1H), 7.98 (dd, J = 9.0, 5.9 Hz, 1H), 7.47 (t, J = 9.0 Hz, 1H), 7.40 (d, J = 2.4 Hz, 1H), 7.19 (s, 1H), 4.55-4.45 (m, 1H), 4.26 (br d, J = 8.9 Hz, 1H), 4.19-4.06 (m, 4H), 4.00-3.91 (m, 3H), 3.77 (br t, J = 5.1 Hz, 2H), 3.03-2.83 (m, 3H), 2.47-2.30 (m, 5H), 2.27-2.20 (m, 1H), 2.14-2.08 (m, 2H), 1.88-1.34 (m, 15H |
| 1-84 | 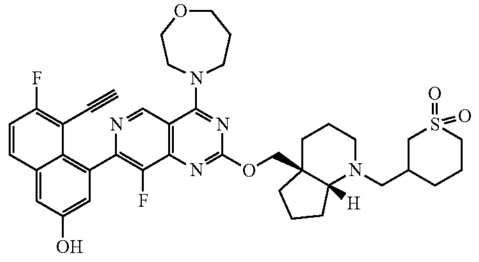 Diastereomer Mixture | 3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-1,6-thiane-1,1-dione | 732.2 | $^1$H NMR (500 MHz, DMSO-$d_6$) δ 9.14-9.06 (m, 1H), 8.00-7.94 (m, 2H), 7.47 (t, J = 8.9 Hz, 1H), 7.40 (d, J = 2.1 Hz, 1H), 7.19 (s, 1H), 4.62-4.43 (m, 1H), 4.36-4.24 (m, 1H), 4.21-4.09 (m, 5H), 3.99-3.93 (m, 4H), 3.80-3.76 (m, 2H), 3.02-2.93 (m, 4H), 2.40 (br s, 1H), 2.35-2.29 (m, 1H), 2.26-2.18 (m, 1H), 2.12 (br s, 3H), 1.85-1.44 (m, 13H), 1.41-1.28 (m, 1H), 1.16-1.06 (m, 1H) |
| 1-85 | 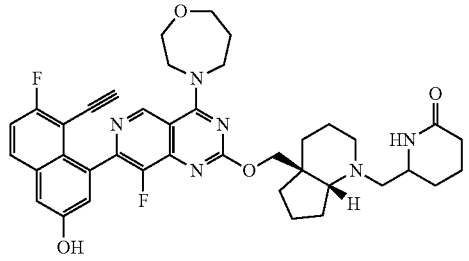 Diastereomer Mixture | 6-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}piperidin-2-one | 697.6 | |
| 1-86 | 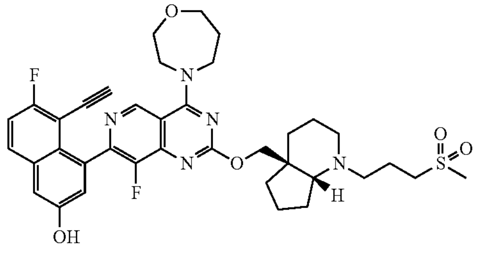 [SMILES: C#Cc1c(F)ccc2cc(O)cc(-c3ncc4c(N5CCCOCC5)nc(OC[C@]56CCC[C@H]5N(CCCS(C)(=O)=O)CCC6)nc4c3F)c12] | 4-(2-{[(4aS,7aR)-1-(3-methanesulfonylpropyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 706.2 | $^1$H NMR (500 MHz, DMSO-$d_6$) δ 10.21 (s, 1H), 9.09 (s, 1H), 7.98 (dd, J = 8.9, 5.9 Hz, 1H), 7.47 (t, J = 9.0 Hz, 1H), 7.40 (d, J = 2.5 Hz, 1H), 7.19 (s, 1H), 4.60-4.46 (m, 1H), 4.27-4.21 (m, 1H), 4.20-4.10 (m, 4H), 4.01-3.93 (m, 3H), 3.84-3.75 (m, 2H), 3.57-3.50 (m, 1H), 3.12-3.02 (m, 2H), 2.92 (br s, 4H), 2.48-2.37 (m, 3H), 2.11 (br s, |

TABLE 1-continued

| # | Structure | IUPAC | LCMS (M + H)+ | 1H NMR |
|---|---|---|---|---|
| | | | | 2H), 1.92-1.47 (m, 11H), 1.42-1.29 (m, 1H) |
| 1-87 | 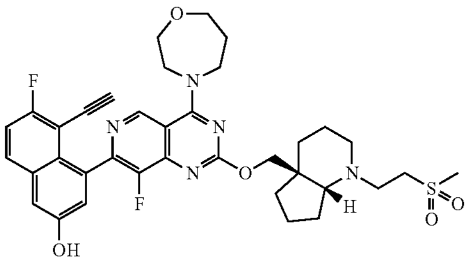 [SMILES: C#Cc1c(F)ccc2cc(O)cc(-c3ncc4c(N5CCCOCC5)nc(OC[C@]56CCC[C@H]5N(CCS(C)(=O)=O)CCC6)nc4c3F)c12] | 4-(2-{[(4aS,7aR)-1-(2-methanesulfonylethyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 692.2 | $^1$H NMR (500 MHz, DMSO-$d_6$) δ 10.21 (s, 1H), 9.09 (s, 1H), 8.00-7.92 (m, 1H), 7.46 (t, J = 9.0 Hz, 1H), 7.40 (d, J = 2.4 Hz, 1H), 7.19 (d, J = 2.4 Hz, 1H), 4.55 (br dd, J = 10.8, 3.2 Hz, 1H), 4.19-4.08 (m, 5H), 4.01-3.91 (m, 3H), 3.77 (br t, J = 5.1 Hz, 2H), 3.57-3.52 (m, 1H), 3.24 (br s, 2H), 2.99 (d, J = 2.4 Hz, 3H), 2.93 (br d, J = 3.0 Hz, 1H), 2.75 (br d, J = 4.6 Hz, 1H), 2.46 (br s, 2H), 2.15-2.05 (m, 2H), 1.90-1.84 (m, 1H), 1.77-1.67 (m, 1H), 1.63-1.55 (m, 5H), 1.51-1.43 (m, 1H), 1.42-1.30 (m, 2H) |
| 1-88 | 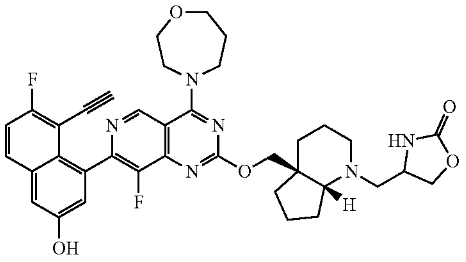 Diastereomer Mixture | 4-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-1,3-oxazolidin-2-one | 685.2 | $^1$H NMR (500 MHz, DMSO-$d_6$) δ 9.11 (s, 1H), 8.02-7.94 (m, 1H), 7.55 (s, 1H), 7.50-7.44 (m, 1H), 7.40 (d, J = 2.4 Hz, 1H), 7.19 (s, 1H), 4.65-4.56 (m, 1H), 4.34-4.09 (m, 7H), 4.02-3.93 (m, 4H), 3.88-3.83 (m, 1H), 3.77 (br d, J = 4.7 Hz, 2H), 3.00-2.88 (m, 1H), 2.48-2.37 (m, 4H), 2.12 (br s, 2H), 1.89-1.79 (m, 1H), 1.78-1.69 (m, 1H), 1.64-1.48 (m, 6H), 1.48-1.40 (m, 1H), 1.37-1.27 (m, 1H) |
| 1-89 | 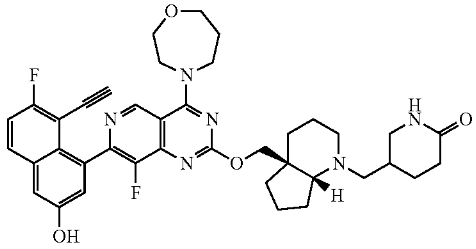 Diastereomer Mixture | 5-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-piperidin-2-one | 697.2 | $^1$H NMR (500 MHz, DMSO-$d_6$) δ 10.21 (s, 1H), 9.10 (s, 1H), 7.98 (dd, J = 9.0, 6.0 Hz, 1H), 7.47 (t, J = 9.1 Hz, 1H), 7.40 (d, J = 2.4 Hz, 1H), 7.37-7.29 (m, 1H), 7.19 (br d, J = 2.4 Hz, 1H), 4.69-4.52 (m, 1H), 4.29-4.07 (m, 6H), 4.05-3.92 (m, 3H), 3.77 (br t, J = 4.5 Hz, 2H), 3.22-3.12 (m, 1H), 2.93-2.85 (m, 1H), 2.82-2.72 (m, 1H), 2.45-2.39 (m, 1H), 2.37-2.24 (m, 2H), 2.11 (br s, 4H), 1.88-1.45 (m, 11H), 1.40-1.26 (m, 2H) |

TABLE 1-continued

| # | Structure | IUPAC | LCMS (M + H)+ | 1H NMR |
|---|---|---|---|---|
| 1-90 | 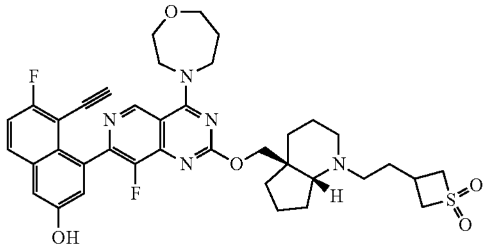 [SMILES: C#Cc1c(F)ccc2cc(O)cc(-c3ncc4c(N5CCCOCC5)nc(OC[C@]56CCC[C@H]5N(CCC5CS(=O)(=O)C5)CCC6)nc4c3F)c12] | 3-{2-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]ethyl}-1,6-thietane-1,1-dione | 718.2 | $^1$H NMR (500 MHz, DMSO-$d_6$) δ 9.09 (d, J = 0.8 Hz, 1H), 7.97 (dd, J = 9.2, 6.0 Hz, 1H), 7.46 (t, J = 9.0 Hz, 1H), 7.40 (d, J = 2.4 Hz, 1H), 7.19 (s, 1H), 4.50 (dd, J = 10.5, 5.9 Hz, 1H), 4.23 (br dd, J = 10.6, 2.9 Hz, 1H), 4.19-4.02 (m, 7H), 3.98-3.91 (m, 3H), 3.89-3.80 (m, 2H), 3.79-3.73 (m, 2H), 2.95-2.87 (m, 1H), 2.47-2.30 (m, 4H), 2.12 (br d, J = 5.9 Hz, 2H), 1.88-1.79 (m, 1H), 1.76-1.44 (m, 11H), 1.38-1.29 (m, 1H) |
| 1-91 | 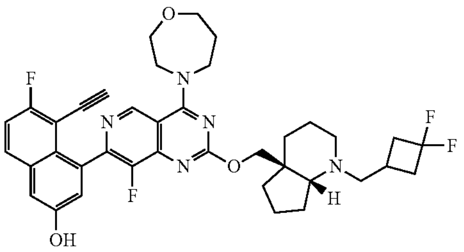 [SMILES: C#Cc1c(F)ccc2cc(O)cc(-c3ncc4c(N5CCCOCC5)nc(OC[C@]56CCC[C@H]5N(CC5CC(F)(F)C5)CCC6)nc4c3F)c12] | 4-(2-{[(4aS,7aR)-1-[(3,3-difluorocyclobutyl)-methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 690.3 | $^1$H NMR (500 MHz, DMSO-$d_6$) δ 9.10 (s, 1H), 7.98 (dd, J = 9.1, 5.9 Hz, 1H), 7.47 (t, J = 9.0 Hz, 1H), 7.40 (d, J = 2.4 Hz, 1H), 7.19 (d, J = 2.2 Hz, 1H), 4.56 (br d, J = 10.5 Hz, 1H), 4.25-4.09 (m, 5H), 4.03-3.92 (m, 3H), 3.77 (br t, J = 4.9 Hz, 2H), 2.88 (br t, J = 7.4 Hz, 1H), 2.59 (br d, J = 6.2 Hz, 1H), 2.49-2.40 (m, 3H), 2.40-2.34 (m, 1H), 2.28 (br d, J = 1.1 Hz, 1H), 2.24-2.05 (m, 4H), 1.90-1.79 (m, 1H), 1.77-1.66 (m, 1H), 1.64-1.48 (m, 7H), 1.48-1.40 (m, 1H), 1.38-1.26 (m, 1H) |
| 1-92 | 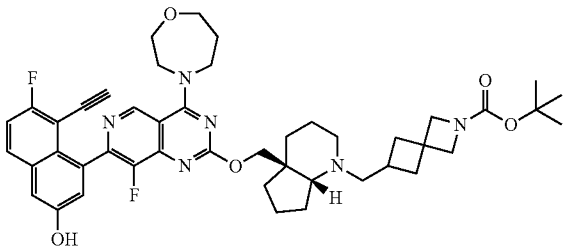 [SMILES: C#Cc1c(F)ccc2cc(O)cc(-c3ncc4c(N5CCCOCC5)nc(OC[C@]56CCC[C@H]5N(CC5CC7(C5)CN(C(=O)OC(C)(C)C)C7)CCC6)nc4c3F)c12] | tert-butyl 6-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-2-azaspiro[3.3]heptane-2-carboxylate | 795.4 | $^1$H NMR (500 MHz, DMSO-$d_6$) δ 10.19 (br s, 1H), 9.10 (d, J = 3.1 Hz, 1H), 7.98 (dd, J = 9.1, 5.9 Hz, 1H), 7.47 (t, J = 8.9 Hz, 1H), 7.40 (d, J = 2.5 Hz, 1H), 7.19 (br d, J = 1.9 Hz, 1H), 4.55 (br d, J = 10.3 Hz, 1H), 4.26-4.09 (m, 5H), 4.00-3.92 (m, 3H), 3.83-3.73 (m, 4H), 3.66 (br d, J = 1.1 Hz, 2H), 2.90-2.79 (m, 1H), 2.43-2.22 (m, 5H), 2.20-2.07 (m, 4H), 1.87-1.65 (m, 4H), 1.63-1.38 (m, 8H), 1.33 (s, 9H) |

TABLE 1-continued

| # | Structure | IUPAC | LCMS (M + H)+ | 1H NMR |
|---|---|---|---|---|
| 1-93 | 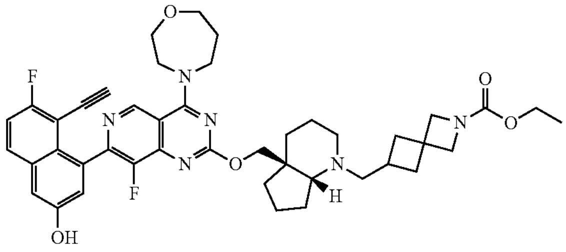 [SMILES: C#Cc1c(F)ccc2cc(O)cc(-c3ncc4c(N5CCCOCC5)nc(OC[C@]56CCC[C@H]5N(CC5CC7(C5)CN(C(=O)OCC)C7)CCC6)nc4c3F)c12] | ethyl 6-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-2-azaspiro[3.3]heptane-2-carboxylate | 767.1 | $^1$H NMR (500 MHz, DMSO-$d_6$) δ 10.18 (br s, 1H), 9.10 (d, J = 3.7 Hz, 1H), 7.98 (dd, J = 9.2, 6.0 Hz, 1H), 7.47 (t, J = 9.0 Hz, 1H), 7.40 (d, J = 2.4 Hz, 1H), 7.19 (br s, 1H), 4.54 (br d, J = 10.6 Hz, 1H), 4.26-4.09 (m, 5H), 4.01-3.92 (m, 5H), 3.85 (br s, 2H), 3.79-3.69 (m, 4H), 2.90-2.79 (m, 1H), 2.46-2.22 (m, 5H), 2.21-2.07 (m, 4H), 1.88-1.65 (m, 4H), 1.63-1.39 (m, 7H), 1.37-1.27 (m, 1H), 1.16-1.07 (m, 3H). |
| 1-94 | 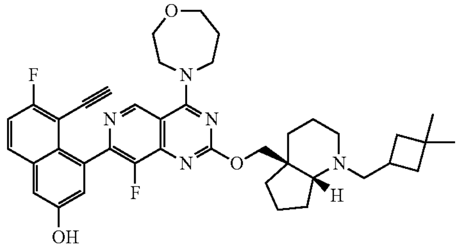 [SMILES: C#Cc1c(F)ccc2cc(O)cc(-c3ncc4c(N5CCCOCC5)nc(OC[C@]56CCC[C@H]5N(CC5CC(C)(C)C5)CCC6)nc4c3F)c12] | 4-(2-{[(4aS,7aR)-1-[(3,3-dimethylcyclobutyl)-methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 682.1 | $^1$H NMR (499 MHz, DMSO-$d_6$) δ 9.10 (d, J = 1.9 Hz, 1H), 7.98 (dd, J = 9.2, 6.0 Hz, 1H), 7.47 (t, J = 8.9 Hz, 1H), 7.40 (d, J = 2.6 Hz, 1H), 7.18 (dd, J = 4.7, 2.5 Hz, 1H), 4.54 (dd, J = 13.5, 10.8 Hz, 1H), 4.26-4.08 (m, 6H), 3.99 (dd, J = 3.5, 0.8 Hz, 1H), 3.97-3.91 (m, 2H), 3.77 (t, J = 5.2 Hz, 2H), 2.85 (t, J = 8.1 Hz, 1H), 2.39-2.31 (m, 4H), 2.11 (br s, 2H), 1.89-1.65 (m, 5H), 1.63-1.48 (m, 6H), 1.46-1.29 (m, 4H), 1.06 (d, J = 13.5 Hz, 3H), 0.98 (d, J = 3.9 Hz, 3H) |
| 1-95$^C$ | 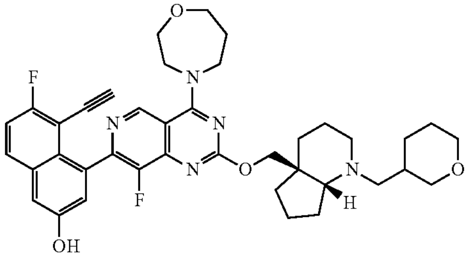 Diastereomer 1 | 4-(2-{[(4aS,7aR)-1-[(oxan-3-yl)-methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 684.3 | $^1$H NMR (499 MHz, DMSO-$d_6$) δ 10.13 (s, 1H), 9.10 (s, 1H), 7.98 (dd, J = 9.2, 5.9 Hz, 1H), 7.47 (t, J = 9.0 Hz, 1H), 7.40 (d, J = 2.5 Hz, 1H), 7.18 (d, J = 2.4 Hz, 1H), 4.62-4.51 (m, 1H), 4.25-4.10 (m, 5H), 3.99-3.90 (m, 3H), 3.81-3.73 (m, 3H), 3.68 (br d, J = 11.2 Hz, 1H), 3.28-3.19 (m, 1H), 3.00 (br t, J = 8.7 Hz, 1H), 2.89 (br d, J = 4.0 Hz, 1H), 2.49-2.42 (m, 1H), 2.33-2.25 (m, 1H), 2.22-2.15 (m, 2H), 2.11 (br dd, J = 9.6, 5.3 Hz, 2H), 1.85-1.06 (m, 13H), 0.91-0.76 (m, 1H) |

TABLE 1-continued

| # | Structure | IUPAC | LCMS (M + H)$^+$ | $^1$H NMR |
|---|---|---|---|---|
| 1-96$^C$ | 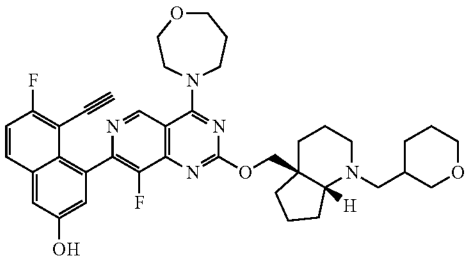 Diastereomer 2 | 4-(2-{[(4aS,7aR)-1-[(oxan-3-yl)-methyl]-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 684.4 | $^1$H NMR (499 MHz, DMSO-$d_6$) δ 10.13 (s, 1H), 9.10 (s, 1H), 7.98 (dd, J = 9.2, 6.0 Hz, 1H), 7.47 (t, J = 9.0 Hz, 1H), 7.40 (d, J = 2.5 Hz, 1H), 7.18 (d, J = 2.5 Hz, 1H), 4.61 (br d, J = 10.7 Hz, 1H), 4.25-4.10 (m, 5H), 4.02-3.92 (m, 3H), 3.79-3.65 (m, 4H), 3.26-3.21 (m, 1H), 3.01-2.96 (m, 1H), 2.85 (br d, J = 6.9 Hz, 1H), 2.45-2.33 (m, 2H), 2.21-2.08 (m, 4H), 1.87-1.02 (m, 13H), 0.91-0.68 (m, 1H) |
| 1-97 | 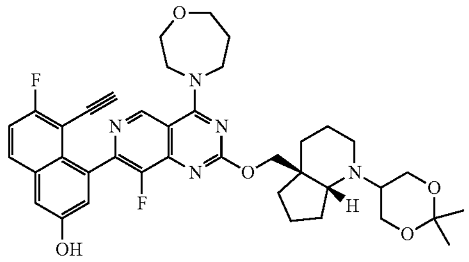 [SMILES: C#Cc1c(F)ccc2cc(O)cc(-c3ncc4c(N5CCCOCC5)nc(OC[C@]56CCC[C@H]5N(C5COC(C)(C)OC5)CCC6)nc4c3F)c12] | 4-(2-{[(4aS,7aR)-1-(2,2-dimethyl-1,3-dioxan-5-yl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 700.5 | $^1$H NMR (500 MHz, DMSO-$d_6$) δ 9.10 s, 1H), 7.97 (dd, J = 9.1, 6.1 Hz, 1H), 7.47 (t, J = 9.0 Hz, 1H), 7.40 (d, J = 2.4 Hz, 1H), 7.19 (br s, 1H), 4.58 (br dd, J = 17.2, 10.7 Hz, 1H), 4.31-4.21 (m, 1H), 4.20-4.10 (m, 4H), 4.02-3.91 (m, 3H), 3.82-3.73 (m, 4H), 3.70-3.53 (m, 3H), 3.04-2.94 (m, 1H), 2.64-2.57 (m, 2H), 2.11 (br d, J = 3.7 Hz, 2H), 1.98-1.88 (m, 1H), 1.76-1.67 (m, 1H), 1.61-1.48 (m, 5H), 1.47-1.37 (m, 2H), 1.35-1.26 (m, 4H), 1.23 (s, 3H) |
| 1-98 | 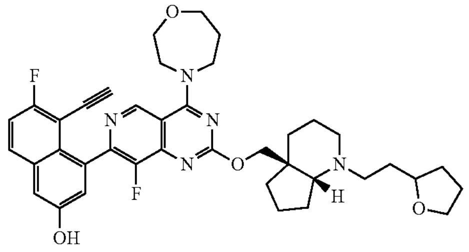 Diastereomer Mixture | 4-(2-{[(4aS,7aR)-1-[2-(oxolan-2-yl)ethyl]-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 683.3 | $^1$H NMR (500 MHz, DMSO-$d_6$) δ 9.10 (s, 1H), 7.97 (dd, J = 8.9, 6.1 Hz, 1H), 7.46 (t, J = 8.9 Hz, 1H), 7.39 (d, J = 2.3 Hz, 1H), 7.19 (d, J = 2.1 Hz, 1H), 4.60-4.47 (m, 1H), 4.26-4.09 (m, 5H), 4.02-3.92 (m, 3H), 3.77 (br t, J = 4.8 Hz, 2H), 3.74-3.66 (m, 2H), 3.53-3.49 (m, 1H), 2.92 (br t, J = 8.0 Hz, 1H), 2.45-2.33 (m, 4H), 2.11 (br s, 2H), 1.92-1.81 (m, 2H), 1.80-1.67 (m, 3H), 1.63-1.49 (m, 8H), 1.48-1.41 (m, 1H), 1.40-1.29 (m, 2H) |

TABLE 1-continued

| # | Structure | IUPAC | LCMS (M + H)+ | $^1$H NMR |
|---|---|---|---|---|
| 1-99[D] | 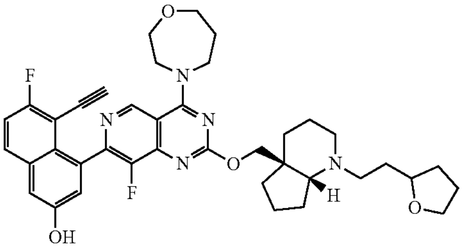<br>Diastereomer 1 | 4-(2-{[(4aS,7aR)-1-[2-(oxolan-2-yl)ethyl]-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 683.3 | $^1$H NMR (500 MHz, DMSO-$d_6$) δ 9.09 (s, 1H), 7.97 (dd, J = 9.0, 6.0 Hz, 1H), 7.46 (br t, J = 8.9 Hz, 1H), 7.40 (d, J = 2.0 Hz, 1H), 7.19 (d, J = 2.3 Hz, 1H), 4.55 (br d, J = 10.8 Hz, 1H), 4.24-4.11 (m, 5H), 4.01-3.93 (m, 3H), 3.79-3.75 (m, 2H), 3.72-3.66 (m, 2H), 3.52-3.48 (m, 1H), 2.95-2.89 (m, 1H), 2.44-2.30 (m, 4H), 2.14-2.05 (m, 2H), 1.92-1.83 (m, 2H), 1.79-1.67 (m, 3H), 1.61-1.42 (m, 9H), 1.39-1.30 (m, 2H) |
| 1-100[D] | 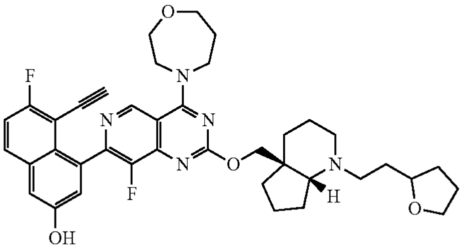<br>Diastereomer 2 | 4-(2-{[(4aS,7aR)-1-[2-(oxolan-2-yl)ethyl]-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethyn-yl-6-fluoro-naphthalen-2-ol | 683.3 | $^1$H NMR (500 MHz, DMSO-$d_6$) δ 9.08 (s, 1H), 7.95 (br dd, J = 9.0, 6.0 Hz, 1H), 7.45 (br t, J = 9.0 Hz, 1H), 7.39 (br d, J = 2.1 Hz, 1H), 7.18 (br s, 1H), 4.50 (br d, J = 10.5 Hz, 1H), 4.27-4.07 (m, 5H), 3.99-3.90 (m, 3H), 3.80-3.73 (m, 2H), 3.73-3.62 (m, 2H), 3.54-3.45 (m, 1H), 2.94-2.88 (m, 1H), 2.38 (br d, J = 5.5 Hz, 4H), 2.14-2.04 (m, 2H), 1.90-1.79 (m, 2H), 1.77-1.67 (m, 3H), 1.63-1.41 (m, 9H), 1.39-1.30 (m, 2H) |
| 1-101 | 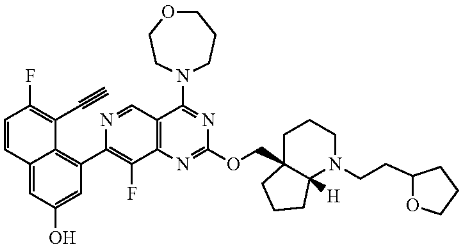<br>Diastereomer Mixture | 5-{[(4aS,7aR)-4a-({[7-(8-ethynyl-7-fluoro-3-hydroxynaph-thalen-1-yl)-8-fluoro-4-(1,4-oxazepan-4-yl)pyrido[4,3-d]pyrimidin-2-yl]oxy}meth-yl)-octahydro-1H-cyclopenta[b]pyridin-1-yl]methyl}-1-methylpyrrol-idin-2-one | 696.3 | $^1$H NMR (500 MHz, DMSO-$d_6$) δ 9.10 (s, 1H), 8.00-7.93 (m, 2H), 7.47 (t, J = 9.0 Hz, 1H), 7.40 (d, J = 2.4 Hz, 1H), 7.19 (d, J = 1.8 Hz, 1H), 4.65-4.56 (m, 1H), 4.24-4.09 (m, 5H), 4.02-3.98 (m, 1H), 3.95 (t, J = 4.6 Hz, 2H), 3.77 (t, J = 5.1 Hz, 2H), 3.67-3.57 (m, 1H), 3.00-2.92 (m, 1H), 2.77-2.68 (m, 3H), 2.45-2.34 (m, 2H), 2.31-2.21 (m, 1H), 2.14-1.97 (m, 4H), 1.89-1.81 (m, 1H), 1.78-1.69 (m, 1H), 1.66-1.49 (m, 8H), 1.48-1.41 (m, 1H), 1.39-1.30 (m, 1H) |

TABLE 1-continued

| # | Structure | IUPAC | LCMS (M + H)+ | 1H NMR |
|---|---|---|---|---|
| 1-102[E] | 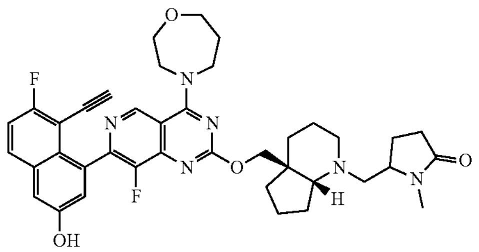 Diastereomer 1 | 5-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-1-methylpyrrolidin-2-one | 696.3 | $^1$H NMR (500 MHz, DMSO-$d_6$) δ 9.09 (s, 1H), 7.97 (dd, J = 9.2, 5.9 Hz, 1H), 7.46 (t, J = 9.0 Hz, 1H), 7.40 (d, J = 2.4 Hz, 1H), 7.19 (d, J = 2.4 Hz, 1H), 4.61 (dd, J = 10.6, 6.3 Hz, 1H), 4.21-4.11 (m, 5H), 3.99 (d, J = 9.2 Hz, 1H), 3.94 (t, J = 4.6 Hz, 2H), 3.77 (t, J = 5.2 Hz, 2H), 3.65-3.59 (m, 1H), 2.99-2.93 (m, 1H), 2.74 (d, J = 4.3 Hz, 3H), 2.45-2.35 (m, 2H), 2.31-2.21 (m, 1H), 2.14-1.95 (m, 4H), 1.88-1.81 (m, 1H), 1.77-1.68 (m, 1H), 1.66-1.51 (m, 8H), 1.48-1.42 (m, 1H), 1.37-1.29 (m, 1H). |
| 1-103[E] | 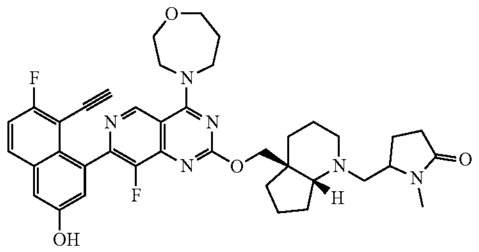 Diastereomer 2 | 5-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]methyl}-1-methylpyrrolidin-2-one | 696.3 | $^1$H NMR (500 MHz, DMSO-$d_6$) δ 9.10 (s, 1H), 7.96 (dd, J = 9.1, 5.8 Hz, 1H), 7.46 (t, J = 9.0 Hz, 1H), 7.39 (d, J = 2.4 Hz, 1H), 7.19 (s, 1H), 4.60 (dd, J = 10.5, 4.7 Hz, 1H), 4.24-4.10 (m, 5H), 3.99 (d, J = 1.8 Hz, 1H), 3.95 (br t, J = 4.5 Hz, 2H), 3.77 (br t, J = 5.1 Hz, 2H), 3.65-3.61 (m, 1H), 2.97-2.89 (m, 1H), 2.73 (d, J = 7.6 Hz, 3H), 2.46-2.34 (m, 2H), 2.32-2.21 (m, 1H), 2.14-2.02 (m, 3H), 2.01-1.93 (m, 1H), 1.91-1.81 (m, 1H), 1.75-1.69 (m, 1H), 1.66-1.43 (m, 8H), 1.37-1.28 (m, 1H) |
| 1-110 | 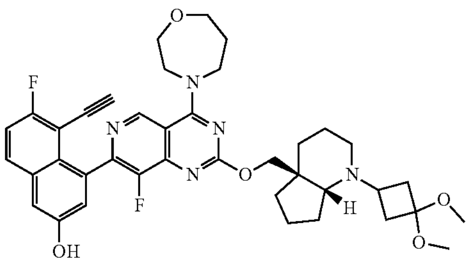 [SMILES: C#Cc1c(F)ccc2cc(O)cc(-c3ncc4c(N5CCCOCC5)nc(OC[C@]56CCC[C@H]5N(C5CC(OC)(OC)C5)CCC6)nc4c3F)c12] | 4-(2-{[(4aS,7aR)-1-(3,3-dimethoxycyclobutyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 700.2 | H NMR (500 MHz, DMSO-$d_6$) δ 9.09 (s, 1H), 8.01-7.92 (m, 2H), 7.46 (t, J = 9.1 Hz, 1H), 7.40 (d, J = 2.2 Hz, 1H), 7.22-7.12 (m, 1H), 4.55 (br dd, J = 10.7, 6.6 Hz, 1H), 4.29 (br dd, J = 10.6, 5.0 Hz, 1H), 4.21-4.10 (m, 4H), 4.00-3.92 (m, 3H), 3.77 (br t, J = 4.7 Hz, 2H), 3.04-2.93 (m, 7H), 2.66 (br t, J = 7.2 Hz, 1H), 2.44 (br d, J = 10.6 Hz, 1H), 2.31-2.15 (m, 3H), 2.14-2.07 (m, 2H), 1.83 (br d, J = 11.0 Hz, 1H), 1.74-1.61 (m, 4H), 1.60-1.49 (m, |

TABLE 1-continued

| # | Structure | IUPAC | LCMS (M + H)+ | $^1$H NMR |
|---|---|---|---|---|
| | | | | 3H), 1.47-1.33 (m, 3H), 1.33-1.24 (m, 1H) |
| 1-115 | 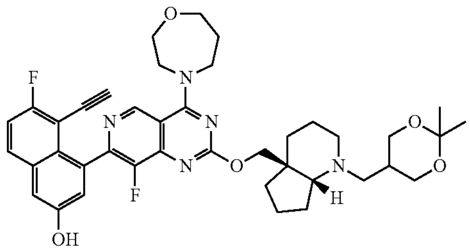 [SMILES: C#Cc1c(F)ccc2cc(O)cc(-c3ncc4c(N5CCCOCC5)nc(OC[C@]56CCC[C@H]5N(CC5COC(C)(C)OC5)CCC6)nc4c3F)c12] | 4-(2-{[(4aS,7aR)-1-[(2,2-dimethyl-1,3-dioxan-5-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoro-naphthalen-2-ol | 714.2 | $^1$H NMR (500 MHz, DMSO-$d_6$) δ 9.09 (s, 1H), 7.97 (dd, J = 9.2, 6.0 Hz, 1H), 7.46 (t, J = 9.0 Hz, 1H), 7.40 (d, J = 2.4 Hz, 1H), 7.18 (br d, J = 2.5 Hz, 1H), 4.55 (br d, J = 10.5 Hz, 1H), 4.25-4.07 (m, 6H), 4.00-3.93 (m, 3H), 3.81-3.72 (m, 5H), 3.57-3.50 (m, 1H), 2.90-2.82 (m, 1H), 2.46-2.40 (m, 1H), 2.33 (br dd, J = 12.0, 8.2 Hz, 2H), 2.24 (br dd, J = 12.3, 6.8 Hz, 1H), 2.11 (br s, 2H), 1.89-1.79 (m, 2H), 1.75-1.66 (m, 1H), 1.63-1.49 (m, 6H), 1.47-1.41 (m, 1H), 1.26 (br d, J = 3.1 Hz, 6H) |
| 1-118 | 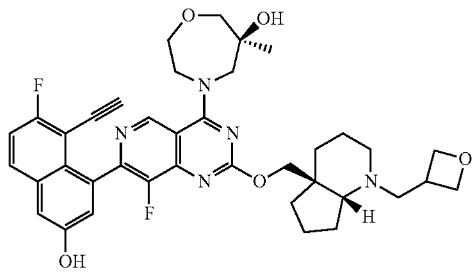 [SMILES: C#Cc1c(F)ccc2cc(O)cc(-c3ncc4c(N5CCOC[C@@](C)(O)C5)nc(OC[C@]56CCC[C@H]5N(CC5COC5)CCC6)nc4c3F)c12] | (6S)-4-(2-{[(4aS,7aR)-1-[(oxetan-3-yl)methyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol | 686.1 | $^1$H NMR (500 MHz, DMSO-$d_6$) δ 9.46-9.27 (m, 1H), 7.97 (dd, J = 9.2, 5.9 Hz, 1H), 7.46 (t, J = 9.0 Hz, 1H), 7.40 (d, J = 2.4 Hz, 1H), 7.20 (dd, J = 12.6, 2.4 Hz, 1H), 5.57-4.97 (m, 1H), 4.67-4.39 (m, 4H), 4.39-4.28 (m, 1H), 4.28-4.13 (m, 4H), 4.13-4.02 (m, 2H), 4.02-3.94 (m, 2H), 3.94-3.81 (m, 2H), 3.71-3.47 (m, 2H), 2.76-2.59 (m, 1H), 2.47-2.35 (m, 1H), 2.35-2.20 (m, 1H), 1.97-1.80 (m, 1H), 1.80-1.66 (m, 1H), 1.66-1.27 (m, 9H), 1.21-1.13 (m, 3H) |
| 1-119 | 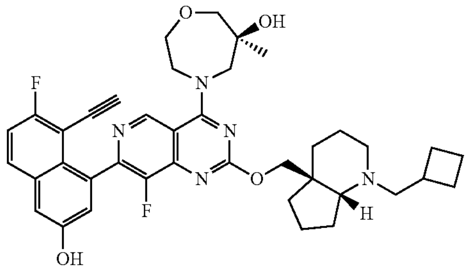 [SMILES: C#Cc1c(F)ccc2cc(O)cc(-c3ncc4c(N5CCOC[C@@](C)(O)C5)nc(OC[C@]56CCC[C@H]5N(CC5CCC5)CCC6)nc4c3F)c12] | (6S)-4-(2-{[(4aS,7aR)-1-(cyclobutylmethyl)-octahydro-1H-cyclopenta[b]pyridin-4a-yl]-methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol | 684.6 | $^1$H NMR (500 MHz, DMSO-$d_6$) δ 9.46-9.28 (m, 1H), 7.98 (dd, J = 9.0, 5.9 Hz, 1H), 7.47 (t, J = 8.9 Hz, 1H), 7.40 (d, J = 2.4 Hz, 1H), 7.20 (dd, J = 11.6, 2.4 Hz, 1H), 5.58-5.01 (m, 1H), 4.66-4.52 (m, 1H), 4.50-4.39 (m, 1H), 4.39-4.30 (m, 1H), 4.23-4.02 (m, 3H), 4.01-3.93 (m, 2H), 3.93-3.81 (m, 2H), 3.67-3.50 (m, 2H), 2.04-1.69 (m, 8H), 1.69-1.29 (m, 12H), 1.21-1.12 (m, 3H) |

TABLE 1-continued

| # | Structure | IUPAC | LCMS (M + H)+ | $^1$H NMR |
|---|---|---|---|---|
| I-120 | 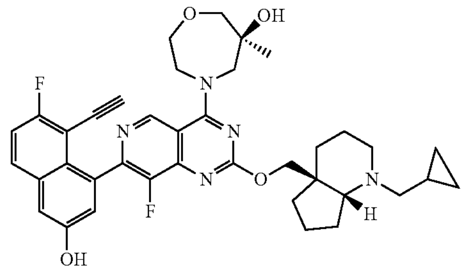 [SMILES: C#Cc1c(F)ccc2cc(O)cc(-c3ncc4c(N5CCOC[C@@](C)(O)C5)nc(OC[C@]56CCC[C@H]5N(CC5CC5)CCC6)nc4c3F)c12] | (6S)-4-(2-{[(4aS,7aR)-1-(cyclopropyl-methyl)-octa-hydro-1H-cyclopenta[b]pyridin-4a-yl]methoxy}-7-(8-ethynyl-7-fluoro-3-hydroxynaph-thalen-1-yl)-8-fluoropyrido[4,3-d]pyrimi-din-4-yl)-6-methyl-1,4-oxazepan-6-ol | 670.0 | $^1$H NMR (500 MHz, DMSO-$d_6$) δ 9.40-9.21 (m, 1H), 7.91 (dd, J = 9.8, 3.9 Hz, 1H), 7.41 (t, J = 9.0 Hz, 1H), 7.35 (d, J = 2.4 Hz, 1H), 7.15 (dd, J = 11.5, 2.5 Hz, 1H), 4.61-4.50 (m, 1H), 4.42-4.23 (m, 2H), 4.21-3.98 (m, 3H), 3.98-3.87 (m, 2H), 3.87-3.74 (m, 2H), 3.63-3.46 (m, 1H), 3.07-2.95 (m, 1H), 2.63-2.53 (m, 1H), 2.38-2.30 (m, 1H), 2.25-2.13 (m, 1H), 1.86-1.75 (m, 1H), 1.75-1.62 (m, 1H), 1.62-1.26 (m, 9H), 1.15-1.08 (m, 3H), 0.81-0.71 (m, 1H), 0.46-0.31 (m, 2H), 0.12-−0.06 (m, 2H) |
| 1-121 | 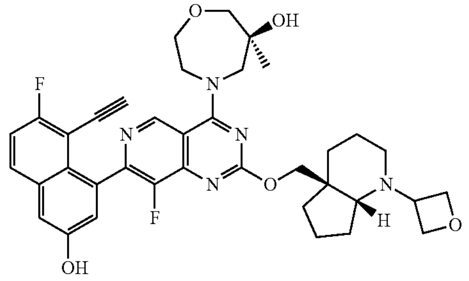 [SMILES: C#Cc1c(F)ccc2cc(O)cc(-c3ncc4c(N5CCOC[C@@](C)(O)C5)nc(OC[C@]56CCC[C@H]5N(C5COC5)CCC6)nc4c3F)c12] | (6S)-4-(2-{[(4aS,7aR)-1-(oxetan-3-yl)-octahydro-1H-cyclopenta[b]pyridin-4a-yl]methoxy}-7-(8-ethynyl-7-fluoro-3-hydroxynaph-thalen-1-yl)-8-fluoropyrido[4,3-d]pyrimi-din-4-yl)-6-methyl-1,4-oxazepan-6-ol | 672.2 | $^1$H NMR (499 MHz, DMSO-$d_6$) δ 10.15 (br d, J = 4.9 Hz, 1H), 9.47-9.29 (m, 1H), 7.98 (dd, J = 9.2, 6.0 Hz, 1H), 7.47 (br t, J = 8.9 Hz, 1H), 7.40 (d, J = 2.2 Hz, 1H), 7.20 (dd, J = 13.2, 2.2 Hz, 1H), 5.54-4.92 (m, 1H), 4.70-4.59 (m, 1H), 4.57-4.48 (m, 1H), 4.48-4.40 (m, 3H), 4.40-4.31 (m, 1H), 4.31-4.24 (m, 1H), 4.22-3.80 (m, 5H), 3.79-3.68 (m, 1H), 3.68-3.50 (m, 2H), 3.01-2.85 (m, 1H), 2.48-2.41 (m, 1H), 2.36-2.24 (m, 1H), 1.90-1.26 (m, 11H), 1.22-1.13 (m, 3H) |
| 1-122 | 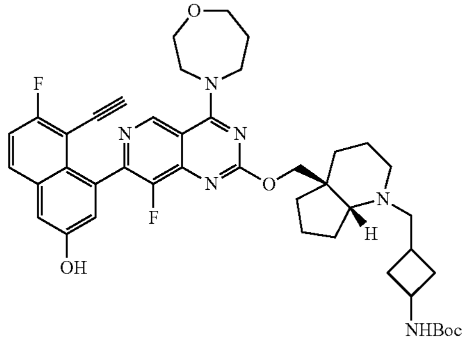 [SMILES: C#Cc1c(F)ccc2cc(O)cc(-c3ncc4c(N5CCCOCC5)nc(OC[C@]56CCC[C@H]5N(CC5CC(NC(=O)OC(C)(C)C)C5)CCC6)nc4c3F)c12] | tert-butyl N-(3-{[(4aS,7aR)-4a-({[7-(8-ethynyl-7-fluoro-3-hydroxynaph-thalen-1-yl)-8-fluoro-4-(1,4-oxazepan-4-yl)pyrido[4,3-d]pyrimidin-2-yl]oxy}meth-yl)-octahydro-1H-cyclopenta[b]pyridin-1-yl]methyl}-cyclobutyl)carbamate | 769.4 | $^1$H NMR (500 MHz, DMSO-$d_6$) δ 9.09 (s, 1H), 8.00-7.96 (m, 1H), 7.46 (t, J = 9.0 Hz, 1H), 7.39 (d, J = 2.4 Hz, 1H), 7.18 (d, J = 2.1 Hz, 1H), 6.96 (br d, J = 8.3 Hz, 1H), 4.61-4.44 (m, 2H), 4.41-4.23 (m, 4H), 4.18-4.04 (m, 2H), 4.00-3.84 (m, 3H), 3.51-3.42 (m, 2H), 2.99-2.81 (m, 4H), 2.53-2.02 (m, 8H), 1.93-1.87 (m, 2H), 1.86-1.61 (m, 9H), 1.49-1.41 (m, 9H) |

TABLE 1-continued

| # | Structure | IUPAC | LCMS (M + H)+ | 1H NMR |
|---|---|---|---|---|
| 1-123 | 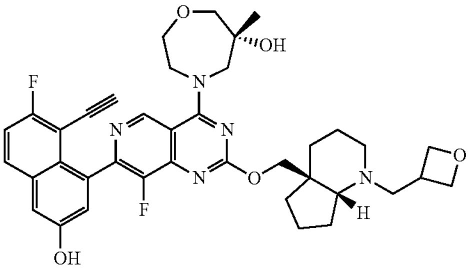 [SMILES: C#Cc1c(F)ccc2cc(O)cc(-c3ncc4c(N5CCOC[C@](C)(O)C5)nc(OC[C@]56CCC[C@H]5N(CC5COC5)CCC6)nc4c3F)c12] | (6R)-4-(2-{[(4aS,7aR)-1-[(oxetan-3-yl)methyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol | 686.3 | $^1$H NMR (499 MHz, METHANOL-$d_4$) δ 9.50-9.36 (m, 1H), 7.91-7.84 (m, 1H), 7.40-7.31 (m, 2H), 7.25 (br dd, J = 15.3, 2.3 Hz, 1H), 4.80-4.71 (m, 2H), 4.68-4.53 (m, 3H), 4.53-4.36 (m, 3H), 4.35-4.17 (m, 1H), 4.13-4.02 (m, 2H), 4.02-3.86 (m, 2H), 3.80-3.61 (m, 2H), 3.58-3.44 (m, 1H), 3.17-3.02 (m, 1H), 2.94-2.77 (m, 2H), 2.70-2.55 (m, 1H), 2.55-2.38 (m, 1H), 2.12-1.97 (m, 1H), 1.90-1.51 (m, 11H), 1.34-1.28 (m, 3H) |
| 1-124 | 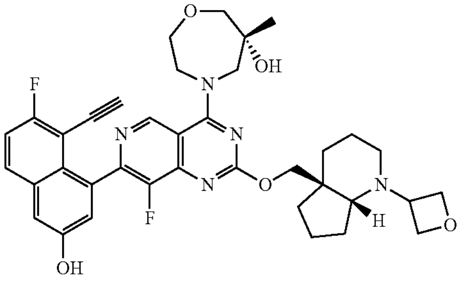 [SMILES: C#Cc1c(F)ccc2cc(O)cc(-c3ncc4c(N5CCOC[C@](C)(O)C5)nc(OC[C@]56CCC[C@H]5N(C5COC5)CCC6)nc4c3F)c12] | (6R)-4-(2-{[(4aS,7aR)-1-(oxetan-3-yl)-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol | 672.2 | $^1$H NMR (499 MHz, DMSO-$d_6$) δ 10.14 (d, J = 3.1 Hz, 1H), 9.45-9.26 (m, 1H), 7.98 (dd, J = 9.2, 5.9 Hz, 1H), 7.47 (t, J = 9.0 Hz, 1H), 7.40 (d, J = 2.6 Hz, 1H), 7.20 (dd, J = 13.9, 2.5 Hz, 1H), 5.35-5.00 (m, 1H), 4.66-4.58 (m, 1H), 4.54-4.48 (m, 1H), 4.48-4.41 (m, 3H), 4.41-4.32 (m, 1H), 4.32-4.24 (m, 1H), 4.19-3.95 (m, 4H), 3.95-3.81 (m, 2H), 3.78-3.67 (m, 1H), 3.65-3.53 (m, 2H), 3.03-2.88 (m, 1H), 2.48-2.39 (m, 1H), 2.35-2.25 (m, 1H), 1.89-1.78 (m, 1H), 1.75-1.54 (m, 5H), 1.50-1.43 (m, 2H), 1.39-1.28 (m, 2H), 1.21-1.16 (m, 3H) |
| 1-125 | 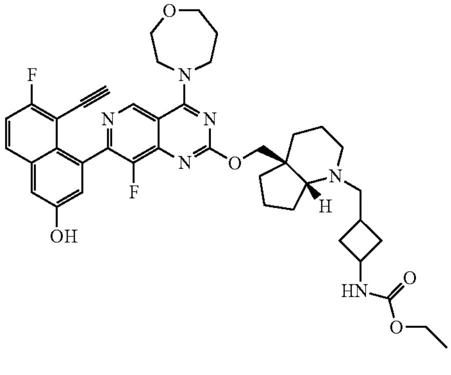 [SMILES: C#Cc1c(F)ccc2cc(O)cc(-c3ncc4c(N5CCCOCC5)nc(OC[C@]56CCC[C@H]5N(CC5CC(NC(=O)OCC)C5)CCC6)nc4c3F)c12] | ethyl N-(3-{[(4aS,7aR)-4a-({[7-(8-ethynyl-7-fluoro-3-hydroxy-naphthalen-1-yl)-8-fluoro-4-(1,4-oxazepan-4-yl)pyrido[4,3-d]pyrimidin-2-yl]oxy}-methyl)-octahydro-1H-cyclopenta[b]pyridin-1-yl]methyl}cyclobutyl)carbamate | 742.3 | $^1$H NMR (499 MHz, METHANOL-$d_4$) δ 9.65 (s, 1H), 9.15 (s, 1H), 7.89 (dd, J = 9.0, 5.7 Hz, 1H), 7.41-7.31 (m, 2H), 7.25 (s, 1H), 4.72-4.57 (m, 1H), 4.57-4.43 (m, 1H), 4.43-4.23 (m, 4H), 4.17-3.84 (m, 8H), 3.53-3.39 (m, 2H), 3.31-3.02 (m, 4H), 2.65-2.40 (m, 3H), 2.35-1.70 (m, 14H), 1.28-1.17 (m, 3H) |

TABLE 1-continued

| # | Structure | IUPAC | LCMS (M + H)+ | $^1$H NMR |
|---|---|---|---|---|
| 1-126 | 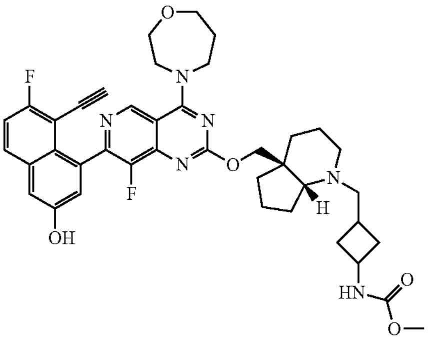 [SMILES: C#Cc1c(F)ccc2cc(O)cc(-c3ncc4c(N5CCCOCC5)nc(OC[C@]56CCC[C@H]5N(CC5CC(NC(=O)OC)C5)CCC6)nc4c3F)c12] | methyl N-(3-{[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yloxy}methyl)-octahydro-1H-cyclopenta[b]pyridin-1-yl]methyl}cyclobutyl)carbamate | 727.1 | $^1$H NMR (500 MHz, DMSO-$d_6$) δ 9.09 (s, 1H), 8.00-7.96 (m, 1H), 7.46 (t, J = 9.0 Hz, 1H), 7.39 (d, J = 2.5 Hz, 1H), 7.26 (br d, J = 7.2 Hz, 1H), 7.18 (d, J = 2.4 Hz, 1H), 4.64-4.45 (m, 2H), 4.40-4.20 (m, 4H), 4.14-4.02 (m, 2H), 4.02-3.79 (m, 4H), 3.67-3.55 (m, 5H), 3.49-3.40 (m, 1H), 3.13-2.95 (m, 4H), 2.59-2.31 (m, 3H), 2.31-2.18 (m, 2H), 2.18-2.02 (m, 3H), 1.89-1.63 (m, 9H) |
| 1-130 | 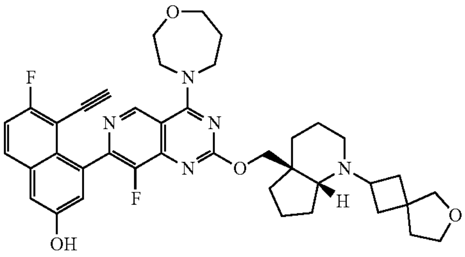 Diastereomer Mixture | 4-(2-{[(4aS,7aR)-1-{6-oxaspiro[3.4]octan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 696.2 | |
| 1-131$^O$ | 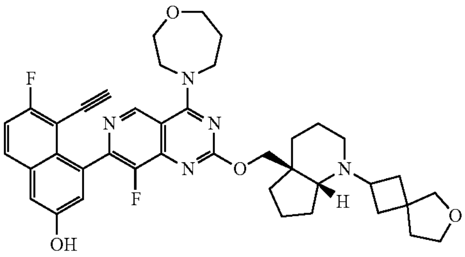 Diastereomer 1 | 4-(2-{[(4aS,7aR)-1-{6-oxaspiro[3.4]octan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 696.4 | $^1$H NMR (500 MHz, DMSO-$d_6$) δ 8.86 (s, 1H), 7.77-7.70 (m, 1H), 7.22 (br t, J = 9.0 Hz, 1H), 7.15 (d, J = 2.2 Hz, 1H), 6.94 (d, J = 2.4 Hz, 1H), 4.40-4.30 (m, 1H), 4.02 (br t, J = 10.5 Hz, 1H), 3.97-3.83 (m, 4H), 3.77-3.65 (m, 4H), 3.58-3.49 (m, 2H), 3.36-3.25 (m, 3H), 2.74 (br t, J = 8.3 Hz, 1H), 2.61-2.52 (m, 1H), 2.23-2.16 (m, 1H), 1.93-1.83 (m, 3H), 1.81-1.70 (m, 2H), 1.58-0.97 (m, 14H) |
| 1-132$^O$ | 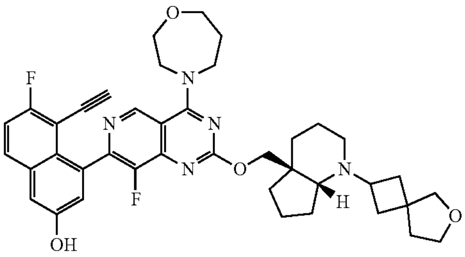 Diastereomer 2 | 4-(2-{[(4aS,7aR)-1-{6-oxaspiro[3.4]octan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 696.4 | $^1$H NMR (500 MHz, DMSO-$d_6$) δ 8.90 (s, 1H), 7.77 (dd, J = 9.1, 6.1 Hz, 1H), 7.26 (t, J = 9.0 Hz, 1H), 7.19 (d, J = 2.1 Hz, 1H), 6.99 (s, 1H), 4.44-4.33 (m, 1H), 4.06 (br dd, J = 10.7, 5.1 Hz, 1H), 4.00-3.88 (m, 4H), 3.82-3.71 (m, 3H), 3.57 (br t, J = 5.2 Hz, 2H), 3.46-3.28 (m, 3H), 2.83-2.68 (m, 2H), 2.25 (br d, J = 9.4 Hz, 1H), |

TABLE 1-continued

| # | Structure | IUPAC | LCMS $(M + H)^+$ | $^1H$ NMR |
|---|---|---|---|---|
| | | | | 1.99-1.88 (m, 3H), 1.83-1.72 (m, 2H), 1.65 (br t, J = 6.5 Hz, 2H), 1.56-0.99 (m, 12H) |
| 1-134$^G$ | 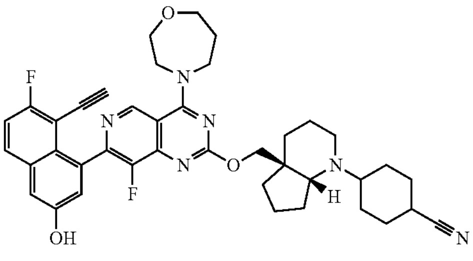 Diastereomer 1 | 4-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]cyclohexane-1-carbonitrile | 693.3 | $^1H$ NMR (500 MHz, DMSO-$d_6$) δ 9.09 (s, 1H), 8.01-7.96 (m, 1H), 7.47 (t, J = 8.9 Hz, 1H), 7.40 (d, J = 2.4 Hz, 1H), 7.19 (s, 1H), 4.59 (br t, J = 9.3 Hz, 1H), 4.27 (br dd, J = 10.3, 5.8 Hz, 1H), 4.15 (br s, 4H), 4.02-3.90 (m, 3H), 3.77 (br s, 2H), 3.12 (br t, J = 8.8 Hz, 1H), 2.95 (br s, 1H), 2.49-2.41 (m, 1H), 2.36 (br d, J = 2.7 Hz, 1H), 2.12 (br s, 2H), 1.95-1.40 (m, 18H), 1.37-1.28 (m, 1H), 1.16-1.08 (m, 1H) |
| 1-135$^G$ | 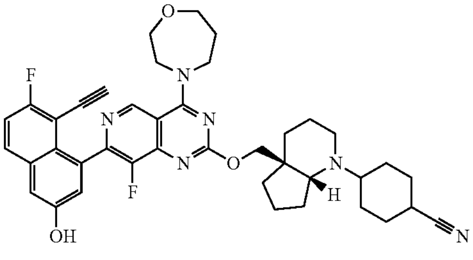 Diastereomer 2 | 4-[(4aS,7aR)-4a-({[7-(8-ethynyl-7-fluoro-3-hydroxynaphthalen-1-yl)-8-fluoro-4-(1,4-oxazepan-4-yl)pyrido[4,3-d]pyrimidin-2-yl]oxy}methyl)-octahydro-1H-cyclopenta[b]pyridin-1-yl]cyclohexane-1-carbonitrile | 693.4 | $^1H$ NMR (500 MHz, DMSO-$d_6$) δ 9.09 (s, 1H), 7.97 (br dd, J = 9.1, 6.1 Hz, 1H), 7.47 (br t, J = 9.0 Hz, 1H), 7.40 (d, J = 2.2 Hz, 1H), 7.18 (br s, 1H), 4.58 (br dd, J = 10.5, 5.1 Hz, 1H), 4.24-4.07 (m, 5H), 4.02-3.92 (m, 3H), 3.76 (br d, J = 4.7 Hz, 2H), 3.05 (br t, J = 8.6 Hz, 1H), 2.39-2.30 (m, 1H), 2.10 (br s, 2H), 1.98 (br dd, J = 9.7, 7.3 Hz, 2H), 1.78-1.64 (m, 3H), 1.61-1.18 (m, 15H) |
| 1-136$^Y$ | 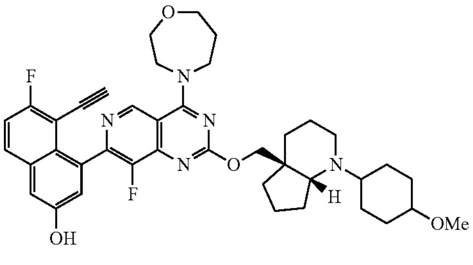 Diastereomer 1 | 4-(2-{[(4aS,7aR)-1-(4-methoxycyclohexyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 698.4 | $^1H$ NMR (500 MHz, DMSO-$d_6$) δ 8.89 (s, 1H), 7.77 (dd, J = 9.2, 5.9 Hz, 1H), 7.26 (t, J = 9.0 Hz, 1H), 7.19 (d, J = 2.5 Hz, 1H), 6.98 (s, 1H), 4.39 (d, J = 10.8 Hz, 1H), 4.05-3.85 (m, 5H), 3.80-3.68 (m, 3H), 3.57 (br t, J = 5.2 Hz, 2H), 2.98 (s, 3H), 2.91-2.76 (m, 2H), 2.28-2.23 (m, 1H), 2.14-2.04 (m, 1H), 1.95-1.86 (m, 2H), 1.78-1.67 (m, 3H), 1.58-1.45 (m, 3H), 1.37-0.83 (m, 13H) |

TABLE 1-continued

| # | Structure | IUPAC | LCMS $(M + H)^+$ | $^1H$ NMR |
|---|---|---|---|---|
| 1-137[Y] | 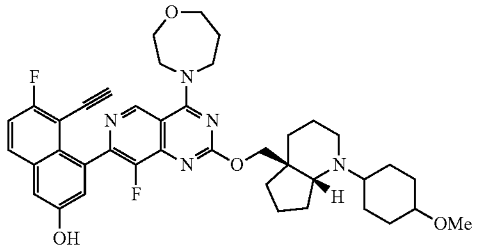<br>Diastereomer 2 | 4-(2-{[(4aS,7aR)-1-(4-methoxy-cyclohexyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 698.1 | $^1H$ NMR (500 MHz, DMSO-$d_6$) δ 9.10 (s, 1H), 8.00-7.95 (m, 1H), 7.46 (t, J = 9.0 Hz, 1H), 7.39 (d, J = 2.4 Hz, 1H), 7.19 (s, 1H), 4.60 (dd, J = 10.6, 7.0 Hz, 1H), 4.23 (d, J = 10.5 Hz, 1H), 4.19-4.11 (m, 3H), 4.01-3.89 (m, 3H), 3.76 (br t, J = 5.1 Hz, 2H), 3.24-3.20 (m, 1H), 3.14 (d, J = 3.2 Hz, 3H), 2.59 (br d, J = 10.5 Hz, 1H), 2.42-2.28 (m, 2H), 2.14-2.06 (m, 2H), 1.95-1.86 (m, 2H), 1.75-1.27 (m, 16H) |
| 1-140 | 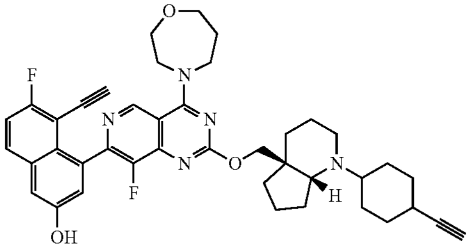<br>Diastereomer Mixture | 4-(2-{[(4aS,7aR)-1-(4-ethynyl-cyclohexyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 692.1 | |
| 1-141[G] | 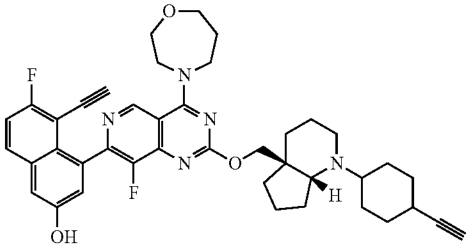<br>Diastereomer 2 | 4-(2-{[(4aS,7aR)-1-(4-ethynyl-cyclohexyl)-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 692.2 | |
| 1-144[AB] | 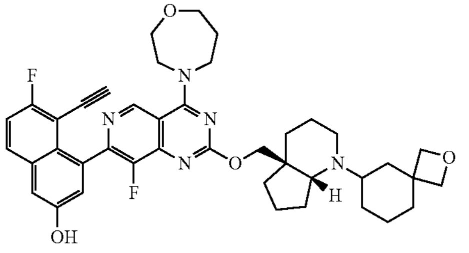<br>Diastereomer 2 | 4-(2-{[(4aS,7aR)-1-{2-oxaspiro[3.5]nonan-6-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 710.4 | |

TABLE 1-continued

| # | Structure | IUPAC | LCMS (M + H)+ | 1H NMR |
|---|---|---|---|---|
| 1-152 | 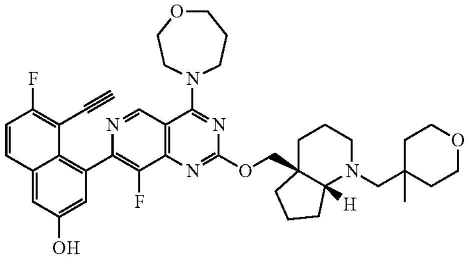 [SMILES: C#Cc1c(F)ccc2cc(O)cc(-c3ncc4c(N5CCCOCC5)nc(OC[C@]56CCC[C@H]5N(CC5(C)CCOCC5)CCC6)nc4c3F)c12] | 4-(2-{[(4aS,7aR)-1-[(4-methyl-oxan-4-yl)-methyl]-octa-hydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaph-thalen-2-ol | 698.3 | $^1$H NMR (500 MHz, DMSO-$d_6$) δ 9.10 (s, 1H), 8.00-7.94 (m, 1H), 7.46 (br t, J = 9.0 Hz, 1H), 7.40 (d, J = 2.2 Hz, 1H), 7.18 (br s, 1H), 4.67 (br d, J = 10.5 Hz, 1H), 4.29 (br t, J = 9.4 Hz, 1H), 4.15 (br s, 4H), 3.95 (br t, J = 9.8 Hz, 3H), 3.76 (br d, J = 3.7 Hz, 2H), 3.54-3.48 (m, 1H), 3.46-3.39 (m, 1H), 2.94 (br t, J = 6.1 Hz, 1H), 2.69-2.58 (m, 1H), 2.42-2.35 (m, 1H), 2.31 (br d, J = 14.0 Hz, 1H), 2.15-2.02 (m, 3H), 1.93-1.84 (m, 1H), 1.80-1.35 (m, 10H), 1.32-1.22 (m, 1H), 1.14-1.05 (m, 2H), 0.89 (s, 3H) |
| 1-205[AC] | 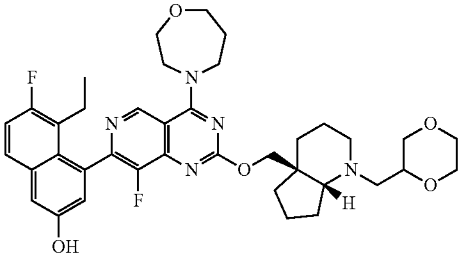 Diastereomer 1 | 4-(2-{[(4aS,7aR)-1-[(1,4-dioxan-2-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethyl-6-fluoronaph-thalen-2-ol | 690.6 | $^1$H NMR (500 MHz, DMSO-$d_6$) δ 9.16 (s, 1H), 7.77 (dd, J = 9.0, 6.0 Hz, 1H), 7.39-7.31 (m, 2H), 7.03 (s, 1H), 4.60 (d, J = 10.8 Hz, 1H), 4.27-4.11 (m, 5H), 3.95 (br t, J = 4.6 Hz, 2H), 3.75 (br t, J = 5.1 Hz, 2H), 3.72-3.46 (m, 4H), 3.22-3.10 (m, 1H), 2.94-2.84 (m, 1H), 2.49-2.27 (m, 5H), 2.20-2.06 (m, 3H), 1.89-1.79 (m, 1H), 1.75-1.65 (m, 1H), 1.62-1.38 (m, 7H), 1.34-1.24 (m, 1H), 0.79-0.69 (m, 3H) |
| 1-206 | 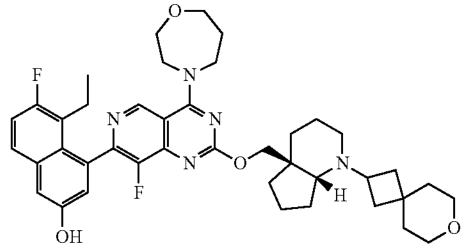 [SMILES: CCc1c(F)ccc2cc(O)cc(-c3ncc4c(N5CCCOCC5)nc(OC[C@]56CCC[C@H]5N(C5CC7(CCOCC7)C5)CCC6)nc4c3F)c12] | 4-(2-{[(4aS,7aR)-1-{7-oxaspiro[3.5]nonan-2-yl}-octahydro-1H-cyclopenta[b]pyridin-4a-yl]methoxy}-8-fluoro-4-(1,4-oxazepan-4-yl)pyrido[4,3-d]pyrimi-din-7-yl)-5-ethyl-6-fluoro-naphthalen-2-ol | 714.4 | $^1$H NMR (500 MHz, DMSO-$d_6$) δ 9.16 (s, 1H), 7.76 (dd, J = 9.1, 6.0 Hz, 1H), 7.40-7.27 (m, 2H), 7.02 (d, J = 2.6 Hz, 1H), 4.62-4.34 (m, 2H), 4.20-4.04 (m, 4H), 3.95 (br s, 2H), 3.75 (br t, J = 5.2 Hz, 2H), 3.39-3.29 (m, 1H), 2.43-2.32 (m, 1H), 2.21-2.05 (m, 4H), 2.00-1.79 (m, 3H), 1.74-1.25 (m, 15H), 0.73 (td, J = 7.3, 3.2 Hz, 3H) |

TABLE 1-continued

| # | Structure | IUPAC | LCMS (M + H)+ | $^1$H NMR |
|---|---|---|---|---|
| 1-213 | 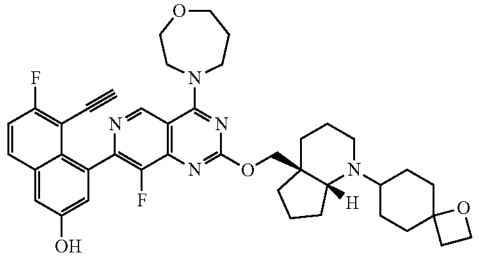 Diastereomer Mixture | 4-(2-{[(4aS,7aR)-1-{1-oxaspiro[3.5]nonan-7-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 710.3 | |
| 1-214[K] | 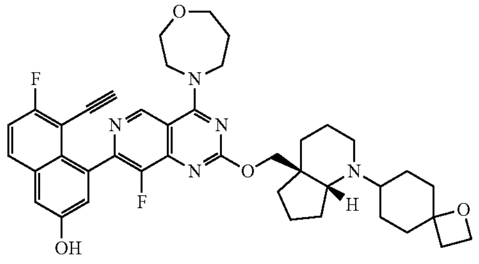 Diastereomer 1 | 4-(2-{[(4aS,7aR)-1-{1-oxaspiro[3.5]nonan-7-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 710.3 | $^1$H NMR (500 MHz, DMSO-$d_6$) δ 9.09 (s, 1H), 7.97 (dd, J = 9.2, 5.9 Hz, 1H), 7.46 (t, J = 9.0 Hz, 1H), 7.40 (d, J = 2.4 Hz, 1H), 7.19 (d, J = 2.2 Hz, 1H), 4.64-4.54 (m, 1H), 4.29 (t, J = 7.7 Hz, 2H), 4.25-4.07 (m, 5H), 4.01-3.90 (m, 3H), 3.76 (br t, J = 4.8 Hz, 2H), 2.34-2.21 (m, 3H), 2.14-2.07 (m, 2H), 1.99-1.85 (m, 3H), 1.75-1.66 (m, 1H), 1.62-1.27 (m, 16H) |
| 1-215 | 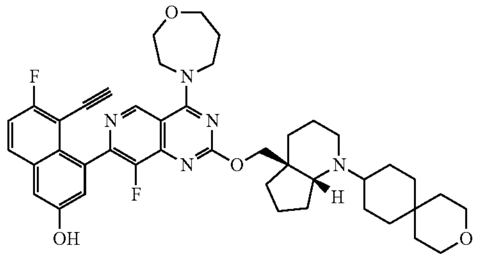 [SMILES: C#Cc1c(F)ccc2cc(O)cc(-c3ncc4c(N5CCCOCC5)nc(OC[C@]56CCC[C@H]5N(C5CCC7(CCOCC7)CC5)CCC6)nc4c3F)c12] | 4-(2-{[(4aS,7aR)-1-{3-oxaspiro[5.5]undecan-9-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 738.2 | $^1$H NMR (500 MHz, DMSO-$d_6$) δ 9.10 (s, 1H), 7.97 (dd, J = 9.2, 5.9 Hz, 1H), 7.46 (t, J = 9.0 Hz, 1H), 7.40 (d, J = 2.4 Hz, 1H), 7.19 (s, 1H), 4.73-4.59 (m, 1H), 4.29 (br t, J = 10.0 Hz, 1H), 4.20-4.07 (m, 5H), 3.99-3.91 (m, 3H), 3.76 (br d, J = 4.7 Hz, 2H), 3.57-3.43 (m, 4H), 3.14 (br d, J = 7.0 Hz, 1H), 2.14-1.93 (m, 5H), 1.82-1.34 (m, 18H), 1.25 (br s, 2H), 1.14-1.03 (m, 2H) |
| 1-218 | 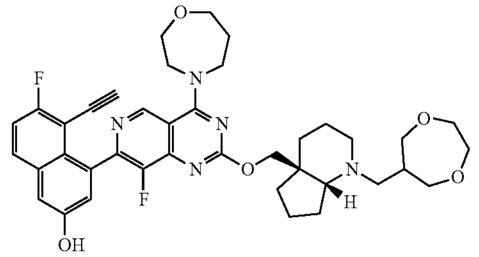 [SMILES: C#Cc1c(F)ccc2cc(O)cc(-c3ncc4c(N5CCCOCC5)nc(OC[C@]56CCC[C@H]5N(CC5COCCOC5)CCC6)nc4c3F)c12] | 4-(2-{[(4aS,7aR)-1-[(1,4-dioxepan-6-yl)methyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 700.3 | $^1$H NMR (500 MHz, DMSO-$d_6$) δ 9.08 (s, 1H), 7.96 (dd, J = 9.2, 6.1 Hz, 1H), 7.46 (t, J = 9.1 Hz, 1H), 7.39 (d, J = 2.4 Hz, 1H), 7.18 (s, 1H), 4.56 (br dd, J = 10.7, 4.1 Hz, 1H), 4.25-4.07 (m, 5H), 3.99-3.93 (m, 3H), 3.78-3.66 (m, 3H), 3.61-3.54 (m, 1H), 3.41 (ddd, J = 12.8, 8.6, 5.2 Hz, 2H), 2.88-2.81 (m, 1H), 2.45-2.30 (m, 3H), 2.25-2.06 (m, 6H), |

TABLE 1-continued

| # | Structure | IUPAC | LCMS (M + H)+ | $^1$H NMR |
|---|---|---|---|---|
| | | | | 1.72-1.66 (m, 1H), 1.62-1.39 (m, 9H), 1.36-1.30 (m, 1H) |
| 1-219 | 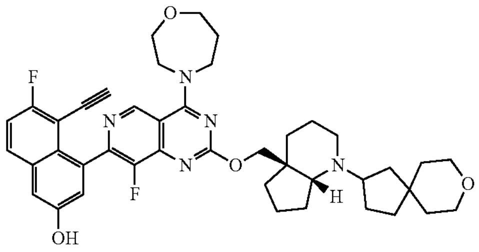 Diastereomer Mixture | 4-(2-{[(4aS,7aR)-1-{8-oxaspiro[4.5]decan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 724.1 | |
| 1-220[J] | 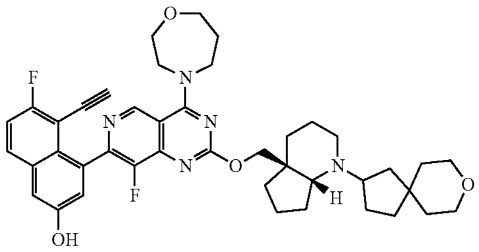 Diastereomer 1 | 4-(2-{[(4aS,7aR)-1-{8-oxaspiro[4.5]decan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 724.1 | $^1$H NMR (500 MHz, DMSO-$d_6$) δ 9.10 (s, 1H), 8.01-7.94 (m, 2H), 7.47 (t, J = 9.0 Hz, 1H), 7.40 (d, J = 2.4 Hz, 1H), 7.17 (t, J = 2.5 Hz, 1H), 4.62-4.53 (m, 1H), 4.37-4.23 (m, 1H), 4.19-4.07 (m, 4H), 4.02-3.87 (m, 5H), 3.76 (br t, J = 5.1 Hz, 2H), 3.55-3.46 (m, 4H), 2.34-2.25 (m, 1H), 2.14-2.04 (m, 2H), 1.83-1.75 (m, 2H), 1.69-1.22 (m, 18H) |
| 1-221[J] | 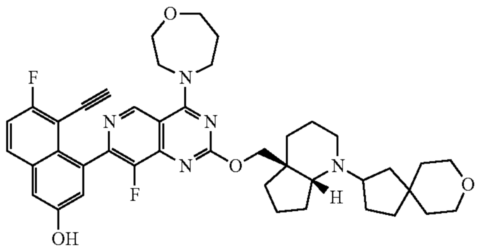 Diastereomer 2 | 4-(2-{[(4aS,7aR)-1-{8-oxaspiro[4.5]decan-2-yl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 724.1 | |
| 1-224 | 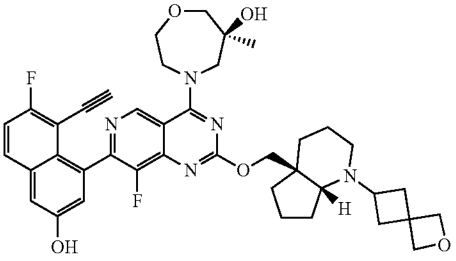 [SMILES: C#Cc1c(F)ccc2cc(O)cc(-c3ncc4c(N5CCOC[C@@](C)(O)C5)nc(OC[C@]56CCC[C@H]5N(C5CC7(COC7)C5)CCC6)nc4c3F)c12] | (6S)-4-(2-{[(4aS,7aR)-1-{2-oxaspiro[3.3]heptan-6-yl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol | 712.2 | $^1$H NMR (500 MHz, DMSO-$d_6$) δ 9.65-9.06 (m, 1H), 7.97 (dd, J = 9.0, 5.9 Hz, 1H), 7.46 (t, J = 9.0 Hz, 1H), 7.40 (d, J = 2.4 Hz, 1H), 7.21 (br d, J = 2.4 Hz, 1H), 4.66-4.49 (m, 3H), 4.46-4.27 (m, 3H), 4.25-3.11 (m, 13H), 3.00-2.93 (m, 1H), 2.77-2.65 (m, 1H), 2.45-2.36 (m, 1H), 2.32-2.18 (m, 2H), 2.15-2.02 (m, 1H), 1.89-1.74 (m, 3H), 1.74-1.22 (m, 10H), 1.21-1.11 (m, 3H) |

TABLE 1-continued

| # | Structure | IUPAC | LCMS (M + H)$^+$ | $^1$H NMR |
|---|---|---|---|---|
| 1-225 | 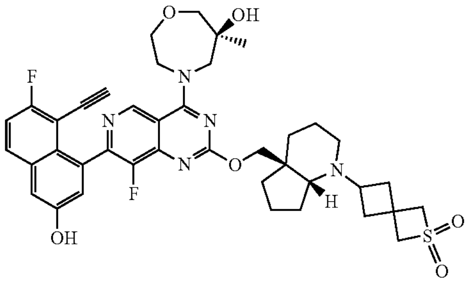 [SMILES: C#Cc1c(F)ccc2cc(O)cc(-c3ncc4c(N5CCOC[C@@](C)(O)C5)nc(OC[C@]56CCC[C@H]5N(C5CC7(C5)CS(=O)(=O)C7)CCC6)nc4c3F)c12] | 6-[(4aS,7aR)-4a-({[7-(8-ethynyl-7-fluoro-3-hydroxynaphthalen-1-yl)-8-fluoro-4-[(6S)-6-hydroxy-6-methyl-1,4-oxazepan-4-yl]pyrido[4,3-d]pyrimidin-2-yl]oxy}-methyl)-octahydro-1H-cyclopenta[b]pyridin-1-yl]-2¿6-thiaspiro[3.3]heptane-2,2-dione | 760.4 | $^1$H NMR (500 MHz, DMSO-$d_6$) δ 9.53-9.24 (m, 1H), 7.97 (br dd, J = 8.9, 6.0 Hz, 1H), 7.46 (t, J = 8.9 Hz, 1H), 7.40 (s, 1H), 7.21 (s, 1H), 5.59-5.01 (m, 1H), 4.66-4.54 (m, 1H), 4.49-4.28 (m, 2H), 4.24-3.15 (m, 10H), 3.06-2.92 (m, 1H), 2.49-2.42 (m, 1H), 2.42-2.27 (m, 2H), 2.27-2.14 (m, 1H), 2.14-1.96 (m, 2H), 1.88-1.25 (m, 13H), 1.21-1.14 (m, 3H) |
| 1-226 | 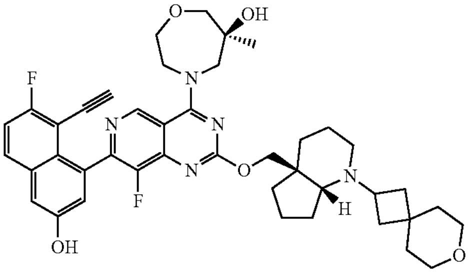 [SMILES: C#Cc1c(F)ccc2cc(O)cc(-c3ncc4c(N5CCOC[C@@](C)(O)C5)nc(OC[C@]56CCC[C@H]5N(C5CC7(CCOCC7)C5)CCC6)nc4c3F)c12] | (6S)-4-(2-{[(4aS,7aR)-1-{7-oxaspiro[3.5]nonan-2-yl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol | 740.1 | $^1$H NMR (500 MHz, DMSO-$d_6$) δ 10.10 (s, 1H), 9.48-9.26 (m, 1H), 7.98 (dd, J = 9.2, 6.0 Hz, 1H), 7.47 (t, J = 9.0 Hz, 1H), 7.40 (d, J = 2.4 Hz, 1H), 7.20 (dd, J = 10.1, 2.3 Hz, 1H), 5.28-5.02 (m, 1H), 4.61 (br d, J = 11.3 Hz, 1H), 4.47-4.29 (m, 2H), 4.29-4.15 (m, 2H), 4.15-3.94 (m, 4H), 3.94-3.79 (m, 2H), 3.65-3.29 (m, 4H), 3.10-2.84 (m, 2H), 2.25-2.05 (m, 1H), 2.05-1.81 (m, 4H), 1.77-1.27 (m, 17H), 1.17 (d, J = 10.5 Hz, 3H) |
| 1-227 | 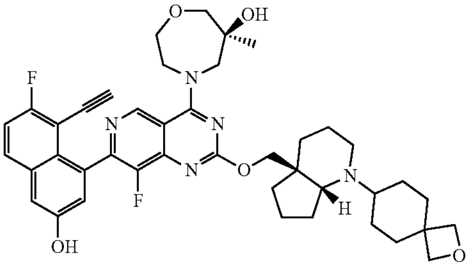 [SMILES: C#Cc1c(F)ccc2cc(O)cc(-c3ncc4c(N5CCOC[C@@](C)(O)C5)nc(OC[C@]56CCC[C@H]5N(C5CCC7(CC5)COC7)CCC6)nc4c3F)c12] | (6S)-4-(2-{[(4aS,7aR)-1-{2-oxaspiro[3.5]nonan-7-yl}-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol | 740.1 | $^1$H NMR (500 MHz, DMSO-$d_6$) δ 9.50-9.14 (m, 1H), 7.97 (br dd, J = 9.1, 6.1 Hz, 1H), 7.46 (br t, J = 9.0 Hz, 1H), 7.40 (d, J = 2.1 Hz, 1H), 7.20 (dd, J = 10.1, 2.2 Hz, 1H), 4.61-4.53 (m, 1H), 4.45-4.26 (m, 2H), 4.25-4.14 (m, 4H), 4.13-4.01 (m, 1H), 4.01-3.69 (m, 9H), 3.65-3.57 (m, 1H), 3.54-3.45 (m, 1H), 3.12-3.02 (m, 1H), 2.47-2.39 (m, 1H), 2.28-2.20 (m, 1H), 2.02-1.85 (m, 2H), 1.75-1.20 (m, 12H), 1.16 (br d, J = 11.3 Hz, 3H) |

TABLE 1-continued

| # | Structure | IUPAC | LCMS $(M + H)^+$ | $^1H$ NMR |
|---|---|---|---|---|
| 1-268 | 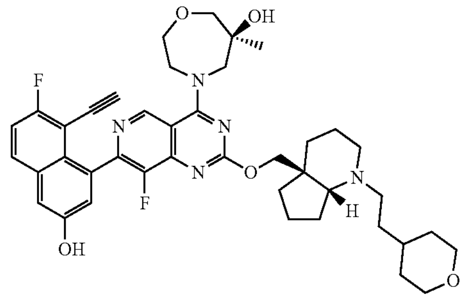 [SMILES: C#Cc1c(F)ccc2cc(O)cc(-c3ncc4c(N5CCOC[C@@](C)(O)C5)nc(OC[C@]56CCC[C@H]5N(CCC5CCOCC5)CCC6)nc4c3F)c12] | (6S)-4-(2-{[(4aS,7aR)-1-[2-(oxan-4-yl)ethyl]-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol | 728.1 | $^1H$ NMR (500 MHz, DMSO-$d_6$) δ 10.25-10.12 (m, 1H), 9.60-9.18 (m, 1H), 8.21-7.77 (m, 1H), 7.56-7.44 (m, 1H), 7.40 (d, J = 2.1 Hz, 1H), 7.20 (dd, J = 13.3, 1.9 Hz, 1H), 5.31-5.02 (m, 1H), 4.52 (br d, J = 10.4 Hz, 1H), 4.42 (br d, J = 14.3 Hz, 1H), 4.34 (br dd, J = 13.4, 3.5 Hz, 1H), 4.28-4.21 (m, 1H), 4.19-4.13 (m, 1H), 4.12-4.01 (m, 2H), 4.01-3.94 (m, 2H), 3.94-3.81 (m, 2H), 3.78-3.66 (m, 2H), 3.64-3.57 (m, 2H), 3.56-3.49 (m, 1H), 3.20-3.05 (m, 2H), 3.02-2.91 (m, 1H), 2.46-2.29 (m, 4H), 1.89-1.79 (m, 1H), 1.77-1.67 (m, 1H), 1.66-1.42 (m, 10H), 1.39-1.29 (m, 3H), 1.17 (br d, J = 10.4 Hz, 3H), 1.13-1.05 (m, 2H) |
| 1-322 | 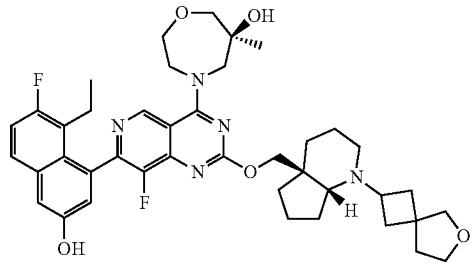 Diastereomer Mixture | (6S)-4-(2-{[(4aS,7aR)-1-{6-oxaspiro[3.4]octan-2-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol | 730.4 | |
| 1-323[P] | 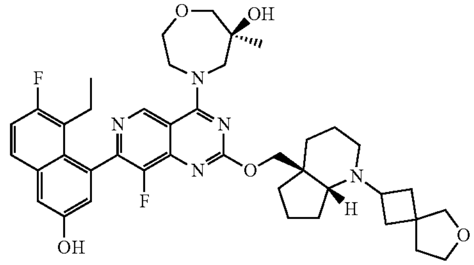 Diastereomer 1 | (6S)-4-(2-{[(4aS,7aR)-1-{6-oxaspiro[3.4]octan-2-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol | 730.4 | $^1H$ NMR (500 MHz, DMSO-$d_6$) δ 9.46 (s, 1H), 7.75 (dd, J = 9.0, 6.1 Hz, 1H), 7.39-7.30 (m, 2H), 7.08-6.96 (m, 1H), 4.70-4.52 (m, 1H), 4.42-3.73 (m, 7H), 3.63-3.46 (m, 2H), 3.08-2.92 (m, 1H), 2.87-2.74 (m, 1H), 2.49-2.31 (m, 2H), 2.20-1.93 (m, 4H), 1.89-1.19 (m, 16H), 1.16 (br d, J = 4.2 Hz, 3H), 0.73 (br t, J = 7.4 Hz, 3H) |

TABLE 1-continued

| # | Structure | IUPAC | LCMS (M + H)+ | $^1$H NMR |
|---|---|---|---|---|
| 1-324 | 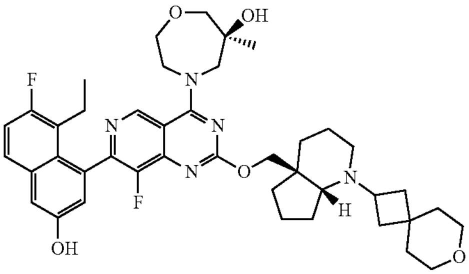 [SMILES: CCc1c(F)ccc2cc(O)cc(-c3ncc4c(N5CCOC[C@@](C)(O)C5)nc(OC[C@]56CCC[C@H]5N(C5CC7(CCOCC7)C5)CCC6)nc4c3F)c12] | (6S)-4-(2-{[(4aS,7aR)-1-{7-oxaspiro[3.5]nonan-2-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol | 744.2 | $^1$H NMR (500 MHz, DMSO-$d_6$) δ 9.45 (s, 1H), 7.76 (br dd, J = 8.8, 6.2 Hz, 1H), 7.45-7.24 (m, 2H), 7.02 (br d, J = 15.9 Hz, 1H), 4.71-4.48 (m, 1H), 4.47-4.26 (m, 2H), 4.25-4.11 (m, 1H), 4.10-3.81 (m, 3H), 3.63-3.43 (m, 1H), 3.41-3.28 (m, 1H), 3.00 (br d, J = 8.1 Hz, 1H), 2.95-2.81 (m, 1H), 2.51 (br d, J = 1.6 Hz, 6H), 2.49-2.40 (m, 1H), 2.39-2.30 (m, 1H), 2.22-2.05 (m, 2H), 1.98-1.76 (m, 3H), 1.72-1.23 (m, 14H), 1.16 (br d, J = 4.8 Hz, 3H), 0.73 (br t, J = 7.1 Hz, 3H) |
| 1-326 | 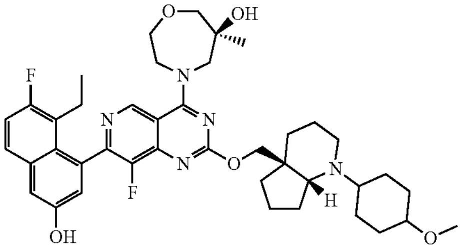 Diastereomer Mixture | (6S)-4-(2-{[(4aS,7aR)-1-(4-methoxycyclohexyl)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol | 732.3 | |
| 1-327[AJ] | 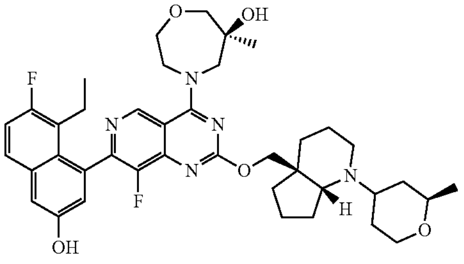 Diastereomer 1 | (6S)-4-(2-{[(4aS,7aR)-1-[(2R)-2-methyloxan-4-yl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol | 718.4 | $^1$H NMR (500 MHz, DMSO-$d_6$) δ 9.45 (s, 1H), 7.75 (dd, J = 9.1, 5.9 Hz, 1H), 7.47-7.24 (m, 2H), 7.02 (br d, J = 19.6 Hz, 1H), 5.23-5.04 (m, 1H), 4.60 (br dd, J = 10.9, 3.3 Hz, 1H), 4.42-4.23 (m, 3H), 4.22-4.09 (m, 1H), 3.85-3.78 (m, 1H), 3.63-3.53 (m, 3H), 3.28 (br d, J = 11.1 Hz, 3H), 3.11 (br s, 1H), 2.65-2.55 (m, 1H), 2.44-2.26 (m, 1H), 2.24-2.01 (m, 1H), 2.01-1.83 (m, 1H), 1.81-1.65 (m, 3H), 1.65-1.38 (m, 8H), 1.38-1.20 (m, 2H), 1.19-1.09 (m, 3H), 1.09-1.00 (m, 3H), 1.00-0.87 (m, 1H), 0.73 (br t, J = 6.5 Hz, 3H) |

TABLE 1-continued

| # | Structure | IUPAC | LCMS (M + H)$^+$ | $^1$H NMR |
|---|---|---|---|---|
| 1-328 | 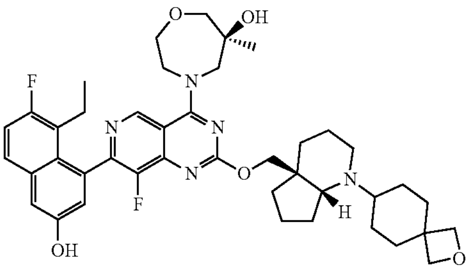 [SMILES: CCc1c(F)ccc2cc(O)cc(-c3ncc4c(N5CCOC[C@@](C)(O)C5)nc(OC[C@]56CCC[C@H]5N(C5CCC7(CC5)COC7)CCC6)nc4c3F)c12] | (6S)-4-(2-{[(4aS,7aR)-1-{2-oxaspiro[3.5]nonan-7-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol | 744.4 | $^1$H NMR (500 MHz, DMSO-$d_6$) δ 10.15-9.88 (m, 1H), 9.45 (s, 1H), 7.76 (br dd, J = 8.9, 6.0 Hz, 1H), 7.47-7.22 (m, 2H), 7.12-6.88 (m, 1H), 5.18 (br d, J = 18.0 Hz, 1H), 4.56 (br dd, J = 18.8, 10.5 Hz, 1H), 4.46-3.89 (m, 10H), 3.08 (br t, J = 8.0 Hz, 1H), 2.46-2.30 (m, 2H), 2.29-2.04 (m, 2H), 2.02-1.79 (m, 3H), 1.78-1.20 (m, 12H), 1.15 (br d, J = 6.2 Hz, 3H), 0.85-0.61 (m, 3H) |
| 1-329 | 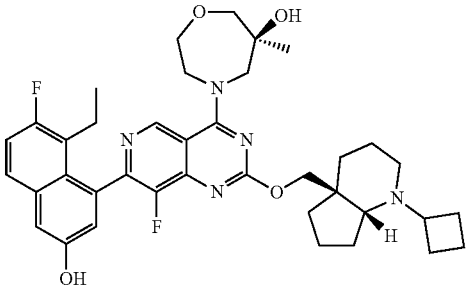 [SMILES: CCc1c(F)ccc2cc(O)cc(-c3ncc4c(N5CCOC[C@@](C)(O)C5)nc(OC[C@]56CCC[C@H]5N(C5CCC5)CCC6)nc4c3F)c12] | (6S)-4-(2-{[(4aS,7aR)-1-cyclobutyl-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol | 674.6 | $^1$H NMR (500 MHz, DMSO-$d_6$) δ 9.47 (s, 1H), 7.76 (br dd, J = 8.9, 5.8 Hz, 1H), 7.59-7.24 (m, 2H), 7.03 (br dd, J = 17.4, 1.9 Hz, 1H), 5.17 (br d, J = 16.9 Hz, 1H), 4.62 (br t, J = 10.0 Hz, 1H), 4.42-4.23 (m, 2H), 4.23-4.10 (m, 1H), 4.09-3.82 (m, 3H), 3.62-3.52 (m, 2H), 3.04-2.84 (m, 2H), 2.51 (br s, 4H), 2.48-2.30 (m, 2H), 2.22-2.07 (m, 2H), 1.97-1.49 (m, 9H), 1.48-1.34 (m, 2H), 1.28 (br d, J = 4.0 Hz, 1H), 1.16 (br d, J = 5.4 Hz, 2H), 0.74 (br t, J = 7.2 Hz, 2H) |
| 1-331[4K] | 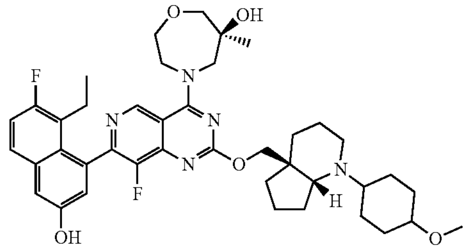 Diastereomer 2 | (6S)-4-(2-{[(4aS,7aR)-1-(4-methoxy-cyclohexyl)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol | 732.4 | $^1$H NMR (500 MHz, DMSO-$d_6$) δ 9.45 (s, 1H), 7.73 (dd, J = 8.7, 6.1 Hz, 1H), 7.43-7.25 (m, 2H), 7.05-7.05 (m, 1H), 7.08-6.99 (m, 1H), 4.60 (br t, J = 9.5 Hz, 1H), 4.44-3.75 (m, 8H), 3.73-3.63 (m, 1H), 3.61-3.54 (m, 1H), 3.20-3.16 (m, 2H), 3.12-2.95 (m, 2H), 2.48-2.44 (m, 1H), 2.42-2.25 (m, 2H), 2.22-2.03 (m, 1H), 1.92 (br s, 3H), 1.79-1.03 (m, 21H), 0.93-0.81 (m, 1H), 0.74 (br t, J = 7.1 Hz, 3H) |

TABLE 1-continued

| # | Structure | IUPAC | LCMS (M + H)+ | 1H NMR |
|---|---|---|---|---|
| 1-332[AL] | 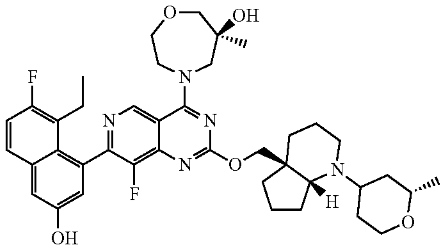 Diastereomer 2 | (6S)-4-(2-{[(4aS,7aR)-1-[(2S)-2-methyloxan-4-yl]-octa-hydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol | 718.4 | $^1$H NMR (500 MHz, DMSO-$d_6$) δ 9.47 (s, 1H), 7.74 (dd, J = 9.1, 6.1 Hz, 1H), 7.42-7.25 (m, 2H), 7.09-6.88 (m, 1H), 4.64-4.29 (m, 3H), 4.27-3.79 (m, 4H), 3.66 (br d, J = 1.6 Hz, 1H), 3.61-3.49 (m, 2H), 3.20-3.10 (m, 1H), 2.78-2.69 (m, 1H), 2.41-2.29 (m, 1H), 2.22-2.07 (m, 2H), 1.94-1.79 (m, 2H), 1.76-1.20 (m, 13H), 1.15 (d, J = 7.8 Hz, 3H), 0.90 (dd, J = 18.5, 6.2 Hz, 3H), 0.73 (br t, J = 7.4 Hz, 3H) |
| 1-333[AJ] | 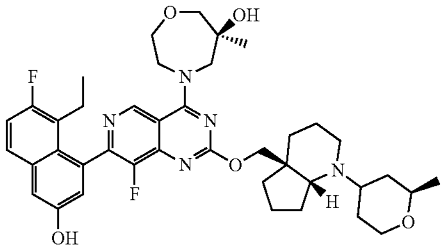 Diastereomer 2 | (6S)-4-(2-{[(4aS,7aR)-1-[(2R)-2-methyloxan-4-yl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol | 718.4 | $^1$H NMR (500 MHz, DMSO-$d_6$) δ 9.48 (s, 1H), 7.76 (dd, J = 9.0, 6.1 Hz, 1H), 7.49-7.27 (m, 2H), 7.04 (dd, J = 17.3, 2.3 Hz, 1H), 4.79-4.58 (m, 1H), 4.45-4.28 (m, 3H), 4.23 (br d, J = 15.0 Hz, 1H), 4.16-4.01 (m, 2H), 4.00-3.90 (m, 2H), 3.92-3.83 (m, 1H), 3.81-3.74 (m, 2H), 3.64-3.56 (m, 7H), 3.18 (br s, 3H), 2.79-2.71 (m, 2H), 2.61-2.55 (m, 1H), 2.43-2.28 (m, 2H), 2.26-2.13 (m, 2H), 1.86-1.77 (m, 3H), 1.75-1.68 (m, 1H), 1.67-1.37 (m, 9H), 1.37-1.20 (m, 3H), 1.16 (br d, J = 6.9 Hz, 3H), 1.01 (t, J = 5.9 Hz, 3H), 0.74 (br t, J = 7.1 Hz, 3H) |
| 1-334[AL] | 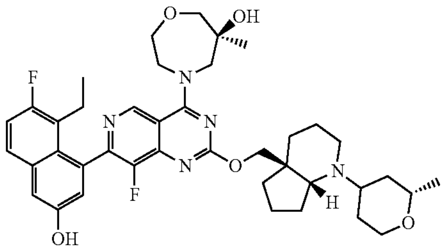 Diastereomer 1 | (6S)-4-(2-{[(4aS,7aR)-1-[(2S)-2-methyloxan-4-yl]-octa-hydro-1H-cyclopenta[b]pyridin-4a-yl]methoxy}-7-(8-ethyl-7-fluoro-3-hydroxynaphthalen-1-yl)-8-fluoropyrido | 718.4 | $^1$H NMR (500 MHz, DMSO-$d_6$) δ 9.46 (s, 1H), 7.76 (dd, J = 9.0, 6.0 Hz, 1H), 7.44-7.24 (m, 2H), 7.03 (dd, J = 18.0, 2.5 Hz, 1H), 5.15 (br dd, J = 4.5, 2.4 Hz, 1H), 4.61 (dd, J = 10.6, 3.4 Hz, 1H), 4.41-4.23 (m, 3H), 4.22-4.10 (m, 1H), 4.09-3.77 (m, 5H), 3.59-3.54 (m, |

TABLE 1-continued

| # | Structure | IUPAC | LCMS (M + H)$^+$ | $^1$H NMR |
|---|---|---|---|---|
| | | [4,3-d]pyrimidin-4-yl)-6-methyl-1,4-oxazepan-6-ol | | 3H), 3.25 (br s, 2H), 3.15-3.08 (m, 2H), 2.49-2.40 (m, 2H), 2.39-2.31 (m, 1H), 2.23-2.06 (m, 1H), 1.96-1.84 (m, 1H), 1.77-1.37 (m, 12H), 1.36-1.28 (m, 1H), 1.27-1.19 (m, 1H), 1.16 (br d, J = 6.5 Hz, 3H), 1.07-1.02 (m, 4H), 0.74 (br t, J = 6.5 Hz, 3H) |

Preparation of Intermediate 30: tert-butyl 6-methylene-1,4-oxazepane-4-carboxylate

30

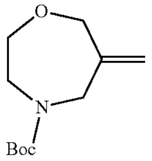

The intermediate tert-butyl 6-methylene-1,4-oxazepane-4-carboxylate was synthesized according to the literature procedure: Bioorg. Med. Chem. Lett. 2019, 29, 2405-2409.

Preparation of Intermediate 31: tert-butyl 6-oxo-1,4-oxazepane-4-carboxylate

31

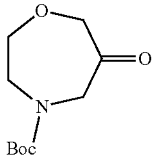

To a stirred solution of tert-butyl 6-methylene-1,4-oxazepane-4-carboxylate (6 g, 28.1 mmol) in THF (40 mL) and water (40 mL) was added sodium metaperiodate (12.03 g, 56.3 mmol) followed by an osmium tetroxide solution in tert-butanol (2 mL, 0.141 mmol) at 0° C. The reaction mixture was stirred at room temperature for 16 hours. Then, the reaction mixture was concentrated to afford the crude product. The mixture was extracted with EtOAc (60 mL×3). The combined extracts were washed with brine, dried over anhydrous $Na_2SO_4$, filtered, and concentrated under reduced pressure to afford a crude residue, which was purified by COMBIFLASH™ chromatography (Teledyne ISO, Lincoln, NE) (pet. ether/EtOAc=30%) to afford the title compound tert-butyl 6-oxo-1,4-oxazepane-4-carboxylate (2 g, 9.29 mmol, 33.0% yield) as a colorless liquid. $^1$H NMR (300 MHz, $CDCl_3$) δ ppm=4.02-4.17 (m, 4H), 3.91 (br d, J=3.78 Hz, 2H), 3.70 (br s, 2H) 1.45 (br s, 9H).

Preparation of Intermediate 32a and 32b: tert-butyl (S)-6-hydroxy-6-methyl-1,4-oxazepane-4-carboxylate and tert-butyl (R)-6-hydroxy-6-methyl-1,4-oxazepane-4-carboxylate Isomer-1 (32a)

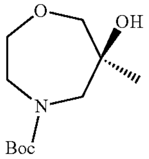

and

Isomer-2 (32b)

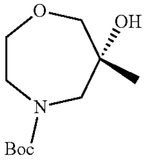

To a stirred solution of tert-butyl 6-oxo-1,4-oxazepane-4-carboxylate (2.5 g, 11.61 mmol) in THF (150 mL), was added methylmagnesium chloride solution in THF (46.5 mL, 46.5 mmol) drop wise at 0° C. The reaction mixture was stirred for 2 h. The reaction mixture was then quenched with saturated $NH_4Cl$ solution and extracted with ethyl acetate (100 mL). The combined organic layers were dried over anhydrous $Na_2SO_4$, filtered, and concentrated under reduced pressure to afford the product. The racemic compound was purified by SFC chiral separation to afford Isomer-1: tert-butyl (S)-6-hydroxy-6-methyl-1,4-oxazepane-4-carboxylate (1 g, 4.32 mmol, 37.2% yield) and Isomer-2: tert-butyl (R)-6-hydroxy-6-methyl-1,4-oxazepane-4-carboxylate (1 g, 4.32 mmol, 37.2% yield). [Method; Column/dimensions: CHIRALPAK™ IG (Daicel, Japan) (250×50) mm, 5 μm, % CO2: 60% Co solvent: 40% OF 4M Methanolic ammonia in MeOH, Total Flow: 280.0 g/min, Back Pressure: 100 bar, Temperature: 40° C., UV: 205 nm, Retention time=4.15 min (isomer-1) & retention time=6.01 min (isomer-2)].

Isomer-1: $^1$H NMR (400 MHz, DMSO-$d_6$) δ ppm=4.60-4.66 (m, 1H), 3.48-3.73 (m, 3H), 3.35-3.44 (m, 2H), 3.04-3.20 (m, 3H), 1.41 (s, 9H), 1.02-1.15 (m, 3H).

Isomer-2: $^1$H NMR (400 MHz, DMSO-$d_6$) δ ppm=4.57-4.73 (m, 1H), 3.49-3.77 (m, 3H), 3.35-3.48 (m, 2H), 3.06-3.25 (m, 3H), 1.41 (s, 9H), 1.07-1.08 (m, 3H).

Preparation of Intermediate 33a and 33b: (S)-6-methyl-1,4-oxazepan-6-ol hydrochloride and (R)-6-methyl-1,4-oxazepan-6-ol hydrochloride Isomer-1 (33a)

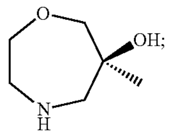

and

Isomer-2 (33b)

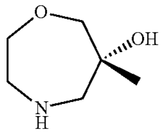

To a stirred solution of tert-butyl (S)-6-hydroxy-6-methyl-1,4-oxazepane-4-carboxylate [Intermediate 32a (isomer-1), 1 g, 4.32 mmol] in acetonitrile (10 mL) was added HCl (4M in dioxane) (5.40 mL, 21.62 mmol). The resulting reaction mixture was stirred at 0° C. for 2 h. The reaction mixture was concentrated and co-evaporated with toluene (two times) to afford (S)-6-methyl-1,4-oxazepan-6-ol hydrochloride (550 mg, 3.28 mmol, 76% yield) as white solid. MS (ESI) m/z: 132.1 $[M+H]^+$.

To a stirred solution of tert-butyl (R)-6-hydroxy-6-methyl-1,4-oxazepane-4-carboxylate [Intermediate 32b (isomer-2), 1 g, 4.32 mmol] in acetonitrile (10 mL) was added HCl (4M in dioxane) (5.40 mL, 21.62 mmol). The resulting reaction mixture was stirred at 0° C. for 2 h. The reaction mixture was concentrated and co-evaporated with toluene (two times) to afford (R)-6-methyl-1,4-oxazepan-6-ol hydrochloride (550 mg, 3.28 mmol, 76% yield). MS (ESI) m/z: 132.2 $[M+H]^+$.

Preparation of Intermediate 43: 1-(tert-butyl) 3-methyl 5-oxopiperidine-1,3-dicarboxylate

43

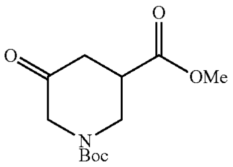

To a stirred solution of 1-(tert-butyl) 3-methyl 5-hydroxypiperidine-1,3-dicarboxylate (5 g, 19.28 mmol) in DCM (60 mL) under an argon atmosphere at 0° C., was added Dess-Martin periodinane (8.18 g, 19.28 mmol). The reaction mixture was gradually warmed to room temperature over a period of 2 hours. Then, the reaction mixture was quenched with aqueous saturated $Na_2S_2O_3$ solution followed by $NaHCO_3$ solution. The reaction mixture was extracted with DCM and the combined organic layers were washed with brine, dried over $Na_2SO_4$, filtered, concentrated under reduced pressure to afford a crude residue, which was purified through silica gel column chromatography using COMBIFLASH™ chromatography (Teledyne ISO, Lincoln, NE) (15% Solvent-solvent, 40 g RediSep® silica gel column; silica gel column) to afford 1-(tert-butyl) 3-methyl 5-oxopiperidine-1,3-dicarboxylate (3.9 g, 15.16 mmol, 79% yield). $^1H$ NMR (300 MHz, chloroform-d) δ ppm=3.95 (s, 2H), 3.85-3.72 (m, 2H), 3.60 (s, 3H), 3.12-2.91 (m, 1H), 2.80-2.48 (m, 2H), 1.46-1.29 (m, 9H).

Preparation of Intermediate 44: 1-(tert-butyl) 3-methyl 5,5-difluoropiperidine-1,3-dicarboxylate

44

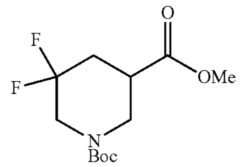

To a stirred solution of 1-(tert-butyl) 3-methyl 5-oxopiperidine-1,3-dicarboxylate (1 g, 3.89 mmol) in DCM (20 mL) at −78° C., was added DAST (1.027 mL, 7.77 mmol) and the reaction mixture was gradually warm to room temperature over a period of 3 hours. The reaction mixture was quenched with aqueous sat. $NaHCO_3$ solution, extracted with DCM, washed with brine, dried with anhydrous $Na_2SO_4$, filtered and concentrated under reduced pressure to afford a crude residue, which was purified by silica gel chromatography using COMBIFLASH™ chromatography (Teledyne ISO, Lincoln, NE) (15% EtOAc-Hexane, 24 g RediSep® silica gel column; evaporative light scatting detection (ELSD) purification). The fractions containing product were concentrated to afford 1-(tert-butyl) 3-methyl 5,5-difluoropiperidine-1,3-dicarboxylate (750 mg, 2.69 mmol, 69.1% yield). $^1H$ NMR (300 MHz, chloroform-d) δ ppm=4.57-4.12 (m, 2H), 3.72 (s, 3H), 3.09-2.66 (m, 3H), 2.60-2.39 (m, 1H), 2.15-1.83 (m, 1H), 1.47 (s, 9H).

Preparation of Intermediate 45a and 45b: tert-butyl 3,3-difluoro-5-(hydroxymethyl)piperidine-1-carboxylate 45a & 45b

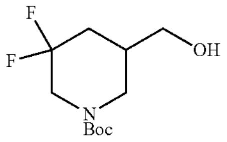

To a stirred solution of 1-(tert-butyl) 3-methyl 5,5-difluoropiperidine-1,3-dicarboxylate (500 mg, 1.790 mmol) in tetrahydrofuran (10 mL) under an argon atmosphere at 0° C., was added 2M LAH in THF (0.716 mL, 1.432 mmol) solution. The reaction mixture was gradually warm to room temperature over a period of 2 hours. Then, the reaction mixture was quenched with aqueous saturated $Na_2SO_4$ solution. The reaction mixture was filtered through a CELITE™ (Sigma Aldrich, St. Louis, MO) pad, washed with EtOAc (50 mL) and the filtrate was concentrated under reduced pressure to afford a crude residue, which was purified by silica gel column chromatography using COMBIFLASH™ chromatography (Teledyne ISO, Lincoln, NE) (60% Solvent-solvent, 12 g RediSep® silica gel column, ELSD purification) to afford racemic tert-butyl 3,3-difluoro-5-(hydroxymethyl)piperidine-1-carboxylate as a colourless liquid. The racemic compound was purified by chiral SFC to afford tert-butyl 3,3-difluoro-5-(hydroxymethyl)piperidine-1-carboxylate, 45a (150 mg, 0.597 mmol, 33.3% yield) and tert-butyl 3,3-difluoro-5-(hydroxymethyl)piperidine-1-carboxylate, 45b (150 mg, 0.597 mmol, 33.3% yield) as a colourless liquid. SFC chiral separation method: Peak-1 (45a): retention time 6.3 min; Peak-2 (45b): retention time 7.7 min; Column/dimension: Chiralpak AD-H (250×4.6) mm, 5 μm; % $CO_2$: 90%; % Co solvent: 10% 0.2% ammonia in MeOH; Total Flow: 2.0 g/min; Back Pressure: 100 bar; Temperature: 35° C.; UV: 200 nm. Peak-1 (45a): $^1$H NMR (300 MHz, DMSO-$d_6$) δ ppm=4.69 (t, J=5.21 Hz, 1H), 4.21-3.82 (m, 2H), 3.41-3.32 (m, 1H), 3.30-3.21 (m, 1H), 3.20-3.05 (m, 1H), 2.73-2.51 (m, 1H), 2.15-1.99 (m, 1H), 1.85-1.55 (m, 2H), 1.40 (s, 9H). Peak-2 (45b): $^1$H NMR (300 MHz, DMSO-$d_6$) δ ppm=4.69 (t, J=5.39 Hz, 1H), 4.20-3.81 (m, 2H), 3.43-3.32 (m, 1H), 3.30-3.21 (m, 1H), 3.20-3.05 (m, 1H), 2.73-2.51 (m, 1H), 2.15-1.99 (m, 1H), 1.86-1.52 (m, 2H), 1.40 (s, 9H).

Preparation of Intermediate 46a: (5,5-difluoropiperidin-3-yl)methanol hydrochloride 46a

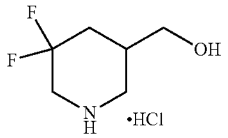

To an ice cooled solution of tert-butyl 3,3-difluoro-5-(hydroxymethyl)piperidine-1-carboxylate (Intermediate 45a, 60 mg, 0.239 mmol) in ethyl acetate (0.5 mL) under an argon atmosphere at room temperature, was added 4M HCl (0.725 mL, 23.88 mmol) in EtOAc and the mixture was stirred at room temperature for 2 hours. The solvent was evaporated under reduced pressure. The residue was further triturated with diethyl ether and dried to afford (5,5-difluoropiperidin-3-yl)methanol hydrochloride (35 mg, 0.232 mmol, 97% yield). $^1$H NMR (300 MHz, DMSO-$d_6$) δ ppm=11.02-8.01 (brs, 2H), 4.05-4.01 (m, 1H) 3.73-3.53 (m, 1H), 3.45-3.18 (m, 3H), 2.90-2.67 (m, 1H), 2.33-1.75 (m, 4H).

Example 2-7 was synthesized using this fragment.

Preparation of Intermediate 46b: (5,5-difluoropiperidin-3-yl)methanol hydrochloride 46b

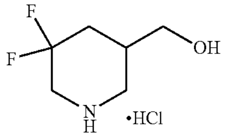

To an ice cooled solution of tert-butyl 3,3-difluoro-5-(hydroxymethyl)piperidine-1-carboxylate (Intermediate 45b, 60 mg, 0.239 mmol) in ethyl acetate under an argon atmosphere at room temperature, was added 4M HCl (7.25 μl, 0.239 mmol) in EtOAc and the mixture was stirred at room temperature for 2 hours. The solvent was evaporated under reduced pressure. The residue was further triturated with diethyl ether and dried to afford the (5,5-difluoropiperidin-3-yl)methanol hydrochloride (35 mg, 0.232 mmol, 97% yield). $^1$H NMR (300 MHz, DMSO-$d_6$) δ ppm=10.52-8.10 (brs, 2H), 4.05-4.01 (m, 1H) 3.71-3.58 (m, 1H), 3.50-3.34 (m, 3H), 3.31-3.16 (m, 1H), 2.84-2.68 (m, 1H), 2.39-1.78 (m, 4H).

Examples 2-7, and 2-8 were synthesized using this fragment.

Preparation of Intermediate 47a and 47b: 1-benzyl-3-ethylpiperidin-3-ol

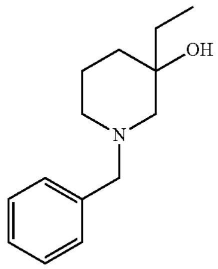

Peak-1; 47a
Peak-2; 47b

To a stirred solution of 1-benzylpiperidin-3-one (1 g, 5.28 mmol) in tetrahydrofuran (5 mL) at 0° C. under an argon atmosphere, was added ethyl magnesium bromide solution (42.3 mL, 21.14 mmol) in diethyl ether. The reaction mixture was stirred at 0° C. for 1 hour. The reaction mixture was quenched with $NH_4Cl$ solution and extracted with ethyl acetate. The organic layer was washed with brine, dried over anhydrous sodium sulfate, filtered and concentrated under reduced pressure to afford the crude racemic 1-benzyl-3-ethylpiperidin-3-ol (900 mg, 4.10 mmol, 78% yield). The racemic compound was purified by chiral super critical fluid chromatography (SFC) to afford Peak-1 (47a) 1-benzyl-3-ethylpiperidin-3-ol (375 mg, 1.710 mmol, 32.4% yield) and Peak-2 (47b) 1-benzyl-3-ethylpiperidin-3-ol (395 mg, 1.801 mmol, 34.1% yield). SFC chiral separation method: Peak-1 retention time: 3.41 min; Peak-2: retention time 4.98 min; Column/dimension: Chiralpak AD-H (250×50) mm, 5 μm; % $CO_2$: 85%; % Co-solvent: 15% of 0.2% ammonia in MeOH; Total Flow: 280.0 g/min; Back Pressure: 100 bar; Temperature: 30° C.; UV: 220 nm. Peak-1 (47a): $^1$H NMR (400 MHz, chloroform-d) δ ppm=7.43-7.22 (m, 5H), 3.63-3.54 (s, 2H), 3.41-3.24 (m, 1H), 2.87-2.67 (m, 2H), 2.47-2.31 (m, 2H), 2.21-2.06 (m, 1H), 1.99-1.87 (m, 1H), 1.87-1.74 (m, 1H), 1.70-1.45 (m, 5H) [exchangeable OH proton not appeared]. Peak-2 (47b): $^1$H NMR (400 MHz, chloroform-d) δ ppm=7.44-7.24 (m, 5H), 3.62-3.54 (s, 2H), 3.44-3.21 (m, 1H), 2.90-2.68 (m, 2H), 2.46-2.30 (m, 2H), 2.22-2.05 (m, 1H), 2.01-1.86 (m, 1H), 1.87-1.74 (m, 1H), 1.70-1.46 (m, 5H) [exchangeable OH proton not appeared].

Preparation of Intermediate 48a: 3-ethylpiperidin-3-ol

48a

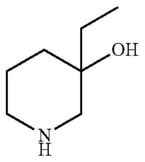

To a stirred solution of 1-benzyl-3-ethylpiperidin-3-ol (intermediate 47a, 375 mg, 1.710 mmol) in MeOH (4 mL) at room temperature under an argon atmosphere, was added Pd-C (184 mg, 1.733 mmol). The reaction mixture was purged with $H_2$, and the reaction mixture was stirred for 6 hours under $H_2$ bladder. The reaction mixture was filtered through a CELITE™ (Sigma Aldrich, St. Louis, MO) pad, and the filtrate was concentrated under reduced pressure to afford crude 3-ethylpiperidin-3-ol (195 mg, 1.512 mmol, 88% yield). MS (ESI) m/z: 130.2 $[M+H]^+$.

Examples 2-6 and 4-7 were synthesized using this fragment.

Preparation of Intermediate 48b: 3-ethylpiperidin-3-ol

48b

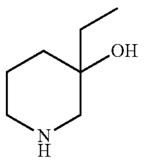

To a stirred solution of 1-benzyl-3-ethylpiperidin-3-ol (Intermediate 47b, 380 mg, 1.733 mmol) in MeOH (4 mL) at room temperature under an argon atmosphere, was added Pd-C (184 mg, 1.733 mmol). The reaction mixture was purged with $H_2$ and the reaction mixture was stirred for 6 hours under an $H_2$ balloon. The reaction mixture was filtered through a CELITE™ (Sigma Aldrich, St. Louis, MO) bed, and the filtrate was concentrated under reduced pressure to afford crude 3-ethylpiperidin-3-ol (200 mg, 1.548 mmol, 89% yield). MS (ESI) m/z: 130.2 $[M+H]^+$.

Examples 2-5 and 4-8 were synthesized using this fragment.

Preparation of Intermediate 49a: ethyl (4aS,7aR)-1-methyl-2-oxooctahydro-4aH-cyclopenta[b]pyridine-4a-carboxylate 49a

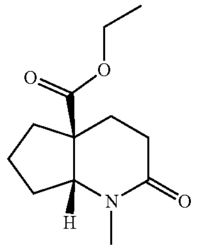

To a stirred suspension of NaH (3.79 g, 95 mmol) in THF (100 mL) at 0° C., was added ethyl (4aS,7aR)-2-oxooctahydro-4aH-cyclopenta[b]pyridine-4a-carboxylate (10 g, 47.3 mmol) and the reaction mixture was stirred for 30 min. Then, Mel (3.85 mL, 61.5 mmol) was added and the mixture was gradually warm to room temperature over a period of 2 hours. The reaction mixture was then quenched with ice cold water, extracted with ethyl acetate. The organic layer was washed with brine, dried over anhydrous $Na_2SO_4$, filtered and concentrated under reduced pressure to afford a crude residue, which was purified using COMBIFLASH™ chromatography (Teledyne ISO, Lincoln, NE) (using 30% ethyl acetate/petroleum ether) to provide ethyl (4aS,7aR)-1-methyl-2-oxooctahydro-4aH-cyclopenta[b]pyridine-4a-carboxylate (7.5 g, 33.0 mmol, 69.6% yield). MS (ESI) m/z: 226.2 $[M+H]^+$. $^1H$ NMR (400 MHz, $CDCl_3$) δ ppm=4.25 (q, J=4.0 Hz, 2H), 4.09 (t, J=8.0 Hz, 1H), 2.95 (s, 3H), 2.45-2.35 (m, 3H), 2.25-2.08 (m, 2H), 1.92-1.56 (m, 5H), 1.27 (t, J=7.2 Hz, 3H).

Preparation of Intermediate 49b: ethyl (4aS,7aR)-1-methyl-3-(methylsulfanyl)-2-oxo-octahydro-1H-cyclopenta[b]pyridine-4a-carboxylate 49b

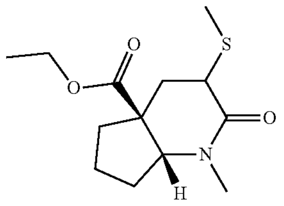

To a stirred solution of ethyl (4aS,7aR)-1-methyl-2-oxo-octahydro-1H-cyclopenta[b]pyridine-4a-carboxylate (800 mg, 3.55 mmol) in THF (20 mL) at −30° C. under an argon atmosphere, was added lithium diisopropylamide (LDA) (2 M in THF) (2.66 mL, 5.33 mmol), and the reaction mixture was stirred for 15 min. Then, a solution of S-methyl methanethiosulfonate (0.517 mL, 5.33 mmol) was added, and the resulting reaction mixture was gradually brought to room temperature over a period of 16 hours. The reaction mixture was quenched with saturated aqueous $NH_4Cl$ solution and extracted with EtOAc. The combined organic layers were washed with brine, dried over anhydrous $Na_2SO_4$, filtered and evaporated under reduced pressure to afford a crude residue, which was purified by silica gel column chromatography using COMBIFLASH™ chromatography (Teledyne ISO, Lincoln, NE) (40-60% EtOAc in petroleum ether, 40 g RediSep® column, ELSD purification). Fractions containing the desired product were evaporated to afford ethyl (4aS,7aR)-1-methyl-3-(methylsulfanyl)-2-oxo-octahydro-1H-cyclopenta[b]pyridine-4a-carboxylate (400 mg, 1.474 mmol, 41.5% yield) as a major isomer and ethyl (4aS,7aR)-1-methyl-3-(methylsulfanyl)-2-oxo-octahydro-1H-cyclopenta[b]pyridine-4a-carboxylate (180 mg, 0.663 mmol, ~9% yield; 50% purity) as a minor isomer. Major isomer: MS (ESI) m/z: 272.2 $[M+H]^+$ $^1H$ NMR (300 MHz, chloroform-d) 8 ppm=4.29-4.13 (m, 2H), 4.09-4.00 (m, 1H), 3.33 (dd, J=12.4, 5.9 Hz, 1H), 3.02-2.94 (m, 3H), 2.58-2.52 (m, 1H), 2.42-2.26 (m, 3H), 2.15-1.59 (m, 6H), 1.33-1.22 (m, 4H).

Preparation of Intermediate 50: ethyl (4aS,7aR)-3-methanesulfonyl-1-methyl-2-oxo-octahydro-1H-cyclopenta[b]pyridine-4a-carboxylate

50

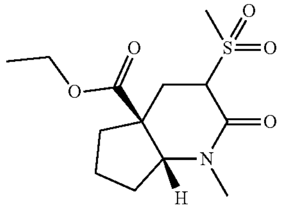

To a stirred solution of ethyl (4aS,7aR)-1-methyl-3-(methylsulfanyl)-2-oxo-octahydro-1H-cyclopenta[b]pyridine-4a-carboxylate (major isomer 49b, 10.0 g, 17.84 mmol) in MeOH (5 mL)-water (5 mL) under an argon atmosphere, was added OXONE™ (Sigma Aldrich, St. Louis, MO) (1.99 g, 3.24 mmol) and the reaction mixture was stirred at room temperature for 2 hours. Then, volatiles were removed under reduced pressure and the crude residue was dissolved in EtOAc. The organic layer was washed with water, brine, dried over anhydrous $Na_2SO_4$ filtered and concentrated under reduced pressure to afford crude ethyl (4aS,7aR)-3-methanesulfonyl-1-methyl-2-oxo-octahydro-1H-cyclopenta[b]pyridine-4a-carboxylate (400 mg, 1.319 mmol, 81% yield). MS (ESI) m/z: 304.2 $(M+H)^+$; $^1H$ NMR (300 MHz, chloroform-d) δ ppm=4.26-4.16 (m, 2H), 4.06-3.89 (m, 2H), 3.36 (s, 3H), 2.99 (s, 3H), 2.72-2.66 (m, 1H), 2.42-2.26 (m, 2H), 2.20-2.07 (m, 1H), 2.04-1.70 (m, 4H), 1.27 (t, J=7.2 Hz, 3H).

Preparation of Intermediate 51: [(4aS,7aR)-3-methanesulfonyl-1-methyl-octahydro-1H-cyclopenta[b]pyridin-4a-yl]methanol

51

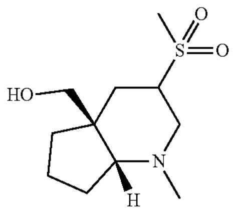

To a stirred solution of ethyl (4aS,7aR)-3-methanesulfonyl-1-methyl-2-oxo-octahydro-1H-cyclopenta[b]pyridine-4a-carboxylate (260 mg, 0.857 mmol) in THF (5 mL) at 0° C. under an argon atmosphere, was added 1M diisobutylaluminum hydride (DIBAL-H) in THF (8.57 mL, 8.57 mmol) and the mixture was stirred for an additional 4 hours. The reaction mixture was quenched with saturated sodium potassium tartrate solution and extracted with EtOAC. The organic layer was washed with brine, dried over anhydrous sodium sulfate, filtered and evaporated to afford the crude residue, which was purified by silica gel column chromatography using COMBIFLASH™ chromatography (Teledyne ISO, Lincoln, NE) (40-60% EtOAc in petroleum Ether, 12 g RediSep® column, ELSD purification). Fractions containing the desired product were evaporated to afford [(4aS,7aR)-3-methanesulfonyl-1-methyl-octahydro-1H-cyclopenta[b]pyridin-4a-yl]methanol (60 mg, 0.243 mmol, 28.3% yield). MS (ESI) m/z: 248.2 $[M+H]^+$; $^1H$ NMR (300 MHz, chloroform-d) δ ppm=3.83-3.67 (m, 1H), 3.64 (s, 2H), 3.02-2.82 (m, 2H), 2.82-2.78 (m, 3H), 2.69-2.59 (m, 1H), 2.31 (s, 3H), 1.95-1.54 (m, 7H), 1.42-1.32 (m, 2H).

Example 2-4 was synthesized using this fragment.

Preparation of Intermediate 52a & 52b: ethyl (3S,4aS,7aR)-3-fluoro-1-methyl-2-oxooctahydro-4aH-cyclopenta[b]pyridine-4a-carboxylate & ethyl (3R,4aS,7aR)-3-fluoro-1-methyl-2-oxooctahydro-4aH-cyclopenta[b]pyridine-4a-carboxylate 52a

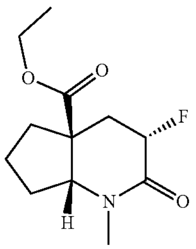

and

52b

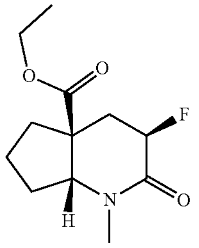

To a stirred solution of ethyl (4aS,7aR)-1-methyl-2-oxooctahydro-4aH-cyclopenta[b]pyridine-4a-carboxylate (5 g, 22.19 mmol) in tetrahydrofuran (50 ml) at −78° C. under an argon atmosphere, was added LDA (16.65 ml, 33.3 mmol). The reaction mixture was stirred at −76° C. for 60 min. Then, a solution of N-fluorobenzenesulfonimide (8.40 g, 26.6 mmol) in tetrahydrofuran (50 mL) was added to the reaction mixture and it was slowly warm to 0° C. over a period of 2 hours. The reaction mixture was quenched with ice water and extracted with ethyl acetate. The organic layer was washed with brine, dried over anhydrous sodium sulfate, filtered and evaporated under reduced pressure to afford a crude product, which was purified by silica gel column chromatography using a CombiFlash instrument (25% Ethyl Acetate/Hexane, 120 g RediSep® column, ELSD purification) to afford the major isomer ethyl (3S,4aS,7aR)-3-fluoro-1-methyl-2-oxooctahydro-4aH-cyclopenta[b]pyridine-4a-carboxylate, Intermediate 52a (1.25 g, 5.14 mmol, 23.15% yield) and the minor isomer ethyl (3R,4aS,7aR)-3-fluoro-1-methyl-2-oxooctahydro-4aH-cyclopenta[b]pyridine-4a-carboxylate, Intermediate 52b (500 mg, 2.055 mmol, 9.26% yield). Major isomer: $^1$H-NMR (300 MHz, CHLOROFORM-d) δ ppm=4.90-4.74 (m, 1H), 4.30-4.18 (m, 2H), 4.08 (t, J=8.4 Hz, 1H), 2.97 (s, 3H), 2.72-2.63 (m, 1H), 2.40-2.28 (m, 1H), 2.23-2.05 (m, 2H), 1.98-1.54 (m, 5H), 1.25 (t, J=6.0 Hz, 3H). Minor isomer: $^1$H NMR (300 MHz, CHLOROFORM-d) δ ppm=4.92-4.67 (m, 1H), 4.29-4.08 (m, 3H), 3.06-2.97 (s, 3H), 2.59-2.40 (m, 1H), 2.38-2.10 (m, 2H), 1.95-1.68 (m, 2H), 1.67-1.40 (m, 3H), 1.36-1.16 (m, 3H).

Preparation of Intermediate 53a: ((3S,4aS,7aR)-3-fluoro-1-methyloctahydro-4aH-cyclopenta[b]pyridin-4a-yl)methanol 53a

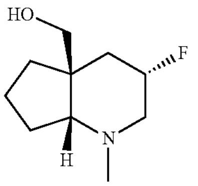

To a stirred solution ethyl (3S,4aS,7aR)-3-fluoro-1-methyl-2-oxooctahydro-4aH-cyclopenta[b]pyridine-4a-carboxylate (3 g, 12.33 mmol) in tetrahydrofuran (60 mL) at 0° C. under an argon atmosphere, was added DIBAL-H (61.7 ml, 61.7 mmol) and the mixture was stirred for 2 hours. The reaction mixture was then quenched with saturated aqueous potassium sodium tartarate solution and stirred at room temperature for 1 hour. The organic layer was washed with brine, dried over anhydrous sodium sulfate, filtered, and concentrated under reduced pressure to afford the crude ((3S,4aS,7aR)-3-fluoro-1-methyloctahydro-4aH-cyclopenta[b]pyridin-4a-yl)methanol (1.8 g, 9.61 mmol, 78% yield), which progressed to the next step without further purification. $^1$H NMR (300 MHz, chloroform-d) δ ppm=5.5-5.0 (m, 1H), 3.60-3.40 (m, 2H), 3.00-2.85 (m, 1H), 2.85-2.71 (m, 1H), 2.34 (s, 3H), 2.04-1.76 (m, 3H), 1.74-1.51 (m, 4H), 1.49-1.30 (m, 2H).

Preparation of Intermediate 53b: ((3R,4aS,7aR)-3-fluoro-1-methyloctahydro-4aH-cyclopenta[b]pyridin-4a-yl)methanol 53b

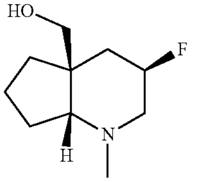

To a stirred solution of ethyl (3R,4aS,7aR)-3-fluoro-1-methyl-2-oxooctahydro-4aH-cyclopenta[b]pyridine-4a-carboxylate (800 mg, 3.29 mmol) in THF (20 mL) at 0° C. under an argon atmosphere, was added lithium aluminum hydride (499 mg, 13.15 mmol) and heated at 75° C. for 4 hours. The reaction mixture was cooled to 0° C., quenched with water (1.2 mL), 10% NaOH (3 mL) and water (3 mL). Then, the reaction mass was stirred for an additional 10 min and filtered through a CELITE™ (Sigma Aldrich, St. Louis, MO) pad. The CELITE™ pad was washed with EtOAc and the filtrate was concentrated under reduced pressure to afford crude ((3R,4aS,7aR)-3-fluoro-1-methyloctahydro-4aH-cyclopenta[b]pyridin-4a-yl)methanol (400 mg, 2.136 mmol, 65.0% yield) as a colorless liquid. The crude material was taken to the next step without further purification. $^1$H NMR (300 MHz, chloroform-d) δ ppm=4.59-4.52 (m, 2H), 3.20-3.10 (m, 2H), 2.90-2.80 (m, 1H), 2.37-2.24 (m, 1H), 2.26 (s, 3H), 2.22-2.03 (m, 2H), 2.01-1.93 (m, 1H), 1.81-1.71 (m, 2H), 1.51-1.49 (m, 3H). (Exchangeable OH proton was not present).

Preparation of Intermediate 54a and 54b: ethyl (4aS,7aR)-3-fluoro-1,3-dimethyl-2-oxooctahydro-4aH-cyclopenta[b]pyridine-4a-carboxylate 54a

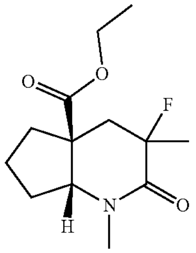

and

54b

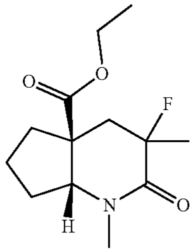

To a stirred solution of ethyl (3R,4aS,7aR)-3-fluoro-1-methyl-2-oxooctahydro-4aH-cyclopenta[b]pyridine-4a-carboxylate (1.2 g, 4.93 mmol) in THF (15 mL) at −78° C. under an argon atmosphere, was added LDA (3.70 mL, 7.40 mmol). The reaction mixture was stirred at −78° C. for 1.5 hours, and then a solution of methyl iodide (0.370 mL, 5.92 mmol) in THF (5 mL) was added dropwise. The reaction mixture was gradually warm to −20° C. over a period of 2 hours, and then for another 0.5 hours at same temperature. The reaction mixture was quenched with saturated ammonium chloride solution and extracted with EtOAc. The combined organic layers were washed with brine and dried over $Na_2SO_4$, concentrated under reduced pressure to afford a crude residue, which was purified by silica gel column chromatography using COMBIFLASH™ chromatography (Teledyne ISO, Lincoln, NE) (15 to 40% ethyl acetate/pet ether, 12 g RediSep® column, ELSD purification) to afford Isomer-1, ethyl (4aS,7aR)-3-fluoro-1,3-dimethyl-2-oxooctahydro-4aH-cyclopenta[b]pyridine-4a-carboxylate (0.6 g, 2.332 mmol, 47.3% yield and Isomer-2, ethyl (4aS,7aR)-3- fluoro-1,3-dimethyl-2-oxooctahydro-4aH-cyclopenta[b]pyridine-4a-carboxylate (0.1 g, 0.389 mmol, 7.88% yield). Isomer-1: $^{1}$H NMR (300 MHz, DMSO-$d_6$) δ ppm=4.17-4.08 (m, 3H), 2.86 (d, J=0.7 Hz, 3H), 2.42 (d, J=3.2 Hz, 1H), 2.37 (d, J=2.2 Hz, 1H), 2.23-2.26 (m, 1H), 2.01-1.88 (m, 2H), 1.81-1.74 (m, 1H), 1.66-1.50 (m, 2H), 1.39-1.32 (s, 3H), 1.21 (t, J=7.2 Hz, 3H). Isomer-2: $^{1}$H NMR (300 MHz, DMSO-$d_6$) δ ppm=4.19-3.89 (m, 3H), 2.87 (d, J=0.7 Hz, 3H), 2.86-2.72 (m, 1H), 2.48-2.42 (m, 2H), 2.40-2.07 (m, 2H), 1.92-1.54 (m, 3H), 1.48-1.31 (m, 3H), 1.19 (t, J=7.2 Hz, 3H).

Preparation of Intermediate 55a: ((4aS,7aR)-3-fluoro-1,3-dimethyloctahydro-4aH-cyclopenta[b]pyridin-4a-yl)methanol 55a

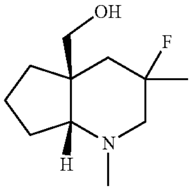

To a stirred solution of ethyl (4aS,7aR)-3-fluoro-1,3-dimethyl-2-oxooctahydro-4aH-cyclopenta[b]pyridine-4a-carboxylate (Intermediate 54a, 200 mg, 0.777 mmol) in THF (2 mL) at 0° C. under an argon atmosphere, was added lithium aluminum hydride (73.8 mg, 1.943 mmol) and heated at 50° C. for 4 hours. The reaction mixture was cooled to 0° C., quenched with water (0.6 mL), 10% NaOH (1.2 mL) and water (1.2 mL). Then, the reaction mass was stirred for 10 min and filtered through a CELITE™ (Sigma Aldrich, St. Louis, MO) pad and the CELITE™ pad was washed with EtOAc. The filtrate was concentrated under reduced pressure to afford ((4aS,7aR)-3-fluoro-1,3-dimethyloctahydro-4aH-cyclopenta[b]pyridin-4a-yl)methanol (100 mg, 0.497 mmol, 63.9% yield) as a colorless liquid. $^{1}$H NMR (400 MHz, chloroform-d) δ ppm=3.56 (br d, J=11 Hz, 1H), 3.41 (d, J=11 Hz, 1H), 2.98-2.72 (m, 1H), 2.37-2.24 (m, 3H), 2.22-2.03 (m, 4H), 2.01-1.93 (m, 1H), 1.91-1.71 (m, 2H), 1.68-1.51 (m, 3H), 1.46-1.31 (m, 3H). (Exchangeable OH proton not appeared).

Preparation of Intermediate 55b: ((4aS,7aR)-3-fluoro-1,3-dimethyloctahydro-4aH-cyclopenta[b]pyridin-4a-yl)methanol 55b

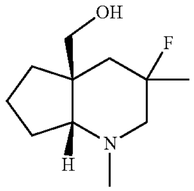

To a stirred solution of ethyl (4aS,7aR)-3-fluoro-1,3-dimethyl-2-oxooctahydro-4aH-cyclopenta[b]pyridine-4a-carboxylate (intermediate 54b, 100 mg, 0.389 mmol) in THF (10 mL) at 0° C., was added lithium aluminum hydride (36.9 mg, 0.972 mmol) and slowly heated at 50° C. for 4 hours. The reaction mixture was cooled to 0° C., quenched with water (0.5 mL), 10% NaOH (1 mL) and water (1 mL). Then, the reaction mass was stirred for 10 min and filtered through a CELITE™ (Sigma Aldrich, St. Louis, MO) pad, and the CELITE™ pad was washed with EtOAc. The filtrate was concentrated under reduced pressure to afford ((4aS,7aR)-3-fluoro-1,3-dimethyloctahydro-4aH-cyclopenta[b]pyridin-4a-yl)methanol (65 mg, 0.323 mmol, 83% yield) as a colorless liquid. $^{1}$H NMR (400 MHz, chloroform-d) δ ppm=3.61 (br d, J=11 Hz, 1H), 3.44 (d, J=11 Hz, 1H), 2.80-2.79 (m, 1H), 2.35-2.22 (m, 3H), 2.20-2.00 (m, 4H), 1.90-1.93 (m, 1H), 1.88-1.69 (m, 2H), 1.62-1.48 (m, 3H), 1.31-1.24 (m, 3H). (Exchangeable OH proton not appeared).

The compounds in Table 2 were prepared according to procedures described herein from appropriate starting materials. Mixtures of diastereomers were purified by either chiral HPLC or SFC as noted to provide single diastereomers. Superscripts appearing after the example number in the table designate which of the chiral separation conditions were used (following the table). For those compounds that are noted as diastereomer 1 or diastereomer 2, but without superscripts, were purified by the general conditions: Column Info: X-Select C18 (250×20×5 nm) Mobile Phase A: 10 mm Ammonium bicarbonate in Milli-Q-Water pH-9.5Mobile Phase B: ACN;MeOH (1:1) Flow: 20 mL\min.

TABLE 2

| # | Structure | IUPAC | LCMS (M + H)$^{+}$ | $^{1}$H NMR |
|---|---|---|---|---|
| 2-3 | 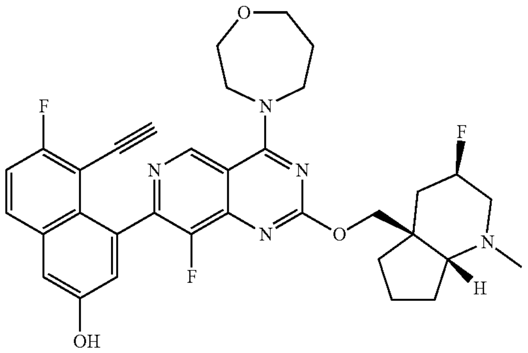 [SMILES: C#Cc1c(F)ccc2cc(O)cc(-c3ncc4c(N5CCCOCC5)nc(OC[C@]56CCC[C@H]5N(C)C[C@H](F)C6)nc4c3F)c12] | 5-ethynyl-6-fluoro-4-(8-fluoro-2-(((3R,4aS,7aR)-3-fluoro-1-methyloctahydro-4aH-cyclopenta[b]pyridin-4a-yl)methoxy)-4-(1,4-oxazepan-4-yl)pyrido[4,3-d]pyrimidin-7-yl)naphthalen-2-ol | 618.3 | $^{1}$H NMR (400 MHz, DMSO-$d_6$) δ ppm = 10.31 (s, 1H), 9.12 (s, 1H), 7.99-7.95 (m, 1H), 7.49-7.45 (m, 1H), 7.39-7.39 (m, 1H), 7.18-7.18 (m, 1H), 4.81-4.69 (m, 1H), 4.38-4.35 (m, 1H), 4.27-4.23 (m, 1H), 4.21-4.10 (m, 4H), 4.02 (s, 1H), 3.96-3.94 (m, 2H), 3.78-3.75 (m, 2H), 2.75-2.71 (m, 1H), 2.23 (s, 3H), 2.13-2.08 (m, 2H), 1.87-1.59 (m, 10H). |

TABLE 2-continued

| # | Structure | IUPAC | LCMS (M + H)+ | $^1$H NMR |
|---|---|---|---|---|
| 2-4 | 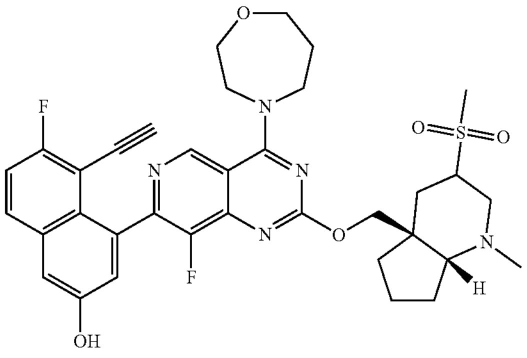 [SMILES: C#Cc1c(F)ccc2cc(O)cc(-c3ncc4c(N5CCCOCC5)nc(OC[C@]56CCC[C@H]5N(C)CC(S(C)(=O)=O)C6)nc4c3F)c12] | 5-ethynyl-6-fluoro-4-(8-fluoro-2-(((4aS,7aR)-1-methyl-3-(methylsulfonyl)octahydro-4aH-cyclopenta[b]pyridin-4a-yl)methoxy)-4-(1,4-oxazepan-4-yl)pyrido[4,3-d]pyrimidin-7-yl)naphthalen-2-ol | 678.2 | $^1$H NMR (400 MHz, DMSO-$d_6$) δ ppm = 10.15 (s, 1H), 9.11-9.08 (m, 1H), 7.98 (dd, J = 9.1, 5.9 Hz, 1H), 7.47 (t, J = 9.0 Hz, 1H), 7.40 (d, J = 2.5 Hz, 1H), 7.18 (t, J = 3.0 Hz, 1H), 4.67-4.53 (m, 1H), 4.22-4.08 (m, 5H), 4.02-3.92 (m, 3H), 3.81-3.74 (m, 2H), 3.59-3.43 (m, 1H), 2.95-2.86 (m, 4H), 2.79 (br dd, J = 11.3, 4.3 Hz, 1H), 2.31-2.26 (m, 3H), 2.15-2.09 (m, 2H), 2.07-1.92 (m, 2H), 1.81-1.69 (m, 3H), 1.66-1.54 (m, 3H), 1.50-1.39 (m, 1H). |
| 2-5 | 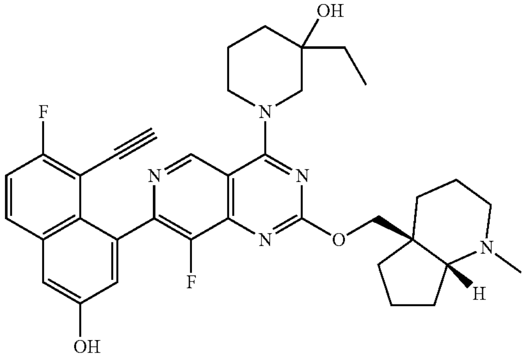 [SMILES: C#Cc1c(F)ccc2cc(O)cc(-c3ncc4c(N5CCCC(O)(CC)C5)nc(OC[C@]56CCC[C@H]5N(C)CCC6)nc4c3F)c12] Single Diastereomer | 3-ethyl-1-(7-(8-ethynyl-7-fluoro-3-hydroxy-naphthalen-1-yl)-8-fluoro-2-(((4aS,7aR)-1-methyloctahydro-4aH-cyclopenta[b]pyridin-4a-yl)methoxy)pyrido[4,3-d]pyrimidin-4-yl)piperidin-3-ol | 628.3 | $^1$H NMR (400 MHz, DMSO-$d_6$) δ ppm = 9.23 (s, 1H), 8.76 (br s, 1H), 7.99-7.95 (dd, J = 9.1, 6.1 Hz, 1H), 7.46 (t, J = 9.0 Hz, 1H), 7.40 (d, J = 2.3 Hz, 1H), 7.24-7.20 (m, 1H), 4.49-4.46 (m, 2H), 4.15-4.12 (m, 2H), 3.95-3.94 (m, 2H), 3.58-3.50 (m, 1H), 3.30-3.25 (m, 2H), 2.73-2.70 (m, 1H), 2.32-2.21 (m, 1H), 2.21 (s, 3H), 2.13-1.96 (m, 1H), 1.89-1.79 (m, 1H), 1.77-1.35 (m, 14H), 0.95-0.79 (m, 3H). |
| 2-6 | 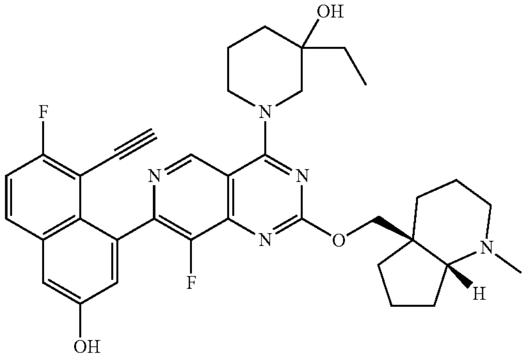 [SMILES: C#Cc1c(F)ccc2cc(O)cc(-c3ncc4c(N5CCCC(O)(CC)C5)nc(OC[C@]56CCC[C@H]5N(C)CCC6)nc4c3F)c12] Single Diastereomer | 3-ethyl-1-(7-(8-ethynyl-7-fluoro-3-hydroxy-naphthalen-1-yl)-8-fluoro-2-(((4aS,7aR)-1-methyloctahydro-4aH-cyclopenta[b]pyridin-4a-yl)methoxy)pyrido[4,3-d]pyrimidin-4-yl)piperidin-3-ol | 628.3 | $^1$H NMR (400 MHz, DMSO-$d_6$) δ ppm = 9.32-9.22 (m, 1H), 8.75 (br s, 1H), 7.98 (dd, J = 9.1, 5.9 Hz, 1H), 7.48 (dt, J = 9.0, 1.3 Hz, 1H), 7.40 (dd, J = 2.4, 1.1 Hz, 1H), 7.28-7.20 (m, 1H), 4.48-4.40 (m, 2H), 4.20-4.10 (m, 2H), 4.04-3.90 (m, 2H), 3.55-3.52 (m, 1H), 3.30-3.25 (m, 2H), 2.77-2.68 (m, 1H), 2.33-2.29 (m, 1H), 2.20 (s, 3H), 2.10-1.91 (m, 1H), 1.71-1.41 (m, 15H), 0.92-0.85 (m, 3H). |

TABLE 2-continued

| # | Structure | IUPAC | LCMS (M + H)+ | 1H NMR |
|---|---|---|---|---|
| 2-7 | 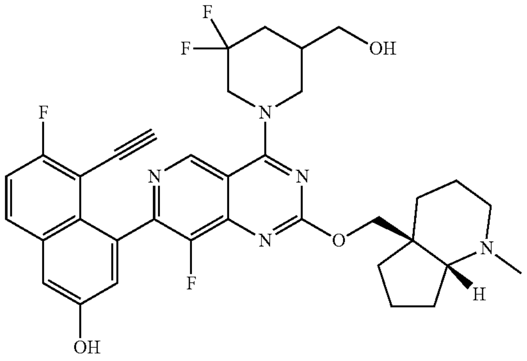 [SMILES: C#Cc1c(F)ccc2cc(O)cc(-c3ncc4c(N5CC(CO)CC(F)(F)C5)nc(OC[C@]56CCC[C@H]5N(C)CCC6)nc4c3F)c12] Single Diastereomer | 4-(4-(3,3-difluoro-5-(hydroxymethyl)piperidin-1-yl)-8-fluoro-2-(((4aS,7aR)-1-methyloctahydro-4aH-cyclopenta[b]pyridin-4a-yl)methoxy)pyrido[4,3-d]pyrimidin-7-yl)-5-ethynyl-6-fluoronaphthalen-2-ol | 650.3 | $^1$H NMR (400 MHz, DMSO-$d_6$) δ ppm = 10.19 (br s, 1H), 9.12-9.06 (m, 1H), 8.03-7.95 (m, 1H), 7.47 (t, J = 9.0 Hz, 1H), 7.41 (d, J = 1.8 Hz, 1H), 7.22 (dd, J = 9.3, 2.5 Hz, 1H), 4.97 (br s, 1H), 4.74-4.56 (m, 1H), 4.54-4.39 (m, 2H), 4.19 (t, J = 10.1 Hz, 1H), 4.02-3.90 (m, 1H), 3.87-3.65 (m, 1H), 3.59-3.51 (m, 1H), 3.47-3.40 (m, 1H), 2.79-2.72 (m, 1H), 2.41-2.22 (m, 3H), 2.22 (br s, 3H), 2.01-1.72 (m, 3H), 1.69-1.49 (m, 9H), 1.46-1.33 (m, 1H). |
| 2-8 | 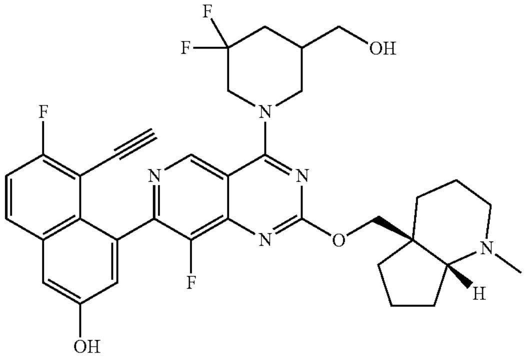 [SMILES: C#Cc1c(F)ccc2cc(O)cc(-c3ncc4c(N5CC(CO)CC(F)(F)C5)nc(OC[C@]56CCC[C@H]5N(C)CCC6)nc4c3F)c12] Single Diastereomer | 4-(4-(3,3-difluoro-5-(hydroxymethyl)piperidin-1-yl)-8-fluoro-2-(((4aS,7aR)-1-methyloctahydro-4aH-cyclopenta[b]pyridin-4a-yl)methoxy)pyrido[4,3-d]pyrimidin-7-yl)-5-ethynyl-6-fluoronaphthalen-2-ol | 650.3 | $^1$H NMR (400 MHz, DMSO-$d_6$) δ ppm = 10.20 (br s, 1H), 9.08 (d, J = 17.3 Hz, 1H), 8.02-7.97 (m, 1H), 7.47 (t, J = 9.0 Hz, 1H), 7.41 (d, J = 2.0 Hz, 1H), 7.22 (dd, J = 9.9, 2.6 Hz, 1H), 4.93 (br s, 1H), 4.74-4.55 (m, 1H), 4.50 (t, J = 10.6 Hz, 2H), 4.19 (t, J = 10.6 Hz, 1H), 4.04-3.90 (m, 1H), 3.87-3.66 (m, 1H), 3.53 (br dd, J = 10.1, 5.1 Hz, 1H), 3.48-3.38 (m, 1H), 2.79-2.64 (m, 1H), 2.36-2.21 (m, 3H), 2.18 (d, J = 2.0 Hz, 3H), 2.06-1.70 (m, 2H), 1.66-1.34 (m, 10H), 1.46-1.33 (m, 1H). |
| 2-9 | 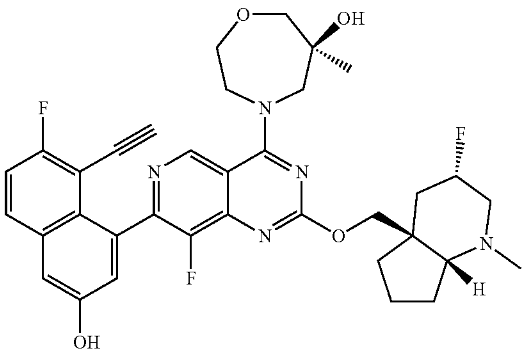 [SMILES: C#Cc1c(F)ccc2cc(O)cc(-c3ncc4c(N5CCOC[C@@](C)(O)C5)nc(OC[C@]56CCC[C@H]5N(C)C[C@@H](F)C6)nc4c3F)c12] | (S)-4-(7-(8-ethynyl-7-fluoro-3-hydroxy-naphthalen-1-yl)-8-fluoro-2-(((3S,4aS,7aR)-3-fluoro-1-methyloctahydro-4aH-cyclopenta[b]pyridin-4a-yl)methoxy)pyrido[4,3-d]pyrimidin-4-yl)-6-methyl-1,4-oxazepan-6-ol | 648.2 | $^1$H NMR (400 MHz, DMSO-$d_6$) δ ppm = 10.66-9.67 (m, 1H), 9.47-9.30 (m, 1H), 7.97 (dd, J = 9.2, 5.9 Hz, 1H), 7.50-7.37 (m, 2H), 7.19 (dd, J = 11.0, 2.5 Hz, 1H), 4.94-4.69 (m, 1H), 4.45-4.33 (m, 3H), 4.20-4.03 (m, 2H), 4.01-3.83 (m, 4H), 3.63-3.48 (m, 2H), 2.66-2.49 (m, 4H), 2.13 (s, 3H), 1.89-1.46 (m, 8H), 1.17 (d, J = 7.8 Hz, 3H). |

TABLE 2-continued

| # | Structure | IUPAC | LCMS (M + H)+ | $^1H$ NMR |
|---|---|---|---|---|
| 2-10 | 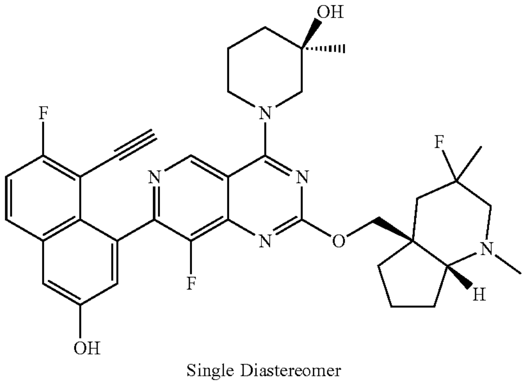 Single Diastereomer | (3R)-1-(7-(8-ethynyl-7-fluoro-3-hydroxy-naphthalen-1-yl)-8-fluoro-2-(((4aS,7aR)-3-fluoro-1,3-dimethylocta-hydro-4aH-cyclopenta[b] pyridin-4a-yl)methoxy) pyrido[4,3-d]pyrimidin-4-yl)-3-methylpiperidin-3-ol | 646.3 | $^1H$ NMR (400 MHz, DMSO-$d_6$) δ ppm = 10.16 (br d, J = 3.5 Hz, 1H), 9.24-9.05 (m, 1H), 8.03-7.94 (m, 1H), 7.46 (t, J = 8.9 Hz, 1H), 7.40 (d, J = 2.1 Hz, 1H), 7.26-7.17 (m, 1H), 4.73-4.69 (m, 1H), 4.43-4.32 (m, 1H), 4.22-4.16 (m, 1H), 4.12-4.05 (m, 2H), 4.01-3.93 (m, 2H), 3.63-3.53 (m, 1H), 2.83-2.73 (m, 1H), 2.29-2.25 (m, 1H), 2.23-2.15 (m, 3H), 2.11-1.84 (m, 7H), 1.81-1.58 (m, 8H), 1.52-1.45 (m, 2H), 1.37-1.14 (m, 6H). |
| 2-11 | 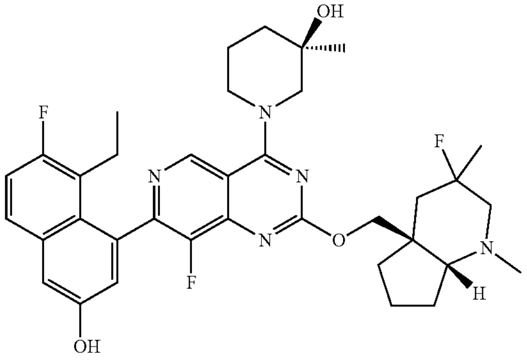 [SMILES: CCc1c(F)ccc2cc(O)cc(-c3ncc4c(N5CCC[C@@](C)(O)C5)nc(OC[C@]56CCC[C@H]5N(C)CC(C)(F)C6)nc4c3F)c12] Single Diastereomer | (3R)-1-(7-(8-ethyl-7-fluoro-3-hydroxy-naphthalen-1-yl)-8-fluoro-2-(((4aS,7aR)-3-fluoro-1,3-dimethylocta-hydro-4aH-cyclopenta[b] pyridin-4a-yl)methoxy) pyrido[4,3-d]pyrimidin-4-yl)-3-methylpiperidin-3-ol | 650.3 | $^1H$ NMR (400 MHz, DMSO-$d_6$) δ ppm = 9.95-9.90 (m, 1H), 9.27-9.22 (m, 1H), 7.77 (dd, J = 9.0, 6.0 Hz, 1H), 7.39-7.32 (m, 2H), 7.03 (d, J = 2.3 Hz, 1H), 4.79-4.72 (m, 1H), 4.42-4.31 (m, 1H), 4.28-4.17 (m, 1H), 4.13-4.01 (m, 2H), 3.64 (br d, J = 13.5 Hz, 1H), 3.54 (br d, J = 13.5 Hz, 1H), 2.82-2.74 (m, 1H), 2.41-2.25 (m, 2H), 2.23 (s, 3H), 2.22-1.98 (m, 4H), 1.95-1.41 (m, 10H), 1.38-1.24 (m, 3H), 1.23-1.15 (m, 3H), 0.79-0.68 (m, 3H). |
| 2-12 | 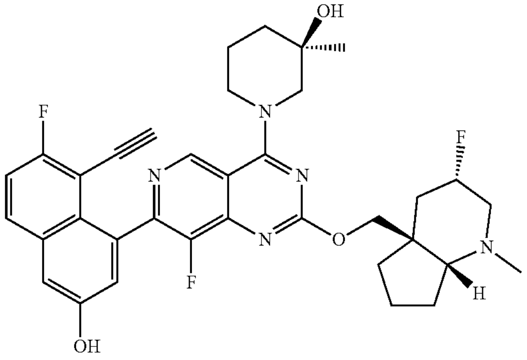 [SMILES: C#Cc1c(F)ccc2cc(O)cc(-c3ncc4c(N5CCC[C@@](C)(O)C5)nc(OC[C@]56CCC[C@H]5N(C)C[C@@H](F)C6)nc4c3F)c12] | (R)-1-(7-(8-ethynyl-7-fluoro-3-hydroxy-naphthalen-1-yl)-8-fluoro-2-(((3S,4aS,7aR)-3-fluoro-1-methyloctahydro-4aH-cyclopenta[b] pyridin-4a-yl)methoxy) pyrido[4,3-d]pyrimidin-4-yl)-3-methylpiperidin-3-ol | 632.3 | $^1H$ NMR (400 MHz, DMSO-$d_6$) δ ppm = 10.42-10.16 (m, 1H), 9.24-9.05 (m, 1H), 7.97 (dd, J = 9.1, 5.9 Hz, 1H), 7.49-7.36 (m, 2H), 7.24-7.19 (m, 1H), 4.91-4.71 (m, 2H), 4.49-4.32 (m, 2H), 4.15-3.92 (m, 3H), 3.61-3.53 (m, 1H), 2.77-2.57 (m, 3H), 2.23 (d, J = 1.1 Hz, 3H), 2.11-1.89 (m, 2H), 1.89-1.40 (m, 11H), 1.25-1.12 (m, 3H). |

TABLE 2-continued

| # | Structure | IUPAC | LCMS (M + H)+ | 1H NMR |
| --- | --- | --- | --- | --- |
| 2-13 | 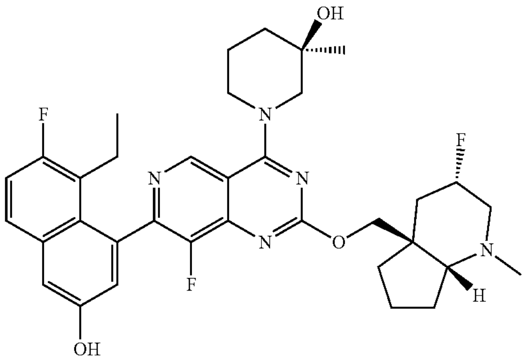 [SMILES: CCc1c(F)ccc2cc(O)cc(-c3ncc4c(N5CCC[C@@](C)(O)C5)nc(OC[C@]56CCC[C@H]5N(C)C[C@@H](F)C6)nc4c3F)c12] | (R)-1-(7-(8-ethyl-7-fluoro-3-hydroxy-naphthalen-1-yl)-8-fluoro-2-(((3S,4aS,7aR)-3-fluoro-1-methyloctahydro-4aH-cyclopenta[b]pyridin-4a-yl)methoxy)pyrido[4,3-d]pyrimidin-4-yl)-3-methylpiperidin-3-ol | 636.3 | $^1$H NMR (400 MHz, DMSO-$d_6$) δ ppm = 9.99 (br s, 1H), 9.23 (d, J = 1.6 Hz, 1H), 7.76 (dd, J = 9.1, 6.0 Hz, 1H), 7.37-7.31 (m, 2H), 7.03 (s, 1H), 4.92-4.83 (m, 1H), 4.75 (d, J = 6.5 Hz, 1H), 4.47 (t, J = 11.0 Hz, 1H), 4.35 (br t, J = 14.1 Hz, 1H), 4.15-4.00 (m, 2H), 3.67-3.48 (m, 1H), 2.74-2.67 (m, 1H), 2.66-2.54 (m, 2H), 2.39-2.31 (m, 1H), 2.23 (s, 3H), 2.22-1.98 (m, 3H), 1.90-1.46 (m, 11H), 1.19-1.15 (m, 3H), 0.77-0.70 (m, 3H). |
| 2-14[1] | 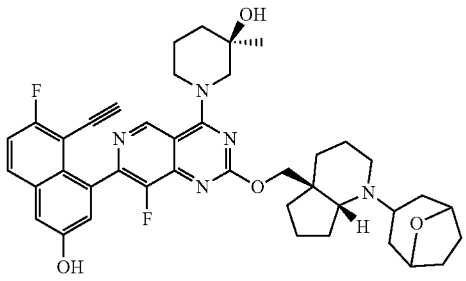 [SMILES: C#Cc1c(F)ccc2cc(O)cc(-c3ncc4c(N5CCC[C@@](C)(O)C5)nc(OC[C@]56CCC[C@H]5N(C5CC7CCC(C5)O7)CCC6)nc4c3F)c12] Diastereomer 1 | (3R)-1-(2-{[(4aS,7aR)-1-{8-oxabicyclo[3.2.1]octan-3-yl}-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-3-methylpiperidin-3-ol | 710.3 | $^1$H NMR (400 MHz, DMSO-$d_6$) δ ppm = 10.16 (s, 1H), 9.23-9.10 (m, 1H), 8.86-8.84 (m, 1H), 8.01-7.97 (m, 1H), 7.49-7.44 (m, 1H), 7.41-7.39 (m, 1H), 7.23-7.19 (m, 1H), 4.66-4.61 (m, 1H), 4.46-4.39 (m, 3H), 4.34-4.26 (m, 1H), 4.16-3.98 (m, 1H), 3.95 (s, 1H), 3.79-3.71 (m, 1H), 3.61-3.55 (m, 1H), 3.15-2.96 (m, 2H), 2.75-2.71 (m, 1H), 2.61-2.57 (m, 1H), 2.21-2.12 (m, 1H), 2.08-1.99 (m, 3H), 1.89-1.56 (m, 15H), 1.54-1.45 (m, 2H), 1.37-1.24 (m, 2H), 1.20-1.16 (m, 3H). TFA salt, 1 proton excess for TFA proton. |
| 2-15[1] | 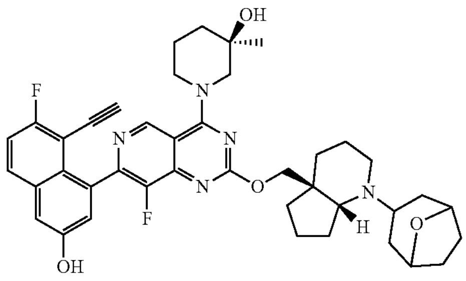 [SMILES: C#Cc1c(F)ccc2cc(O)cc(-c3ncc4c(N5CCC[C@@](C)(O)C5)nc(OC[C@]56CCC[C@H]5N(C5CC7CCC(C5)O7)CCC6)nc4c3F)c12] Diastereomer 2 | (3R)-1-(2-{[(4aS,7aR)-1-{8-oxabicyclo[3.2.1]octan-3-yl}-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-3-methylpiperidin-3-ol | 710.3 | $^1$H NMR (400 MHz, DMSO-$d_6$) δ ppm = 10.17 (s, 1H), 9.24-9.10 (m, 1H), 8.96-8.94 (m, 1H), 8.01-7.97 (m, 1H), 7.49-7.45 (m, 1H), 7.41-7.40 (m, 1H), 7.24-7.19 (m, 1H), 4.66-4.61 (m, 1H), 4.46-4.41 (m, 3H), 4.34-4.26 (m, 1H), 4.16-3.98 (m, 1H), 3.95 (s, 1H), 3.79-3.71 (m, 1H), 3.61-3.55 (m, 2H), 3.31-3.27 (m, 2H), 3.01-2.96 (m, 1H), 2.18-1.99 (m, 4H), 1.95-1.90 (m, 1H), 1.85-1.61 (m, 16H), 1.57-1.49 (m, 2H), 1.20-1.16 (m, 3H). TFA salt, 1 proton excess for TFA proton. |

TABLE 2-continued

| # | Structure | IUPAC | LCMS (M + H)+ | 1H NMR |
|---|---|---|---|---|
| 2-16 | 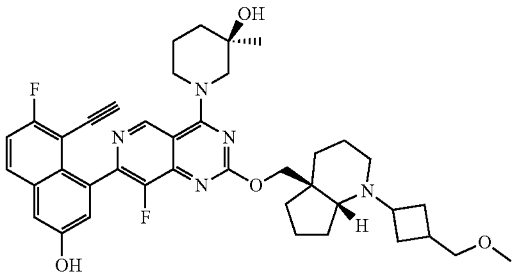 [SMILES: C#Cc1c(F)ccc2cc(O)cc(-c3ncc4c(N5CCC[C@@](C)(O)C5)nc(OC[C@]56CCC[C@H]5N(C5CC(COC)C5)CCC6)nc4c3F)c12] Diastereomer 1 | (3R)-1-(2-{[(4aS,7aR)-1-[3-(methoxymethyl) cyclobutyl]-octahydro-1H-cyclopenta[b] pyridin-4a-yl]methoxy}-7-(8-ethynyl-7-fluoro-3-hydroxy-naphthalen-1-yl)-8-fluoropyrido[4,3-d]pyrimidin-4-yl)-3-methylpiperidin-3-ol | 698.4 | $^1$H NMR (400 MHz, DMSO-$d_6$) δ ppm = 10.15 (s, 1H), 9.21 (s, 1H), 7.98-7.96 (m 1H), 7.46 (t, J = 8.8 Hz, 1H), 7.39 (s, 1H), 7.23 (s, 1H), 4.76 (s, 1H), 4.7-4.55 (m, 1H), 4.4-4.2 (m, 1H), 4.18-4.15 (m, 2H), 3.95-3.93 (m, 1H), 3.5-3.4 (m, 1H), 3.30-3.21 (m, 2H), 3.19-3.17 (m, 3H), 3.05-2.93 (m, 1H), 2.25-2.0 (m, 6H), 1.95-1.8 (m, 3H), 1.75-1.30 (m, 15H), 1.28-1.1 (m, 3H). |
| 2-17 | 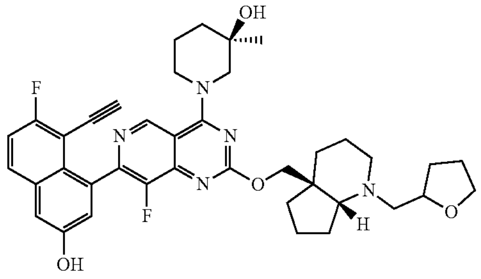 [SMILES: C#Cc1c(F)ccc2cc(O)cc(-c3ncc4c(N5CCC[C@@](C)(O)C5)nc(OC[C@]56CCC[C@H]5N(CC5CCCO5)CCC6)nc4c3F)c12] Diastereomer 1 | (3R)-1-(2-{[(4aS,7aR)-1-[(oxolan-2-yl)methyl]-octahydro-1H-cyclopenta[b] pyridin-4a-yl]methoxy}-7-(8-ethynyl-7-fluoro-3-hydroxy-naphthalen-1-yl)-8-fluoropyrido[4,3-d]pyrimidin-4-yl)-3-methylpiperidin-3-ol | 684.2 | $^1$H NMR (400 MHz, DMSO-$d_6$) δ ppm = 10.15 (brs, 1H), 9.21-9.05 (m, 1H), 8.00-7.96 (m, 1H), 7.47 (t, J = 8.8 Hz, 1H), 7.40 (d, J = 2.0 Hz, 1H), 7.22 (dd, J = 18.4, 2.4 Hz, 1H), 4.71-4.63 (m, 1H), 4.41-4.30 (m, 1H), 4.19-4.08 (m, 2H), 4.00-3.93 (m, 2H), 3.89-3.82 (m, 1H), 3.74-3.68 (m, 2H), 3.61-3.51 (m, 2H), 2.98-2.92 (m, 1H), 2.59-2.54 (m, 1H), 2.48-2.39 (m, 1H), 2.12-1.97 (m, 1H), 2.05-2.02 (m, 2H), 1.91-1.82 (m, 3H), 1.79-1.40 (m, 15H), 1.37-1.24 (m, 1H), 1.18-1.16 (m, 1H). |
| 2-18# | 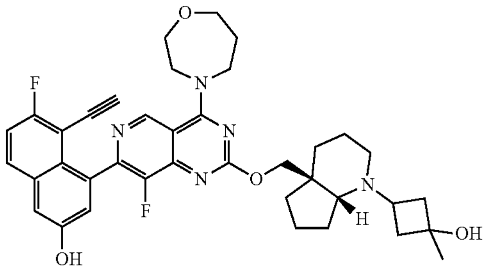 [SMILES: C#Cc1c(F)ccc2cc(O)cc(-c3ncc4c(N5CCCOCC5)nc(OC[C@]56CCC[C@H]5N(C5CC(C)(O)C5)CCC6)nc4c3F)c12] Diastereomer 1 | 4-(2-{[(4aS,7aR)-1-(3-hydroxy-3-methylcyclo-butyl)-octahydro-1H-cyclopenta[b] pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 670.3 | $^1$H NMR (400 MHz, DMSO-$d_6$) δ ppm = 10.14 (s, 1H), 9.10 (s, 1H), 8.01-7.96 (m, 1H), 7.49-7.45 (m, 1H), 7.40 (d, J = 4.0 Hz, 1H), 7.19 (d, J = 2.4 Hz, 1H), 4.81 (s, 1H), 4.63-4.56 (m, 1H), 4.20-4.02 (m, 5H), 3.96-3.94 (m, 2H), 3.79-3.76 (m, 3H), 3.06-2.98 (m, 2H), 2.47-2.42 (m, 1H), 2.16-1.99 (m, 6H), 1.86-1.25 (m, 11H), 1.15-1.13 (m, 4H). |
| 2-19# | 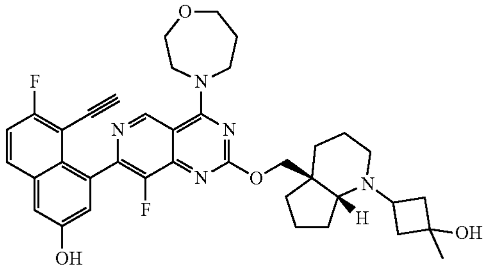 [SMILES: C#Cc1c(F)ccc2cc(O)cc(-c3ncc4c(N5CCCOCC5)nc(OC[C@]56CCC[C@H]5N(C5CC(C)(O)C5)CCC6)nc4c3F)c12] Diastereomer 2 | 4-(2-{[(4aS,7aR)-1-(3-hydroxy-3-methylcyclo-butyl)-octahydro-1H-cyclopenta[b] pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 670.3 | $^1$H NMR (400 MHz, DMSO-$d_6$) δ ppm = 10.14 (s, 1H), 9.10 (s, 1H), 8.01-7.96 (m, 1H), 7.49-7.45 (m, 1H), 7.40 (d, J = 4 Hz, 1H), 7.18-7.17 (m, 1H), 4.63-4.60 (m, 2H), 4.27-4.21 (m, 1H), 4.19-4.11 (m, 4H), 3.97-3.91 (m, 3H), 3.78-3.72 (m, 2H), 3.06-2.98 (m, 2H), 2.15-2.07 (m, 3H), 1.98-1.92 (m, 2H), 1.87-1.82 (m, 2H), 1.72-1.25 (m, 11H), 1.15-1.13 (m, 3H). |

TABLE 2-continued

| # | Structure | IUPAC | LCMS (M + H)$^+$ | $^1$H NMR |
|---|---|---|---|---|
| 2-20 | 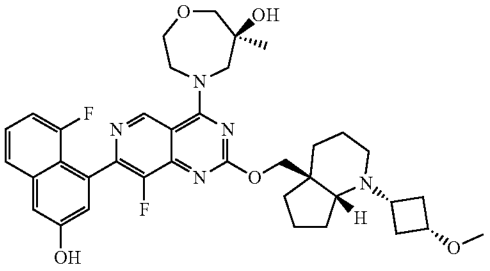 [SMILES: CO[C@H]1C[C@@H](N2CCC[C@@]3(COc4nc(N5CCOC[C@@](C)(O)C5)c5cnc(-c6cc(O)cc7cccc(F)c67)c(F)c5n4)CCC[C@@H]23)C1] | (6S)-4-(2-{[(4aS,7aR)-1-[(1s,3s)-3-methoxycyclo-butyl]-octahydro-1H-cyclopenta[b]pyridin-4a-yl]methoxy}-8-fluoro-7-(8-fluoro-3-hydroxy-naphthalen-1-yl)pyrido[4,3-d]pyrimidin-4-yl)-6-methyl-1,4-oxazepan-6-ol | 676.3 | $^1$H NMR (400 MHz, DMSO-$d_6$) δ ppm 10.23 (s, 1H), 9.46 (s, 1H), 7.68 (d, J = 8.0 Hz, 1H), 7.46-7.40 (m, 1H), 7.36 (s, 1H), 7.20 (d, J = 2.8 Hz, 1H), 7.14 (d, J = 2.4 Hz, 1H), 5.17 (s, 1H), 4.72-4.51 (m, 1H), 4.52-4.21 (m, 3H), 4.10-3.85 (m, 3H), 3.50-3.41 (m, 3H), 3.06-3.05 (m, 3H), 3.01-2.98 (m, 2H), 2.52-2.41 (m, 1H), 2.20-2.10 (m, 2H), 1.90-1.81 (m, 1H), 1.70-1.44 (m, 13H), 1.17-1.15 (m, 3H). |
| 2-21 | 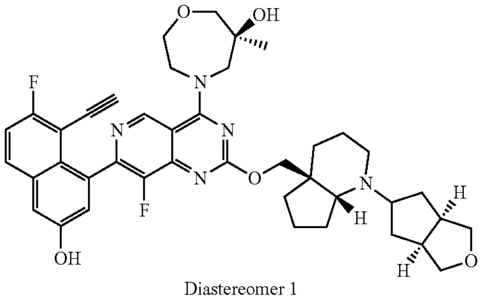 [SMILES: C#Cc1c(F)ccc2cc(O)cc(-c3ncc4c(N5CCOC[C@@](C)(O)C5)nc(OC[C@]56CCC[C@H]5N(C5C[C@H]7COC[C@H]7C5)CCC6)nc4c3F)c12] Diastereomer 1 | (6S)-4-(2-{[(4aS,7aR)-1-[(3aR,6aS)-hexahydro-1H-cyclopenta[c]furan-5-yl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 726.2 | $^1$H NMR (400 MHz, METHANOL-$d_4$) δ ppm = 9.55-9.40 (m, 1H), 7.87-7.91 (m, 1H), 7.39-7.31 (m, 2H), 7.24 (dd, J = 11.1, 2.6 Hz, 1H), 4.72-4.45 (m, 6H), 4.33-4.18 (m, 1H), 4.09-4.00 (m, 2H), 3.97-3.82 (m, 4H), 3.75-3.71 (m, 2H), 3.69-3.63 (m, 1H), 3.48-3.45 (m, 1H), 2.41-1.48 (m, 20H), 1.30 (m, 3H). (Two exchangeable protons not appeared). |
| 2-22 | 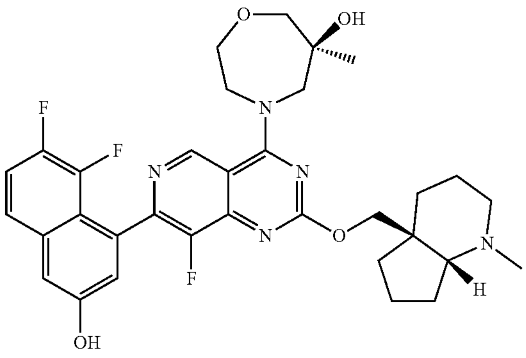 [SMILES: CN1CCC[C@@]2(COc3nc(N4CCOC[C@@](C)(O)C4)c4cnc(-c5cc(O)cc6ccc(F)c(F)c56)c(F)c4n3)CCC[C@@H]12] | (6S)-4-(2-{[(4aS,7aR)-1-methyl-octahydro-1H-cyclopenta[b]pyridin-4a-yl]methoxy}-7-(7,8-difluoro-3-hydroxy-naphthalen-1-yl)-8-fluoropyrido[4,3-d]pyrimidin-4-yl)-6-methyl-1,4-oxazepan-6-ol | 624.3 | $^1$H NMR (400 MHz, METHANOL-$d_4$) δ ppm = 9.60 (s, 1H), 7.66-7.63 (m, 1H), 7.46-7.41 (m, 1H), 7.37-7.36 (m, 1H), 7.27 (dd, J = 15.8, 2.4 Hz, 1H), 4.63-4.56 (m, 4H), 4.46-4.43 (m, 2H), 4.26-4.18 (m, 1H), 4.09-3.90 (m, 3H), 3.73-3.68 (m, 2H), 2.85-2.65 (m, 3H), 2.18-2.05 (m, 2H), 2.14-2.02 (m, 2H), 1.97-1.71 (m, 6H), 1.41-1.21 (m, 4H). (Two exchangeable protons not appeared). |
| 2-23 | 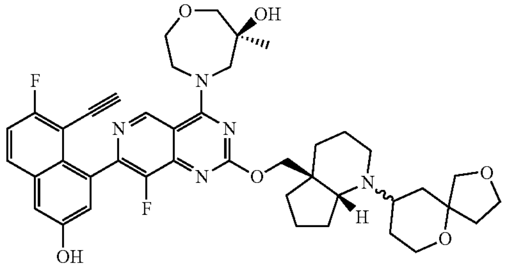 Diastereomer Mixture | (6S)-4-(2-{[(4aS,7aR)-1-{2,6-dioxaspiro[4.5]decan-9-yl}-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 756.2 | $^1$H NMR (400 MHz, DMSO-$d_6$) δ ppm = 10.16 (brs, 1H), 9.49-9.28 (m, 1H), 8.01-7.94 (m, 1H), 7.46 (t, J = 9.0 Hz, 1H), 7.39 (d, J = 2.5 Hz, 1H), 7.21-7.16 (m, 1H), 5.25-5.03 (m, 1H), 4.65-4.57 (m, 1H), 4.46-4.27 (m, 3H), 4.24-3.85 (m, 5H), 3.76-3.65 (m, 3H), 3.63-3.57 (m, 2H), 3.54-3.34 (m, 4H), 3.16-3.06 (m, 1H), 2.64-2.55 (m, 1H), 2.45-2.37 (m, 2H), 2.13-2.04 (m, 2H), 1.95-1.87 (m, 2H), 1.84-1.78 (m, 1H), 1.75-1.39 (m, 5H), 1.38- |

TABLE 2-continued

| # | Structure | IUPAC | LCMS (M + H)+ | $^1$H NMR |
|---|---|---|---|---|
| | | | | 1.26 (m, 3H), 1.25-1.10 (m, 5H). (Diastereomeric mixture) |
| 2-24# | 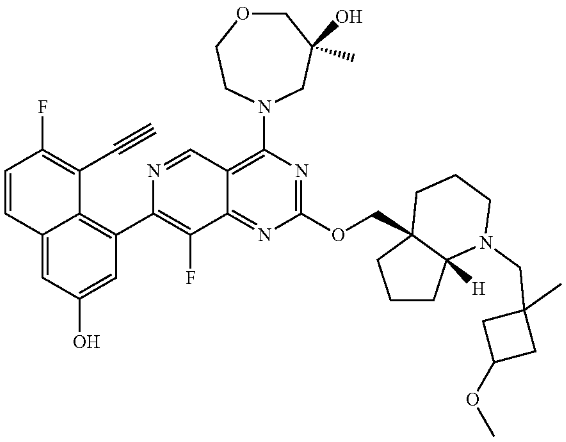 Diastereomer 1 | (6S)-4-(2-{[(4aS,7aR)-1-[(3-methoxy-1-methylcyclobutyl)methyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 728.4 | $^1$H NMR (400 MHz, DMSO-$d_6$) δ ppm = 10.13 (m, 1H), 9.36-9.32 (m, 1H), 7.97 (m, 1H), 7.46 (t, J = 9.2 Hz, 1H), 7.39 (d, J = 2.8 Hz, 1H), 7.18 (dd, J = 10.0, 2.4 Hz, 1H), 4.7-4.6 (m, 1H), 4.48-4.40 (m, 1H), 4.30-4.20 (m, 1H), 4.19-4.0 (m, 1H), 4.0-3.8 (m, 4H), 3.65-3.50 (m, 3H), 2.99-3.03 (m, 4H), 2.45-2.35 (m, 4H), 2.2-2.0 (m, 2H), 1.98-1.80 (m, 1H), 1.7-1.6 (m, 1H), 1.52-1.49 (m, 9H), 1.45-1.40 (m, 1H), 1.38-1.30 (m, 2H), 1.16-1.10 (m, 3H), 1.05-1.01 (m, 3H). |
| 2-25# | 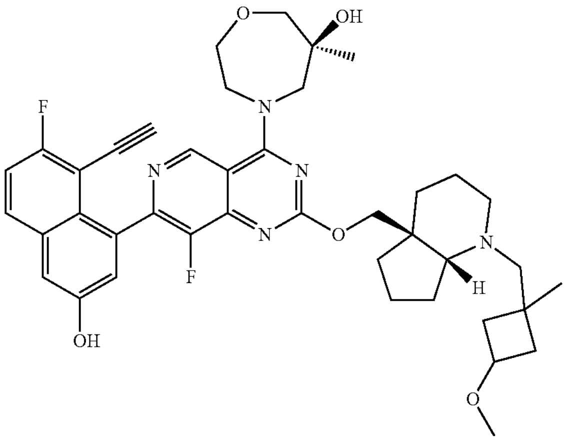 Diastereomer 2 | (6S)-4-(2-{[(4aS,7aR)-1-[(3-methoxy-1-methylcyclobutyl)methyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 728.4 | $^1$H NMR (400 MHz, DMSO-$d_6$) δ ppm = 10.13 (m, 1H), 9.36-9.32 (m, 1H), 7.97 (m, 1H), 7.46 (t, J = 9.2 Hz, 1H), 7.39 (d, J = 2.8 Hz, 1H), 7.18 (dd, J = 10.0, 2.4 Hz, 1H), 4.7-4.6 (m, 1H), 4.48-4.40 (m, 1H), 4.30-4.20 (m, 2H), 4.19-4.0 (m, 2H), 4.0-3.8 (m, 4H), 3.65-3.50 (m, 3H), 2.99-3.03 (m, 4H), 2.45-2.35 (m, 2H), 2.21-2.02 (m, 2H), 1.98-1.80 (m, 1H), 1.7-1.6 (m, 1H), 1.52-1.49 (m, 9H), 1.45-1.40 (m, 2H), 1.38-1.30 (m, 2H), 1.17-1.15 (m, 3H), 1.04-1.02 (m, 3H). |
| 2-26 | 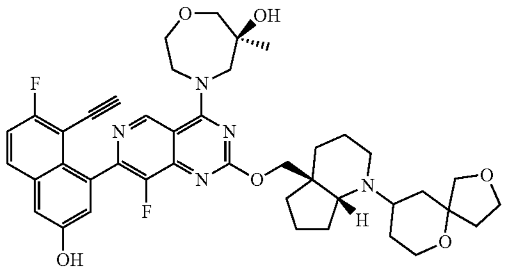 Diastereomer 1 | (6S)-4-(2-{[(4aS,7aR)-1-{2,6-dioxaspiro[4.5]decan-9-yl}-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 756.3 | $^1$H NMR (400 MHz, DMSO-$d_6$) δ ppm = 10.16 (brs, 1H), 9.43-9.25 (m, 1H), 7.97-7.84 (m, 1H), 7.46 (t, J = 9.0 Hz, 1H), 7.39 (d, J = 2.5 Hz, 1H), 7.19 (dd, J = 11.0, 2.5 Hz, 1H), 5.23-5.03 (m, 1H), 4.62-4.57 (m, 1H), 4.47-4.01 (m, 5H), 4.00-3.80 (m, 3H), 3.73-3.61 (m, 2H), 3.59 (s, 2H), 3.54-3.51 (m, 2H), 3.45-3.37 (m, 1H), 3.15-3.06 (m, 1H), 2.62-2.54 (m, 2H), 2.46-2.38 (m, 2H), 1.97-1.83 (m, 2H), 1.81-1.62 (m, 3H), 1.61-1.52 (m, 2H), 1.50-1.39 (m, 4H), 1.38-1.22 (m, 4H), 1.18-1.13 (m, 4H). |

TABLE 2-continued

| # | Structure | IUPAC | LCMS (M + H)+ | 1H NMR |
|---|---|---|---|---|
| 2-27# | 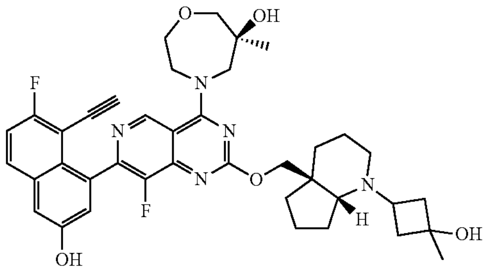 Diastereomer 2 | (6S)-4-(2-{[(4aS,7aR)-1-(3-hydroxy-3-methylcyclobutyl)-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 700.4 | $^1$H NMR (400 MHz, METHANOL-$d_4$) δ ppm = 9.52-9.42 (m, 1H), 7.91-7.86 (m, 1H), 7.38-7.32 (m, 2H), 7.26-7.26 (m, 1H), 4.68-4.47 (m, 5H), 4.30-4.28 (m, 1H), 4.06-3.93 (m, 2H), 3.77-3.68 (m, 2H), 3.50-3.45 (m, 1H), 2.13-1.75 (m, 5H), 1.71-1.42 (m, 10H), 1.35-1.29 (m, 9H). (Three exchangeable protons not appeared) |
| 2-28# | 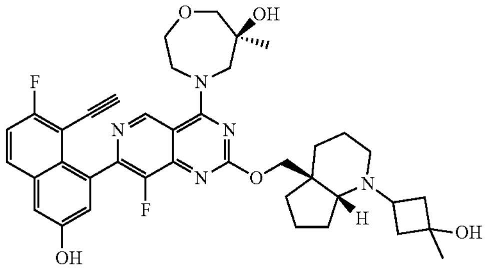 Diastereomer 1 | (6S)-4-(2-{[(4aS,7aR)-1-(3-hydroxy-3-methylcyclo-butyl)-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 700.4 | $^1$H NMR (400 MHz, METHANOL-$d_4$) δ ppm = 9.40-9.30 (m, 1H), 7.78-7.73 (m, 1H), 7.26-7.20 (m, 2H), 7.13 (dd, J = 14.0, 2.8 Hz, 1H), 4.52-4.37 (m, 4H), 3.96-3.92 (m, 1H), 3.85-3.81 (m, 2H), 3.65-3.56 (m, 3H), 3.34-3.33 (m, 1H), 2.20-1.77 (m, 5H), 1.62-1.42 (m, 10H), 1.23-1.17 (m, 9H). (Three exchangeable protons not appeared). |
| 2-29 | 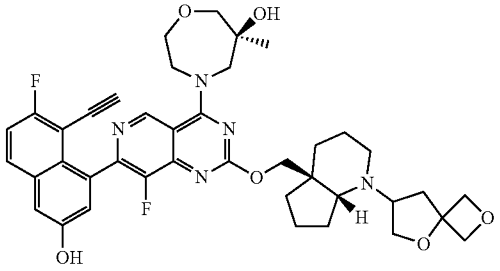 Diastereomer 1 | (6S)-4-(2-{[(4aS,7aR)-1-{2,5-dioxaspiro[3.4]octan-7-yl}-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 728.2 | $^1$H NMR (400 MHz, DMSO-$d_6$) δ ppm = 10.14 (s, 1H), 9.42-9.30 (m, 1H), 7.99-7.96 (m, 1H), 7.48-7.39 (m, 2H), 7.20-7.18 (m, 1H), 5.23-5.06 (m, 1H), 4.52-4.44 (m, 5H), 4.23-4.05 (m, 3H), 3.99-3.84 (m, 5H), 3.56 (s, 2H), 3.51-3.47 (m, 2H), 3.12-2.97 (m, 2H), 2.34-2.32 (m, 1H), 1.61-1.47 (m, 12H), 1.24-1.15 (m, 4H). |

TABLE 2-continued

| # | Structure | IUPAC | LCMS (M + H)+ | $^1$H NMR |
|---|---|---|---|---|
| 2-30 | 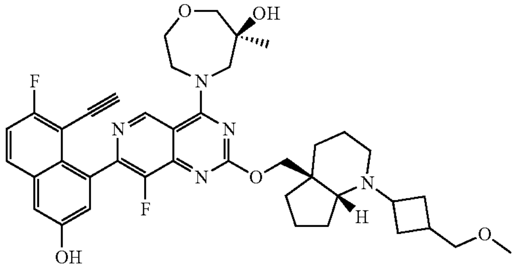 Diastereomer 1 | (6S)-4-(2-{[(4aS,7aR)-1-[3-(methoxymethyl)cyclobutyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 714.4 | $^1$H NMR (400 MHz, METHANOL-$d_4$) δ ppm = 9.39 (s, 1H), 7.78-7.74 (m, 1H), 7.26-7.20 (m, 2H), 7.14-7.11 (m, 1H), 4.54-4.52 (m, 2H), 4.48-4.40 (m, 4H), 4.38-4.35 (m, 2H), 3.95-3.91 (m, 2H), 3.84-3.81 (m, 2H), 3.65-3.55 (m, 3H), 3.35-3.33 (m, 2H), 2.15-2.12 (m, 4H), 1.93-1.92 (m, 3H), 1.76-1.50 (m, 6H), 1.50-1.28 (m, 4H), 1.20-1.17 (m, 4H). (Two exchangeable protons not appeared). |
| 2-31 | 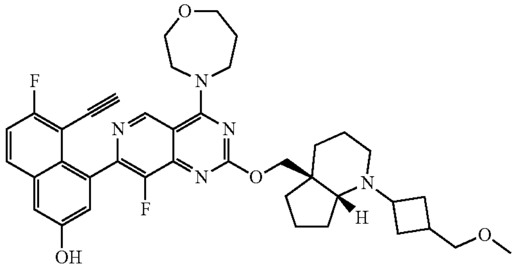 Diastereomer 1 | 4-(2-{[(4aS,7aR)-1-[3-(methoxymethyl)cyclobutyl]-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 684.3 | $^1$H NMR (400 MHz, DMSO-$d_6$) δ ppm = 10.14 (s, 1H), 9.10 (s, 1H), 8.00-7.96 (m, 1H), 7.47 (t, J = 9.2 Hz, 1H), 7.40 (d, J = 2.8 Hz, 1H), 7.18 (s, 1H), 4.59-4.58 (m, 1H), 4.25-4.23 (m, 2H), 4.16-4.15 (m, 4H), 4.01-3.94 (m, 2H), 3.78 (t, J = 4.8, 2H), 3.20-3.16 (m, 5H), 3.10-2.9 (m, 3H), 2.12-2.10 (m, 4H), 2.03-2.02 (m, 3H), 1.9-1.8 (m, 2H), 1.62-1.52 (m, 4H), 1.5-1.3 (m, 5H). |
| 2-32# | 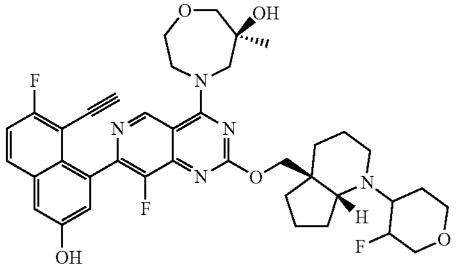 Diastereomer 4 | (6S)-4-(2-{[(4aS,7aR)-1-(3-fluorooxan-4-yl)-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 718.3 | $^1$H NMR (400 MHz, METHANOL-$d_4$) δ ppm = 9.49-9.38 (m, 1H), 7.89-7.85 (m, 1H), 7.36-7.23 (m, 3H), 4.74-4.62 (m, 1H), 4.58-4.42 (m, 4H), 4.29-4.21 (m, 1H), 4.07-3.81 (m, 4H), 3.74-3.61 (m, 3H), 3.46-3.41 (m, 2H), 3.27-3.22 (m, 2H), 2.82-2.71 (m, 3H), 2.17-2.11 (m, 1H), 1.82-1.62 (m, 8H), 1.59-1.49 (m, 5H), 1.34-1.27 (m, 3H). (Two exchangeable protons not appeared). |

TABLE 2-continued

| # | Structure | IUPAC | LCMS (M + H)+ | 1H NMR |
|---|---|---|---|---|
| 2-33# | 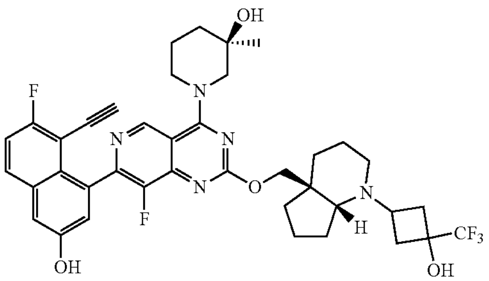 Diastereomer 2 | (3R)-1-(2-{[(4aS,7aR)-1-[3-hydroxy-3-(trifluoromethyl)cyclobutyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-3-methylpiperidin-3-ol | 738.3 | $^1$H NMR (400 MHz, DMSO-$d_6$) δ ppm = 10.19-10.16 (m, 1H), 9.24-9.04 (m, 1H), 8.01-7.95 (m, 1H), 7.50-7.43 (m, 1H), 7.41-7.38 (m, 1H), 7.26-7.18 (m, 1H), 6.46 (s, 1H), 4.81-4.71 (m, 1H), 4.69-4.60 (m, 1H), 4.42-4.27 (m, 1H), 4.21-4.08 (m, 2H), 4.00-3.92 (m, 2H), 3.62-3.52 (m, 1H), 3.28-3.25 (m, 1H), 3.07-2.99 (m, 1H), 2.56-2.53 (m, 1H), 2.22-2.11 (m, 1H), 2.06-1.95 (m, 3H), 1.90-1.79 (m, 1H), 1.76-1.26 (m, 14H), 1.21-1.15 (m, 3H). |
| 2-34# | 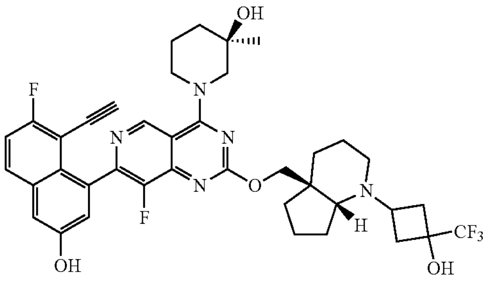 Diastereomer 1 | (3R)-1-(2-{[(4aS,7aR)-1-[3-hydroxy-3-(trifluoromethyl)cyclobutyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-3-methylpiperidin-3-ol | 738.3 | $^1$H NMR (400 MHz, DMSO-$d_6$) δ ppm = 10.18-10.14 (m, 1H), 9.22-9.03 (m, 1H), 7.97-7.94 (m, 1H), 7.46 (dd, J = 9.0, 1.0 Hz, 1H), 7.41-7.38 (m, 1H), 7.24-7.17 (m, 1H), 6.30 (m, 1H), 4.78-4.63 (m, 2H), 4.42-4.28 (m, 1H), 4.19-4.06 (m, 2H), 4.00-3.91 (m, 2H), 3.62-3.53 (m, 1H), 3.03-2.94 (m, 1H), 2.56-2.53 (m, 2H), 2.47-2.40 (m, 1H), 2.25-2.15 (m, 1H), 2.09-1.99 (m, 3H), 1.92-1.80 (m, 1H), 1.78-1.23 (m, 13H), 1.21-1.13 (m, 3H). |
| 2-35# | 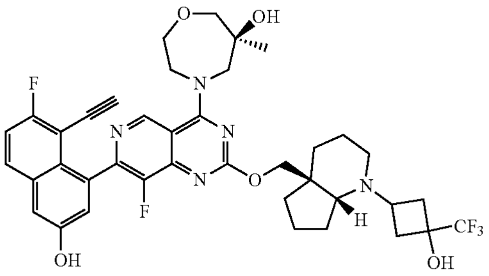 Diastereomer 2 | (6S)-4-(2-{[(4aS,7aR)-1-[3-hydroxy-3-(trifluoromethyl)cyclobutyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 754.2 | $^1$H NMR (400 MHz, DMSO-$d_6$) δ ppm = 10.18-10.13 (m, 1H), 9.46-9.30 (m, 1H), 8.01-7.95 (m, 1H), 7.50-7.44 (m, 1H), 7.41-7.38 (m, 1H), 7.23-7.17 (m, 1H), 6.44 (s, 1H), 5.27-5.06 (m, 1H), 4.66-4.56 (m, 1H), 4.46-4.31 (m, 2H), 4.28-4.20 (m, 1H), 4.19-4.02 (m, 3H), 4.02-3.78 (m, 3H), 3.66-3.50 (m, 2H), 3.07-2.99 (m, 1H), 2.56-2.52 (m, 2H), 2.19-2.15 (m, 1H), 2.03-1.92 (m, 2H), 1.89-1.79 (m, 1H), 1.76-1.51 (m, 6H), 1.51-1.41 (m, 2H), 1.39-1.27 (m, 2H), 1.20-1.15 (m, 3H). |

TABLE 2-continued

| # | Structure | IUPAC | LCMS (M + H)$^+$ | $^1$H NMR |
|---|---|---|---|---|
| 2-36# | 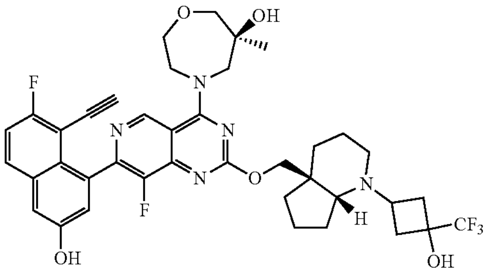 Diastereomer 1 | (6S)-4-(2-{[(4aS,7aR)-1-[3-hydroxy-3-(trifluoromethyl) cyclobutyl]-octahydro-1H-cyclopenta[b] pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 754.2 | $^1$H NMR (400 MHz, DMSO-$d_6$) δ ppm = 10.18-10.14 (m, 1H), 9.42-9.29 (m, 1H), 8.02-7.94 (m, 1H), 7.50-7.43 (m, 1H), 7.41-7.38 (m, 1H), 7.22-7.16 (m, 1H), 6.31 (s, 1H), 5.23-5.04 (m, 1H), 4.67-4.61 (m, 1H), 4.48-4.28 (m, 2H), 4.22-4.01 (m, 3H), 4.00-3.81 (m, 3H), 3.64-3.58 (m, 2H), 3.26-3.19 (m, 2H), 3.03-2.95 (m, 1H), 2.47-2.41 (m, 1H), 2.25-2.15 (m, 1H), 2.07-1.99 (m, 2H), 1.94-1.81 (m, 1H), 1.80-1.65 (m, 2H), 1.64-1.22 (m, 8H), 1.19-1.14 (m, 3H). |
| 2-37 | 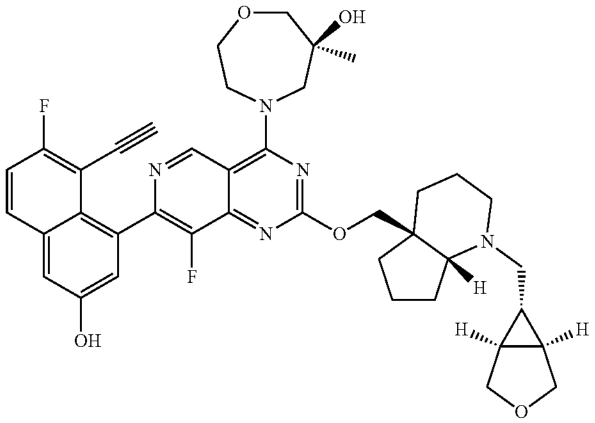 [SMILES: C#Cc1c(F)ccc2cc(O)cc(-c3ncc4c(N5CCOC[C@@](C)(O)C5)nc(OC[C@]56CCC[C@H]5N(C[C@H]5[C@@H]7COC[C@@H]75)CCC6)nc4c3F)c12] | (6S)-4-(2-{[(4aS,7aR)-1-{[(1R,5S,6R)-3-oxabicyclo[3.1.0] hexan-6-yl]methyl}-octahydro-1H-cyclopenta[b] pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 712.2 | $^1$H NMR (400 MHz, DMSO-$d_6$) δ ppm = 10.16 (s, 1H), 9.47-9.29 (m, 1H), 8.01-7.92 (m, 1H), 7.46 (t, J = 9.0 Hz, 1H), 7.39 (d, J = 2.5 Hz, 1H), 7.23-7.15 (m, 1H), 5.28-5.02 (m, 1H), 4.59-4.50 (m, 1H), 4.48-4.22 (m, 2H), 4.19-3.80 (m, 4H), 3.72-3.64 (m, 2H), 3.64-3.56 (m, 2H), 3.55-3.47 (m, 2H), 3.07-3.00 (m, 2H), 2.27-2.20 (m, 2H), 1.91-1.71 (m, 3H), 1.66-1.28 (m, 11H), 1.17 (d, J = 9.0 Hz, 3H), 0.71-0.56 (m, 2H). |
| 2-38# | 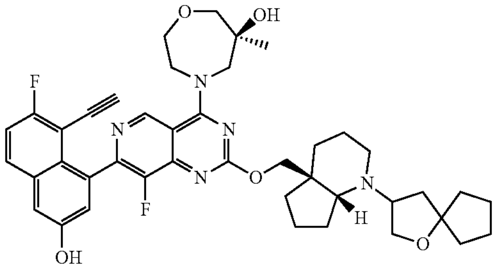 Diastereomer 2 | (6S)-4-(2-{[(4aS,7aR)-1-{1-oxaspiro[4.4] nonan-3-yl}-octahydro-1H-cyclopenta[b] pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 740.5 | $^1$H NMR (400 MHz, DMSO-$d_6$) δ ppm = 10.19 (brs, 1H), 9.43-9.26 (m, 1H), 8.01-7.93 (m, 1H), 7.52-7.43 (m, 1H), 7.39 (d, J = 2.5 Hz, 1H), 7.19 (dd, J = 9.5, 2.5 Hz, 1H), 5.25-5.03 (m, 1H), 4.65-4.52 (m, 1H), 4.42-4.21 (m, 2H), 4.12-3.77 (m, 6H), 3.63-3.50 (m, 3H), 3.12-3.05 (m, 1H), 2.96-2.86 (m, 1H), 2.41-2.34 (m, 1H), 2.02-1.89 (m, 2H), 1.83-1.36 (m, 17H), 1.35-1.22 (m, 3H), 1.17-1.13 (m, 3H). |

TABLE 2-continued

| # | Structure | IUPAC | LCMS (M + H)+ | $^1$H NMR |
|---|---|---|---|---|
| 2-39# | 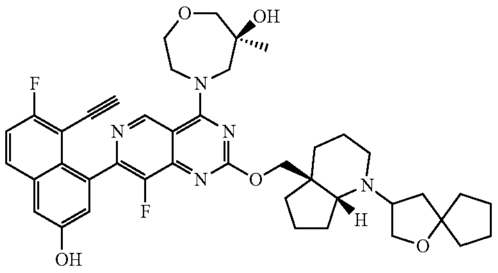 Diastereomer 1 | (6S)-4-(2-{[(4aS,7aR)-1-{1-oxaspiro[4.4]nonan-3-yl}-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 740.4 | $^1$H NMR (400 MHz, DMSO-$d_6$) δ ppm = 10.19 (brs, 1H), 9.43-9.26 (m, 1H), 8.01-7.93 (m, 1H), 7.52-7.43 (m, 1H), 7.39 (d, J = 2.5 Hz, 1H), 7.19 (dd, J = 9.5, 2.5 Hz, 1H), 5.25-5.03 (m, 1H), 4.65-4.52 (m, 1H), 4.42-4.21 (m, 3H), 4.12-3.77 (m, 6H), 3.63-3.50 (m, 1H), 3.12-3.05 (m, 2H), 2.96-2.86 (m, 1H), 2.41-2.34 (m, 1H), 2.02-1.89 (m, 2H), 1.83-1.36 (m, 17H), 1.35-1.22 (m, 2H), 1.17 (d, J = 9.0 Hz, 3H). |
| 2-40 | 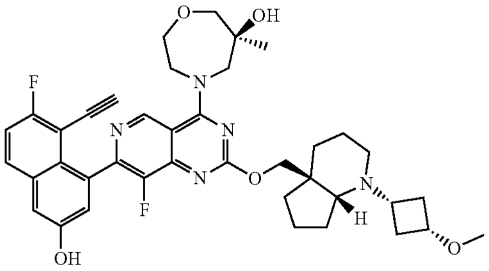 [SMILES: C#Cc1c(F)ccc2cc(O)cc(-c3ncc4c(N5CCOC[C@@](C)(O)C5)nc(OC[C@]56CCC[C@H]5N([C@H]5C[C@@H](OC)C5)CCC6)nc4c3F)c12] | (6S)-4-(2-{[(4aS,7aR)-1-[(1s,3s)-3-methoxycyclo-butyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 700.3 | $^1$H NMR (400 MHz, DMSO-$d_6$) δ ppm = 10.15-10.13 (m, 1H), 9.42-9.31 (m, 1H), 8.00-7.96 (m, 1H), 7.46 (t, J = 8.8 Hz, 1H), 7.39 (d, J = 2.8 Hz, 1H), 7.19 (dd, J = 10.0, 2.4 Hz, 1H), 5.23-5.06 (m, 1H), 4.62-4.61 (m, 1H), 4.40-3.87 (m, 10H), 3.09 (s, 3H), 3.08-3.01 (m, 2H), 2.14-2.10 (m, 1H), 1.94-1.93 (m, 5H), 1.58-1.33 (m, 11H), 1.18-1.14 (m, 3H). |
| 2-41# | 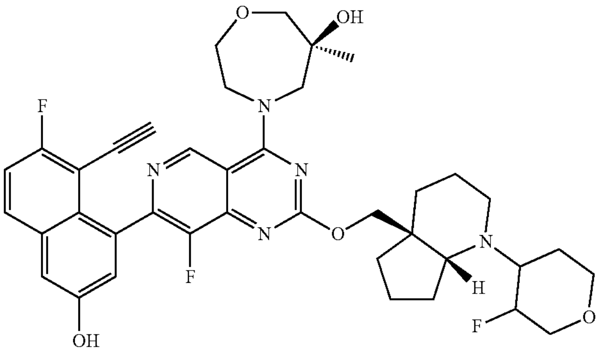 Diastereomer 3 | (6S)-4-(2-{[(4aS,7aR)-1-(3-fluorooxan-4-yl)-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 718.2 | $^1$H NMR (400 MHz, METHANOL-$d_4$) δ ppm = 9.49-9.38 (m, 1H), 7.89-7.85 (m, 1H), 7.36-7.23 (m, 3H), 4.74-4.62 (m, 1H), 4.58-4.42 (m, 4H), 4.29-4.21 (m, 1H), 4.07-3.81 (m, 5H), 3.74-3.61 (m, 2H), 3.46-3.41 (m, 2H), 3.27-3.22 (m, 2H), 2.82-2.71 (m, 3H), 2.17-2.11 (m, 1H), 1.82-1.62 (m, 8H), 1.59-1.49 (m, 3H), 1.34-1.27 (m, 3H). (Two exchangeable protons not appeared). |

TABLE 2-continued

| # | Structure | IUPAC | LCMS (M + H)+ | $^1$H NMR |
|---|---|---|---|---|
| 2-42# | 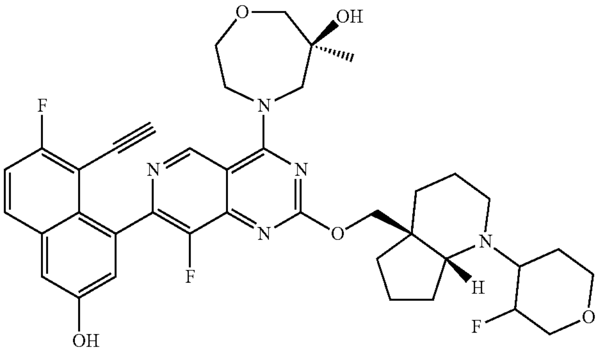 Diastereomer 2 | (6S)-4-(2-{[(4aS,7aR)-1-(3-fluorooxan-4-yl)-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 718.2 | $^1$H NMR (400 MHz, DMSO-$d_6$) δ ppm = 10.14-10.13 (m, 1H), 9.42-9.30 (m, 1H), 7.99-7.95 (m, 1H), 7.48-7.39 (m, 2H), 7.19 (dd, J = 9.2, 2.4 Hz, 1H), 5.23-5.06 (m, 1H), 4.81-4.60 (m, 2H), 4.35-4.32 (m, 1H), 4.22-3.88 (m, 9H), 3.59-3.34 (m, 4H), 3.19-3.17 (m, 1H), 2.74-2.72 (m, 1H), 2.64-2.61 (m, 1H), 1.97-1.72 (m, 3H), 1.58-1.46 (m, 10H), 1.17-1.15 (m, 3H). |
| 2-43# | 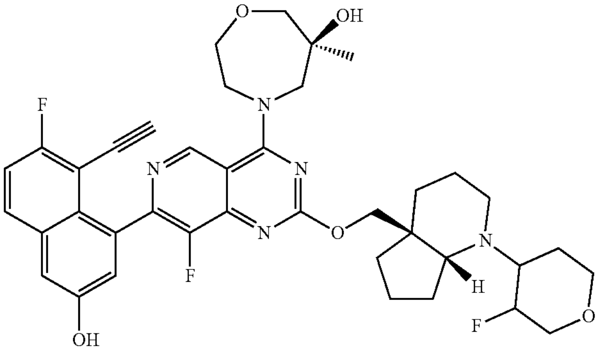 Diastereomer 1 | (6S)-4-(2-{[(4aS,7aR)-1-(3-fluorooxan-4-yl)-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 718.2 | $^1$H NMR (400 MHz, DMSO-$d_6$) δ ppm = 10.14 (s, 1H), 9.43-9.31 (m, 1H), 8.00-7.96 (m, 1H), 7.49-7.44 (m, 1H), 7.40-7.39 (m, 1H), 7.20 (dd, J = 9.4, 2.40 Hz 1H), 5.23-5.06 (m, 1H), 4.68-4.65 (m, 2H), 4.42-4.41 (m, 1H), 4.22-3.85 (m, 10H), 3.60-3.35 (m, 5H), 2.69-2.67 (m, 2H), 1.19-1.72 (m, 3H), 1.60-1.55 (m, 8H), 1.24-1.16 (m, 4H). |
| 2-44 | 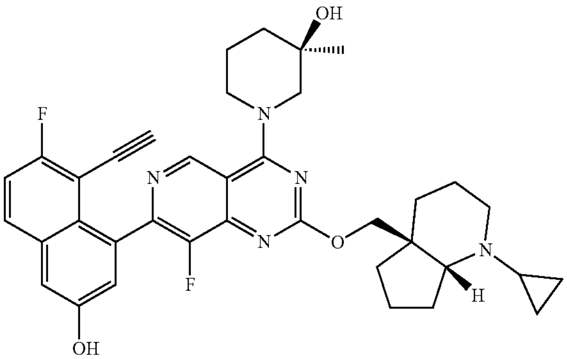 [SMILES: C#Cc1c(F)ccc2cc(O)cc(-c3ncc4c(N5CCC[C@@](C)(O)C5)nc(OC[C@]56CCC[C@H]5N(C5CC5)CCC6)nc4c3F)c12] | (3R)-1-(2-{[(4aS,7aR)-1-cyclopropyl-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-3-methylpiperidin-3-ol | 640.4 | $^1$H NMR(400 MHz, DMSO-$d_6$) δ ppm = 10.29-10.14 (m, 1H), 9.23-9.02 (m, 1H), 8.02-7.93 (m, 1H), 7.50-7.43 (m, 1H), 7.41-7.37 (m, 1H), 7.25-7.16 (m, 1H), 4.81-4.70 (m, 1H), 4.54-4.46 (m, 1H), 4.42-4.25 (m, 1H), 4.18-4.04 (m, 2H), 4.00-3.89 (m, 2H), 3.07-2.95 (m, 2H), 2.65-2.56 (m, 1H), 2.07-1.96 (m, 1H), 1.81-1.27 (m, 14H), 1.25-1.22 (m, 1H), 1.20-1.12 (m, 3H), 0.46-0.32 (m, 2H), 0.31-0.13 (m, 2H). |

TABLE 2-continued

| # | Structure | IUPAC | LCMS (M + H)+ | 1H NMR |
|---|---|---|---|---|
| 2-45 | 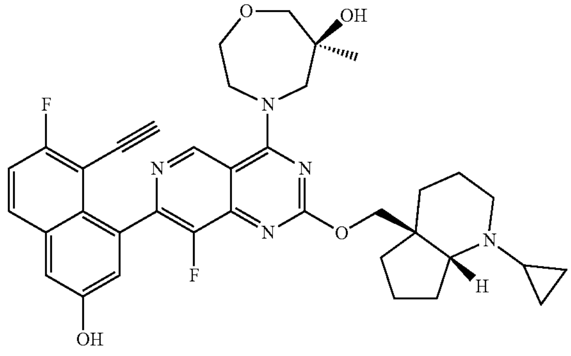 [SMILES: C#Cc1c(F)ccc2cc(O)cc(-c3ncc4c(N5CCOC[C@@](C)(O)C5)nc(OC[C@]56CCC[C@H]5N(C5CC5)CCC6)nc4c3F)c12] | (6S)-4-(2-{[(4aS,7aR)-1-cyclopropyl-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 656.2 | $^1$H NMR (400 MHz, DMSO-$d_6$) δ ppm = 10.23-10.10 (m, 1H), 9.42-9.29 (m, 1H), 8.01-7.93 (m, 1H), 7.49-7.43 (m, 1H), 7.39 (d, J = 2.5 Hz, 1H), 7.21-7.17 (m, 1H), 5.24-5.04 (m, 1H), 4.52-4.38 (m, 1H), 4.37-4.26 (m, 1H), 4.21-3.78 (m, 6H), 3.62-3.56 (m, 2H), 3.54-3.48 (m, 1H), 3.06-2.99 (m, 1H), 2.64-2.56 (m, 1H), 2.05-1.98 (m, 1H), 1.77-1.69 (m, 2H), 1.66-1.28 (m, 8H), 1.26-1.22 (m, 1H), 1.20-1.12 (m, 3H), 0.45-0.33 (m, 2H), 0.29-0.13 (m, 2H). |
| 2-46 | 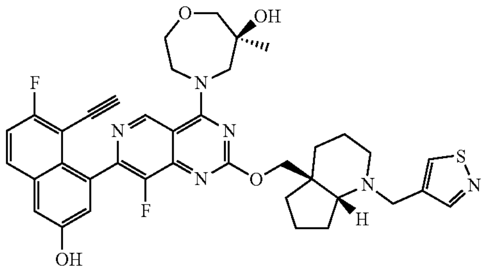 [SMILES: C#Cc1c(F)ccc2cc(O)cc(-c3ncc4c(N5CCOC[C@@](C)(O)C5)nc(OC[C@]56CCC[C@H]5N(Cc5cnsc5)CCC6)nc4c3F)c12] | (6S)-4-(2-{[(4aS,7aR)-1-[(1,2-thiazol-4-yl)methyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 713.2 | $^1$H NMR (400 MHz, DMSO-$d_6$) δ ppm = 10.14 (d, J = 3.0 Hz, 1H), 9.44-9.30 (m, 1H), 8.78-8.74 (m, 1H), 8.44-8.41 (m, 1H), 8.00-7.93 (m, 1H), 7.49-7.43 (m, 1H), 7.40-7.38 (m, 1H), 7.23-7.17 (m, 1H), 5.25-5.04 (m, 1H), 4.58-4.53 (m, 1H), 4.47-4.30 (m, 2H), 4.26-4.21 (m, 1H), 4.18-4.01 (m, 3H), 4.01-3.94 (m, 2H), 3.92-3.79 (m, 2H), 3.67-3.63 (m, 2H), 3.61-3.58 (m, 1H), 2.92-2.84 (m, 1H), 2.43-2.36 (m, 1H), 1.98-1.86 (m, 1H), 1.81-1.69 (m, 1H), 1.63-1.51 (m, 6H), 1.51-1.33 (m, 2H), 1.20-1.14 (m, 3H). |
| 2-47 | 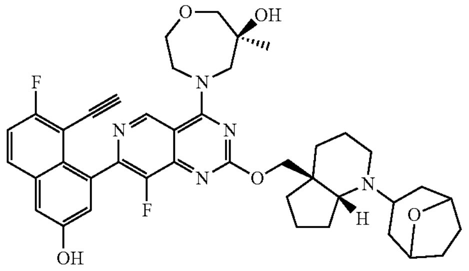 Diastereomer Mixture | (6S)-4-(2-{[(4aS,7aR)-1-{8-oxabicyclo[3.2.1]octan-3-yl}-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 726.2 | $^1$H NMR (400 MHz, DMSO-$d_6$) δ ppm = 10.24-10.13 (m, 1H), 9.42-9.28 (m, 1H), 8.16 (s, 1H), 7.97 (dd, J = 9.3, 5.8 Hz, 1H), 7.46 (t, J = 9.0 Hz, 1H), 7.39 (d, J = 2.5 Hz, 1H), 7.19 (dd, J = 10.0, 2.5 Hz, 1H), 5.26-5.04 (m, 1H), 4.63-4.57 (m, 1H), 4.35-4.24 (m, 3H), 4.20-4.15 (m, 2H), 4.10-3.93 (m, 3H), 3.92-3.85 (m, 3H), 3.63-3.57 (m, 2H), 3.11-3.04 (m, 1H), 1.94-1.83 (m, 1H), 1.77-1.68 (m, 3H), 1.66-1.51 (m, 9H), 1.49-1.36 (m, 8H), 1.33-1.22 (m, 1H), 1.18-1.14 (m, 3H). Formic acid salt. 1 proton excess for formic acid. (Diastereomeric mixture) |

TABLE 2-continued

| # | Structure | IUPAC | LCMS (M + H)$^+$ | $^1$H NMR |
|---|---|---|---|---|
| 2-48 | 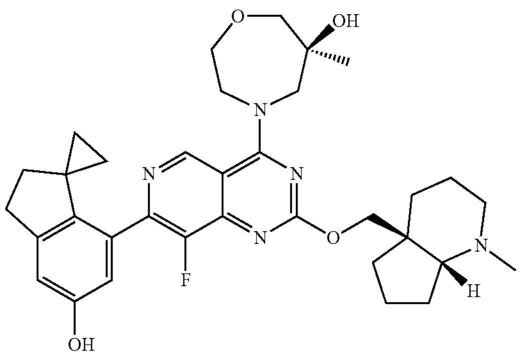 [SMILES: CN1CCC[C@@]2(COc3nc(N4CCOC[C@@](C)(O)C4)c4cnc(-c5cc(O)cc6c5C5(CC6)CC5)c(F)c4n3)CCC[C@@H]12] | (6S)-4-(2-{[(4aS,7aR)-1-methyl-octahydro-1H-cyclopenta[b]pyridin-4a-yl]methoxy}-8-fluoro-7-{5'-hydroxy-2',3'-dihydrospiro[cyclopropane-1,1'-inden]-7'-yl}pyrido[4,3-d]pyrimidin-4-yl)-6-methyl-1,4-oxazepan-6-ol | 604.4 | $^1$H NMR (400 MHz, DMSO-$d_6$) δ ppm = 9.35 (s, 2H), 6.74 (d, J = 2.4 Hz, 1H), 6.36 (d, J = 2.4 Hz, 1H), 5.15 (s, 1H), 4.46 (d, J = 10.8 Hz, 1H), 4.40-4.20 (m, 1H), 4.19-4.10 (m, 2H), 4.10-3.90 (m, 3H), 3.85-3.75 (m. 2H), 3.6-3.5 (m, 2H), 2.91 (t, J = 7.6 Hz, 2H), 2.66 (t, J = 6.0 Hz, 1H), 2.51-2.41 (m, 1H), 2.38-2.2 (m, 4H), 1.95 (t, J = 7.6 Hz, 2H), 1.90-1.71 (m, 2H), 1.65-1.51 (m, 7H), 1.42-1.31 (m, 1H), 1.15 (s, 3H), 0.51-0.39 (m, 4H). |
| 2-49$^{\#}$ | 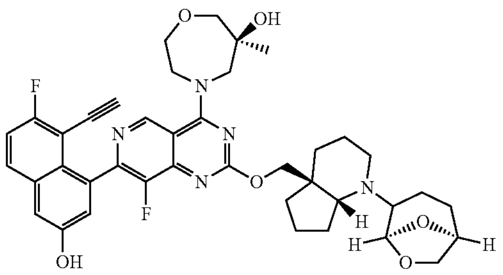 Diastereomer 2 | (6S)-4-(2-{[(4aS,7aR)-1-[(1S,5R)-6,8-dioxabicyclo[3.2.1]octan-4-yl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 728.2 | $^1$H NMR (400 MHz, DMSO-$d_6$) δ ppm = 10.14 (s, 1H), 9.41-9.30 (m, 1H), 7.99-7.96 (m, 1H), 7.46 (t, J = 9.2 Hz, 1H), 7.39 (d, J = 2.4 Hz, 1H), 7.22-7.15 (m, 1H), 5.23 (d, J = 4.5 Hz, 2H), 4.69-4.61 (m, 1H), 4.42-4.41 (m, 2H), 4.25-4.14 (m, 2H), 4.07-4.03 (m, 2H), 3.99 (s, 1H), 3.91-3.86 (m, 2H), 3.79 (d, J = 7.0 Hz, 1H), 3.61-3.52 (m, 3H), 3.09-2.99 (m, 2H), 2.80-2.77 (m, 1H), 1.96-1.84 (m, 2H), 1.77-1.65 (m, 4H), 1.61-1.48 (m, 7H), 1.47-1.34 (m, 1H), 1.27-1.24 (m, 1H), 1.18-1.15 (m, 3H). |
| 2-50$^{\#}$ | 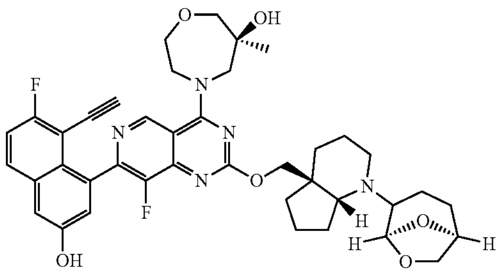 Diastereomer 1 | (6S)-4-(2-{[(4aS,7aR)-1-[(1S,5R)-6,8-dioxabicyclo[3.2.1]octan-4-yl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 728.2 | $^1$H NMR (400 MHz, METHANOL-$d_4$) δ ppm = 9.48-9.34 (m, 1H), 7.78-7.74 (m, 1H), 7.36-7.29 (m, 1H), 7.21 (d, J = 8.80 Hz, 1H), 7.24-7.21 (dd, J = 12.2, 2.40 Hz, 1H), 5.46 (s, 1H), 4.54-4.35 (m, 5H), 4.39-4.32 (m, 2H), 3.80-3.62 (m, 3H), 3.61-3.54 (m, 4H), 3.38-3.36 (m, 1H), 2.88-2.75 (m, 2H), 2.49-2.48 (m, 1H), 2.06-1.29 (m, 17H). |

TABLE 2-continued

| # | Structure | IUPAC | LCMS (M + H)+ | $^1$H NMR |
|---|---|---|---|---|
| 2-51 | 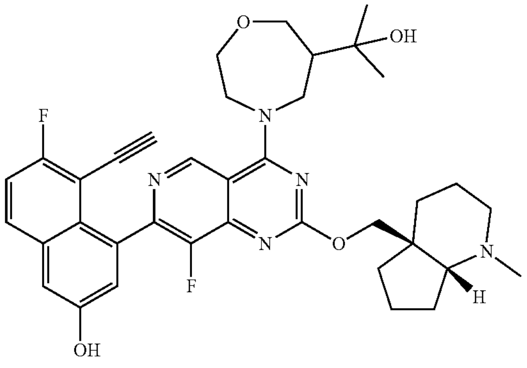 Diastereomer 1 | 4-(2-{[(4aS,7aR)-1-methyl-octahydro-1H-cyclopenta[b]pyridin-4a-yl]methoxy}-8-fluoro-4-[6-(2-hydroxypropan-2-yl)-1,4-oxazepan-4-yl]pyrido[4,3-d]pyrimidin-7-yl)-5-ethynyl-6-fluoronaphthalen-2-ol | 658.2 | $^1$H NMR (400 MHz, METHANOL-$d_4$) δ ppm = 9.19-9.18 (m, 1H), 7.90-7.86 (m, 1H), 7.38-7.32 (m, 2H), 7.21-7.25 (m, 1H), 4.94-4.91 (m, 1H), 4.58-4.54 (m, 2H), 4.37-4.32 (m, 1H), 4.09-4.01 (m, 3H), 3.96-3.81 (m, 3H), 3.51-3.50 (m, 1H), 3.04-3.02 (m, 1H), 2.81-2.79 (m, 1H), 2.48-2.44 (m, 4H), 1.96-1.89 (m, 3H), 1.76-1.61 (m, 6H), 1.42-1.31 (m, 8H). (Two exchangeable protons not appeared). |
| 2-52 | 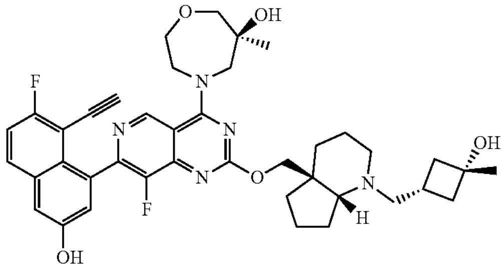 [SMILES: C#Cc1c(F)ccc2cc(O)cc(-c3ncc4c(N5CCOC[C@@](C)(O)C5)nc(OC[C@]56CCC[C@H]5N(C[C@H]5C[C@@](C)(O)C5)CCC6)nc4c3F)c12] | (6S)-4-(2-{[(4aS,7aR)-1-{[(1r,3s)-3-hydroxy-3-methylcyclobutyl]methyl}-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 714.4 | $^1$H NMR (400 MHz, DMSO-$d_6$) δ ppm = 10.18-10.11 (m, 1H), 9.45-9.30 (m, 1H), 8.01-7.94 (m, 1H), 7.50-7.43 (m, 1H), 7.41-7.37 (m, 1H), 7.23-7.15 (m, 1H), 5.25-5.04 (m, 1H), 4.72-4.69 (m, 1H), 4.57-4.51 (m, 1H), 4.48-4.30 (m, 2H), 4.22-3.80 (m, 7H), 3.64-3.49 (m, 2H), 3.32 (s, 1H), 2.90-2.81 (m, 1H), 2.42-2.35 (m, 3H), 2.01-1.77 (m, 1H), 1.76-1.66 (m, 1H), 1.64-1.39 (m, 10H), 1.37-1.29 (m, 1H), 1.25-1.21 (m, 1H), 1.19-1.14 (m, 6H). |
| 2-53 | 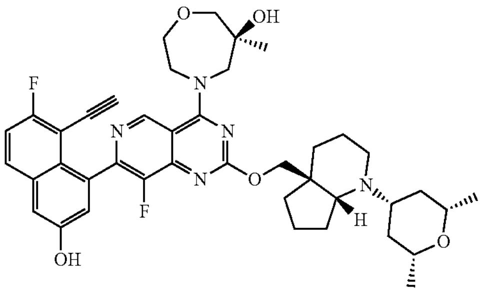 [SMILES: C#Cc1c(F)ccc2cc(O)cc(-c3ncc4c(N5CCOC[C@@](C)(O)C5)nc(OC[C@]56CCC[C@H]5N([C@H]5C[C@@H](C)O[C@@H](C)C5)CCC6)nc4c3F)c12] | (6S)-4-(2-{[(4aS,7aR)-1-[(2R,4r,6S)-2,6-dimethyl-oxan-4-yl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 728.4 | $^1$H NMR (400 MHz, DMSO-$d_6$) δ ppm = 10.15-10.12 (m, 1H), 9.47-9.30 (m, 1H), 8.02-7.93 (m, 1H), 7.49-7.42 (m, 1H), 7.41-7.38 (m, 1H), 7.22-7.15 (m, 1H), 5.25-5.01 (m, 1H), 4.59-4.53 (m, 1H), 4.49-4.30 (m, 2H), 4.14-3.92 (m, 4H), 3.90-3.71 (m, 3H), 3.64-3.49 (m, 3H), 3.21-3.13 (m, 1H), 2.80-2.73 (m, 1H), 2.20-2.10 (m, 1H), 1.96-1.81 (m, 3H), 1.77-1.26 (m, 10H), 1.21-1.12 (m, 5H), 0.99-0.95 (m, 3H), 0.94-0.89 (m, 3H). |

TABLE 2-continued

| # | Structure | IUPAC | LCMS (M + H)+ | 1H NMR |
|---|---|---|---|---|
| 2-54 | 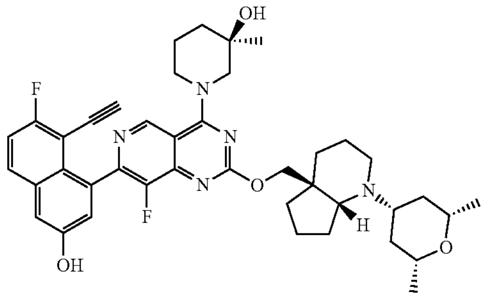 [SMILES: C#Cc1c(F)ccc2cc(O)cc(-c3ncc4c(N5CCC[C@@](C)(O)C5)nc(OC[C@]56CCC[C@H]5N([C@H]5C[C@@H](C)O[C@@H](C)C5)CCC6)nc4c3F)c12] | (3R)-1-(2-{[(4aS,7aR)-1-[(2R,4r,6S)-2,6-dimethyloxan-4-yl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-3-methylpiperidin-3-ol | 712.2 | 1H NMR (400 MHz, METHANOL-$d_4$) δ ppm = 9.21-9.00 (m, 1H), 7.89-7.83 (m, 1H), 7.37-7.28 (m, 2H), 7.27-7.19 (m, 1H), 4.46-4.24 (m, 2H), 3.69-3.63 (m, 2H), 3.55-3.30 (m, 5H), 2.25-1.97 (m, 7H), 2.74-2.63 (m, 1H), 2.32-2.22 (m, 1H), 1.87-1.52 (m, 9H), 1.77-1.26 (m, 9H), 0.97-0.89 (m, 4H), Two exchangeable protons not appeared). |
| 2-55 | 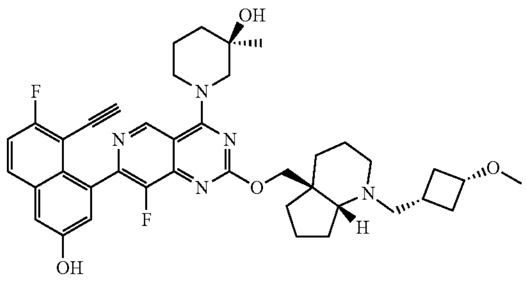 [SMILES: C#Cc1c(F)ccc2cc(O)cc(-c3ncc4c(N5CCC[C@@](C)(O)C5)nc(OC[C@]56CCC[C@H]5N(C[C@H]5C[C@@H](OC)C5)CCC6)nc4c3F)c12] | (3R)-1-(2-{[(4aS,7aR)-1-{[(1s,3s)-3-methoxycyclo-butyl]methyl}-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-3-methylpiperidin-3-ol | 698.2 | 1H NMR (400 MHz, METHANOL-$d_4$) δ ppm = 9.28-9.07 (m, 1H), 7.87 (dd, J = 9.0, 5.5 Hz, 1H), 7.38-7.23 (m, 3H), 4.75-4.51 (m, 2H), 4.49-4.29 (m, 2H), 3.82-3.71 (m, 1H), 3.70-3.62 (m, 1H), 3.59-3.55 (m, 1H), 3.50-3.40 (m, 1H), 3.24-3.09 (m, 6H), 2.56-2.42 (m, 2H), 2.36-2.03 (m, 8H), 1.92-1.63 (m, 11H), 1.33-1.27 (m, 3H). (Two exchangeable protons not appeared) |
| 2-56 | 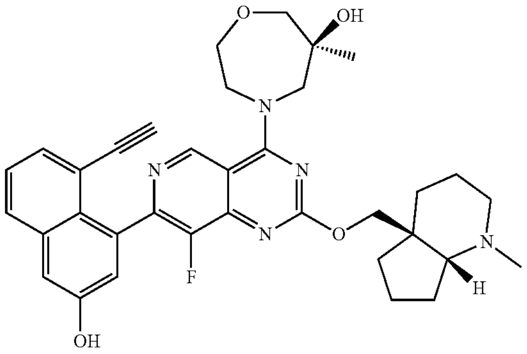 [SMILES: C#Cc1cccc2cc(O)cc(-c3ncc4c(N5CCOC[C@@](C)(O)C5)nc(OC[C@]56CCC[C@H]5N(C)CCC6)nc4c3F)c12] | (6S)-4-(2-{[(4aS,7aR)-1-methyl-octahydro-1H-cyclopenta[b]pyridin-4a-yl]methoxy}-7-(8-ethynyl-3-hydroxy-naphthalen-1-yl)-8-fluoropyrido[4,3-d]pyrimidin-4-yl)-6-methyl-1,4-oxazepan-6-ol | 612.2 | 1H NMR (400 MHz, METHANOL-$d_4$) δ ppm = 9.52-9.41 (m, 1H), 8.52 (s, 1H), 7.85-7.83 (m, 1H), 7.54-7.52 (m, 1H), 7.43-7.39 (m, 1H), 7.21-7.18 (m, 1H), 4.66-4.54 (m, 4H), 4.32-4.25 (m, 1H), 4.1-4.0 (m, 2H), 3.95-3.91 (m, 2H), 3.8-3.6 (m, 3H), 3.21-3.0 (m, 2H), 2.67 (s, 3H), 2.09 (s, 2H), 1.95-1.94 (m, 2H), 1.92-1.74 (m, 6H), 1.31-1.28 (m, 3H). (Two exchangeable protons not appeared). |

TABLE 2-continued

| # | Structure | IUPAC | LCMS (M + H)+ | $^1$H NMR |
|---|---|---|---|---|
| 2-57 | 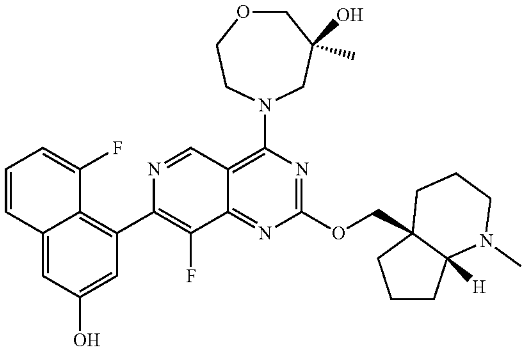 [SMILES: CN1CCC[C@@]2(COc3nc(N4CCOC[C@@](C)(O)C4)c4cnc(-c5cc(O)cc6cccc(F)c56)c(F)c4n3)CCC[C@@H]12] | (6S)-4-(2-{[(4aS,7aR)-1-methyl-octahydro-1H-cyclopenta[b]pyridin-4a-yl]methoxy}-8-fluoro-7-(8-fluoro-3-hydroxy-naphthalen-1-yl)pyrido[4,3-d]pyrimidin-4-yl)-6-methyl-1,4-oxazepan-6-ol | 606.2 | $^1$H NMR (400 MHz, METHANOL-$d_4$) δ ppm = 9.45 (s, 1H), 7.50 (d, J = 8.1 Hz, 1H), 7.32-7.26 (m, 1H), 7.24-7.23 (m, 1H), 7.10 (d, J = 2.4 Hz, 1H), 6.85-6.80 (m, 1H) 4.49-4.53 (m, 2H), 4.49-4.42 (m, 2H), 4.33-4.30 (m, 1H), 4.20-4.00 (m, 1H), 3.95-3.87 (m, 2H), 3.59-3.51 (m, 2H), 3.0-2.8 (m, 2H), 2.61 (s, 3H), 2.1-1.9 (m, 2H), 1.84-1.82 (m, 3H), 1.75-1.70 (m, 6H), 1.19 (d, J = 2.8 Hz, 3H). (Two exchangeable protons not appeared). |
| 2-58 | 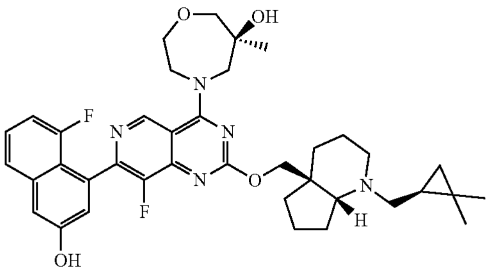 [SMILES: CC1(C)C[C@@H]1CN1CCC[C@@]2(COc3nc(N4CCOC[C@@](C)(O)C4)c4cnc(-c5cc(O)cc6cccc(F)c56)c(F)c4n3)CCC[C@@H]12] | (6S)-4-(2-{[(4aS,7aR)-1-{[(1S)-2,2-dimethylcyclo-propyl]methyl}-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 698.4 | $^1$H NMR (400 MHz, DMSO-$d_6$) δ ppm = 10.19-10.13 (m, 1H), 9.46-9.31 (m, 1H), 8.01-7.95 (m, 1H), 7.51-7.43 (m, 1H), 7.42-7.38 (m, 1H), 7.23-7.16 (m, 1H), 5.26-5.05 (m, 1H), 4.67-4.57 (m, 1H), 4.47-4.31 (m, 2H), 4.26-4.18 (m, 1H), 4.17-4.01 (m, 2H), 4.00-3.93 (m, 2H), 3.91-3.81 (m, 2H), 3.63-3.50 (m, 3H), 1.95-1.85 (m, 2H), 1.81-1.70 (m, 1H), 1.69-1.47 (m, 9H), 1.45-1.33 (m, 1H), 1.20-1.14 (m, 3H), 1.03-0.97 (m, 6H), 0.69-0.60 (m, 1H), 0.47-0.40 (m, 1H), 0.09-0.03 (m, 1H). |
| 2-59 | 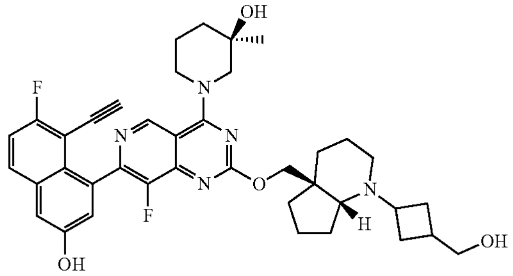 Diastereomer 1 | (3R)-1-(2-{[(4aS,7aR)-1-[3-(hydroxymethyl)cyclobutyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-3-methylpiperidin-3-ol | 684.3 | $^1$H NMR (400 MHz, DMSO-$d_6$) δ ppm = 10.21-10.17 (m, 1H), 9.22-9.04 (m, 1H), 7.97-7.91 (m, 1H), 7.49-7.42 (m, 1H), 7.40-7.37 (m, 1H), 7.21 (dd, J = 19.0, 2.5 Hz, 1H), 6.52 (s, 1H), 4.79-4.71 (m, 1H), 4.62-4.59 (m, 1H), 4.42-4.29 (m, 2H), 4.20-4.07 (m, 2H), 4.00-3.91 (m, 2H), 3.61-3.52 (m, 3H), 3.08-2.99 (m, 1H), 2.87-2.77 (m, 1H), 2.25-2.15 (m, 1H), 2.05-1.79 (m, 6H), 1.76-1.38 (m, 11H), 1.33-1.22 (m, 2H), 1.20-1.13 (m, 3H). |

TABLE 2-continued

| # | Structure | IUPAC | LCMS (M + H)+ | $^1$H NMR |
|---|---|---|---|---|
| 2-60 | 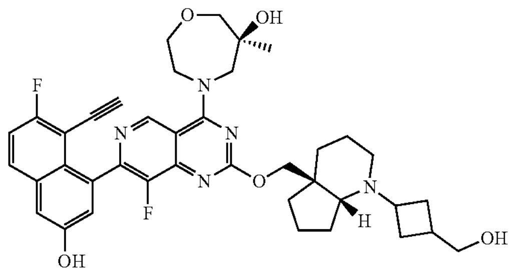 Diastereomer 1 | (6S)-4-(2-{[(4aS,7aR)-1-[3-(hydroxymethyl)cyclobutyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 700.4 | $^1$H NMR (400 MHz, DMSO-$d_6$) δ ppm = 10.25-10.16 (m, 1H), 9.45-9.29 (m, 1H), 8.00-7.94 (m, 1H), 7.50-7.42 (m, 1H), 7.39 (d, J = 2.5 Hz, 1H), 7.23-7.17 (m, 1H), 5.27-5.07 (m, 1H), 4.61-4.58 (m, 1H), 4.47-4.29 (m, 2H), 4.24-4.02 (m, 4H), 4.00-3.78 (m, 4H), 3.03-2.96 (m, 1H), 2.82-2.73 (m, 2H), 2.22-2.11 (m, 2H), 2.04-1.78 (m, 5H), 1.75-1.34 (m, 10H), 1.33-1.22 (m, 2H), 1.21-1.12 (m, 3H). |
| 2-61 | 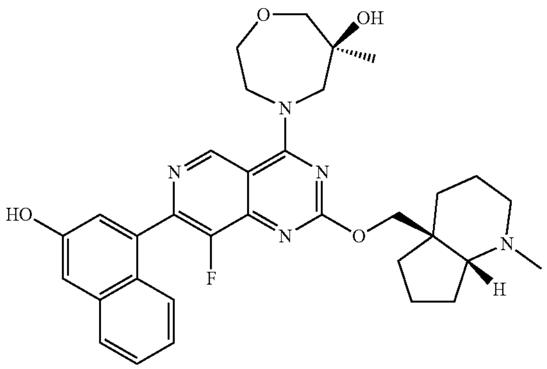 [SMILES: CN1CCC[C@@]2(COc3nc(N4CCOC[C@@](C)(O)C4)c4cnc(-c5cc(O)cc6ccccc56)c(F)c4n3)CCC[C@@H]12] | (6S)-4-(2-{[(4aS,7aR)-1-methyl-octahydro-1H-cyclopenta[b]pyridin-4a-yl]methoxy}-8-fluoro-7-(3-hydroxy-naphthalen-1-yl)pyrido[4,3-d]pyrimidin-4-yl)-6-methyl-1,4-oxazepan-6-ol | 588.2 | $^1$H NMR (400 MHz, METHANOL-$d_4$) δ ppm = 9.55-9.52 (m, 1H), 7.67 (d, J = 8.4 Hz, 1H), 7.43 (d, J = 8.4 Hz, 1H), 7.34 (t, J = 8.4 Hz, 1H), 7.21 (s, 1H), 7.16-7.13 (m, 2H), 4.49-4.53 (m, 2H), 4.53-4.49 (m, 1H), 4.32-4.25 (m, 1H), 4.20-4.15 (m, 1H), 3.91-3.80 (m, 4H), 3.62-3.59 (m, 2H), 2.83 (s, 1H), 2.77 (s, 3H), 2.35-2.0 (m, 3H), 1.90-1.61 (m, 7H), 1.20 (s, 4H). (Two exchangeable protons not appeared). |
| 2-62 | 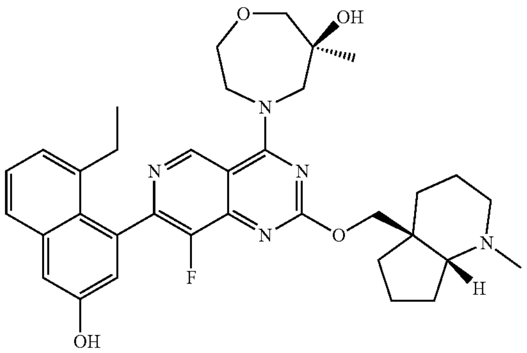 [SMILES: CCc1cccc2cc(O)cc(-c3ncc4c(N5CCOC[C@@](C)(O)C5)nc(OC[C@]56CCC[C@H]5N(C)CCC6)nc4c3F)c12] | (6S)-4-(2-{[(4aS,7aR)-1-methyl-octahydro-1H-cyclopenta[b]pyridin-4a-yl]methoxy}-7-(8-ethyl-3-hydroxy-naphthalen-1-yl)-8-fluoropyrido[4,3-d]pyrimidin-4-yl)-6-methyl-1,4-oxazepan-6-ol | 616.2 | $^1$H NMR (400 MHz, METHANOL-$d_4$) δ ppm = 9.52 (m, 1H), 7.63 (d, J = 7.0 Hz, 1H), 7.36 (t, J = 7.8 Hz, 1H), 7.29 (d, J = 3.0 Hz, 1H), 7.16 (d, J = 6.5 Hz, 1H), 7.02 (dd, J = 14.3, 2.8 Hz, 1H), 4.58-4.47 (m, 1H), 4.40-4.34 (m, 1H), 4.25-4.14 (m, 1H), 4.08-3.90 (m, 3H), 3.62-3.60 (m, 2H), 3.49-3.46 (m, 1H), 3.14-3.12 (m, 1H), 2.44-2.21 (m, 4H), 1.98-195 (m, 1H), 1.91-1.84 (m, 3H), 1.80-1.70 (m, 6H), 1.64-1.58 (m, 2H), 1.29-1.28 (m, 4H), 0.93-0.88 (m, 4H). (Two exchangeable protons not appeared). |

TABLE 2-continued

| # | Structure | IUPAC | LCMS (M + H)+ | 1H NMR |
|---|---|---|---|---|
| 2-63 | 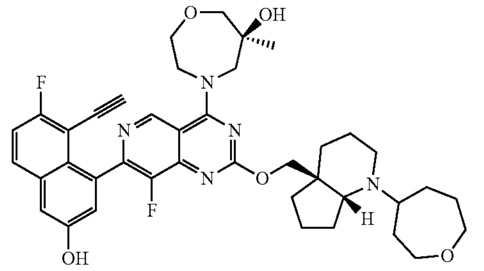 Diastereomer Mixture | (6S)-4-(2-{[(4aS,7aR)-1-(oxepan-4-yl)-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 714.2 | $^1$H NMR (400 MHz, DMSO-$d_6$) δ ppm = 10.14-10.15 (m, 1H), 9.42-9.29 (m, 1H), 7.98 (dd, J = 9.3, 5.8 Hz, 1H), 7.50-7.43 (m, 1H), 7.39 (d, J = 2.5 Hz, 1H), 7.19 (dd, J = 9.0, 2.5 Hz, 1H), 5.23-5.04 (m, 1H), 4.63-4.54 (m, 1H), 4.46-4.28 (m, 1H), 4.27-4.14 (m, 1H), 4.12-4.01 (m, 2H), 4.01-3.93 (m, 2H), 3.91-3.85 (m, 2H), 3.64-3.42 (m, 7H), 3.12-2.98 (m, 1H), 2.02-1.90 (m, 2H), 1.86-1.31 (m, 15H), 1.27-1.20 (m, 1H), 1.19-1.12 (m, 3H). (Diastereomeric mixture) |
| 2-64 | 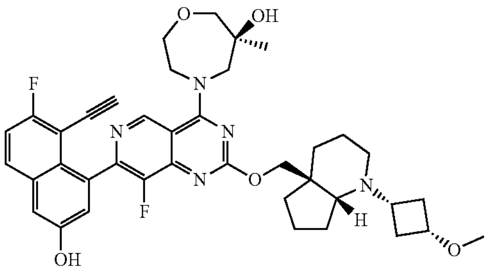 [SMILES: C#Cc1c(F)ccc2cc(O)cc(-c3ncc4c(N5CCOC[C@@](C)(O)C5)nc(OC[C@]56CCC[C@H]5N([C@H]5C[C@@H](OC)C5)CCC6)nc4c3F)c12] | (6S)-4-(2-{[(4aS,7aR)-1-[(1s,3s)-3-methoxycyclo-butyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 700.2 | $^1$H NMR (400 MHz, DMSO-$d_6$) δ ppm = 10.15 (m, 1H), 9.46-9.29 (m, 1H), 8.02-7.93 (m, 1H), 7.50-7.43 (m, 1H), 7.41-7.38 (m, 1H), 7.23-7.16 (m, 1H), 5.26-5.04 (m, 1H), 4.65-4.51 (m, 1H), 4.46-4.23 (m, 3H), 4.21-3.84 (m, 6H), 3.64-3.50 (m, 3H), 3.14-3.04 (m, 4H), 2.43-2.23 (m, 3H), 1.94-1.26 (m, 13H), 1.20-1.13 (m, 3H). |
| 2-65 | 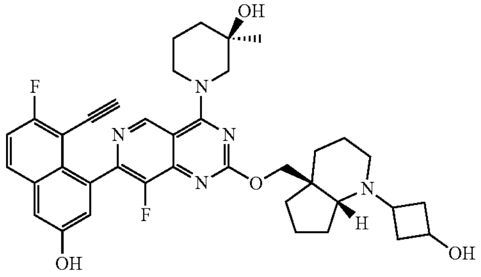 Diastereomer 1 | (3R)-1-(2-{[(4aS,7aR)-1-(3-hydroxycyclo-butyl)-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-3-methylpiperidin-3-ol | 670.2 | $^1$H NMR (400 MHz, METHANOL-$d_4$) δ ppm = 9.22-9.02 (m, 1H), 7.90-7.81 (m, 1H), 7.37-7.28 (m, 2H), 7.27-7.20 (m, 1H), 4.47-4.40 (m, 1H), 4.36-4.24 (m, 1H), 3.99-3.89 (m, 1H), 3.69-3.62 (m, 1H), 3.51-3.34 (m, 2H), 3.19-3.11 (m, 2H), 2.78-2.67 (m, 1H), 2.56-2.41 (m, 3H), 2.27-2.13 (m, 1H), 2.03-1.95 (m, 1H), 1.91-1.56 (m, 14H), 1.53-1.42 (m, 1H), 1.33-1.23 (m, 4H). (Three exchangeable protons not appeared). |

TABLE 2-continued

| # | Structure | IUPAC | LCMS (M + H)+ | 1H NMR |
|---|---|---|---|---|
| 2-66 | 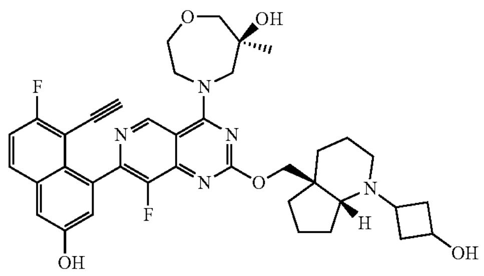 Diastereomer 1 | (6S)-4-(2-{[(4aS,7aR)-1-(3-hydroxycyclo-butyl)-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 686.3 | $^1H$ NMR (400 MHz, METHANOL-$d_4$) δ ppm = 9.45-9.41 (m, 1H), 7.90-7.86 (m, 1H), 7.38-7.32 (m, 2H), 7.24 (dd, J = 13.2, 2.4 Hz, 1H), 4.66-4.47 (m, 4H), 4.28-4.21 (m, 1H), 4.09-3.91 (m, 4H), 3.74-3.65 (m, 2H), 3.54-3.46 (m, 1H), 3.27-3.19 (m, 1H), 2.64-2.55 (m, 2H), 2.51-2.43 (m, 2H), 2.38-2.31 (m, 1H), 2.01-1.92 (m, 1H), 1.83-1.62 (m, 6H), 1.61-1.52 (m, 3H), 1.49-1.44 (m, 1H), 1.32-1.29 (m, 4H). (Three exchangeable protons not appeared). |
| 2-67# | 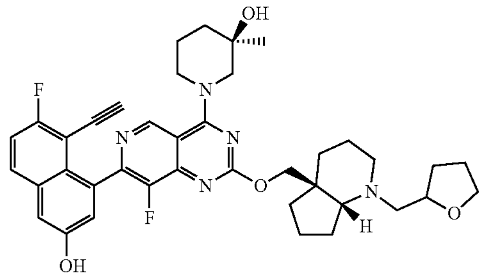 Diastereomer 2 | (3R)-1-(2-{[(4aS,7aR)-1-[(oxolan-2-yl)methyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-3-methylpiperidin-3-ol | 684.2 | $^1H$ NMR (400 MHz, METHANOL-$d_4$) δ ppm = 9.25-9.08 (m, 1H), 7.91-7.87 (m, 1H), 7.38-7.20 (m, 3H), 4.79-4.63 (m, 2H), 4.48-4.08 (m, 5H), 3.91-3.77 (m, 3H), 3.75-3.60 (m, 2H), 3.28-3.19 (m, 1H), 2.32-2.07 (m, 5H), 2.05-1.71 (m, 13H), 1.66-1.46 (m, 2H), 1.36-1.17 (m, 3H). (Two exchangeable protons not appeared). |
| 2-69 | 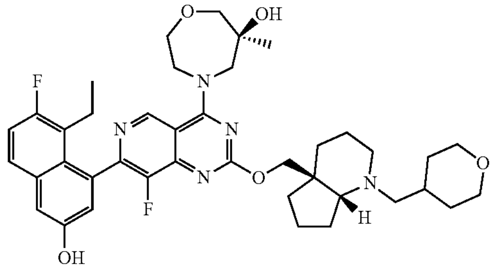 [SMILES: CCc1c(F)ccc2cc(O)cc(-c3ncc4c(N5CCOC[C@@](C)(O)C5)nc(OC[C@]56CCC[C@H]5N(CC5CCOCC5)CCC6)nc4c3F)c12] | (6S)-4-(2-{[(4aS,7aR)-1-[(oxan-4-yl)methyl]-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 718.2 | $^1H$ NMR (400 MHz, DMSO-$d_6$) δ ppm = 9.93-9.92 (m, 1H), 9.52-9.47 (m, 1H), 7.79-7.76 (m, 1H), 7.38-7.33 (m, 2H), 7.04-7.01 (m, 1H), 5.16-5.12 (m, 1H), 4.61-4.55 (m, 1H), 4.48-4.32 (m, 2H), 4.21-3.68 (m, 8H), 3.58-3.52 (m, 2H), 3.22-3.18 (m, 2H), 2.92-2.89 (m, 2H), 2.34-2.33 (m, 3H), 2.20-2.18 (m, 3H), 2.01-1.51 (m, 13H), 1.17-1.16 (m, 3H), 0.74 (t, J = 7.6 Hz, 3H). |

TABLE 2-continued

| # | Structure | IUPAC | LCMS (M + H)$^+$ | $^1$H NMR |
|---|---|---|---|---|
| 2-70 | 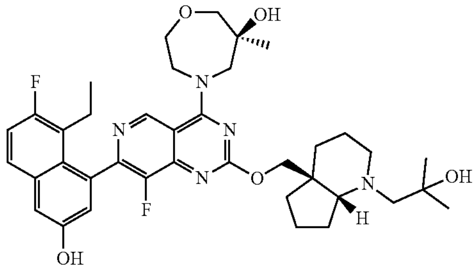 [SMILES: CCc1c(F)ccc2cc(O)cc(-c3ncc4c(N5CCOC[C@@](C)(O)C5)nc(OC[C@]56CCC[C@H]5N(CC(C)(C)O)CCC6)nc4c3F)c12] | (6S)-4-(2-{[(4aS,7aR)-1-(2-hydroxy-2-methylpropyl)-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 692.2 | $^1$H NMR (400 MHz, DMSO-$d_6$) δ ppm = 9.93-9.91 (m, 1H), 9.48 (s, 1H), 7.79-7.75 (m, 1H), 7.39-7.33 (m, 2H), 7.03 (dd, J = 13.6, 2.4 Hz, 1H), 5.15-5.12 (m, 1H), 4.71-4.68 (m, 1H), 4.40-3.81 (m, 8H), 3.56 (s, 1H), 3.01-2.93 (m, 1H), 2.55-2.53 (m, 2H), 2.34-2.33 (m, 3H), 2.29-2.19 (m, 3H), 1.81-1.35 (m, 10H), 1.24-1.19 (m, 3H), 1.16-1.15 (m, 5H), 0.74 (t, J = 7.2 Hz, 3H). |
| 2-71 | 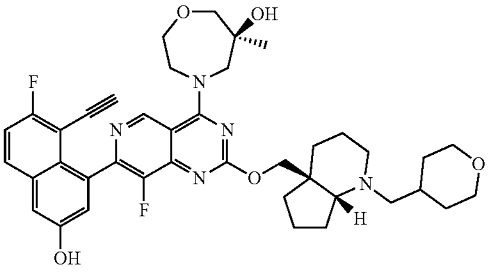 [SMILES: C#Cc1c(F)ccc2cc(O)cc(-c3ncc4c(N5CCOC[C@@](C)(O)C5)nc(OC[C@]56CCC[C@H]5N(CC5CCOCC5)CCC6)nc4c3F)c12] | (6S)-4-(2-{[(4aS,7aR)-1-[(oxan-4-yl)methyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 714.2 | $^1$H NMR (400 MHz, METHANOL-$d_4$) δ ppm = 9.51-9.41 (m, 1H), 7.90-7.87 (m, 1H), 7.38-7.32 (m, 2H), 7.25 (dd, J = 9.8, 2.4 Hz, 1H), 4.58-4.52 (m, 4H), 4.30-4.21 (m, 1H), 4.08-4.04 (m, 2H), 3.96-3.90 (m, 4H), 3.78-3.66 (m, 2H), 3.48-3.40 (m, 2H), 2.52-2.49 (m, 1H), 1.90-1.65 (m, 13H), 1.32-1.28 (m, 9H). (Two exchangeable protons not appeared). |
| 2-72 | 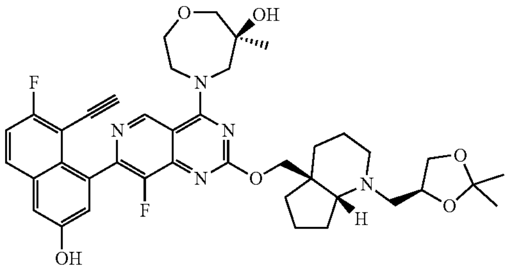 [SMILES: C#Cc1c(F)ccc2cc(O)cc(-c3ncc4c(N5CCOC[C@@](C)(O)C5)nc(OC[C@]56CCC[C@H]5N(C[C@H]5COC(C)(C)O5)CCC6)nc4c3F)c12] | (6S)-4-(2-{[(4aS,7aR)-1-{[(4S)-2,2-dimethyl-1,3-dioxolan-4-yl]methyl}-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 730.3 | $^1$H NMR (400 MHz, DMSO-$d_6$) δ ppm = 10.19-10.18 (m, 1H), 9.43-9.32 (m, 1H), 8.00-7.96 (m, 1H), 7.47 (t, J = 9.2 Hz, 1H), 7.40 (d, J = 2.4 Hz, 1H), 7.20 (dd, J = 10.4, 2.4 Hz, 1H), 5.25-5.08 (m, 1H), 4.61-4.32 (m, 2H), 4.22-3.86 (m, 10H), 3.61-3.52 (m, 3H), 1.89-1.45 (m, 13H), 1.23-1.14 (m, 9H). |

TABLE 2-continued

| # | Structure | IUPAC | LCMS (M + H)$^+$ | $^1$H NMR |
|---|---|---|---|---|
| 2-73 | 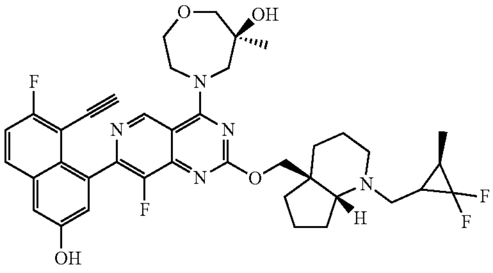 Diastereomer Mixture | (6S)-4-(2-{[(4aS,7aR)-1-{[(3R)-2,2-difluoro-3-methylcyclo-propyl]methyl}-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 720.2 | $^1$H NMR (400 MHz, DMSO-$d_6$) δ ppm = 10.15-10.14 (m, 1H), 9.43-9.32 (m, 1H), 8.00-7.96 (m, 1H), 7.47 (t, J = 9.2 Hz, 1H), 7.40 (d, J = 2.40 Hz, 1H), 7.20 (dd, J = 10.0, 2.4 Hz, 1H), 5.24-5.06 (m, 1H), 4.59-4.42 (m, 3H), 4.34-3.86 (m, 5H), 3.60 (m, 2H), 2.98-2.90 (m, 1H), 2.61-2.52 (m, 2H), 2.50-2.42 (m, 3H), 1.84-1.51 (m, 10H), 1.35-1.27 (m, 2H), 1.24-1.00 (m, 6H). (Diastereomeric mixture) |
| 2-74 | 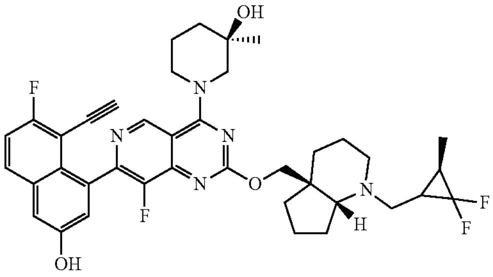 Diastereomer Mixture | (3R)-1-(2-{[(4aS,7aR)-1-{[(3R)-2,2-difluoro-3-methylcyclo-propyl]methyl}-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-3-methylpiperidin-3-ol | 704.2 | $^1$H NMR (400 MHz, DMSO-$d_6$) δ ppm = 10.15-10.14 (m, 1H), 9.22-9.06 (m, 1H), 8.00-7.96 (m, 1H), 7.47 (t, J = 9.2 Hz, 1H), 7.40 (s, 1H), 7.24-7.23 (m, 1H), 4.77-4.71 (m, 1H), 4.61-4.57 (m, 1H), 4.19-4.09 (m, 2H), 3.95-3.94 (m, 1H), 3.58-3.55 (m, 1H), 2.97-2.95 (m, 1H), 2.57-2.52 (m, 1H), 2.44-2.39 (m, 2H), 2.09-2.03 (m, 2H), 1.84-1.50 (m, 14H), 1.36-1.24 (m, 3H), 1.20-1.02 (m, 6H). (Diastereomeric mixture) |
| 2-75 | 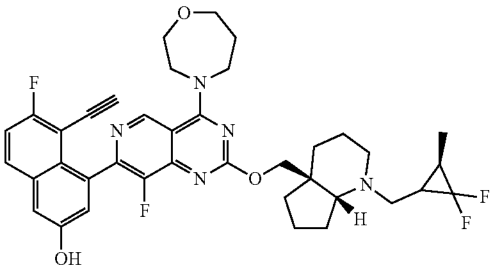 Diastereomer Mixture | 4-(2-{[(4aS,7aR)-1-{[(3R)-2,2-difluoro-3-methylcyclo-propyl]methyl}-octahydro-1H-cyclopenta[b]pyridin-4a-yl]methoxy}-8-fluoro-4-(1,4-oxazepan-4-yl)pyrido[4,3-d]pyrimidin-7-yl)-5-ethynyl-6-fluoronaphthalen-2-ol | 690.2 | $^1$H NMR (400 MHz, DMSO-$d_6$) δ ppm = 10.14 (s, 1H), 9.09 (s, 1H), 7.99-7.96 (m, 1H), 7.46 (t, J = 8.8 Hz, 1H), 7.39 (d, J = 2.4 Hz, 1H), 7.17 (d, J = 2.4 Hz, 1H), 4.55 (t, J = 8.0 Hz, 1H), 4.22-4.12 (m, 5H), 4.00-3.94 (m, 3H), 3.78-3.75 (m, 2H), 2.97-2.94 (m, 1H), 2.42-2.38 (m, 3H), 2.12-2.10 (m, 2H), 1.83-1.50 (m, 10H), 1.36-1.32 (m, 3H), 1.10-1.00 (m, 3H). (Diastereomeric mixture) |

TABLE 2-continued

| # | Structure | IUPAC | LCMS (M + H)+ | 1H NMR |
|---|---|---|---|---|
| 2-76 | 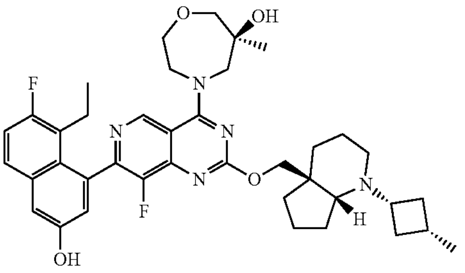 [SMILES: CCc1c(F)ccc2cc(O)cc(-c3ncc4c(N5CCOC[C@@](C)(O)C5)nc(OC[C@]56CCC[C@H]5N([C@H]5C[C@@H](C)C5)CCC6)nc4c3F)c12] | (1s,3s)-3-[(4aS,7aR)-4a-({[7-(8-ethyl-7-fluoro-3-hydroxy-naphthalen-1-yl)-8-fluoro-4-[(6S)-6-hydroxy-6-methyl-1,4-oxazepan-4-yl]pyrido[4,3-d]pyrimidin-2-yl]oxy}methyl)-octahydro-1H-cyclopenta[b]pyridin-1-yl]cyclobutane-1-carbonitrile | 699.3 | $^1$H NMR (400 MHz, DMSO-$d_6$) δ ppm = 9.93 (d, J = 6.5 Hz, 1H), 9.47 (s, 1H), 7.77 (dd, J = 9.0, 6.0 Hz, 1H), 7.42-7.30 (m, 2H), 7.03 (dd, J = 14.0, 2.5 Hz, 1H), 5.15 (d, J = 12.3 Hz, 1H), 4.63-4.56 (m, 1H), 4.46-3.80 (m, 7H), 3.63-3.49 (m, 2H), 3.07-2.81 (m, 3H), 2.47-2.30 (m, 4H), 2.26-2.04 (m, 2H), 2.03-1.73 (m, 3H), 1.70-1.25 (m, 9H), 1.17 (d, J = 3.0 Hz, 3H), 0.74 (t, J = 7.4 Hz, 3H). |
| 2-77 | 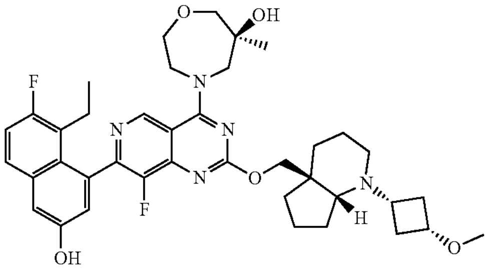 [SMILES: CCc1c(F)ccc2cc(O)cc(-c3ncc4c(N5CCOC[C@@](C)(O)C5)nc(OC[C@]56CCC[C@H]5N([C@H]5C[C@@H](OC)C5)CCC6)nc4c3F)c12] | (6S)-4-(2-{[(4aS,7aR)-1-[(1s,3s)-3-methoxycyclo-butyl]-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 704.3 | $^1$H NMR (400 MHz, DMSO-$d_6$) δ ppm = 9.93 (d, J = 7.0 Hz, 1H), 9.47 (s, 1H), 7.77 (dd, J = 9.3, 6.0 Hz, 1H), 7.49-7.23 (m, 2H), 7.03 (dd, J = 16.5, 2.5 Hz, 1H), 5.15 (d, J = 12.8 Hz, 1H), 4.57 (dd, J = 15.9, 10.6 Hz, 1H), 4.47-4.26 (m, 3H), 4.24-3.83 (m, 5H), 3.66-3.46 (m, 3H), 3.14-2.89 (m, 4H), 2.47-2.24 (m, 3H), 2.24-2.05 (m, 2H), 1.89-1.22 (m, 13H), 1.17 (d, J = 4.0 Hz, 3H), 0.74 (t, J = 7.3 Hz, 3H). |
| 2-78 | 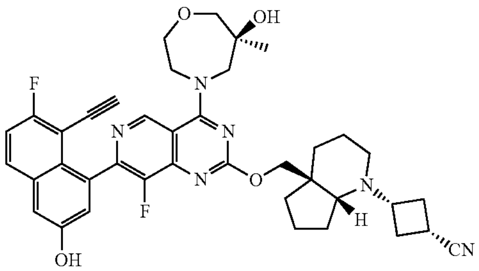 [SMILES: C#Cc1c(F)ccc2cc(O)cc(-c3ncc4c(N5CCOC[C@@](C)(O)C5)nc(OC[C@]56CCC[C@H]5N([C@H]5C[C@@H](C#N)C5)CCC6)nc4c3F)c12] | (1s,3s)-3-[(4aS,7aR)-4a-({[7-(8-ethynyl-7-fluoro-3-hydroxy-naphthalen-1-yl)-8-fluoro-4-[(6S)-6-hydroxy-6-methyl-1,4-oxazepan-4-yllpyrido[4,3-d]pyrimidin-2-yl]oxy}methyl)-octahydro-1H-cyclopenta[b]pyridin-1-yl]cyclobutane-1-carbonitrile | 695.3 | $^1$H NMR (400 MHz, DMSO-$d_6$) δ ppm = 10.16 (d, J = 4.5 Hz, 1H), 9.51-9.22 (m, 1H), 7.98 (dd, J = 9.0, 6.0 Hz, 1H), 7.47 (t, J = 9.0 Hz, 1H), 7.40 (d, J = 2.5 Hz, 1H), 7.20 (dd, J = 10.0, 2.5 Hz, 1H), 5.35-4.97 (m, 1H), 4.68-4.55 (m, 1H), 4.49-4.14 (m, 3H), 4.12-3.79 (m, 5H), 3.67-3.50 (m, 2H), 3.10-2.88 (m, 4H), 2.47-2.31 (m, 3H), 2.27-2.13 (m, 1H), 2.09-1.92 (m, 2H), 1.86-1.25 (m, 9H), 1.18-1.10 (m, 3H). |

TABLE 2-continued

| # | Structure | IUPAC | LCMS (M + H)+ | 1H NMR |
|---|---|---|---|---|
| 2-79 | 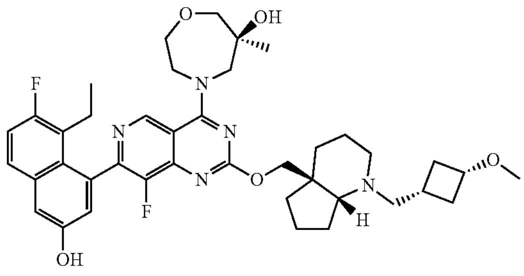 [SMILES: CCc1c(F)ccc2cc(O)cc(-c3ncc4c(N5CCOC[C@@](C)(O)C5)nc(OC[C@]56CCC[C@H]5N(C[C@H]5C[C@@H](OC)C5)CCC6)nc4c3F)c12] | (6S)-4-(2-{[(4aS,7aR)-1-{[(1s,3s)-3-methoxycyclo-butyl]methyl}-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 718.3 | $^1$H NMR (400 MHz, DMSO-$d_6$) δ ppm = 9.93 (d, J = 6.0 Hz, 1H), 9.47 (s, 1H), 7.77 (dd, J = 9.0, 6.0 Hz, 1H), 7.44-7.24 (m, 2H), 7.03 (dd, J = 15.0, 2.5 Hz, 1H), 5.15 (d, J = 13.0 Hz, 1H), 4.56 (dd, J = 10.9, 1.6 Hz, 1H), 4.43-3.81 (m, 7H), 3.66-3.49 (m, 3H), 3.05 (d, J = 3.0 Hz, 3H), 2.87 (br t, J = 7.3 Hz, 1H), 2.45-2.31 (m, 5H), 2.30-2.09 (m, 3H), 1.96-1.77 (m, 2H), 1.75-1.66 (m, 1H), 1.62-1.26 (m, 10H), 1.16 (d, J = 5.0 Hz, 3H), 0.74 (t, J = 7.3 Hz, 3H). |
| 2-81 | 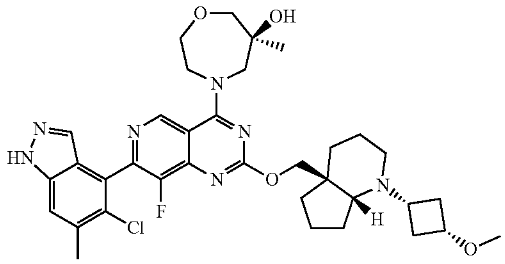 [SMILES: CO[C@H]1C[C@@H](N2CCC[C@@]3(COc4nc(N5CCOC[C@@](C)(O)C5)c5cnc(-c6c(Cl)c(C)cc7[nH]ncc67)c(F)c5n4)CCC[C@@H]23)C1] | (6S)-4-(2-{[(4aS,7aR)-1-[(1s,3s)-3-methoxycyclo-butyl]-octahydro-1H-cyclopenta[b]pyridin-4a-yl]methoxy}-7-(5-chloro-6-methyl-1H-indazol-4-yl)-8-fluoropyrido[4,3-d]pyrimidin-4-yl)-6-methyl-1,4-oxazepan-6-ol | 680.3 | $^1$H NMR (400 MHz, DMSO-$d_6$) δ ppm = 13.29 (s, 1H), 9.53 (d, J = 9.5 Hz, 1H), 7.71-7.67 (m, 2H), 5.21-5.12 (m, 1H), 4.59 (br dd, J = 18.8, 10.8 Hz, 1H), 4.41-4.16 (m, 3H), 4.14-3.89 (m, 5H), 3.62-3.48 (m, 3H), 3.10-2.99 (m, 4H), 2.55 (s, 3H), 2.40-2.28 (m, 2H), 2.24-2.07 (m, 1H), 1.95-1.78 (m, 1H), 1.75-1.23 (m, 12H), 1.20-1.16 (m, 3H). |
| 2-82 | 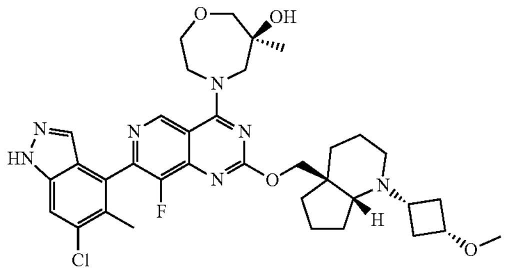 [SMILES: CO[C@H]1C[C@@H](N2CCC[C@@]3(COc4nc(N5CCOC[C@@](C)(O)C5)c5cnc(-c6c(C)c(Cl)cc7[nH]ncc67)c(F)c5n4)CCC[C@@H]23)C1] | (6S)-4-(2-{[(4aS,7aR)-1-[(1s,3s)-3-methoxycyclo-butyl]-octahydro-1H-cyclopenta[b]pyridin-4a-yl]methoxy}-7-(6-chloro-5-methyl-1H-indazol-4-yl)-8-fluoropyrido[4,3-d]pyrimidin-4-yl)-6-methyl-1,4-oxazepan-6-ol | 680.3 | $^1$H NMR (400 MHz, DMSO-$d_6$) δ ppm = 13.56-12.90 (br s, 1H), 9.54 (d, J = 4.0 Hz, 1H), 7.83 (s, 1H), 7.70 (d, J = 3.5 Hz, 1H), 5.16 (br d, J = 15.3 Hz, 1H), 4.63-4.54 (m, 1H), 4.41-4.18 (m, 3H), 4.14-3.90 (m, 4H), 3.63-3.48 (m, 3H), 3.09-2.98 (m, 4H), 2.49-2.42 (m, 1H), 2.39-2.25 (m, 5H), 2.22-2.11 (m, 1H), 1.89-1.78 (m, 1H), 1.74-1.22 (m, 12H), 1.18 (s, 3H). |

TABLE 2-continued

| # | Structure | IUPAC | LCMS (M + H)$^+$ | $^1$H NMR |
|---|---|---|---|---|
| 2-83 | 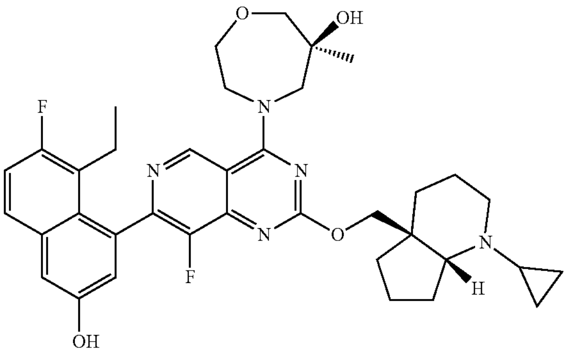 [SMILES: CCc1c(F)ccc2cc(O)cc(-c3ncc4c(N5CCOC[C@@](C)(O)C5)nc(OC[C@]56CCC[C@H]5N(C5CC5)CCC6)nc4c3F)c12] | (6S)-4-(2-{[(4aS,7aR)-1-cyclopropyl-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 660.4 | $^1$H NMR (400 MHz, DMSO-$d_6$) δ ppm = 9.91 (d, J = 6.6 Hz, 1H), 9.48-9.44 (m, 1H), 7.80-7.74 (m, 1H), 7.38-7.31 (m, 2H), 7.06-6.99 (m, 1H), 5.17-5.11 (m, 1H), 4.53-4.46 (m, 1H), 4.37-4.27 (m, 1H), 4.23-4.12 (m, 2H), 4.09-3.84 (m, 4H), 3.60-3.52 (m, 2H), 3.07-2.99 (m, 1H), 2.64-2.56 (m, 1H), 2.43-2.36 (m, 1H), 2.21-1.95 (m, 2H), 1.78-1.68 (m, 2H), 1.66-1.58 (m, 3H), 1.57-1.47 (m, 3H), 1.45-1.22 (m, 3H), 1.17-1.14 (m, 3H), 0.77-0.69 (m, 3H), 0.45-0.32 (m, 2H), 0.30-0.21 (m, 1H), 0.20-0.11 (m, 1H). |
| 2-86 | 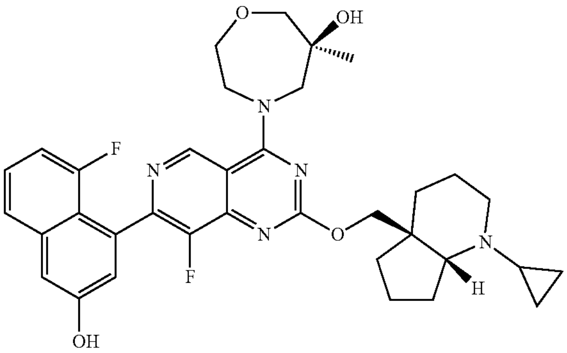 [SMILES: C[C@@]1(O)COCCN(c2nc(OC[C@]34CCC[C@H]3N(C3CC3)CCC4)nc3c(F)c(-c4cc(O)cc5cccc(F)c45)ncc23)C1] | (6S)-4-(2-{[(4aS,7aR)-1-cyclopropyl-octahydro-1H-cyclopenta[b]pyridin-4a-yl]methoxy}-8-fluoro-7-(8-fluoro-3-hydroxy-naphthalen-1-yl)pyrido[4,3-d]pyrimidin-4-yl)-6-methyl-1,4-oxazepan-6-ol | 632.2 | $^1$H NMR (400 MHz, DMSO-$d_6$) δ ppm = 10.27-10.18 (m, 1H), 9.47-9.42 (m, 1H), 7.68 (d, J = 7.9 Hz, 1H), 7.47-7.40 (m, 1H), 7.38-7.35 (m, 1H), 7.20-7.13 (m, 1H), 7.05-6.97 (m, 1H), 5.17-5.13 (m, 1H), 4.54-4.46 (m, 1H), 4.37-4.29 (m, 1H), 4.26-4.14 (m, 2H), 4.12-4.01 (m, 2H), 4.00-3.85 (m, 2H), 3.61-3.52 (m, 2H), 3.07-3.00 (m, 1H), 2.66-2.58 (m, 1H), 2.08-1.99 (m, 1H), 1.78-1.69 (m, 2H), 1.67-1.29 (m, 8H), 1.19-1.15 (m, 4H), 0.45-0.34 (m, 2H), 0.29-0.22 (m, 1H), 0.21-0.13 (m, 1H). |
| 2-87[A] | 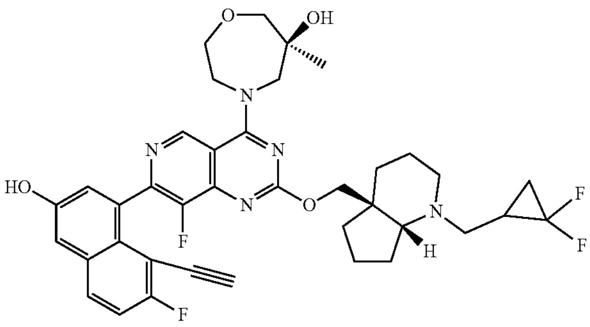 Diastereomer 1 | (6S)-4-(2-{[(4aS,7aR)-1-[(2,2-difluorocyclo-propyl)methyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 706.2 | $^1$H NMR (400 MHz, DMSO-$d_6$) δ ppm = 10.22 (br s, 1H), 9.56-9.07 (m, 1H), 7.98 (dd, J = 9.1, 5.9 Hz, 1H), 7.47 (t, J = 9.1 Hz, 1H), 7.40 (d, J = 2.5 Hz, 1H), 7.20 (dd, J = 9.8, 2.5 Hz, 1H), 5.37-4.94 (m, 1H), 4.60 (d, J = 10.8 Hz, 1H), 4.49-4.12 (m, 2H), 4.10-3.76 (m, 5H), 3.63-3.53 (m, 2H), 3.01-2.92 (m, 1H), 2.67-2.55 (m, 1H), 2.47-2.34 (m, 2H), 1.91-1.68 (m, 3H), 1.67-1.43 (m, 9H), 1.39-1.29 (m, 1H), 1.20-1.04 (m, 5H). |

TABLE 2-continued

| # | Structure | IUPAC | LCMS (M + H)$^+$ | $^1$H NMR |
|---|---|---|---|---|
| 2-88[A] | 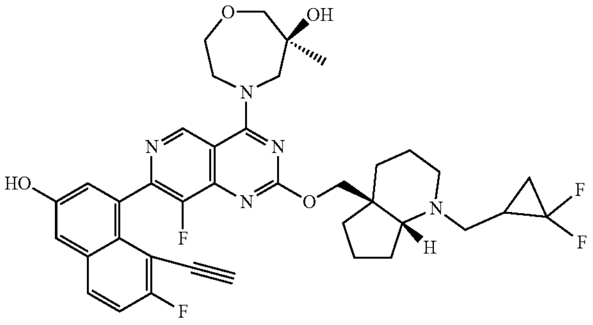<br>Diastereomer 2 | (6S)-4-(2-{[(4aS,7aR)-1-[(2,2-difluorocyclo-propyl)methyl]-octahydro-1H-cyclopenta[b]pyridin-4a-yl]methoxy}-7-(8-ethynyl-7-fluoro-3-hydroxy-naphthalen-1-yl)-8-fluoropyrido[4,3-d]pyrimidin-4-yl)-6-methyl-1,4-oxazepan-6-ol | 706.2 | $^1$H NMR (400 MHz, DMSO-$d_6$) δ ppm = 10.16 (br s, 1H), 9.47-9.13 (m, 1H), 7.98 (dd, J = 9.3, 6.0 Hz, 1H), 7.47 (t, J = 9.0 Hz, 1H), 7.40 (d, J = 2.5 Hz, 1H), 7.20 (dd, J = 10.4, 2.4 Hz, 1H), 5.34-5.03 (m, 1H), 4.55 (dd, J = 11.0, 2.3 Hz, 1H), 4.48-3.75 (m, 8H), 3.65-3.53 (m, 2H), 2.92 (br t, J = 7.1 Hz, 1H), 2.48-2.41 (m, 2H), 1.89-1.68 (m, 4H), 1.66-1.46 (m, 9H), 1.42-1.36 (m, 1H), 1.20-1.07 (m, 4H). |
| 2-89[A] | 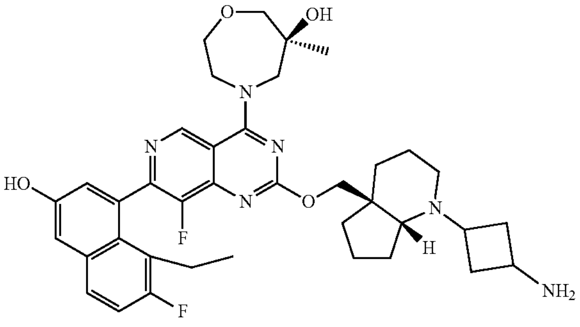<br>Homochiral isomer | (6S)-4-(2-{[(4aS,7aR)-1-(3-aminocyclobutyl)-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 689.1 | $^1$H NMR (400 MHz, DMSO-$d_6$) δ ppm = 9.48 (s, 1H), 8.40 (s, 1H), 7.76 (dd, J = 9.0, 6.0 Hz, 1H), 7.47-7.26 (m, 2H), 7.04 (dd, J = 13.4, 2.6 Hz, 1H), 5.17 (br s, 1H), 4.65-4.60 (m, 1H), 4.42-4.17 (m, 3H), 4.14-3.83 (m, 3H), 3.61-3.56 (m, 3H), 3.13-3.07 (m, 1H), 2.99-2.90 (m, 1H), 2.62-2.55 (m, 1H), 2.40-2.22 (m, 3H), 2.21-2.11 (m, 3H), 1.86-1.26 (m, 12H), 1.25-1.20 (m, 2H), 1.17 (d, J = 3.8 Hz, 3H), 0.74 (t, J = 7.3 Hz, 3H). |
| 2-90[A] | 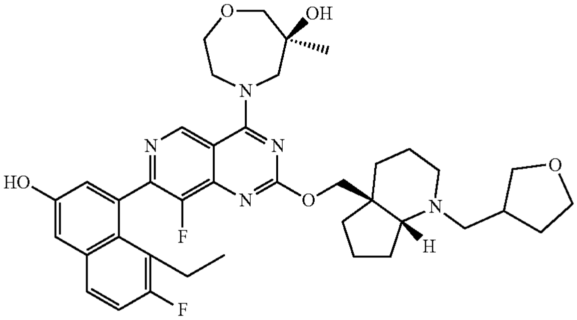<br>Homochiral isomer | (6S)-4-(2-{[(4aS,7aR)-1-[(oxolan-3-yl)methyl]-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 704.3 | $^1$H NMR (400 MHz, DMSO-$d_6$) δ ppm = 9.96 (br s, 1H), 9.47 (s, 1H), 7.77 (dd, J = 9.0, 6.0 Hz, 1H), 7.45-7.26 (m, 2H), 7.03 (dd, J = 13.8, 2.8 Hz, 1H), 5.14 (br d, J = 12.5 Hz, 1H), 4.70-4.53 (m, 1H), 4.45-3.78 (m, 7H), 3.71-3.53 (m, 5H), 2.94 (br t, J = 7.9 Hz, 1H), 2.47-2.28 (m, 6H), 2.21-2.08 (m, 1H), 1.91-1.67 (m, 4H), 1.65-1.40 (m, 8H), 1.37-1.26 (m, 1H), 1.16 (d, J = 5.0 Hz, 3H), 0.74 (t, J = 7.4 Hz, 3H). |

TABLE 2-continued

| # | Structure | IUPAC | LCMS (M + H)+ | 1H NMR |
|---|---|---|---|---|
| 2-91[A] | 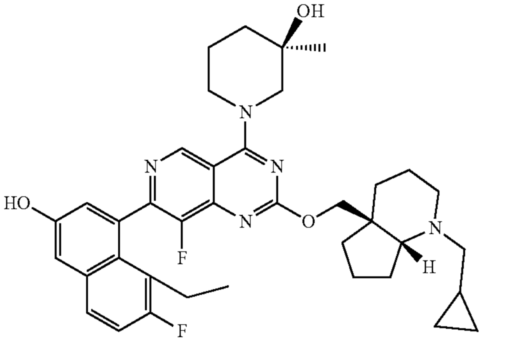 [SMILES: CCc1c(F)ccc2cc(O)cc(-c3ncc4c(N5CCC[C@@](C)(O)C5)nc(OC[C@]56CCC[C@H]5N(CC5CC5)CCC6)nc4c3F)c12] | (3R)-1-(2-{[(4aS,7aR)-1-(cyclopropyl-methyl)-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-3-methylpiperidin-3-ol | 658.3 | $^1$H NMR (400 MHz, DMSO-$d_6$) δ ppm = 9.97 (br s, 1H), 9.22 (s, 1H), 7.77 (dd, J = 9.0, 6.0 Hz, 1H), 7.45-7.25 (m, 2H), 7.04 (d, J = 2.5 Hz, 1H), 4.74 (br d, J = 6.3 Hz, 1H), 4.63 (dd, J = 10.8, 5.3, Hz, 1H), 4.43-4.27 (m, 1H), 4.20 (dd, J = 10.8, 1.8 Hz, 1H), 4.08-4.03 (m, 1H), 3.63-3.52 (m, 1H), 3.44-3.39 (m, 1H), 3.02 (br t, J = 7.5 Hz, 1H), 2.62-2.54 (m, 1H), 2.48-2.40 (m, 1H), 2.39-2.30 (m, 2H), 2.22-1.95 (m, 3H), 1.94-1.89 (m, 2H), 1.87-1.79 (m, 1H), 1.76-1.41 (m, 9H), 1.40-1.31 (m, 1H), 1.18 (d, J = 8.3 Hz, 3H), 0.83-0.68 (m, 4H), 0.45-0.30 (m, 2H), 0.13-0.01 (m, 2H). |
| 2-92[A] | 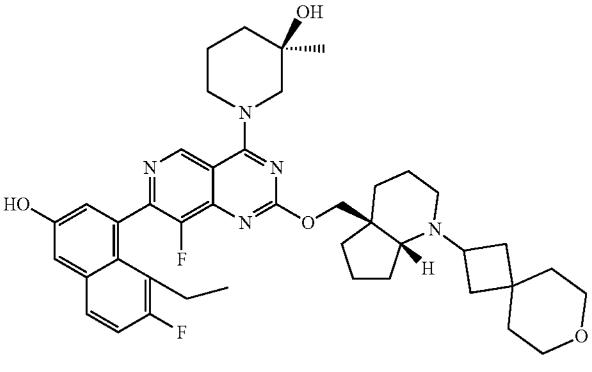 [SMILES: CCc1c(F)ccc2cc(O)cc(-c3ncc4c(N5CCC[C@@](C)(O)C5)nc(OC[C@]56CCC[C@H]5N(C5CC7(CCOCC7)C5)CCC6)nc4c3F)c12] | (3R)-1-(2-{[(4aS,7aR)-1-{7-oxaspiro[3.5]nonan-2-yl}-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-3-methylpiperidin-3-ol | 728.4 | $^1$H NMR (400 MHz, DMSO-$d_6$) δ ppm = 9.95 (br s, 1H), 9.22 (s, 1H), 7.77 (dd, J = 9.0, 6.0 Hz, 1H), 7.42-7.26 (m, 2H), 7.03 (t, J = 2.3 Hz, 1H), 4.73 (br d, J = 7.3 Hz, 1H), 4.65-4.59 (m, 1H), 4.45-4.20 (m, 2H), 4.15-3.98 (m, 1H), 3.66-3.53 (m, 1H), 3.50-3.39 (m, 4H), 3.07-2.88 (m, 2H), 2.48-2.26 (m, 2H), 2.21-1.78 (m, 5H), 1.76-1.26 (m, 20H), 1.18 (d, J = 8.3 Hz, 3H), 0.74 (td, J = 10.3, 7.4 Hz, 3H). |
| 2-93[A] | 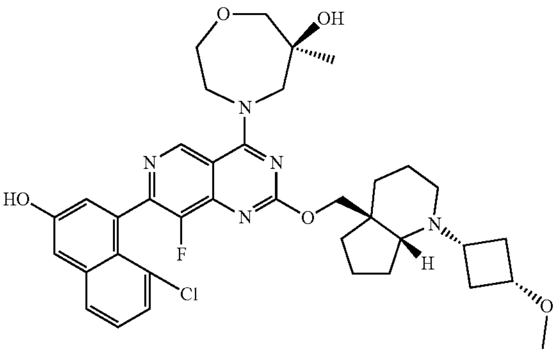 [SMILES: CO[C@H]1C[C@@H](N2CCC[C@@]3(COc4nc(N5CCOC[C@@](C)(O)C5)c5cnc(-c6cc(O)cc7cccc(Cl)c67)c(F)c5n4)CCC[C@@H]23)C1] | (6S)-4-(2-{[(4aS,7aR)-1-[(1s,3s)-3-methoxycyclo-butyl]-octahydro-1H-cyclopenta[b]pyridin-4a-yl]methoxy}-7-(8-chloro-3-hydroxy-naphthalen-1-yl)-8-fluoropyrido[4,3-d]pyrimidin-4-yl)-6-methyl-1,4-oxazepan-6-ol | 692.2 | $^1$H NMR (400 MHz, DMSO-$d_6$) δ ppm = 10.27 (br s, 1H), 9.43 (s, 1H), 7.85 (dd, J = 8.3, 1.3 Hz, 1H), 7.46-7.32 (m, 3H), 7.19-7.05 (m, 1H), 5.15 (d, J = 8.3 Hz, 1H), 4.64-4.47 (m, 1H), 4.40-3.83 (m, 7H), 3.60-3.48 (m, 3H), 3.06 (d, J = 3.0 Hz, 3H), 3.04-2.93 (m, 1H), 2.48-2.43 (m, 1H), 2.39-2.25 (m, 2H), 2.23-2.11 (m, 1H), 1.90-1.78 (m, 1H), 1.74-1.25 (m, 12H), 1.17 (d, J = 4.5 Hz, 3H). |

TABLE 2-continued

| # | Structure | IUPAC | LCMS (M + H)+ | 1H NMR |
|---|---|---|---|---|
| 2-94[A] | 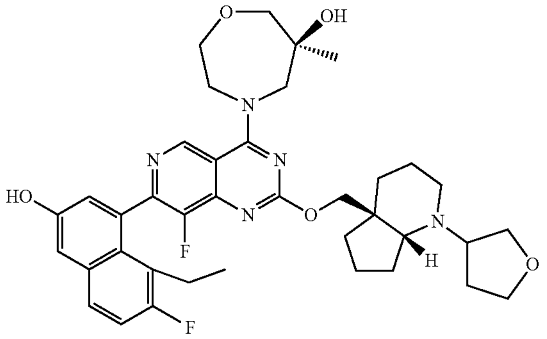 Diastereomer 1 | (6S)-4-(2-{[(4aS,7aR)-1-(oxolan-3-yl)-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 690.3 | $^1$H NMR (400 MHz, DMSO-$d_6$) δ ppm = 9.93 (s, 1H), 9.47 (s, 1H), 7.77 (dd, J = 9.1, 6.0 Hz, 1H), 7.41-7.29 (m, 2H), 7.03 (dd, J = 13.6, 2.4 Hz, 1H), 5.15 (d, J = 13.8 Hz, 1H), 4.63 (br d, J = 10.8 Hz, 1H), 4.44-3.70 (m, 10H), 3.67-3.53 (m, 2H), 3.12-2.98 (m, 1H), 2.96-2.86 (m, 1H), 2.63-2.54 (m, 1H), 2.44-2.34 (m, 1H), 2.20-2.09 (m, 1H), 2.03-1.89 (m, 3H), 1.77-1.38 (m, 9H), 1.35-1.26 (m, 1H), 1.20-1.11 (m, 4H), 0.74 (br t, J = 7.1 Hz, 3H). |
| 2-95[A] | 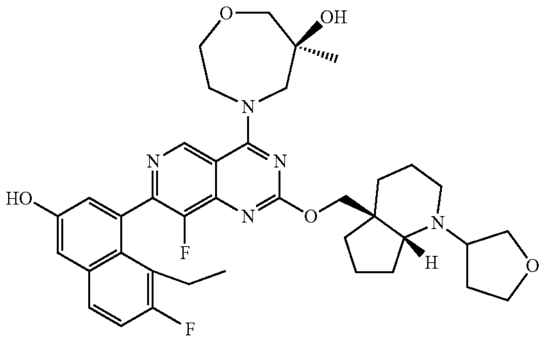 Diastereomer 2 | (6S)-4-(2-{[(4aS,7aR)-1-(oxolan-3-yl)-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 690.3 | $^1$H NMR (400 MHz, DMSO-$d_6$) δ ppm = 9.95 (br s, 1H), 9.51 (br s, 1H), 7.77 (dd, J = 9.0, 6.0 Hz, 1H), 7.54-7.30 (m, 1H), 7.12-6.94 (m, 2H), 5.16 (d, J = 13.8 Hz, 1H), 4.73-4.66 (m, 1H), 4.42-4.28 (m, 2H), 4.22-3.73 (m, 9H), 3.68-3.52 (m, 2H), 2.99-2.89 (m, 1H), 2.43-2.36 (m, 1H), 2.16-2.01 (m, 1H), 1.88-1.42 (m, 5H), 1.30-0.96 (m, 10H), 0.90-0.62 (m, 6H). |
| 2-96[A] | 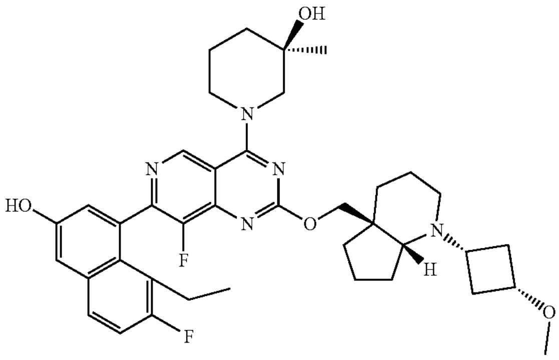 [SMILES: CCc1c(F)ccc2cc(O)cc(-c3ncc4c(N5CCC[C@@](C)(O)C5)nc(OC[C@]56CCC[C@H]5N([C@H]5C[C@@H](OC)C5)CCC6)nc4c3F)c12] | (3R)-1-(2-{[(4aS,7aR)-1-[(1s,3s)-3-methoxycyclo-butyl]-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-3-methylpiperidin-3-ol | 688.3 | $^1$H NMR (400 MHz, DMSO-$d_6$) δ ppm = 9.93 (br d, J = 4.0 Hz, 1H), 9.22 (s, 1H), 7.77 (dd, J = 9.1, 6.1 Hz, 1H), 7.42-7.25 (m, 2H), 7.04 (d, J = 2.8 Hz, 1H), 4.74 (d, J = 4.5 Hz, 1H), 4.63 (dd, J = 10.8, 2.3 Hz, 1H), 4.44-4.22 (m, 2H), 4.17-3.96 (m, 1H), 3.67-3.40 (m, 3H), 3.11-2.91 (m, 4H), 2.47-2.28 (m, 4H), 2.24-1.78 (m, 4H), 1.76-1.23 (m, 15H), 1.18 (d, J = 8.0 Hz, 3H), 0.74 (td, J = 9.8, 7.5 Hz, 3H). |

TABLE 2-continued

| # | Structure | IUPAC | LCMS (M + H)+ | $^1H$ NMR |
|---|---|---|---|---|
| 2-97[A] | 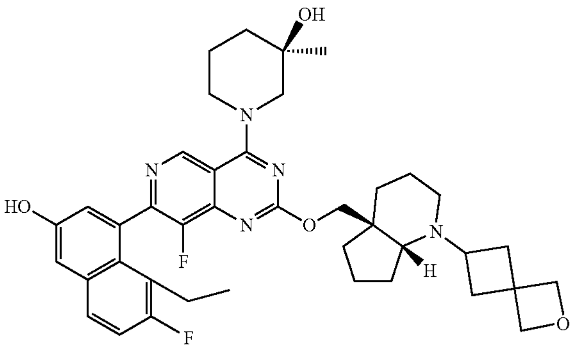 [SMILES: CCc1c(F)ccc2cc(O)cc(-c3ncc4c(N5CCC[C@@](C)(O)C5)nc(OC[C@]56CCC[C@H]5N(C5CC7(COC7)C5)CCC6)nc4c3F)c12] | (3R)-1-(2-{[(4aS,7aR)-1-{2-oxaspiro[3.3]heptan-6-yl}-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-3-methylpiperidin-3-ol | 700.3 | $^1H$ NMR (400 MHz, DMSO-$d_6$) δ ppm = 9.73 (br s, 1H), 9.22 (s, 1H), 7.77 (dd, J = 9.3, 6.0 Hz, 1H), 7.45-7.27 (m, 2H), 7.04 (d, J = 2.5 Hz, 1H), 4.86-4.48 (m, 4H), 4.45-4.17 (m, 4H), 4.09-4.01 (m, 1H), 3.66-3.56 (m, 2H), 3.00-2.92 (m, 1H), 2.75-2.67 (m, 1H), 2.45-2.20 (m, 4H), 2.17-1.93 (m, 4H), 1.87-1.23 (m, 14H), 1.18 (d, J = 8.0 Hz, 3H), 0.83-0.64 (m, 3H). |
| 2-98[A] | 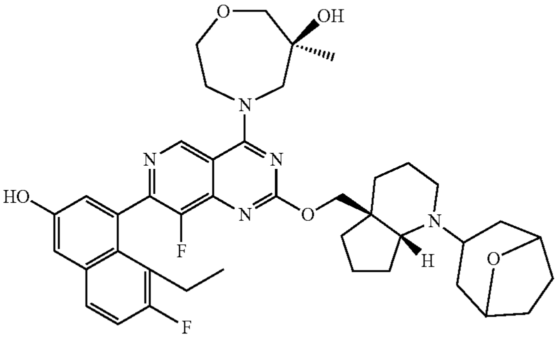 Diastereomer 1 | (6S)-4-(2-{[(4aS,7aR)-1-{8-oxabicyclo[3.2.1]octan-3-yl}-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 730.4 | $^1H$ NMR (400 MHz, DMSO-$d_6$) δ ppm = 9.99 (s, 1H), 9.46 (s, 1H), 7.77 (dd, J = 9.3, 6.0 Hz, 1H), 7.46-7.25 (m, 2H), 7.03 (dd, J = 14.4, 2.6 Hz, 1H), 5.28-4.99 (m, 1H), 4.61 (dd, J = 10.8, 7.3 Hz, 1H), 4.42-3.78 (m, 9H), 3.60-3.54 (m, 2H), 3.12-3.03 (m, 1H), 2.73-2.65 (m, 1H), 2.61-2.54 (m, 1H), 2.40-2.28 (m, 2H), 2.21-2.10 (m, 1H), 1.94-1.85 (m, 1H), 1.78-1.25 (m, 17H), 1.16 (d, J = 5.0 Hz, 3H), 0.74 (dt, J = 7.3, 1.4 Hz, 3H). |
| 2-99[A] | 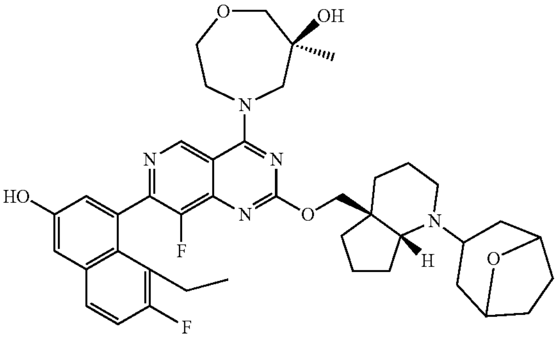 Diastereomer 2 | (6S)-4-(2-{[(4aS,7aR)-1-{8-oxabicyclo[3.2.1]octan-3-yl}-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 730.4 | $^1H$ NMR (400 MHz, DMSO-$d_6$) δ ppm = 10.08-9.77 (m, 1H), 9.50 (d, J = 2.8 Hz, 1H), 7.77 (dd, J = 9.3, 6.0 Hz, 1H), 7.44-7.20 (m, 2H), 7.03 (dd, J = 13.5, 2.8 Hz, 1H), 5.16 (d, J = 10.0 Hz, 1H), 4.69 (dd, J = 10.8, 6.0 Hz, 1H), 4.43-3.81 (m, 9H), 3.62-3.52 (m, 2H), 2.99-2.84 (m, 1H), 2.49-2.44 (m, 1H), 2.40-2.31 (m, 1H), 2.22-1.44 (m, 19H), 1.41-1.25 (m, 2H), 1.15 (d, J = 6.0 Hz, 3H), 0.78-0.65 (m, 3H). |

TABLE 2-continued

| # | Structure | IUPAC | LCMS (M + H)+ | 1H NMR |
|---|---|---|---|---|
| 2-100[A] | 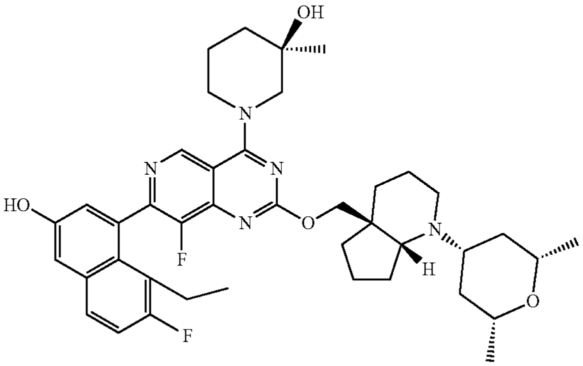 [SMILES: CCc1c(F)ccc2cc(O)cc(-c3ncc4c(N5CCC[C@@](C)(O)C5)nc(OC[C@]56CCC[C@H]5N([C@H]5C[C@@H](C)O[C@@H](C)C5)CCC6)nc4c3F)c12] | (3R)-1-(2-{[(4aS,7aR)-1-[(2R,4r,6S)-2,6-dimethyloxan-4-yl]-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-3-methylpiperidin-3-ol | 716.3 | $^1$H NMR (400 MHz, DMSO-$d_6$) δ ppm = 9.93 (br s, 1H), 9.22 (s, 1H), 7.77 (dd, J = 9.0, 6.0 Hz, 1H), 7.48-7.24 (m, 2H), 7.04 (d, J = 2.5 Hz, 1H), 4.73 (br d, J = 2.8 Hz, 1H), 4.62 (dd, J = 10.5, 6.5 Hz, 1H), 4.40-4.28 (m, 1H), 4.24 (d, J = 10.8 Hz, 1H), 4.08-4.02 (m, 1H), 3.66-3.51 (m, 1H), 3.45-3.40 (m, 1H), 3.14 (br d, J = 9.0 Hz, 1H), 2.65-2.54 (m, 2H), 2.48-2.31 (m, 2H), 2.21-1.86 (m, 3H), 1.82-1.39 (m, 14H), 1.38-1.25 (m, 1H), 1.21-1.15 (m, 4H), 1.07 (d, J = 6.0 Hz, 6H), 1.02-0.84 (m, 2H), 0.79-0.65 (m, 3H). |
| 2-101[A] | 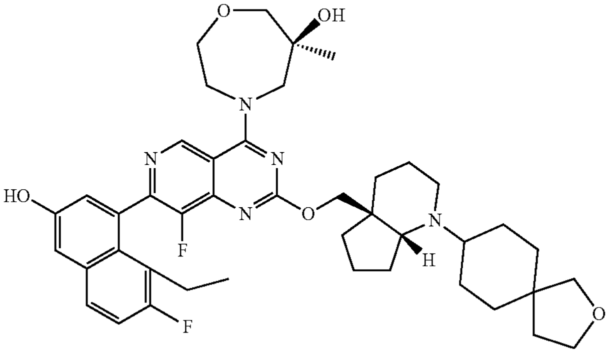<br>Diastereomer 1 | (6S)-4-(2-{[(4aS,7aR)-1-{2-oxaspiro[4.5]decan-8-yl}-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 758.3 | $^1$H NMR (400 MHz, DMSO-$d_6$) δ ppm = 9.95 (br s, 1H), 9.46 (s, 1H), 7.77 (dd, J = 9.0, 6.0 Hz, 1H), 7.47-7.22 (m, 2H), 7.03 (dd, J = 13.3, 2.5 Hz, 1H), 5.14 (br d, J = 12.3 Hz, 1H), 4.62-4.55 (m, 1H), 4.44-4.11 (m, 4H), 4.08-3.85 (m, 4H), 3.71-3.64 (m, 2H), 3.58-3.51 (m, 2H), 3.18-3.11 (m, 1H), 2.63-2.54 (m, 1H), 2.56-2.51 (m, 1H), 2.47-2.26 (m, 2H), 2.22-2.06 (m, 1H), 1.98-1.87 (m, 1H), 1.78-1.39 (m, 15H), 1.36-1.19 (m, 5H), 1.16 (d, J = 5.3 Hz, 3H), 0.74 (t, J = 7.4 Hz, 3H). |
| 2-102[A] | 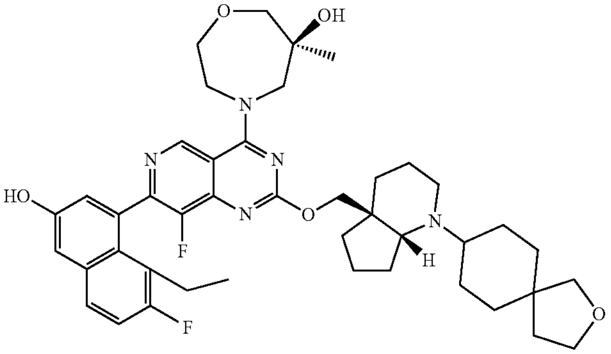<br>Diastereomer 2 | (6S)-4-(2-{[(4aS,7aR)-1-{2-oxaspiro[4.5]decan-8-yl}-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 758.3 | $^1$H NMR (400 MHz, DMSO-$d_6$) δ ppm = 9.94 (br s, 1H), 9.46 (s, 1H), 7.77 (dd, J = 9.0, 6.0 Hz, 1H), 7.48-7.23 (m, 2H), 7.05-6.98 (m, 1H), 5.14 (br d, J = 12.0 Hz, 1H), 4.69-4.50 (m, 1H), 4.43-3.80 (m, 7H), 3.66-3.60 (m, 2H), 3.58-3.52 (m, 2H), 3.39-3.35 (m, 2H), 3.12 (br t, J = 7.4 Hz, 1H), 2.62-2.55 (m, 1H), 2.46-2.25 (m, 3H), 2.21-2.05 (m, 1H), 2.01-1.86 (m, 1H), 1.76-1.39 (m, 14H), 1.36-1.19 (m, 5H), 1.16 (d, J = 5.3 Hz, 3H), 0.74 (t, J = 7.4 Hz, 3H). |

TABLE 2-continued

| # | Structure | IUPAC | LCMS (M + H)+ | 1H NMR |
|---|---|---|---|---|
| 2-103A | 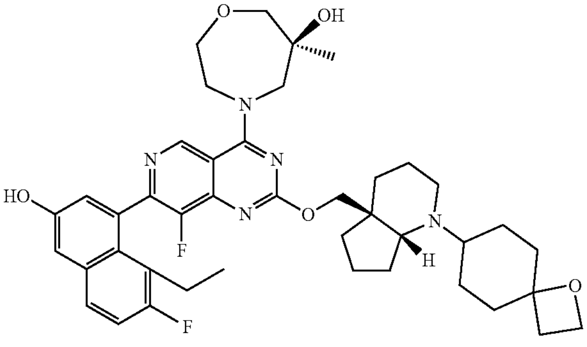 Diastereomer 1 | (6S)-4-(2-{[(4aS,7aR)-1-{1-oxaspiro[3.5]nonan-7-yl}-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 744.3 | $^1H$ NMR (400 MHz, DMSO-$d_6$) δ ppm = 9.92 (br s, 1H), 9.47 (s, 1H), 7.77 (dd, J = 9.0, 6.0 Hz, 1H), 7.48-7.26 (m, 2H), 7.03 (dd, J = 13.9, 2.6 Hz, 1H), 5.14 (br d, J = 12.3 Hz, 1H), 4.60-4.50 (m, 1H), 4.43-3.82 (m, 9H), 3.61-3.53 (m, 2H), 3.12-3.03 (m, 1H), 2.60-2.53 (m, 1H), 2.45-1.82 (m, 9H), 1.76-1.21 (m, 15H), 1.16 (d, J = 5.3 Hz, 3H), 0.74 (t, J = 7.4 Hz, 3H). |
| 2-104A | 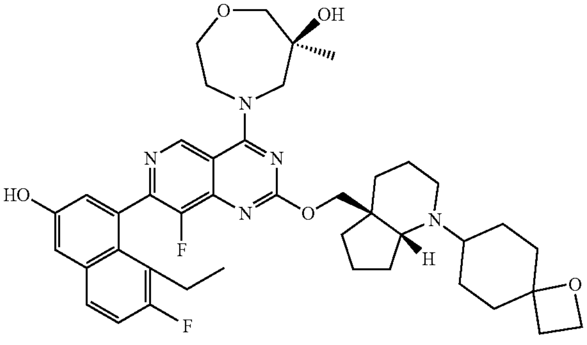 Diastereomer 2 | (6S)-4-(2-{[(4aS,7aR)-1-{1-oxaspiro[3.5]nonan-7-yl}-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 744.3 | $^1H$ NMR (400 MHz, DMSO-$d_6$) δ ppm = 9.98 (br s, 1H), 9.47 (d, J = 1.3 Hz, 1H), 7.77 (dd, J = 9.3, 6.0 Hz, 1H), 7.48-7.26 (m, 2H), 7.03 (dd, J = 14.9, 2.2 Hz, 1H), 5.14 (br d, J = 14.5 Hz, 1H), 4.68-4.50 (m, 1H), 4.41-3.81 (m, 9H), 3.59-3.52 (m, 2H), 3.10 (br t, J = 8.9 Hz, 1H), 2.59-2.54 (m, 1H), 2.47-2.06 (m, 6H), 2.01-1.83 (m, 3H), 1.75-1.26 (m, 15H), 1.16 (d, J = 5.3 Hz, 3H), 0.74 (t, J = 7.4 Hz, 3H). |
| 2-105A | 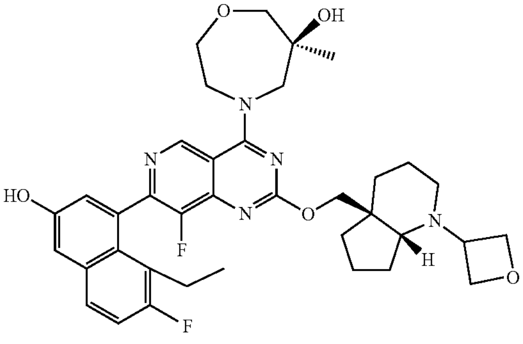 [SMILES: CCc1c(F)ccc2cc(O)cc(-c3ncc4c(N5CCOC[C@@](C)(O)C5)nc(OC[C@]56CCC[C@H]5N(C5COC5)CCC6)nc4c3F)c12] | (6S)-4-(2-{[(4aS,7aR)-1-(oxetan-3-yl)-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 676.3 | $^1H$ NMR (400 MHz, DMSO-$d_6$) δ ppm = 9.93 (d, J = 6.5 Hz, 1H), 9.48 (s, 1H), 7.77 (dd, J = 9.1, 5.9 Hz, 1H), 7.47-7.24 (m, 2H), 7.06-6.97 (m, 1H), 5.16 (d, J = 13.3 Hz, 1H), 4.63 (dd, J = 10.5, 4.0 Hz, 1H), 4.54-4.47 (m, 1H), 4.46-4.28 (m, 6H), 4.19-4.13 (m, 1H), 4.08-3.85 (m, 3H), 3.76-3.65 (m, 1H), 3.62-3.48 (m, 2H), 3.00-2.86 (m, 1H), 2.46-2.24 (m, 3H), 2.21-2.03 (m, 1H), 1.83-1.41 (m, 8H), 1.38-1.26 (m, 2H), 1.17 (d, J = 4.5 Hz, 3H), 0.75 (t, J = 7.3 Hz, 3H). |

TABLE 2-continued

| # | Structure | IUPAC | LCMS (M + H)+ | 1H NMR |
|---|---|---|---|---|
| 2-106[A] | 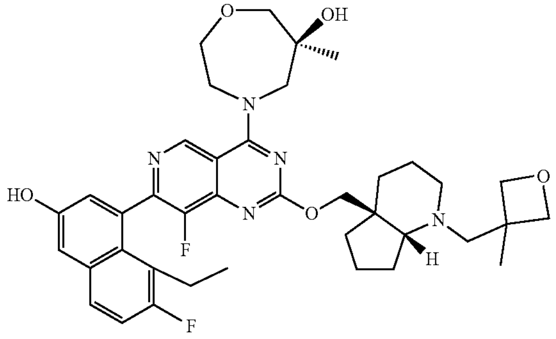 [SMILES: CCc1c(F)ccc2cc(O)cc(-c3ncc4c(N5CCOC[C@@](C)(O)C5)nc(OC[C@]56CCC[C@H]5N(CC5(C)COC5)CCC6)nc4c3F)c12] | (6S)-4-(2-{[(4aS,7aR)-1-[(3-methyloxetan-3-yl)methyl]-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 704.4 | $^1$H NMR (400 MHz, DMSO-$d_6$) δ ppm = 9.92 (d, J = 7.5 Hz, 1H), 9.48 (s, 1H), 7.77 (dd, J = 9.0, 6.0 Hz, 1H), 7.41-7.26 (m, 2H), 7.05-6.98 (m, 1H), 5.14 (d, J = 11.3 Hz, 1H), 4.72-4.60 (m, 1H), 4.44-4.17 (m, 8H), 4.15-3.82 (m, 4H), 3.66-3.48 (m, 2H), 2.83-2.73 (m, 1H), 2.60-2.54 (m, 1H), 2.48-2.34 (m, 2H), 2.25-2.07 (m, 2H), 1.96-1.82 (m, 1H), 1.79-1.66 (m, 1H), 1.65-1.28 (m, 8H), 1.26-1.14 (m, 6H), 0.74 (t, J = 7.4 Hz, 3H). |
| 2-107[A] | 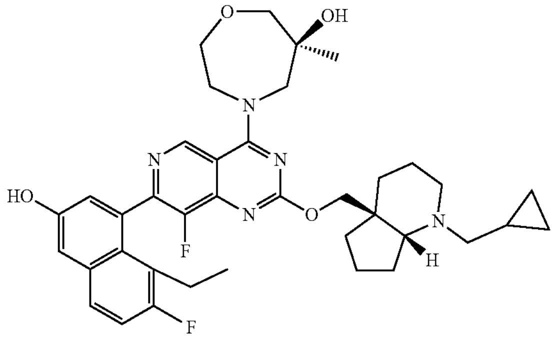 [SMILES: CCc1c(F)ccc2cc(O)cc(-c3ncc4c(N5CCOC[C@@](C)(O)C5)nc(OC[C@]56CCC[C@H]5N(CC5CC5)CCC6)nc4c3F)c12] | (6S)-4-(2-{[(4aS,7aR)-1-(cyclopropyl-methyl)-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 674.3 | $^1$H NMR (400 MHz, DMSO-$d_6$) δ ppm = 9.94 (br s, 1H), 9.47 (s, 1H), 7.77 (dd, J = 9.1, 6.0 Hz, 1H), 7.45-7.26 (m, 2H), 7.03 (dd, J = 14.3, 2.8 Hz, 1H), 5.16 (d, J = 11.3 Hz, 1H), 4.61 (d, J = 10.5 Hz, 1H), 4.44-4.16 (m, 3H), 4.15-3.81 (m, 3H), 3.61-3.53 (m, 2H), 3.03 (br t, J = 7.5 Hz, 1H), 2.63-2.54 (m, 2H), 2.48-2.28 (m, 3H), 2.23-2.07 (m, 2H), 1.89-1.78 (m, 1H), 1.76-1.42 (m, 8H), 1.41-1.29 (m, 1H), 1.16 (d, J = 4.8 Hz, 3H), 0.84-0.68 (m, 4H), 0.41-0.39 (m, 2H), 0.17-0.01 (m, 2H). |
| 2-108[A] | 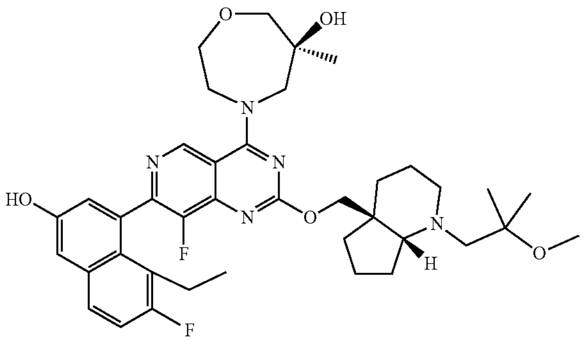 [SMILES: CCc1c(F)ccc2cc(O)cc(-c3ncc4c(N5CCOC[C@@](C)(O)C5)nc(OC[C@]56CCC[C@H]5N(CC(C)(C)OC)CCC6)nc4c3F)c12] | (6S)-4-(2-{[(4aS,7aR)-1-(2-methoxy-2-methylpropyl)-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 706.3 | $^1$H NMR (400 MHz, DMSO-$d_6$) δ ppm = 9.93 (d, J = 7.0 Hz, 1H), 9.49 (s, 1H), 7.77 (dd, J = 9.3, 6.0 Hz, 1H), 7.48-7.22 (m, 2H), 7.03 (dd, J = 13.6, 2.6 Hz, 1H), 5.14 (d, J = 10.3 Hz, 1H), 4.69 (t, J = 10.8 Hz, 1H), 4.49-4.22 (m, 3H), 4.21-3.82 (m, 5H), 3.66-3.51 (m, 2H), 3.06 (d, J = 2.0 Hz, 3H), 2.97 (br d, J = 6.3 Hz, 1H), 2.65-2.53 (m, 2H), 2.42-2.30 (m, 2H), 2.28-2.03 (m, 1H), 1.95-1.81 (m, 1H), 1.78-1.46 (m, 7H), 1.41-1.37 (m, 1H), 1.33-1.24 (m, 1H), 1.16 (d, J = 5.5 Hz, 3H), 1.11-0.97 (m, 6H), 0.74 (t, J = 7.4 Hz, 3H). |

TABLE 2-continued

| # | Structure | IUPAC | LCMS (M + H)+ | ¹H NMR |
|---|---|---|---|---|
| 2-109[A] | 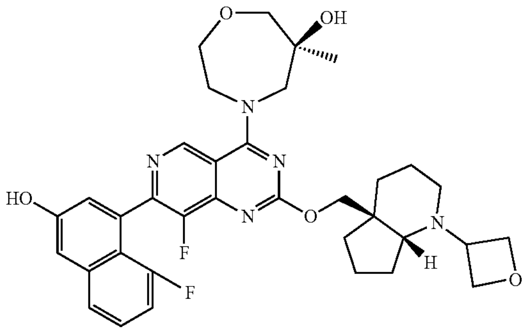 [SMILES: C[C@@]1(O)COCCN(c2nc(OC[C@]34CCC[C@H]3N(C3COC3)CCC4)nc3c(F)c(-c4cc(O)cc5cccc(F)c45)ncc23)C1] | (6S)-4-(2-{[(4aS,7aR)-1-(oxetan-3-yl)-octahydro-1H-cyclopenta[b]pyridin-4a-yl]methoxy}-8-fluoro-7-(8-fluoro-3-hydroxy-naphthalen-1-yl)pyrido[4,3-d]pyrimidin-4-yl)-6-methyl-1,4-oxazepan-6-ol | 648.3 | ¹H NMR (400 MHz, DMSO-$d_6$) δ ppm = 10.24 (br s, 1H), 9.47 (s, 1H), 7.73-7.62 (m, 1H), 7.43 (dt, J = 8.0, 5.3 Hz, 1H), 7.36 (s, 1H), 7.21-7.10 (m, 1H), 7.02 (dd, J = 13.0. 8.0 Hz, 1H), 5.18 (d, J = 6.0 Hz, 1H), 4.66-4.59 (m, 1H), 4.54-4.39 (m, 4H), 4.38-4.17 (m, 3H), 4.12-3.83 (m, 4H), 3.75-3.70 (m, 1H), 3.65-3.50 (m, 2H), 2.96-2.88 (m, 1H), 2.47-2.40 (m, 1H), 2.33-2.25 (m, 1H), 1.89-1.77 (m, 1H), 1.75-1.52 (m, 5H), 1.51-1.40 (m, 2H), 1.38-1.26 (m, 2H), 1.18 (d, J = 2.3 Hz, 3H). |
| 2-110[A] | 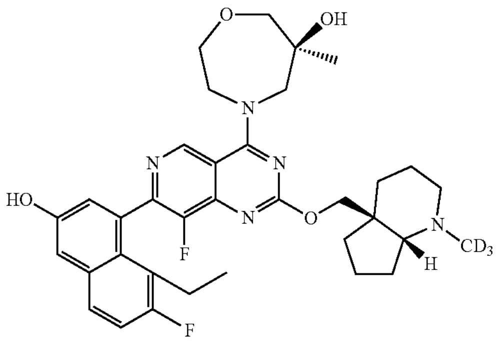 [SMILES: [2H]C([2H])([2H])N1CCC[C@@]2(COc3nc(N4CCOC[C@@](C)(O)C4)c4cnc(-c5cc(O)cc6ccc(F)c(CC)c56)c(F)c4n3)CCC[C@@H]12] | (6S)-4-(2-{[(4aS,7aR)-1-(2H3)methyl-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 637.3 | ¹H NMR (400 MHz, DMSO-$d_6$) δ ppm = 10.38-9.64 (m, 1H), 9.48 (br s, 1H), 7.77 (dd, J = 8.4, 6.6 Hz, 1H), 7.38-7.31 (m, 2H), 7.05-7.00 (m, 1H), 5.18 (br s, 1H), 4.48 (br d, J = 11.0 Hz, 1H), 4.41-4.16 (m, 3H), 4.14-3.80 (m, 4H), 3.61-3.52 (m, 2H), 2.69-2.63 (m, 1H), 2.49-2.44 (m, 1H), 2.38-2.33 (m, 1H), 2.23-2.06 (m, 2H), 1.89-1.36 (m, 10H), 1.16 (d, J = 5.8 Hz, 3H), 0.78-0.71 (m, 3H). |
| 2-111[A] | 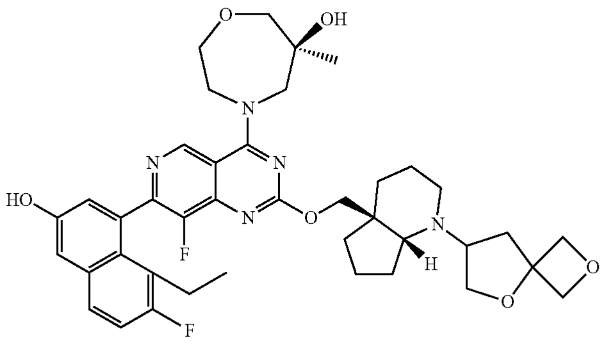 Diastereomer 1 | (6S)-4-(2-{[(4aS,7aR)-1-{2,5-dioxaspiro[3.4]octan-7-yl}-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 732.3 | ¹H NMR (400 MHz, DMSO-$d_6$) δ ppm = 9.97-9.89 (m, 1H), 9.47 (s, 1H), 7.77 (dd, J = 9.0, 6.0 Hz, 1H), 7.40-7.31 (m, 2H), 7.05-6.99 (m, 1H), 5.15 (d, J = 13.3 Hz, 1H), 4.62 (t, J = 10.5 Hz, 1H), 4.54-4.44 (m, 4H), 4.30 (br dd, J = 14.3, 2.8 Hz, 2H), 4.16 (br d, J = 10.5 Hz, 1H), 4.07-3.83 (m, 5H), 3.59-3.55 (m, 2H), 3.51-3.46 (m, 1H), 3.14-3.06 (m, 1H), 3.01-2.93 (m, 1H), 2.39 (br dd, J = 6.0, 1.0 Hz, 1H), 2.34 (br dd, J = 3.5, 1.8 Hz, 2H), 2.13-2.09 (m, 1H), 2.03-1.87 (m, 2H), 1.78-1.28 (m, 11H), 0.91-0.81 (m, 2H), 0.74 (br t, J = 7.1 Hz, 3H). |

TABLE 2-continued

| # | Structure | IUPAC | LCMS (M + H)+ | 1H NMR |
|---|---|---|---|---|
| 2-112[A] | 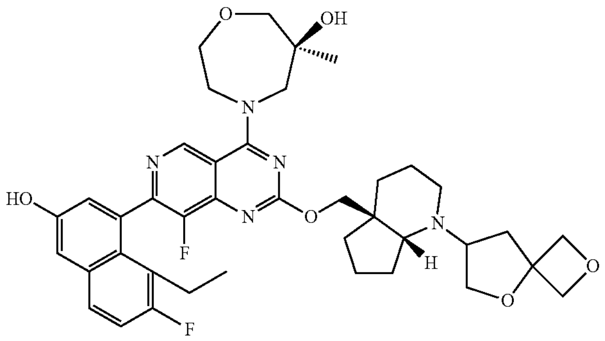 Diastereomer 2 | (6S)-4-(2-{[(4aS,7aR)-1-{2,5-dioxaspiro[3.4]octan-7-yl}-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 732.3 | $^1$H NMR (400 MHz, DMSO-$d_6$) δ ppm = 10.11-9.86 (m, 1H), 9.47 (s, 1H), 7.77 (dd, J = 9.1, 5.9 Hz, 1H), 7.41-7.31 (m, 2H), 7.03 (dd, J = 13.4, 2.4 Hz, 1H), 5.15 (br d, J = 12.8 Hz, 1H), 4.61 (br dd, J = 10.8, 3.8 Hz, 1H), 4.55-3.85 (m, 12H), 3.57-3.46 (m, 3H), 3.06-2.99 (m, 1H), 2.92-2.83 (m, 1H), 2.40-2.34 (m, 3H), 2.22-2.06 (m, 1H), 2.00-1.90 (m, 2H), 1.80-1.30 (m, 11H), 0.91-0.83 (m, 2H), 0.78-0.73 (m, 3H). |
| 2-113[B] | 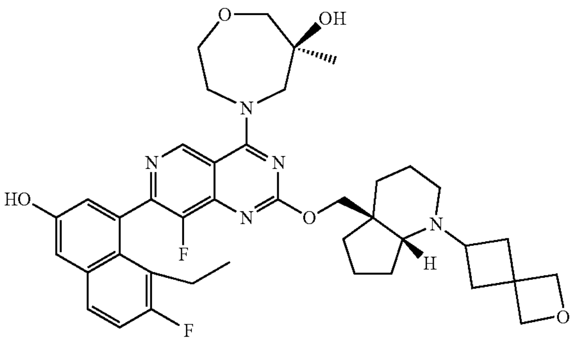 [SMILES: CCc1c(F)ccc2cc(O)cc(-c3ncc4c(N5CCOC[C@@](C)(O)C5)nc(OC[C@]56CCC[C@H]5N(C5CC7(COC7)C5)CCC6)nc4c3F)c12] | (6S)-4-(2-{[(4aS,7aR)-1-{2-oxaspiro[3.3]heptan-6-yl}-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-6-methyl-1,4-oxazepan-6-ol | 716.3 | $^1$H NMR (400 MHz, DMSO-$d_6$) δ ppm = 9.97 (br s, 1H), 9.47 (s, 1H), 7.77 (dd, J = 9.1, 6.1 Hz, 1H), 7.41-7.28 (m, 2H), 7.06-7.00 (m, 1H), 5.19-5.05 (m, 1H), 4.63-4.50 (m, 3H), 4.44-4.11 (m, 6H), 4.10-3.81 (m, 4H), 3.60-3.54 (m, 2H), 3.02-2.92 (m, 1H), 2.76-2.66 (m, 1H), 2.46-2.31 (m, 2H), 2.29-2.05 (m, 4H), 1.86-1.50 (m, 7H), 1.49-1.23 (m, 4H), 1.16 (d, J = 3.8 Hz, 3H), 0.79-0.62 (m, 3H). |
| 2-114[A] | 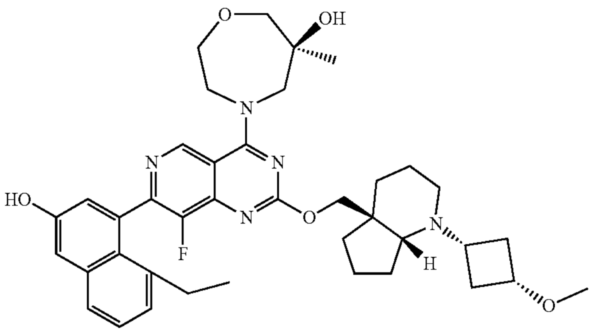 [SMILES: CCc1cccc2cc(O)cc(-c3ncc4c(N5CCOC[C@@](C)(O)C5)nc(OC[C@]56CCC[C@H]5N([C@H]5C[C@@H](OC)C5)CCC6)nc4c3F)c12] | (6S)-4-(2-{[(4aS,7aR)-1-[(1s,3s)-3-methoxycyclo-butyl]-octahydro-1H-cyclopenta[b]pyridin-4a-yl]methoxy}-7-(8-ethyl-3-hydroxy-naphthalen-1-yl)-8-fluoropyrido[4,3-d]pyrimidin-4-yl)-6-methyl-1,4-oxazepan-6-ol | 686.3 | $^1$H NMR (400 MHz, DMSO-$d_6$) δ ppm = 9.89 (d, J = 6.5 Hz, 1H), 9.45 (d, J = 5.0 Hz, 1H), 7.67 (d, J = 8.0 Hz, 1H), 7.43-7.34 (m, 1H), 7.29 (d, J = 2.5 Hz, 1H), 7.13 (br d, J = 7.0 Hz, 1H), 6.98 (dd, J = 16.9, 2.6 Hz, 1H), 5.15 (d, J = 5.5 Hz, 1H), 4.65-4.51 (m, 1H), 4.43-4.11 (m, 3H), 4.10-3.82 (m, 4H), 3.61-3.47 (m, 3H), 3.06 (d, J = 2.3 Hz, 3H), 3.06-2.95 (m, 2H), 2.39-2.11 (m, 4H), 1.89-1.78 (m, 1H), 1.76-1.25 (m, 13H), 1.16 (d, J = 4.3 Hz, 3H), 0.83 (t, J = 7.4 Hz, 3H). |

TABLE 2-continued

| # | Structure | IUPAC | LCMS (M + H)+ | $^1$H NMR |
|---|---|---|---|---|
| 2-115[A] | 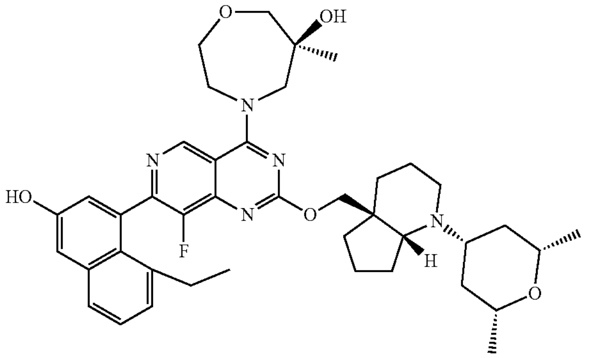 [SMILES: CCc1cccc2cc(O)cc(-c3ncc4c(N5CCOC[C@@](C)(O)C5)nc(OC[C@]56CCC[C@H]5N([C@H]5C[C@@H](C)O[C@@H](C)C5)CCC6)nc4c3F)c12] | (6S)-4-(2-{[(4aS,7aR)-1-[(2R,4r,6S)-2,6-dimethyloxan-4-yl]-octahydro-1H-cyclopenta[b]pyridin-4a-yl]methoxy}-7-(8-ethyl-3-hydroxy-naphthalen-1-yl)-8-fluoropyrido[4,3-d]pyrimidin-4-yl)-6-methyl-1,4-oxazepan-6-ol | 714.2 | $^1$H NMR (400 MHz, DMSO-$d_6$) δ ppm = 9.90 (d, J = 5.5 Hz, 1H), 9.45 (br d, J = 5.3 Hz, 1H), 7.67 (d, J = 8.0 Hz, 1H), 7.42-7.32 (m, 1H), 7.29 (d, J = 2.5 Hz, 1H), 7.13 (br d, J = 7.3 Hz, 1H), 7.02-6.93 (m, 1H), 5.15 (d, J = 7.3 Hz, 1H), 4.59 (br t, J = 11.0 Hz, 1H), 4.43-3.84 (m, 8H), 3.63-3.50 (m, 3H), 3.13-3.09 (m, 1H), 2.64-2.54 (m, 1H), 2.40-2.10 (m, 4H), 1.81-1.29 (m, 11H), 1.18-1.13 (m, 6H), 1.06 (br d, J = 6.0 Hz, 3H), 0.98-0.78 (m, 6H). |
| 2-116[A] | 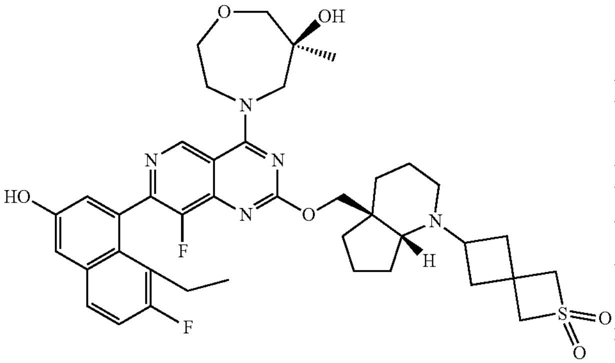 [SMILES: CCc1c(F)ccc2cc(O)cc(-c3ncc4c(N5CCOC[C@@](C)(O)C5)nc(OC[C@]56CCC[C@H]5N(C5CC7(C5)CS(=O)(=O)C7)CCC6)nc4c3F)c12] | 6-[(4aS,7aR)-4a-({[7-(8-ethyl-7-fluoro-3-hydroxy-naphthalen-1-yl)-8-fluoro-4-[(6S)-6-hydroxy-6-methyl-1,4-oxazepan-4-yl]pyrido[4,3-d]pyrimidin-2-yl]oxy}methyl)-octahydro-1H-cyclopenta[b]pyridin-1-yl]-2lambda6-thiaspiro[3.3] heptane-2,2-dione | 764.2 | $^1$H NMR (400 MHz, DMSO-$d_6$) δ ppm = 9.93 (d, J = 6.5 Hz, 1H), 9.47 (s, 1H), 7.77 (dd, J = 9.1, 6.1 Hz, 1H), 7.44-7.28 (m, 2H), 7.03 (dd, J = 13.6, 2.4 Hz, 1H), 5.15 (d, J = 13.8 Hz, 1H), 4.61 (dd, J = 10.6, 5.9 Hz, 1H), 4.43-3.79 (m, 11H), 3.65-3.51 (m, 2H), 3.05-2.83 (m, 2H), 2.46-2.24 (m, 4H), 2.23-1.94 (m, 4H), 1.87-1.77 (m, 1H), 1.74-1.24 (m, 9H), 1.17 (d, J = 3.8 Hz, 3H), 0.74 (t, J = 7.3 Hz, 3H). |
| 2-117[X] | 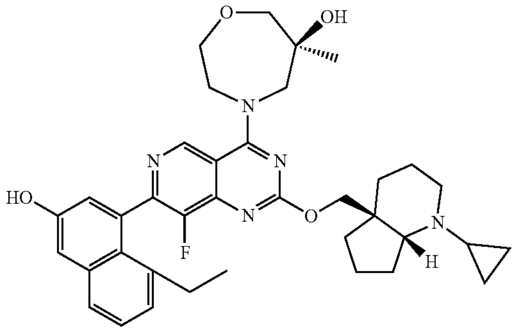 [SMILES: CCc1cccc2cc(O)cc(-c3ncc4c(N5CCOC[C@@](C)(O)C5)nc(OC[C@]56CCC[C@H]5N(C5CC5)CCC6)nc4c3F)c12] | (6S)-4-(2-{[(4aS,7aR)-1-cyclopropyl-octahydro-1H-cyclopenta[b]pyridin-4a-yl]methoxy}-7-(8-ethyl-3-hydroxy-naphthalen-1-yl)-8-fluoropyrido[4,3-d]pyrimidin-4-yl)-6-methyl-1,4-oxazepan-6-ol | 642.3 | $^1$H NMR (400 MHz, DMSO-$d_6$) δ ppm = 9.89 (d, J = 6.5 Hz, 1H), 9.44 (d, J = 5.8 Hz, 1H), 7.67 (d, J = 7.8 Hz, 1H), 7.42-7.33 (m, 1H), 7.29 (d, J = 2.5 Hz, 1H), 7.13 (br d, J = 6.5 Hz, 1H), 6.98 (dd, J = 14.8, 2.5 Hz, 1H), 5.14 (d, J = 5.8 Hz, 1H), 4.61-4.43 (m, 1H), 4.42-4.12 (m, 3H), 4.11-3.75 (m, 5H), 3.62-3.52 (m, 2H), 3.09-2.93 (m, 1H), 2.65-2.53 (m, 1H), 2.31-2.10 (m, 2H), 2.09-1.94 (m, 1H), 1.80-1.69 (m, 3H), 1.67-1.33 (m, 7H), 1.16 (d, J = 5.5 Hz, 3H), 0.83 (t, J = 7.4 Hz, 3H), 0.47-0.31 (m, 2H), 0.28-0.09 (m, 2H). |

TABLE 2-continued

| # | Structure | IUPAC | LCMS (M + H)$^+$ | $^1$H NMR |
| --- | --- | --- | --- | --- |
| 2-120$^F$ | 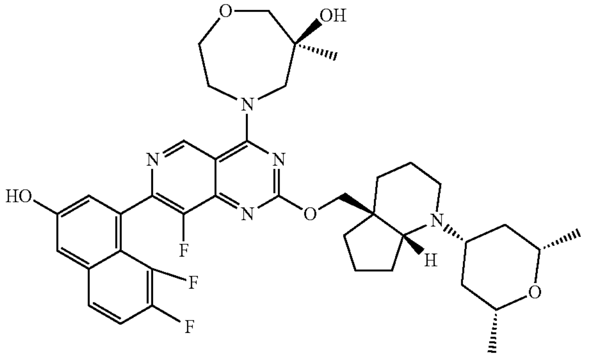 [SMILES: C[C@@H]1C[C@H](N2CCC[C@@]3(COc4nc(N5CCOC[C@@](C)(O)C5)c5cnc(-c6cc(O)cc7ccc(F)c(F)c67)c(F)c5n4)CCC[C@@H]23)C[C@H](C)O1] | (6S)-4-(2-{[(4aS,7aR)-1-[(2R,4r,6S)-2,6-dimethyloxan-4-yl]-octahydro-1H-cyclopenta[b]pyridin-4a-yl]methoxy}-7-(7,8-difluoro-3-hydroxy-naphthalen-1-yl)-8-fluoropyrido[4,3-d]pyrimidin-4-yl)-6-methyl-1,4-oxazepan-6-ol | 722.2 | $^1$H NMR (400 MHz, DMSO-$d_6$) δ ppm = 9.49-9.47 (m, 1H), 7.54-7.51 (m, 1H), 7.34-7.30 (m, 1H), 7.24 (s, 1H), 7.18-7.18 (m, 1H), 7.13-7.13 (m, 1H), 4.47-4.44 (m, 4H), 4.12-4.05 (m, 1H), 3.96-3.91 (m, 3H), 3.61-3.59 (m, 3H), 3.43-3.38 (m, 4H), 3.02-3.00 (m, 1H), 2.30-2.00 (m, 4H), 1.90-1.50 (m, 8H), 1.38-1.12 (m, 12H). |
| 2-124 | 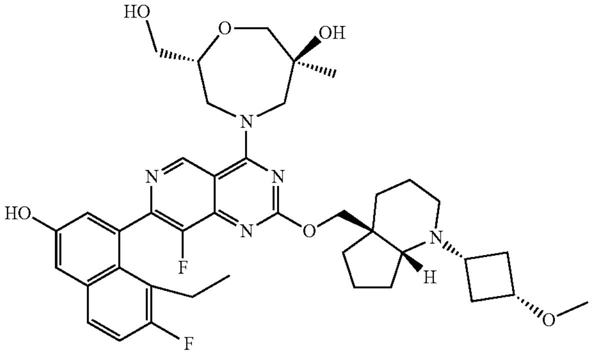 [SMILES: CCc1c(F)ccc2cc(O)cc(-c3ncc4c(N5C[C@H](CO)OC[C@@](C)(O)C5)nc(OC[C@]56CCC[C@H]5N([C@H]5C[C@@H](OC)C5)CCC6)nc4c3F)c12] | (2R,6S)-4-(2-{[(4aS,7aR)-1-[(1s,3s)-3-methoxycyclo-butyl]-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-2-(hydroxymethyl)-6-methyl-1,4-oxazepan-6-ol | 734.3 | $^1$H NMR (400 MHz, $CD_3CN$) δ ppm = 9.46-9.45 (m, 1H), 7.75 (dd, J = 9.1, 5.9 Hz, 1H), 7.37 (d, J = 2.6 Hz, 1H), 7.32 (t, J = 9.4 Hz, 1H), 7.20-7.03 (m, 1H), 5.03-4.87 (m, 1H), 4.76-4.68 (m, 1H), 4.66-4.52 (m, 2H), 4.46-4.31 (m, 1H), 4.08-3.98 (m, 1H), 3.93-3.86 (m, 1H), 3.68-3.53 (m, 4H), 3.51-3.41 (m, 2H), 3.14-3.13 (m, 3H), 2.72-2.59 (m, 2H), 2.46-2.38 (m, 3H), 2.29-2.23 (m, 2H), 1.81-1.70 (m, 3H), 1.70-1.45 (m, 7H), 1.46-1.39 (m, 2H), 1.31-1.29 (m, 3H), 0.90-0.75 (m, 3H). (Three OH protons not appeared). |
| 2-126$^\#$ | 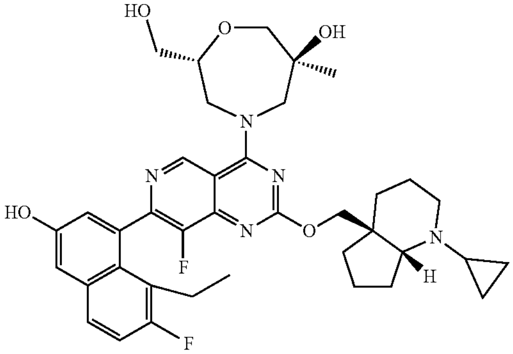 [SMILES: CCc1c(F)ccc2cc(O)cc(-c3ncc4c(N5C[C@H](CO)OC[C@@](C)(O)C5)nc(OC[C@]56CCC[C@H]5N(C5CC5)CCC6)nc4c3F)c12] | (2R,6S)-4-(2-{[(4aS,7aR)-1-cyclopropyl-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-2-(hydroxymethyl)-6-methyl-1,4-oxazepan-6-ol | 690.3 | $^1$H NMR (400 MHz, $CD_3CN$) δ ppm = 9.20-9.17 (m, 1H), 7.53-7.47 (m, 1H), 7.14-7.03 (m, 2H), 6.90-6.82 (m, 1H), 4.90-4.52 (m, 1H), 4.39-4.22 (m, 2H), 4.00-3.98 (m, 1H), 3.78-3.66 (m, 1H), 3.65-3.60 (m, 1H), 3.39-3.28 (m, 3H), 3.25-3.16 (m, 2H), 2.93-2.78 (m, 1H), 2.45-2.38 (m, 1H), 2.20-2.14 (m, 1H), 2.02-1.97 (m, 1H), 1.61-1.49 (m, 3H), 1.46-1.42 (m, 3H), 1.37-1.32 (m, 3H), 1.27-1.23 (m, 3H), 1.06-1.01 (m, 5H), 0.19-0.02 (m, 4H). (Three OH protons not appeared). |

TABLE 2-continued

| # | Structure | IUPAC | LCMS (M + H)+ | 1H NMR |
|---|---|---|---|---|
| 2-127# | 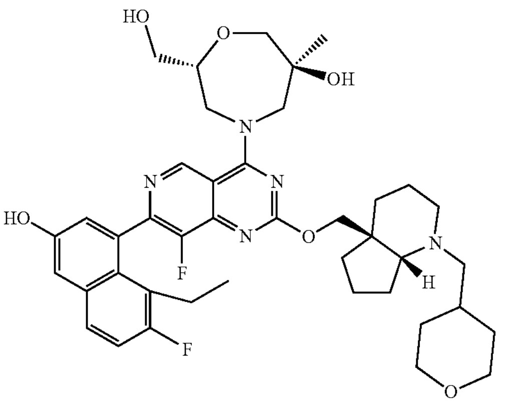 [SMILES: CCc1c(F)ccc2cc(O)cc(-c3ncc4c(N5C[C@H](CO)OC[C@@](C)(O)C5)nc(OC[C@]56CCC[C@H]5N(CC5CCOCC5)CCC6)nc4c3F)c12] | (2R,6S)-4-(2-{[(4aS,7aR)-1-[(oxan-4-yl)methyl]-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-2-(hydroxymethyl)-6-methyl-1,4-oxazepan-6-ol | 748.3 | $^1$H NMR (400 MHz, $CD_3CN$) δ ppm = 9.46-9.42 (m, 1H), 7.78-7.73 (m, 1H), 7.39-7.37 (m, 1H), 7.35-7.30 (m, 1H), 7.14-7.09 (m, 1H), 4.97-4.88 (m, 1H), 4.64-4.58 (m, 2H), 4.47-4.40 (m, 1H), 4.02-3.95 (m, 1H), 3.91-3.87 (m, 3H), 3.81-3.77 (m, 1H), 3.63-3.43 (m, 6H), 3.32-3.26 (m, 2H), 2.46-2.41 (m, 2H), 2.28-2.22 (m, 2H), 2.13-2.07 (m, 2H), 1.82-1.57 (m, 9H), 1.30-1.28 (m, 4H), 1.19-1.11 (m, 3H), 0.83-0.79 (m, 4H). (Three OH protons not appeared). |
| 2-128# | 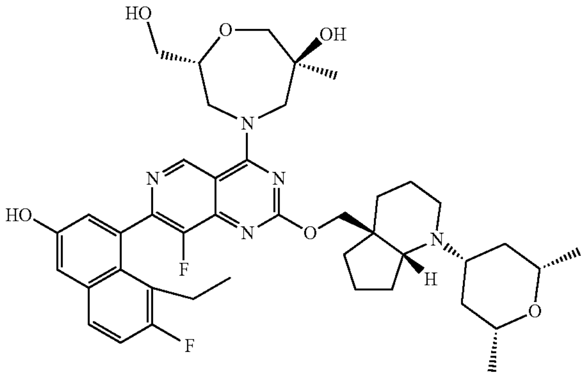 [SMILES: CCc1c(F)ccc2cc(O)cc(-c3ncc4c(N5C[C@H](CO)OC[C@@](C)(O)C5)nc(OC[C@]56CCC[C@H]5N([C@H]5C[C@@H](C)O[C@@H](C)C5)CCC6)nc4c3F)c12] | (2R,6S)-4-(2-{[(4aS,7aR)-1-[(2R,4r,6S)-2,6-dimethyloxan-4-yl]-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-2-(hydroxymethyl)-6-methyl-1,4-oxazepan-6-ol | 762.2 | $^1$H NMR (400 MHz, DMSO-$d_6$) δ ppm = 9.92-9.91 (m, 1H), 9.57-9.52 (m, 1H), 7.79-7.75 (m, 1H), 7.38-7.32 (m, 2H), 7.04-7.01 (m, 1H), 5.16-5.09 (m, 1H), 4.95-4.78 (m, 2H), 4.66-4.55 (m, 2H), 4.29 (d, J = 10.6 Hz, 1H), 4.05-4.01 (m, 1H), 3.81-3.75 (m, 1H), 3.68-3.54 (m, 2H), 3.50-3.42 (m, 2H), 3.39-3.33 (m, 2H), 3.15-3.08 (m, 1H), 2.57-2.54 (m, 1H), 2.53-2.53 (m, 1H), 2.39-2.28 (m, 1H), 2.21-2.12 (m, 1H), 1.94-1.92 (m, 1H), 1.78-1.63 (m, 3H), 1.62-1.52 (m, 4H), 1.48-1.46 (m, 2H), 1.40-1.17 (m, 6H), 1.10-1.02 (m, 7H), 1.02-0.83 (m, 2H), 0.74 (t, J = 7.2 Hz, 3H). |

TABLE 2-continued

| # | Structure | IUPAC | LCMS (M + H)+ | $^{1}$H NMR |
|---|---|---|---|---|
| 2-129[#] | 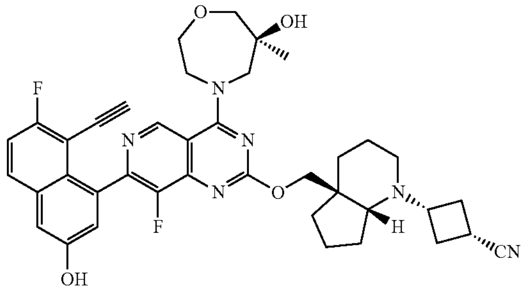 [SMILES: C#Cc1c(F)ccc2cc(O)cc(-c3ncc4c(N5CCOC[C@@](C)(O)C5)nc(OC[C@]56CCC[C@H]5N([C@H]5C[C@@H](C#N)C5)CCC6)nc4c3F)c12] | (2R,6S)-4-(2-{[(4aS,7aR)-1-[(2R,4s,6S)-2,6-dimethyloxan-4-yl]-octahydro-1H-cyclopenta[b]pyridin-4a-yl]methoxy}-7-(8-ethyl-7-fluoro-3-hydroxy-naphthalen-1-yl)-8-fluoropyrido[4,3-d]pyrimidin-4-yl)-2-(hydroxymethyl)-6-methyl-1,4-oxazepan-6-ol | 762.2 | $^{1}$H NMR (400 MHz, DMSO-$d_6$) δ ppm = 9.91 (s, 1H), 9.56-9.51 (m, 1H), 7.79-7.75 (m, 1H), 7.38-7.32 (m, 2H), 7.05-7.01 (m, 1H), 5.15-5.07 (m, 1H), 4.94-4.89 (m, 1H), 4.88-4.76 (m, 1H), 4.69-4.45 (m, 3H), 4.08-4.01 (m, 1H), 3.82-3.73 (m, 2H), 3.66-3.52 (m, 3H), 3.50-3.38 (m, 3H), 3.20 (br t, J = 9.1 Hz, 1H), 2.78-2.77 (m, 1H), 2.56-2.54 (m, 1H), 2.53-2.53 (m, 1H), 2.21-2.10 (m, 2H), 1.94-1.81 (m, 3H), 1.77-1.65 (m, 2H), 1.64-1.59 (m, 2H), 1.51-1.30 (m, 5H), 1.26-1.19 (m, 3H), 1.19-1.05 (m, 2H), 1.01-0.93 (m, 3H), 0.90-0.82 (m, 3H), 0.74 (t, J = 7.4 Hz, 3H). |

[#]Prep-HPLC [HPLC Method: Preparative column: X Bridge C18 (150 * 19 * 5); Mobile Phase A: 10 mm ammonium bicarbonate in water pH-9.5; Mobile Phase B: ACN; temperature: 27° C.; Flow rate: 15.0 mL/min; detection: UV at 220 nm];
[!]Prep-HPLC [HPLC Method: Preparative Column: Kinetex Bi phenyl (250 * 21.2) Mobile phase A: 0.1% TFA in water, Mobile phase B: Acetonitrile, Temperature: 27° C., Flow rate: 15 mL/min, detection: UV at 220 nm];
[X]Prep-HPLC [HPLC Method: Preparative column: Gemini NX C18 (250 * 21.2 * 5); Mobile Phase A: 10 mM ammonium bicarbonate in water pH-9.5; Mobile Phase B: ACN:MeOH (1:1) Flow: 20 ml/min; Temperature: 27° C.; Flow rate: 19.0 mL/min; Detection: UV at 220 nm];
[A]Prep-HPLC [HPLC Method: Preparative column: X Select C18 (250 mm * 20 mm * 5 μm); Mobile phase A: 10 mM ammonium bicarbonate in water pH-9.5; Mobile phase B: ACN:MeOH (1:1); Flow rate: 20 mL/min; Temperature: 27° C.; Detection: UV at 220 nm];
[B]Prep-HPLC [HPLC Method: Preparative column: Cellulose C5 (250 mm * 21.2 mm * 5 μm); Mobile phase A: 10 mM ammonium bicarbonate in water pH-9.5; Mobile Phase B: ACN: MeOH (1:1); Flow rate: 20 mL\min; Temperature: 27° C.; Detection: UV at 220 nm]; and
[F]Prep-HPLC [HPLC Method: Preparative column: X select C18 (250 mm * 20 mm * 5 μm); Mobile phase A: 5 mM ammonium bicarbonate in water pH-3.5; Mobile phase B: acetonitrile; Flow rate: 15 mL\min; Temperature: 27° C.; Detection: UV at 220 nm].

Preparation of Intermediate 66: 7-bromo-5-(methoxymethoxy)-2,3-dihydro-1H-inden-1-one

66

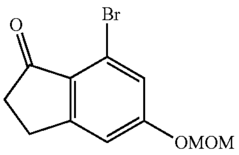

To a stirred solution of 7-bromo-5-hydroxy-2,3-dihydro-1H-inden-1-one (1 g, 4.40 mmol) and DIPEA (1.54 mL, 8.81 mmol) in dichloromethane (20 mL) under a nitrogen atmosphere at 0° C., was added MOM-Cl (0.401 mL, 5.29 mmol). The reaction mixture was gradually warmed to room temperature and stirred for 2 hours. Then, the reaction mixture was diluted with dichloromethane, washed with water, brine, dried over anhydrous $Na_2SO_4$, filtered and concentrated under reduced pressure to provide a crude residue, which was purified through silica gel column chromatography using a CombiFlash instrument (24 g RediSep® silica gel column, 10% EtOAc-Pet Ether) to afford 7-bromo-5-(methoxymethoxy)-2,3-dihydro-1H-inden-1-one (1.1 g, 4.02 mmol, 91% yield). $^{1}$H NMR (400 MHz, DMSO-$d_6$) δ ppm=7.22 (d, J=2.0 Hz, 1H), 7.18 (d, J=2.0 Hz, 1H), 5.32 (s, 2H), 3.39 (s, 3H), 3.02-2.99 (m, 2H), 2.64-2.62 (m, 2H).

Preparation of Intermediate 67:7-bromo-5-(methoxymethoxy)-1-methylene-2,3-dihydro-1H-indene

67

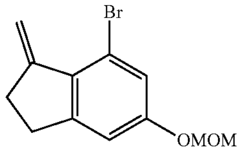

To a stirred solution of methyltriphenylphosphonium bromide (1.32 g, 3.69 mmol) in methyl tert-butyl ether (8 mL) under a nitrogen atmosphere at 0° C., was added 3M potassium tert-butoxide in THF (1.5 mL, 2.77 mmol) and the mixture was stirred for 15 min. Next, 7-bromo-5-(methoxymethoxy)-2,3-dihydro-1H-inden-1-one (250 mg, 0.92 mmol) was added to that reaction mixture and gradually warmed to room temperature over a period of 1 hour. The reaction mixture was quenched with water, extracted with ethyl acetate, washed with brine, dried over anhydrous $Na_2SO_4$, and concentrated under reduced pressure to afford a crude residue, which was purified through silica gel column chromatography using a CombiFlash instrument (24 g RediSep® silica gel column, 10% EtOAc-Pet Ether, ELSD) to afford 7-bromo-5-(methoxymethoxy)-1-methylene-2,3-dihydro-1H-indene (180 mg, 0.67 mmol, 72.5% yield) a colorless liquid. $^{1}$H NMR (400 MHz, DMSO-$d_6$) δ ppm=7.11 (d, J=2.4 Hz, 1H), 7.01 (d, J=1.2 Hz, 1H), 5.99-5.98 (m, 1H), 5.09-5.08 (m, 1H), 5.22 (s, 2H), 3.38 (s, 3H), 2.92-2.89 (m, 2H), 2.80-2.75 (m, 2H).

Preparation of Intermediate 68: 7'-bromo-5'-(methoxymethoxy)-2',3'-dihydrospiro[cyclopropane-1,1'-indene]

68

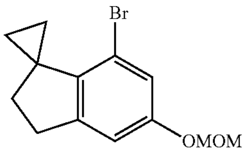

To a stirred solution of 1M diethylzinc in hexanes (4.01 mL, 4.01 mmol) in dichloromethane (3 mL) under a nitrogen atmosphere at 0° C., was added diiodomethane (0.27 mL, 3.34 mmol). Next, 7-bromo-5-(methoxymethoxy)-1-methylene-2,3-dihydro-1H-indene (180 mg, 0.67 mmol) was added to that reaction mixture and gradually warmed to room temperature over a period of 3 hours. Then, the reaction mixture was quenched with water, and extracted with dichloromethane. The organic layer was separated, dried over anhydrous $Na_2SO_4$, filtered and was concentrated under reduced pressure to provide a crude residue, which was purified through silica gel column chromatography using a CombiFlash instrument (12 g RediSep® silica gel column, to 5% EtOAc-Pet Ether, ELSD) afford 7'-bromo-5'-(methoxymethoxy)-2',3'-dihydrospiro[cyclopropane-1,1'-indene] (120 mg, 0.42 mmol, 63.4% yield) a colorless liquid. $^1H$ NMR (400 MHz, DMSO-$d_6$) δ ppm=6.93-6.91 (m, 2H), 5.15 (s, 2H), 3.36 (s, 3H), 2.92 (t, J=8.0 Hz, 2H), 2.04 (t, J=8.0 Hz, 2H), 1.54 (q, J=4.4 Hz, 2H), 0.75 (q, J=4.0 Hz, 2H).

Preparation of Intermediate 69: 2-(5'-(methoxymethoxy)-2',3'-dihydrospiro[cyclopropane-1,1'-inden]-7'-yl)-4,4,5,5-tetramethyl-1,3,2-dioxaborolane

69

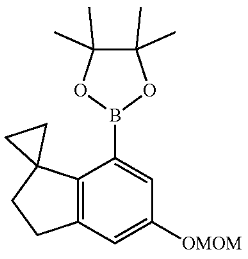

To a stirred solution of 7'-bromo-5'-(methoxymethoxy)-2',3'-dihydrospiro[cyclopropane-1,1'-indene] (110 mg, 0.39 mmol) and bis(pinacolato)diboron (128 mg, 0.51 mmol) in 1,4-dioxane (2.5 mL), was added potassium acetate (114 mg, 1.17 mmol) and the reaction mixture was purged with argon for 5 min. Then, the reaction mixture was charged with Pd(dppf)$Cl_2$·DCM complex (28.4 mg, 0.039 mmol) and again purged with argon for 3 min. The reaction mixture was heated at 80° C. over a period of 16 hours. Then, the reaction mixture was diluted with water and extracted with ethyl acetate. The organic layer was separated, dried over anhydrous sodium sulphate, filtered and concentrated under reduced pressure to provide a crude residue, which was purified through silica gel column chromatography using a CombiFlash instrument (12 g RediSep® silica gel column, 5% EtOAc-Pet Ether, ELSD) to afford 2-(5'-(methoxymethoxy)-2',3'-dihydrospiro[cyclopropane-1,1'-inden]-7'-yl)-4,4,5,5-tetramethyl-1,3,2-dioxaborolane (70 mg, 0.21 mmol, 54.6% yield) as a colorless liquid. $^1H$ NMR (400 MHz, DMSO-$d_6$) δ ppm=6.94 (d, J=2.4 Hz, 1H), 6.91 (d, J=2.4 Hz, 1H), 5.11 (s, 2H), 3.35 (s, 3H), 2.88 (t, J=7.6 Hz, 2H), 1.98 (t, J=7.6 Hz, 2H), 1.27 (s, 14H), 0.77 (q, J=4.0 Hz, 2H).

Preparation of Intermediate 70:1,1-dimethoxy-3-(methoxymethyl)cyclobutene

70

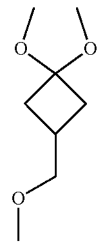

To a stirred solution of (3,3-dimethoxycyclobutyl)methanol (1.0 g, 6.84 mmol) in DMF (8.0 mL) under a nitrogen atmosphere at 0° C., was added NaH (0.328 g, 13.68 mmol) and stirred for 10 min. Then, methyl iodide (1.07 g, 7.52 mmol) was added to the reaction mixture and gradually warmed to room temperature over a period of 2 hours. The reaction mixture was quenched with ice cold water and extracted with EtOAc. The organic layer was separated, dried over $Na_2SO_4$ and was concentrated under reduced pressure to afford a crude residue, which was purified through silica gel column chromatography using a CombiFlash instrument (40 g RediSep® silica gel column, 10% Solvent-solvent, ELSD) to afford 1,1-dimethoxy-3-(methoxymethyl)cyclobutane (830 mg, 5.19 mmol, 76% yield) as a colorless liquid. $^1H$ NMR (300 MHz, DMSO-$d_6$) δ ppm=3.31-3.29 (m, 2H), 3.23 (s, 3H), 3.04 (s, 3H), 3.01 (s, 3H), 2.17-2.15 (m, 3H), 1.75-1.72 (m, 2H).

Preparation of Intermediate 71: 3-(methoxymethyl)cyclobutan-1-one

71

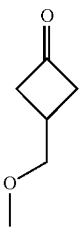

To a stirred solution of 1,1-dimethoxy-3-(methoxymethyl)cyclobutane (830 mg, 5.18 mmol) in diethyl ether (13 mL) and water (1 mL) at room temperature, was added p-toluenesulfonic acid monohydrate (99 mg, 0.52 mmol) and stirred for 2 hours. Then, the reaction mixture was quenched with water and extracted with diethyl ether. The organic layer was separated, dried over anhydrous $Na_2SO_4$ and was concentrated under reduced pressure to afford 1,1-dimethoxy-3-(methoxymethyl)cyclobutane (830 mg, crude) as a colorless crude liquid which was taken for next step without further purification.

Preparation of Intermediate 72: 3-hydroxy-3-methylcyclobutyl pivalate

72

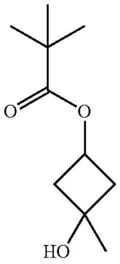

To a stirred solution of 3-oxocyclobutyl pivalate (500 mg, 2.94 mmol) in tetrahydrofuran (6 mL) under a nitrogen atmosphere at 0° C., was added 3M methylmagnesium bromide in diethyl ether (1.96 mL, 5.88 mmol). The reaction mixture was gradually warmed to room temperature over a period of 2 hours. Then, the reaction mixture was quenched with saturated $NH_4Cl$ solution, filtered through a Celite pad, washed with EtOAc and the filtrate was extracted with EtOAc. The combined organic layers were dried over anhydrous sodium sulphate, filtered and concentrated under reduced pressure to afford a crude residue, which was purified through silica gel column chromatography using a CombiFlash instrument (12 g RediSep® silica gel column, 60% Solvent-solvent, ELSD) to afford diastereomeric mixture of 3-hydroxy-3-methylcyclobutyl pivalate (270 mg, 1.44 mmol, 49.3% yield). $^1H$ NMR (300 MHz, DMSO-$d_6$) δ ppm=5.11-5.10 (m, 1H), 4.57-4.50 (m, 1H), 2.40-2.35 (m, 2H), 2.04-2.02 (m, 2H), 1.21-1.18 (m, 3H), 1.14-1.10 (m, 9H).

Preparation of Intermediate 73: 1-methylcyclobutane-1,3-diol

73

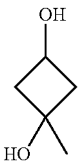

To a stirred solution of 3-hydroxy-3-methylcyclobutyl pivalate (270 mg, 1.45 mmol) in MeOH (1.5 mL) and water (1.5 mL) at room temperature under a nitrogen atmosphere, was added NaOH (232 mg, 5.80 mmol) and stirred for 16 hours. The reaction mixture was concentrated under reduced pressure to afford a crude residue, which was diluted with ice-water and acidified with 1.5M HCl to PH ~5. The aqueous layer was extracted with dichloromethane, dried over anhydrous $Na_2SO_4$, filtered and concentrated under reduced pressure to afford a diastereomeric mixture of 1-methylcyclobutane-1,3-diol (120 mg, 1.18 mmol, 95% yield).

Preparation of Intermediate 74: 3-hydroxy-3-methylcyclobutan-1-one

74

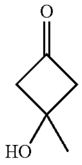

To a stirred solution of 1-methylcyclobutane-1,3-diol (125 mg, 1.22 mmol) in dichloromethane (3.0 mL) under a nitrogen atmosphere at 0° C., was added Dess Martin periodinane (519 mg, 1.22 mmol). The reaction mixture was gradually warmed to room temperature over a period of 2 hours. Then, the reaction mixture was filtered through a CELITE pad, and concentrated to afford a crude residue. The crude residue was re-dissolved in $Et_2O$ and again filtered through that Celite pad. The filtrate was evaporated to dryness under reduced pressure to afford 3-hydroxy-3-methylcyclobutan-1-one (100 mg, 1.01 mmol, 82% yield) as a colorless liquid, which was taken for next step without further purification.

Preparation of Intermediate 76: tert-butyl 6-(hydroxymethyl)-1,4-oxazepane-4-carboxylate

76

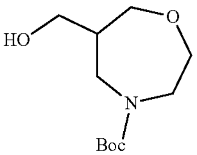

To a stirred solution of tert-butyl 6-methylene-1,4-oxazepane-4-carboxylate (3 g, 14.07 mmol) in tetrahydrofuran (30 mL) under a nitrogen atmosphere at 0° C., was added 1M $BH_3$·THF complex in tetrahydrofuran (14.07 mL, 14.07 mmol) and gradually warmed to room temperature over a period of 4 hours. Then, the reaction mixture was cooled to 0° C., and 3N aqueous NaOH solution (4.69 mL, 14.07 mmol) and hydrogen peroxide (2.16 mL, 21.10 mmol) were added in sequence. The reaction mixture was gradually warmed to room temperature and stirred for 16 hours. Then, the reaction mixture was diluted with water and extracted with ethyl acetate. The combined organic layers were washed with saturated brine, dried over anhydrous $Na_2SO_4$, filtered and concentrated under reduced pressure to afford a crude residue, which was purified through silica gel column chromatography using Biotage instrument (80 g RediSep® silica gel column, 0-60% ethyl acetate in petroleum ether, ELSD) to afford tert-butyl 6-(hydroxymethyl)-1,4-oxazepane-4-carboxylate (2.6 g, 10.5 mmol, 75% yield) as colorless liquid. MS (ESI) m/z: 132.2 $[M+H-Boc]^+$. $^1H$ NMR (400 MHz, $CDCl_3$) δ ppm=3.99 (dd, J=14.8, 4.0 Hz, 1H), 3.86-3.57 (m, 8H), 3.34 (dd, J=14.8, 5.2 Hz, 1H), 3.23-3.17 (m, 1H), 2.20-2.16 (m, 1H), 1.50 (s, 9H).

Preparation of Intermediate 77: tert-butyl 6-formyl-1,4-oxazepane-4-carboxylate

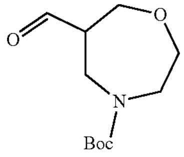

77

To a stirred solution of tert-butyl 6-(hydroxymethyl)-1,4-oxazepane-4-carboxylate (2.6 g, 11.24 mmol) in dichloromethane (40 mL) under a nitrogen atmosphere at room temperature, was added Dess-Martin periodinane (9.54 g, 22.48 mmol) and the mixture was stirred for 48 hours. Then, the reaction mixture was filtered through a CELITE pad, and the filtrate was basified with 10% aqueous $NaHCO_3$ solution. The biphasic mixture was extracted with dichloromethane, washed with brine, dried over anhydrous $Na_2SO_4$, filtered and concentrated under reduced pressure to afford crude tert-butyl 6-formyl-1,4-oxazepane-4-carboxylate (3 g, crude) as a white gummy solid.

Preparation of Intermediate 78: 4-(tert-butoxycarbonyl)-1,4-oxazepane-6-carboxylic Acid

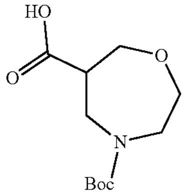

78

To a stirred solution of tert-butyl 6-formyl-1,4-oxazepane-4-carboxylate (3 g, 13.08 mmol) in t-BuOH (30 mL) and water (6 mL) at 0° C. under a nitrogen atmosphere, were added sodium chlorite (1.78 g, 19.63 mmol) and sodium phosphate monobasic (2.36 g, 19.63 mmol). The reaction mixture was gradually warmed up to room temperature and stirred for 16 hours. Then, the reaction mixture was filtered, diluted with water, and extracted with ethyl acetate. The, combined organic layers were washed with brine, dried over anhydrous $Na_2SO_4$, filtered and concentrated under reduced pressure to afford crude 4-(tert-butoxycarbonyl)-1,4-oxazepane-6-carboxylic acid (1.5 g, 5.98 mmol, 45.7% yield). MS (ESI) m/z: 146.6 [M+H−Boc]$^+$.

Preparation of Intermediate 79a & 79b: 4-(tert-butyl) 6-methyl 1,4-oxazepane-4,6-dicarboxylate 79a & 79b

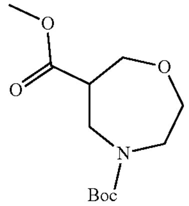

To a stirred solution of 4-(tert-butoxycarbonyl)-1,4-oxazepane-6-carboxylic acid (1.5 g, 6.12 mmol) in DMF (20 mL) under an argon atmosphere at 0° C., were added $K_2CO_3$ (1.69 g, 12.23 mmol) and methyl iodide (0.765 mL, 12.23 mmol). The reaction mixture was gradually warmed to room temperature and stirred for 2 hours. Then, the reaction mixture was diluted with water and extracted with ethyl acetate. The combined organic layers were washed with saturated brine solution, dried over anhydrous $Na_2SO_4$, filtered, and concentrated under reduced pressure to afford a crude residue, which was purified through silica gel column chromatography using a Biotage instrument (80 g RediSep® silica gel column, 0-30% ethyl acetate in petroleum ether, ELSD) to afford racemic 4-(tert-butyl) 6-methyl 1,4-oxazepane-4,6-dicarboxylate (700 mg, 2.63 mmol, 43.1% yield) as a colorless liquid. The racemic compound was purified by chiral SFC to afford 4-(tert-butyl) 6-methyl 1,4-oxazepane-4,6-dicarboxylate (300 mg, 18.90% yield) as colorless liquid and 4-(tert-butyl) 6-methyl 1,4-oxazepane-4,6-dicarboxylate (300 mg, 15.09% yield) as colorless liquid. SFC chiral separation method: Peak-1 (79a) retention time 4.5 min; Peak-2 (79b) retention time 6.1 min; column/dimension: Lux i-Amylose-3 (250×4.6) mm, 5 μm; % $CO_2$: 70%; 30% of 0.1% $NH_4OH$ in MeOH; Total Flow: 3.0 g/min; Back Pressure: 100 bar; Temperature: 40° C.; UV: 220 nm. Peak-1: MS (ESI) m/z: 160.2 [M+H−Boc]$^+$. $^1H$ NMR (400 MHz, $CDCl_3$) δ ppm=4.18-3.89 (m, 2H), 3.84-3.46 (m, 10H), 3.33-3.21 (m, 1H), 3.14-2.96 (m, 1H), 1.49 (s, 9H), 0.98-0.91 (m, 1H). Peak-2: MS (ESI) m/z: 160.2 [M+H−Boc]$^+$. $^1H$ NMR (400 MHz, $CDCl_3$) δ ppm=4.18-3.89 (m, 2H), 3.84-3.46 (m, 10H), 3.33-3.21 (m, 1H), 3.14-2.96 (m, 1H), 1.49 (s, 9H), 0.98-0.91 (m, 1H).

Preparation of Intermediate 80: tert-butyl 6-(2-hydroxypropan-2-yl)-1,4-oxazepane-4-carboxylate

80

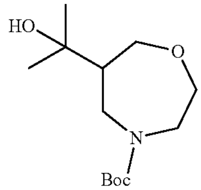

To a stirred solution of 4-(tert-butyl) 6-methyl 1,4-oxazepane-4,6-dicarboxylate (300 mg, 1.16 mmol, Intermediate 79a) in tetrahydrofuran (5 mL) under a nitrogen atmosphere at 0° C., was added 3M MeMgBr in diethyl ether (1.55 mL, 4.63 mmol). The reaction mixture was gradually warmed up to room temperature and stirred for 16 hours. Then, the reaction mixture quenched with saturated aqueous ammonium chloride solution, diluted with water and extracted with ethyl acetate. The combined organic layers were washed with water, brine, dried over anhydrous $Na_2SO_4$, filtered and concentrated under reduced pressure to afford a crude residue, which was purified through silica gel column chromatography using Biotage instrument (40 g RediSep® silica gel column, 0-30% ethyl acetate in petroleum ether, ELSD) to afford tert-butyl 6-(2-hydroxypropan-2-yl)-1,4-oxazepane-4-carboxylate (250 mg, 0.96 mmol, 83% yield) as colorless liquid. $^1$H NMR (400 MHz, $CDCl_3$) δ ppm=3.99-3.85 (m, 2H), 3.82-3.51 (m, 4H), 3.47-3.10 (m, 2H), 2.13-1.97 (m, 1H), 1.49 (s, 9H), 1.29 (s, 3H), 1.23 (s, 3H).

Preparation of Intermediate 81: 2-(1,4-oxazepan-6-yl) propan-2-ol, HCl

81

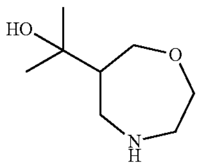

To a stirred solution of tert-butyl 6-(2-hydroxypropan-2-yl)-1,4-oxazepane-4-carboxylate (250 mg, 0.96 mmol) in dichloromethane (5 mL) under a nitrogen atmosphere at 0° C., was added 4M HCl in 1,4-dioxane (1.21 mL, 4.82 mmol). The reaction mixture was gradually warmed to room temperature and stirred for 2 hours. Then, the reaction mixture was concentrated under reduced pressure and the crude residue was triturated with diethyl ether (5 mL) and dried under reduced pressure to afford 2-(1,4-oxazepan-6-yl) propan-2-ol, HCl (250 mg) as a colorless gum. MS (ESI) m/z: 160.2 $[M+H]^+$. $^1$H NMR (400 MHz, DMSO-$d_6$) δ ppm=9.24 (brs, 1H), 8.89 (brs, 1H), 4.70 (brs, 1H), 3.89-3.78 (m, 2H), 3.75-3.68 (m, 1H), 3.64-3.55 (m, 3H), 3.38-3.32 (m, 1H), 3.26-3.17 (m, 1H), 3.09-2.93 (m, 2H), 2.26-2.17 (m, 1H), 1.08 (s, 3H), 1.05 (s, 3H).

Preparation of Intermediate 92: ethyl (4aS,7aR)-1-benzyl-2-oxooctahydro-4aH-cyclopenta[b]pyridine-4a-carboxylate

92

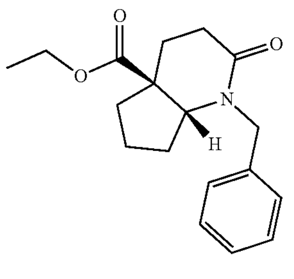

To a stirred solution of ethyl (4aS,7aR)-2-oxooctahydro-4aH-cyclopenta[b]pyridine-4a-carboxylate (5.00 g, 23.67 mmol) in THF under an argon atmosphere at 0° C., was added sodium hydride (0.947 g, 23.67 mmol) and stirred for 1 hour. Then, (bromomethyl)benzene (5.62 mL, 47.30 mmol) was added at 0° C. and stirred for additional 2 hours. After completion, the reaction mixture was quenched with saturated aqueous ammonium chloride solution and extracted with EtOAc. The combined organic layers were dried over anhydrous $Na_2SO_4$, filtered, dried, and purified through silica gel column chromatography using a CombiFlash instrument (80 g RediSep® column, 30% EtOAc-pet ether) to afford the ethyl (4aS,7aR)-1-benzyl-2-oxooctahydro-4aH-cyclopenta[b]pyridine-4a-carboxylate (7 g, 23.23 mmol, 98% yield) as a colorless liquid. $^1$H NMR (300 MHz, $CDCl_3$) δ ppm=7.27-7.14 (m, 5H), 4.18-3.92 (m, 2H), 2.37 (dd, J=7.9, 5.4 Hz, 2H), 2.14-1.92 (m, 4H), 1.89-1.62 (m, 4H), 1.59-1.40 (m, 2H), 1.27-1.03 (m, 3H).

Preparation of Intermediate 192a: 2,7-dichloro-8-fluoro-N,N-dimethylpyrido[4,3-d]pyrimidin-4-amine 192a

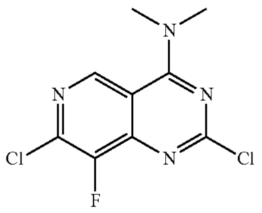

To a solution of 2,4,7-trichloro-8-fluoropyrido[4,3-d]pyrimidine (2.0 g, 7.81 mmol) in DCM (25 mL) at −40° C. under a nitrogen atmosphere, were added dimethylamine hydrochloride (0.57 g, 7.03 mmol) and N,N-diisopropylethylamine (5.43 mL, 31.24 mmol). The reaction mixture was stirred at the same temperature for 1 hour. Then, the reaction mixture was quenched with ice cold water and extracted with DCM. The organic layer was separated and dried over anhydrous $Na_2SO_4$, filtered and concentrated under reduced pressure to afford a crude residue, which was purified by silica gel column chromatography using a CombiFlash instrument (40 g RediSep® column, 40% EtOAc in pet-ether) to afford 2,7-dichloro-8-fluoro-N,N-dimethylpyrido[4,3-d]pyrimidin-4-amine (1.24 g, 4.77 mmol, 68% yield) as a pale yellow solid. MS (ESI) m/z: 261.0 $[M+H]^+$.

Preparation of Intermediate 192b: tert-butyl (4aS,7aR)-4a-({[7-chloro-4-(dimethylamino)-8-fluoropyrido[4,3-d]pyrimidin-2yl]oxy}methyl)-octahydro-1H-cyclopenta[b]pyridine-1-carboxylate 192b

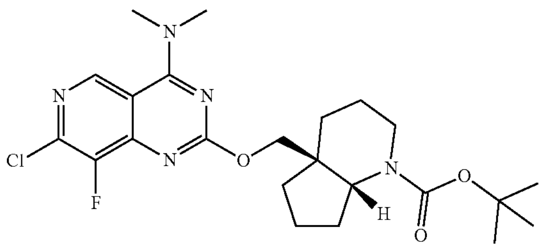

To a stirred solution of tert-butyl (4aS,7aR)-4a-(hydroxymethyl)-octahydro-1H-cyclopenta[b]pyridine-1-carboxylate (1.0 g, 3.92 mmol) in THF (15 mL) at 0° C. under a nitrogen atmosphere, was added 1M LiHMDS in THF (7.84 mL, 7.84 mmol) and the mixture was stirred at the same temperature for 15 min. Then, a solution of 2,7-dichloro-8-fluoro-N,N-dimethylpyrido[4,3-d]pyrimidin-4-amine (1.01 g, 3.92 mmol) in THF (5 mL) was added to the reaction mixture and it was gradually warmed to room temperature over a period of 16 hours. Next, the reaction mixture was quenched with ice cold water and extracted with DCM. The organic layer was separated, dried over anhydrous $Na_2SO_4$, filtered and concentrated under reduced pressure to afford a crude residue, which was purified by silica gel column chromatography using a CombiFlash instrument (40 g RediSep® column, 30% EtOAc in pet-ether) to afford tert-butyl (4aS,7aR)-4a-({[7-chloro-4-(dimethylamino)-8-fluoropyrido[4,3-d]pyrimidin-2-yl] oxy}methyl)-octahydro-1H-cyclopenta[b]pyridine-1-carboxylat (1.0 g, 2.12 mmol, 54% yield) as a pale yellow solid. MS (ESI) m/z: 480.4 $[M+H]^+$.

Preparation of Intermediate 93: ethyl (3S,4aS,7aR)-1-benzyl-3-fluoro-2-oxooctahydro-4aH-cyclopenta [b]pyridine-4a-carboxylate

93

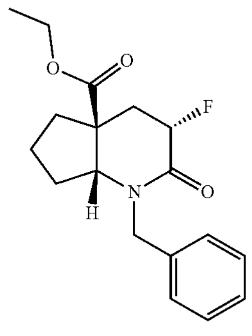

To a stirred solution of ethyl (4aS,7aR)-1-benzyl-2-oxooctahydro-4aH-cyclopenta[b]pyridine-4a-carboxylate (7 g, 23.23 mmol) in THE under an argon atmosphere at −78° C., was added 2M LDA in THF (17.42 mL, 34.80 mmol) and stirred for 1 hour. Then, N-fluorobenzenesulfonimide (9.52 g, 30.20 mmol) was added in a portion and stirred for an additional 2 hours at the same temperature. After completion, the reaction mixture was quenched with saturated aqueous ammonium chloride solution and extracted with ethyl acetate. The combined organic layers were washed with brine, dried over anhydrous $Na_2SO_4$, filtered, concentrated under reduced pressure to afford a crude residue, which was purified by silica gel column chromatography using a CombiFlash instrument (120 g RediSep® column, 30% EtOAc-pet ether) to afford ethyl (4aS,7aR)-1-benzyl-3-fluoro-2-oxo-octahydro-1H-cyclopenta[b]pyridine-4a-carboxylate (2.4 g, 7.50 mmol, 32.4%) as a pale yellow liquid. $^1$H NMR (300 MHz, $CDCl_3$) δ ppm=7.30-7.12 (m, 5H), 5.05-4.72 (m, 1H), 4.19-3.88 (m, 3H), 2.67-2.44 (m, 1H), 2.26-1.92 (m, 4H), 1.88-1.55 (m, 4H), 1.21-1.03 (m, 3H), −0.01-0.08 (m, 1H).

Preparation of Intermediate 94: ((3S,4aS,7aR)-1-benzyl-3-fluorooctahydro-4aH-cyclopenta[b]pyridin-4a-yl)methanol

94

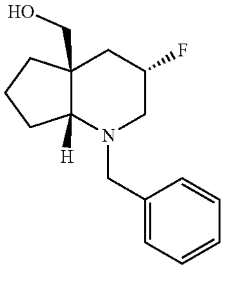

To a stirred solution of ethyl (4aS,7aR)-1-benzyl-3-fluoro-2-oxooctahydro-4aH-cyclopenta[b]pyridine-4a-carboxylate (1.0 g, 3.13 mmol) in THF (10 mL) under an argon atmosphere at 0° C., was added 2M LAH in THF (6.26 mL, 12.52 mmol) and stirred at room temperature for 15 hours. The reaction mixture was cooled to 0° C., quenched with water (6 mL), 10% NaOH (12 mL) and water (12 mL). Then, the reaction mixture was stirred for 10 min and filtered through a CELITE pad. The CELITE pad was washed with EtOAc. The filtrate was concentrated under reduced pressure to afford [(3S,4aS,7aR)-1-benzyl-3-fluoro-octahydro-1H-cyclopenta[b]pyridin-4a-yl]methanol (450 mg, 1.709 mmol, 54.6% yield) as a colorless liquid. $^1$H NMR (400 MHz, CHLOROFORM-d) δ ppm=7.48-7.19 (m, 5H), 5.30-5.02 (m, 1H), 3.91-3.79 (m, 1H), 3.76-3.53 (m, 3H), 3.13-2.89 (m, 2H), 2.56-2.41 (m, 1H), 2.14-1.95 (m, 2H), 1.91-1.53 (m, 5H), 1.45-1.32 (m, 2H).

Preparation of Intermediate 99: (1s,3s)-3-hydroxy-3-(trifluoromethyl)cyclobutane-1-carboxylic Acid

99

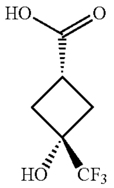

The intermediate (1s,3s)-3-hydroxy-3-(trifluoromethyl) cyclobutane-1-carboxylic acid was synthesized according to the literature procedure: J. Med. Chem., 2022, 65, 8948-8960.

Preparation of Intermediate 100: (1s,3s)-3-(hydroxymethyl)-1-(trifluoromethyl)cyclobutan-1-ol

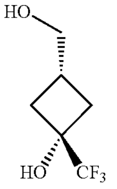

100

To a stirred solution of (1s,3s)-3-hydroxy-3-(trifluoromethyl)cyclobutane-1-carboxylic acid (450 mg, 2.45 mmol) in THF (9 mL) under an argon atmosphere at 0° C., was added 1M Borane·THF complex (9.78 mL, 9.78 mmol). The reaction mixture was gradually warmed to room temperature over a period of 16 hours. Then, the reaction mixture was quenched with MeOH. The reaction mixture was diluted with EtOAc and washed with water, brine, dried over anhydrous $Na_2SO_4$, concentrated under reduced pressure to afford a crude residue, which was purified through silica gel column chromatography using a CombiFlash instrument (12 g RediSep® column, 80% EtOAc-pet ether, ELSD) to afford (1s,3s)-3-(hydroxymethyl)-1-(trifluoromethyl)cyclobutan-1-ol (380 mg, 2.24 mmol, 91% yield) as a white solid. $^1H$ NMR (300 MHz, DMSO-$d_6$) δ ppm=6.32 (s, 1H), 4.60 (t, J=5.39 Hz, 1H), 3.43-3.33 (m, 2H), 2.43-2.30 (m, 2H), 2.14-1.97 (m, 1H), 1.97-1.84 (m, 2H).

Preparation of Intermediate 101: (1s,3s)-3-hydroxy-3-(trifluoromethyl)cyclobutane-1-carbaldehyde

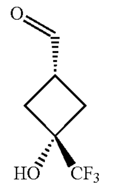

101

To a stirred solution of (1s,3s)-3-(hydroxymethyl)-1-(trifluoromethyl)cyclobutan-1-ol (170 mg, 1.00 mmol) in DCM (3 mL) under an argon atmosphere at room temperature, was added PCC (431 mg, 2.00 mmol) and stirred for 4 hours. Then, the reaction mixture was diluted with DCM and washed with water, brine, dried over $Na_2SO_4$, concentrated under reduced pressure to afford a crude residue, which purified by silica gel column chromatography using a CombiFlash instrument (12 g RediSep® column, 20% EtOAC-Pet ether, ELSD) to afford (1s,3s)-3-hydroxy-3-(trifluoromethyl)cyclobutane-1-carbaldehyde (100 mg, 0.60 mmol, 59.5% yield) as a colorless liquid. $^1H$ NMR (300 MHz, DMSO-$d_6$) δ ppm=9.71 (s, 1H), 6.60 (s, 1H), 4.09 (d, J=6.46 Hz, 1H), 3.02-2.82 (m, 1H), 2.76-2.56 (m, 1H), 2.39-2.25 (m, 2H).

Examples 5-59, 5-60, 5-110, 5-118, and 5-135 were synthesized using this fragment.

Preparation of Intermediate 102: (1s,3s)-3-hydroxy-3-methylcyclobutane-1-carboxylic Acid

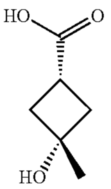

102

The intermediate (1s,3s)-3-hydroxy-3-methylcyclobutane-1-carboxylic acid was synthesized according to the procedure described in WO2015005901A1.

Preparation of Intermediate 103: (1s,3s)-3-(hydroxymethyl)-1-methylcyclobutan-1-ol

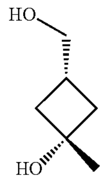

103

To a stirred solution of (1s,3s)-3-hydroxy-3-methylcyclobutane-1-carboxylic acid (180 mg, 1.38 mmol) in THF (5 mL) under an argon atmosphere at 0° C., was added 1M $BH_3$·THF in THF (6.92 mL, 6.92 mmol) and the reaction mixture was gradually warmed up to room temperature over a period of 16 hours. The reaction mixture was quenched with MeOH and volatiles were removed under reduced pressure. The crude residue was dissolved in ethyl acetate, washed with water, brine, dried over $Na_2SO_4$ and concentrated under reduced pressure to afford a crude residue, which was purified by silica gel column chromatography using a CombiFlash instrument (12 g RediSep® column, 40 to 60% EtOAc-pet ether, ELSD) to afford (1s,3s)-3-(hydroxymethyl)-1-methylcyclobutan-1-ol (120 mg, 1.03 mmol, 74.7% yield) as a colorless liquid. $^1H$ NMR (300 MHz, DMSO-$d_6$) δ ppm=4.85-4.63 (m, 1H), 4.50-4.28 (m, 1H), 3.33 (d, J=5.4 Hz, 2H), 1.97-1.81 (m, 3H), 1.67 (br d, J=9.3 Hz, 2H), 1.20 (s, 3H).

Preparation of Intermediate 104: (1s,3s)-3-hydroxy-3-methylcyclobutane-1-carbaldehyde

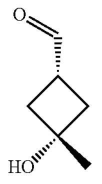

104

To a stirred solution of (1s,3s)-3-(hydroxymethyl)-1-methylcyclobutan-1-ol (120 mg, 1.03 mmol) in DCM (4 mL) under an argon atmosphere at room temperature, was added PCC (445 mg, 2.07 mmol) and the reaction mixture was stirred for 3 hours. The reaction mixture was diluted with DCM and washed with water, brine, dried over $Na_2SO_4$ and concentrated under reduced pressure to afford a crude residue, which was purified by silica gel column chromatography using a CombiFlash instrument (12 g RediSep® column, 30 to 40% EtOAc-pet ether, ELSD) to afford (1s,3s)-3-hydroxy-3-methylcyclobutane-1-carbaldehyde (21 mg, 0.18 mmol, 17.80% yield) as a colorless liquid (desired product is volatile). $^1$H NMR (300 MHz, CHLOROFORM-d) δ ppm=9.75-9.71 (m, 1H), 2.34-2.21 (m, 5H), 1.88-1.77 (m, 1H), 1.44 (s, 3H).

Preparation of Intermediate 105: 6-chloro-4-fluoro-1H-indazole

105

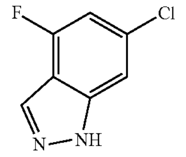

To a stirred solution of 4-chloro-2,6-difluorobenzaldehyde (15 g, 85.00 mmol) in 1,4-dioxane (56.60 mL) at room temperature under an argon atmosphere, was added hydrazine monohydrate (11.33 mL, 234.00 mmol) and the reaction mixture was stirred at 95° C. for 16 hours. Then, the reaction mixture was cooled to room temperature and water (400 mL) was added. The precipitate was filtered off, washed with additional water and dried under vacuum. The solid was dissolved in ethyl acetate and dried over anhydrous $Na_2SO_4$. The resulting mixture was filtered and filtrate was concentrated to afford 6-chloro-4-fluoro-1H-indazole (12 g, 70.40 mmol, 83% yield) as an off-white solid. MS (ESI) m/z: 169.0 $[M-H]^+$; $^1$H NMR (300 MHz, DMSO-$d_6$) δ ppm=13.62-13.45 (m, 1H), 8.27-8.18 (m, 1H), 7.54-7.47 (m, 1H), 7.10-7.04 (m, 1H).

Preparation of Intermediate 106: 6-chloro-4-fluoro-1-(tetrahydro-2H-pyran-2-yl)-1H-indazole

106

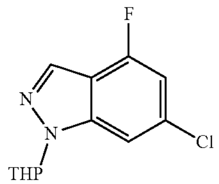

To a stirred solution of 6-chloro-4-fluoro-1H-indazole (15 g, 88.00 mmol) and 3,4-dihydro-2H-pyran (12.03 ml, 132.00 mmol) in DCM (176 mL) at room temperature under an argon atmosphere, was added 4-methylbenzenesulfonic acid hydrate (1.67 g, 8.79 mmol). The resulting mixture was stirred for 2 hours. Then, the reaction mixture was quenched with ice cold water, and extracted with DCM. The organic layer was washed with brine, dried over anhydrous $Na_2SO_4$, filtered and concentrated under reduced pressure to generate a crude residue, which was purified by silica gel column chromatography using a CombiFlash instrument (80 g RediSep® column, 5 to 10% EtOAc-pet ether) to afford 6-chloro-4-fluoro-1-(tetrahydro-2H-pyran-2-yl)-1H-indazole (12 g, 47.10 mmol, 53.6% yield). MS (ESI) m/z: 254.9 $[M+H]^+$; $^1$H NMR (300 MHz, DMSO-$d_6$) δ ppm=8.28 (s, 1H), 7.80 (s, 1H), 7.16 (dd, J=9.8, 1.3 Hz, 1H), 5.90 (dd, J=9.5, 2.1 Hz, 1H), 3.92-3.69 (m, 2H), 2.46-2.26 (m, 1H), 2.13-1.91 (m, 1H), 1.82-1.43 (m, 4H).

Preparation of Intermediate 107: 6-chloro-4-fluoro-5-methyl-1-(tetrahydro-2H-pyran-2-yl)-1H-indazole

107

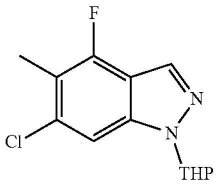

To a stirred solution of 6-chloro-4-fluoro-1-(tetrahydro-2H-pyran-2-yl)-1H-indazole (10 g, 39.30 mmol) in THF (100 mL) at −78° C. under an argon atmosphere, were added lithium chloride (1.99 g, 47.10 mmol) and LDA (51.0 mL, 102 mmol). The reaction mixture was stirred for 2 hours at the same temperature and methyl iodide (3.93 mL, 62.80 mmol) was added. The reaction mixture was stirred for an additional 1 hour, diluted with aqueous ammonium chloride solution and extracted with ethyl acetate. The combined organic layers were washed with brine, dried over anhydrous $Na_2SO_4$, filtered and concentrated under reduced pressure to afford a crude residue, which was purified by silica gel column chromatography using a CombiFlash instrument (80 g RediSep® column, 0 to 100% EtOAc-pet ether) to afford 6-chloro-4-fluoro-5-methyl-1-(tetrahydro-2H-pyran-2-yl)-1H-indazole (3.2 g, 11.91 mmol, 76% yield). MS (ESI) m/z: 269.0 $[M+H]^+$.

Preparation of Intermediate 108: 6-chloro-5-methyl-1-(tetrahydro-2H-pyran-2-yl)-1H-indazol-4-ol

108

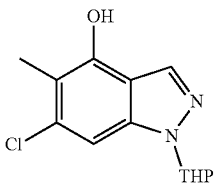

To a stirred solution of 6-chloro-4-fluoro-5-methyl-1-(tetrahydro-2H-pyran-2-yl)-1H-indazole (8.0 g, 29.80 mmol) in DMSO (104 mL) at room temperature under an argon atmosphere, were added water (10.73 mL, 595.00 mmol) and potassium hydroxide (10.02 g, 179.00 mmol). The reaction mixture was heated to 100° C. for 16 hours. Then, the reaction mixture was cooled to room temperature, diluted with water, acidified using 1.5M HCl, and extracted with ethyl acetate. The organic layer was washed with brine, dried over anhydrous $Na_2SO_4$, filtered and concentrated under reduced pressure to afford a crude residue, which was purified by silica gel column chromatography using a CombiFlash instrument (80 g RediSep® column, 50 to 100% EtOAc-pet ether) to afford 6-chloro-5-methyl-1-(tetrahydro-2H-pyran-2-yl)-1H-indazol-4-ol (4 g, 15.00 mmol, 50.4% yield) as a pale-yellow solid. MS (ESI) m/z: 267.0 $[M+H]^+$.

Preparation of Intermediate 109: 6-chloro-5-methyl-1-(tetrahydro-2H-pyran-2-yl)-1H-indazol-4-yl trifluoromethanesulfonate

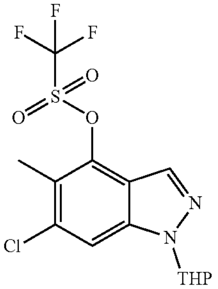

109

To a stirred solution of 6-chloro-5-methyl-1-(tetrahydro-2H-pyran-2-yl)-1H-indazol-4-ol (1 g, 3.75 mmol) and DIPEA (3.93 mL, 22.50 mmol) in DCM (20 mL) at −78° C. under an argon atmosphere, was added $Tf_2O$ (0.95 mL, 5.62 mmol) and stirred for an additional 1 hour. Then, the reaction mixture was diluted with DCM. The organic layer was washed successively with water and brine, dried over anhydrous $Na_2SO_4$, filtered, and concentrated under reduced pressure to generate a crude residue, which was purified by silica gel column chromatography using a CombiFlash instrument (40 g RediSep® column, 10 to 20% EtOAc-pet ether). Fractions containing the desired product were evaporated to afford 6-chloro-5-methyl-1-(tetrahydro-2H-pyran-2-yl)-1H-indazol-4-yl trifluoromethanesulfonate (1.20 g, 3.01 mmol, 80% yield). MS (ESI) m/z: 398.9 $[M+H]^+$; $^1H$ NMR (300 MHz, DMSO-$d_6$) δ ppm=8.21 (s, 1H), 8.11 (s, 1H), 5.95 (dd, J=9.6, 2.3 Hz, 1H), 3.93-3.73 (m, 2H), 2.42 (s, 3H), 2.09-1.95 (m, 2H), 1.81-1.65 (m, 1H), 1.64-1.54 (m, 3H).

Preparation of Intermediate 110: 6-chloro-5-methyl-1-(tetrahydro-2H-pyran-2-yl)-4-(4,4,5,5-tetramethyl-1,3,2-dioxaborolan-2-yl)-1H-indazole

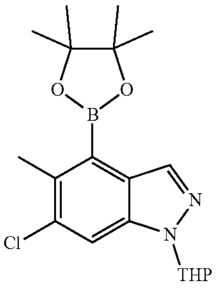

110

To a degassed solution of 6-chloro-5-methyl-1-(tetrahydro-2H-pyran-2-yl)-1H-indazol-4-yl-trifluoromethanesulfonate (1.2 g, 3.01 mmol) in 1,4-dioxane (24 mL) were added bis(pinacolato)diboron (1.91 g, 7.52 mmol), potassium acetate (0.74 g, 7.52 mmol) and $PdCl_2$(dppf) (0.22 g, 0.30 mmol). The reaction mixture was stirred at 100° C. for 16 hours. Then, the reaction mixture was filtered through a CELITE pad and concentrated under reduced pressure to generate a crude residue, which was purified by silica gel column chromatography using a CombiFlash instrument (40 g RediSep® column, 0-10% EtOAc-pet ether). Fractions containing the desired product were evaporated to afford 6-chloro-5-methyl-1-(tetrahydro-2H-pyran-2-yl)-4-(4,4,5,5-tetramethyl-1,3,2-dioxaborolan-2-yl)-1H-indazole (1 g, 2.65 mmol, 88% yield). MS (ESI) m/z: 377.3, $[M+H]^+$; $^1H$ NMR (300 MHz, DMSO-$d_6$) δ ppm=8.18 (s, 1H), 8.00 (s, 1H), 5.85 (dd, J=9.6, 2.6 Hz, 1H), 3.91-3.70 (m, 2H), 2.59 (s, 3H), 2.43-2.30 (m, 1H), 2.08-1.88 (m, 2H), 1.63-1.53 (m, 3H), 1.42-1.35 (m, 12H).

Preparation of Intermediate 126: ((1r,3s)-3-methoxy-3-methylcyclobutyl)methanol

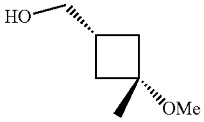

126

The intermediate ((1r,3s)-3-methoxy-3-methylcyclobutyl)methanol was synthesized according to the literature procedure: WO2017147102A1.

Preparation of Intermediate 127: (1r,3s)-3-methoxy-3-methylcyclobutane-1-carbaldehyde

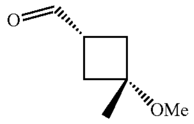

127

To a stirred solution of ((1r,3s)-3-methoxy-3-methylcyclobutyl)methanol (50 mg, 0.38 mmol) in DCM (2 mL) at room temperature under an argon atmosphere, was added PCC (248 mg, 1.15 mmol) in three portions with an interval of 1 hour. The reaction mixture was diluted with DCM and filtered through a CELITE pad. The volatiles were removed under reduced pressure to afford a crude residue, which was re-dissolved in diethyl ether and filtered. The filtrate was concentrated under reduced pressure to afford crude (1r,3s)-3-methoxy-3-methylcyclobutane-1-carbaldehyde (45 mg), which was used for the next step without further purification. $^1H$ NMR (300 MHz, DMSO-$d_6$) δ ppm=9.68 (s, 1H), 3.20 (s, 3H), 2.82-2.56 (m, 1H), 2.39-2.21 (m, 2H), 2.21-1.91 (m, 2H), 1.30 (s, 3H).

Preparation of Intermediate 142: tert-butyl (3-((tert-butyldiphenylsilyl)oxy)-2-hydroxypropyl)carbamate

142

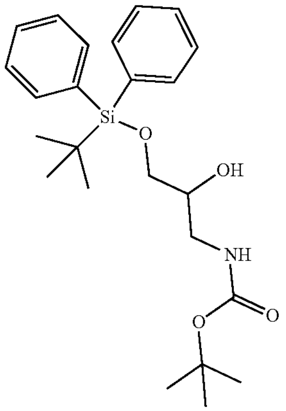

To a stirred solution of tert-butyl (2,3-dihydroxypropyl) carbamate (50 g, 261 mmol) and imidazole (21.36 g, 314 mmol) in DCM at 0° C. under a nitrogen atmosphere, was added tert-butyl(chloro)diphenylsilane (75 ml, 288 mmol). The reaction mixture was stirred at the same temperature for 16 hours. Then, the reaction mixture was quenched with ice cooled water and extracted with DCM. The combined organic extract was washed with water, brine, dried over anhydrous $Na_2SO_4$, filtered and concentrated under reduced pressure to afford a crude residue, which was purified by silica gel column chromatography using a CombiFlash instrument (240 g RediSep® column, 40-60% EtOAc-pet ether) to afford tert-butyl (3-((tert-butyldiphenylsilyl)oxy)-2-hydroxypropyl) carbamate (100 g, 231 mmol, 89% yield) as a colorless gummy liquid. MS (ESI) m/z: 428.7 $[M-H]^+$.

Preparation of Intermediate 143: tert-butyl 2-(((tert-butyldiphenylsilyl)oxy)methyl)-6-methylene-1,4-oxazepane-4-carboxylate

143

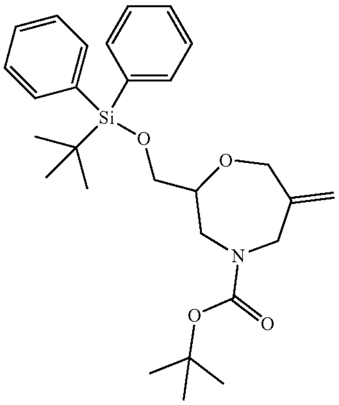

To a stirred solution of tert-butyl (3-((tert-butyldiphenylsilyl)oxy)-2-hydroxypropyl) carbamate (20 g, 46.6 mmol) in THF (200 mL) at 0° C. under a nitrogen atmosphere, was added NaH (4.10 g, 102 mmol, ~60% dispersion in mineral oil) followed by 3-chloro-2-(chloromethyl) prop-1-ene (5.82 g, 46.6 mmol). The resulting reaction mixture was gradually allowed to attain room temperature and stirred for 16 hours. The reaction mixture was cooled to 0° C. and quenched with ice cold water. The biphasic layer was extracted with ethyl acetate, washed with brine, dried over anhydrous $Na_2SO_4$, filtered and concentrated under reduced pressure to afford a crude residue, which was purified by reverse-phase silica gel flash chromatography [Redisep 415 gm, C18, 20-40 micron; Mobile phase A: 5% ammonium formate in water; Mobile phase B: acetonitrile; (80-100%, Flow: 100 ml/min)] to afford tert-butyl 2-(((tert-butyldiphenylsilyl)oxy)methyl)-6-methylene-1,4-oxazepane-4-carboxylate (4.2 g, 8.72 mmol, 18.7% yield). MS (ESI) m/z: 482.2 $[M+H]^+$; $^1H$ NMR (400 MHz, $CDCl_3$) δ ppm=7.68-7.61 (m, 4H), 7.42-7.35 (m, 6H), 5.02-4.89 (m, 2H), 4.65-4.23 (m, 3H), 4.03-3.97 (m, 1H), 3.75-3.50 (m, 4H), 2.80-2.79 (m, 1H), 1.46 (s, 9H), 1.05 (s, 9H).

Preparation of Intermediate 144 and 145: tert-butyl (S)-2-(((tert-butyldiphenylsilyl)oxy)methyl)-6-oxo-1,4-oxazepane-4-carboxylate and tert-butyl (R)-2-(((tert-butyldiphenylsilyl)oxy)methyl)-6-oxo-1,4-oxazepane-4-carboxylate

144

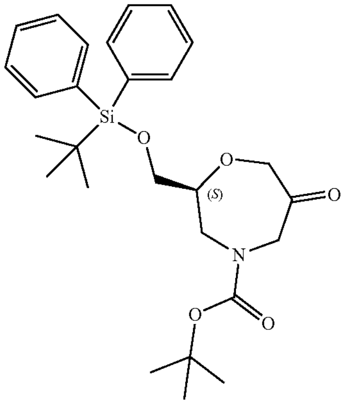

145

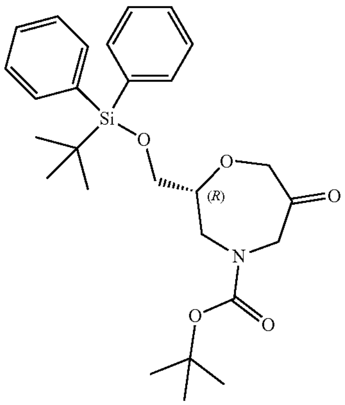

To a stirred solution of tert-butyl 2-(((tert-butyldiphenylsilyl)oxy)methyl)-6-methylene-1,4-oxazepane-4-carboxylate (4.2 g, 8.72 mmol) in a 1:1 THF-water (90 mL) mixture at room temperature under a nitrogen atmosphere, were added potassium osmate (VI) dihydrate (0.16 g, 0.44 mmol) and sodium periodate (4.66 g, 21.80 mmol). The reaction mixture was stirred at the same temperature for 16 hours and quenched by addition of ice-cold water. The reaction mixture was diluted with ethyl acetate, and stirred for an additional 15 min. The organic layer was separated, washed with brine, dried over anhydrous $Na_2SO_4$, filtered and concentrated to afford a crude residue, which was purified by chiral SFC [Chiral SFC method: Column: (R,R)WHELK-O1 (250×4.6) mm, 5μ; Solvent: 0.1% TFA in IPA; Co-Solvent: 20.0%; Flowrate: 3.0 mL/min; Temperature: 40° C.; Pressure: 100.0 bar; First eluting isomer retention time-3.296 min. and second eluting isomer retention time-3.584 min. to afford tert-butyl (S)-2-(((tert-butyldiphenylsilyl)oxy) methyl)-6-oxo-1,4-oxazepane-4-carboxylate (2 g, 4.13 mmol, 47.4% yield) as the first eluting isomer-1 (144) and tert-butyl (R)-2-(((tert-butyldiphenylsilyl)oxy)methyl)-6-oxo-1,4-oxazepane-4-carboxylate (2 g, 4.13 mmol, 47.4% yield) as the second eluting isomer-2 (145), both as a colorless gummy liquid. Isomer-1: MS (ESI) m/z: 484.2 $[M+H]^+$; $^1H$ NMR (400 MHz, $CDCl_3$) δ ppm=7.70-7.66 (m, 4H), 7.47-7.40 (m, 6H), 4.49-4.42 (m, 1H), 4.28-4.24 (m, 2H), 4.05-3.97 (m, 2H), 3.87-3.50 (m, 5H), 3.05-2.99 (m, 1H), 1.47 (s, 9H), 1.08 (s, 9H). Isomer-2: MS (ESI) m/z: 484.2 $[M+H]^+$; $^1H$ NMR (400 MHz, $CDCl_3$) δ ppm=7.70-7.66 (m, 4H), 7.47-7.40 (m, 6H), 4.49-4.42 (m, 1H), 4.28-4.24 (m, 2H), 4.05-3.97 (m, 2H), 3.87-3.50 (m, 5H), 3.05-2.99 (m, 1H), 1.47 (s, 9H), 1.08 (s, 9H).

Preparation of Intermediate 146 and 147: tert-butyl (2R,6S)-2-(((tert-butyldiphenylsilyl)oxy)methyl)-6-hydroxy-6-methyl-1,4-oxazepane-4-carboxylate and tert-butyl (2R,6R)-2-(((tert-butyldiphenylsilyl)oxy) methyl)-6-hydroxy-6-methyl-1,4-oxazepane-4-carboxylate

146

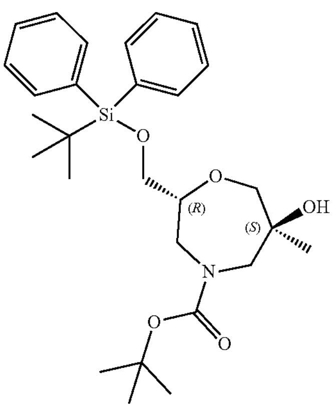

147

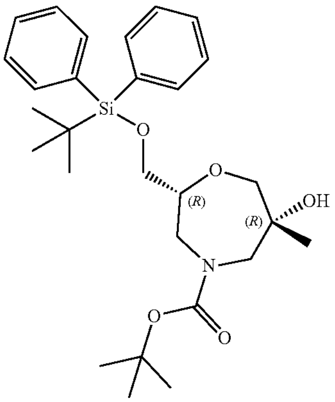

To a stirred solution of tert-butyl (R)-2-(((tert-butyldiphenylsilyl)oxy)methyl)-6-oxo-1,4-oxazepane-4-carboxylate (2 g, 4.13 mmol) in THF (30 mL) at 0° C. under a nitrogen atmosphere, was added 3M MeMgBr in diethyl ether (1.79 mL, 5.38 mmol). The reaction mixture was gradually warmed to room temperature and stirred for an additional 5 h. The reaction mixture was then cooled to 0° C., quenched with saturated aqueous $NH_4Cl$ solution and extracted with ethyl acetate. The combined organic layers were washed with brine, dried over $Na_2SO_4$, filtered and concentrated under reduced pressure to afford a crude residue, which was purified by silica gel column chromatography using a CombiFlash instrument (40 g RediSep® column, 10-15% EtOAc—pet ether) to afford tert-butyl (2R,6S)-2-(((tert-butyldiphenylsilyl)oxy)methyl)-6-hydroxy-6-methyl-1,4-oxazepane-4-carboxylate (550 mg, 1.07 mmol, 25.8% yield) as the first eluting diastereomer-1 (146) and tert-butyl (2R, 6R)-2-(((tert-butyldiphenylsilyl)oxy)methyl)-6-hydroxy-6-methyl-1,4-oxazepane-4-carboxylate (250 mg, 0.48 mmol, 11.7% yield) as the second eluting diastereomer-2 (147), both as a colorless gummy liquid. MS (ESI) m/z: 500.3 $[M+H]^+$;

Preparation of Intermediate 148: (2R,6S)-2-(hydroxymethyl)-6-methyl-1,4-oxazepan-6-ol.hydrochloride

148

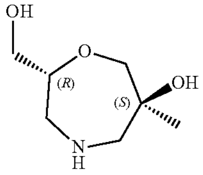

To a stirred solution of tert-butyl (2R,6S)-2-(((tert-butyldiphenylsilyl)oxy)methyl)-6-hydroxy-6-methyl-1,4-oxazepane-4-carboxylate (300 mg, 0.66 mmol) in DCM (5 mL) at 0° C. under an argon atmosphere, was added 4M HCl in 1,4-dioxane (3.00 mL, 12.01 mmol). The resulting reaction mixture was gradually warmed to room temperature and stirred for 16 h. The volatiles were then removed under reduced pressure and the residue triturated with diethyl ether to afford (2R,6S)-2-(hydroxymethyl)-6-methyl-1,4-oxazepan-6-ol hydrochloride (75 mg, 0.37 mmol, 61.3% yield) as a colorless liquid. MS (ESI) m/z: 162.2 $[M+H]^+$.

Preparation of Intermediate 179: (6S)-4-(2,7-dichloro-8-fluoropyrido[4,3-d]pyrimidin-4-yl)-6-methyl-1,4-oxazepan-6-ol

179

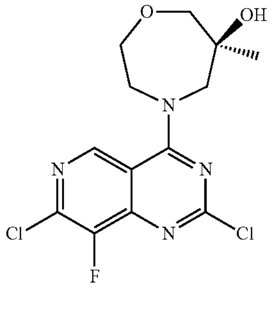

To a stirred solution of commercially available 2,4,7-trichloro-8-fluoropyrido[4,3-d]pyrimidine (5.0 g, 19.81 mmol) in DCM (100 mL) at −40° C. under an argon atmosphere, were added DIPEA (10.38 mL, 59.4 mmol) and (S)-6-methyl-1,4-oxazepan-6-ol hydrochloride (3.98 g, 23.77 mmol). The reaction mixture was stirred at the same temperature for 30 minutes. Then, the reaction mixture was quenched with water and extracted with DCM. The organic layer was washed with brine, dried over anhydrous $Na_2SO_4$, filtered, and concentrated under reduced pressure to get a crude residue, which was purified by silica gel column chromatography using a CombiFlash instrument (40 g RediSep® column, 50-80% EtOAc in pet.-ether) to afford (6S)-4-(2,7-dichloro-8-fluoropyrido[4,3-d]pyrimidin-4-yl)-6-methyl-1,4-oxazepan-6-ol (3.5 g, 10.08 mmol, 50.9% yield) as a yellow solid. MS (ESI) m/z: 347.2 $[M+H]^+$; $^1H$ NMR (400 MHz, DMSO-$d_6$) δ ppm=9.48 (br s, 1H), 5.20 (s, 1H), 4.41-4.18 (m, 2H), 4.07-3.73 (m, 4H), 3.64-3.47 (m, 2H), 1.15 (s, 3H).

Preparation of Intermediate 181: (6S)-6-[(tert-butyldimethylsilyl)oxy]-4-{2,7-dichloro-8-fluoro-pyrido[4,3-d]pyrimidin-4-yl}-6-methyl-1,4-oxazepane

181

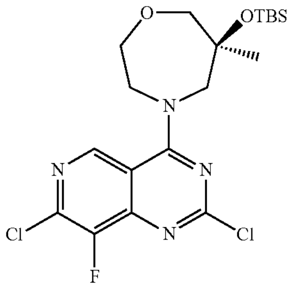

To a stirred solution of (6S)-4-(2,7-dichloro-8-fluoro-pyrido[4,3-d]pyrimidin-4-yl)-6-methyl-1,4-oxazepan-6-ol (7.5 g, 21.60 mmol) in DCM (50 mL) at 0° C. under an argon atmosphere, were added 2,6-lutidine (5.01 mL, 43.20 mmol) and tert-butyldimethylsilyl trifluoromethanesulfonate (7.45 mL, 32.40 mmol). Then, the reaction mixture was gradually warmed up to room temperature over a period of 10 hours. The reaction mixture was quenched with water and extracted with DCM. The combined organic extract was washed with brine, dried over anhydrous $Na_2SO_4$, and concentrated under reduced pressure to get a crude residue, which was purified by silica gel column chromatography using a CombiFlash instrument (80 g RediSep® column, 50% EtOAc-pet.ether) to afford (6S)-6-[(tert-butyldimethylsilyl)oxy]-4-{2,7-dichloro-8-fluoropyrido[4,3-d]pyrimidin-4-yl}-6-methyl-1,4-oxazepane (8.0 g, 17.34 mmol, 80% yield) as an off-white solid. MS (ESI) m/z: 461.2 $[M+H]^+$; $^1H$ NMR (400 MHz, DMSO-$d_6$) δ ppm=9.19 (s, 1H), 4.40 (d, J=14.4 Hz, 1H), 4.19-3.84 (m, 5H), 3.58-3.47 (m, 2H), 1.22 (s, 3H), 0.57 (s, 9H), 0.06-0.01 (m, 6H).

Preparation of Intermediate 182: tert-butyl (4aS,7aR)-4a-[({4-[(6S)-6-[(tert-butyldimethylsilyl)oxy]-6-methyl-1,4-oxazepan-4-yl]-7-chloro-8-fluoro-pyrido[4,3-d]pyrimidin-2-yl}oxy)methyl]-octahydro-1H-cyclopenta[b]pyridine-1-carboxylate

182

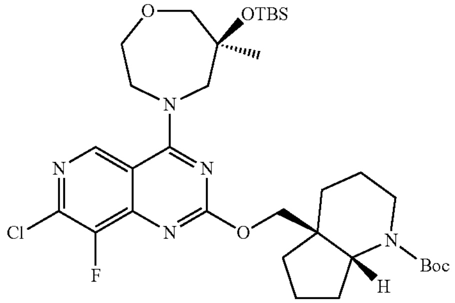

To a stirred solution of tert-butyl (4aS,7aR)-4a-(hydroxymethyl) octahydro-1H-cyclopenta[b]pyridine-1-carboxylate (1.66 g, 6.50 mmol) in THF (25 mL) at 0° C. under an argon atmosphere, was added NaH (0.52 g, 13.00 mmol) and stirred for 30 min. Then, (6S)-6-[(tert-butyldimethylsilyl)oxy]-4-{2,7-dichloro-8-fluoropyrido[4,3-d]pyrimidin-4-yl}-6-methyl-1,4-oxazepane (3.0 g, 6.50 mmol) was added in a portion and the reaction mixture gradually warmed up to room temperature over a period of 2 hours. The reaction was quenched with ice cold saturated $NH_4Cl$ solution and extracted with EtOAc. The organic layer was washed with brine, dried over anhydrous $Na_2SO_4$, filtered and concentrated under reduced pressure to get a crude residue, which was purified by silica gel column chromatography using a CombiFlash instrument (80 g RediSep® column, 5-20% EtOAc in DCM) to afford tert-butyl (4aS,7aR)-4a-[({4-[(6S)-6-[(tert-butyldimethylsilyl)oxy]-6-methyl-1,4-oxazepan-4-yl]-7-chloro-8-fluoropyrido[4,3-d]pyrimidin-2-yl}oxy)methyl]-octahydro-1H-cyclopenta[b]pyridine-1-carboxylate (3 g, 4.41 mmol, 67.8% yield) as an off white solid. MS (ESI) m/z: 680.3 $[M+H]^+$; $^1H$ NMR (400 MHz, DMSO-$d_6$) δ ppm=9.16 (s, 1H), 4.53-4.36 (m, 2H), 4.35-4.13 (m, 4H), 4.10-3.87 (m, 4H), 3.69-3.57 (m, 2H), 1.99-1.73 (m, 5H), 1.70-1.45 (m, 6H), 1.43-1.31 (m, 9H), 1.32-1.18 (m, 3H), 0.71-0.64 (m, 9H), 0.12-0.02 (m, 6H).

Preparation of Intermediate 183: (6S)-4-(2-{[(4aS,7aR)-octahydro-1H-cyclopenta[b]pyridin-4a-yl]methoxy}-7-chloro-8-fluoropyrido[4,3-d]pyrimidin-4-yl)-6-[(tert-butyldimethylsilyl)oxy]-6-methyl-1,4-oxazepane hydrochloride

183

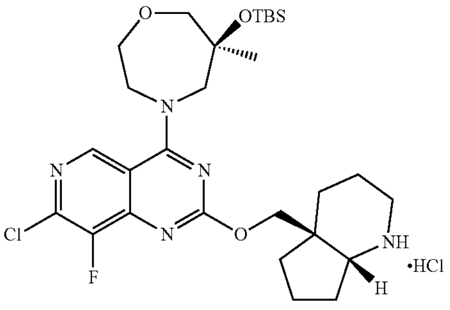

To a stirred solution of tert-butyl (4aS,7aR)-4a-[({4-[(6S)-6-[(tert-butyldimethylsilyl)oxy]-6-methyl-1,4-oxazepan-4-yl]-7-chloro-8-fluoropyrido[4,3-d]pyrimidin-2-yl}oxy)methyl]-octahydro-1H-cyclopenta[b]pyridine-1-carboxylate (1.7 g, 2.25 mmol) in acetonitrile (17 mL) at 0° C. under a nitrogen atmosphere, was added 4M HCl in 1,4-dioxane (5.62 mL, 22.49 mmol). The reaction mixture was gradually allowed to reach room temperature and stirred for 3 hours. Then, the volatiles were removed under reduced pressure to get a crude residue, which was triturated with pet. ether and dried to afford the hydrochloride salt of (6S)-4-(2-{[(4aS,7aR)-octahydro-1H-cyclopenta[b]pyridin-4a-yl]methoxy}-7-chloro-8-fluoropyrido[4,3-d]pyrimidin-4-yl)-6-[(tert-butyldimethylsilyl)oxy]-6-methyl-1,4-oxazepane (1.5 g, 1.90 mmol, 84% yield) as an off-white solid. MS (ESI) m/z: 580.2 $[M+H]^+$.

Preparation of Intermediate 185: (6S)-4-(2-{[(4aS,7aR)-1-cyclopropyl-octahydro-1H-cyclopenta[b]pyridin-4a-yl]methoxy}-7-chloro-8-fluoropyrido[4,3-d]pyrimidin-4-yl)-6-[(tert-butyldimethylsilyl)oxy]-6-methyl-1,4-oxazepane

185

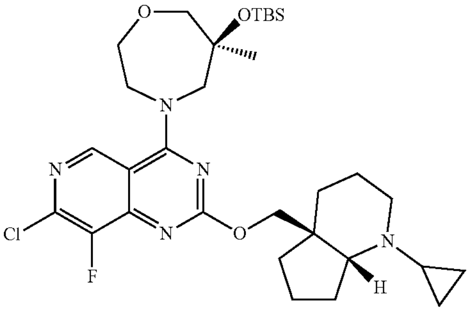

To a stirred solution of (6S)-4-(2-{[(4aS,7aR)-octahydro-1H-cyclopenta[b]pyridin-4a-yl]methoxy}-7-chloro-8-fluoropyrido[4,3-d]pyrimidin-4-yl)-6-[(tert-butyldimethylsilyl)oxy]-6-methyl-1,4-oxazepane (1.5 g, 1.95 mmol) and (1-ethoxycyclopropoxy)trimethylsilane (1.96 mL, 9.73 mmol) in DMSO (10 mL), were added acetic acid (0.5 mL)

and MP-cyanoborohydride (4.5 g, 9.73 mmol). Then, the reaction mixture was stirred at 60° C. for 16 hours. The reaction mixture was filtered through a CELITE pad and the washed with DCM. The combined filtrate was washed with water, brine, dried over anhydrous $Na_2SO_4$, filtered and concentrated under reduced pressure to get a crude residue, which was purified by silica gel column chromatography using CombiFlash instrument (24 g RediSep® column, 20-30% EtOAc in pet.-ether), to afford (6S)-4-(2-{[(4aS,7aR)-1-cyclopropyl-octahydro-1H-cyclopenta[b]pyridin-4a-yl]methoxy}-7-chloro-8-fluoropyrido[4,3-d]pyrimidin-4-yl)-6-[(tert-butyldimethylsilyl)oxy]-6-methyl-1,4-oxazepane (0.95 g, 1.47 mmol, 76% yield) as an off-white solid. MS (ESI) m/z: 620.2 $[M+H]^+$.

Preparation of Intermediate 187: (6S)-4-(2-{[(4aS,7aR)-1-cyclopropyl-octahydro-1H-cyclopenta[b]pyridin-4a-yl]methoxy}-7-[7,8-difluoro-3-(methoxymethoxy) naphthalen-1-yl]-8-fluoropyrido[4,3-d]pyrimidin-4-yl)-6-[(tert-butyldimethylsilyl)oxy]-6-methyl-1,4-oxazepane

187

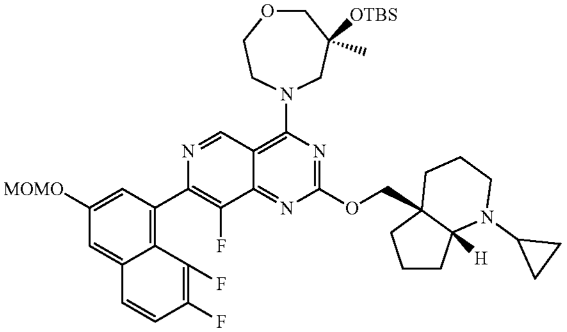

To a stirred solution of (6S)-4-(2-{[(4aS,7aR)-1-cyclopropyl-octahydro-1H-cyclopenta[b]pyridin-4a-yl]methoxy}-7-[7,8-difluoro-3-(methoxymethoxy) naphthalen-1-yl]-8-fluoropyrido[4,3-d]pyrimidin-4-yl)-6-[(tert-butyldimethylsilyl)oxy]-6-methyl-1,4-oxazepane (100 mg, 0.16 mmol) in 1,4-dioxane (2 mL) at room temperature under a nitrogen atmosphere, were added 2-[7,8-difluoro-3-(methoxymethoxy) naphthalen-1-yl]-4,4,5,5-tetramethyl-1,3,2-dioxaborolane (Synthesized as reported in WO2023284881) (113 mg, 0.32 mmol) and 1.5M aqueous potassium phosphate tribasic (0.24 mL, 0.48 mmol). The reaction mixture was purged with nitrogen and charged with CataCXium A Pd G3 (11.74 mg, 0.02 mmol). The reaction mixture was again purged with nitrogen and heated at 85° C. under microwave condition for 3 hours. The reaction mixture was diluted with EtOAc, washed with brine, dried over anhydrous $Na_2SO_4$, filtered and concentrated under reduced pressure to get a crude residue, which was purified by silica gel column chromatography using a CombiFlash instrument (12 g RediSep® column, 30% EtOAc in pet.-ether), to afford (6S)-4-(2-{[(4aS,7aR)-1-cyclopropyl-octahydro-1H-cyclopenta[b]pyridin-4a-yl]methoxy}-7-[7,8-difluoro-3-(methoxymethoxy) naphthalen-1-yl]-8-fluoropyrido[4,3-d]pyrimidin-4-yl)-6-[(tert-butyldimethylsilyl)oxy]-6-methyl-1,4-oxazepane (90 mg, 0.09 mmol, 55.1% yield) as a brown solid. MS (ESI) m/z: 808.4 $[M+H]^+$.

Preparation of Intermediate 188: (6S)-4-(2-{[(4aS,7aR)-1-cyclopropyl-octahydro-1H-cyclopenta[b]pyridin-4a-yl]methoxy}-7-[7,8-difluoro-3-(methoxymethoxy) naphthalen-1-yl]-8-fluoropyrido[4,3-d]pyrimidin-4-yl)-6-methyl-1,4-oxazepan-6-ol

188

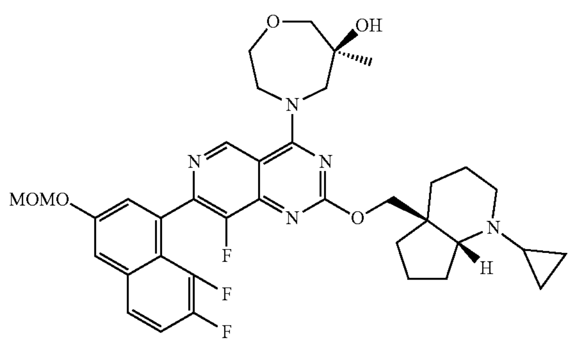

To a stirred solution of (6S)-4-(2-{[(4aS,7aR)-1-cyclopropyl-octahydro-1H-cyclopenta[b]pyridin-4a-yl]methoxy}-7-[7,8-difluoro-3-(methoxymethoxy) naphthalen-1-yl]-8-fluoropyrido[4,3-d]pyrimidin-4-yl)-6-[(tert-butyldimethylsilyl)oxy]-6-methyl-1,4-oxazepane (90 mg, 0.11 mmol) in DMF (2 mL) at room temperature under a nitrogen atmosphere, was added CsF (85 mg, 0.56 mmol) and stirred for 16 hours. The reaction mixture was quenched with water and extracted with EtOAc. The organic layer was separated, dried over anhydrous $Na_2SO_4$, filtered, and concentrated under reduced pressure to get (6S)-4-(2-{[(4aS,7aR)-1-cyclopropyl-octahydro-1H-cyclopenta[b]pyridin-4a-yl]methoxy}-7-[7,8-difluoro-3-(methoxymethoxy) naphthalen-1-yl]-8-fluoropyrido[4,3-d]pyrimidin-4-yl)-6-methyl-1,4-oxazepan-6-ol (80 mg, 0.06 mmol, 56.4% yield) as a brown solid. MS (ESI) m/z: 694.2 $[M+H]^+$.

Example 16-1: (6S)-4-(2-{[(4aS,7aR)-1-cyclopropyl-octahydro-1H-cyclopenta[b]pyridin-4a-yl]methoxy}-7-(7,8-difluoro-3-hydroxynaphthalen-1-yl)-8-fluoropyrido[4,3-d]pyrimidin-4-yl)-6-methyl-1,4-oxazepan-6-ol Example 16-1

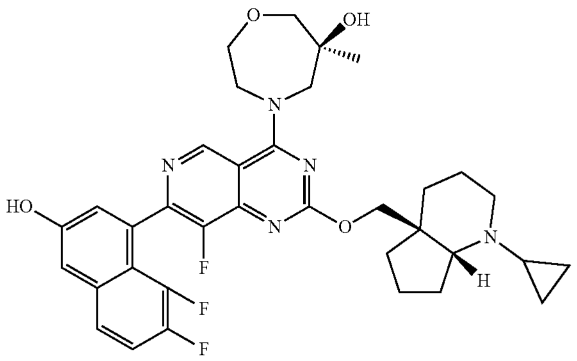

To a stirred solution of (6S)-4-(2-{[(4aS,7aR)-1-cyclopropyl-octahydro-1H-cyclopenta[b]pyridin-4a-yl]methoxy}-7-[7,8-difluoro-3-(methoxymethoxy) naphthalen-1-yl]-8-fluoropyrido[4,3-d]pyrimidin-4-yl)-6-methyl-1,4-oxazepan-6-ol (80 mg, 0.06 mmol) in acetonitrile (2 mL) at 0° C. under a nitrogen atmosphere, was added 4M HCl in 1,4-dioxane (0.08 mL, 0.32 mmol). The reaction mixture was gradually warmed to room temperature and stirred for 2 hours and after completion the mixture was purified by prep-HPLC [HPLC Method: Preparative column: X-Bridge C18 (150 mm×19 mm×5 μm); Mobile phase A: 5 mM ammonium formate in water pH-3.5; Mobile phase B: acetonitrile; Flow rate: 15 mL\min; Temperature: 27° C.; Detection: UV at 220 nm] to afford (6S)-4-(2-{[(4aS,7aR)-1-cyclopropyl-octahydro-1H-cyclopenta[b]pyridin-4a-yl]methoxy}-7-(7,8-difluoro-3-hydroxynaphthalen-1-yl)-8-fluoropyrido[4,3-d]pyrimidin-4-yl)-6-methyl-1,4-oxazepan-6-ol (200 mg, 0.33 mmol, 86% yield). MS (ESI) m/z: 650.2 $[M+H]^+$; $^1H$ NMR (400 MHz, DMSO-$d_6$) δ ppm=10.22-10.21 (m, 1H), 9.46 (s, 1H), 7.78-7.69 (m, 1H), 7.62-7.53 (m, 1H), 7.39 (s, 1H), 7.28-7.20 (m, 1H), 5.15-5.14 (m, 1H), 4.53-4.43 (m, 1H), 4.39-4.27 (m, 1H), 4.25-4.13 (m, 2H), 4.11-3.83 (m, 4H), 3.61-3.51 (m, 2H), 3.02-2.99 (m, 1H), 2.63-2.57 (m, 1H), 2.07-1.97 (m, 1H), 1.80-1.29 (m, 11H), 1.16 (s, 3H), 0.46-0.31 (m, 2H), 0.29-0.21 (m, 1H), 0.20-0.12 (m, 1H).

Preparation of Intermediate 189: tert-butyl (4aS,7aR)-4a-[({4-[(6S)-6-[(tert-butyldimethylsilyl)oxy]-6-methyl-1,4-oxazepan-4-yl]-7-[7,8-difluoro-3-(methoxymethoxy) naphthalen-1-yl]-8-fluoropyrido[4,3-d]pyrimidin-2-yl}oxy)methyl]-octahydro-1H-cyclopenta[b]pyridine-1-carboxylate

189

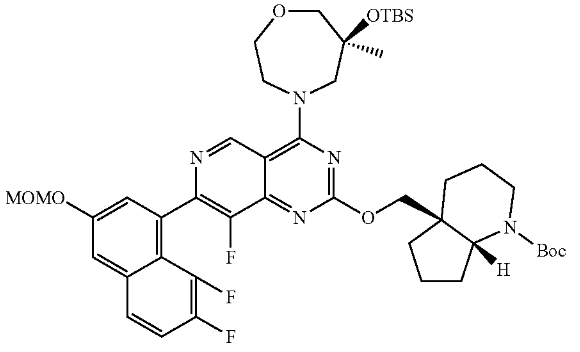

To a stirred solution of tert-butyl (4aS,7aR)-4a-[({4-[(6S)-6-[(tert-butyldimethylsilyl)oxy]-6-methyl-1,4-oxazepan-4-yl]-7-chloro-8-fluoropyrido[4,3-d]pyrimidin-2-yl}oxy)methyl]-octahydro-1H-cyclopenta[b]pyridine-1-carboxylate (400 mg, 0.59 mmol) in 1,4-dioxane (5 mL) at room temperature under a nitrogen atmosphere, were added 2-[7,8-difluoro-3-(methoxymethoxy) naphthalen-1-yl]-4,4,5,5-tetramethyl-1,3,2-dioxaborolane (Synthesized as reported in WO2023284881) (185 mg, 0.53 mmol) and 1.5M aqueous potassium phosphate tribasic solution (1.18 mL, 1.76 mmol). Then, the reaction mixture was purged with nitrogen and charged with CataCXium A Pd G3 (42.8 mg, 0.06 mmol). The reaction mixture was again purged with nitrogen and heated at 85° C. under a microwave condition over a period of 3 hours. The reaction mixture was quenched with water and extracted with EtOAc. The organic layer was separated, dried over anhydrous $Na_2SO_4$, filtered and concentrated under reduced pressure to get a crude residue, which was purified by silica gel column chromatography using CombiFlash instrument (12 g RediSep® column, 20% EtOAc in pet.-ether), to afford tert-butyl (4aS,7aR)-4a-[({4-[(6S)-6-[(tert-butyldimethylsilyl)oxy]-6-methyl-1,4-oxazepan-4-yl]-7-[7,8-difluoro-3-(methoxymethoxy) naphthalen-1-yl]-8-fluoropyrido[4,3-d]pyrimidin-2-yl}oxy)methyl]-octahydro-1H-cyclopenta[b]pyridine-1-carboxylate (350 mg, 0.37 mmol, 62.8% yield) as a brown solid. MS (ESI) m/z: 868.3 [M+H]$^+$.

Preparation of Intermediate 190: tert-butyl (4aS,7aR)-4a-[({7-[7,8-difluoro-3-(methoxymethoxy) naphthalen-1-yl]-8-fluoro-4-[(6S)-6-hydroxy-6-methyl-1,4-oxazepan-4-yl]pyrido[4,3-d]pyrimidin-2-yl}oxy)methyl]-octahydro-1H-cyclopenta[b]pyridine-1-carboxylate

190

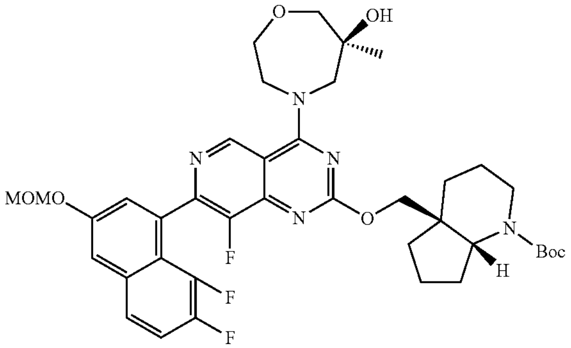

To a stirred solution of tert-butyl (4aS,7aR)-4a-[({4-[(6S)-6-[(tert-butyldimethylsilyl)oxy]-6-methyl-1,4-oxazepan-4-yl]-7-[7,8-difluoro-3-(methoxymethoxy) naphthalen-1-yl]-8-fluoropyrido[4,3-d]pyrimidin-2-yl}oxy)methyl]-octahydro-1H-cyclopenta[b]pyridine-1-carboxylate (350 mg, 0.40 mmol) in DMF (2 mL) at room temperature under a nitrogen atmosphere, was added CsF (306 mg, 2.02 mmol), and stirred for 16 hours. Then, the reaction mixture was quenched with water and extracted with EtOAc. The organic layer was separated, dried over anhydrous $Na_2SO_4$, filtered, and concentrated under reduced pressure to get a crude residue, which was purified by silica gel column chromatography using a Biotage instrument (12 g RediSep® column, 65% EtOAc in pet.-ether) to afford tert-butyl (4aS,7aR)-4a-[({7-[7,8-difluoro-3-(methoxymethoxy) naphthalen-1-yl]-8-fluoro-4-[(6S)-6-hydroxy-6-methyl-1,4-oxazepan-4-yl]pyrido[4,3-d]pyrimidin-2-yl}oxy)methyl]-octahydro-1H-cyclopenta[b]pyridine-1-carboxylate (240 mg, 0.30 mmol, 75% yield) as a colourless gummy solid. MS (ESI) m/z: 754.3 [M+H]$^+$.

Preparation of Intermediate 191: (6S)-4-(2-{[(4aS,7aR)-octahydro-1H-cyclopenta[b]pyridin-4a-yl]methoxy}-7-(7,8-difluoro-3-hydroxynaphthalen-1-yl)-8-fluoropyrido[4,3-d]pyrimidin-4-yl)-6-methyl-1,4-oxazepan-6-ol

191

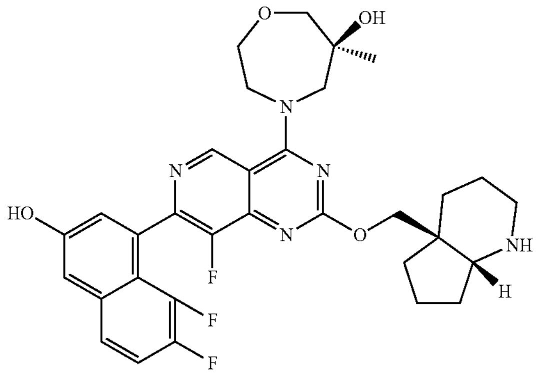

To a stirred solution of tert-butyl (4aS,7aR)-4a-[({7-[7,8-difluoro-3-(methoxymethoxy) naphthalen-1-yl]-8-fluoro-4-[(6S)-6-hydroxy-6-methyl-1,4-oxazepan-4-yl]pyrido[4,3-d]pyrimidin-2-yl}oxy)methyl]-octahydro-1H-cyclopenta[b]pyridine-1-carboxylate (250 mg, 0.33 mmol) in acetonitrile (3 mL) at 0° C. under a nitrogen atmosphere, was added 4M HCl in 1,4-dioxane (0.9 mL, 3.6 mmol). The reaction mixture was gradually warmed to room temperature and stirred for 1 hour. Then, the reaction mixture was quenched with 10% aqueous $NaHCO_3$ solution and extracted with DCM. The organic layer was separated, dried over anhydrous $Na_2SO_4$, filtered and concentrated under reduced pressure to get crude (6S)-4-(2-{[(4aS,7aR)-octahydro-1H-cyclopenta[b]pyridin-4a-yl]methoxy}-7-(7,8-difluoro-3-hydroxynaphthalen-1-yl)-8-fluoropyrido[4,3-d]pyrimidin-4-yl)-6-methyl-1,4-oxazepan-6-ol (200 mg, 0.33 mmol, 86% yield). MS (ESI) m/z: 610.3 [M+H]$^+$.

Example 16-2: (6S)-4-(2-{[(4aS,7aR)-1-[(1s,3s)-3-methoxycyclobutyl]-octahydro-1H-cyclopenta[b]pyridin-4a-yl]methoxy}-7-(7,8-difluoro-3-hydroxynaphthalen-1-yl)-8-fluoropyrido[4,3-d]pyrimidin-4-yl)-6-methyl-1,4-oxazepan-6-ol Example 16-2

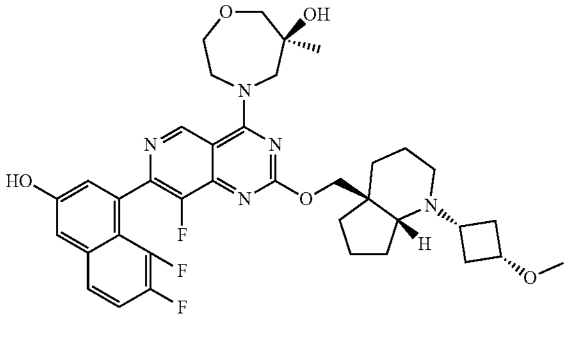

To a stirred solution of (6S)-4-(2-{[(4aS,7aR)-octahydro-1H-cyclopenta[b]pyridin-4a-yl]methoxy}-7-(7,8-difluoro-3-hydroxynaphthalen-1-yl)-8-fluoropyrido[4,3-d]pyrimidin-4-yl)-6-methyl-1,4-oxazepan-6-ol (30 mg, 0.05 mmol) in THF-MeOH (1 mL, 4:1 mixture) at room temperature under a nitrogen atmosphere, were added 3-methoxycyclobutan-1-one (7.39 mg, 0.07 mmol), acetic acid (0.01 mL) and sodium cyanoborohydride (7.73 mg, 0.12 mmol). Then, the reaction mixture was stirred at 65° C. for 3 hours. After completion, the reaction mixture was purified by prep-HPLC [HPLC Method: Preparative column: Sunfire C18 (150 mm×19 mm×5 μm); Mobile phase A: 5 mM ammonium formate in water pH-3.5; Mobile phase B: acetonitrile; Flow rate: 15 mL\min; Temperature: 27° C.; Detection: UV at 220 nm] to afford (6S)-4-(2-{[(4aS,7aR)-1-[(1s,3s)-3-methoxycyclobutyl]-octahydro-1H-cyclopenta[b]pyridin-4a-yl]methoxy}-7-(7,8-difluoro-3-hydroxynaphthalen-1-yl)-8-fluoropyrido[4,3-d]pyrimidin-4-yl)-6-methyl-1,4-oxazepan-6-ol (3.06 mg, 4.32 μmol, 8.8% yield) as an off-white solid. MS (ESI) m/z: 694.3 $[M+H]^+$; $^1H$ NMR (400 MHz, $CD_3CN$) δ ppm=9.45-9.42 (m, 1H), 7.71-7.66 (m, 1H), 7.50-7.39 (m, 2H), 7.38-7.24 (m, 1H), 4.73-4.63 (m, 1H), 4.60-4.51 (m, 1H), 4.50-4.33 (m, 2H), 4.09-4.02 (m, 1H), 4.01-3.94 (m, 1H), 3.91-3.78 (m, 2H), 3.70-3.64 (m, 1H), 3.60-3.52 (m, 2H), 3.19-3.08 (m, 3H), 2.66-2.52 (m, 2H), 2.46-2.34 (m, 3H), 2.33-2.26 (m, 2H), 2.25-2.07 (m, 2H), 2.06-1.99 (m, 1H), 1.95-1.87 (m, 1H), 1.81-1.70 (m, 2H), 1.70-1.47 (m, 4H), 1.45-1.41 (m, 1H), 1.26 (s, 3H). Two OH protons did not appear.

Example 17-1: (6S)-4-(2-{[(4aS,7aR)-1-propyl-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol Example 17-1

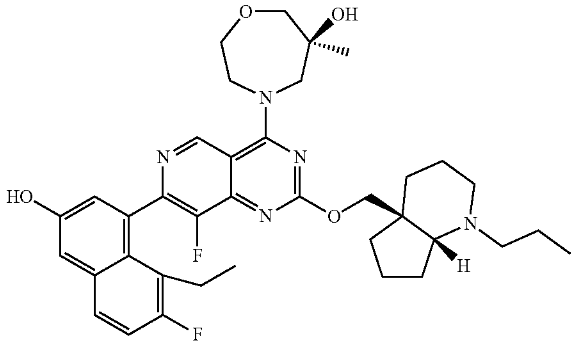

To a stirred solution of ((6S)-4-(2-{[(4aS,7aR)-1-cyclopropyl-octahydro-1H-cyclopenta[b]pyridin-4a-yl]methoxy}-7-(8-ethynyl-7-fluoro-3-hydroxynaphthalen-1-yl)-8-fluoropyrido[4,3-d]pyrimidin-4-yl)-6-methyl-1,4-oxazepan-6-ol) (290 mg, 0.42 mmol) in THF-MeOH (12 mL, 1:1 mixture) under a nitrogen atmosphere, was added 10% Pd—C(224 mg, 0.210 mmol). The reaction mixture was purged with hydrogen, placed under hydrogen bladder, and stirred at room temperature for 16 hours. The reaction mixture was filtered and the filtrate was concentrated to get a crude residue, which was purified by prep-HPLC [HPLC Method: Preparative column: X-Bridge C18 (150 mm×19 mm×5 μm); Mobile phase A: 5 mM ammonium formate in water; Mobile phase B: acetonitrile; Flow rate: 15 mL\min; Temperature: 27° C.; Detection: UV at 220 nm] to afford (6S)-4-(2-{[(4aS,7aR)-1-propyl-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (99 mg, 0.14 mmol, 33.2% yield) as an off-white solid. MS (ESI) m/z: 662.2 $[M+H]^+$; $^1H$ NMR (400 MHz, DMSO-$d_6$) δ ppm=10.09-9.80 (m, 1H), 9.48 (s, 1H), 7.77 (dd, J=9.1, 6.0 Hz, 1H), 7.42-7.27 (m, 2H), 7.03 (dd, J=13.8, 2.6 Hz, 1H), 5.15 (br s, 1H), 4.62 (d, J=10.6 Hz, 1H), 4.41-4.16 (m, 3H), 4.11-3.80 (m, 4H), 3.63-3.49 (m, 2H), 2.94 (t, J=7.4 Hz, 1H), 2.46-2.27 (m, 4H), 2.23-2.06 (m, 1H), 1.90-1.79 (m, 1H), 1.76-1.67 (m, 1H), 1.65-1.30 (m, 11H), 1.16 (d, J=5.0 Hz, 3H), 0.82 (t, J=7.3 Hz, 3H), 0.74 (t, J=7.3 Hz, 3H).

Preparation of Intermediate 192: tert-butyl (4aS,7aR)-4a-({[4-(dimethylamino)-7-[8-ethyl-7-fluoro-3-(methoxymethoxy) naphthalen-1-yl]-8-fluoropyrido[4,3-d]pyrimidin-2-yl]oxy}methyl)-octahydro-1H-cyclopenta[b]pyridine-1-carboxylate

192

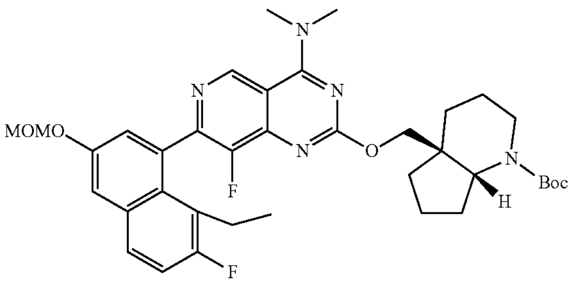

To a stirred solution of tert-butyl (4aS,7aR)-4a-({[7-chloro-4-(dimethylamino)-8-fluoropyrido[4,3-d]pyrimidin-2-yl]oxy}methyl)-octahydro-1H-cyclopenta[b]pyridine-1-carboxylate (1.0 g, 2.08 mmol) in 1,4-dioxane (5 mL) at room temperature, were added 2-[8-ethyl-7-fluoro-3-(methoxymethoxy) naphthalen-1-yl]-4,4,5,5-tetramethyl-1,3,2-dioxaborolane (1.13 g, 3.13 mmol) and 1.5M aqueous potassium phosphate tribasic solution (4.17 mL, 6.25 mmol) and the reaction mixture was purged with nitrogen. Then, the reaction mixture was charged with CataCXium A Pd G3 (0.15 g, 0.21 mmol), purged with nitrogen and heated at 80° C. under a microwave condition for 2 hours. The reaction mixture was quenched with water and extracted with EtOAc. The organic layer was separated, dried over anhydrous $Na_2SO_4$, filtered and concentrated under reduced pressure to get a crude residue, which was purified by silica gel column chromatography using a Biotage instrument (40 g RediSep® column, 80% EtOAc in pet.-ether), to afford tert-butyl (4aS,7aR)-4a-({[4-(dimethylamino)-7-[8-ethyl-7-fluoro-3-(methoxymethoxy) naphthalen-1-yl]-8-fluoropyrido[4,3-d]pyrimidin-2-yl]oxy}methyl)-octahydro-1H-cyclopenta[b]pyridine-1-carboxylate (1.2 g, 1.24 mmol, 59.5% yield) as an off-white solid. MS (ESI) m/z: 678.4 $[M+H]^+$.

Preparation of Intermediate 193: tert-butyl (4aS,7aR)-4a-[({7-[8-ethyl-7-fluoro-3-(methoxymethoxy) naphthalen-1-yl]-8-fluoro-4-hydroxypyrido[4,3-d]pyrimidin-2-yl}oxy)methyl]-octahydro-1H-cyclopenta[b]pyridine-1-carboxylate

193

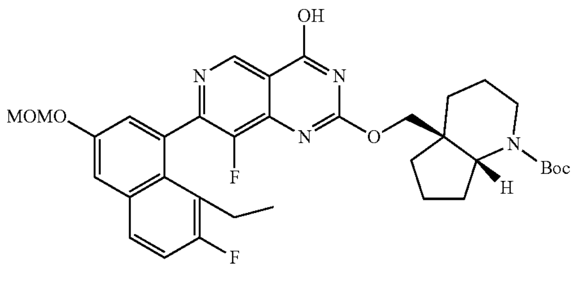

To a stirred solution of tert-butyl (4aS,7aR)-4a-({[4-(dimethylamino)-7-[8-ethyl-7-fluoro-3-(methoxymethoxy) naphthalen-1-yl]-8-fluoropyrido[4,3-d]pyrimidin-2-yl]oxy}methyl)-octahydro-1H-cyclopenta[b]pyridine-1-carboxylate (1.18 g, 1.22 mmol) in DMSO (3 mL) under a nitrogen atmosphere, was added 5N aqueous sodium hydroxide solution (2.44 mL, 12.19 mmol) and the reaction mixture was heated at 80° C. for 1 hour. Then, the reaction mixture was diluted with ice cold water and extracted with EtOAc. The organic layer was separated, dried over anhydrous $Na_2SO_4$, filtered and concentrated under reduced pressure to get a crude residue, which was purified by silica gel column chromatography using a CombiFlash instrument (12 g RediSep® column, 60% EtOAc in pet.-ether), to afford tert-butyl (4aS,7aR)-4a-[({7-[8-ethyl-7-fluoro-3-(methoxymethoxy) naphthalen-1-yl]-8-fluoro-4-hydroxypyrido[4,3-d]pyrimidin-2-yl}oxy)methyl]-octahydro-1H-cyclopenta[b]pyridine-1-carboxylate (600 mg, 0.82 mmol, 67.3% yield) as an off-white solid. MS (ESI) m/z: 651.2 $[M+H]^+$.

Preparation of Intermediate 194: tert-butyl (4aS,7aR)-4a-[({7-[8-ethyl-7-fluoro-3-(methoxymethoxy) naphthalen-1-yl]-8-fluoro-4-[(2R,6S)-6-hydroxy-2-(hydroxymethyl)-6-methyl-1,4-oxazepan-4-yl]pyrido[4,3-d]pyrimidin-2-yl}oxy)methyl]-octahydro-1H-cyclopenta[b]pyridine-1-carboxylate

194

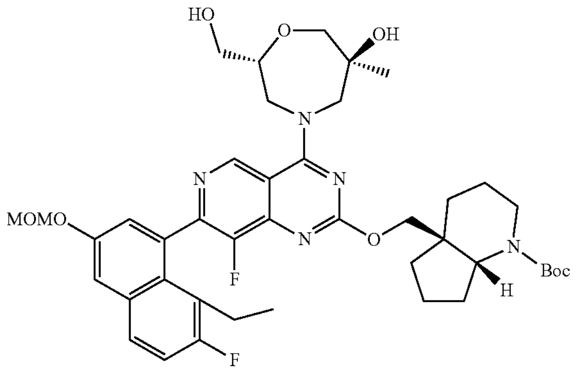

To a stirred solution of tert-butyl (4aS,7aR)-4a-[({7-[8-ethyl-7-fluoro-3-(methoxymethoxy) naphthalen-1-yl]-8-fluoro-4-hydroxypyrido[4,3-d]pyrimidin-2-yl}oxy)methyl]-octahydro-1H-cyclopenta[b]pyridine-1-carboxylate (200 mg, 0.31 mmol) in acetonitrile (2 mL) at 0° C. under a nitrogen atmosphere, were added (2R,6S)-2-(hydroxymethyl)-6-methyl-1,4-oxazepan-6-ol hydrochloride (91 mg, 0.46 mmol), DIPEA (0.27 mL, 1.54 mmol) and PyBOP (400 mg, 0.77 mmol). The reaction mixture was stirred at room temperature for 16 hours. Then, the reaction mixture was quenched with water and extracted with EtOAc. The organic layer was separated, dried over anhydrous $Na_2SO_4$, filtered, and concentrated under reduced pressure to get a crude residue, which was purified by silica gel column chromatography using a Biotage instrument (40 g RediSep® column, 100% EtOAc in pet.-ether), to afford tert-butyl (4aS,7aR)-4a-[({7-[8-ethyl-7-fluoro-3-(methoxymethoxy) naphthalen-1-yl]-8-fluoro-4-[(2R,6S)-6-hydroxy-2-(hydroxymethyl)-6-methyl-1,4-oxazepan-4-yl]pyrido[4,3-d]pyrimidin-2-yl}oxy)methyl]-octahydro-1H-cyclopenta[b]pyridine-1-carboxylate (220 mg, 0.23 mmol, 76% yield) as a brown solid. MS (ESI) m/z: 794.3 $[M+H]^+$.

Preparation of Intermediate 195: (2R,6S)-4-(2-{[(4aS,7aR)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-2-(hydroxymethyl)-6-methyl-1,4-oxazepan-6-ol hydrochloride

195

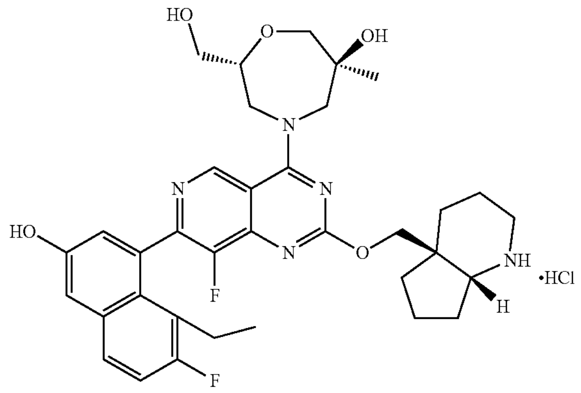

To a stirred solution of tert-butyl (4aS,7aR)-4a-[({7-[8-ethyl-7-fluoro-3-(methoxymethoxy) naphthalen-1-yl]-8-fluoro-4-[(2R,6S)-6-hydroxy-2-(hydroxymethyl)-6-methyl-1,4-oxazepan-4-yl]pyrido[4,3-d]pyrimidin-2-yl}oxy) methyl]-octahydro-1H-cyclopenta[b]pyridine-1-carboxylate (220 mg, 0.23 mmol) in acetonitrile (3 mL) at 0° C. under a nitrogen atmosphere, was added 4M HCl in 1,4-dioxane (0.58 mL, 2.33 mmol). The reaction mixture was gradually warmed to room temperature and stirred for 1 hour. The volatiles were then removed under reduced pressure to get a crude residue, which was triturated with pet.-ether and dried to afford the hydrochloride salt of (2R,6S)-4-(2-{[(4aS,7aR)-octahydro-1H-cyclopenta[b]pyridin-4a-yl]methoxy}-7-(8-ethyl-7-fluoro-3-hydroxynaphthalen-1-yl)-8-fluoro-pyrido[4,3-d]pyrimidin-4-yl)-2-(hydroxymethyl)-6-methyl-1,4-oxazepan-6-ol as a pale-brown solid. MS (ESI) m/z: 650.2 $[M+H]^+$.

Example 18-1: (2R,6S)-4-(2-{[(4aS,7aR)-1-{2-oxaspiro[3.3]heptan-6-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-2-(hydroxymethyl)-6-methyl-1,4-oxazepan-6-ol Example 18-1

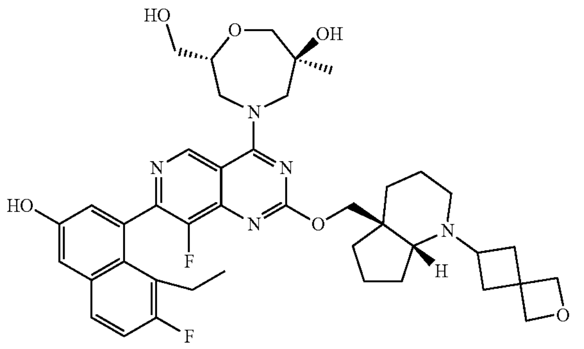

To a stirred solution of (2R,6S)-4-(2-{[(4aS,7aR)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-2-(hydroxymethyl)-6-methyl-1,4-oxazepan-6-ol (25 mg, 0.04 mmol) in THF-MeOH (0.5 mL, 4:1 mixture) at room temperature a under nitrogen atmosphere, were added 2-oxaspiro[3.3]heptan-6-one (6.47 mg, 0.06 mmol), acetic acid (0.02 mL) and sodium cyanoborohydride (7.25 mg, 0.12 mmol). The reaction mixture was stirred at 80° C. for 2 hours and purified by prep-HPLC [HPLC Method: Preparative column: X-Bridge C18 (150 mm×19 mm×5 μm); Mobile phase A: 5 mM ammonium bicarbonate in water pH-3.5; Mobile phase B: acetonitrile; Flow rate: 15 mL\min; Temperature: 27° C.; Detection: UV at 220 nm] to (2R,6S)-4-(2-{[(4aS,7aR)-1-{2-oxaspiro[3.3]heptan-6-yl}-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-2-(hydroxymethyl)-6-methyl-1,4-oxazepan-6-ol (4.7 mg, 5.94 μmol, 15.4% yield) as an off-white solid. MS (ESI) m/z: 746.3 $[M+H]^+$; $^1H$ NMR (400 MHz, $CD_3CN$) δ ppm=9.46-9.45 (m, 1H), 7.75 (dd, J=9.1, 5.9 Hz, 1H), 7.37 (d, J=2.6 Hz, 1H), 7.32 (t, J=9.4 Hz, 1H), 7.20-7.03 (m, 1H), 5.03-4.87 (m, 1H), 4.76-4.68 (m, 1H), 4.66-4.52 (m, 2H), 4.46-4.31 (m, 1H), 4.08-3.98 (m, 1H), 3.93-3.86 (m, 1H), 3.68-3.53 (m, 3H), 3.51-3.41 (m, 2H), 3.14-3.13 (m, 3H), 2.72-2.59 (m, 2H), 2.46-2.38 (m, 2H), 2.29-2.23 (m, 2H), 1.93-1.90 (m, 1H), 1.81-1.70 (m, 4H), 1.70-1.45 (m, 7H), 1.46-1.39 (m, 2H), 1.31-1.29 (m, 3H), 0.90-0.75 (m, 3H). Three OH protons not appeared in $^1H$ NMR.

Preparation of Intermediate 196: tert-butyl 1,5-dioxa-8-azaspiro[2.6]nonane-8-carboxylate

196

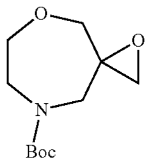

To a stirred solution of trimethylsulfonium iodide (6.16 g, 30.20 mmol) in DMSO (50 mL) at 0° C. under an argon atmosphere, was added 60% NaH in mineral oil (1.21 g, 30.20 mmol) and stirred for 10 min. Then, a solution of tert-butyl 6-oxo-1,4-oxazepane-4-carboxylate (5.0 g, 23.23 mmol) in DMSO (5 mL) was added to the reaction mixture and gradually warmed up to room temperature over a period of 16 hours. The reaction mixture was diluted with water and extracted with EtOAc. The organic layer was washed with brine, dried over anhydrous $Na_2SO_4$, filtered and concentrated under reduced pressure to get crude tert-butyl 1,5-dioxa-8-azaspiro[2.6]nonane-8-carboxylate (5.0 g, 21.81 mmol, 94% yield) as a brown liquid. $^1H$ NMR (400 MHz, DMSO-$d_6$) δ ppm=3.88-3.80 (m, 1H), 3.77-3.47 (m, 5H), 3.43-3.26 (m, 2H), 2.81-2.59 (m, 2H), 1.41 (s, 9H).

Preparation of Intermediate 197: tert-butyl 6-(aminomethyl)-6-hydroxy-1,4-oxazepane-4-carboxylate

197

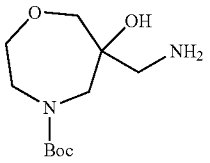

To a stirred solution of tert-butyl 1,5-dioxa-8-azaspiro[2.6]nonane-8-carboxylate (1.0 g, 4.36 mmol) in MeOH (5 mL) at 0° C. under an argon atmosphere, was added 7M ammonia in methanol (6.2 mL, 43.60 mmol). Then, the reaction mixture was gradually warmed up to room temperature and stirred for 16 hours. The reaction mixture was concentrated under reduced pressure to get a crude residue, which was purified by silica gel column chromatography using a CombiFlash instrument (12 g RediSep® column, 0 to 20% methanol in DCM) to afford tert-butyl 6-(aminomethyl)-6-hydroxy-1,4-oxazepane-4-carboxylate (400 mg, 1.62 mmol, 37.2% yield) as a colourless liquid. $^1H$ NMR (400 MHz, DMSO-$d_6$) δ ppm=3.83-3.76 (m, 1H), 3.72-3.41 (m, 7H), 2.96-2.82 (m, 1H), 2.81-2.58 (m, 1H), 2.58-2.34 (br s, 3H), 1.48 (s, 9H).

Preparation of Intermediate 198-1 and 198-2: tert-butyl (5S)-2-oxo-1,7-dioxa-3,10-diazaspiro[4.6]undecane-10-carboxylate and tert-butyl (5R)-2-oxo-1,7-dioxa-3,10-diazaspiro[4.6]undecane-10-carboxylate 198-1

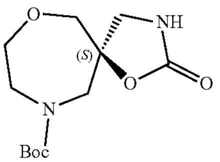

and 198-2

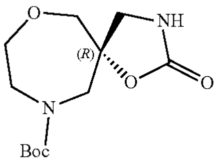

To a stirred solution of tert-butyl 6-(aminomethyl)-6-hydroxy-1,4-oxazepane-4-carboxylate (600 mg, 2.44 mmol) in DCM (2 mL) at room temperature under an argon atmosphere, were added DIPEA (1.3 mL, 7.31 mmol) and CDI (592 mg, 3.65 mmol), The reaction mixture was stirred at room temperature for 16 hours. Then, the reaction mixture was diluted with water and extracted with DCM. The organic layer was washed with brine, dried over anhydrous sodium sulphate, filtered and concentrated under reduced pressure to get a crude residue, which was purified by silica gel column chromatography using a CombiFlash instrument (40 g RediSep® column, 25-100% EtOAc in pet.-ether) to get tert-butyl-2-oxo-1,7-dioxa-3,10-diazaspiro[4.6]undecane-10-carboxylate (400 mg, 1.47 mmol, 60.3% yield) as an off white solid. The racemic product was re-purified by chiral SFC [SFC Method: Preparative column: Lux Cellulose C4 (250 mm×4.6 mm×5 μm); Co-solvent name: 5 mM ammonium acetate in ACN: methanol (1:1); Co-solvent percentage: 30%; Flow rate: 3 mL/min; Back pressure: 100 bar] to afford Isomer-1 (198-1) tert-butyl (S)-2-oxo-1,7-dioxa-3,10-diazaspiro[4.6]undecane-10-carboxylate (170 mg, 0.62 mmol, 25.6% yield) and Isomer-2 (198-2) tert-butyl (R)-2-oxo-1,7-dioxa-3,10-diazaspiro[4.6]undecane-10-carboxylate (150 mg, 0.55 mmol, 22.6% yield) as a colourless liquid.

Isomer-1: MS (ESI) m/z: 273.2 $[M+H]^+$; $^1H$ NMR (400 MHz, DMSO-$d_6$) δ ppm=7.55 (s, 1H), 3.83-3.76 (m, 2H), 3.66-3.50 (m, 4H), 3.50-3.41 (m, 2H), 3.33-3.30 (m, 1H), 3.19-3.14 (m, 1H), 1.40 (s, 9H).

Isomer-2: MS (ESI) m/z: 273.2 $[M+H]^+$; $^1H$ NMR (400 MHz, DMSO-$d_6$) δ ppm=7.55 (s, 1H), 3.88-3.72 (m, 2H), 3.68-3.50 (m, 4H), 3.50-3.28 (m, 3H), 3.24-3.09 (m, 1H), 1.40 (s, 9H).

Preparation of Intermediate 199: (5R)-1,7-dioxa-3,10-diazaspiro[4.6]undecan-2-one hydrochloride

199

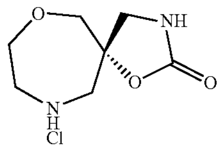

To a stirred solution of tert-butyl (5R)-2-oxo-1,7-dioxa-3,10-diazaspiro[4.6]undecane-10-carboxylate 198-2 (0.3 g, 1.10 mmol) in EtOAc (3 mL) at 0° C. under an argon atmosphere, was added 1M HCl in EtOAc (11.02 mL, 11.02 mmol). The reaction mixture was gradually warmed up to room temperature over a period of 3 hours. The volatiles were removed under reduced pressure at a lower temperature and triturated with diethyl ether to afford (5R)-1,7-dioxa-3,10-diazaspiro[4.6]undecan-2-one hydrochloride (0.20 g, 0.96 mmol, 87% yield) as an off white solid. MS (ESI) m/z: 173.0 $[M+H]^+$; $^1H$ NMR (400 MHz, DMSO-$d_6$) δ ppm=7.83 (s, 1H), 4.00-3.74 (m, 4H), 3.56-3.39 (m, 2H), 3.36-3.18 (m, 6H).

Preparation of Intermediate 205: tert-butyl (4aS,7aR)-4a-(hydroxymethyl)-2-methyl-octahydro-1H-cyclopenta[b]pyridine-1-carboxylate

205

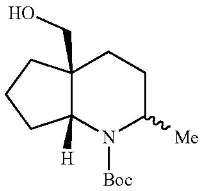

Nickel (II) chloride ethylene glycol dimethyl ether complex (34.4 mg, 0.16 mmol), $Ir[dF(CF_3)ppy]_2(dtbbpy)PF_6$ (43.9 mg, 0.04 mmol), tris(2-pyridylmethyl)amine (45.5 mg, 0.16 mmol) and tert-butyl (4aS,7aR)-4a-(hydroxymethyl) octahydro-1H-cyclopenta[b]pyridine-1-carboxylate (500 mg, 1.96 mmol) were taken in a 40 mL screw cap vial and dissolved in 5 mL 2,2,2-trifluoroethanol. Then, di-tert-butyl peroxide (2.15 mL, 11.75 mmol) was added to the reaction mixture, and the reaction vial was irradiated in a blue LED (427 nm) chamber over a period of 24 hours. The reaction mixture was diluted with DCM, filtered through a CELITE pad and the filtrate was concentrated under reduced pressure to afford a crude residue, which was purified by silica gel column chromatography using a CombiFlash instrument (40 g RediSep® column, 22% EtOAc in pet.-ether), to afford a mixture of diastereomers of tert-butyl (4aS,7aR)-4a-(hydroxymethyl)-2-methyl-octahydro-1H-cyclopenta[b]pyridine-1-carboxylate (500 mg, 1.26 mmol, 64.5% yield) as a colorless liquid. MS (ESI) m/z: 270.2 $[M+H]^+$.

Preparation of Intermediate 230: tert-butyl (4aS,7aR)-4a-[({4-[(6S)-6-[(tert-butyldimethylsilyl)oxy]-6-methyl-1,4-oxazepan-4-yl]-7-[8-ethyl-7-fluoro-3-(methoxymethoxy) naphthalen-1-yl]-8-fluoropyrido[4,3-d]pyrimidin-2-yl}oxy)methyl]-octahydro-1H-cyclopenta[b]pyridine-1-carboxylate

230

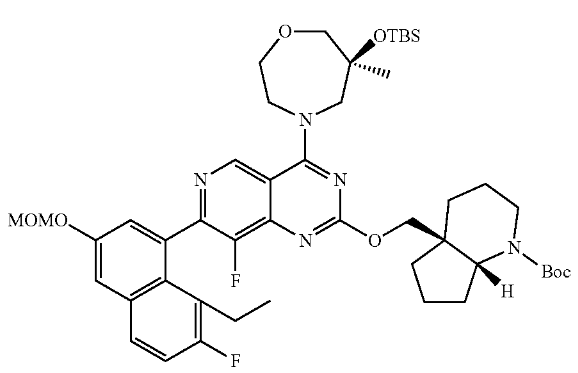

To a stirred solution of tert-butyl (4aS,7aR)-4a-[({4-[(6S)-6-[(tert-butyldimethylsilyl)oxy]-6-methyl-1,4-oxazepan-4-yl]-7-chloro-8-fluoropyrido[4,3-d]pyrimidin-2-yl}oxy)methyl]-octahydro-1H-cyclopenta[b]pyridine-1-carboxylate (5.0 g, 7.35 mmol) in 1,4-dioxane (50 mL) at room temperature under argon atmosphere, were added 2-(8-ethyl-7-fluoro-3-(methoxymethoxy) naphthalen-1-yl)-4,4,5,5-tetramethyl-1,3,2-dioxaborolane (2.91 g, 8.08 mmol), and 1.5M aqueous solution of potassium phosphate tribasic (14.7 mL, 22.05 mmol) aqueous solution. The reaction mixture was purged with argon for 5 min and charged with [1,1'-bis(di-tert-butylphosphino) ferrocene]dichloropalladium (II) (0.48 g, 0.74 mmol). The reaction mixture was again purged with argon and heated at 95° C. for 18 hours. The reaction mixture was cooled to room temperature, diluted with water, and extracted with EtOAc. The organic layer was washed with brine, dried over anhydrous $Na_2SO_4$, filtered and concentrated under reduced pressure to get a crude residue, which was purified by silica gel column chromatography using CombiFlash instrument (120 g RediSep® column, 50-80% EtOAc-pet.-ether) to get tert-butyl (4aS,7aR)-4a-[({4-[(6S)-6-[(tert-butyldimethylsilyl)oxy]-6-methyl-1,4-oxazepan-4-yl]-7-[8-ethyl-7-fluoro-3-(methoxymethoxy) naphthalen-1-yl]-8-fluoropyrido[4,3-d]pyrimidin-2-yl}oxy)methyl]-octahydro-1H-cyclopenta[b]pyridine-1-carboxylate (3.5 g, 3.99 mmol, 54.2% yield) as a brown solid. $^1H$ NMR (400 MHz, DMSO-$d_6$) δ ppm=9.27 (s, 1H), 7.90 (dd, J=9.0, 6.0 Hz, 1H), 7.68 (d, J=2.5 Hz, 1H), 7.44 (t, J=9.3 Hz, 1H), 7.21-7.16 (m, 1H), 5.34 (s, 2H), 4.65-4.48 (m, 1H), 4.49-4.13 (m, 6H), 4.07-3.80 (m, 5H), 3.68-3.57 (m, 2H), 2.86-2.69 (m, 1H), 2.42-2.32 (m, 1H), 2.23-2.10 (m, 2H), 1.82-1.57 (m, 7H), 1.54-1.35 (m, 6H), 1.34-1.15 (m, 12H), 0.76-0.60 (m, 9H), 0.09-0.05 (m, 6H).

Preparation of Intermediate 231: tert-butyl (4aS,7aR)-4a-[({7-[8-ethyl-7-fluoro-3-(methoxymethoxy) naphthalen-1-yl]-8-fluoro-4-[(6S)-6-hydroxy-6-methyl-1,4-oxazepan-4-yl]pyrido[4,3-d]pyrimidin-2-yl}oxy)methyl]-octahydro-1H-cyclopenta[b]pyridine-1-carboxylate

231

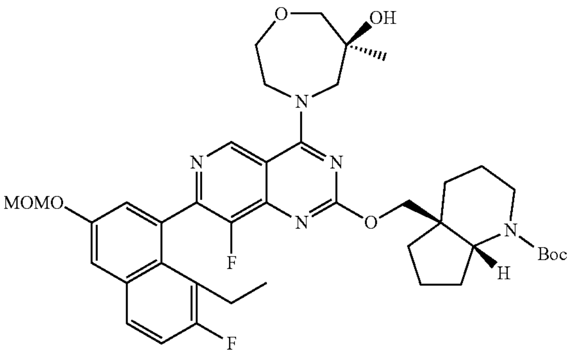

To a stirred solution of tert-butyl (4aS,7aR)-4a-[({4-[(6S)-6-[(tert-butyldimethylsilyl)oxy]-6-methyl-1,4-oxazepan-4-yl]-7-[8-ethyl-7-fluoro-3-(methoxymethoxy) naphthalen-1-yl]-8-fluoropyrido[4,3-d]pyrimidin-2-yl}oxy) methyl]-octahydro-1H-cyclopenta[b]pyridine-1-carboxylate (3.5 g, 3.99 mmol) in DMF (5 mL) at room temperature under argon atmosphere, was added CsF (6.05 g, 39.90 mmol) and stirred at 65° C. for 2 hours. The reaction mixture was filtered through a CELITE pad, and the pad washed with EtOAc. The combined filtrate was concentrated under reduced pressure to get a crude residue, which was purified by silica gel column chromatography using CombiFlash instrument (80 g RediSep® column, 50-100% EtOAc-pet.-ether) to afford tert-butyl (4aS,7aR)-4a-[({7-[8-ethyl-7-fluoro-3-(methoxymethoxy) naphthalen-1-yl]-8-fluoro-4-[(6S)-6-hydroxy-6-methyl-1,4-oxazepan-4-yl]pyrido[4,3-d]pyrimidin-2-yl}oxy)methyl]-octahydro-1H-cyclopenta[b]pyridine-1-carboxylate (2.7 g, 3.53 mmol, 89% yield) as a light yellow solid. MS (ESI) m/z: 764.3 $[M+H]^+$;

Preparation of Intermediate 233: (6S)-4-(2-{[(4aS,7aR)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol

233

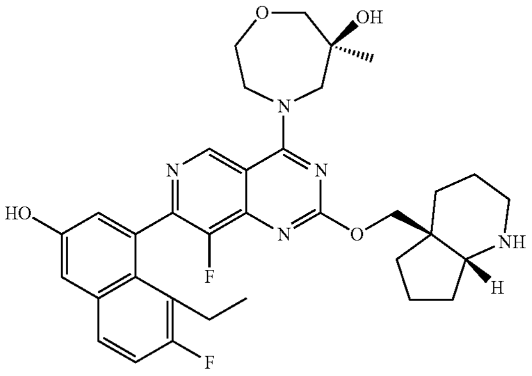

To a stirred solution of tert-butyl (4aS,7aR)-4a-[({7-[8-ethyl-7-fluoro-3-(methoxymethoxy) naphthalen-1-yl]-8-fluoro-4-[(6S)-6-hydroxy-6-methyl-1,4-oxazepan-4-yl]pyrido[4,3-d]pyrimidin-2-yl}oxy)methyl]-octahydro-1H-cyclopenta[b]pyridine-1-carboxylate (2.7 g, 3.53 mmol) in EtOAc (35 mL) at 0° C. under argon atmosphere, was added 1M HCl in EtOAc (70.7 mL, 70.70 mmol). The reaction mixture was gradually warmed up to room temperature over a period of 3 hours. The volatiles were removed under reduced pressure at a lower temperature, dissolved in DCM and basified with triethyl amine. The DCM layer was washed successively with a saturated $NaHCO_3$ solution followed by brine, dried over anhydrous $Na_2SO_4$, filtered and concentrated under reduced pressure to get crude (6S)-4-(2-{[(4aS,7aR)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (2.0 g, 3.23 mmol, 91% yield) as a yellow solid. MS (ESI) m/z: 620.2 $[M+H]^+$.

Example-26-1 and 26-2: (6S)-4-(2-{[(4aS,7aR)-1-[(2R,4s,6S)-2,6-dimethyloxan-4-yl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol and (6S)-4-(2-{[(4aS,7aR)-1-[(2R,4r,6S)-2,6-dimethyloxan-4-yl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol 26-1

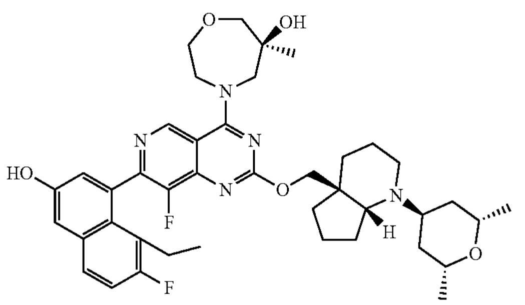

and 26-2

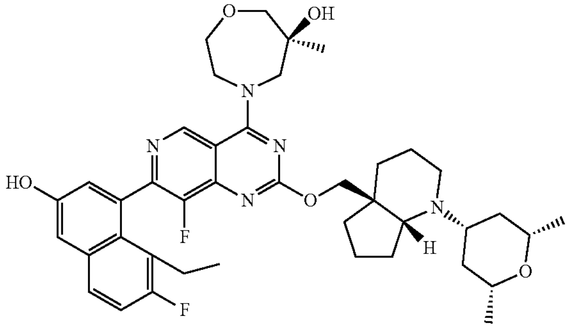

To a stirred solution of (6S)-4-(2-{[(4aS,7aR)-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (1.0 g, 1.61 mmol) in DMSO (10 mL) at room temperature under argon atmosphere, were added cis-2,6-dimethyltetrahydro-4H-pyran-4-one (0.31 g, 2.42 mmol), acetic acid (0.46 mL, 8.07 mmol) and sodium triacetoxyborohydride (1.03 g, 4.84 mmol). The reaction mixture was stirred at room temperature for 15 hours. Then, the reaction mixture was diluted with EtOAc, washed with saturated aqueous $NaHCO_3$ solution followed by brine, dried over anhydrous $Na_2SO_4$, filtered and concentrated under reduced pressure to afford a crude residue, which was purified by silica gel column chromatography using CombiFlash instrument (40 g RediSep® column, 60-100% EtOAc-pet.-ether) to afford isomer-1 (6S)-4-(2-{[(4aS,7aR)-1-[(2R,4s,6S)-2,6-dimethyloxan-4-yl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (0.14 g, 0.19 mmol, 12% yield) and isomer-2 (0.57 g, 80% purity). Isomer-2 was re-purified by SFC [SFC method: preparative column: GreenSep SFC Diol (250 mm*4.6 mm*5 μm); co-solvent name: 0.2% ammonia in methanol; flow: 3 mL/min; co-solvent percentage: 30%; back pressure: 100 bar] to afford (6S)-4-(2-{[(4aS,7aR)-1-[(2R,4r,6S)-2,6-dimethyloxan-4-yl]-octahydro-1H-cyclopenta[b]pyridin-4a-yl]methoxy}-7-(8-ethyl-7-fluoro-3-hydroxynaphthalen-1-yl)-8-fluoropyrido[4,3-d]pyrimidin-4-yl)-6-methyl-1,4-oxazepan-6-ol (400 mg, 0.544 mmol, 33.7% yield) as an off white solid.

Isomer-1 (26-1): MS (ESI) m/z: 732.3 $[M+H]^+$; $^1H$ NMR (400 MHz, DMSO-$d_6$) δ ppm=9.92 (d, J=6.0 Hz, 1H), 9.49 (d, J=2.0 Hz, 1H), 7.77 (dd, J=9, 0, 6.0 Hz, 1H), 7.40-7.30 (m, 2H), 7.04 (dd, J=16.0, 2.5 Hz, 1H), 5.13 (br d, J=16 Hz, 1H), 4.60-4.47 (m, 2H), 4.46-4.30 (m, 2H), 4.27-3.70 (m, 6H), 3.65-3.51 (m, 3H), 3.22-3.14 (m, 1H), 2.82-2.79 (m, 1H), 2.43-2.30 (m, 1H), 2.24-2.05 (m, 2H), 1.97-1.80 (m, 3H), 1.79-1.28 (m, 9H), 1.21-1.07 (m, 5H), 0.99 (d, J=6.0 Hz, 3H), 0.89 (d, J=6.0 Hz, 3H), 0.71 (br t, J=7.1 Hz, 3H).

Isomer-2 (26-2): MS (ESI) m/z: 732.3 $[M+H]^+$; $^1H$ NMR (400 MHz, DMSO-$d_6$) δ ppm=10.08 (s, 1H), 9.46 (s, 1H), 7.77 (dd, J=9.0, 6.0 Hz, 1H), 7.42-7.29 (m, 2H), 7.03 (dd, J=16.0, 2.5 Hz, 1H), 5.15 (br d, J=14.5 Hz, 1H), 4.67-4.54 (m, 1H), 4.41-3.81 (m, 9H), 3.60-3.52 (m, 2H), 3.11 (br t, J=7.6 Hz, 1H), 2.61-2.54 (m, 2H), 2.45-2.31 (m, 2H), 2.24-2.07 (m, 1H), 1.96-1.84 (m, 1H), 1.79-1.25 (m, 11H), 1.16 (d, J=5.3 Hz, 3H), 1.06 (d, J=6.0 Hz, 6H), 1.00-0.84 (m, 2H), 0.74 (br t, J=7.1 Hz, 3H).

Preparation of Intermediate 237: 6-chloro-4-fluoro-1H-indazole

237

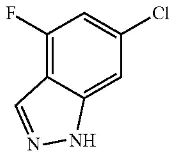

To a stirred solution of 4-chloro-2,6-difluorobenzaldehyde (15 g, 85.0 mmol) in 1,4-dioxane (56.6 mL) at room temperature under argon atmosphere, was added hydrazine monohydrate (11.33 mL, 234.0 mmol) and the reaction mixture was stirred at 95° C. for 16 hours. Then, the reaction mixture was cooled to room temperature and water was added. The resulting precipitate was filtered, washed with water, and dried under vacuum. The solid was diluted with EtOAc, dried over anhydrous $Na_2SO_4$, and concentrated to afford 6-chloro-4-fluoro-1H-indazole (12 g, 70.40 mmol, 83% yield) as an off-white solid. MS (ESI) m/z: 169.0 $[M-H]^+$; $^1H$ NMR (300 MHz, DMSO-$d_6$) δ ppm=13.62-13.45 (m, 1H), 8.27-8.18 (m, 1H), 7.54-7.47 (m, 1H), 7.10-7.04 (m, 1H).

Preparation of Intermediate 238: 6-chloro-4-fluoro-1-(oxan-2-yl)-1H-indazole

238

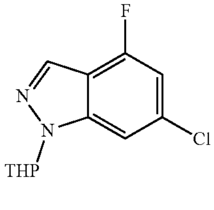

To a stirred solution of 6-chloro-4-fluoro-1H-indazole (15 g, 88.0 mmol) and 3,4-dihydro-2H-pyran (12.0 mL, 132.0 mmol) in DCM (176 mL) at room temperature under argon atmosphere, was added 4-methylbenzenesulfonic acid hydrate (1.67 g, 8.79 mmol). The resulting mixture was stirred for 2 hours. Then, the reaction mixture was quenched with ice cold water, and extracted with DCM. The organic layer was washed with brine, dried over anhydrous $Na_2SO_4$, filtered and concentrated under reduced pressure to get a crude residue, which was purified by silica gel column chromatography using CombiFlash instrument (80 g RediSep® column, 5-10% EtOAc-pet.-ether) to afford 6-chloro-4-fluoro-1-(oxan-2-yl)-1H-indazole (12 g, 47.1 mmol, 53.6% yield) as a pale-yellow solid. MS (ESI) m/z: 254.9 $[M+H]^+$; $^1H$ NMR (300 MHz, DMSO-$d_6$) δ ppm=8.28 (s, 1H), 7.80 (s, 1H), 7.16 (dd, J=9.8, 1.3 Hz, 1H), 5.90 (dd, J=9.5, 2.1 Hz, 1H), 3.92-3.69 (m, 2H), 2.46-2.26 (m, 1H), 2.13-1.91 (m, 1H), 1.82-1.43 (m, 4H).

Preparation of Intermediate 239: 6-chloro-4-fluoro-5-methyl-1-(oxan-2-yl)-1H-indazole

239

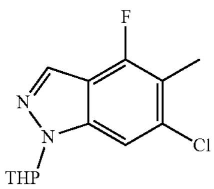

To a stirred solution of 6-chloro-4-fluoro-1-(oxan-2-yl)-1H-indazole (10 g, 39.3 mmol) in THF (100 mL) under argon atmosphere at −78° C. were added lithium chloride (1.99 g, 47.10 mmol) and 2M solution of LDA in THF (51.0 mL, 102.0 mmol). The reaction mixture was stirred for 2 hours at the same temperature after which methyl iodide (3.93 mL, 62.8 mmol) was added. The reaction mixture was stirred for an additional 1 hour. Then, the reaction mixture was diluted with $NH_4Cl$ solution and extracted with EtOAc. The organic layer was washed with brine, dried over anhydrous $Na_2SO_4$, filtered and concentrated under reduced pressure to get the crude residue, which was purified through silica gel column chromatography using CombiFlash instrument (80 g RediSep® column, 0-100% EtOAc-pet.-ether) to get 6-chloro-4-fluoro-5-methyl-1-(oxan-2-yl)-1H-indazole (3.2 g, 11.91 mmol, 76% yield) as a brown semi-solid. MS (ESI) m/z: 269.0 $[M+H]^+$.

Preparation of Intermediate 239-1: 6-chloro-5-methyl-1-(oxan-2-yl)-1H-indazol-4-ol 239-1

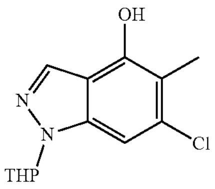

To a stirred solution of 6-chloro-4-fluoro-5-methyl-1-(oxan-2-yl)-1H-indazole (8.0 g, 29.8 mmol) in DMSO (104 mL) at room temperature under argon atmosphere, were added water (10.7 mL, 595.0 mmol) and potassium hydroxide (10.0 g, 179.0 mmol), The reaction mixture was heated to 100° C. for 16 hours. Then, the reaction mixture was cooled to room temperature, diluted with water, acidified using 1.5N aq. HCl solution, and extracted with EtOAc. The organic layer was washed with brine, dried over anhydrous $Na_2SO_4$, filtered and concentrated under reduced pressure to get a crude residue, which was purified through silica gel column chromatography using CombiFlash instrument (80 g RediSep® column, 50-100% EtOAc-pet.-ether) to get 6-chloro-5-methyl-1-(oxan-2-yl)-1H-indazol-4-ol (4 g, 15.0 mmol, 50.4% yield) as a pale yellow solid. MS (ESI) m/z: 267.0 $[M+H]^+$.

Preparation of Intermediate 240: 6-chloro-5-methyl-1-(oxan-2-yl)-1H-indazol-4-yl trifluoromethanesulfonate

240

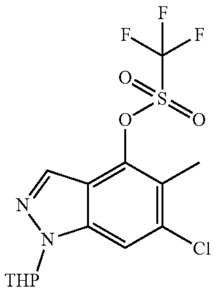

To a stirred solution of 6-chloro-5-methyl-1-(oxan-2-yl)-1H-indazol-4-ol (1 g, 3.75 mmol) and DIPEA (3.93 mL, 22.50 mmol) in DCM (20 mL) at −78° C. under argon atmosphere, was added $Tf_2O$ (0.95 mL, 5.62 mmol) and stirred for 1 hour. Then, the reaction mixture was diluted with DCM, washed with water, brine, dried over anhydrous $Na_2SO_4$ and concentrated under reduced pressure to get a crude residue, which was purified by silica gel column chromatography using CombiFlash instrument (40 g RediSep® column, 10-20% EtOAc-pet.-ether). Fractions containing the desired product were evaporated to afford 6-chloro-5-methyl-1-(oxan-2-yl)-1H-indazol-4-yl trifluoromethanesulfonate (1.2 g, 3.01 mmol, 80% yield) as a colourless solid. MS (ESI) m/z: 398.9 $[M+H]^+$; $^1H$ NMR (300 MHz, DMSO-$d_6$) δ ppm=8.21 (s, 1H), 8.11 (s, 1H), 5.95 (dd, J=9.6, 2.3 Hz, 1H), 3.93-3.73 (m, 2H), 2.42 (s, 3H), 2.09-1.95 (m, 2H), 1.81-1.65 (m, 1H), 1.64-1.54 (m, 3H).

Preparation of Intermediate 241: 6-chloro-5-methyl-1-(oxan-2-yl)-4-(4,4,5,5-tetramethyl-1,3,2-dioxaborolan-2-yl)-1H-indazole

241

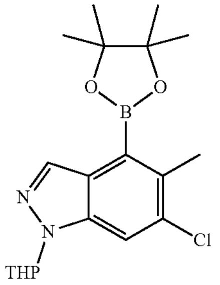

To a stirred solution of 6-chloro-5-methyl-1-(oxan-2-yl)-1H-indazol-4-yl trifluoromethanesulfonate (1.2 g, 3.01 mmol) in 1,4-dioxane (24 mL) under argon atmosphere, were added bis(pinacolato)diboron (1.91 g, 7.52 mmol) and potassium acetate (0.74 g, 7.52 mmol). The reaction mixture was purged with argon and charged with $PdCl_2$(dppf) (0.22 g, 0.30 mmol). The reaction mixture was again purged with argon and stirred at 100° C. for 16 hours. Then, the reaction mixture was filtered through a Celite pad and concentrated under reduced pressure to get a crude residue, which was purified by silica gel column chromatography using CombiFlash instrument (40 g RediSep® column, 0-10% EtOAc-pet.-ether). Fractions containing the desired product were evaporated to afford 6-chloro-5-methyl-1-(oxan-2-yl)-4-(4,4,5,5-tetramethyl-1,3,2-dioxaborolan-2-yl)-1H-indazole (1 g, 2.65 mmol, 88% yield) as a colourless solid. MS (ESI) m/z: 377.3 $[M+H]^+$; $^1H$ NMR (300 MHz, DMSO-$d_6$) δ ppm=8.18 (s, 1H), 8.00 (s, 1H), 5.85 (dd, J=9.6, 2.6 Hz, 1H), 3.91-3.70 (m, 2H), 2.59 (s, 3H), 2.43-2.30 (m, 1H), 2.08-1.88 (m, 2H), 1.63-1.53 (m, 3H), 1.42-1.35 (m, 12H).

BIOLOGICAL ACTIVITY

$KRAS^{G12D}$ RAF Disruption Assay

Recombinant GMPPNP-loaded KRAS G12D (5 nM) was treated with compound at room temperature for 20 minutes in assay buffer (50 mM Tris pH 7.5, 100 mM NaCl, 1 mM $MgCl_2$, 1 mM DTT, 100 μg/ml BSA). Recombinant GST-RAF1 RBD (9 nM) was added, followed by the addition of SA-Tb (0.25 nM), and the reaction mixture was incubated for 3 hours. The homogeneous time resolved fluorescence (HTRF) signal was measured (PerkinElmer Envision), the signal ratio ($\lambda_{em}$ 520/$\lambda_{em}$ 495) was calculated, and $IC_{50}$ values were calculated from the dose-response curve.

$KRAS^{G12D}$ Nucleotide Exchange Assay

Recombinant GDP-loaded KRAS G12D (20 nM) was treated with compound at room temperature for 20 minutes in assay buffer (10 mM Hepes pH 7.4, 150 mM NaCl, 5 mM $MgCl_2$, 0.0025% Igepal-CA630, 0.05% BSA, 1 mM DTT, 0.5 nM SA-Tb). BIODIPY-labeled GDP (400 nM) and recombinant SOS (10 nM) were added, and the reaction was incubated for 30 minutes. HTRF signal was measured (PerkinElmer Envision), the signal ratio ($\lambda_{em}$ 520/$\lambda_{em}$ 495) was calculated, and $IC_{50}$ values were calculated from the dose-response curve.

The $IC_{50}$ values for compounds described herein is shown in Table 6.

TABLE 6

| Example # | KRASG12D RAF Disruption Assay ($IC_{50}$, μM) | KRASG12D Nucleotide Exchange Assay ($IC_{50}$, μM) |
|---|---|---|
| 1-1 | 0.026 | 0.010 |
| 1-2 | 0.059 | 0.012 |
| 1-3 | 0.507 | 0.024 |
| 1-4 | 0.069 | 0.017 |
| 1-5 | 0.169 | 0.009 |
| 1-6 | 0.063 | 0.013 |
| 1-7 | 0.048 | 0.009 |
| 1-8 | 0.236 | 0.011 |
| 1-9 | 0.026 | 0.006 |
| 1-10 | 0.067 | 0.009 |
| 1-11 | 0.147 | 0.011 |
| 1-12 | 0.036 | 0.010 |
| 1-13 | 0.071 | 0.010 |
| 1-14 | 0.142 | 0.011 |
| 1-15 | 0.265 | 0.013 |
| 1-16 | 1.543 | 0.039 |
| 1-17 | 0.081 | 0.011 |
| 1-18 | 0.150 | 0.010 |
| 1-19 | 0.296 | 0.010 |
| 1-20 | 0.368 | 0.014 |
| 1-21 | 0.209 | 0.014 |
| 1-22 | 2.157 | 0.035 |
| 1-23 | 0.028 | 0.009 |
| 1-24 | 0.155 | 0.021 |
| 1-25 | 0.179 | 0.020 |
| 1-26 | 0.060 | 0.019 |
| 1-27 | 0.117 | 0.012 |
| 1-28 | 0.035 | 0.014 |
| 1-29 | 0.044 | 0.012 |
| 1-30 | 0.177 | 0.015 |
| 1-31 | 0.658 | 0.032 |
| 1-32 | 0.062 | 0.008 |
| 1-33 | 0.064 | 0.010 |
| 1-34 | 0.059 | 0.015 |
| 1-35 | 0.394 | 0.037 |
| 1-36 | 0.105 | 0.022 |
| 1-37 | 0.175 | 0.024 |
| 1-38 | 0.019 | 0.009 |
| 1-39 | 0.020 | 0.016 |
| 1-40 | 0.038 | 0.012 |
| 1-41 | 0.638 | 0.025 |
| 1-42 | 0.687 | 0.025 |
| 1-43 | 0.673 | 0.023 |
| 1-44 | 0.714 | 0.023 |
| 1-45 | 0.017 | 0.013 |
| 1-46 | 0.214 | 0.016 |
| 1-47 | 0.055 | 0.011 |
| 1-48 | 0.012 | 0.012 |
| 1-49 | 0.015 | 0.012 |
| 1-50 | 0.025 | 0.013 |
| 1-51 | 0.108 | 0.017 |
| 1-52 | 0.053 | 0.011 |
| 1-53 | 0.031 | 0.012 |
| 1-54 | 0.113 | 0.019 |
| 1-55 | 0.036 | 0.007 |
| 1-56 | 0.031 | 0.014 |
| 1-57 | 0.012 | 0.018 |
| 1-58 | 0.054 | 0.020 |
| 1-59 | 0.013 | 0.013 |
| 1-60 | 0.024 | 0.017 |
| 1-61 | 0.036 | 0.009 |
| 1-62 | 0.046 | 0.010 |
| 1-63 | 0.039 | 0.022 |
| 1-64 | 0.011 | 0.014 |
| 1-65 | 0.015 | 0.013 |
| 1-66 | 0.849 | 0.059 |
| 1-67 | 0.478 | 0.043 |
| 1-68 | 0.079 | 0.013 |
| 1-69 | 0.103 | 0.016 |
| 1-70 | 0.100 | 0.010 |
| 1-71 | 0.021 | 0.007 |
| 1-72 | 0.079 | 0.015 |

TABLE 6-continued

| Example # | KRASG12D RAF Disruption Assay ($IC_{50}$, μM) | KRASG12D Nucleotide Exchange Assay ($IC_{50}$, μM) |
|---|---|---|
| 1-73 | 0.024 | 0.011 |
| 1-74 | 0.087 | 0.013 |
| 1-75 | 0.097 | 0.013 |
| 1-76 | 0.083 | 0.013 |
| 1-77 | 0.388 | 0.025 |
| 1-78 | 0.089 | 0.009 |
| 1-79 | 0.093 | 0.011 |
| 1-80 | 0.293 | 0.032 |
| 1-81 | 0.701 | 0.026 |
| 1-82 | 0.047 | 0.009 |
| 1-83 | 0.046 | 0.024 |
| 1-84 | 0.288 | 0.017 |
| 1-85 | 0.596 | 0.024 |
| 1-86 | 0.024 | 0.010 |
| 1-87 | 0.182 | 0.014 |
| 1-88 | 0.212 | 0.013 |
| 1-89 | 0.062 | 0.013 |
| 1-90 | 0.012 | 0.009 |
| 1-91 | 0.108 | 0.008 |
| 1-92 | 0.249 | 0.014 |
| 1-93 | 0.091 | 0.010 |
| 1-94 | 0.188 | 0.012 |
| 1-95 | 0.067 | 0.009 |
| 1-96 | 0.081 | 0.015 |
| 1-97 | 0.302 | 0.013 |
| 1-98 | 0.024 | 0.008 |
| 1-99 | 0.025 | 0.011 |
| 1-100 | 0.033 | 0.018 |
| 1-101 | 0.152 | 0.013 |
| 1-102 | 0.207 | 0.015 |
| 1-103 | 0.092 | 0.015 |
| 1-110 | 0.015 | 0.010 |
| 1-115 | 0.092 | 0.012 |
| 1-118 | 0.020 | 0.014 |
| 1-119 | 0.048 | 0.014 |
| 1-120 | 0.040 | 0.012 |
| 1-121 | 0.069 | 0.008 |
| 1-122 | 0.240 | 0.013 |
| 1-123 | 0.059 | 0.018 |
| 1-124 | 0.201 | 0.017 |
| 1-125 | 0.058 | 0.011 |
| 1-126 | 0.097 | 0.024 |
| 1-130 | 0.014 | 0.008 |
| 1-131 | 0.009 | 0.006 |
| 1-132 | 0.005 | 0.003 |
| 1-134 | 0.061 | 0.009 |
| 1-135 | 0.063 | 0.010 |
| 1-136 | 0.049 | 0.013 |
| 1-137 | 0.041 | 0.011 |
| 1-140 | 0.600 | 0.032 |
| 1-141 | 0.156 | 0.015 |
| 1-144 | 0.078 | 0.014 |
| 1-152 | 2.600 | 0.023 |
| 1-205 | 0.652 | 0.011 |
| 1-206 | 0.165 | 0.005 |
| 1-213 | 0.018 | 0.011 |
| 1-214 | 0.061 | 0.007 |
| 1-215 | 0.017 | 0.004 |
| 1-218 | 0.077 | 0.011 |
| 1-219 | 0.015 | 0.008 |
| 1-220 | 0.023 | 0.016 |
| 1-221 | 0.029 | 0.009 |
| 1-224 | 0.006 | 0.010 |
| 1-225 | 0.004 | 0.007 |
| 1-226 | 0.006 | 0.008 |
| 1-227 | 0.010 | 0.009 |
| 1-268 | 0.007 | 0.005 |
| 1-322 | 0.013 | 0.011 |
| 1-323 | 0.015 | 0.010 |
| 1-324 | 0.014 | 0.011 |
| 1-326 | 0.047 | 0.014 |
| 1-327 | 0.025 | 0.014 |
| 1-328 | 0.024 | 0.014 |
| 1-329 | 0.040 | 0.011 |
| 1-331 | 0.092 | 0.017 |
| 1-332 | 0.101 | 0.013 |

TABLE 6-continued

| Example # | KRASG12D RAF Disruption Assay ($IC_{50}$, μM) | KRASG12D Nucleotide Exchange Assay ($IC_{50}$, μM) |
|---|---|---|
| 1-333 | 0.156 | 0.024 |
| 1-334 | 0.041 | 0.015 |
| 2-3 | 0.078 | 0.016 |
| 2-4 | 0.053 | 0.005 |
| 2-5 | 0.045 | 0.016 |
| 2-6 | 0.726 | 0.082 |
| 2-7 | 0.533 | 0.025 |
| 2-8 | 0.059 | 0.008 |
| 2-9 | 0.191 | 0.020 |
| 2-10 | 2.038 | 0.300 |
| 2-11 | 2.198 | 0.234 |
| 2-12 | 0.070 | 0.009 |
| 2-13 | 0.183 | 0.008 |
| 2-14 | 0.008 | 0.023 |
| 2-15 | 0.009 | 0.013 |
| 2-16 | 0.004 | 0.018 |
| 2-17 | 0.014 | 0.013 |
| 2-18 | 0.012 | 0.017 |
| 2-19 | 0.006 | 0.019 |
| 2-20 | 0.027 | 0.019 |
| 2-21 | 0.006 | 0.015 |
| 2-22 | 0.075 | 0.028 |
| 2-23 | 0.026 | 0.022 |
| 2-24 | 0.093 | 0.016 |
| 2-25 | 0.055 | 0.012 |
| 2-26 | 0.025 | 0.018 |
| 2-27 | 0.015 | 0.039 |
| 2-28 | 0.023 | 0.044 |
| 2-29 | 0.016 | 0.014 |
| 2-30 | 0.004 | 0.013 |
| 2-31 | 0.012 | 0.021 |
| 2-32 | 0.913 | 0.009 |
| 2-33 | 0.014 | 0.006 |
| 2-34 | 0.015 | 0.014 |
| 2-35 | 0.018 | 0.007 |
| 2-36 | 0.007 | 0.004 |
| 2-37 | 0.020 | 0.014 |
| 2-38 | 0.043 | 0.006 |
| 2-39 | 0.015 | 0.004 |
| 2-40 | 0.007 | 0.005 |
| 2-41 | 0.200 | 0.007 |
| 2-42 | 0.048 | 0.005 |
| 2-43 | 0.305 | 0.007 |
| 2-44 | 0.024 | 0.007 |
| 2-45 | 0.030 | 0.013 |
| 2-46 | 0.041 | 0.009 |
| 2-47 | 0.027 | 0.009 |
| 2-48 | 1.653 | 0.014 |
| 2-49 | 0.133 | 0.004 |
| 2-50 | 0.194 | 0.005 |
| 2-51 | 0.073 | 0.007 |
| 2-52 | 0.014 | 0.007 |
| 2-53 | 0.106 | 0.004 |
| 2-54 | 0.001 | 0.006 |
| 2-55 | 0.013 | 0.008 |
| 2-56 | 0.048 | 0.009 |
| 2-57 | 0.189 | 0.009 |
| 2-58 | 0.027 | 0.006 |
| 2-59 | 0.002 | 0.003 |
| 2-60 | 0.008 | 0.007 |
| 2-61 | 0.324 | 0.007 |
| 2-62 | 0.050 | 0.007 |
| 2-63 | 0.051 | 0.011 |
| 2-64 | 0.006 | 0.008 |
| 2-65 | 0.008 | 0.010 |
| 2-66 | 0.016 | 0.014 |
| 2-67 | 0.029 | 0.006 |
| 2-69 | 0.028 | 0.004 |
| 2-70 | 0.195 | 0.006 |
| 2-71 | 0.025 | 0.008 |
| 2-72 | 0.050 | 0.005 |
| 2-73 | 0.080 | 0.006 |
| 2-74 | 0.041 | 0.004 |
| 2-75 | 0.164 | 0.008 |
| 2-76 | 0.026 | 0.007 |
| 2-77 | 0.011 | 0.007 |

TABLE 6-continued

| Example # | KRASG12D RAF Disruption Assay ($IC_{50}$, μM) | KRASG12D Nucleotide Exchange Assay ($IC_{50}$, μM) |
|---|---|---|
| 2-78 | 0.013 | 0.008 |
| 2-79 | 0.021 | 0.005 |
| 2-81 | 2.055 | 0.011 |
| 2-82 | 1.324 | 0.016 |
| 2-83 | 0.066 | 0.006 |
| 2-86 | 0.192 | 0.007 |
| 2-87 | 0.014 | 0.005 |
| 2-88 | 0.042 | 0.006 |
| 2-89 | 0.012 | 0.007 |
| 2-90 | 0.015 | 0.006 |
| 2-91 | 0.027 | 0.007 |
| 2-92 | 0.007 | 0.006 |
| 2-93 | 0.016 | 0.005 |
| 2-94 | 0.062 | 0.014 |
| 2-95 | 0.067 | 0.014 |
| 2-96 | 0.011 | 0.008 |
| 2-97 | 0.005 | 0.006 |
| 2-98 | 0.025 | 0.005 |
| 2-99 | 0.016 | 0.007 |
| 2-100 | 0.012 | 0.005 |
| 2-101 | 0.017 | 0.007 |
| 2-102 | 0.013 | 0.006 |
| 2-103 | 0.007 | 0.005 |
| 2-104 | 0.033 | 0.005 |
| 2-105 | 0.134 | 0.007 |
| 2-106 | 0.112 | 0.007 |
| 2-107 | 0.037 | 0.007 |
| 2-108 | 0.233 | 0.005 |
| 2-109 | 0.402 | 0.007 |
| 2-110 | 0.017 | 0.005 |
| 2-111 | 0.061 | 0.010 |
| 2-112 | 0.078 | 0.015 |
| 2-113 | 0.011 | 0.008 |
| 2-114 | 0.016 | 0.009 |
| 2-115 | 0.045 | 0.015 |
| 2-116 | 0.014 | 0.007 |
| 2-117 | 0.147 | 0.009 |
| 2-120 | 0.058 | 0.017 |
| 2-124 | 0.001 | 0.005 |
| 2-126 | 0.014 | 0.012 |
| 2-127 | 0.007 | 0.009 |
| 2-128 | 0.004 | 0.008 |
| 2-129 | 0.063 | 0.009 |
| 16-1 | 0.109 | 0.009 |
| 16-2 | 0.014 | 0.006 |
| 17-1 | 0.036 | 0.007 |
| 18-1 | 0.001 | 0.006 |
| 26-1 | 0.320 | 0.007 |
| 26-2 | 0.013 | 0.007 |

Cell Proliferation Assay

Cell lines were purchased from ATCC and cultured according to provider recommendations. Cell lines used: HPAC (ATCC, CRL-2119); NCI-H727 (ATCC, CRL-5815), GP2D (Millipore/Sigma, 95090714), H358 (ATCC, CRL-5807). Cells were seeded in 384-well plates (Greiner 3B) at 200-750 cells/well, a density determined previously to show a linear response over the 5-day culture (37°/5% $CO_2$; 80% humidity). following an overnight recovery, compounds dissolved in DMSO were added at 1/400 volume of media in well using acoustic dispensing. Camptothecin (5 μM) was added as a positive control on each plate. At the end of the 4 day treatment time, CellTiter-Glo® (Promega Corp.) was added and signal was detected on reader adapted with luminescence mode. Results were normalized as percent inhibition relative to DMSO treated cells [% Inhibition=(1−(Test−Average positive control)/(Average DMSO−Average positive control))*100]. Curves were analyzed using non-linear regression analysis and fitted to the standard 4-parameter hyperbola. $IC_{50}$ values are reported in Table 7 and are reported as concentration of compound that generates a 50% decrease in signal relative to DMSO-alone treated control. Empty boxes indicate the compound was not tested against a particular mutation/cell line.

TABLE 7

| | $IC_{50}$ (μM) (mutation/cell line) | | | |
|---|---|---|---|---|
| Example # | G12D (HPAC) | G12V (H727) | G12D (GP2D) | G12C (H358) |
| 1-1 | 0.278 | 0.048 | 0.019 | 0.044 |
| 1-2 | 0.964 | | | |
| 1-3 | 2.750 | | | |
| 1-4 | 0.449 | 0.064 | 0.065 | 0.050 |
| 1-5 | 0.865 | | | |
| 1-6 | 0.384 | | | |
| 1-7 | 0.528 | | | |
| 1-8 | 0.744 | | | |
| 1-9 | 1.662 | | | |
| 1-10 | 1.721 | | | |
| 1-11 | 4.639 | | | |
| 1-12 | 0.671 | 0.044 | 0.087 | 0.060 |
| 1-13 | 1.065 | | | |
| 1-14 | 7.478 | | | |
| 1-15 | 0.777 | | | |
| 1-16 | 3.744 | | | |
| 1-17 | 1.020 | | | |
| 1-18 | 2.303 | | | |
| 1-19 | 2.244 | 0.055 | 0.110 | 0.051 |
| 1-20 | 7.443 | | | |
| 1-21 | 0.527 | | | |
| 1-22 | 4.036 | | | |
| 1-23 | 0.302 | | | |
| 1-24 | 1.408 | | | |
| 1-25 | 0.213 | 0.076 | 0.067 | 0.050 |
| 1-26 | 1.579 | | | |
| 1-27 | 0.530 | 0.068 | 0.048 | 0.042 |
| 1-28 | 1.808 | | | |
| 1-29 | 8.797 | 0.081 | 0.068 | 0.079 |
| 1-30 | 5.981 | | | |
| 1-31 | 1.513 | | | |
| 1-32 | | 0.030 | 0.033 | 0.050 |
| 1-33 | 2.993 | | | |
| 1-34 | 4.512 | | | |
| 1-35 | 10.548 | | | |
| 1-36 | 0.964 | | | |
| 1-37 | 1.744 | | | |
| 1-38 | 0.166 | 0.060 | 0.044 | 0.026 |
| 1-39 | 0.156 | | | |
| 1-40 | 2.306 | | | |
| 1-41 | 8.498 | | | |
| 1-42 | 11.554 | | | |
| 1-43 | 12.359 | | | |
| 1-44 | 10.324 | | | |
| 1-45 | 0.416 | | | |
| 1-46 | 5.586 | | | |
| 1-47 | 0.234 | 0.020 | 0.021 | 0.028 |
| 1-48 | 0.189 | 0.021 | 0.002 | 0.007 |
| 1-49 | 1.392 | | | |
| 1-50 | 0.592 | 0.034 | | 0.002 |
| 1-51 | 1.311 | 0.044 | 0.132 | 0.072 |
| 1-52 | 0.326 | | | |
| 1-53 | | 0.050 | 0.019 | 0.038 |
| 1-54 | 0.187 | | | |
| 1-55 | 0.132 | | | |
| 1-56 | 0.103 | | | |
| 1-57 | 0.058 | 0.030 | 0.024 | 0.014 |
| 1-58 | 0.817 | | | |
| 1-59 | 0.079 | 0.015 | 0.009 | 0.011 |
| 1-60 | 0.140 | 0.025 | 0.015 | 0.019 |
| 1-61 | 0.183 | 0.045 | 0.060 | 0.045 |
| 1-62 | 1.118 | 0.074 | 0.084 | 0.054 |
| 1-63 | 0.202 | 0.025 | 0.008 | 0.004 |
| 1-64 | 0.090 | 0.016 | 0.006 | 0.014 |
| 1-65 | 0.107 | 0.015 | 0.019 | 0.012 |
| 1-66 | 6.117 | | | |
| 1-67 | 1.202 | | | |
| 1-68 | 0.184 | 0.053 | 0.056 | 0.059 |

TABLE 7-continued

| Example # | IC50 (μM) (mutation/cell line) G12D (HPAC) | G12V (H727) | G12D (GP2D) | G12C (H358) |
|---|---|---|---|---|
| 1-69 | 0.193 | | | |
| 1-70 | 0.915 | | | |
| 1-71 | 0.157 | | | |
| 1-72 | 0.213 | 0.060 | 0.069 | 0.042 |
| 1-73 | 0.690 | 0.042 | 0.007 | 0.027 |
| 1-74 | 0.214 | 0.052 | 0.083 | 0.077 |
| 1-75 | 0.182 | | | |
| 1-76 | 1.081 | | | |
| 1-77 | 2.814 | | | |
| 1-78 | 1.119 | 0.048 | 0.069 | 0.048 |
| 1-79 | 0.340 | | | |
| 1-80 | 0.663 | | | |
| 1-81 | 1.434 | | | |
| 1-82 | 0.159 | 0.034 | 0.022 | 0.038 |
| 1-83 | 0.266 | | | |
| 1-84 | 0.431 | | | |
| 1-85 | 1.000 | | | |
| 1-86 | 0.147 | | | |
| 1-87 | 0.584 | | | |
| 1-88 | 0.735 | | | |
| 1-89 | 0.199 | | | |
| 1-90 | 0.522 | 0.209 | 0.192 | 0.127 |
| 1-91 | 0.495 | 0.048 | 0.108 | 0.083 |
| 1-92 | 1.070 | | | |
| 1-93 | 0.599 | | | |
| 1-94 | 1.321 | | | |
| 1-95 | 0.247 | | | |
| 1-96 | 0.296 | | | |
| 1-97 | 0.997 | | | |
| 1-98 | 0.209 | | | |
| 1-99 | 0.689 | | | |
| 1-100 | 0.584 | | | |
| 1-101 | 0.333 | | | |
| 1-102 | 0.609 | | | |
| 1-103 | 0.437 | | | |
| 1-110 | 0.086 | 0.024 | 0.024 | 0.024 |
| 1-115 | 0.398 | | | |
| 1-118 | 0.030 | 0.017 | 0.008 | 0.026 |
| 1-119 | 0.026 | | | |
| 1-120 | 0.084 | 0.065 | 0.019 | 0.099 |
| 1-121 | 0.050 | 0.146 | 0.014 | 0.056 |
| 1-122 | 1.453 | | | |
| 1-123 | 0.687 | | | |
| 1-124 | 0.685 | | | |
| 1-125 | 0.724 | | | |
| 1-126 | 0.862 | | | |
| 1-130 | 0.761 | | | |
| 1-131 | 0.981 | 0.045 | 0.011 | 0.079 |
| 1-132 | 0.901 | | | |
| 1-134 | 2.282 | | | |
| 1-135 | 1.049 | | | |
| 1-136 | 3.720 | 0.087 | 0.146 | 0.134 |
| 1-137 | 12.830 | | | |
| 1-140 | 25.000 | | | |
| 1-141 | >2.5 | | | |
| 1-144 | >2.5 | | | |
| 1-152 | >2.5 | | | |
| 1-205 | 13.698 | | | |
| 1-206 | 4.684 | | | |
| 1-213 | 7.216 | | | |
| 1-214 | 14.166 | | | |
| 1-215 | 6.393 | | | |
| 1-218 | 6.856 | | | |
| 1-219 | 1.722 | | | |
| 1-220 | 1.186 | | | |
| 1-221 | 1.469 | | | |
| 1-224 | 0.024 | | | |
| 1-225 | 0.036 | | | |
| 1-226 | 0.018 | | | |
| 1-227 | 0.045 | | | |
| 1-268 | 0.018 | 0.032 | 0.029 | 0.063 |
| 1-322 | 0.006 | 0.007 | | 0.006 |
| 1-323 | 0.003 | | | |
| 1-324 | 0.010 | 0.010 | | 0.007 |
| 1-326 | 0.024 | 0.022 | | 0.011 |

TABLE 7-continued

| Example # | IC50 (μM) (mutation/cell line) G12D (HPAC) | G12V (H727) | G12D (GP2D) | G12C (H358) |
|---|---|---|---|---|
| 1-327 | 0.016 | 0.009 | | 0.011 |
| 1-328 | 0.023 | 0.018 | | 0.013 |
| 1-329 | 0.026 | 0.018 | | 0.030 |
| 1-331 | 0.021 | 0.047 | | 0.029 |
| 1-332 | 0.042 | 0.061 | | 0.082 |
| 1-333 | 0.071 | 0.096 | | 0.124 |
| 1-334 | 0.040 | 0.036 | | 0.040 |
| 2-3 | 2.387 | 0.027 | 0.031 | 0.031 |
| 2-4 | 0.171 | | | |
| 2-5 | 3.167 | | | |
| 2-6 | 11.746 | | | |
| 2-7 | 5.368 | | | |
| 2-8 | 0.584 | | | |
| 2-9 | 0.166 | | | |
| 2-10 | 5.970 | | | |
| 2-11 | 4.288 | | | |
| 2-12 | 0.211 | | | |
| 2-13 | 0.509 | | | |
| 2-14 | 0.061 | | | |
| 2-15 | 0.059 | 0.032 | 0.006 | 0.030 |
| 2-16 | 0.031 | | | 0.003 |
| 2-17 | 0.145 | 0.050 | 0.048 | 0.093 |
| 2-18 | 0.166 | | | |
| 2-19 | 0.188 | | | |
| 2-20 | 0.038 | | | |
| 2-21 | 0.011 | | | |
| 2-22 | 0.137 | | | |
| 2-23 | 0.047 | | | |
| 2-24 | 0.008 | 0.012 | | |
| 2-25 | 0.024 | 0.040 | 0.032 | 0.064 |
| 2-26 | 0.045 | | | |
| 2-27 | 0.140 | | | |
| 2-28 | 0.220 | | | |
| 2-29 | 0.020 | | | |
| 2-30 | 0.009 | | | |
| 2-31 | 0.128 | | | |
| 2-32 | 2.244 | | | |
| 2-33 | 0.074 | | | |
| 2-34 | 0.034 | | | |
| 2-35 | 0.029 | | | |
| 2-36 | 0.020 | | | |
| 2-37 | 0.044 | | | |
| 2-38 | 0.070 | | | |
| 2-39 | 0.024 | | | |
| 2-40 | 0.023 | | | |
| 2-41 | 0.430 | | | |
| 2-42 | 0.110 | | | |
| 2-43 | 0.756 | | | |
| 2-44 | 0.443 | | | |
| 2-45 | 0.050 | | | |
| 2-46 | 0.038 | | | |
| 2-47 | 0.067 | | | |
| 2-48 | 1.417 | | | |
| 2-49 | 0.145 | | | |
| 2-50 | 0.198 | | | |
| 2-51 | 0.407 | | | |
| 2-52 | 0.411 | | | |
| 2-53 | 0.041 | 0.016 | | |
| 2-54 | 0.021 | | | |
| 2-55 | 0.040 | 0.017 | 0.020 | 0.035 |
| 2-56 | 0.192 | | | |
| 2-57 | 0.229 | | | |
| 2-58 | 0.070 | 0.057 | 0.037 | 0.125 |
| 2-59 | 0.054 | | | |
| 2-60 | 0.191 | | | |
| 2-61 | 0.470 | | | |
| 2-62 | 0.078 | 0.090 | 0.029 | 0.131 |
| 2-63 | 0.181 | | | |
| 2-64 | 0.016 | 0.023 | 0.015 | 0.053 |
| 2-65 | 0.118 | | | |
| 2-66 | 0.339 | | | |
| 2-67 | 0.831 | 0.089 | 0.094 | 0.203 |
| 2-69 | 0.013 | 0.009 | | |
| 2-70 | 0.216 | | | |
| 2-71 | 0.031 | | | |

TABLE 7-continued

| Example # | $IC_{50}$ (μM) (mutation/cell line) G12D (HPAC) | G12V (H727) | G12D (GP2D) | G12C (H358) |
|---|---|---|---|---|
| 2-72 | 0.156 | | | |
| 2-73 | 0.109 | | | |
| 2-74 | 0.295 | | | |
| 2-75 | 5.029 | | | |
| 2-76 | 0.015 | 0.013 | 0.007 | 0.018 |
| 2-77 | 0.013 | | | |
| 2-78 | 0.013 | 0.010 | 0.006 | 0.021 |
| 2-79 | 0.034 | 0.028 | 0.009 | 0.033 |
| 2-81 | 0.523 | | | |
| 2-82 | 0.452 | | | |
| 2-83 | 0.040 | 0.029 | 0.011 | 0.053 |
| 2-86 | 0.183 | 0.121 | 0.052 | 0.168 |
| 2-87 | 0.011 | | | |
| 2-88 | 0.011 | | | |
| 2-89 | 0.150 | | | |
| 2-90 | 0.005 | | | |
| 2-91 | 0.022 | | | |
| 2-92 | 0.003 | | | |
| 2-93 | 0.010 | | | |
| 2-94 | 0.008 | | | |
| 2-95 | 0.008 | | | |
| 2-96 | 0.003 | 0.005 | | 0.006 |
| 2-97 | 0.002 | 0.010 | 0.005 | 0.010 |
| 2-98 | 0.007 | 0.021 | 0.014 | 0.026 |
| 2-99 | 0.002 | 0.005 | | 0.007 |
| 2-100 | 0.008 | 0.022 | 0.009 | 0.018 |
| 2-101 | 0.005 | 0.012 | 0.006 | 0.013 |
| 2-102 | 0.006 | 0.014 | 0.006 | 0.012 |
| 2-103 | 0.002 | 0.008 | 0.004 | 0.008 |
| 2-104 | 0.017 | 0.037 | 0.017 | 0.045 |
| 2-105 | 0.013 | 0.026 | 0.018 | 0.041 |
| 2-107 | 0.013 | 0.018 | 0.010 | 0.025 |
| 2-108 | 0.209 | | | |
| 2-109 | 0.169 | | | |
| 2-110 | 0.041 | | | |
| 2-111 | 0.037 | | | |
| 2-112 | 0.029 | | | |
| 2-113 | 0.006 | | | |
| 2-114 | 0.008 | 0.006 | | 0.014 |
| 2-115 | 0.037 | | | |
| 2-116 | 0.010 | 0.011 | | 0.008 |
| 2-117 | 0.062 | | | |
| 2-120 | 0.128 | | | |
| 2-124 | 0.001 | 0.003 | | |
| 2-126 | 0.002 | 0.005 | 0.003 | 0.004 |
| 2-127 | 0.003 | 0.009 | | 0.004 |
| 2-128 | 0.007 | | | |
| 2-129 | 0.009 | | | |
| 16-1 | 0.049 | 0.067 | | 0.094 |
| 16-2 | 0.019 | 0.012 | 0.004 | 0.013 |
| 17-1 | 0.008 | 0.014 | | 0.013 |
| 18-1 | 0.002 | 0.004 | | |
| 26-1 | 0.030 | 0.091 | | |
| 26-2 | 0.010 | 0.021 | 0.009 | 0.017 |

PERK Immunofluorescence Assay

Cells (2000-5000 cells per well) were plated in 384 well plates (Revvity 6057602) and incubated overnight. Cells were treated with compound (2 hours) and fixed with (paraformaldehyde, 4%) for 15 minutes. Cells were washed three times (PBS), permeabilized (0.1% Triton X100) for 15 minutes, and washed three times (PBS). Cells were blocked for 1 hour at room temperature (5% normal goat serum, 0.2 M glycine, PBS) followed by incubation with PERK antibody (CST-4370S, 1:250) overnight at 4° C. Cells were washed three times (PBS) and stained with anti-rabbit secondary antibody (Invitrogen A-11034, 1:1000), Hoechst 33342 (Invitrogen H3570, 1:1000), and CellMask (Invitrogen H32721, 1:15000) for 1 hour at room temperature. Cells were washed three times (PBS) prior to imaging (Opera Phenix). Average pERK intensity per cell was measured, and $IC_{50}$ values were calculated from the dose-response curve. $IC_{50}$ values are shown in Table 8.

TABLE 8

| Ex. | $IC_{50}$ (nM) (mutation/cell line) G12D (GP2D) | G12D (HPAC) | G12V (SW620) | G12V (H727) | G13D (LoVo) | G12A (H2009) | G12S (A549) | Q61H (H460) | WT amplified (MKN1) | G12C (MiaPaCa2) |
|---|---|---|---|---|---|---|---|---|---|---|
| 26-2 | 1.0 | 0.9 | 28.4 | 5.7 | 1.7 | 1.1 | 52.1 | | 0.8 | 0.3 |

Cellular KRAS:RAF Disruption Assay

Stable cell lines (HEK293T) were generated to co-express RAF1 and mutant or wild type KRAS, as indicated, using the BiBRET vector (Promega). Engineered cell lines were suspended in media (OptiMEM, 4% FBS), plated in 384-well plates (8000 cells/well), and allowed to rest for 1.5 hours. Cells were treated with compounds for 24 hours, and NanoBRET NanoGlo substrate (Promega) was added per the manufacturer's instructions. NanoBRET signal was measured (PerkinElmer Envision), the signal ratio ($\lambda_{em}$ 618/$\lambda_{em}$ 460) was calculated, and $IC_{50}$ values were calculated from the dose-response curve. $IC_{50}$ values are shown in Table 9.

TABLE 9

| | $IC_{50}$ (nM) | | | | | | | | |
|---|---|---|---|---|---|---|---|---|---|
| Example # | G12D | G12V | G13D | Q61H | G12A | G12S | A146T | G12C | KRAS WT (4B) |
| 1-11 | 280.7 | | | | | | | | |
| 1-71 | 8.2 | 26.9 | 5.3 | 5.8 | 2.6 | 2.9 | | 2.5 | 1.4 |
| 2-69 | 1.2 | 27.9 | | | 0.7 | | | | 0.6 |
| 26-2 | 0.9 | 12.7 | 2.2 | 1.5 | 0.8 | 0.8 | 4 | 1.2 | 0.6 |

Certain compounds in the present disclosure have favorable pharmacodynamic and pharmacokinetic properties such as enhanced systemic exposure from oral dosing.

It is to be appreciated that the Detailed Description section, and not the Summary and Abstract sections, is intended to be used to interpret the claims. The Summary and Abstract sections can set forth one or more but not all exemplary aspects of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific aspects will so fully reveal the general nature of the disclosure that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

What is claimed is:

1. A compound selected from the group consisting of:

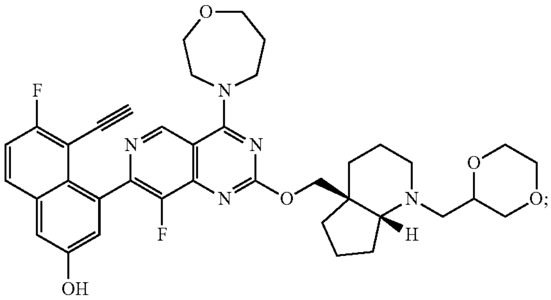

;

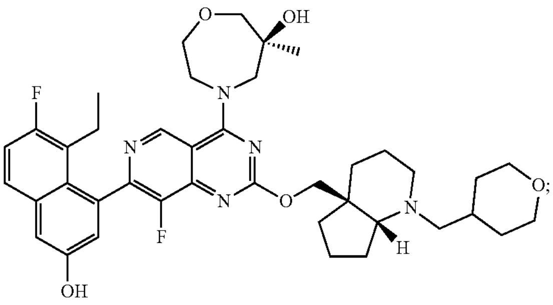

;

-continued
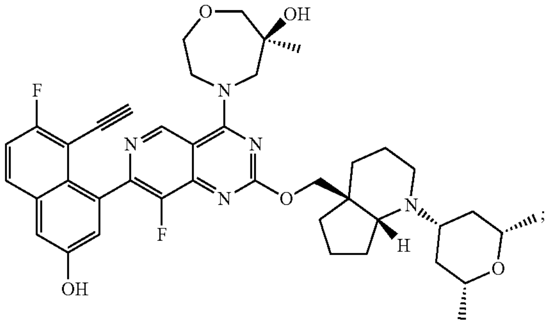
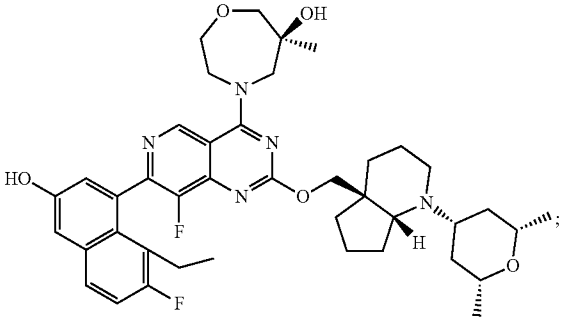
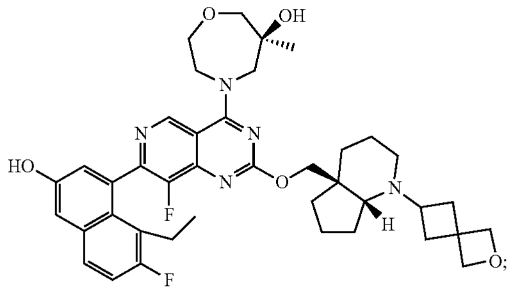
and
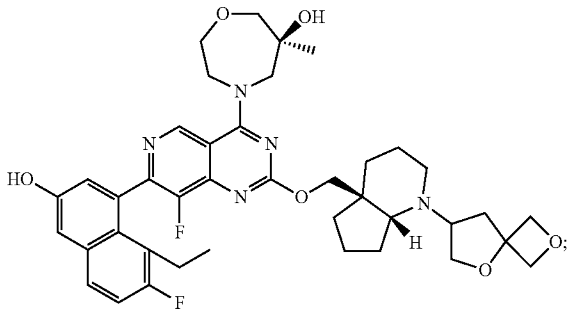
or a pharmaceutically acceptable salt thereof.
2. A compound of claim 1 which is a pharmaceutically acceptable salt.
3. A compound of claim 1 selected from the group consisting of:
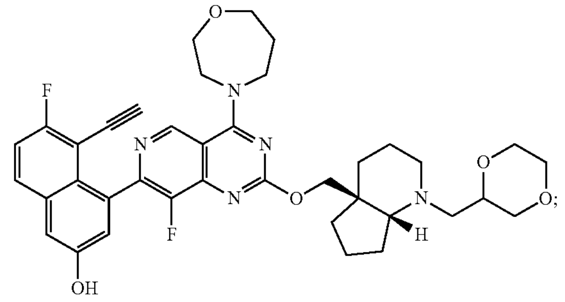
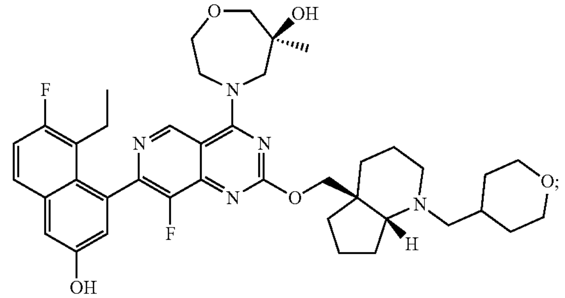
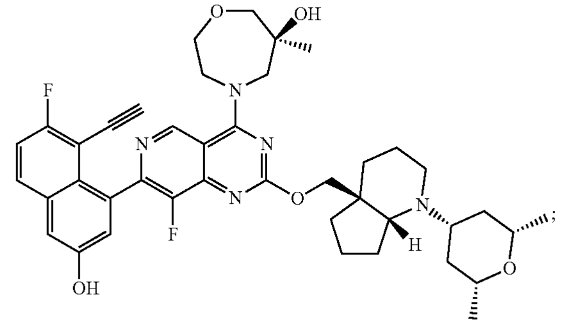
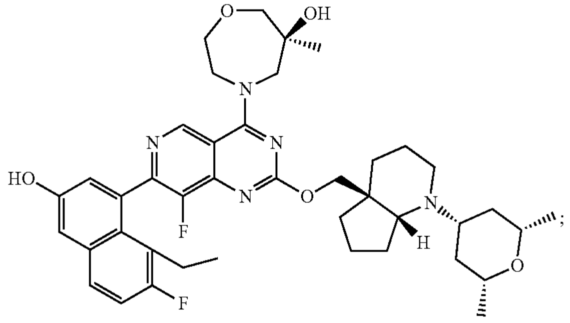
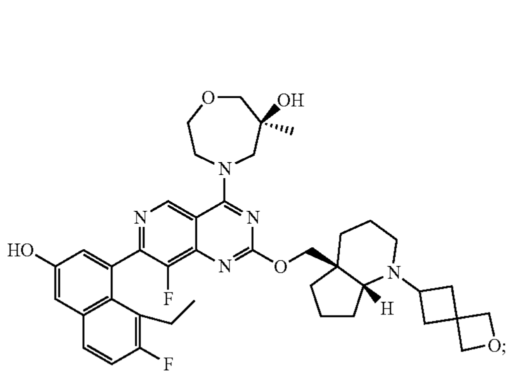
and -continued
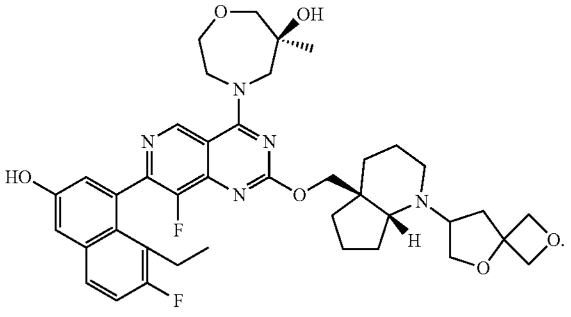
4. The compound of claim 3, which is:
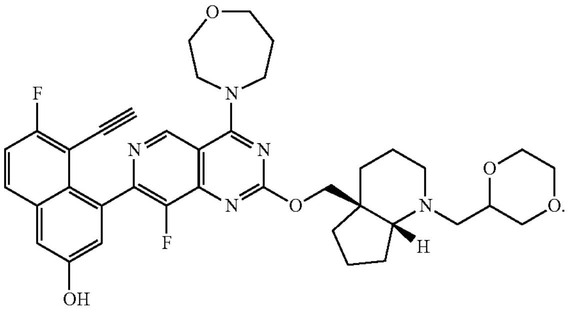 [SMILES: C#Cc1c(F)ccc2cc(O)cc(-c3ncc4c(N5CCCOCC5)nc(OC[C@]56CCC[C@H]5N(CC5COCCO5)CCC6)nc4c3F)c12]
5. The compound of claim 3, which is:
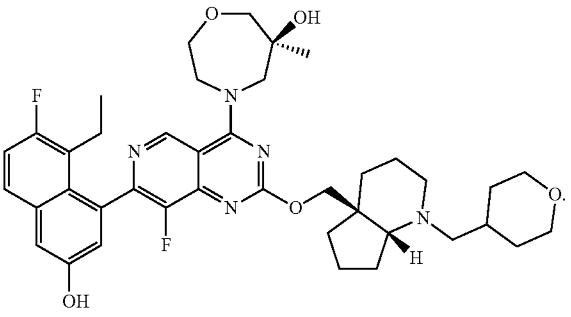 [SMILES: CCc1c(F)ccc2cc(O)cc(-c3ncc4c(N5CCOC[C@@](C)(O)C5)nc(OC[C@]56CCC[C@H]5N(CC5CCOCC5)CCC6)nc4c3F)c12]
6. The compound of claim 3, which is:
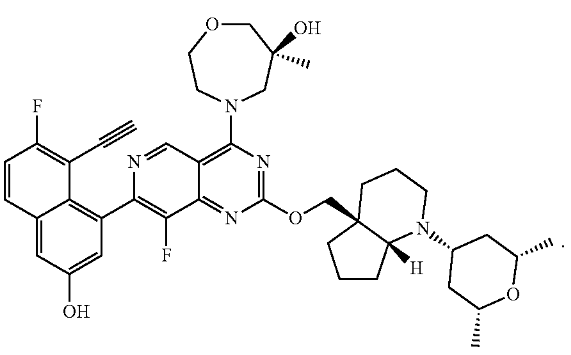 [SMILES: C#Cc1c(F)ccc2cc(O)cc(-c3ncc4c(N5CCOC[C@@](C)(O)C5)nc(OC[C@]56CCC[C@H]5N([C@H]5C[C@@H](C)O[C@@H](C)C5)CCC6)nc4c3F)c12]
7. The compound of claim 3, which is:
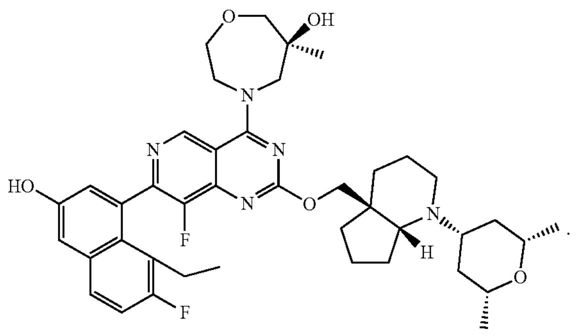 [SMILES: CCc1c(F)ccc2cc(O)cc(-c3ncc4c(N5CCOC[C@@](C)(O)C5)nc(OC[C@]56CCC[C@H]5N([C@H]5C[C@@H](C)O[C@@H](C)C5)CCC6)nc4c3F)c12]
8. The compound of claim 3, which is:
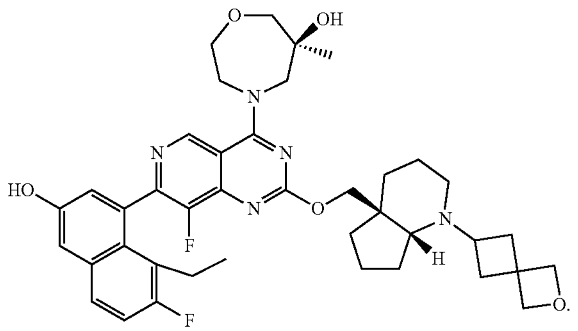 [SMILES: CCc1c(F)ccc2cc(O)cc(-c3ncc4c(N5CCOC[C@@](C)(O)C5)nc(OC[C@]56CCC[C@H]5N(C5CC7(COC7)C5)CCC6)nc4c3F)c12]
9. The compound of claim 3, which is:
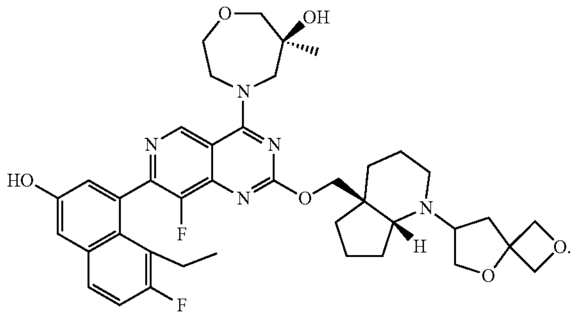 [SMILES: CCc1c(F)ccc2cc(O)cc(-c3ncc4c(N5CCOC[C@@](C)(O)C5)nc(OC[C@]56CCC[C@H]5N(C5COC7(COC7)C5)CCC6)nc4c3F)c12]
10. The compound of claim 1, which is:
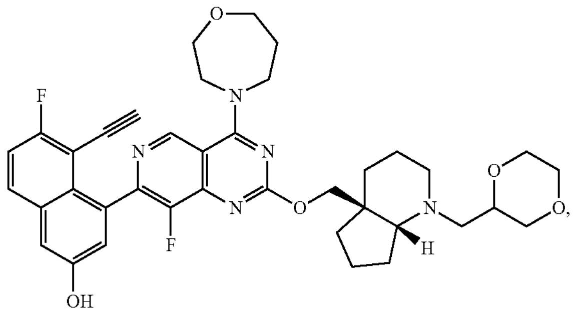 [SMILES: C#Cc1c(F)ccc2cc(O)cc(-c3ncc4c(N5CCCOCC5)nc(OC[C@]56CCC[C@H]5N(CC5COCCO5)CCC6)nc4c3F)c12]
or a pharmaceutically acceptable salt thereof.

11. The compound of claim 1, which is

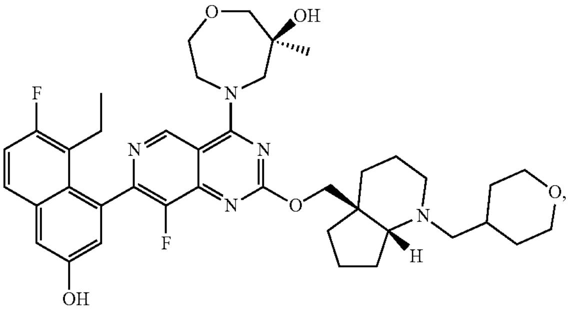 [SMILES: CCc1c(F)ccc2cc(O)cc(-c3ncc4c(N5CCOC[C@@](C)(O)C5)nc(OC[C@]56CCC[C@H]5N(CC5CCOCC5)CCC6)nc4c3F)c12]

or a pharmaceutically acceptable salt thereof.

12. The compound of claim 1, which is

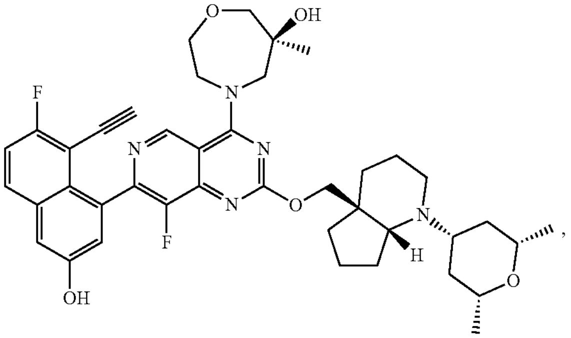 [SMILES: C#Cc1c(F)ccc2cc(O)cc(-c3ncc4c(N5CCOC[C@@](C)(O)C5)nc(OC[C@]56CCC[C@H]5N([C@H]5C[C@@H](C)O[C@@H](C)C5)CCC6)nc4c3F)c12]

or a pharmaceutically acceptable salt thereof.

13. The compound of claim 1, which is

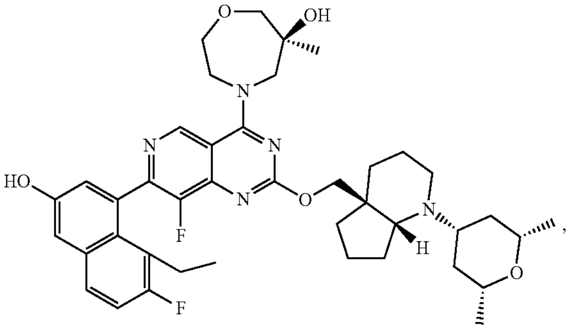 [SMILES: CCc1c(F)ccc2cc(O)cc(-c3ncc4c(N5CCOC[C@@](C)(O)C5)nc(OC[C@]56CCC[C@H]5N([C@H]5C[C@@H](C)O[C@@H](C)C5)CCC6)nc4c3F)c12]

or a pharmaceutically acceptable salt thereof.

14. The compound of claim 1, which is

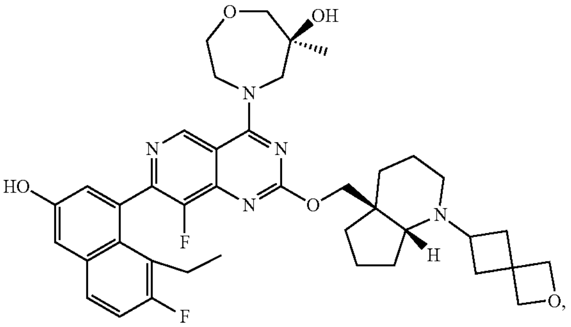 [SMILES: CCc1c(F)ccc2cc(O)cc(-c3ncc4c(N5CCOC[C@@](C)(O)C5)nc(OC[C@]56CCC[C@H]5N(C5CC7(COC7)C5)CCC6)nc4c3F)c12]

or a pharmaceutically acceptable salt thereof.

15. The compound of claim 1, which is

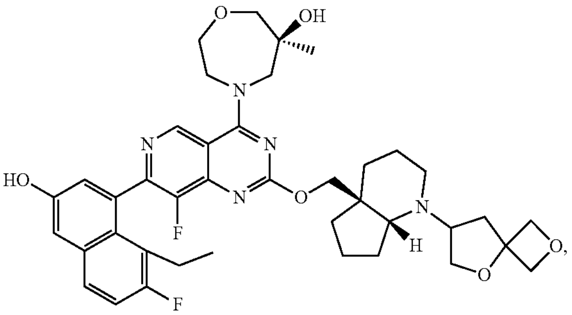 [SMILES: CCc1c(F)ccc2cc(O)cc(-c3ncc4c(N5CCOC[C@@](C)(O)C5)nc(OC[C@]56CCC[C@H]5N(C5COC7(COC7)C5)CCC6)nc4c3F)c12]

or a pharmaceutically acceptable salt thereof.

* * * * *